US011987829B2

(12) United States Patent
Pauthenier et al.

(10) Patent No.: US 11,987,829 B2
(45) Date of Patent: May 21, 2024

(54) METHOD FOR THE BIOSYNTHESIS OF DIOSMIN AND/OR HESPERIDIN IN A MICROORGANISM

(71) Applicant: LES LABORATOIRES SERVIER, Suresnes (FR)

(72) Inventors: Cyrille Pauthenier, Juvisy-sur-Orge (FR); André Le Jeune, Draveil (FR); Hélène Scornec, Longjumeau (FR); Célia Roussel, Saintry sur Seine (FR); Laetitia Joubert, Palaiseau (FR)

(73) Assignee: LES LABORATOIRES SERVIER, Suresnes (FR)

( * ) Notice: Subject to any disclaimer, the term of this patent is extended or adjusted under 35 U.S.C. 154(b) by 450 days.

(21) Appl. No.: 17/429,459

(22) PCT Filed: Feb. 11, 2020

(86) PCT No.: PCT/EP2020/053503
§ 371 (c)(1),
(2) Date: Aug. 9, 2021

(87) PCT Pub. No.: WO2020/165189
PCT Pub. Date: Aug. 20, 2020

(65) Prior Publication Data

US 2022/0042061 A1 Feb. 10, 2022

(30) Foreign Application Priority Data

Feb. 11, 2019 (EP) .................................... 19305163

(51) Int. Cl.

| | |
|---|---|
| ***C12P 19/60*** | (2006.01) |
| ***C12N 9/00*** | (2006.01) |
| ***C12N 9/02*** | (2006.01) |
| ***C12N 9/10*** | (2006.01) |
| ***C12N 9/88*** | (2006.01) |
| ***C12N 9/90*** | (2006.01) |

(52) U.S. Cl.

CPC ............ *C12P 19/60* (2013.01); *C12N 9/0042* (2013.01); *C12N 9/0071* (2013.01); *C12N 9/0073* (2013.01); *C12N 9/1007* (2013.01); *C12N 9/1051* (2013.01); *C12N 9/1085* (2013.01); *C12N 9/88* (2013.01); *C12N 9/90* (2013.01); *C12N 9/93* (2013.01); *C12Y 106/02004* (2013.01); *C12Y 114/11022* (2013.01); *C12Y 114/13011* (2013.01); *C12Y 114/14* (2013.01); *C12Y 204/01* (2013.01); *C12Y 204/01185* (2013.01); *C12Y 205/01006* (2013.01); *C12Y 402/01076* (2013.01); *C12Y 403/01023* (2013.01); *C12Y 403/01024* (2013.01); *C12Y 505/01006* (2013.01); *C12Y 602/01012* (2013.01)

(58) Field of Classification Search
None
See application file for complete search history.

(56) References Cited

FOREIGN PATENT DOCUMENTS

| | | |
|---|---|---|
| CN | 108 504 680 | 9/2018 |
| CN | 109 312 375 | 2/2019 |
| EP | 3 321 273 | 5/2018 |
| WO | WO 2018/039923 | 3/2018 |

OTHER PUBLICATIONS

An, D. G. et al. "Biosynthesis of two quercetin O-diglycosides in *Escherichia coli*" *J Ind Microbial Biotechnol.*, 2016, pp. 841-849, vol. 43, No. 6.

Del Bano, M. J. et al. "Flavonoid Distribution during the Development of Leaves, Flowers, Stems, and Roots of *Rosmarinus officinalis*. Postulation of a Biosynthetic Pathway" *J. Agric. Food Chem.*, 2004, pp. 4987-4992, vol. 52, No. 16.

Kim, B. G. et al. "Biosynthesis and production of glycosylated flavonoids in *Escherichia coli*: current state and perspectives" *Appl Microbial Biotechnol.*, 2015, pp. 2979-2988, vol. 99, No. 7.

Ohashi, T. et al. "Substrate preference of citrus naringenin rhamnosyltransferases and their application to flavonoid glycoside production in fission yeast" *Appl Microbial Biotechnol.*, 2016, pp. 687-696, vol. 100, No. 2.

Trantas, E. A. et al. "When plants produce not enough or at all: rnetabolic engineering of flavonoids in microbial hosts" *Frontiers in Plant Science*, Jan. 29, 2015, pp. 1-16, vol. 6, Article 7.

Database Biosis [Online] Accession No. PREV201000250656, "Biotransformation of hesperidin to hesperetin by microorganisms" Jan. 2010, p. 1, XP002793175.

Written Opinion in International Application No. PCT/EP2020/053503, dated Mar. 19, 2020, pp. 1-8.

*Primary Examiner* — Suzanne M Noakes
*Assistant Examiner* — Jae W Lee
(74) *Attorney, Agent, or Firm* — SALIWANCHIK, LLOYD & EISENSCHENK

(57) ABSTRACT

The present invention relates to a recombinant microorganism which is modified to be capable of producing diosmin and hesperidin and to the use thereof for producing diosmin and/or hesperidin.

18 Claims, 35 Drawing Sheets

Specification includes a Sequence Listing.

[Figure 1]
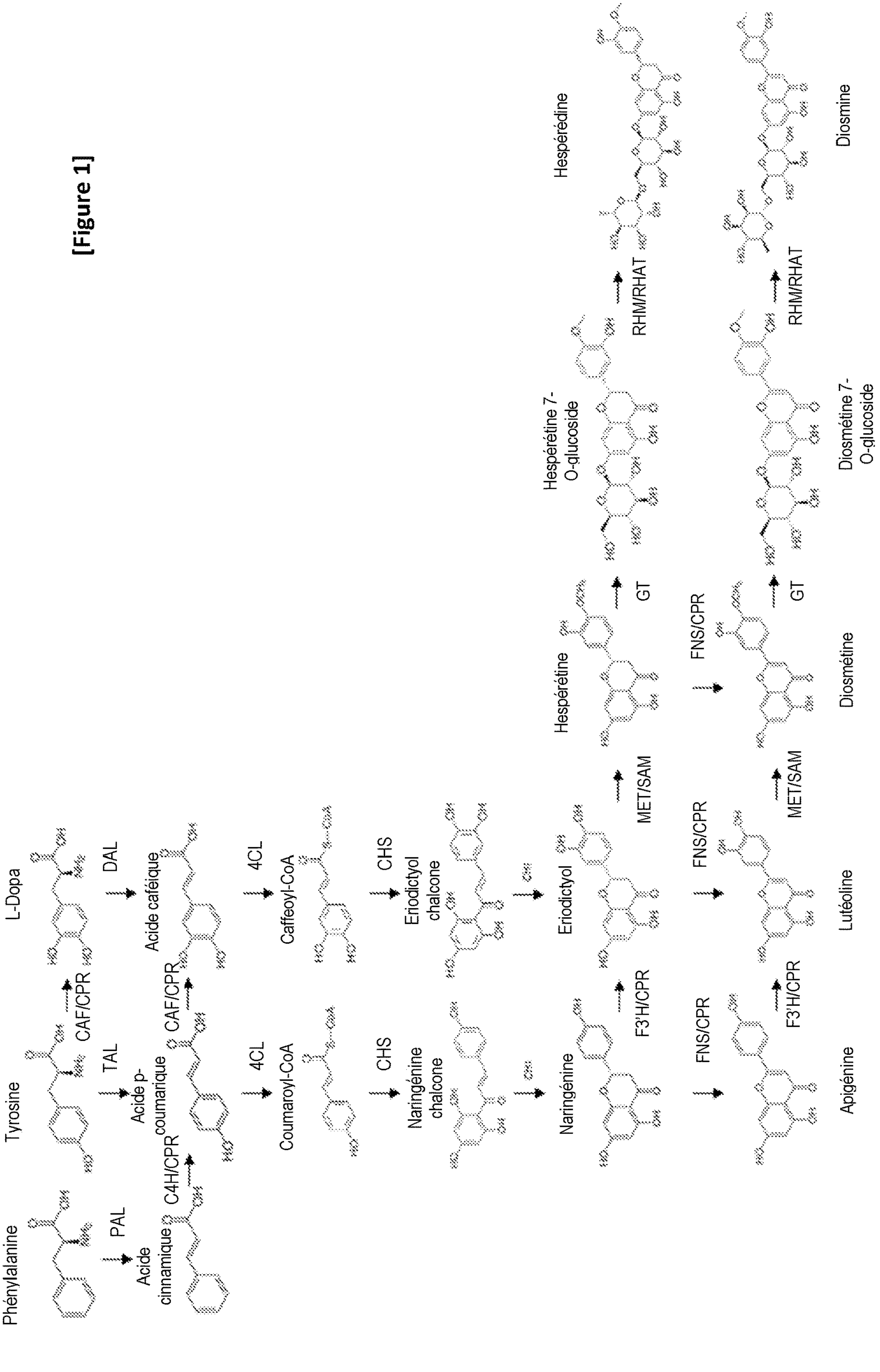
Phénylalanine
Tyrosine
L-Dopa
Acide cinnamique
Acide p-coumarique
Acide caféique
Coumaroyl-CoA
Caffeoyl-CoA
Naringénine chalcone
Eriodictyol chalcone
Naringénine
Eriodictyol
Hespérétine
Hespérétine 7-O-glucoside
Hespérédine
Apigénine
Lutéoline
Diosmétine
Diosmétine 7-O-glucoside
Diosmine

[Figure 2]
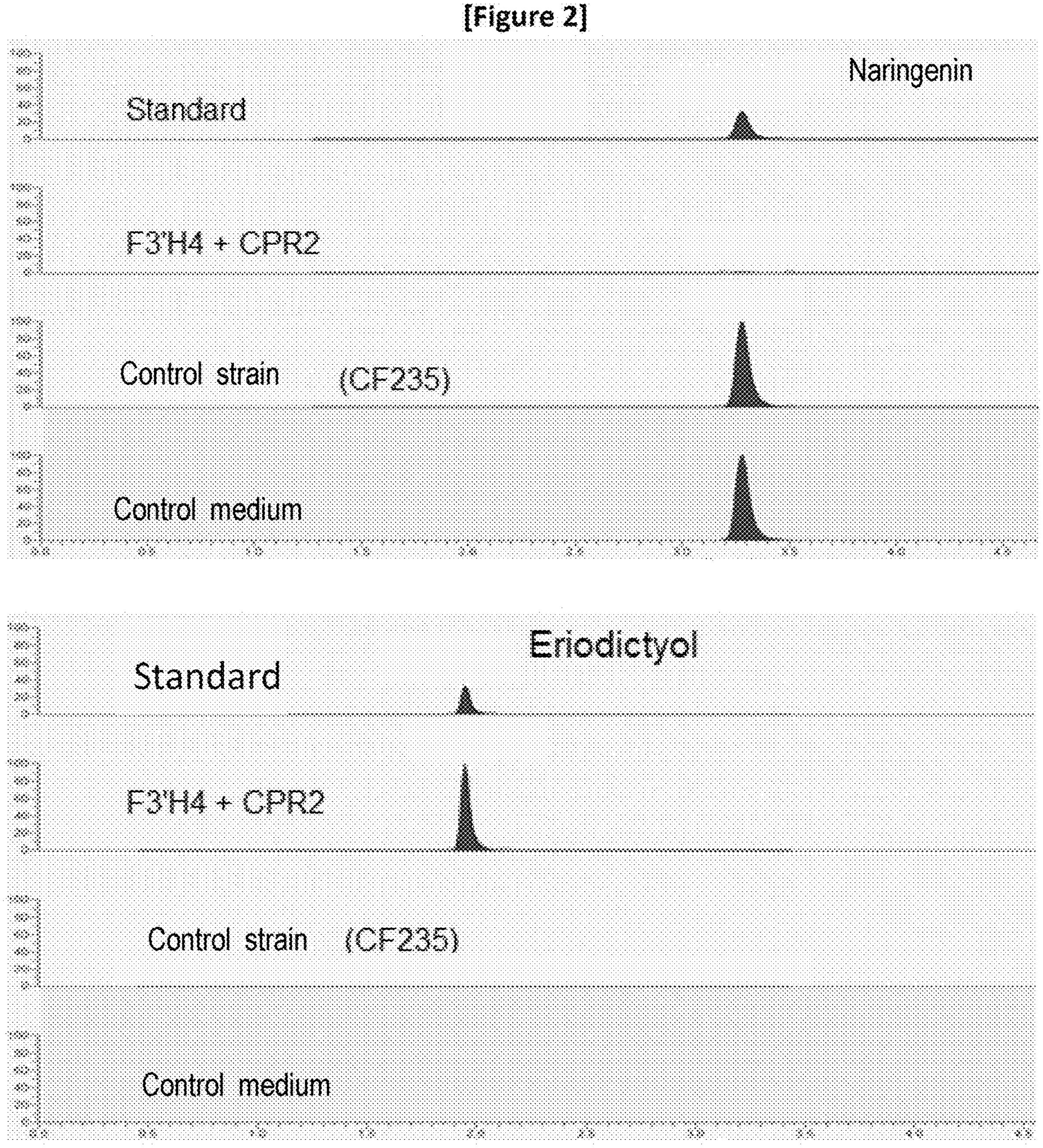

[Figure 3]
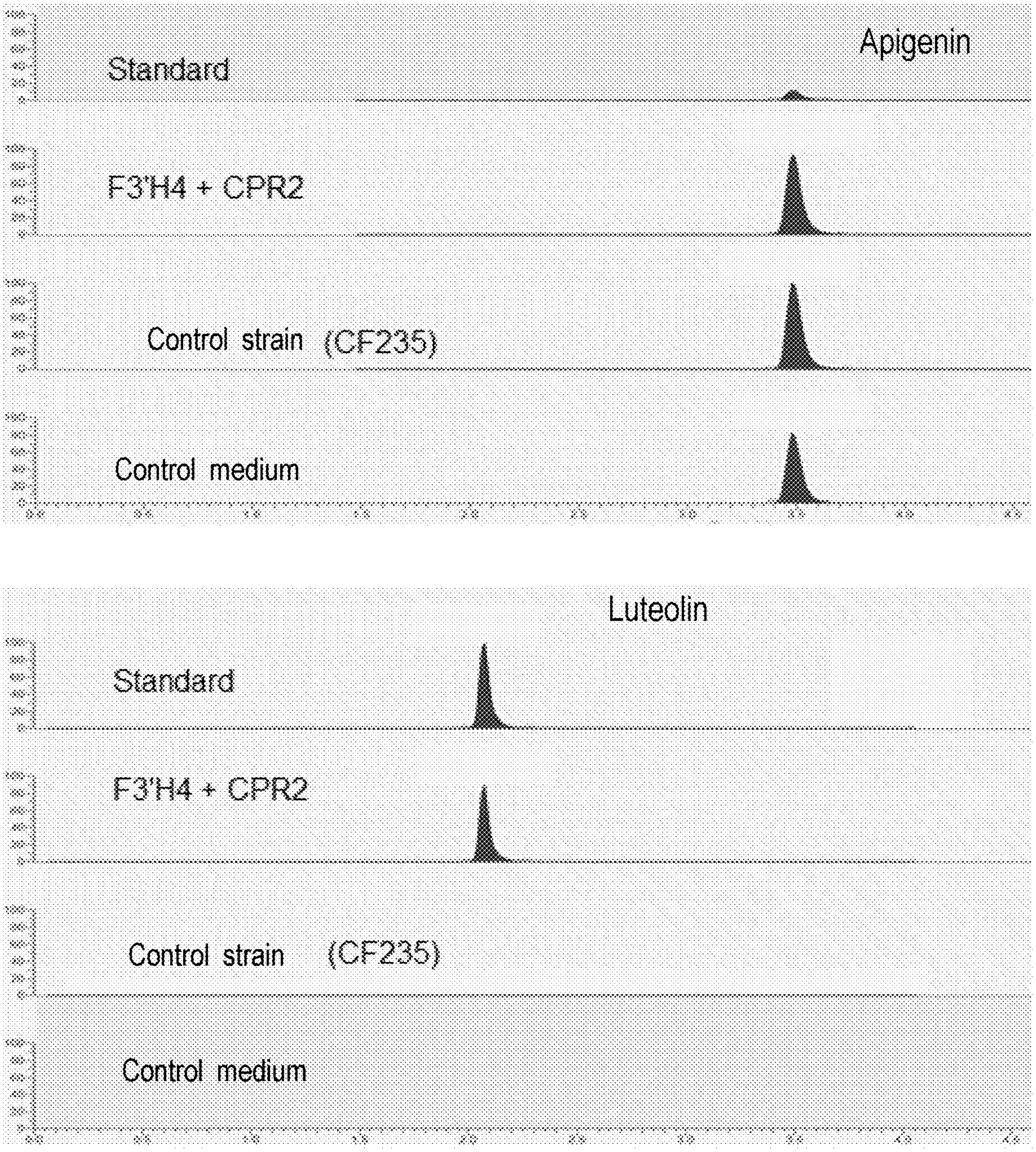

[Figure 4]
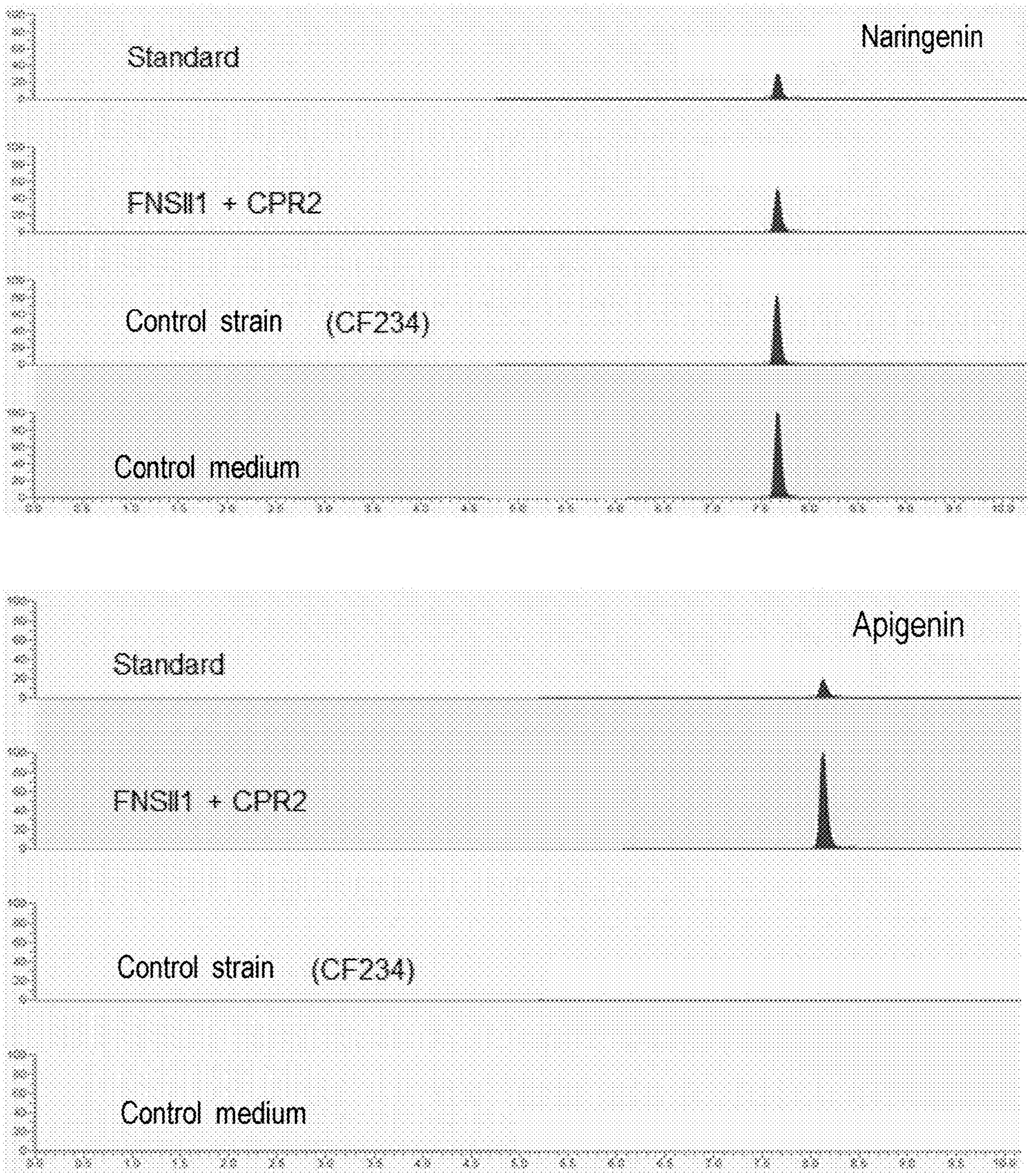

[Figure 5]
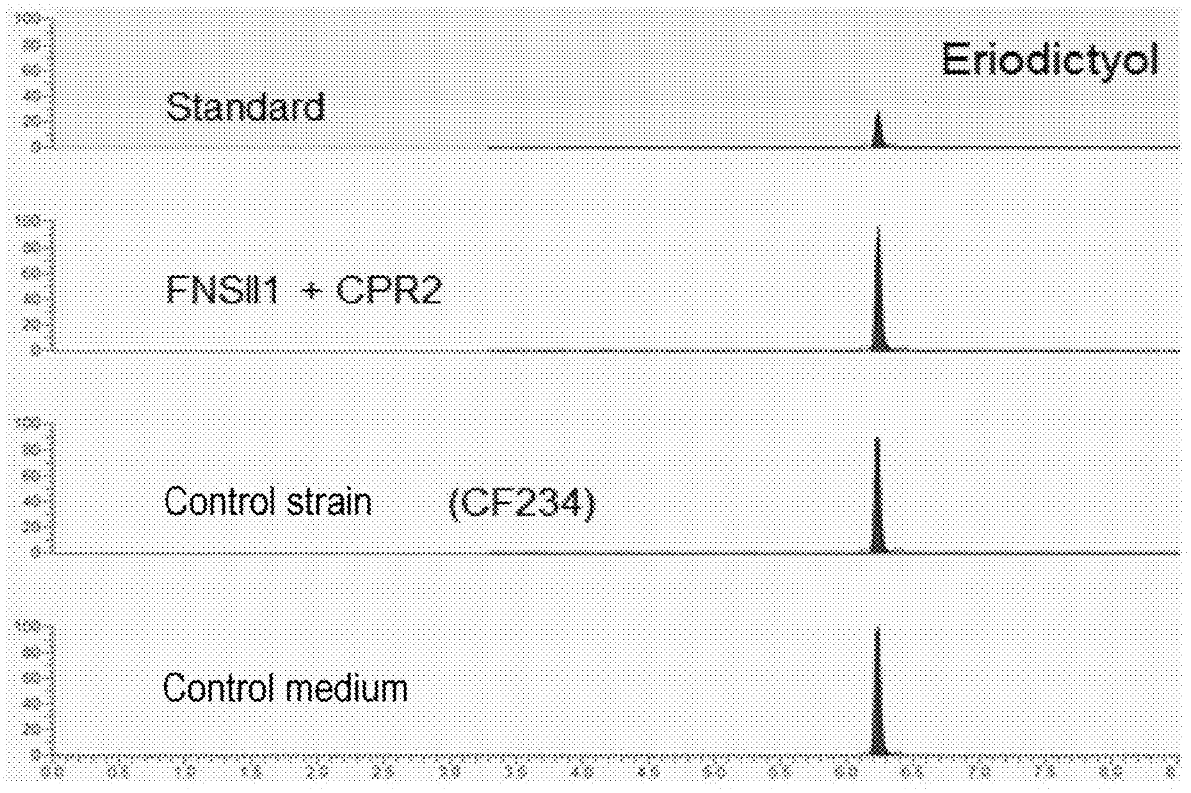
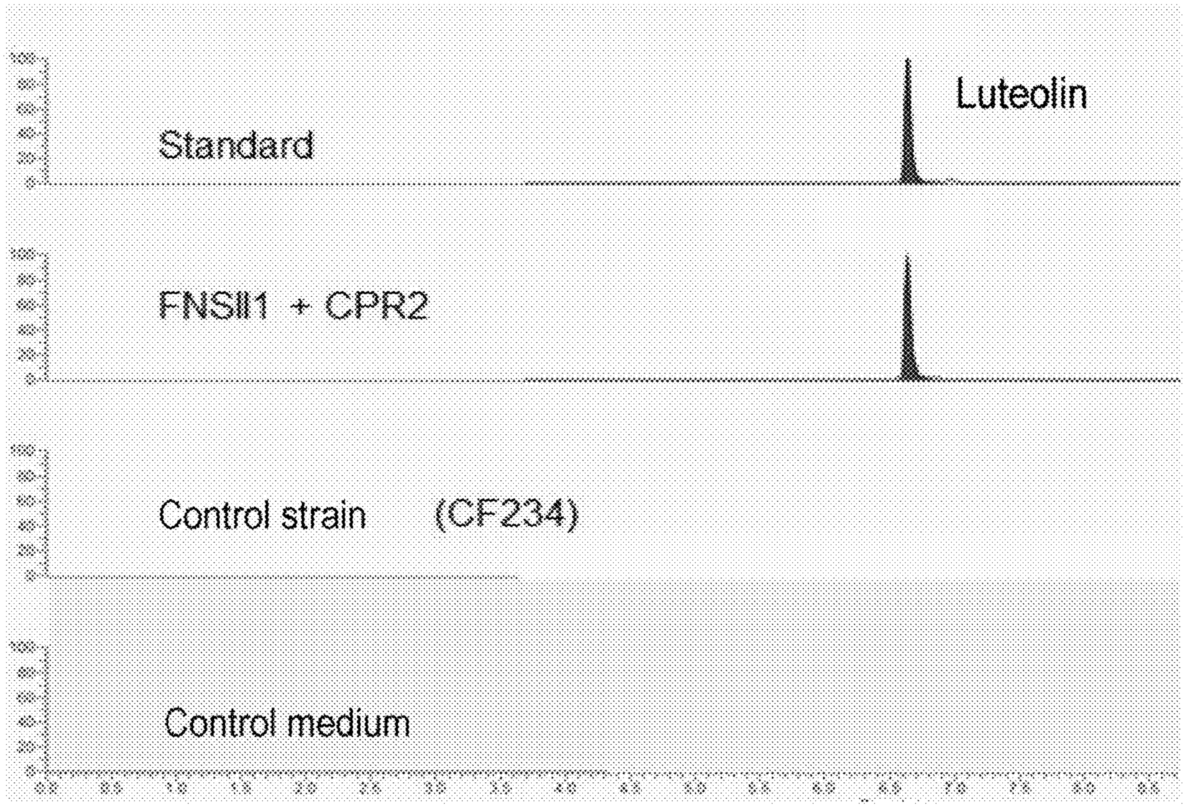

[Figure 6]
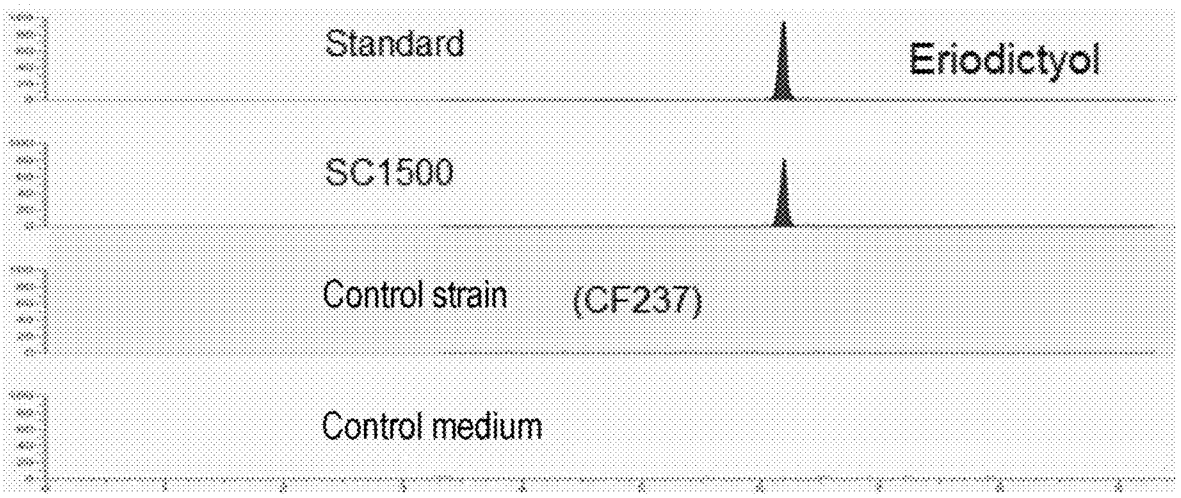
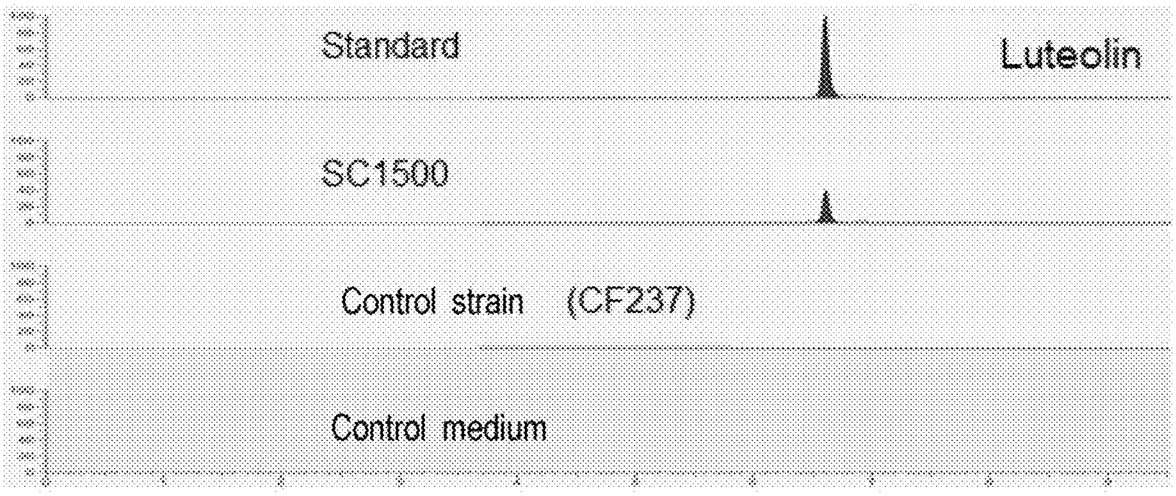

[Figure 7]
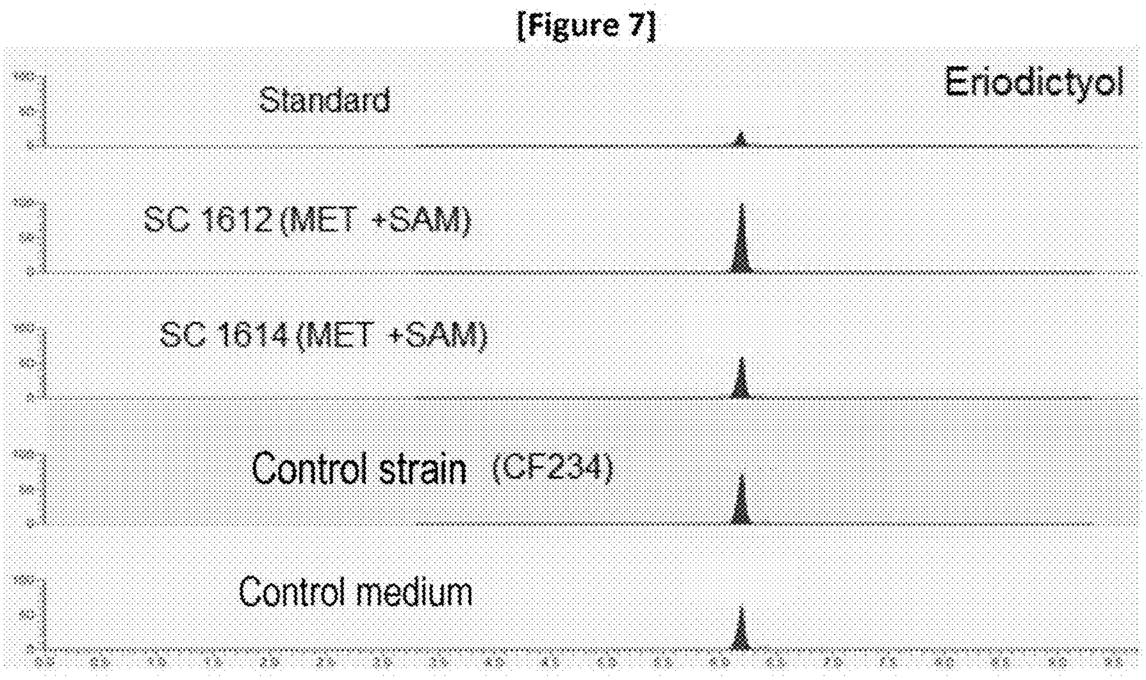
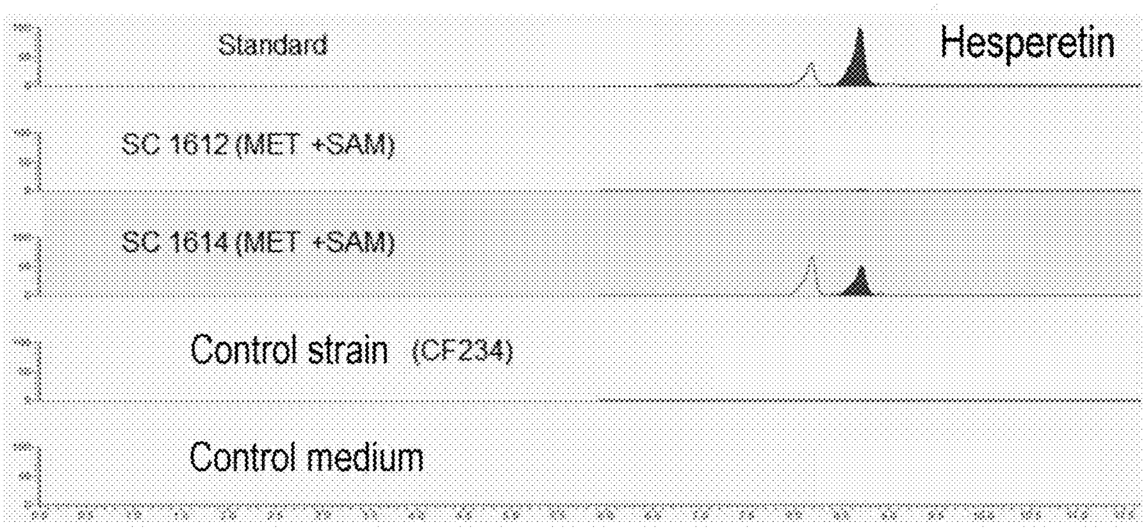

[Figure 8]
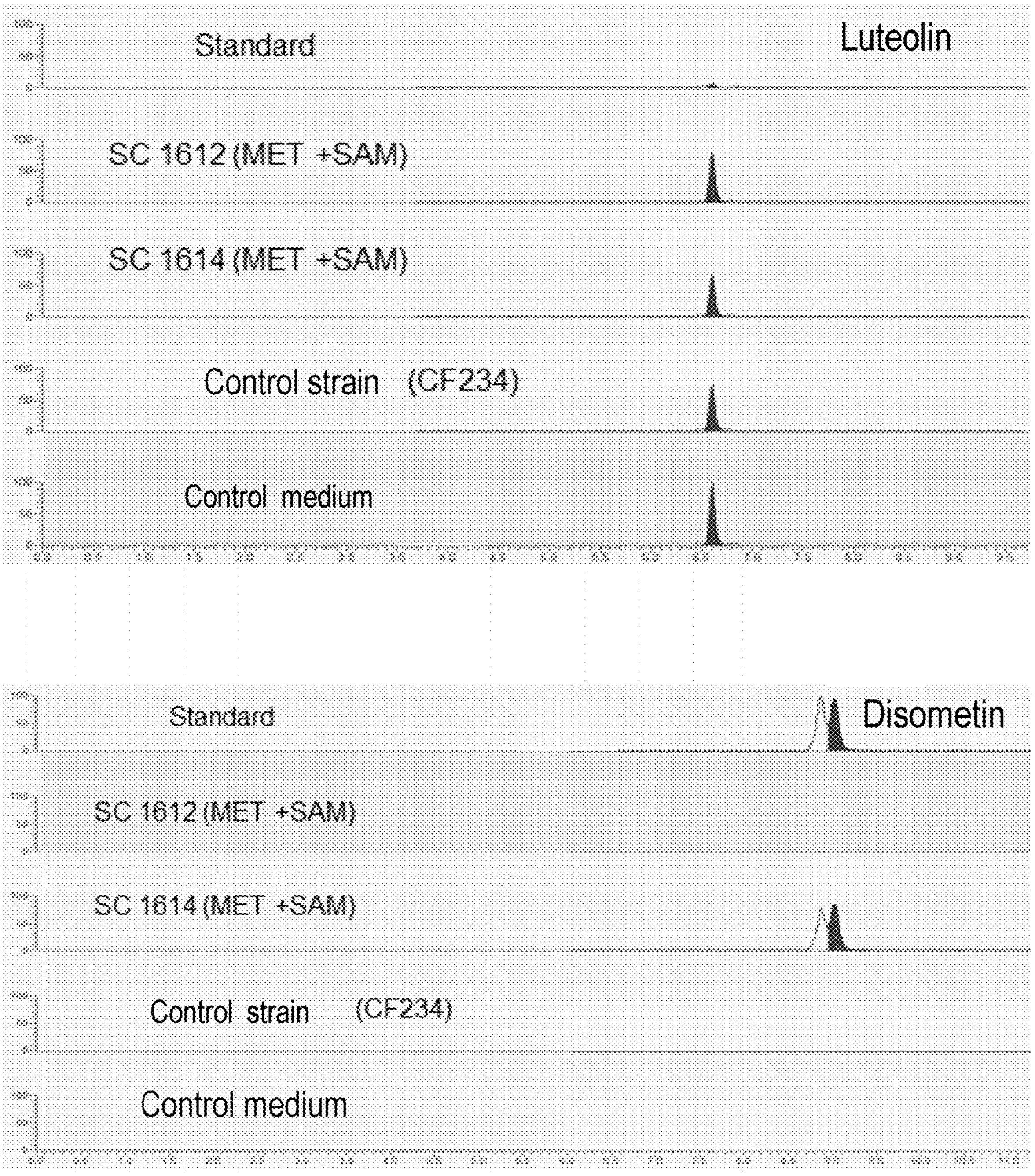

[Figure 9]
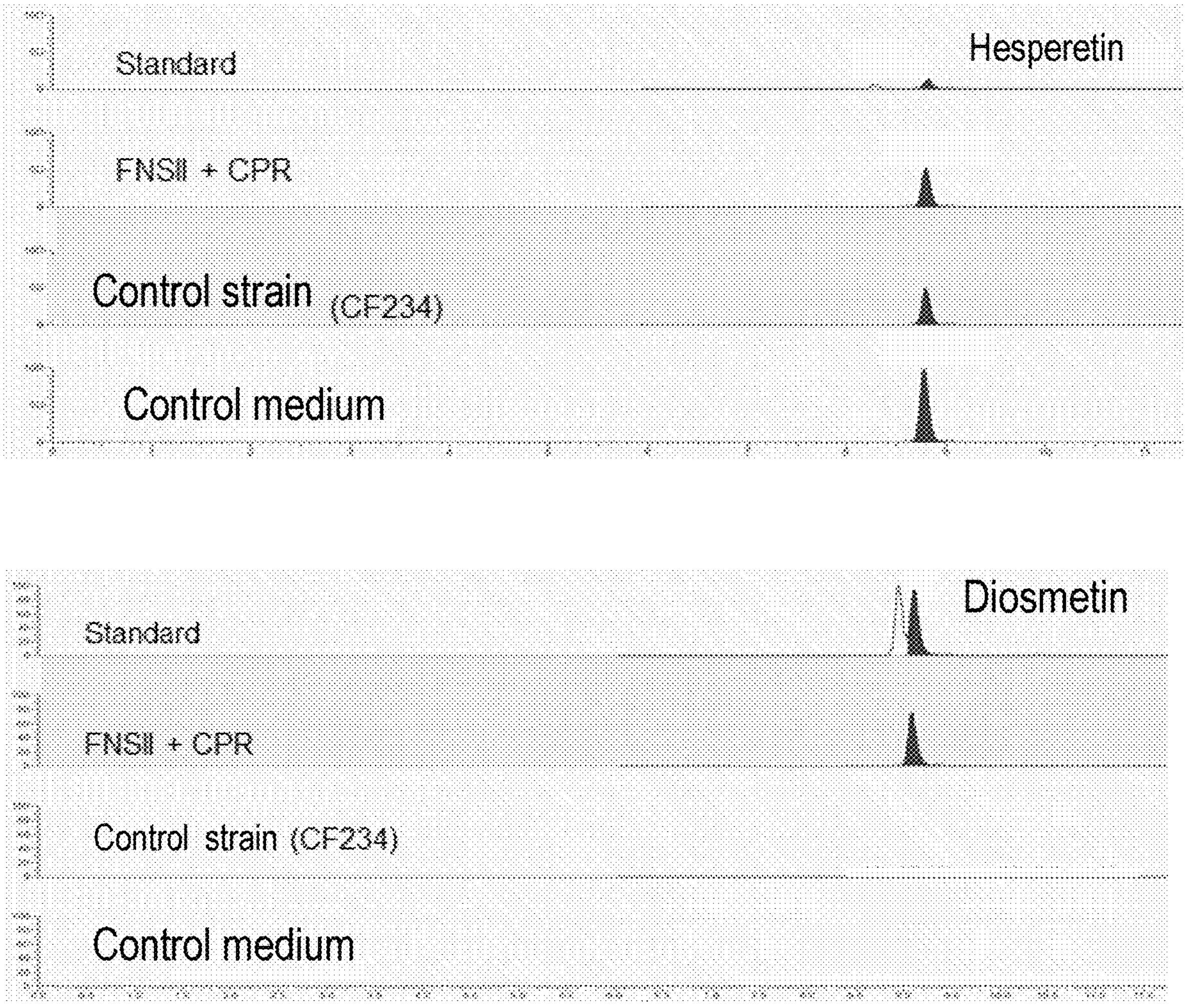

[Figure 10]
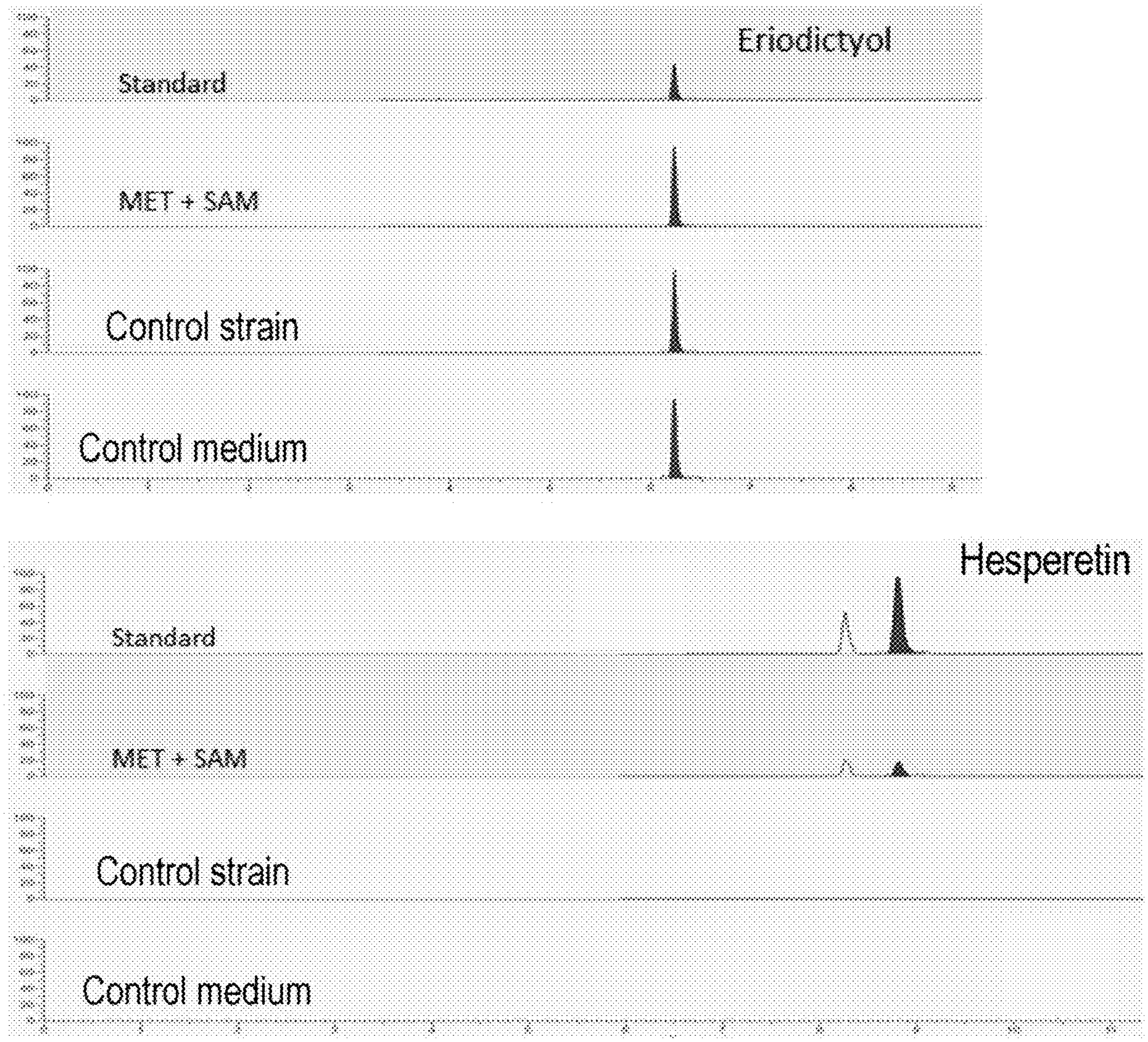

[Figure 11]
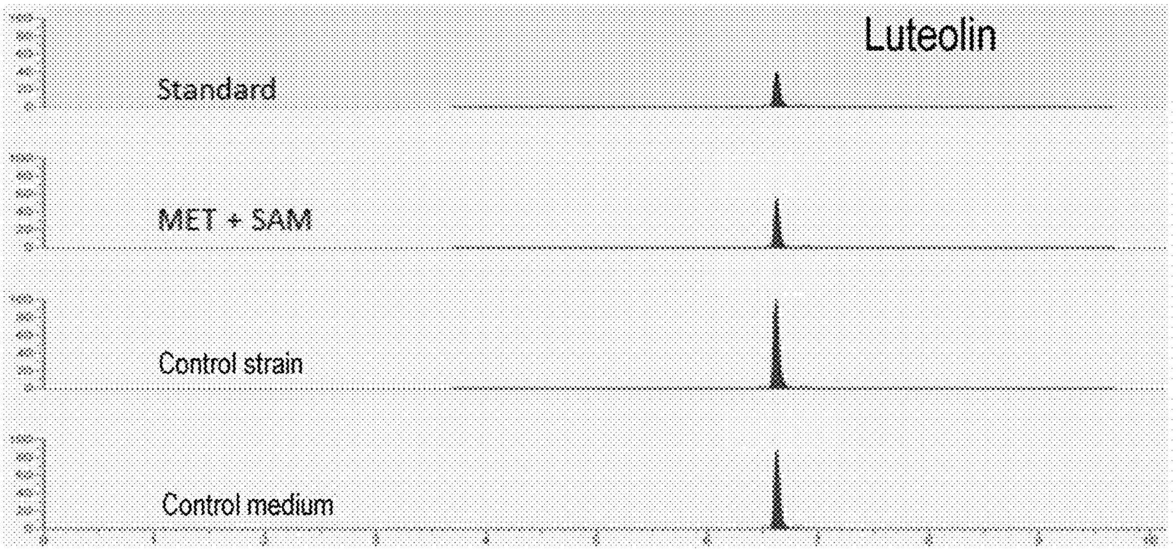
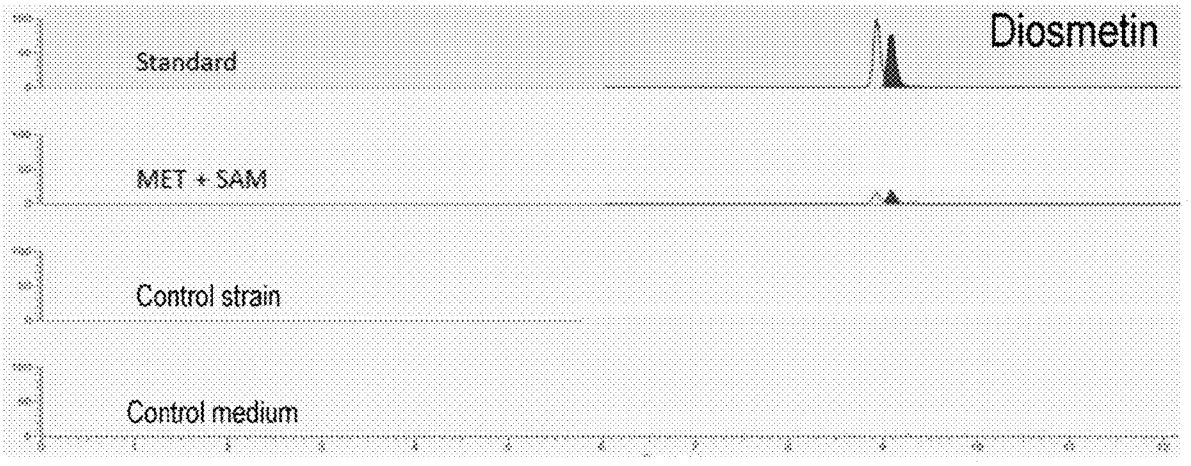

[Figure 12]
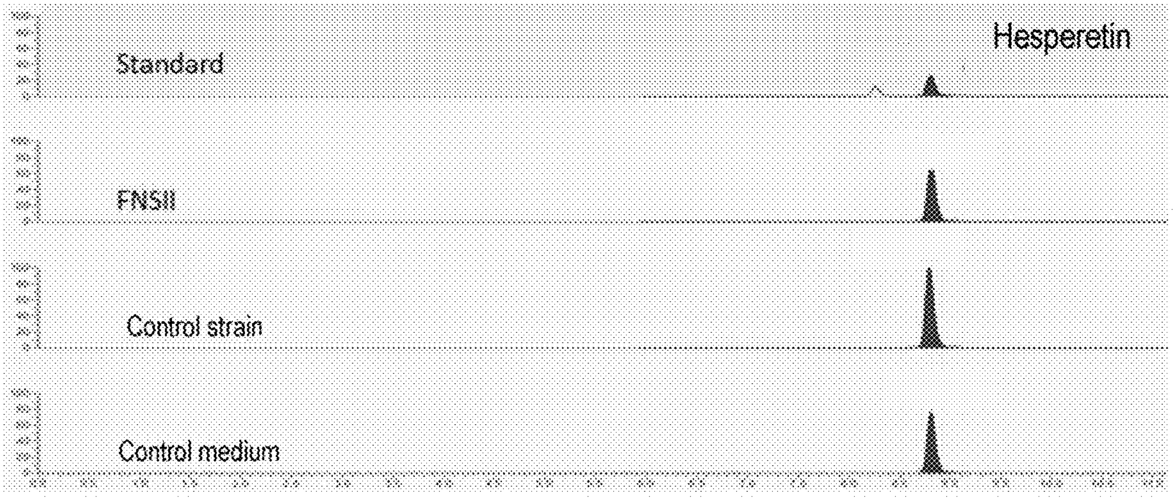
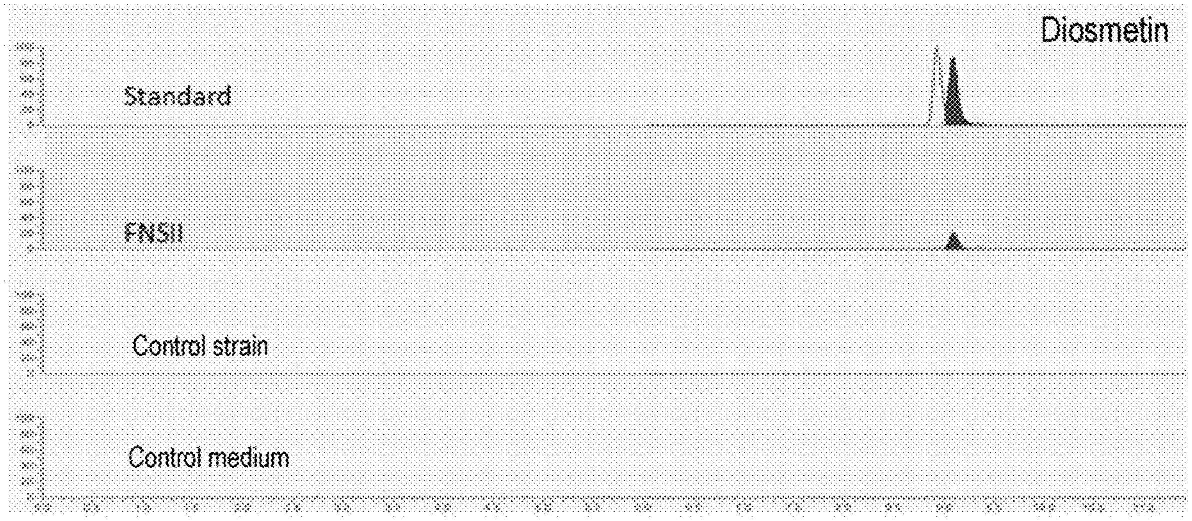

[Figure 13]
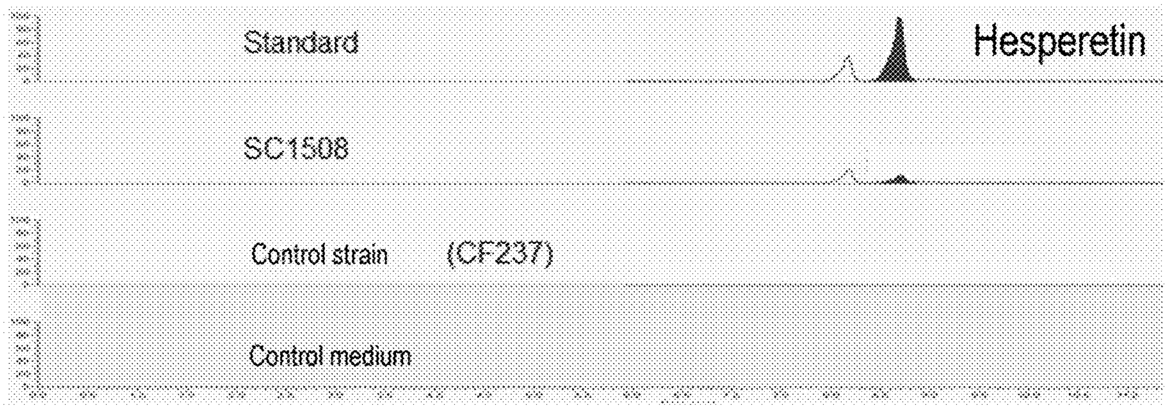
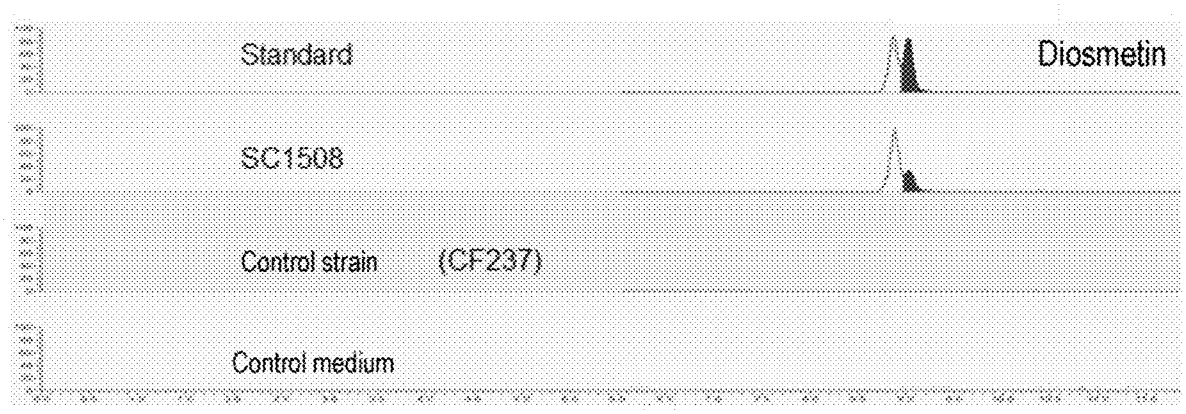

[Figure 14]
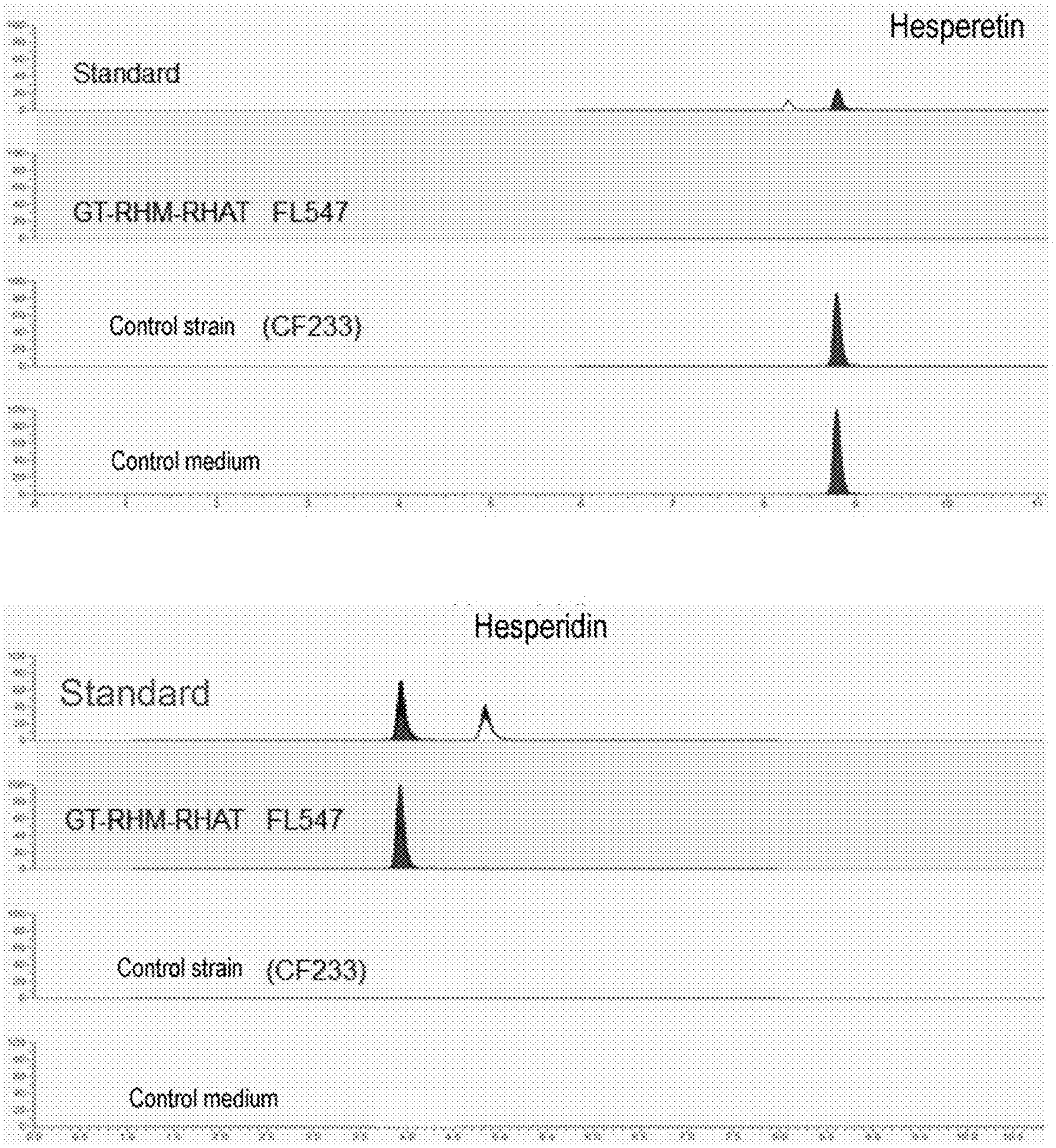

[Figure 15]
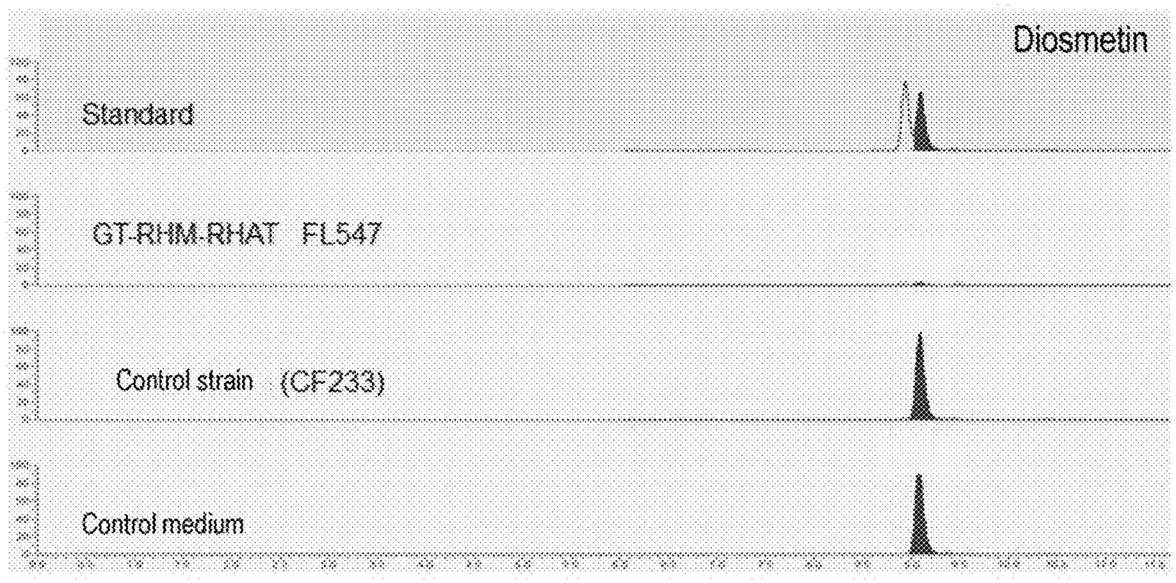
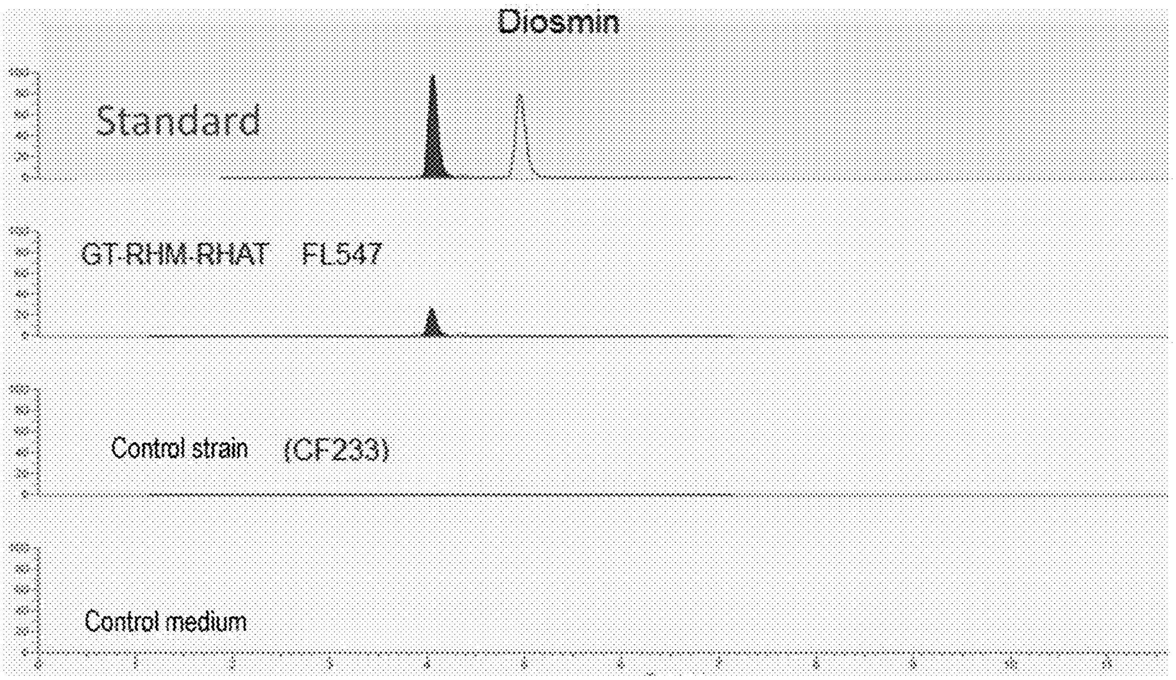

[Figure 16]
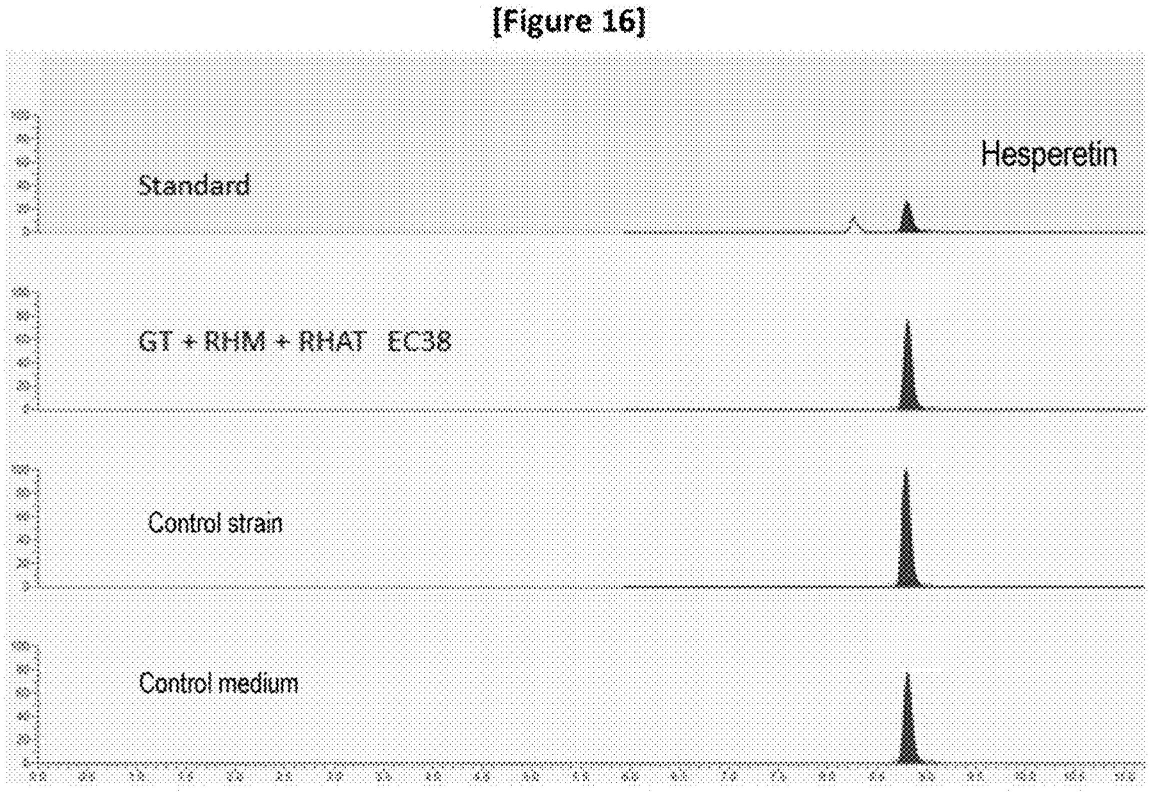
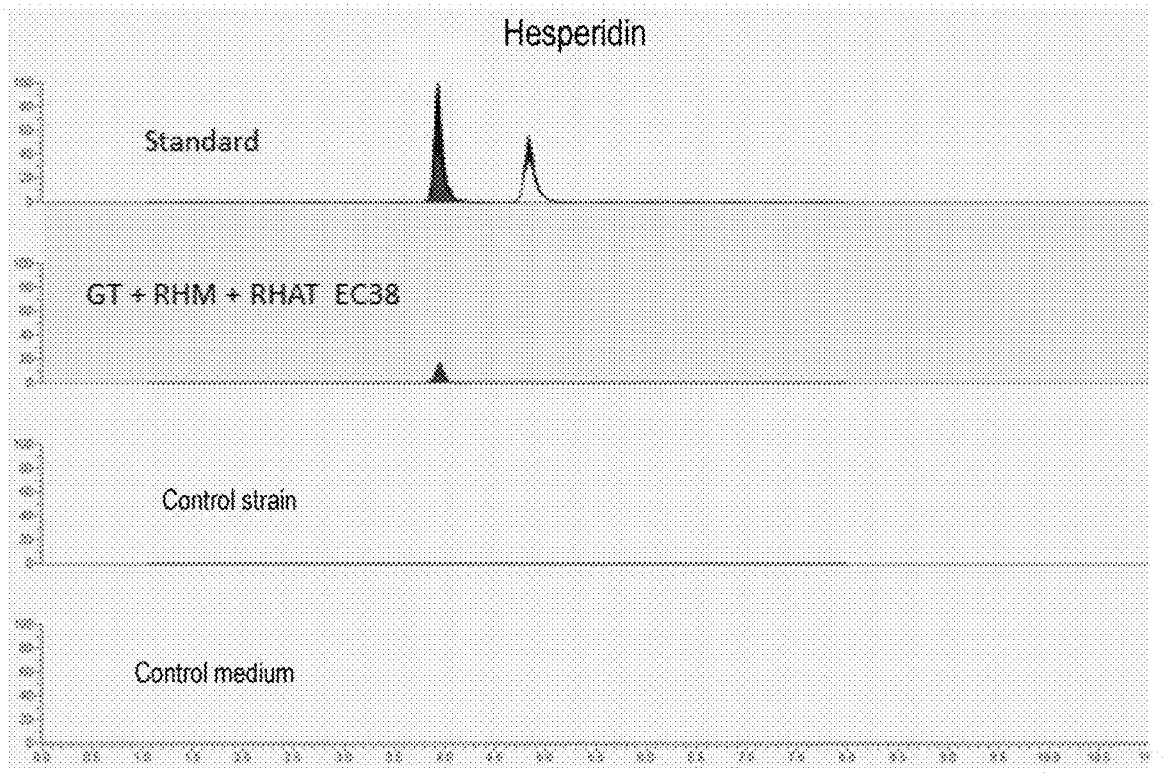

[Figure 16 continued]
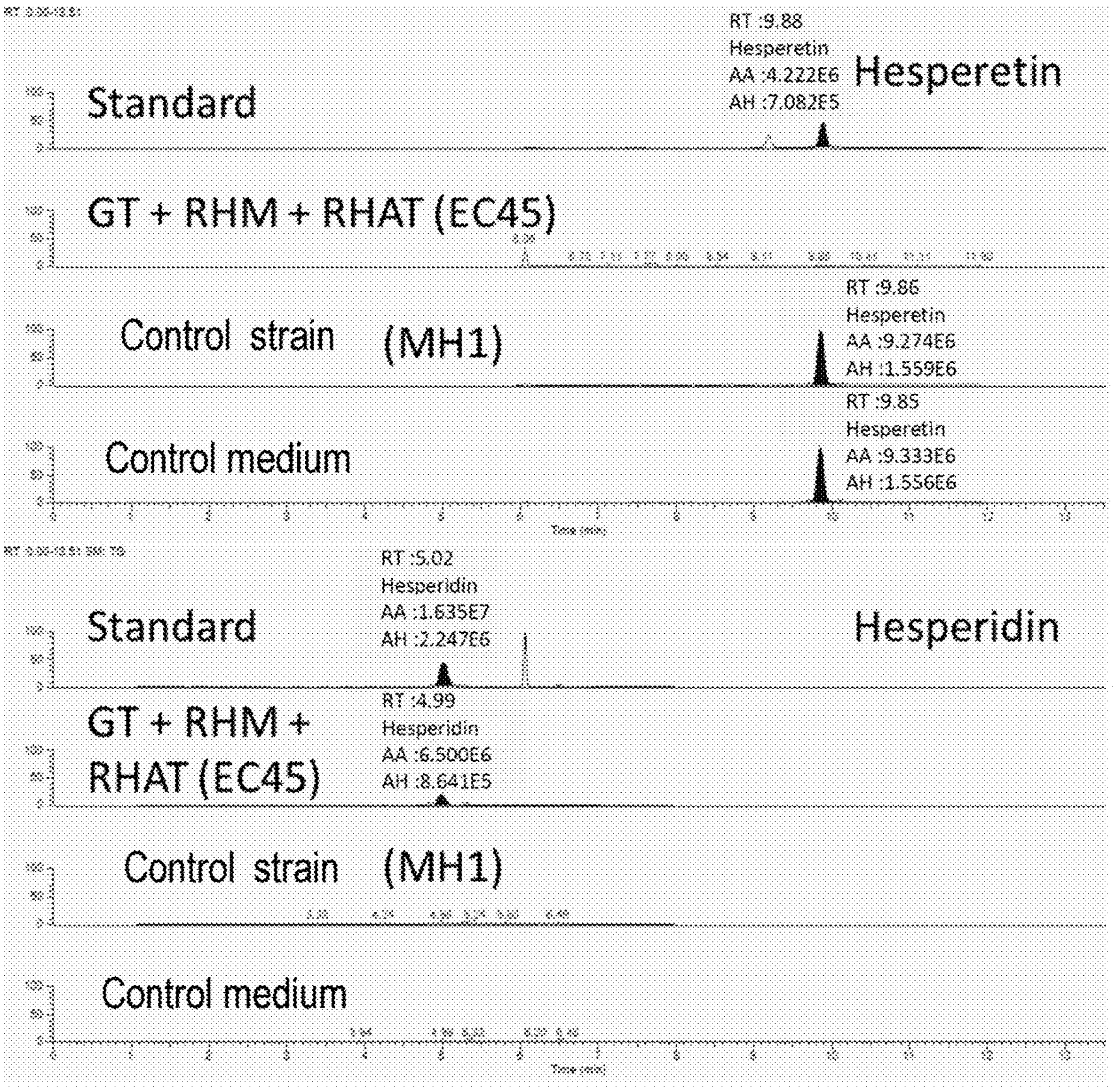

[Figure 16 continued]
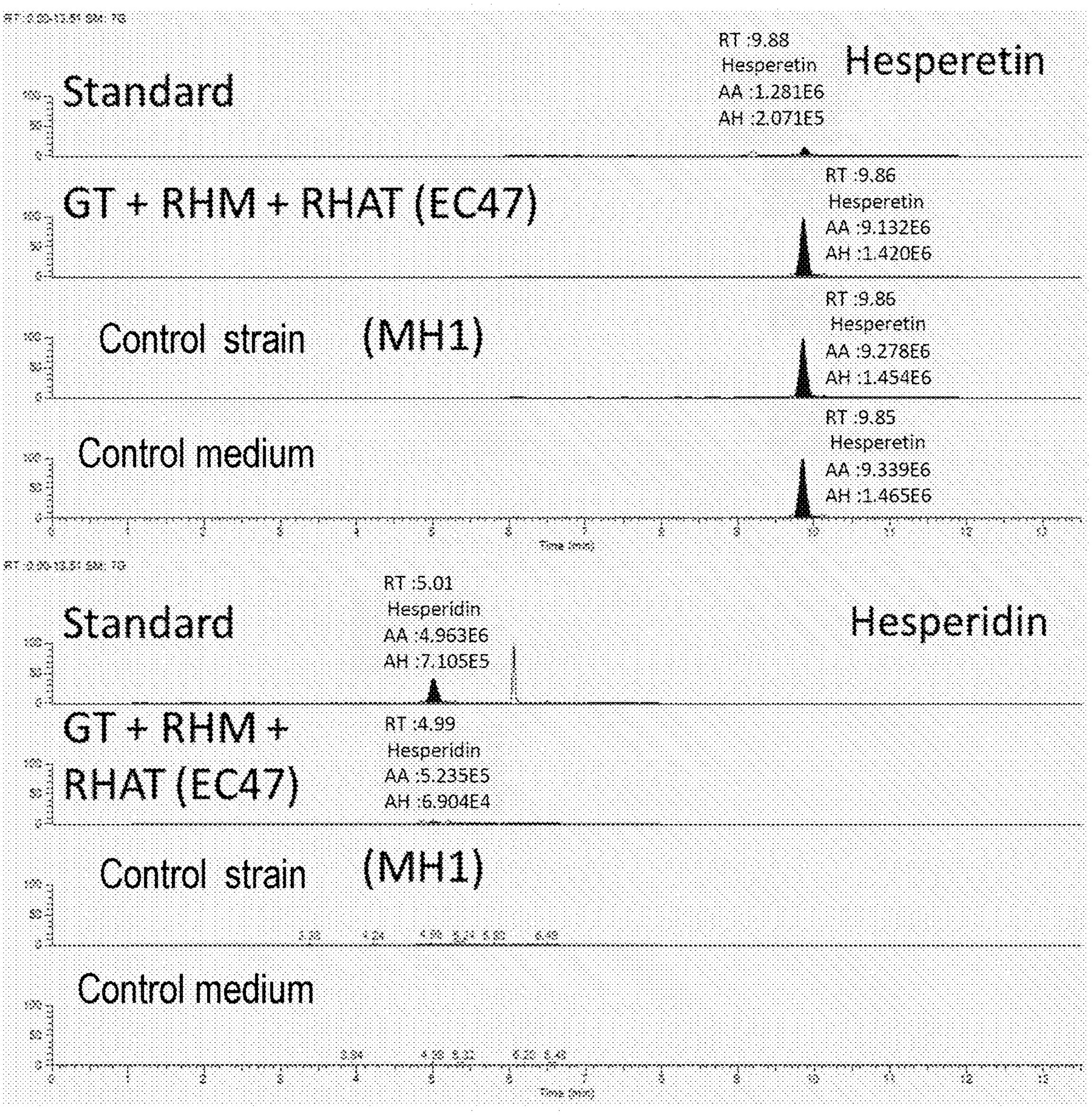

[Figure 17]
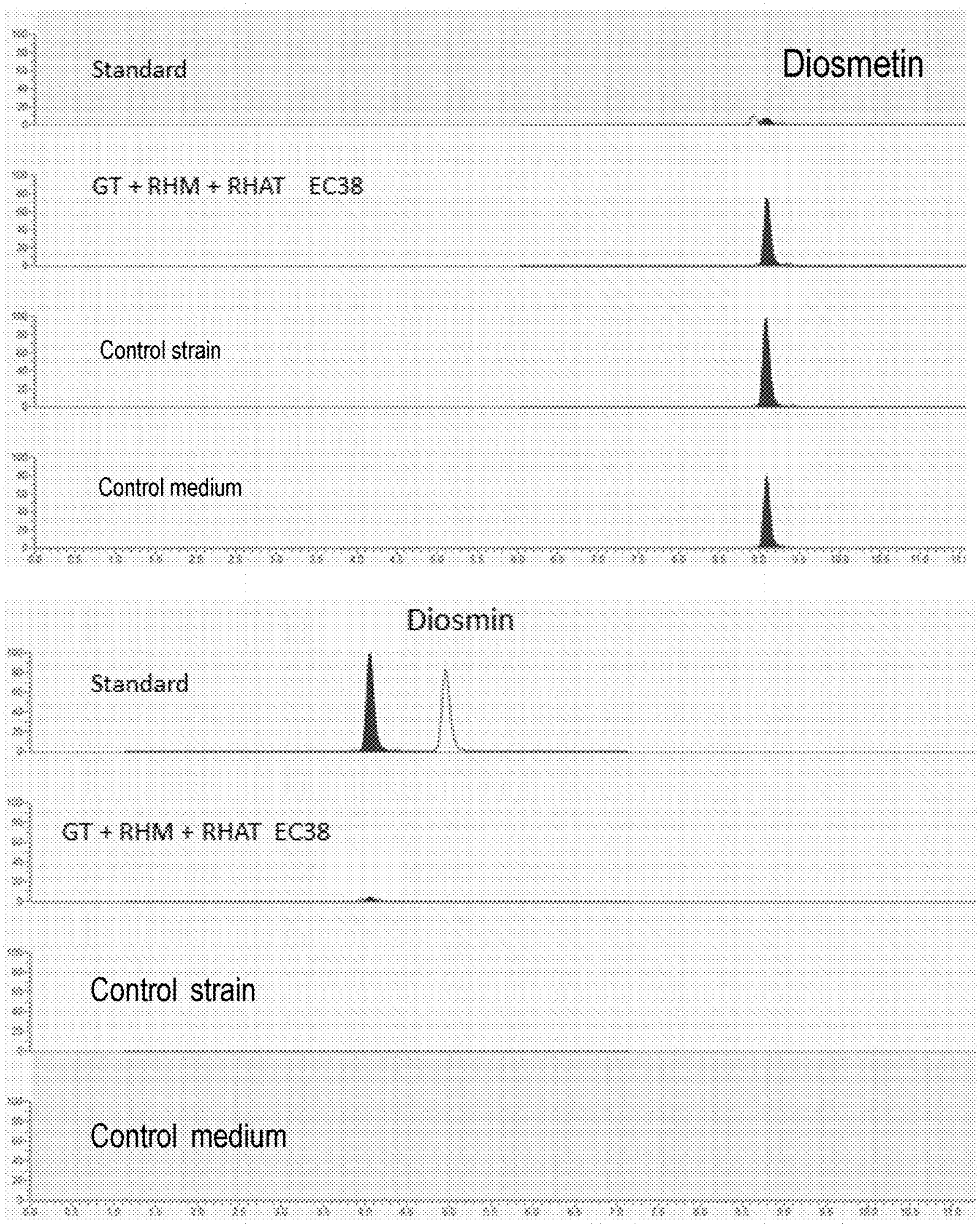

[Figure 17 continued]
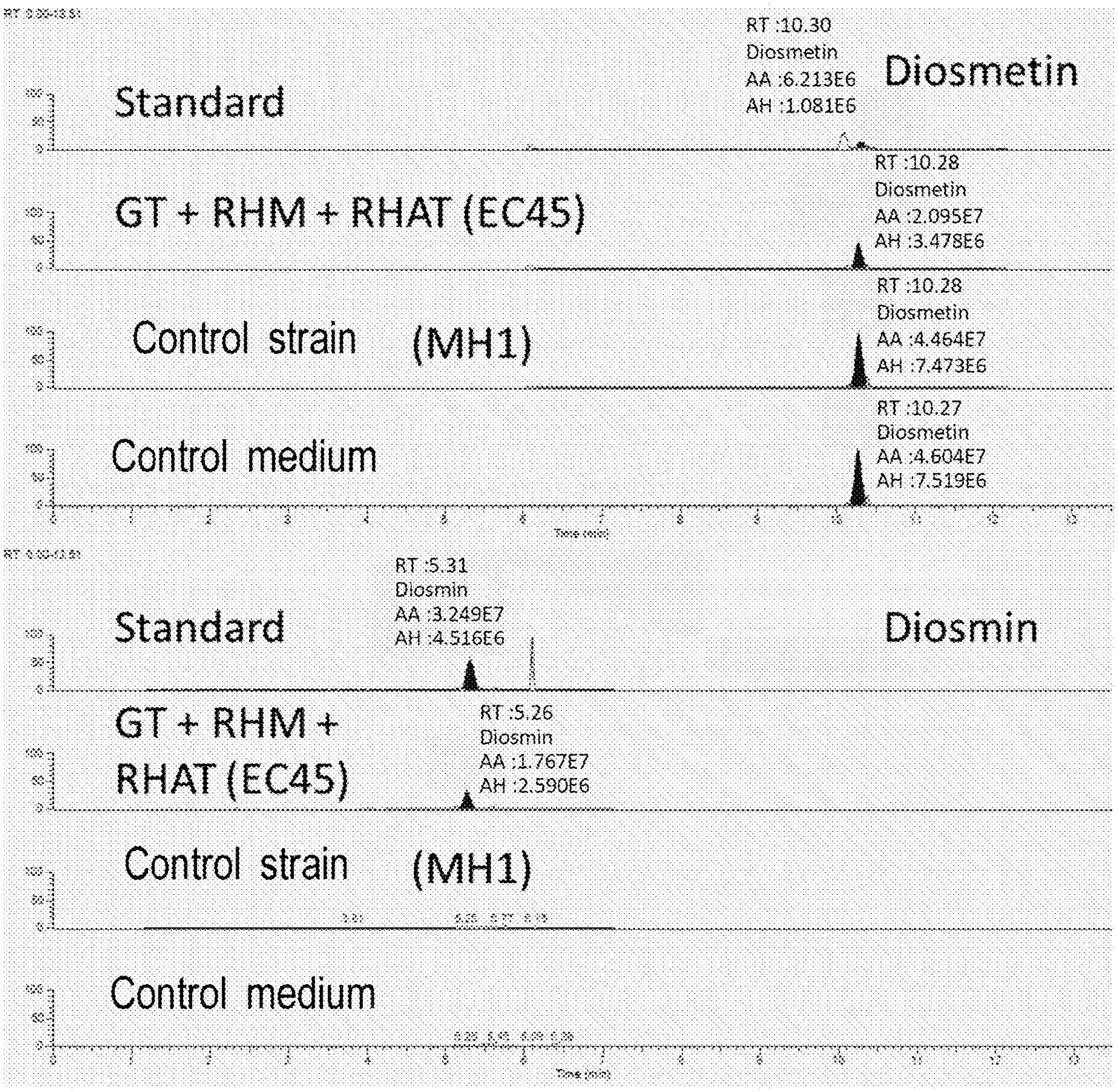

[Figure 17 continued]
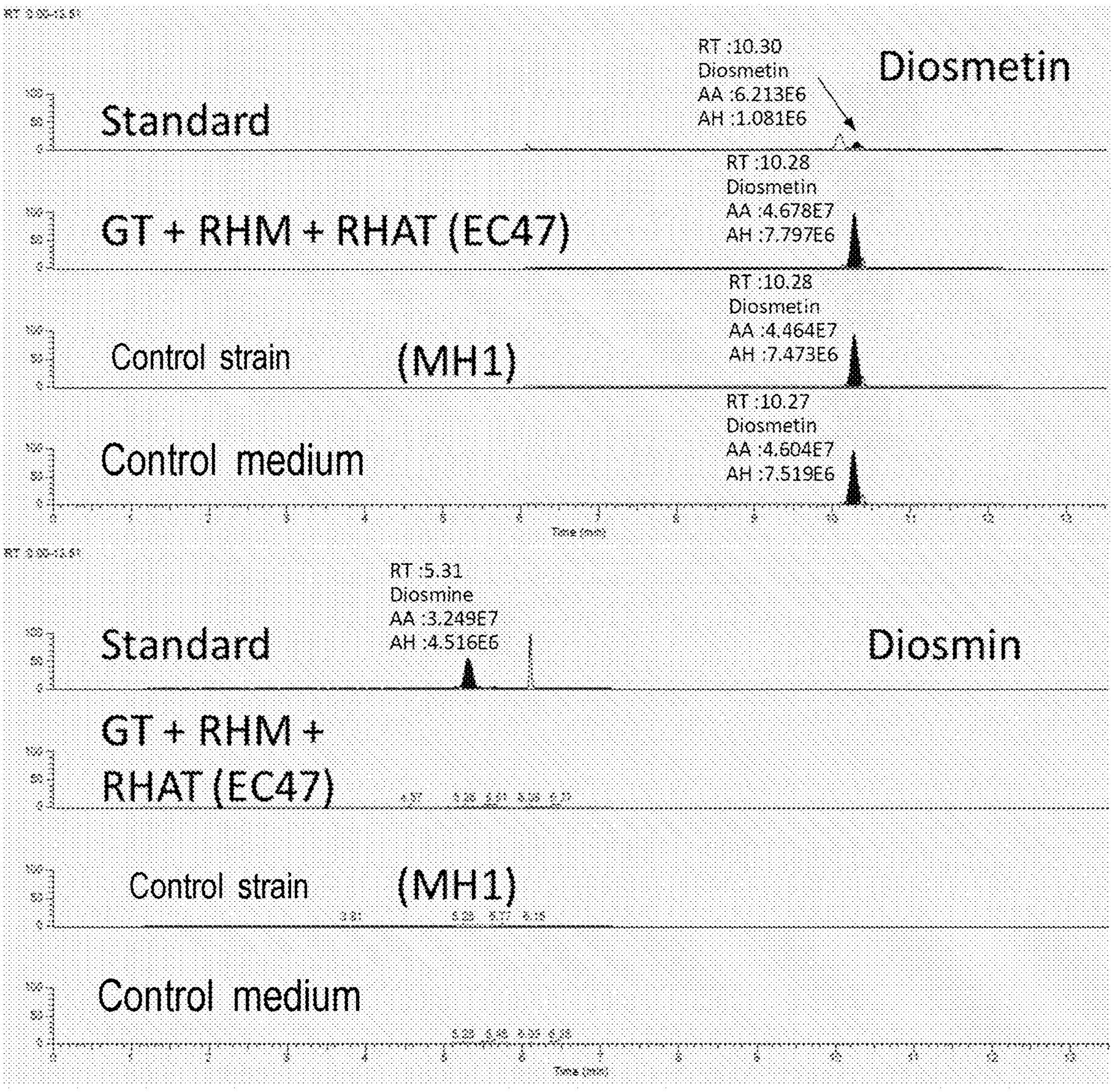

[Figure 18]
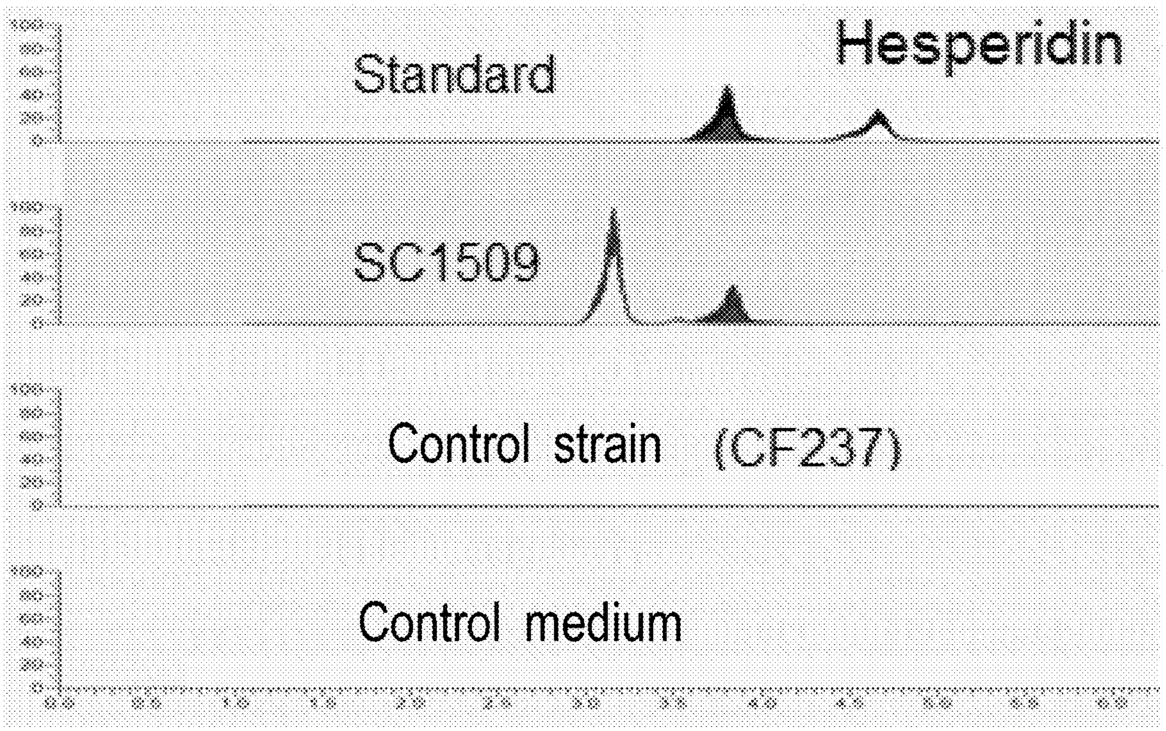
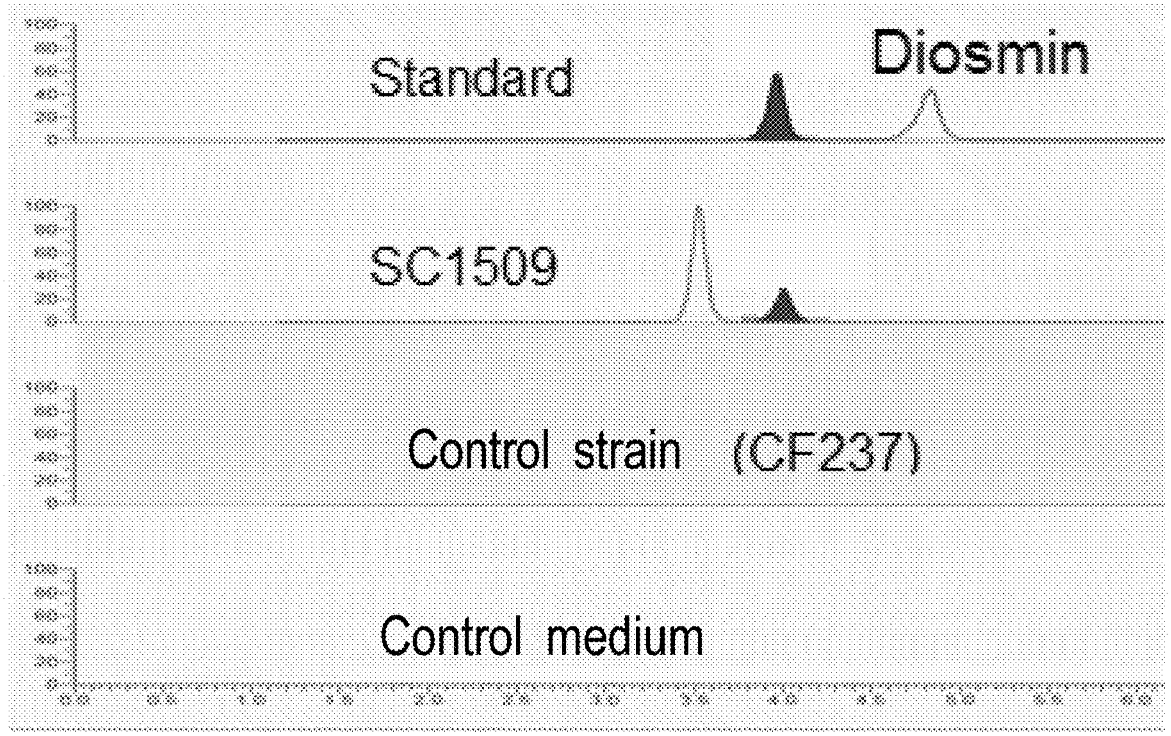

[Figure 18 continued]
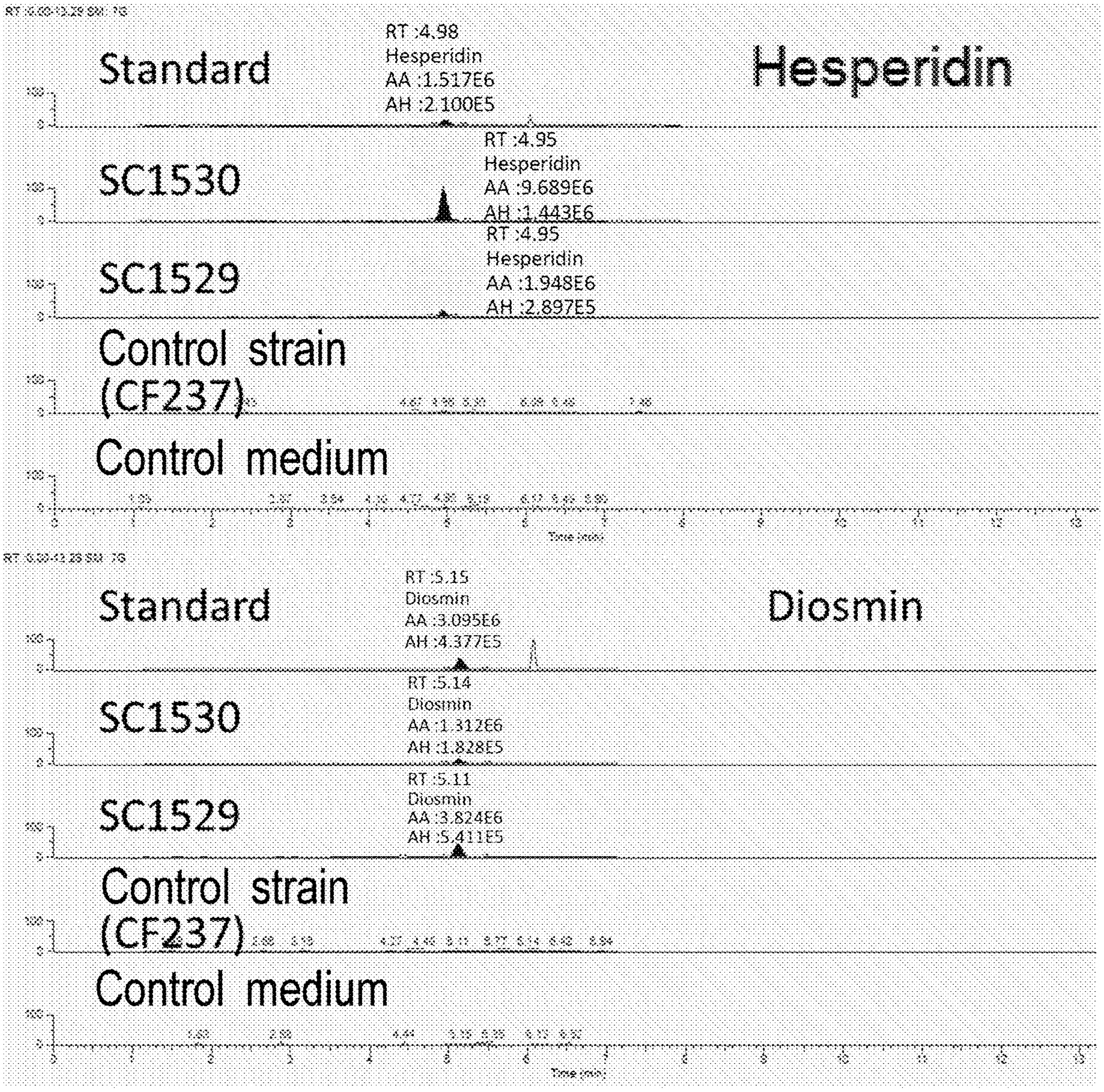

[Figure 18 continued]
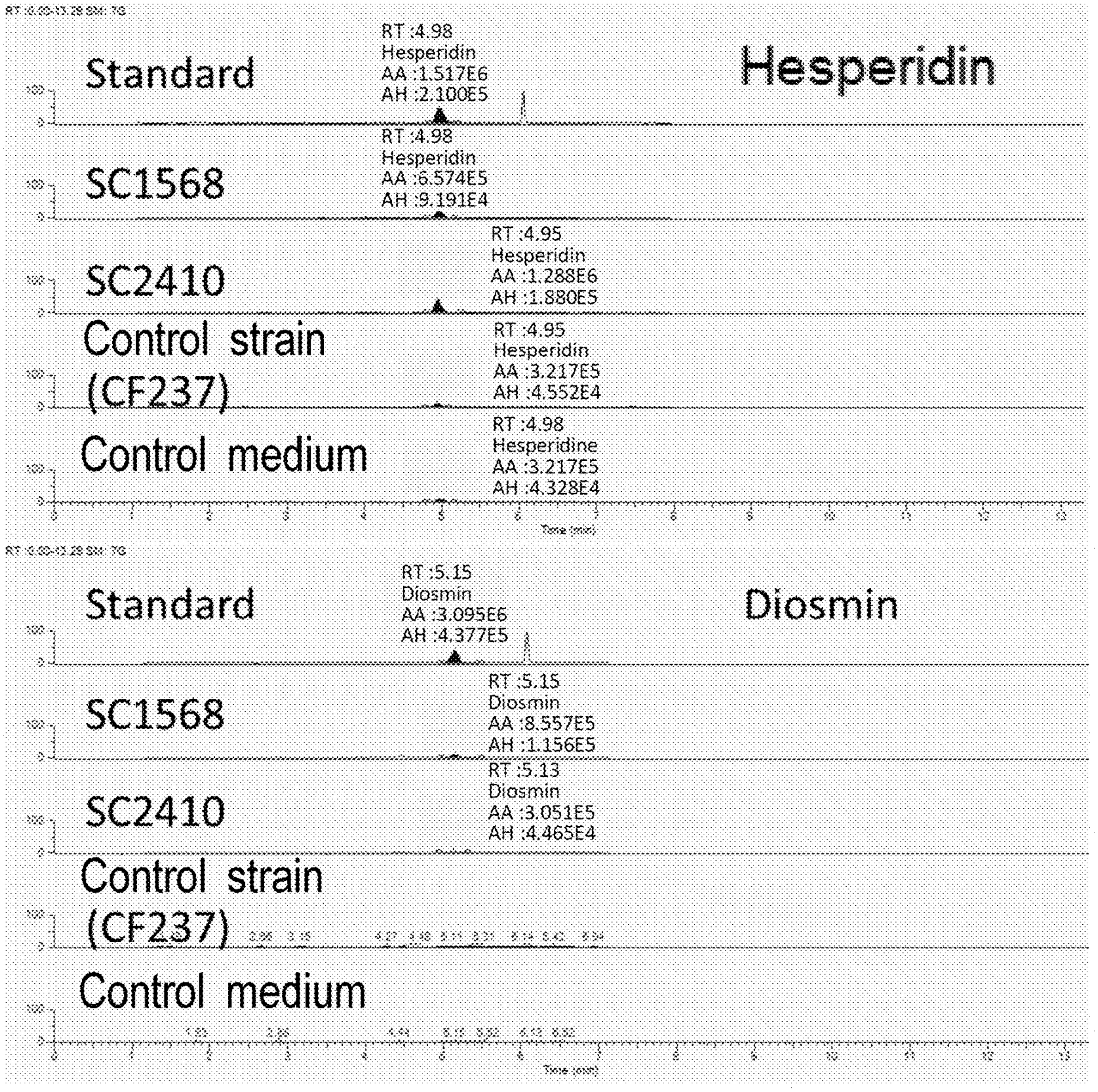

[Figure 19]
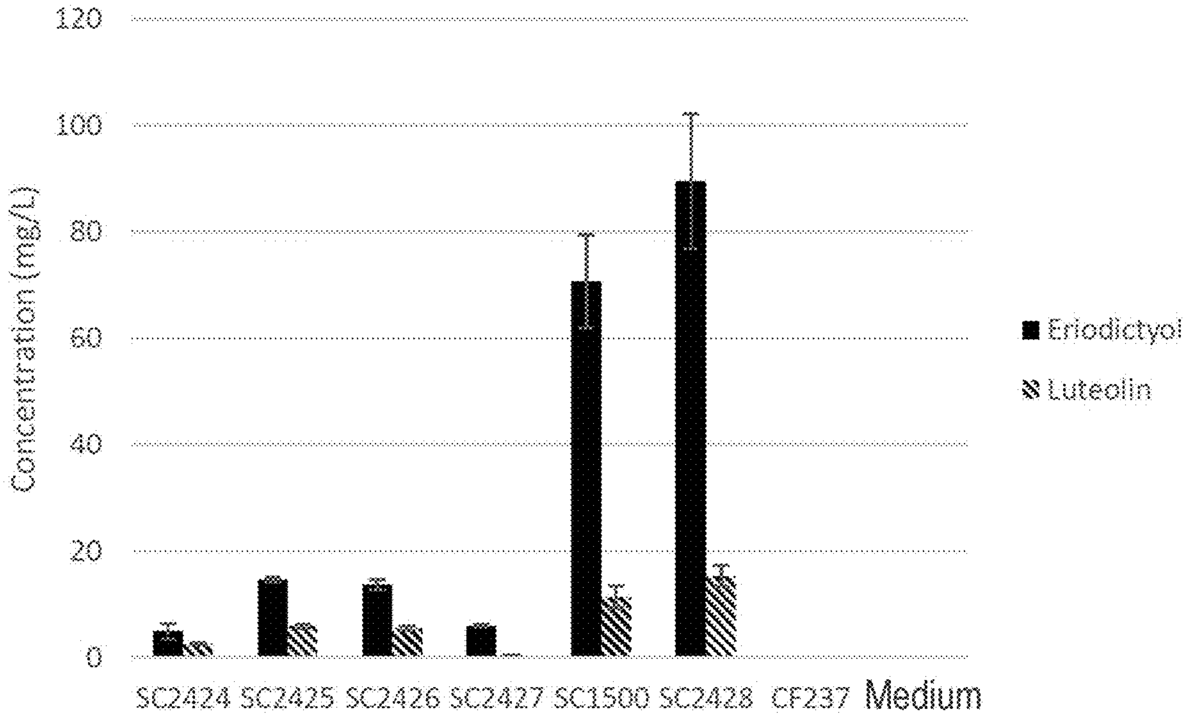

[Figure 20]
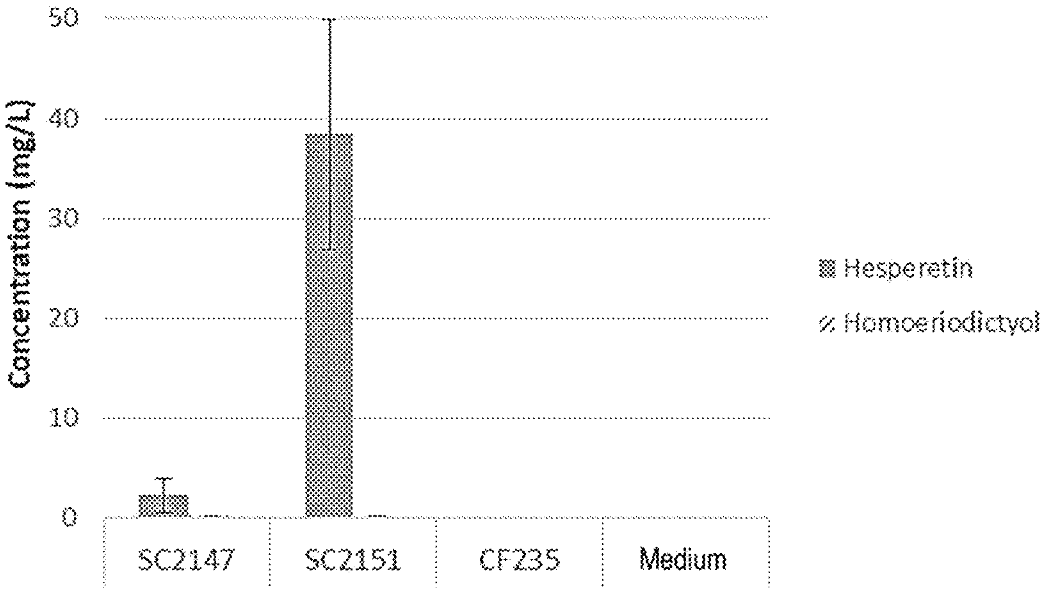
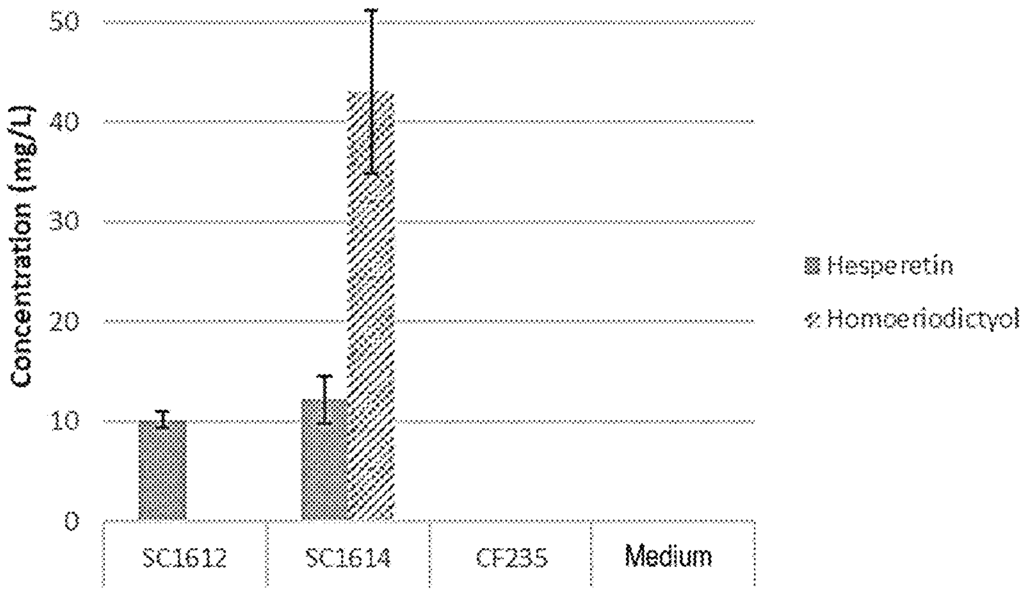

[Figure 21]
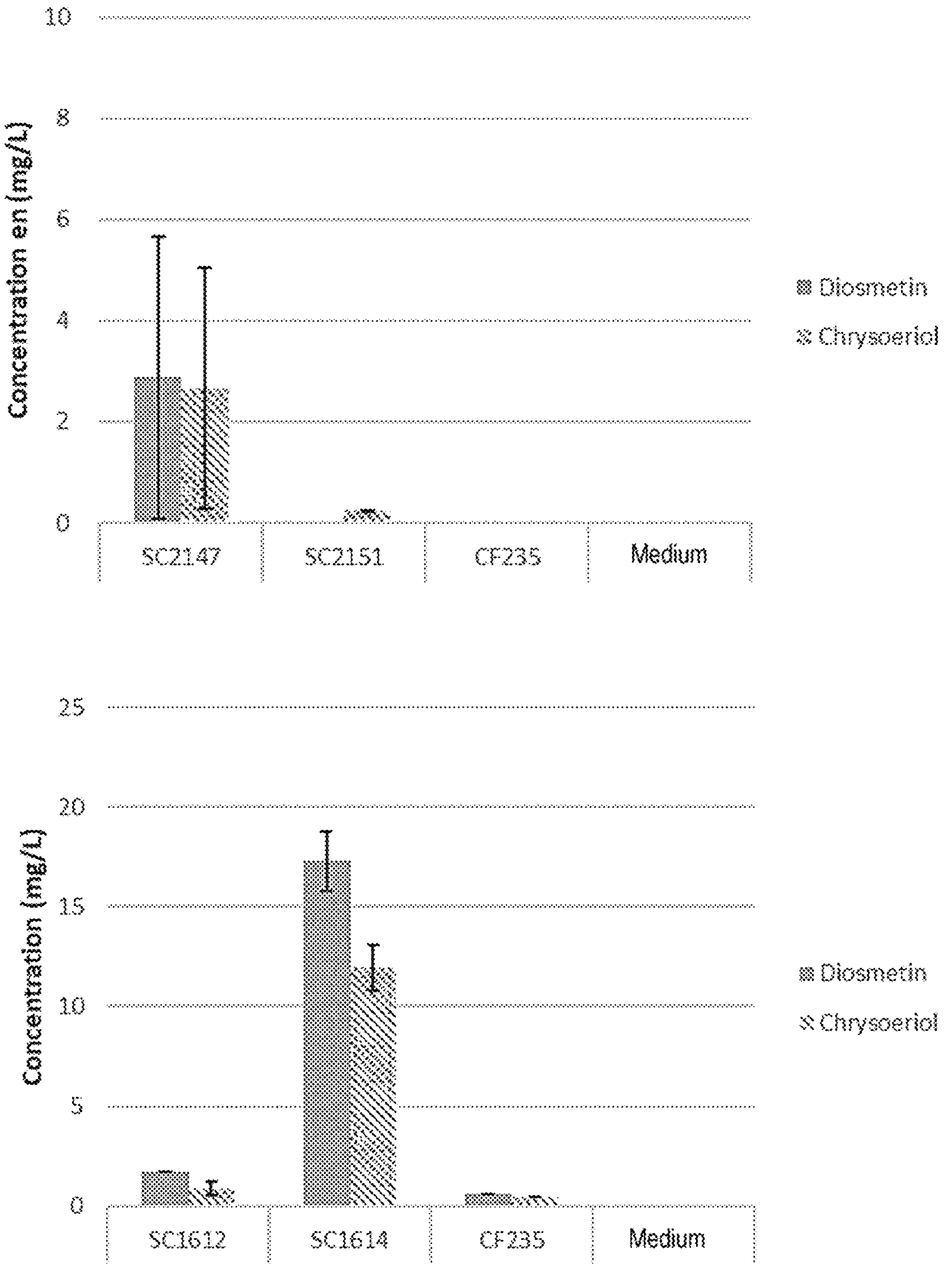

[Figure 22]
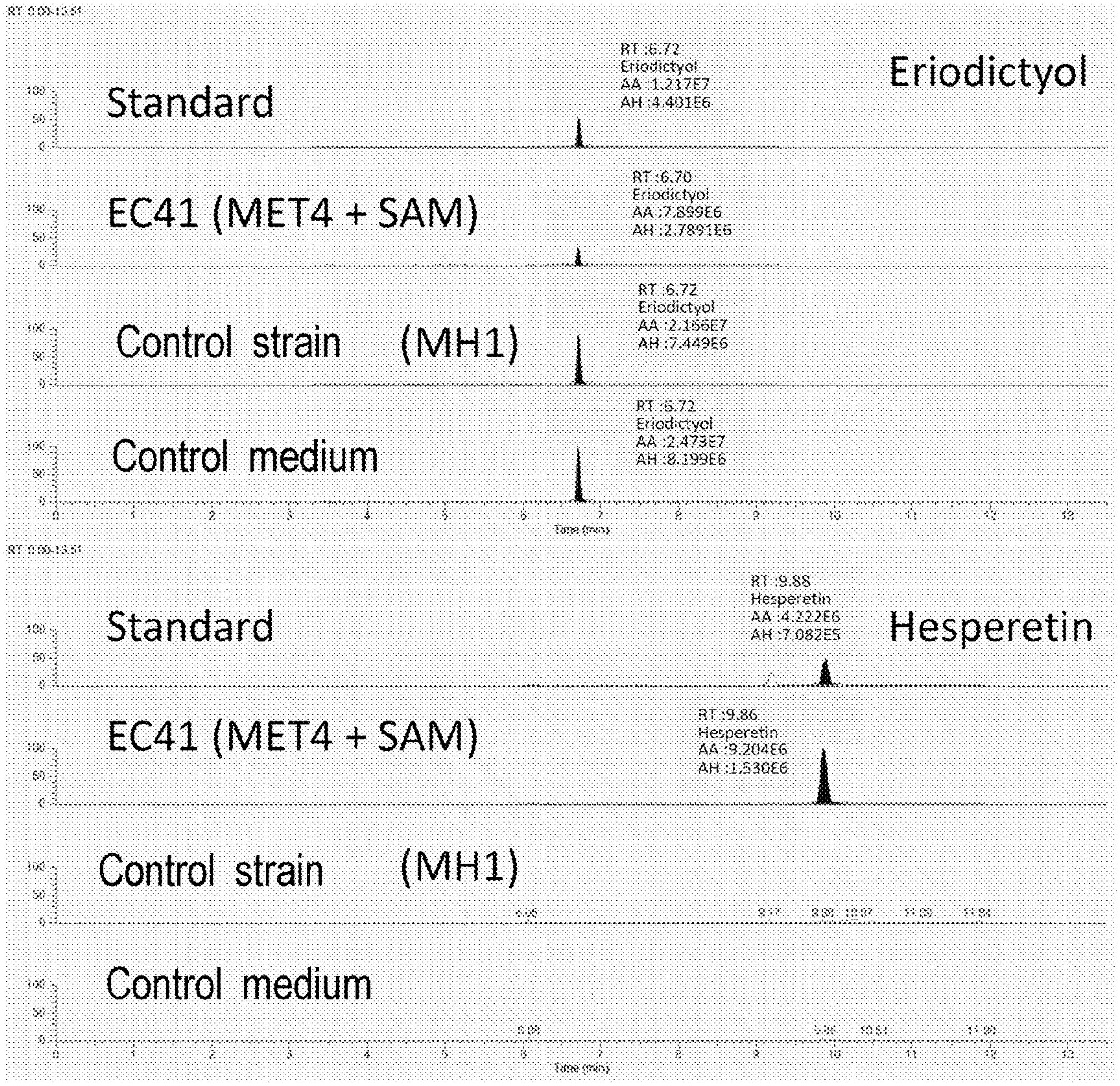

[Figure 23]
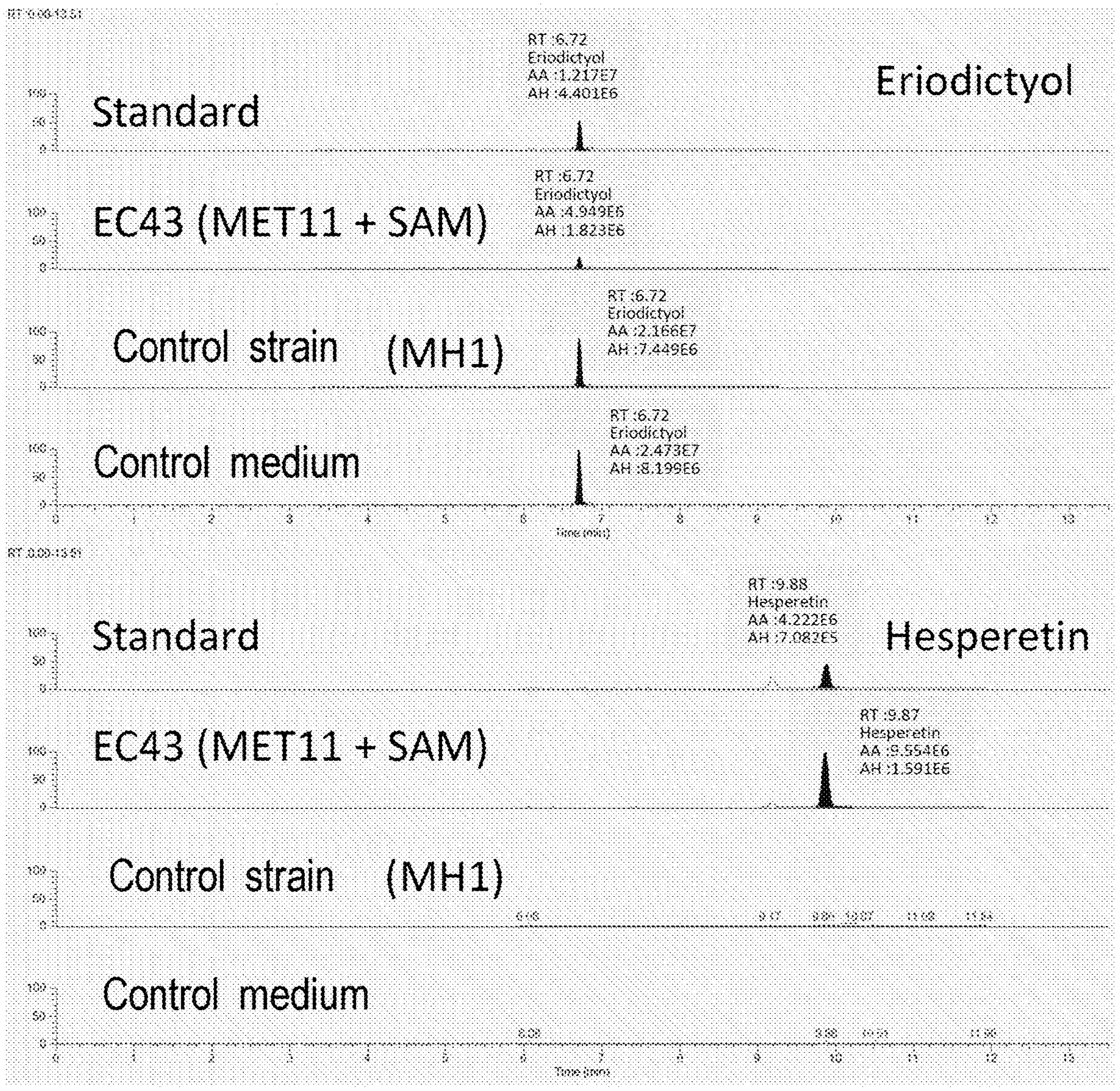

[Figure 24]
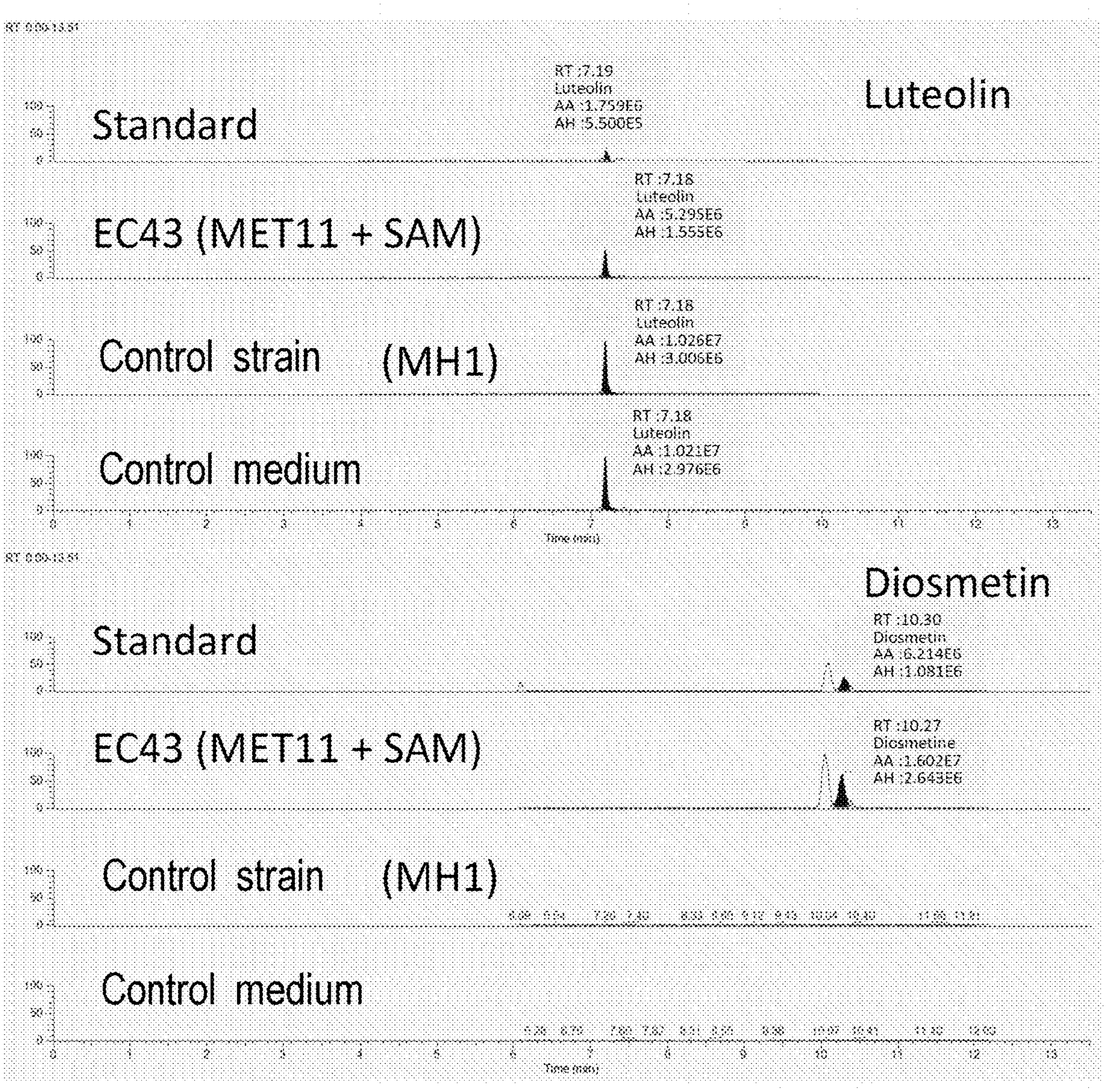

[Figure 25]
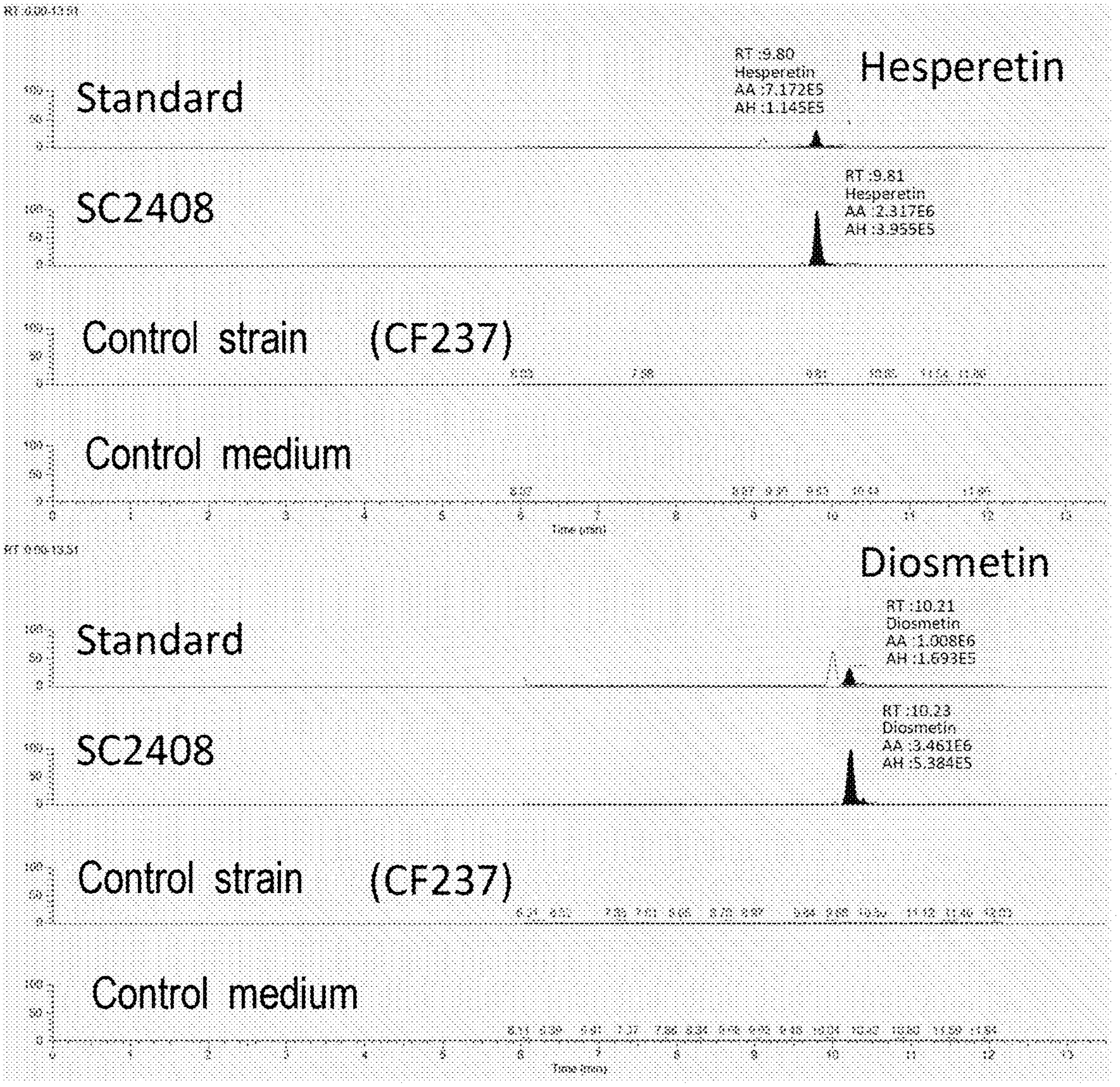

[Figure 26]
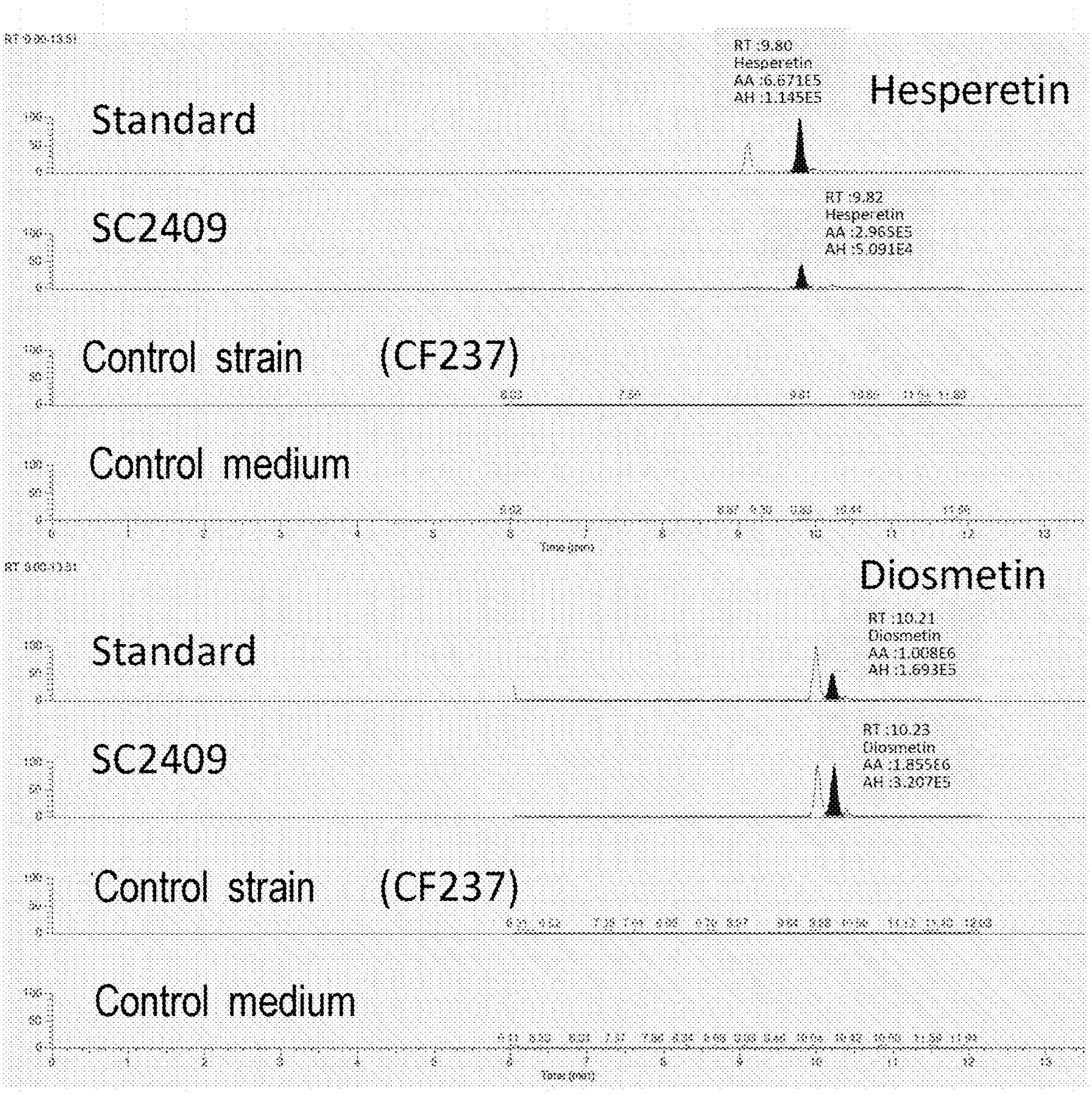

[Figure 27]
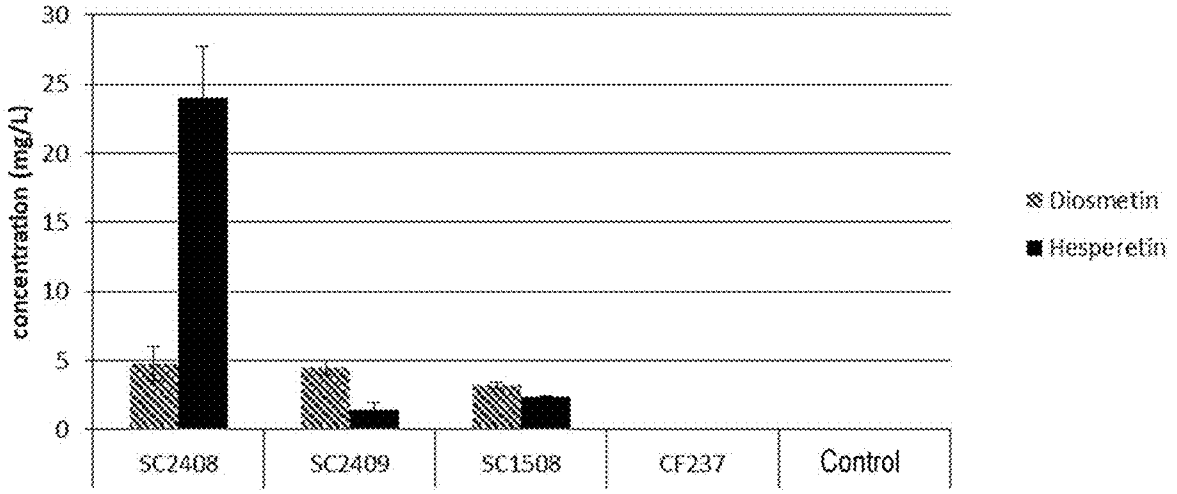
[Figure 28]
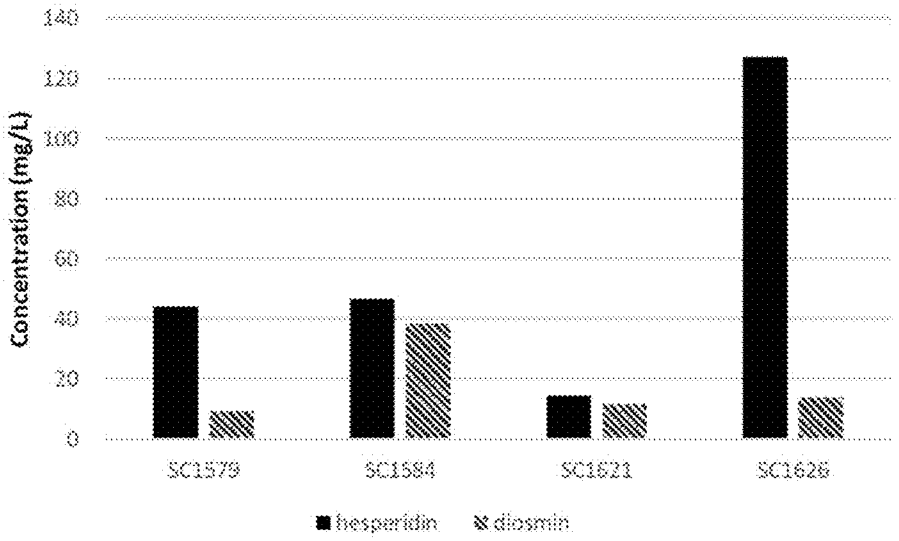

[Figure 29]
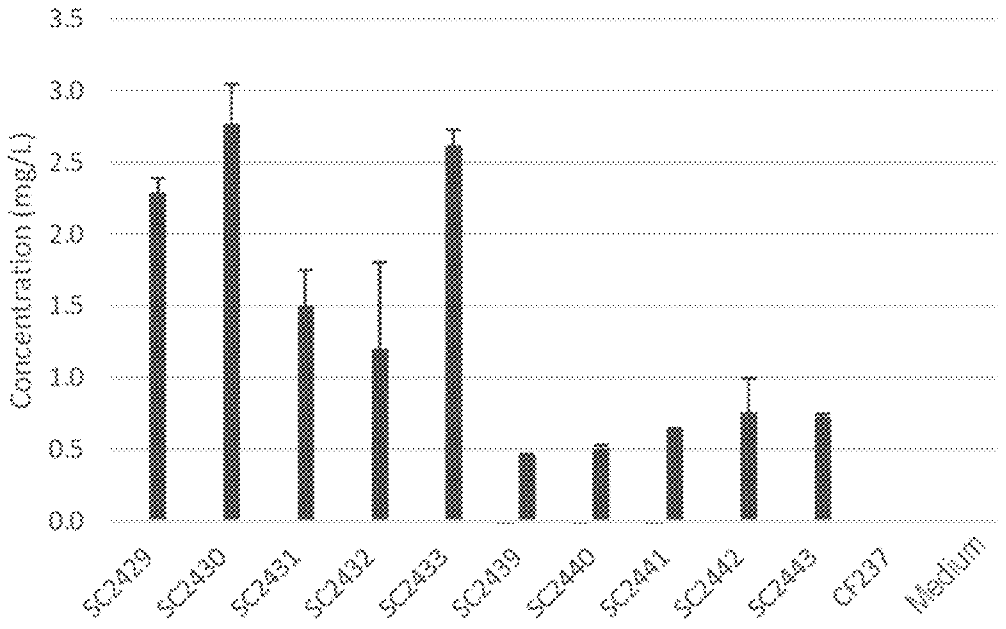
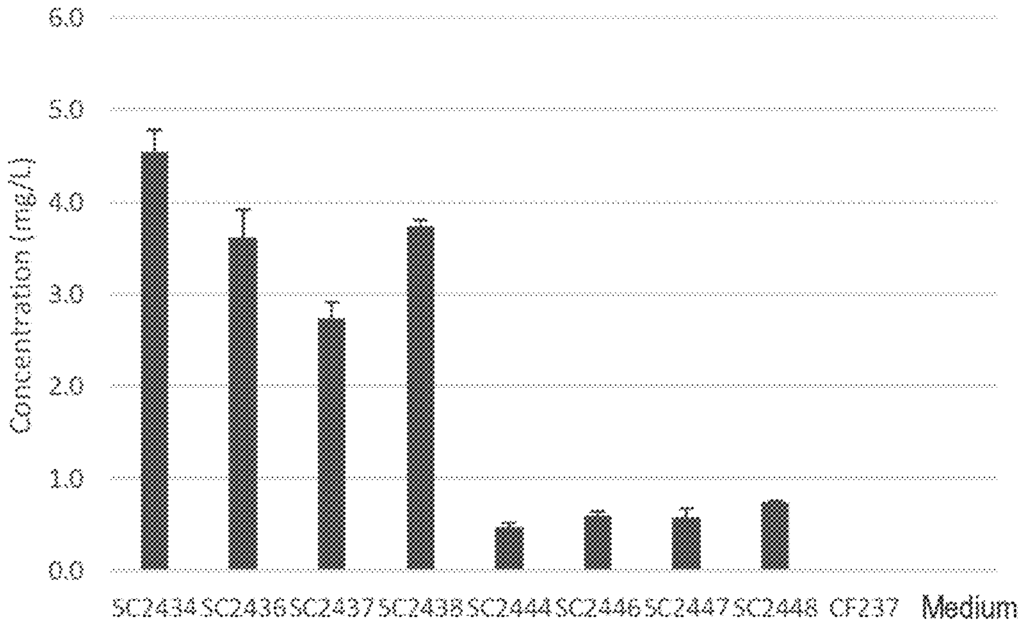

[Figure 29 continued]
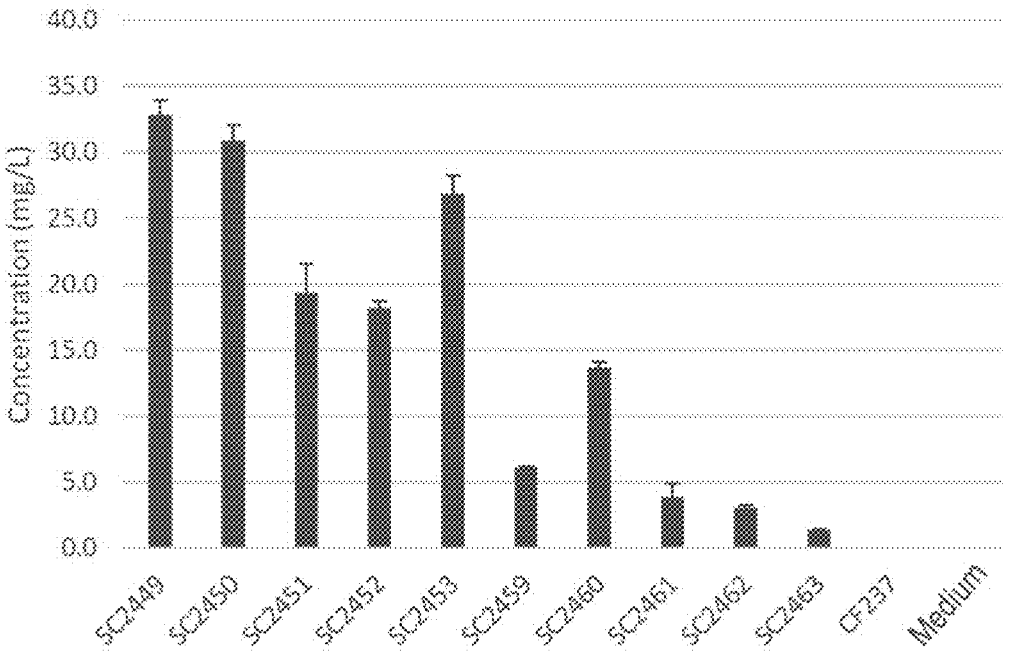
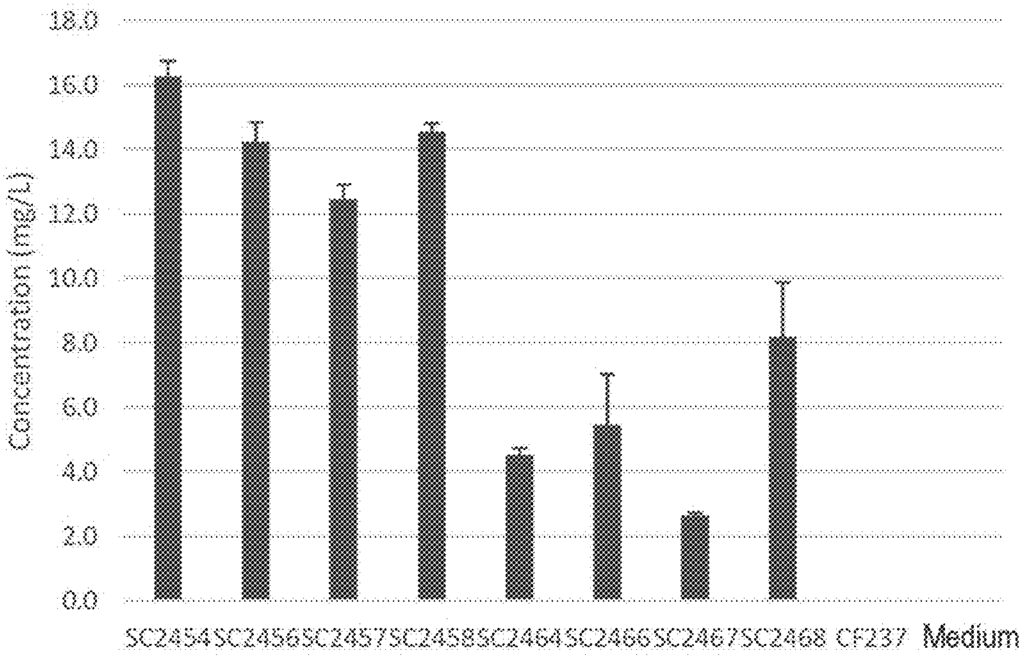

SEQUENCE LISTING

```
<160> NUMBER OF SEQ ID NOS: 160

<210> SEQ ID NO 1
<211> LENGTH: 524
<212> TYPE: PRT
<213> ORGANISM: Perilla frutescens

<400> SEQUENCE: 1

Met Ser Ile Ser Ala Ala Val Ser Leu Ile Ile Cys Thr Ser Ile Leu
1               5                   10                  15

Gly Val Leu Val Tyr Phe Leu Phe Leu Arg Arg Gly Gly Gly Ser Asn
            20                  25                  30

Gly Arg Pro Leu Pro Pro Gly Pro Arg Pro Trp Pro Ile Val Gly Asn
        35                  40                  45

Leu Pro Gln Leu Gly Pro Lys Pro His Gln Ser Met Ala Ala Leu Ala
    50                  55                  60

Arg Val His Gly Pro Leu Met His Leu Lys Met Gly Phe Val His Val
65                  70                  75                  80

Val Val Ala Ala Ser Ala Thr Val Ala Glu Lys Phe Leu Lys Val His
                85                  90                  95

Asp Thr Asn Phe Leu Ser Arg Pro Pro Asn Ser Gly Ala Glu His Ile
            100                 105                 110
```

-continued

```
Ala Tyr Asn Tyr Asn Asp Leu Val Phe Ala Pro His Gly Pro Arg Trp
        115                 120                 125

Arg Leu Leu Arg Lys Ile Cys Ala Leu His Leu Phe Ser Ser Lys Ala
    130                 135                 140

Leu Asp Asp Phe Arg His Val Arg Glu Glu Glu Val Gly Ile Leu Ile
145                 150                 155                 160

Arg Asn Leu Ala Ser Val Gly Glu Met Pro Ala Ser Ile Gly Gln Met
                165                 170                 175

Met Tyr Val Cys Ala Thr Asn Ala Ile Ser Arg Val Met Leu Gly Arg
            180                 185                 190

His Val Leu Gly Asp Glu His Arg Gly Ala Ala Gly Gly Gly Asp Thr
        195                 200                 205

Thr Ala Glu Glu Phe Lys Ala Met Val Val Glu Leu Met Ala Leu Ala
    210                 215                 220

Gly Val Phe Asn Val Gly Asp Phe Ile Pro Pro Leu Lys Gly Leu Asp
225                 230                 235                 240

Leu Gln Gly Val Val Ala Lys Met Lys Lys Leu His Gln Arg Phe Asp
                245                 250                 255

Ala Phe Phe Ser Gly Ile Leu His Asp His Lys Ile Asn Gly Ser Asn
            260                 265                 270

Ala Ala Glu Gly His Val Asp Leu Leu Thr Thr Leu Ile Ser Leu Lys
        275                 280                 285

Asp Val Asp Asn Asn Gly Glu Gly Gly Lys Leu Thr Asp Thr Glu Ile
    290                 295                 300

Lys Ala Leu Leu Leu Asn Leu Phe Thr Ala Gly Thr Asp Thr Thr Ser
305                 310                 315                 320

Ser Thr Val Glu Trp Ala Ile Thr Glu Leu Ile Arg Asn Pro Asn Ile
                325                 330                 335

Leu Ala Arg Val Arg Lys Glu Leu Asp Leu Ile Val Gly Lys Asp Lys
            340                 345                 350

Leu Val Lys Glu Ser Asp Leu Gly Gln Leu Thr Tyr Leu Gln Ala Val
        355                 360                 365

Ile Lys Glu Asn Phe Arg Leu His Pro Ser Thr Pro Leu Ser Leu Pro
    370                 375                 380

Arg Val Ala Gln Glu Ser Cys Glu Ile Asn Gly Tyr Tyr Ile Pro Lys
385                 390                 395                 400

Asp Ser Thr Leu Leu Val Asn Val Trp Ala Ile Gly Arg Asp Pro Asn
                405                 410                 415

Val Trp Pro Asp Pro Leu Glu Phe Arg Pro Glu Arg Phe Leu Met Gly
            420                 425                 430

Gly Glu Lys Pro Asn Val Asp Val Arg Gly Asn Asp Phe Glu Leu Ile
        435                 440                 445

Pro Phe Gly Ser Gly Arg Arg Ile Cys Ala Gly Met Asn Leu Gly Ile
    450                 455                 460

Arg Met Val Gln Leu Leu Ile Ala Thr Met Val His Ala Phe Asp Phe
465                 470                 475                 480

Glu Leu Ala Asn Gly Gln Leu Ala Lys Asp Leu Asn Met Glu Glu Ala
                485                 490                 495

Tyr Gly Ile Thr Leu Gln Arg Ala Asp Pro Leu Val Val His Pro Arg
            500                 505                 510

Pro Arg Leu Ala Arg His Val Tyr Gln Ala Gln Val
        515                 520
```

<210> SEQ ID NO 2
<211> LENGTH: 1575
<212> TYPE: DNA
<213> ORGANISM: artificial sequence
<220> FEATURE:
<223> OTHER INFORMATION: coding sequence for SEQ ID NO: 1

<400> SEQUENCE: 2
atgtccatct ctgccgccgt ttctttgatc atctgtactt ccattttggg tgttttggtt 60
tacttcttgt tcttgagaag aggtggtggt tctaacggta gaccattgcc accaggtcca 120
agaccatggc caattgtcgg taacttgcca caattgggtc caaagccaca ccaatctatg 180
gctgccttgg ccagagttca cggtccattg atgcacttga agatgggttt cgttcacgtt 240
gttgttgccg cctccgccac cgttgctgaa aagttcttga aggttcacga caccaacttc 300
ttgtctagac caccaaactc cggtgccgaa cacattgctt acaactacaa cgacttggtt 360
ttcgctccac acggtccaag atggagattg ttgagaaaga tttgtgcctt gcacttgttc 420
tcctccaagg ccttggatga cttcagacac gttagagaag aagaagttgg tatcttgatt 480
agaaacttgg cttctgttgg tgaaatgcca gcttctatcg gtcaaatgat gtacgtttgt 540
gccactaacg ctatctctag agtcatgttg ggtagacacg ttttgggtga cgaacacaga 600
ggtgccgccg gtggtggtga taccactgct gaagaattca aggctatggt tgttgaattg 660
atggctttgg ccggtgtttt caacgttggt gatttcattc caccattgaa gggtttggac 720
ttgcaaggtg ttgttgctaa gatgaagaag ttgcaccaaa gattcgacgc tttcttctct 780
ggtatcttgc acgatcacaa gatcaacggt tctaacgccg ctgaaggtca cgttgacttg 840
ttgactactt tgatttcttt gaaggacgtt gacaacaacg gtgaaggtgg taagttgacc 900
gatactgaaa ttaaggcttt gttgttgaac ttgttcactg ctggtactga cactacttct 960
tctactgttg aatgggccat cactgaattg atcagaaacc caaacatttt ggctagagtt 1020
agaaaggaat tggacttgat cgttggtaag gataagttgg ttaaggaatc cgatttgggt 1080
caattgacct acttgcaagc cgttatcaag gaaaacttca gattgcaccc atctactcca 1140
ttgtctttgc caagagtcgc tcaagaatct tgtgaaatca acggttacta catcccaaag 1200
gattctacct tgttggtcaa cgtttgggcc atcggtagag atccaaacgt ttggccagat 1260
ccattggaat tcagaccaga aagattcttg atgggtggtg aaaagccaaa cgttgatgtt 1320
agaggtaacg atttcgaatt gattccattc ggttctggta gaagaatttg tgctggtatg 1380
aacttgggta ttagaatggt tcaattgttg attgctacta tggttcacgc tttcgatttc 1440
gaattggcta acggtcaatt ggccaaggac ttgaacatgg aagaagctta cggtattact 1500
ttgcaaagag ccgacccatt ggttgtccac ccaagaccaa gattggccag acacgtttac 1560
caagctcaag tttaa 1575

<210> SEQ ID NO 3
<211> LENGTH: 627
<212> TYPE: PRT
<213> ORGANISM: Phanerochaete chrysosporium

<400> SEQUENCE: 3

Met Ser Pro Leu Leu Ser Ala Val Pro Ala Ala Ala Leu Pro Leu Leu
1 5 10 15

Ala Ala Ala Met Tyr Val Leu Trp Thr Phe Leu Ala Leu Leu Val Arg
20 25 30

Gln Ala Arg Ser Pro Leu Arg His Leu Arg Gly Pro Pro Ser Pro Ser
35 40 45

```
Phe Leu Val Gly Asn Leu Arg Glu Met His Asp Gln Glu Asn Thr Ala
    50                  55                  60

Leu Phe Ala Arg Trp Glu His Arg Tyr Gly Ser Thr Phe Val Tyr His
65                  70                  75                  80

Gly Phe Leu Gly Gly Ala Arg Leu Leu Thr Thr Asp Pro Val Ala Val
                85                  90                  95

Ala His Ile Leu Ala His Gly Tyr Asp Phe Pro Lys Pro Glu Phe Ile
            100                 105                 110

Arg Asp Ala Leu Ala Ser Met Ala Ala Gly His Glu Gly Leu Leu Val
        115                 120                 125

Val Glu Gly Asp Gly His Arg Arg Gln Arg Lys Ile Leu Ser Pro Ala
    130                 135                 140

Phe Ala Thr Pro His Ile Lys Ser Leu Ser Pro Ile Ile Trp Ser Lys
145                 150                 155                 160

Ala Thr Gln Leu Arg Asp Val Trp Ile Asp Leu Ala Ser Ser Pro Ser
                165                 170                 175

Leu Thr Pro Ala Ala Thr Pro Ser Asp Pro Leu Ala His Ala Glu Glu
            180                 185                 190

Gln Pro Ala Arg Ala Ser Gly Phe Leu Pro Asn Pro Phe Ser Ser Phe
        195                 200                 205

Leu Ser Ser Lys Ala His Pro Arg Ser Ala Leu Pro Arg Ala Glu Ala
    210                 215                 220

His Pro Glu Asp Arg Met Ser Ser Pro Gly Thr Lys Val Asp Val Leu
225                 230                 235                 240

Ala Trp Leu Ala Arg Ala Thr Leu Asp Val Ile Gly Glu Ala Gly Phe
                245                 250                 255

Gly Tyr Ala Phe Asn Ser Val Arg Ala Ala Ala Cys Pro Gly Asp Ala
            260                 265                 270

Ala Glu Asp Glu Leu Ala Arg Ala Phe Ala Val Ile Phe Ser Thr Ala
        275                 280                 285

Arg Lys Phe Arg Leu Ile Thr Val Leu Gln Val Trp Phe Pro Phe Leu
    290                 295                 300

Arg Arg Phe Arg Arg Asn Ser Ala Ala Glu Asp His Ala Arg Ala Thr
305                 310                 315                 320

Met Arg Arg Ile Gly Leu Ala Leu Ile Ala Glu Arg Arg Gln Glu Val
                325                 330                 335

Leu Asp Asp Lys Ala His Ala Ser Gln Glu Ala Met Asp Gly Lys Asp
            340                 345                 350

Leu Leu Thr Val Met Ile Lys Ser Ser Leu Ser Ser Asp Pro Ser Gln
        355                 360                 365

Gln Leu Ser Thr Asn Glu Met Leu Cys Gln Ile Ala Thr Phe Leu Ala
    370                 375                 380

Ala Gly His Glu Thr Ser Ala Ser Ala Leu Ser Trp Ala Leu Tyr Ala
385                 390                 395                 400

Leu Ala Arg Ala Pro Ala Cys Gln His Thr Leu Arg Arg Glu Leu Arg
                405                 410                 415

Ala Leu Thr Leu Pro Ala Asp Pro Ser Ala Ala Asp Leu Gln Ala Val
            420                 425                 430

Leu Ala Leu Pro Tyr Leu Asp Ala Val Val Arg Glu Thr Leu Arg Val
        435                 440                 445

His Ala Pro Val Thr Ser Thr Met Arg Val Ala Ala His Asp Ala Ala
    450                 455                 460
```

-continued

```
Val Pro Val Gly Thr Pro Phe Arg Asp Ala His Gly Ala Gln His Ala
465                 470                 475                 480

Ala Ile Arg Leu Arg Ala Gly Asp Val Val Thr Leu Pro Leu Gln Ala
                485                 490                 495

Met Asn Lys Ala Arg Ala Leu Trp Gly Ala Asp Ala Ala Cys Phe Arg
            500                 505                 510

Pro Glu Arg Trp Leu Ala His Gly Asp Ala Pro Arg Glu Pro Arg Gly
        515                 520                 525

Leu Trp Gly Gly Val Met Thr Phe Gly Thr Gly Val Val Ala Asn Gly
    530                 535                 540

Asn Arg Ser Cys Ile Gly Tyr Arg Phe Ala Val Asn Glu Ile Lys Leu
545                 550                 555                 560

Phe Leu Tyr Ala Leu Val Arg Asp Ile Glu Phe Thr Ile Asp Pro Trp
                565                 570                 575

Ile Glu Ile Glu Lys Arg Val Asn Val Val Thr Arg Pro Cys Val Lys
            580                 585                 590

Ser Glu Pro His Leu Gly Asn Gln Met Pro Leu Arg Leu Arg Arg Val
        595                 600                 605

Ala Val Glu Glu Thr Val Gly Asp Ser Ser Gly Asp Gly Ala Pro Arg
    610                 615                 620

Thr Val Ser
625


<210> SEQ ID NO 4
<211> LENGTH: 1884
<212> TYPE: DNA
<213> ORGANISM: artificial
<220> FEATURE:
<223> OTHER INFORMATION: coding sequence for SEQ ID NO: 3

<400> SEQUENCE: 4

atgtccccat tgttgtctgc cgttccagcc gccgctttgc cattgttggc cgccgctatg      60

tacgttttgt ggactttctt ggctttgttg gttagacaag ccagatcccc attgagacac     120

ttgagaggtc caccatctcc atctttcttg gtcggtaact tgagagaaat gcacgaccaa     180

gaaaacaccg ctttgttcgc tagatgggaa cacagatacg gttctacctt cgtctaccac     240

ggtttcttgg gtggtgccag attgttgacc accgacccag tcgccgtcgc ccacatcttg     300

gcccacggtt acgacttccc aaagccagaa ttcatcagag atgccttggc ttctatggcc     360

gccggtcacg aaggtttgtt ggtcgtcgaa ggtgacggtc acaggagaca aagaaagatc     420

ttgtccccag ctttcgccac tccacacatc aagtctttgt ctccaatcat ctggtctaag     480

gctactcaat tgagagatgt ttggattgac ttggcctctt ctccatcctt gactccagct     540

gctaccccat ccgacccatt ggctcacgct gaagaacaac cagctagagc ttctggtttc     600

ttgccaaacc cattctcttc tttcttgtca tctaaggctc acccaagatc cgctttgcca     660

agagctgaag ctcacccaga agatagaatg tcctctccag gtaccaaggt cgacgttttg     720

gcttggttgg ctagagccac tttggacgtc atcggtgaag ccggtttcgg ttacgctttc     780

aactctgtca gagccgctgc ttgtccaggt gacgccgctg aagatgaatt ggctagagct     840

ttcgctgtca tcttctctac tgctagaaag ttcagattga tcactgtctt gcaagtttgg     900

ttcccattct tgagaagatt cagaagaaac tctgctgctg aagatcacgc tagagctact     960

atgagaagaa tcggtttggc tttgatcgct gaaaggagac aagaagtctt ggacgacaag    1020

gctcacgcct ctcaagaagc tatggatggt aaggacttgt tgactgtcat gatcaagtca    1080
```

-continued

```
tctttgtcat ccgatccatc tcaacaattg tctactaacg aaatgttgtg tcaaatcgct   1140

actttcttgg ctgctggtca cgaaacctct gcttctgctt tgtcttgggc cttgtacgcc   1200

ttggctagag ctccagcttg tcaacacact ttgagaagag aattgagagc tttgactttg   1260

ccagctgacc catctgccgc tgacttgcaa gctgttttgg ctttgccata cttggacgcc   1320

gtcgttagag aaactttgag agttcacgct ccagttactt ctactatgag agtcgctgct   1380

cacgacgccg ctgttccagt cggtactcca ttcagagatg ctcacggtgc tcaacacgcc   1440

gctatcagat tgagagctgg tgacgtcgtc actttgccat tgcaagctat gaacaaggcc   1500

agagctttgt ggggtgccga cgccgcttgt ttcagaccag aaagatggtt ggctcacggt   1560

gacgccccaa gagaaccaag aggtttgtgg ggtggtgtca tgactttcgg taccggtgtc   1620

gtcgctaacg gtaacagatc ttgtattggt tacagattcg ctgttaacga aatcaagttg   1680

ttcttgtacg ccttggttag agacatcgaa ttcactatcg acccatggat cgaaatcgaa   1740

aagagagtta acgtcgtcac cagaccatgt gtcaagtccg aaccacactt gggtaaccaa   1800

atgccattga gattgagaag agtcgctgtt gaagaaactg ttggtgattc ttctggtgac   1860

ggtgctccaa gaactgtttc ttaa                                          1884
```

<210> SEQ ID NO 5
<211> LENGTH: 513
<212> TYPE: PRT
<213> ORGANISM: Petunia x hybrida

<400> SEQUENCE: 5

```
Met Ser Glu Ile Leu Ser Leu Ile Leu Tyr Thr Val Ile Phe Ser Phe
1               5                   10                  15

Leu Leu Gln Phe Ile Leu Arg Ser Phe Phe Arg Lys Arg Tyr Pro Leu
            20                  25                  30

Pro Leu Pro Pro Gly Pro Lys Pro Trp Pro Ile Ile Gly Asn Leu Val
        35                  40                  45

His Leu Gly Pro Lys Pro His Gln Ser Thr Ala Ala Met Ala Gln Thr
    50                  55                  60

Tyr Gly Pro Leu Met Tyr Leu Lys Met Gly Phe Val Asp Val Val Val
65                  70                  75                  80

Ala Ala Ser Ala Ser Val Ala Ala Gln Phe Leu Lys Thr His Asp Ala
                85                  90                  95

Asn Phe Ser Ser Arg Pro Pro Asn Ser Gly Ala Glu His Met Ala Tyr
            100                 105                 110

Asn Tyr Gln Asp Leu Val Phe Ala Pro Tyr Gly Pro Arg Trp Arg Met
        115                 120                 125

Leu Arg Lys Ile Cys Ser Val His Leu Phe Ser Thr Lys Ala Leu Asp
    130                 135                 140

Asp Phe Arg His Val Arg Gln Asp Glu Val Lys Thr Leu Thr Arg Ala
145                 150                 155                 160

Leu Ala Ser Ala Gly Gln Lys Pro Val Lys Leu Gly Gln Leu Leu Asn
                165                 170                 175

Val Cys Thr Thr Asn Ala Leu Ala Arg Val Met Leu Gly Lys Arg Val
            180                 185                 190

Phe Ala Asp Gly Ser Gly Asp Val Asp Pro Gln Ala Ala Glu Phe Lys
        195                 200                 205

Ser Met Val Val Glu Met Met Val Val Ala Gly Val Phe Asn Ile Gly
    210                 215                 220

Asp Phe Ile Pro Gln Leu Asn Trp Leu Asp Ile Gln Gly Val Ala Ala
```

```
225                 230                 235                 240

Lys Met Lys Lys Leu His Ala Arg Phe Asp Ala Phe Leu Thr Asp Ile
                245                 250                 255

Leu Glu Glu His Lys Gly Lys Ile Phe Gly Glu Met Lys Asp Leu Leu
            260                 265                 270

Ser Thr Leu Ile Ser Leu Lys Asn Asp Asp Ala Asp Asn Asp Gly Gly
        275                 280                 285

Lys Leu Thr Asp Thr Glu Ile Lys Ala Leu Leu Leu Asn Leu Phe Val
    290                 295                 300

Ala Gly Thr Asp Thr Ser Ser Ser Thr Val Glu Trp Ala Ile Ala Glu
305                 310                 315                 320

Leu Ile Arg Asn Pro Lys Ile Leu Ala Gln Ala Gln Gln Glu Ile Asp
                325                 330                 335

Lys Val Val Gly Arg Asp Arg Leu Val Gly Glu Leu Asp Leu Ala Gln
            340                 345                 350

Leu Thr Tyr Leu Glu Ala Ile Val Lys Glu Thr Phe Arg Leu His Pro
        355                 360                 365

Ser Thr Pro Leu Ser Leu Pro Arg Ile Ala Ser Glu Ser Cys Glu Ile
    370                 375                 380

Asn Gly Tyr Phe Ile Pro Lys Gly Ser Thr Leu Leu Leu Asn Val Trp
385                 390                 395                 400

Ala Ile Ala Arg Asp Pro Asn Ala Trp Ala Asp Pro Leu Glu Phe Arg
                405                 410                 415

Pro Glu Arg Phe Leu Pro Gly Gly Glu Lys Pro Lys Val Asp Val Arg
            420                 425                 430

Gly Asn Asp Phe Glu Val Ile Pro Phe Gly Ala Gly Arg Arg Ile Cys
        435                 440                 445

Ala Gly Met Asn Leu Gly Ile Arg Met Val Gln Leu Met Ile Ala Thr
    450                 455                 460

Leu Ile His Ala Phe Asn Trp Asp Leu Val Ser Gly Gln Leu Pro Glu
465                 470                 475                 480

Met Leu Asn Met Glu Glu Ala Tyr Gly Leu Thr Leu Gln Arg Ala Asp
                485                 490                 495

Pro Leu Val Val His Pro Arg Pro Arg Leu Glu Ala Gln Ala Tyr Ile
            500                 505                 510

Gly


<210> SEQ ID NO 6
<211> LENGTH: 1542
<212> TYPE: DNA
<213> ORGANISM: artificial
<220> FEATURE:
<223> OTHER INFORMATION: coding sequence for SEQ ID NO: 5

<400> SEQUENCE: 6

atgtccgaaa tcttgtcttt gattttgtac accgtcattt tctctttctt gttgcaattc      60

attttgagat ctttcttcag aaagagatac ccattgccat tgccaccagg tccaaagcca     120

tggccaatta tcggtaactt ggtccacttg ggtccaaagc cacaccaatc tactgctgcc     180

atggctcaaa cttacggtcc attgatgtac ttgaagatgg gtttcgttga cgttgttgtt     240

gctgcctctg cttctgttgc tgctcaattc ttaaagactc acgatgctaa cttctcttct     300

agaccaccaa actctggtgc tgaacacatg gcttacaact accaagattt ggttttcgct     360

ccatacggtc caagatggag aatgttgaga aagatttgtt ctgttcactt gttctctacc     420
```

```
aaggctttgg atgacttcag acacgtcaga caagatgaag ttaagacttt gactagagct    480

ttggcttctg ctggtcaaaa gccagtcaag ttgggtcaat tgttgaacgt ttgtactact    540

aacgctttgg ctagagttat gttgggtaag agagttttcg ccgacggttc tggtgatgtt    600

gatccacaag ctgctgaatt caagtctatg gttgttgaaa tgatggttgt cgccggtgtt    660

ttcaacattg gtgatttcat tccacaattg aactggttgg atattcaagg tgttgccgct    720

aagatgaaga agttgcacgc tagattcgac gctttcttga ctgatatctt ggaagaacac    780

aagggtaaga ttttcggtga aatgaaggat ttgttgtcta ctttgatctc tttgaagaac    840

gatgatgctg ataacgatgg tggtaagttg actgatactg aaattaaggc tttgttgttg    900

aacttgttcg ttgctggtac tgacacttct tcttctactg ttgaatgggc cattgctgaa    960

ttgattagaa acccaaagat cttggcccaa gcccaacaag aaatcgacaa ggtcgttggt   1020

agagacagat tggttggtga attggacttg gcccaattga cttacttgga agctatcgtc   1080

aaggaaacct tcagattgca cccatctacc ccattgtctt tgccaagaat tgcttctgaa   1140

tcttgtgaaa tcaacggtta cttcattcca aagggttcta ctttgttgtt gaacgtttgg   1200

gccattgcta gagatccaaa cgcttgggct gatccattgg aattcagacc agaaagattc   1260

ttgccaggtg gtgaaaagcc aaaggttgat gtcagaggta acgacttcga agtcatccca   1320

ttcggtgctg gtagaagaat ttgtgctggt atgaacttgg gtatcagaat ggtccaattg   1380

atgattgcta ctttgatcca cgctttcaac tgggatttgg tatctggtca attgccagaa   1440

atgttgaaca tggaagaagc ttacggtttg accttgcaaa gagctgatcc attggttgtt   1500

cacccaagac caagattgga agcccaagct tacattggtt aa                      1542
```

```
<210> SEQ ID NO 7
<211> LENGTH: 519
<212> TYPE: PRT
<213> ORGANISM: Callistephus chinensis

<400> SEQUENCE: 7

Met Ser Thr Ile Leu Pro Phe Ile Phe Tyr Thr Cys Ile Thr Ala Leu
1               5                   10                  15

Val Leu Tyr Val Leu Leu Asn Leu Leu Thr Arg Asn Pro Asn Arg Leu
            20                  25                  30

Pro Pro Gly Pro Thr Pro Trp Pro Ile Val Gly Asn Leu Pro His Leu
        35                  40                  45

Gly Met Ile Pro His His Ser Leu Ala Ala Leu Ala Gln Lys Tyr Gly
    50                  55                  60

Pro Leu Met His Leu Arg Leu Gly Phe Val Asp Val Val Val Ala Ala
65                  70                  75                  80

Ser Ala Ser Val Ala Ala Gln Phe Leu Lys Thr His Asp Ala Asn Phe
                85                  90                  95

Ala Ser Arg Pro Pro Asn Ser Gly Ala Lys His Ile Ala Tyr Asn Tyr
            100                 105                 110

Gln Asp Leu Val Phe Ala Pro Tyr Gly Pro Arg Trp Arg Met Leu Arg
        115                 120                 125

Lys Ile Cys Ser Val His Leu Phe Ser Thr Lys Ala Leu Asp Asp Phe
    130                 135                 140

Arg His Val Arg Glu Glu Glu Val Ala Ile Leu Thr Arg Val Leu Val
145                 150                 155                 160

His Ala Gly Glu Ser Ala Val Lys Leu Gly Gln Leu Leu Asn Val Cys
                165                 170                 175
```

```
Thr Thr Asn Ala Leu Ala Arg Val Met Leu Gly Arg Arg Val Phe Ala
            180                 185                 190

Asp Gly Ser Glu Gly Arg Gly Val Asp Pro Lys Ala Asp Glu Phe Lys
        195                 200                 205

Asp Met Val Val Glu Leu Met Glu Leu Ala Gly Glu Phe Asn Ile Gly
    210                 215                 220

Asp Phe Ile Pro Pro Leu Asp Cys Leu Asp Leu Gln Gly Ile Thr Lys
225                 230                 235                 240

Lys Met Lys Lys Leu His Ala Arg Phe Asp Lys Phe Leu Asn Ile Ile
                245                 250                 255

Leu Asp Asp His Lys Ile Glu Lys Gly Ala Ala Gly Arg Arg His Ser
            260                 265                 270

Asp Leu Leu Thr Thr Leu Ile Ser Leu Lys Asp Val Asp Ala Ala Asp
        275                 280                 285

Asp Asp Glu Glu Gly Lys Leu Ser Asp Ile Glu Ile Lys Ala Leu Leu
    290                 295                 300

Leu Asn Leu Phe Ala Ala Gly Thr Asp Thr Ser Ser Ser Thr Val Glu
305                 310                 315                 320

Trp Ala Val Ala Glu Leu Ile Arg His Pro Glu Leu Leu Lys Gln Ala
                325                 330                 335

Arg Glu Glu Met Asp Ile Val Val Gly Arg Asp Arg Leu Val Thr Glu
            340                 345                 350

Leu Asp Leu Ser Arg Leu Thr Phe Leu Gln Ala Ile Val Lys Glu Thr
        355                 360                 365

Phe Arg Leu His Pro Ser Thr Pro Leu Ser Leu Pro Arg Met Ala Ser
    370                 375                 380

Glu Ser Cys Glu Val Asp Gly Tyr Tyr Ile Pro Lys Gly Ser Thr Leu
385                 390                 395                 400

Leu Val Asn Val Trp Ala Ile Ala Arg Asp Pro Lys Met Trp Thr Asn
                405                 410                 415

Pro Leu Glu Phe Arg Pro Ser Arg Phe Leu Pro Gly Gly Glu Lys Pro
            420                 425                 430

Asp Ala Asp Ile Lys Gly Asn Asp Phe Glu Val Ile Pro Phe Gly Ala
        435                 440                 445

Gly Arg Arg Ile Cys Ala Gly Met Ser Leu Gly Met Arg Met Val Gln
    450                 455                 460

Leu Leu Ile Ala Thr Leu Val Gln Thr Phe Asp Trp Glu Leu Ala Asn
465                 470                 475                 480

Gly Leu Asp Pro Glu Lys Leu Asn Met Glu Glu Ala Tyr Gly Leu Thr
                485                 490                 495

Leu Gln Arg Ala Glu Pro Leu Met Val His Pro Arg Pro Arg Leu Ser
            500                 505                 510

Pro His Val Tyr Glu Ser Arg
        515
```

<210> SEQ ID NO 8
<211> LENGTH: 1560
<212> TYPE: DNA
<213> ORGANISM: artificial
<220> FEATURE:
<223> OTHER INFORMATION: coding sequence for SEQ ID NO: 7

<400> SEQUENCE: 8

```
atgtccacca ttttgccatt cattttctac acttgtatca ctgccttggt tttgtacgtt      60

ttgttgaact tgttgaccag aaacccaaac agattgccac caggtccaac cccatggcca     120
```

```
atcgttggta acttgccaca cttgggtatg atcccacacc actctttggc tgccttggcc    180
caaaagtacg gtccattgat gcacttgaga ttgggtttcg ttgacgttgt cgttgccgct    240
tctgcttccg ttgctgctca attcttaaag actcacgacg ctaacttcgc ttctagacca    300
ccaaactctg gtgccaagca cattgcctac aactaccaag atttggtttt cgctccatac    360
ggtccaagat ggagaatgtt gagaaagatt tgttctgttc acttgttctc cactaaggct    420
ttggacgact tcagacacgt tagagaagaa gaagttgcta tcttgactag agttttggtc    480
cacgctggtg aatctgctgt taagttgggt caattgttga acgtttgtac cactaacgct    540
ttggctagag ttatgttggg tagaagagtt ttcgctgacg gttctgaagg tagaggtgtc    600
gacccaaagg ctgatgaatt caaggacatg gttgttgaat tgatggaatt ggccggtgaa    660
ttcaacatcg gtgacttcat cccaccattg gactgtttgg atttgcaagg tatcaccaag    720
aagatgaaga agttgcacgc tagattcgac aagttcttga acatcatctt ggacgaccac    780
aagatcgaaa agggtgctgc cggtagaagg cactctgact tgttgaccac tttgatttct    840
ttgaaggatg ttgatgctgc tgatgatgat gaagaaggta agttgtctga cattgaaatc    900
aaggctttgt tgttgaactt gttcgctgct ggtactgaca cttcttcttc taccgttgaa    960
tgggctgttg ccgaattgat tagacaccca gaattgttga agcaagctag agaagaaatg   1020
gatatcgttg ttggtagaga cagattggtt accgaattgg acttgtctag attgactttc   1080
ttgcaagcca ttgttaagga aaccttcaga ttgcacccat ctactccatt gtccttgcca   1140
agaatggctt ctgaatcttg tgaagttgat ggttactaca ttccaaaggg ttccactttg   1200
ttggttaacg tttgggccat cgccagagat ccaaagatgt ggactaaccc attggaattc   1260
agaccatcta gattcttgcc aggtggtgaa aagccagatg ctgatatcaa gggtaacgat   1320
ttcgaagtca tcccattcgg tgccggtaga agaatctgtg ctggtatgtc tttgggtatg   1380
agaatggtcc aattgttgat tgctactttg gtccaaacct tcgattggga attggctaac   1440
ggtttggacc cagaaaagtt gaacatggaa gaagcttacg gtttgacctt gcaaagagct   1500
gaaccattga tggttcaccc aagaccaaga ttgtctccac acgtttacga atctagataa   1560
```

<210> SEQ ID NO 9
<211> LENGTH: 511
<212> TYPE: PRT
<213> ORGANISM: Callistephus chinensis

<400> SEQUENCE: 9

```
Met Ser Ser Ile Leu Ser Leu Leu Val Tyr Phe Cys Ile Ser Leu Leu
1               5                   10                  15

Val Ile Ile Ala Leu Val Asn Met Phe Ile Thr Arg His Thr Asn Arg
            20                  25                  30

Leu Pro Pro Gly Pro Ala Pro Trp Pro Val Val Gly Asn Leu Pro His
        35                  40                  45

Leu Gly Ala Ile Pro His His Thr Leu Ala Ala Leu Ala Thr Lys Tyr
    50                  55                  60

Gly Pro Leu Val Tyr Leu Arg Leu Gly Phe Val His Val Val Val Ala
65                  70                  75                  80

Ser Ser Pro Ser Val Ala Ala Gln Phe Leu Lys Val His Asp Leu Lys
                85                  90                  95

Phe Ala Ser Arg Pro Pro Asn Ser Gly Ala Lys His Ile Ala Tyr Asn
            100                 105                 110

Tyr Gln Asp Met Val Phe Ala Pro Tyr Gly Pro Gln Trp Thr Met Phe
```

-continued

```
        115                 120                 125

Arg Lys Ile Cys Lys Asp His Leu Phe Ser Ser Lys Ala Leu Asp Asp
    130                 135                 140

Phe Arg His Val Arg Gln Glu Glu Val Ala Ile Leu Ala Arg Gly Leu
145                 150                 155                 160

Ala Gly Ala Gly Arg Ser Lys Val Asn Leu Gly Gln Gln Leu Asn Met
                165                 170                 175

Cys Thr Ala Asn Thr Leu Ala Arg Met Met Leu Asp Lys Arg Val Phe
            180                 185                 190

Gly Asn Glu Ser Gly Gly Asp Asp Pro Lys Ala Asn Glu Phe Lys Glu
        195                 200                 205

Met Ala Thr Glu Leu Met Phe Leu Ala Gly Gln Phe Asn Ile Gly Asp
    210                 215                 220

Tyr Ile Pro Val Leu Asp Trp Leu Asp Leu Gln Gly Ile Val Lys Lys
225                 230                 235                 240

Met Lys Lys Leu His Thr Arg Phe Asp Lys Phe Leu Asp Val Ile Leu
                245                 250                 255

Asp Glu His Lys Val Ile Ala Ser Gly His Ile Asp Met Leu Ser Thr
            260                 265                 270

Leu Ile Ser Leu Lys Asp Asp Thr Ser Val Asp Gly Arg Lys Pro Ser
        275                 280                 285

Asp Ile Glu Ile Lys Ala Leu Leu Leu Glu Leu Phe Val Ala Gly Thr
    290                 295                 300

Asp Thr Ser Ser Asn Thr Val Glu Trp Ala Ile Ala Glu Leu Ile Arg
305                 310                 315                 320

Gln Pro His Leu Leu Lys Arg Ala Gln Glu Glu Met Asp Ser Val Val
                325                 330                 335

Gly Gln Asn Arg Leu Val Thr Glu Met Asp Leu Ser Gln Leu Thr Phe
            340                 345                 350

Leu Gln Ala Ile Val Lys Glu Ala Phe Arg Leu His Pro Ser Thr Pro
        355                 360                 365

Leu Ser Leu Pro Arg Ile Ala Ser Glu Ser Cys Glu Val Asp Gly Tyr
    370                 375                 380

Tyr Ile Pro Lys Gly Ser Thr Leu Leu Val Asn Ile Trp Ala Ile Gly
385                 390                 395                 400

Arg His Pro Glu Val Trp Thr Asp Pro Leu Glu Phe Arg Pro Thr Arg
                405                 410                 415

Phe Leu Pro Gly Gly Glu Lys Pro Gly Ile Val Val Lys Val Asn Asp
            420                 425                 430

Phe Glu Val Leu Pro Phe Gly Ala Gly Arg Arg Ile Cys Ala Gly Met
        435                 440                 445

Ser Leu Ala Leu Arg Thr Val Gln Leu Leu Met Gly Thr Leu Val Gln
    450                 455                 460

Ala Phe Asp Trp Glu Leu Ala Asn Gly Ile Lys Pro Glu Lys Leu Asn
465                 470                 475                 480

Met Asp Glu Ala Phe Gly Leu Ser Val Gln Arg Ala Glu Pro Leu Val
                485                 490                 495

Val His Pro Arg Pro Arg Leu Pro Pro His Val Tyr Lys Ser Gly
            500                 505                 510
```

<210> SEQ ID NO 10
<211> LENGTH: 1536
<212> TYPE: DNA
<213> ORGANISM: artificial
<220> FEATURE:
<223> OTHER INFORMATION: coding sequence for SEQ ID NO: 9

<400> SEQUENCE: 10

```
atgtcctcta ttttgtcttt gttggtctac ttctgtatct ctttgttggt tatcattgct     60
ttggttaaca tgttcatcac cagacacacc aacagattgc caccaggtcc agccccatgg    120
ccagtcgtcg gtaacttgcc acacttgggt gctattccac accacacttt ggctgctttg    180
gctactaagt acggtccatt ggtttacttg agattgggtt tcgttcacgt tgttgttgcc    240
tcttctccat ccgttgctgc tcaattcttg aaggttcacg acttgaagtt cgcctctaga    300
ccaccaaact ctggtgctaa gcacatcgct tacaactacc aagatatggt tttcgctcca    360
tacggtccac aatggactat gttcagaaag atttgtaagg atcacttgtt ctcttctaag    420
gctttggatg atttcagaca cgttagacaa gaagaagttg ctatcttggc tagaggtttg    480
gctggtgctg gtagatctaa ggttaacttg ggtcaacaat tgaacatgtg taccgctaac    540
actttggcta gaatgatgtt ggacaagaga gttttcggta acgaatctgg tggtgatgat    600
ccaaaggcta acgaattcaa ggaaatggct actgaattga tgttcttggc tggtcaattc    660
aacattggtg actacatccc agttttggac tggttggact tgcaaggtat tgttaagaag    720
atgaagaagt tgcacactag attcgataag ttcttggacg ttatcttgga tgaacacaag    780
gttatcgctt ctggtcacat cgacatgttg tctactttga tttctttgaa ggatgatacc    840
tctgttgacg gtagaaagcc atccgacatc gaaatcaagg ctttgttgtt ggaattgttc    900
gttgctggta ctgacacttc ttctaacacc gttgaatggg ctatcgctga attgattaga    960
caaccacact tgttgaagag agcccaagaa gaaatggact ctgttgttgg tcaaaacaga   1020
ttggttaccg aaatggactt gtctcaattg actttcttgc aagccattgt taaggaagcc   1080
ttcagattgc acccatctac tccattgtcc ttgccaagaa ttgcttccga atcttgtgaa   1140
gttgatggtt actacatccc aaagggttcc actttgttgg ttaacatctg ggccattggt   1200
agacacccag aagtttggac cgacccattg gaattcagac caactagatt cttgccaggt   1260
ggtgaaaagc caggtattgt cgtcaaggtt aacgatttcg aagtcttgcc attcggtgcc   1320
ggtagaagaa tctgtgctgg tatgtctttg gccttgagaa ctgtccaatt gttgatgggt   1380
actttggtcc aagccttcga ttgggaattg gctaacggta tcaagccaga aaagttgaac   1440
atggacgaag ccttcggttt gtctgttcaa agagctgaac cattggttgt tcacccaaga   1500
ccaagattgc caccacacgt ttacaagtct ggttaa                              1536
```

<210> SEQ ID NO 11
<211> LENGTH: 513
<212> TYPE: PRT
<213> ORGANISM: Gerbera hybrida

<400> SEQUENCE: 11

```
Met Ser Thr Pro Leu Thr Leu Leu Ile Gly Thr Cys Val Thr Gly Leu
1               5                   10                  15

Phe Leu Tyr Val Leu Leu Asn Arg Cys Thr Arg Asn Pro Asn Arg Leu
            20                  25                  30

Pro Pro Gly Pro Thr Pro Trp Pro Val Val Gly Asn Leu Pro His Leu
        35                  40                  45

Gly Thr Ile Pro His His Ser Leu Ala Ala Met Ala Lys Lys Tyr Gly
    50                  55                  60

Pro Leu Met His Leu Arg Leu Gly Phe Val Asp Val Val Val Ala Ala
65                  70                  75                  80
```

```
Ser Ala Ser Val Ala Ala Gln Phe Leu Lys Thr His Asp Ala Asn Phe
                85                  90                  95

Ala Asp Arg Pro Pro Asn Ser Gly Ala Lys His Ile Ala Tyr Asn Tyr
            100                 105                 110

Gln Asp Leu Val Phe Ala Pro Tyr Gly Pro Arg Trp Arg Met Leu Arg
        115                 120                 125

Lys Ile Cys Ser Val His Leu Phe Ser Thr Lys Ala Leu Asp Asp Phe
    130                 135                 140

Arg His Val Arg Gln Glu Glu Val Ala Ile Leu Ala Arg Ala Leu Val
145                 150                 155                 160

Gly Ala Gly Lys Ser Pro Val Lys Leu Gly Gln Leu Leu Asn Val Cys
                165                 170                 175

Thr Thr Asn Ala Leu Ala Arg Val Met Leu Gly Arg Arg Val Phe Asp
            180                 185                 190

Ser Gly Asp Ala Gln Ala Asp Glu Phe Lys Asp Met Val Val Glu Leu
        195                 200                 205

Met Val Leu Ala Gly Glu Phe Asn Ile Gly Asp Phe Ile Pro Val Leu
    210                 215                 220

Asp Trp Leu Asp Leu Gln Gly Val Thr Lys Lys Met Lys Lys Leu His
225                 230                 235                 240

Ala Lys Phe Asp Ser Phe Leu Asn Thr Ile Leu Glu Glu His Lys Thr
                245                 250                 255

Gly Ala Gly Asp Gly Val Ala Ser Gly Lys Val Asp Leu Leu Ser Thr
            260                 265                 270

Leu Ile Ser Leu Lys Asp Asp Ala Asp Gly Glu Gly Gly Lys Leu Ser
        275                 280                 285

Asp Ile Glu Ile Lys Ala Leu Leu Leu Asn Leu Phe Thr Ala Gly Thr
    290                 295                 300

Asp Thr Ser Ser Ser Thr Ile Glu Trp Ala Ile Ala Glu Leu Ile Arg
305                 310                 315                 320

Asn Pro Gln Leu Leu Asn Gln Ala Arg Lys Glu Met Asp Thr Ile Val
                325                 330                 335

Gly Gln Asp Arg Leu Val Thr Glu Ser Asp Leu Gly Gln Leu Thr Phe
            340                 345                 350

Leu Gln Ala Ile Ile Lys Glu Thr Phe Arg Leu His Pro Ser Thr Pro
        355                 360                 365

Leu Ser Leu Pro Arg Met Ala Leu Glu Ser Cys Glu Val Gly Gly Tyr
    370                 375                 380

Tyr Ile Pro Lys Gly Ser Thr Leu Leu Val Asn Val Trp Ala Ile Ser
385                 390                 395                 400

Arg Asp Pro Lys Ile Trp Ala Asp Pro Leu Glu Phe Gln Pro Thr Arg
                405                 410                 415

Phe Leu Pro Gly Gly Glu Lys Pro Asn Thr Asp Ile Lys Gly Asn Asp
            420                 425                 430

Phe Glu Val Ile Pro Phe Gly Ala Gly Arg Arg Ile Cys Val Gly Met
        435                 440                 445

Ser Leu Gly Leu Arg Met Val Gln Leu Leu Thr Ala Thr Leu Ile His
    450                 455                 460

Ala Phe Asp Trp Glu Leu Ala Asp Gly Leu Asn Pro Lys Lys Leu Asn
465                 470                 475                 480

Met Glu Glu Ala Tyr Gly Leu Thr Leu Gln Arg Ala Ala Pro Leu Val
                485                 490                 495
```

```
Val His Pro Arg Pro Arg Leu Ala Pro His Val Tyr Glu Thr Thr Lys
            500                 505                 510

Val


<210> SEQ ID NO 12
<211> LENGTH: 1542
<212> TYPE: DNA
<213> ORGANISM: artificial
<220> FEATURE:
<223> OTHER INFORMATION: coding sequence for SEQ ID NO:11

<400> SEQUENCE: 12

atgtccactc cattgacttt gttgatcggt acctgtgtca ctggtttgtt cttgtacgtt      60

ttgttgaaca gatgtaccag aaacccaaac agattgccac caggtccaac tccatggcca     120

gtcgtcggta acttgccaca cttgggtact atcccacacc actctttggc tgctatggct     180

aagaagtacg gtccattgat gcacttgaga ttgggtttcg tcgacgtcgt tgttgccgcc     240

tccgcctccg tcgccgctca attcttaaag actcacgacg ctaacttcgc cgatagacca     300

ccaaactccg gtgccaagca catcgcttac aactaccaag atttggtttt cgctccatac     360

ggtccaagat ggagaatgtt gagaaagatt tgttctgttc acttgttctc caccaaggct     420

ttggatgatt tcagacacgt cagacaagaa gaagttgcta tcttggctag agctttggtc     480

ggtgccggta agtctccagt taagttgggt caattgttga acgtttgtac cactaacgct     540

ttggctagag ttatgttggg tagaagagtt ttcgactccg gtgatgctca agctgatgaa     600

ttcaaggaca tggttgttga attgatggtt ttggccggtg aattcaacat cggtgacttc     660

atcccagttt ggactggtt ggacttgcaa ggtgttacta agaagatgaa gaagttgcac     720

gctaagttcg actctttctt gaacactatc ttggaagaac acaagaccgg tgccggtgac     780

ggtgtcgctt ctggtaaggt tgacttgttg tctactttga tttctttgaa ggatgacgct     840

gatggtgaag gtggtaagtt gtctgacatt gaaatcaagg ctttgttgtt gaacttgttc     900

actgctggta ctgacacttc ttcttctact attgaatggg ctatcgctga attgattaga     960

aacccacaat tgttgaacca agccagaaag gaaatggaca ccatcgttgg tcaagacaga    1020

ttggttaccg aatctgactt gggtcaattg actttcttgc aagccattat caaggaaact    1080

ttcagattgc acccatctac cccattgtct ttgccaagaa tggctttgga atcttgtgaa    1140

gttggtggtt actacatccc aaagggttcc actttgttgg ttaacgtttg ggccatttct    1200

agagatccaa agatttgggc cgatccattg gaattccaac caactagatt cttgccaggt    1260

ggtgaaaagc caaacactga tatcaagggt aacgatttcg aagtcatccc attcggtgcc    1320

ggtagaagaa tttgtgtcgg tatgtctttg ggtttgagaa tggtccaatt gttgactgct    1380

accttgatcc acgccttcga ttgggaattg gctgatggtt tgaacccaaa gaagttgaac    1440

atggaagaag cttacggttt gaccttgcaa agagccgctc cattggttgt tcacccaaga    1500

ccaagattgg ccccacacgt ttacgaaact actaaggtct aa                        1542


<210> SEQ ID NO 13
<211> LENGTH: 515
<212> TYPE: PRT
<213> ORGANISM: Osteospermum hybrid cultivar

<400> SEQUENCE: 13

Met Ser Thr Ile Leu Pro Leu Val Leu Tyr Ser Cys Ile Thr Gly Leu
1               5                   10                  15

Val Ile Tyr Val Leu Leu Asn Leu Arg Thr Arg His Ser Asn Arg Leu
```

-continued

```
            20                  25                  30

Pro Pro Gly Pro Thr Pro Trp Pro Ile Val Gly Asn Leu Pro His Leu
        35                  40                  45

Gly Val Val Pro His His Ser Leu Ala Ala Met Ala Glu Lys Tyr Gly
    50                  55                  60

Pro Leu Met His Leu Arg Leu Gly Phe Val Asp Val Val Val Ala Ala
65                  70                  75                  80

Ser Ala Ala Val Ala Ala Gln Phe Leu Lys Val His Asp Ala Asn Phe
                85                  90                  95

Ala Ser Arg Pro Pro Asn Ser Gly Ala Lys His Ile Ala Tyr Asn Tyr
            100                 105                 110

Gln Asp Leu Val Phe Ala Pro Tyr Tyr Gly Pro Arg Trp Arg Met Leu
        115                 120                 125

Arg Lys Ile Cys Ser Val His Leu Phe Ser Ser Lys Ala Leu Asp Asp
    130                 135                 140

Phe Arg His Val Arg Gln Glu Glu Val Ala Ile Leu Thr Arg Ala Leu
145                 150                 155                 160

Ile Gly Ala Gly Asp Ser Pro Val Lys Leu Gly Gln Leu Leu Asn Val
                165                 170                 175

Cys Thr Thr Asn Ala Leu Ala Arg Val Met Leu Gly Lys Arg Val Phe
            180                 185                 190

Gly Asp Arg Ser Gly Gly Gly Asp Pro Lys Ala Asp Glu Phe Lys Asp
        195                 200                 205

Met Val Val Glu Val Met Glu Leu Ala Gly Glu Phe Asn Ile Gly Asp
    210                 215                 220

Phe Ile Pro Val Leu Asp Ser Leu Asp Leu Gln Gly Ile Ala Lys Lys
225                 230                 235                 240

Met Lys Glu Leu His Val Arg Phe Asp Ser Phe Leu Gly Lys Ile Leu
                245                 250                 255

Glu Glu His Lys Thr Gly Asn Gly Gly Ala Ser Ser Gln His Thr Asp
            260                 265                 270

Leu Leu Thr Thr Leu Ile Ser Leu Lys Asp Asp Thr Asp Glu Glu Gly
        275                 280                 285

Gly Lys Leu Ser Asp Ile Glu Ile Lys Ala Leu Leu Leu Asn Leu Phe
    290                 295                 300

Thr Ala Gly Thr Asp Thr Ser Ser Ser Thr Val Glu Trp Ala Ile Ala
305                 310                 315                 320

Glu Leu Ile Arg His Pro Gln Leu Leu Lys Gln Ala Gln Glu Glu Ile
                325                 330                 335

Asp Asn Val Val Gly Arg Asp His Leu Val Thr Glu Leu Asp Leu Thr
            340                 345                 350

Gln Leu Pro Phe Leu Gln Ala Ile Val Lys Glu Thr Phe Arg Leu His
        355                 360                 365

Pro Ser Thr Pro Leu Ser Leu Pro Arg Ile Ala Ser Glu Ser Cys Glu
    370                 375                 380

Val Asn Gly Tyr His Ile Pro Lys Gly Ser Thr Leu Leu Val Asn Val
385                 390                 395                 400

Trp Ala Ile Ala Arg Asp Pro Lys Met Trp Ser Glu Pro Leu Glu Phe
                405                 410                 415

Arg Pro Ala Arg Phe Leu Pro Gly Gly Glu Lys Pro Asp Ala Asp Val
            420                 425                 430

Lys Gly Asn Asp Phe Glu Val Ile Pro Phe Gly Ala Gly Arg Arg Ser
        435                 440                 445
```

-continued

```
Cys Ala Gly Met Ser Leu Gly Leu Arg Met Val Gln Leu Leu Val Ala
    450                 455                 460

Thr Leu Val Gln Thr Phe Asp Trp Glu Leu Ala Asn Gly Leu Lys Pro
465                 470                 475                 480

Glu Lys Leu Asn Met Glu Glu Ala Tyr Gly Leu Thr Leu Gln Arg Ala
                485                 490                 495

Ala Pro Leu Leu Val His Pro Lys Pro Arg Leu Ala Pro His Val Tyr
            500                 505                 510

Gly Ser Asn
        515


<210> SEQ ID NO 14
<211> LENGTH: 1548
<212> TYPE: DNA
<213> ORGANISM: artificial
<220> FEATURE:
<223> OTHER INFORMATION: coding sequence for SEQ ID NO: 13

<400> SEQUENCE: 14

atgtccacca ttttgccatt ggttttgtac tcttgtatca ctggtttggt tatctacgtt     60

ttgttgaact tgagaaccag acactctaac agattgccac caggtccaac tccatggcca    120

atcgtcggta acttgccaca cttgggtgtt gttccacacc actctttggc tgctatggct    180

gaaaagtacg gtccattgat gcacttgaga ttgggtttcg ttgacgttgt tgttgctgct    240

tctgctgccg ttgctgctca attcttgaag gttcacgatg ctaacttcgc ttctagacca    300

ccaaactccg gtgctaagca catcgcttac aactaccaag acttggtttt cgctccatac    360

tacggtccaa gatggagaat gttgagaaag atttgttccg ttcacttgtt ctcttctaag    420

gctttggatg atttcagaca cgtcagacaa gaagaagttg ctatcttgac tagagctttg    480

atcggtgccg gtgactctcc agttaagttg ggtcaattgt tgaacgtttg tactactaac    540

gctttggcta gagttatgtt gggtaagaga gttttcggtg acagatctgg tggtggtgat    600

ccaaaggctg atgaattcaa ggatatggtt gttgaagtta tggaattggc cggtgaattc    660

aacatcggtg atttcatccc agttttggat tctttggatt tgcaaggtat cgctaagaag    720

atgaaggaat tgcacgttag attcgattct ttcttgggta agatcttgga agaacacaag    780

accggtaacg gtggtgcttc ttctcaacac actgacttgt tgactacctt gatttctttg    840

aaggatgata ctgatgaaga aggtggtaag ttgtctgaca ttgaaatcaa ggctttgttg    900

ttgaacttgt tcactgctgg tactgacact tcttcttcta ccgttgaatg ggctatcgcc    960

gaattgatta gacacccaca attgttgaag caagcccaag aagaaatcga caacgttgtt   1020

ggtagagatc acttggttac cgaattggac ttgacccaat tgccattctt gcaagccatt   1080

gttaaggaaa ccttcagatt gcacccatct actccattgt ctttgccaag aattgcttcc   1140

gaatcttgtg aagtcaacgg ttaccacatc ccaaagggtt ccactttgtt ggttaacgtt   1200

tgggccatcg ccagagatcc aaagatgtgg tccgaaccat tggaattcag accagccaga   1260

ttcttgccag gtggtgaaaa gccagatgct gatgttaagg gtaacgattt cgaagtcatc   1320

ccattcggtg ccggtagaag atcttgtgct ggtatgtctt tgggtttgag aatggttcaa   1380

ttgttggttg ctactttggt tcaaaccttc gactgggaat tggctaacgg tttgaagcca   1440

gaaaagttga acatggaaga agcttacggt ttgactttgc aaagagctgc tccattgttg   1500

gttcacccaa agccaagatt ggctccacac gtttacggtt ctaactaa                 1548
```

<210> SEQ ID NO 15
<211> LENGTH: 539
<212> TYPE: PRT
<213> ORGANISM: Citrus clementina

<400> SEQUENCE: 15

```
Met Ser Gln Pro Leu Val Arg Leu Leu Val Pro Phe Leu Arg Phe Leu
1               5                   10                  15

Trp Glu Thr Lys Gln Arg Ala Met Ser Thr Leu Pro Leu Leu Ile Leu
            20                  25                  30

Tyr Thr Ser Leu Leu Ala Ile Val Ile Ser Phe Leu Phe Ser Leu Leu
        35                  40                  45

Arg Asn Arg Arg Arg His Ser Ser His Arg Leu Pro Pro Gly Pro Lys
    50                  55                  60

Pro Trp Pro Ile Val Gly Asn Leu Pro His Leu Gly Pro Met Pro His
65                  70                  75                  80

Gln Ser Ile Ala Gly Leu Ala Arg Thr His Gly Pro Leu Met Tyr Leu
                85                  90                  95

Arg Leu Gly Phe Val Asp Val Val Val Ala Ala Ser Ala Ser Val Ala
            100                 105                 110

Ala Gln Phe Leu Lys Ile His Asp Ser Asn Phe Ser Asn Arg Pro Pro
        115                 120                 125

Asn Ser Gly Ala Lys His Ile Ala Tyr Asn Tyr Gln Asp Ile Val Phe
    130                 135                 140

Arg Pro Tyr Gly Pro Arg Trp Arg Met Leu Arg Lys Ile Ser Ser Val
145                 150                 155                 160

His Leu Phe Ser Gly Lys Ala Leu Asp Asp Tyr Arg His Val Arg Gln
                165                 170                 175

Glu Glu Met Ala Val Leu Thr Arg Ala Leu Ala Ser Ala Gly Thr Glu
            180                 185                 190

Pro Val Asn Leu Ala Gln Arg Leu Asn Leu Cys Val Val Asn Ala Leu
        195                 200                 205

Gly Arg Val Met Leu Gly Phe Arg Val Phe Gly Asp Gly Thr Gly Gly
    210                 215                 220

Ser Asp Pro Arg Ala Asp Glu Phe Lys Ser Met Val Val Glu Leu Met
225                 230                 235                 240

Val Leu Ala Gly Val Phe Asn Val Gly Asp Phe Val Pro Ala Leu Glu
                245                 250                 255

Arg Leu Asp Leu Gln Gly Val Ala Arg Lys Met Lys Lys Leu His Lys
            260                 265                 270

Arg Phe Asp Val Phe Leu Ser Asp Ile Leu Glu Glu Arg Lys Met Asn
        275                 280                 285

Gly Arg Asp Gly Gly Asn Lys Leu Thr Asp Leu Leu Gly Thr Leu Ile
    290                 295                 300

Ser Leu Met Asp Asp Ala Asn Gly Glu Glu Lys Leu Thr Glu Thr Glu
305                 310                 315                 320

Ile Lys Ala Leu Leu Leu Asn Met Phe Thr Ala Gly Thr Asp Thr Ser
                325                 330                 335

Ser Ser Thr Ile Glu Trp Ala Ile Ala Glu Leu Ile Arg His Pro Lys
            340                 345                 350

Val Trp Ala Gln Val Gln Gln Glu Leu Asp Ser Val Val Gly Arg Asp
        355                 360                 365

Arg Leu Val Thr Glu Leu Asp Leu Pro Gln Leu Thr Tyr Leu Gln Ala
    370                 375                 380
```

-continued

```
Val Ile Lys Glu Ile Phe Arg Leu His Pro Ser Thr Pro Leu Ser Leu
385                 390                 395                 400

Pro Arg Ala Ala Ser Glu Ser Cys Lys Ile Asn Gly Tyr Asp Ile Pro
                405                 410                 415

Lys Gly Ser Thr Leu Leu Val Asn Ile Trp Ala Ile Ala Arg Asp Pro
            420                 425                 430

Asn Glu Trp Ala Asp Pro Leu Glu Phe Arg Pro Glu Arg Phe Leu Pro
        435                 440                 445

Gly Gly Glu Lys Tyr Asn Val Asp Val Lys Gly Asn Asp Tyr Glu Leu
    450                 455                 460

Ile Pro Phe Gly Ala Gly Arg Arg Ile Cys Ala Gly Leu Ser Trp Gly
465                 470                 475                 480

Leu Arg Met Val Gln Leu Gly Thr Ala Thr Leu Ala His Ala Phe Asn
                485                 490                 495

Trp Glu Leu Pro Gly Gly Leu Lys Pro Glu Lys Leu Asn Met Asp Glu
            500                 505                 510

Ala Tyr Gly Leu Thr Leu Gln Arg Ala Ala Pro Leu Val Val His Pro
        515                 520                 525

Arg Pro Arg Leu Ser Pro Asn Ala Tyr Gln Ala
    530                 535


<210> SEQ ID NO 16
<211> LENGTH: 1620
<212> TYPE: DNA
<213> ORGANISM: artificial
<220> FEATURE:
<223> OTHER INFORMATION: coding sequence for SEQ ID NO: 15

<400> SEQUENCE: 16

atgtcccaac cattggttag attgttggtt ccattcttga gattcttgtg ggaaactaag      60

caaagagcta tgtctacttt gccattgttg atcttgtaca cttctttgtt ggctattgtc     120

atttctttct tgttctcttt gttgagaaac agaaggagac actcctccca cagattgcca     180

ccaggtccaa agccatggcc aatcgtcggt aacttgccac acttgggtcc aatgccacac     240

caatccatcg ctggtttggc cagaacccac ggtccattga tgtacttgag attgggtttc     300

gttgacgtcg tcgttgccgc ttccgcttcc gttgctgccc aattcttgaa gatccacgat     360

tccaacttct ccaacagacc accaaactcc ggtgccaagc acatcgctta caactaccaa     420

gacatcgttt tcagaccata cggtccaaga tggagaatgt tgagaaagat ctcttccgtt     480

cacttgttct ccggtaaggc cttggatgac tacagacacg ttagacaaga agaaatggct     540

gttttgacta gagctttggc ttctgctggt actgaaccag ttaacttggc tcaaagattg     600

aacttgtgtg ttgttaacgc cttgggtaga gttatgttgg gtttcagagt tttcggtgac     660

ggtaccggtg gttctgaccc aagagctgac gaattcaagt ctatggttgt tgaattgatg     720

gttttggctg gtgttttcaa cgtcggtgat ttcgtcccag ccttggaaag attggacttg     780

caaggtgttg ctagaaagat gaagaagttg cacaagagat tcgatgtttt cttgtctgat     840

atcttggaag aaagaaagat gaacggtaga gatggtggta acaagttgac tgacttgttg     900

ggtaccttga tttctttgat ggatgatgct aacggtgaag aaaagttgac tgaaactgaa     960

atcaaggctt tgttgttgaa catgttcact gctggtaccg acacttcttc ttctactatc    1020

gaatgggcca ttgctgaatt gatcagacac ccaaaggtct gggcccaagt ccaacaagaa    1080

ttggattctg ttgttggtag agatagattg gtcaccgaat tggacttgcc acaattgact    1140

tacttgcaag ccgttatcaa ggaaatcttc agattgcacc catctactcc attgtctttg    1200
```

-continued ccaagagctg cttccgaatc ttgtaagatc aacggttacg atattccaaa gggttccact 1260
ttgttggtca acatctgggc cattgctaga gatccaaacg aatgggccga cccattggaa 1320
ttcagaccag aaagattctt gccaggtggt gaaaagtaca acgttgatgt taagggtaac 1380
gattacgaat tgatcccatt cggtgccggt agaagaattt gtgctggttt gtcttggggt 1440
ttgagaatgg ttcaattggg tactgctact ttggcccacg ctttcaactg ggaattgcca 1500
ggtggtttga agccagaaaa gttgaacatg gacgaagctt acggtttgac cttgcaaaga 1560
gctgctccat tggttgttca cccaagacca agattgtctc caaacgctta ccaagcttaa 1620

<210> SEQ ID NO 17
<211> LENGTH: 517
<212> TYPE: PRT
<213> ORGANISM: Citrus sinensis

<400> SEQUENCE: 17

Met Ser Ser Thr Leu Pro Leu Leu Ile Leu Tyr Thr Ser Leu Leu Ala
1 5 10 15

Ile Val Ile Ser Phe Leu Phe Ser Leu Leu Arg Asn Arg Arg Arg His
20 25 30

Ser Ser His Arg Leu Pro Pro Gly Pro Lys Pro Trp Pro Ile Val Gly
35 40 45

Asn Leu Pro His Leu Gly Pro Met Pro His Gln Ser Ile Ala Gly Leu
50 55 60

Ala Arg Thr His Gly Pro Leu Met Tyr Leu Arg Leu Gly Phe Val Asp
65 70 75 80

Val Val Val Ala Ala Ser Ala Ser Val Ala Ala Gln Phe Leu Lys Ile
85 90 95

His Asp Ser Asn Phe Ser Asn Arg Pro Pro Asn Ser Gly Ala Lys His
100 105 110

Ile Ala Tyr Asn Tyr Gln Asp Ile Val Phe Arg Pro Tyr Gly Pro Arg
115 120 125

Trp Arg Met Leu Arg Lys Ile Ser Ser Val His Leu Phe Ser Gly Lys
130 135 140

Ala Leu Asp Asp Tyr Arg His Val Arg Gln Glu Glu Met Ala Val Leu
145 150 155 160

Ala Arg Ala Leu Ala Ser Ala Gly Thr Glu Pro Val Asn Leu Ala Gln
165 170 175

Arg Leu Asn Leu Cys Val Val Asn Ala Leu Gly Arg Val Met Leu Gly
180 185 190

Phe Arg Val Phe Gly Asp Gly Thr Gly Gly Ser Asp Pro Arg Ala Asp
195 200 205

Glu Phe Lys Ser Met Val Val Glu Leu Met Val Leu Ala Gly Val Phe
210 215 220

Asn Val Gly Asp Phe Val Pro Ala Leu Glu Arg Leu Asp Leu Gln Gly
225 230 235 240

Val Ala Arg Lys Met Lys Lys Leu His Lys Arg Phe Asp Val Phe Leu
245 250 255

Ser Asp Ile Leu Glu Glu Arg Lys Met Asn Gly Arg Asp Gly Gly Asn
260 265 270

Lys His Thr Asp Leu Leu Gly Thr Leu Ile Ser Leu Met Asp Asp Ala
275 280 285

Asn Gly Glu Glu Lys Leu Thr Glu Thr Glu Ile Lys Ala Leu Leu Leu
290 295 300

-continued

Asn Met Phe Thr Ala Gly Thr Asp Thr Ser Ser Ser Thr Ile Glu Trp
305 310 315 320

Ala Ile Ala Glu Leu Ile Arg His Pro Lys Val Arg Ala Gln Val Gln
325 330 335

Gln Glu Leu Asp Ser Val Val Gly Arg Asp Arg Leu Val Thr Glu Leu
340 345 350

Asp Leu Pro Gln Leu Thr Tyr Leu Gln Ala Val Ile Lys Glu Ile Phe
355 360 365

Arg Leu His Pro Ser Thr Pro Leu Ser Leu Pro Arg Ala Ala Ser Glu
370 375 380

Ser Cys Lys Ile Asn Gly Tyr Asp Ile Pro Lys Gly Ser Thr Leu Leu
385 390 395 400

Val Asn Ile Trp Ala Ile Ala Arg Asp Pro Asn Glu Trp Ala Asp Pro
405 410 415

Leu Glu Phe Arg Pro Glu Arg Phe Leu Pro Gly Gly Glu Lys Tyr Asn
420 425 430

Val Asp Val Lys Gly Asn Asp Tyr Glu Leu Ile Pro Phe Gly Ala Gly
435 440 445

Arg Arg Ile Cys Ala Gly Leu Ser Trp Gly Leu Arg Met Val Gln Leu
450 455 460

Gly Thr Ala Thr Leu Ala His Ala Phe Asn Trp Glu Leu Pro Gly Gly
465 470 475 480

Leu Lys Pro Glu Lys Leu Ser Met Asp Glu Ala Tyr Gly Leu Thr Leu
485 490 495

Gln Arg Ala Ala Pro Leu Val Val His Pro Arg Pro Arg Leu Ser Pro
500 505 510

Asn Ala Tyr Gln Ala
515

<210> SEQ ID NO 18
<211> LENGTH: 1554
<212> TYPE: DNA
<213> ORGANISM: artificial
<220> FEATURE:
<223> OTHER INFORMATION: coding sequence for SEQ ID NO: 17

<400> SEQUENCE: 18
atgtcctcta ctttgccatt gttgatcttg tacacttctt tgttggctat tgtcatttct 60
ttcttgttct ctttgttgag aaacagaagg agacactcct cccacagatt gccaccaggt 120
ccaaagccat ggccaatcgt cggtaacttg ccacacttgg gtccaatgcc acaccaatcc 180
atcgctggtt tggccagaac ccacggtcca ttgatgtact tgagattggg tttcgttgac 240
gtcgtcgttg ccgcttctgc ttccgttgct gcccaattct tgaagatcca cgattccaac 300
ttctccaaca gaccaccaaa ctccggtgcc aagcacatcg cttacaacta ccaagacatc 360
gttttcagac catacggtcc aagatggaga atgttgagaa agatctcttc cgttcacttg 420
ttctccggta aggccttgga tgactacaga cacgttagac aagaagaaat ggctgttttg 480
gctagagctt tggcttctgc tggtactgaa ccagttaact tggctcaaag attgaacttg 540
tgtgttgtta acgccttggg tagagttatg ttgggtttca gagttttcgg tgacggtacc 600
ggtggttctg acccaagagc tgacgaattc aagtctatgg ttgttgaatt gatggttttg 660
gctggtgttt tcaacgtcgg tgacttcgtc ccagccttgg aaagattgga cttgcaaggt 720
gttgctagaa agatgaagaa gttgcacaag agattcgatg ttttcttgtc tgatatcttg 780
gaagaaagaa agatgaacgg tagagatggt ggtaacaagc acactgactt gttgggtacc 840
ttgatttctt tgatggatga tgctaacggt gaagaaaagt tgactgaaac tgaaatcaag 900
gctttgttgt tgaacatgtt cactgctggt accgacactt cttcttctac tatcgaatgg 960
gccattgctg aattgatcag acacccaaag gtcagagccc aagtccaaca agaattggat 1020
tctgttgttg gtagagatag attggtcacc gaattggact tgccacaatt gacttacttg 1080
caagccgtta tcaaggaaat cttcagattg cacccatcta ctccattgtc tttgccaaga 1140
gctgcttccg aatcttgtaa gatcaacggt tacgatattc caaagggttc cactttgttg 1200
gtcaacatct gggccattgc tagagatcca aacgaatggg ccgacccatt ggaattcaga 1260
ccagaaagat tcttgccagg tggtgaaaag tacaacgttg atgttaaggg taacgattac 1320
gaattgatcc cattcggtgc cggtagaaga atttgtgctg gtttgtcttg ggtttgaga 1380 atggttcaat tgggtactgc tactttggcc cacgctttca actgggaatt gccaggtggt 1440
ttgaagccag aaaagttgtc tatggacgaa gcttacggtt tgaccttgca aagagctgct 1500
ccattggttg ttcacccaag accaagattg tctccaaacg cttaccaagc ttaa 1554

<210> SEQ ID NO 19
<211> LENGTH: 513
<212> TYPE: PRT
<213> ORGANISM: Pilosella officinarum

<400> SEQUENCE: 19

Met Ser Thr Leu Leu Ser Leu Ile Ile Tyr Leu Cys Ile Thr Gly Val
1 5 10 15

Thr Ala Tyr Val Leu Val Asn Leu Arg Thr Arg Arg Ala Asn Arg Leu
20 25 30

Pro Pro Gly Pro Thr Pro Trp Pro Ile Val Gly Asn Leu Pro His Leu
35 40 45

Gly Thr Ile Pro His His Ser Leu Ala Asp Leu Ala Thr Arg Tyr Gly
50 55 60

Pro Leu Met His Leu Arg Leu Gly Phe Val Asp Val Val Val Ala Ala
65 70 75 80

Ser Ala Ser Val Ala Ala Gln Phe Leu Lys Thr His Asp Ala Asn Phe
85 90 95

Ala Ser Arg Pro Pro Asn Ser Gly Ala Lys His Met Ala Tyr Asn Tyr
100 105 110

Gln Asp Leu Val Phe Ala Pro Tyr Gly Pro Arg Trp Arg Met Leu Arg
115 120 125

Lys Ile Cys Ser Val His Leu Phe Ser Ala Lys Ser Leu Asp Asp Phe
130 135 140

Arg His Val Arg Gln Glu Glu Val Ala Ile Leu Thr Arg Ala Leu Val
145 150 155 160

Gly Ala Gly Lys Ser Thr Val Lys Leu Gly Gln Leu Leu His Val Cys
165 170 175

Thr Thr Asn Ala Leu Val Arg Val Met Leu Gly Arg Arg Val Phe Gly
180 185 190

Asp Gly Ser Gly Gly Gly Asp Pro Lys Ala Asp Glu Phe Lys Asn Met
195 200 205

Val Ile Glu Met Met Val Leu Ala Gly Glu Phe Asn Leu Gly Asp Phe
210 215 220

Ile Pro Val Leu Asp Leu Leu Asp Leu Gln Gly Val Thr Lys Lys Met
225 230 235 240

```
Lys Lys Leu His Thr Arg Phe Asp Ser Phe Leu Asn Ser Ile Leu Glu
                245                 250                 255

Glu His Arg Thr Ser Ser Gly Gly Ala Ser Gly His Val Asp Leu Leu
            260                 265                 270

Ser Thr Leu Ile Ser Leu Lys Asp Glu Ala Asp Gly Glu Gly Gly Lys
        275                 280                 285

Leu Thr Asp Thr Glu Ile Lys Ala Leu Leu Leu Asn Leu Phe Val Ala
    290                 295                 300

Gly Thr Asp Thr Ser Ser Ser Thr Val Glu Trp Ala Ile Ala Glu Leu
305                 310                 315                 320

Ile Arg Asn Pro Gln Leu Leu Lys Gln Ala Gln Gln Glu Leu Asp Thr
                325                 330                 335

Val Val Gly Gln Gly Arg Leu Val Asn Glu Ser Asp Leu Ser Gln Leu
            340                 345                 350

Thr Phe Leu Gln Ala Ile Val Lys Glu Thr Phe Arg Leu His Pro Ser
        355                 360                 365

Thr Pro Leu Ser Leu Pro Arg Ile Ala Ser Glu Ser Cys Glu Ile Asn
    370                 375                 380

Gly Tyr Asn Ile Pro Lys Gly Ser Thr Leu Leu Val Asn Val Trp Ala
385                 390                 395                 400

Ile Ala Arg Asp Pro Lys Met Trp Thr Glu Pro Leu Glu Phe Arg Pro
                405                 410                 415

Ser Arg Phe Leu Pro Asp Gly Glu Lys Pro Asn Ala Asp Val Lys Gly
            420                 425                 430

Asn Asp Phe Glu Val Ile Pro Phe Gly Ala Gly Arg Arg Ile Cys Ala
        435                 440                 445

Gly Met Ser Leu Gly Leu Arg Met Val Gln Leu Leu Thr Ala Thr Leu
    450                 455                 460

Ile Gln Ala Phe Asp Trp Glu Leu Ala Asn Gly Leu Glu Pro Arg Asn
465                 470                 475                 480

Leu Asn Met Glu Glu Ala Tyr Gly Leu Thr Leu Gln Arg Ala Gln Pro
                485                 490                 495

Leu Met Val His Pro Arg Pro Arg Leu Ala Pro His Val Tyr Gly Thr
            500                 505                 510

Gly
```

<210> SEQ ID NO 20
<211> LENGTH: 1542
<212> TYPE: DNA
<213> ORGANISM: artificial
<220> FEATURE:
<223> OTHER INFORMATION: coding sequence for SEQ ID NO: 19

<400> SEQUENCE: 20

```
atgtccacct tgttgtcctt gatcatctac ttgtgtatca ctggtgttac tgcctacgtt      60

ttggttaact tgagaactag aagagctaac agattgccac caggtccaac cccatggcca     120

atcgtcggta acttgccaca cttgggtact attccacacc actctttggc tgatttggct     180

actagatacg gtccattgat gcacttgaga ttgggtttcg ttgacgttgt tgttgccgcc     240

tctgcttccg tcgctgctca attcttaaag actcacgacg ctaacttcgc ttctagacca     300

ccaaactctg gtgctaagca catggcttac aactaccaag atttggtttt cgctccatac     360

ggtccaagat ggagaatgtt gagaaagatt tgttccgttc acttgttctc tgccaagtct     420

ttggatgatt tcagacacgt tagacaagaa gaagttgcta tcttgactag agctttggtc     480
```

ggtgccggta agtctactgt taagttgggt caattgttgc acgtttgtac cactaacgct 540
ttggttagag ttatgttggg tagaagagtt ttcggtgatg gttctggtgg tggtgatcca 600
aaggctgatg aattcaagaa catggttatt gaaatgatgg ttttggccgg tgaattcaac 660
ttgggtgatt tcatcccagt tttggatttg ttggacttgc aaggtgttac taagaagatg 720
aagaagttgc acactagatt cgattctttc ttgaactcta tcttggaaga acacagaact 780
tcttctggtg gtgcttctgg tcacgtcgat ttgttgtcta ctttgatttc tttgaaggat 840
gaagccgatg gtgaaggtgg taagttgact gacactgaaa ttaaggcttt gttgttgaac 900
ttgttcgttg ctggtactga cacttcttct tctaccgttg aatgggctat cgctgaattg 960
attagaaacc cacaattgtt gaagcaagcc caacaagaat tggacactgt tgttggtcaa 1020
ggtagattgg ttaacgaatc tgacttgtct caattgacct tcttgcaagc cattgttaag 1080
gaaactttca gattgcaccc atctactcca ttgtccttgc caagaatcgc ttccgaatct 1140
tgtgaaatca acggttacaa cattccaaag ggttccactt tgttggttaa cgtttgggcc 1200
atcgctagag atccaaagat gtggaccgaa ccattggaat tcagaccatc cagattcttg 1260
ccagacggtg aaaagccaaa cgctgatgtt aagggtaacg atttcgaagt catcccattc 1320
ggtgctggta gaagaatttg tgctggtatg tctttgggtt tgagaatggt ccaattgttg 1380
accgctactt tgattcaagc cttcgattgg gaattggcta acggtttgga accaagaaac 1440
ttgaacatgg aagaagccta cggtttgacc ttgcaaagag ctcaaccatt gatggttcac 1500
ccaagaccaa gattggcccc acacgtttac ggtactggtt aa 1542

<210> SEQ ID NO 21
<211> LENGTH: 406
<212> TYPE: PRT
<213> ORGANISM: Streptomyces avermitilis

<400> SEQUENCE: 21

Met Ser Ala Ala Ala Phe Asp Leu Ala Phe Asp Pro Trp Asp Pro Ala
1 5 10 15

Phe Leu Ala Asp Pro Tyr Pro Ala Tyr Ala Asp Leu Arg Ala Lys Gly
20 25 30

Arg Val His Tyr Tyr Glu Pro Thr Asn Gln Trp Leu Val Pro His His
35 40 45

Ala Asp Val Ser Ala Leu Leu Arg Asp Arg Arg Leu Gly Arg Ala Tyr
50 55 60

Gln His Arg Tyr Thr His Glu Asp Phe Gly Arg Thr Ala Pro Pro Ala
65 70 75 80

Glu His Glu Pro Phe His Thr Leu Asn Asp His Gly Met Leu Asp Leu
85 90 95

Glu Pro Pro Asp His Thr Arg Ile Arg Arg Leu Val Ser Lys Ala Phe
100 105 110

Thr Pro Arg Thr Val Glu Gln Leu Lys Pro Tyr Val Ala Lys Leu Ala
115 120 125

Gly Glu Leu Val Asp Arg Leu Val Ala Ala Gly Gly Gly Asp Leu Leu
130 135 140

Ala Asp Val Ala Glu Pro Leu Pro Val Ala Val Ile Ala Glu Met Leu
145 150 155 160

Gly Ile Pro Glu Ser Asp Arg Ala Pro Leu Arg Pro Trp Ser Ala Asp
165 170 175

Ile Cys Gly Met Tyr Glu Leu Asn Pro Pro Lys Asp Val Ala Ala Lys
180 185 190

```
Ala Val Arg Ala Ser Val Glu Phe Ser Asp Tyr Leu Arg Glu Leu Ile
        195                 200                 205

Ala Glu Arg Arg Lys Glu Pro Gly Asp Asp Leu Ile Ser Gly Leu Ile
    210                 215                 220

Ala Ala His Asp Glu Gly Asp Arg Leu Thr Glu Gln Glu Met Ile Ser
225                 230                 235                 240

Thr Cys Val Leu Leu Leu Asn Ala Gly His Glu Ala Thr Val Asn Ala
                245                 250                 255

Thr Val Asn Gly Trp Tyr Ala Leu Phe Arg Asn Pro Asp Gln Leu Ala
            260                 265                 270

Ala Leu Arg Ala Asp His Ser Leu Val Pro Ala Ala Val Glu Glu Leu
        275                 280                 285

Met Arg Tyr Asp Thr Pro Leu Gln Leu Phe Glu Arg Trp Val Leu Asp
    290                 295                 300

Glu Ile Glu Ile Asp Gly Thr Thr Val Pro Arg Gly Ala Glu Ile Ala
305                 310                 315                 320

Met Leu Phe Gly Ser Ala Asn His Asp Pro Glu Val Phe Arg Asn Pro
                325                 330                 335

Glu Lys Leu Asp Leu Thr Arg Glu Asp Asn Pro His Ile Ser Phe Ser
            340                 345                 350

Ala Gly Ile His Tyr Cys Ile Gly Ala Pro Leu Ala Arg Ile Glu Leu
        355                 360                 365

Ala Ala Ser Met Thr Ala Leu Leu Glu Lys Ala Pro Thr Leu Gly Leu
    370                 375                 380

Val Ala Glu Pro Lys Arg Lys Pro Asn Phe Val Ile Arg Gly Leu Glu
385                 390                 395                 400

Gly Leu Ser Val Ala Val
                405
```

<210> SEQ ID NO 22
<211> LENGTH: 1221
<212> TYPE: DNA
<213> ORGANISM: artificial
<220> FEATURE:
<223> OTHER INFORMATION: coding sequence for SEQ ID NO: 21

<400> SEQUENCE: 22

```
atgtccgctg ctgctttcga cttggccttc gacccatggg acccagcttt cttggccgac     60

ccatacccag cctacgccga tttgagagcc aagggtagag ttcactacta cgaaccaact    120

aaccaatggt tggttccaca ccacgctgac gtttctgctt tgttgagaga cagaagattg    180

ggtagagctt accaacacag atacactcac gaagatttcg gtagaaccgc tccaccagct    240

gaacacgaac cattccacac cttgaacgac cacggtatgt tggacttgga accaccagac    300

cacaccagaa tcagaagatt ggtttctaag gctttcactc caagaaccgt tgaacaattg    360

aagccatacg ttgccaagtt ggccggtgaa ttggttgaca gattggtcgc tgctggtggt    420

ggtgatttgt tggctgatgt cgccgaacca ttgccagttg ccgtcatcgc cgaaatgttg    480

ggtatcccag aatccgacag agccccatta agaccatggt ctgctgacat ctgtggtatg    540

tacgaattga acccaccaaa ggacgttgct gctaaggctg ttagagcttc tgttgaattc    600

tccgactact tgagagaatt gatcgccgaa agaagaaagg aaccaggtga cgatttgatc    660

tctggtttga tcgccgccca cgacgaaggt gacagattga ccgaacaaga aatgatctcc    720

acctgtgtct tgttgttgaa cgctggtcac gaagccaccg tcaacgccac tgtcaacggt    780
```

-continued

```
tggtacgcct tgttcagaaa cccagaccaa ttggccgcct tgagagccga ccactctttg    840

gttccagccg ccgttgaaga attgatgaga tacgacactc cattgcaatt gttcgaaaga    900

tgggtcttgg acgaaatcga aatcgacggt actactgtcc caagaggtgc tgaaatcgcc    960

atgttgttcg gttccgccaa ccacgaccca gaagttttca gaaacccaga aaagttggac   1020

ttgaccagag aagataaccc acacatttcc ttctctgctg gtatccacta ctgtatcggt   1080

gctccattgg ctagaatcga attggctgct tctatgactg ccttgttgga aaaggcccca   1140

actttgggtt tggttgctga accaaagaga aagccaaact tcgttatcag aggtttggaa   1200

ggtttgtctg tcgctgtcta a                                             1221


<210> SEQ ID NO 23
<211> LENGTH: 715
<212> TYPE: PRT
<213> ORGANISM: Catharanthus roseus

<400> SEQUENCE: 23

Met Ser Asp Ser Ser Ser Glu Lys Leu Ser Pro Phe Glu Leu Met Ser
1               5                   10                  15

Ala Ile Leu Lys Gly Ala Lys Leu Asp Gly Ser Asn Ser Ser Asp Ser
            20                  25                  30

Gly Val Ala Val Ser Pro Ala Val Met Ala Met Leu Leu Glu Asn Lys
        35                  40                  45

Glu Leu Val Met Ile Leu Thr Thr Ser Val Ala Val Leu Ile Gly Cys
    50                  55                  60

Val Val Val Leu Ile Trp Arg Arg Ser Ser Gly Ser Gly Lys Lys Val
65                  70                  75                  80

Val Glu Pro Pro Lys Leu Ile Val Pro Lys Ser Val Val Glu Pro Glu
                85                  90                  95

Glu Ile Asp Glu Gly Lys Lys Lys Phe Thr Ile Phe Phe Gly Thr Gln
            100                 105                 110

Thr Gly Thr Ala Glu Gly Phe Ala Lys Ala Leu Ala Glu Glu Ala Lys
        115                 120                 125

Ala Arg Tyr Glu Lys Ala Val Ile Lys Val Ile Asp Ile Asp Asp Tyr
    130                 135                 140

Ala Ala Asp Asp Glu Glu Tyr Glu Glu Lys Phe Arg Lys Glu Thr Leu
145                 150                 155                 160

Ala Phe Phe Ile Leu Ala Thr Tyr Gly Asp Gly Glu Pro Thr Asp Asn
                165                 170                 175

Ala Ala Arg Phe Tyr Lys Trp Phe Val Glu Gly Asn Asp Arg Gly Asp
            180                 185                 190

Trp Leu Lys Asn Leu Gln Tyr Gly Val Phe Gly Leu Gly Asn Arg Gln
        195                 200                 205

Tyr Glu His Phe Asn Lys Ile Ala Lys Val Val Asp Glu Lys Val Ala
    210                 215                 220

Glu Gln Gly Gly Lys Arg Ile Val Pro Leu Val Leu Gly Asp Asp Asp
225                 230                 235                 240

Gln Cys Ile Glu Asp Asp Phe Ala Ala Trp Arg Glu Asn Val Trp Pro
                245                 250                 255

Glu Leu Asp Asn Leu Leu Arg Asp Glu Asp Asp Thr Thr Val Ser Thr
            260                 265                 270

Thr Tyr Thr Ala Ala Ile Pro Glu Tyr Arg Val Val Phe Pro Asp Lys
        275                 280                 285

Ser Asp Ser Leu Ile Ser Glu Ala Asn Gly His Ala Asn Gly Tyr Ala
```

-continued

```
    290                 295                 300

Asn Gly Asn Thr Val Tyr Asp Ala Gln His Pro Cys Arg Ser Asn Val
305                 310                 315                 320

Ala Val Arg Lys Glu Leu His Thr Pro Ala Ser Asp Arg Ser Cys Thr
                325                 330                 335

His Leu Asp Phe Asp Ile Ala Gly Thr Gly Leu Ser Tyr Gly Thr Gly
            340                 345                 350

Asp His Val Gly Val Tyr Cys Asp Asn Leu Ser Glu Thr Val Glu Glu
        355                 360                 365

Ala Glu Arg Leu Leu Asn Leu Pro Pro Glu Thr Tyr Phe Ser Leu His
    370                 375                 380

Ala Asp Lys Glu Asp Gly Thr Pro Leu Ala Gly Ser Ser Leu Pro Pro
385                 390                 395                 400

Pro Phe Pro Pro Cys Thr Leu Arg Thr Ala Leu Thr Arg Tyr Ala Asp
                405                 410                 415

Leu Leu Asn Thr Pro Lys Lys Ser Ala Leu Leu Ala Leu Ala Ala Tyr
            420                 425                 430

Ala Ser Asp Pro Asn Glu Ala Asp Arg Leu Lys Tyr Leu Ala Ser Pro
        435                 440                 445

Ala Gly Lys Asp Glu Tyr Ala Gln Ser Leu Val Ala Asn Gln Arg Ser
    450                 455                 460

Leu Leu Glu Val Met Ala Glu Phe Pro Ser Ala Lys Pro Pro Leu Gly
465                 470                 475                 480

Val Phe Phe Ala Ala Ile Ala Pro Arg Leu Gln Pro Arg Phe Tyr Ser
                485                 490                 495

Ile Ser Ser Ser Pro Arg Met Ala Pro Ser Arg Ile His Val Thr Cys
            500                 505                 510

Ala Leu Val Tyr Glu Lys Thr Pro Gly Gly Arg Ile His Lys Gly Val
        515                 520                 525

Cys Ser Thr Trp Met Lys Asn Ala Ile Pro Leu Glu Glu Ser Arg Asp
    530                 535                 540

Cys Ser Trp Ala Pro Ile Phe Val Arg Gln Ser Asn Phe Lys Leu Pro
545                 550                 555                 560

Ala Asp Pro Lys Val Pro Val Ile Met Ile Gly Pro Gly Thr Gly Leu
                565                 570                 575

Ala Pro Phe Arg Gly Phe Leu Gln Glu Arg Leu Ala Leu Lys Glu Glu
            580                 585                 590

Gly Ala Glu Leu Gly Thr Ala Val Phe Phe Phe Gly Cys Arg Asn Arg
        595                 600                 605

Lys Met Asp Tyr Ile Tyr Glu Asp Glu Leu Asn His Phe Leu Glu Ile
    610                 615                 620

Gly Ala Leu Ser Glu Leu Leu Val Ala Phe Ser Arg Glu Gly Pro Thr
625                 630                 635                 640

Lys Gln Tyr Val Gln His Lys Met Ala Glu Lys Ala Ser Asp Ile Trp
                645                 650                 655

Arg Met Ile Ser Asp Gly Ala Tyr Val Tyr Val Cys Gly Asp Ala Lys
            660                 665                 670

Gly Met Ala Arg Asp Val His Arg Thr Leu His Thr Ile Ala Gln Glu
        675                 680                 685

Gln Gly Ser Met Asp Ser Thr Gln Ala Glu Gly Phe Val Lys Asn Leu
    690                 695                 700

Gln Met Thr Gly Arg Tyr Leu Arg Asp Val Trp
705                 710                 715
```

<210> SEQ ID NO 24
<211> LENGTH: 2148
<212> TYPE: DNA
<213> ORGANISM: artificial
<220> FEATURE:
<223> OTHER INFORMATION: coding sequence for SEQ ID NO: 23

<400> SEQUENCE: 24
atgtccgatt cttcttctga aaagttgtct ccattcgaat tgatgtctgc tatcttgaag 60
ggtgctaagt tggatggttc taactcttct gattctggtg ttgctgtttc tccagctgtt 120
atggctatgt tgttggaaaa caaggaattg gttatgattt tgactacttc tgttgctgtt 180
ttgatcggtt gtgtcgttgt tttgatctgg agaagatctt ccggttctgg taagaaggtc 240
gttgaaccac caaagttgat cgttccaaag tctgttgttg aaccagaaga aattgatgaa 300
ggtaagaaga agttcaccat cttcttcggt actcaaactg gtactgctga aggtttcgct 360
aaggctttgg ctgaagaagc caaggctaga tacgaaaagg ctgttatcaa ggttattgat 420
atcgatgatt acgctgctga tgatgaagaa tacgaagaaa agttcagaaa ggaaaccttg 480
gctttcttca tcttggccac ttacggtgat ggtgaaccaa ccgacaacgc tgctagattc 540
tacaagtggt tcgttgaagg taacgataga ggtgactggt tgaagaactt gcaatacggt 600
gttttcggtt tgggtaacag acaatacgaa cacttcaaca agattgctaa ggttgttgat 660
gaaaaggttg ctgaacaagg tggtaagaga attgttccat tggttttggg tgacgatgac 720
caatgtattg aagatgactt cgctgcttgg agagaaaacg tttggccaga attggataac 780
ttgttgagag atgaagatga tactactgtt tctactacct acactgctgc tattccagaa 840
tacagagttg ttttcccaga caagtctgat tctttgattt ctgaagctaa cggtcacgcc 900
aacggttacg ctaacggtaa caccgtttac gatgcccaac acccatgtag atctaacgtt 960
gctgttagaa aggaattgca cactccagct tctgatagat cttgtaccca cttggatttc 1020
gacattgctg gtactggttt gtcttacggt actggtgatc acgttggtgt ttactgtgat 1080
aacttgtctg aaaccgttga agaagctgaa agattgttga acttgccacc agaaacttac 1140
ttctctttgc acgctgataa ggaagatggt accccattgg ctggttcttc tttgccacca 1200
ccattcccac catgtacttt gagaaccgcc ttgactagat acgctgattt gttgaacact 1260
ccaaagaagt ctgctttgtt ggctttggct gcttacgctt ctgatccaaa cgaagccgat 1320
agattgaagt acttggcttc tccagccggt aaggatgaat acgctcaatc tttggttgct 1380
aaccaaagat ctttgttgga agtcatggct gaattcccat ctgctaagcc accattgggt 1440
gttttcttcg ctgctattgc tccaagattg caaccaagat tctactctat ctcttcttct 1500
ccaagaatgg ctccatctag aattcacgtc acttgtgctt tggtttacga aaagactcca 1560
ggtggtagaa ttcacaaggg tgtttgttct acttggatga agaacgccat tccattggaa 1620
gaatctagag actgttcttg ggctccaatc ttcgtcagac aatctaactt caagttgcca 1680
gccgatccaa aggttccagt tatcatgatc ggtccaggta ctggtttggc tccattcaga 1740
ggtttcttgc aagaaagatt ggctttgaag gaagaaggtg ctgaattggg tactgctgtt 1800
ttcttcttcg gttgtagaaa cagaaagatg gattacatct acgaagatga attgaaccac 1860
ttcttggaaa ttggtgcttt gtccgaattg ttggttgctt tctctagaga aggtccaact 1920
aagcaatacg ttcaacacaa gatggctgaa aaggcttctg atatttggag aatgatttct 1980
gatggtgctt acgtttacgt ctgtggtgat gccaagggta tggccagaga tgtccacaga 2040
actttgcaca ccattgctca agaacaaggt tctatggatt ctactcaagc tgaaggtttc 2100
gttaagaact tgcaaatgac cggtagatac ttgagagatg tctggtaa 2148

<210> SEQ ID NO 25
<211> LENGTH: 692
<212> TYPE: PRT
<213> ORGANISM: Saccharomyces cerevisiae

<400> SEQUENCE: 25

Met Ser Pro Phe Gly Ile Asp Asn Thr Asp Phe Thr Val Leu Ala Gly
1 5 10 15

Leu Val Leu Ala Val Leu Leu Tyr Val Lys Arg Asn Ser Ile Lys Glu
20 25 30

Leu Leu Met Ser Asp Asp Gly Asp Ile Thr Ala Val Ser Ser Gly Asn
35 40 45

Arg Asp Ile Ala Gln Val Val Thr Glu Asn Asn Lys Asn Tyr Leu Val
50 55 60

Leu Tyr Ala Ser Gln Thr Gly Thr Ala Glu Asp Tyr Ala Lys Lys Phe
65 70 75 80

Ser Lys Glu Leu Val Ala Lys Phe Asn Leu Asn Val Met Cys Ala Asp
85 90 95

Val Glu Asn Tyr Asp Phe Glu Ser Leu Asn Asp Val Pro Val Ile Val
100 105 110

Ser Ile Phe Ile Ser Thr Tyr Gly Glu Gly Asp Phe Pro Asp Gly Ala
115 120 125

Val Asn Phe Glu Asp Phe Ile Cys Asn Ala Glu Ala Gly Ala Leu Ser
130 135 140

Asn Leu Arg Tyr Asn Met Phe Gly Leu Gly Asn Ser Thr Tyr Glu Phe
145 150 155 160

Phe Asn Gly Ala Ala Lys Lys Ala Glu Lys His Leu Ser Ala Ala Gly
165 170 175

Ala Ile Arg Leu Gly Lys Leu Gly Glu Ala Asp Asp Gly Ala Gly Thr
180 185 190

Thr Asp Glu Asp Tyr Met Ala Trp Lys Asp Ser Ile Leu Glu Val Leu
195 200 205

Lys Asp Glu Leu His Leu Asp Glu Gln Glu Ala Lys Phe Thr Ser Gln
210 215 220

Phe Gln Tyr Thr Val Leu Asn Glu Ile Thr Asp Ser Met Ser Leu Gly
225 230 235 240

Glu Pro Ser Ala His Tyr Leu Pro Ser His Gln Leu Asn Arg Asn Ala
245 250 255

Asp Gly Ile Gln Leu Gly Pro Phe Asp Leu Ser Gln Pro Tyr Ile Ala
260 265 270

Pro Ile Val Lys Ser Arg Glu Leu Phe Ser Ser Asn Asp Arg Asn Cys
275 280 285

Ile His Ser Glu Phe Asp Leu Ser Gly Ser Asn Ile Lys Tyr Ser Thr
290 295 300

Gly Asp His Leu Ala Val Trp Pro Ser Asn Pro Leu Glu Lys Val Glu
305 310 315 320

Gln Phe Leu Ser Ile Phe Asn Leu Asp Pro Glu Thr Ile Phe Asp Leu
325 330 335

Lys Pro Leu Asp Pro Thr Val Lys Val Pro Phe Pro Thr Pro Thr Thr
340 345 350

Ile Gly Ala Ala Ile Lys His Tyr Leu Glu Ile Thr Gly Pro Val Ser

```
        355                 360                 365

Arg Gln Leu Phe Ser Ser Leu Ile Gln Phe Ala Pro Asn Ala Asp Val
    370                 375                 380

Lys Glu Lys Leu Thr Leu Leu Ser Lys Asp Lys Asp Gln Phe Ala Val
385                 390                 395                 400

Glu Ile Thr Ser Lys Tyr Phe Asn Ile Ala Asp Ala Leu Lys Tyr Leu
                405                 410                 415

Ser Asp Gly Ala Lys Trp Asp Thr Val Pro Met Gln Phe Leu Val Glu
            420                 425                 430

Ser Val Pro Gln Met Thr Pro Arg Tyr Tyr Ser Ile Ser Ser Ser Ser
        435                 440                 445

Leu Ser Glu Lys Gln Thr Val His Val Thr Ser Ile Val Glu Asn Phe
    450                 455                 460

Pro Asn Pro Glu Leu Pro Asp Ala Pro Pro Val Val Gly Val Thr Thr
465                 470                 475                 480

Asn Leu Leu Arg Asn Ile Gln Leu Ala Gln Asn Asn Val Asn Ile Ala
                485                 490                 495

Glu Thr Asn Leu Pro Val His Tyr Asp Leu Asn Gly Pro Arg Lys Leu
            500                 505                 510

Phe Ala Asn Tyr Lys Leu Pro Val His Val Arg Arg Ser Asn Phe Arg
        515                 520                 525

Leu Pro Ser Asn Pro Ser Thr Pro Val Ile Met Ile Gly Pro Gly Thr
    530                 535                 540

Gly Val Ala Pro Phe Arg Gly Phe Ile Arg Glu Arg Val Ala Phe Leu
545                 550                 555                 560

Glu Ser Gln Lys Lys Gly Gly Asn Asn Val Ser Leu Gly Lys His Ile
                565                 570                 575

Leu Phe Tyr Gly Ser Arg Asn Thr Asp Asp Phe Leu Tyr Gln Asp Glu
            580                 585                 590

Trp Pro Glu Tyr Ala Lys Lys Leu Asp Gly Ser Phe Glu Met Val Val
        595                 600                 605

Ala His Ser Arg Leu Pro Asn Thr Lys Lys Val Tyr Val Gln Asp Lys
    610                 615                 620

Leu Lys Asp Tyr Glu Asp Gln Val Phe Glu Met Ile Asn Asn Gly Ala
625                 630                 635                 640

Phe Ile Tyr Val Cys Gly Asp Ala Lys Gly Met Ala Lys Gly Val Ser
                645                 650                 655

Thr Ala Leu Val Gly Ile Leu Ser Arg Gly Lys Ser Ile Thr Thr Asp
            660                 665                 670

Glu Ala Thr Glu Leu Ile Lys Met Leu Lys Thr Ser Gly Arg Tyr Gln
        675                 680                 685

Glu Asp Val Trp
    690
```

<210> SEQ ID NO 26
<211> LENGTH: 2079
<212> TYPE: DNA
<213> ORGANISM: artificial
<220> FEATURE:
<223> OTHER INFORMATION: coding sequence for SEQ ID NO: 25

<400> SEQUENCE: 26

```
atgtccccgt ttggaataga caacaccgac ttcactgtcc tggcggggct agtgcttgcc      60

gtgctactgt acgtaaagag aaactccatc aaggaactgc tgatgtccga tgacggagat     120
```

atcacagctg tcagctcggg caacagagac attgctcagg tggtgaccga aaacaacaag 180
aactacttgg tgttgtatgc gtcgcagact gggactgccg aggattacgc caaaaagttt 240
tccaaggagc tggtggccaa gttcaaccta aacgtgatgt gcgcagatgt tgagaactac 300
gactttgagt cgctaaacga tgtgcccgtc atagtctcga tttttatctc tacatatggt 360
gaaggagact tccccgacgg ggcggtcaac tttgaggact ttatttgtaa tgcggaagcg 420
ggtgcactat cgaacctgag gtataaatatg tttggtctgg gaaattctac ttatgaattc 480
tttaatggtg ccgccaagaa ggccgagaag catctctccg ccgcgggcgc tatcagacta 540
ggcaagctcg gtgaagctga tgatggtgca ggaactacag acgaagatta catggcctgg 600
aaggactcca tcctggaggt tttgaaagac gaactgcatt tggacgaaca ggaagccaag 660
ttcacctctc aattccagta cactgtgttg aacgaaatca ctgactccat gtcgcttggt 720
gaaccctctg ctcactattt gccctcgcat cagttgaacc gcaacgcaga cggcatccaa 780
ttgggtccct tcgatttgtc tcaaccgtat attgcaccca tcgtgaaatc tcgcgaactg 840
ttctcttcca atgaccgtaa ttgcatccac tctgaatttg acttgtccgg ctctaacatc 900
aagtactcca ctggtgacca tcttgctgtt tggccttcca acccattgga aaaggtcgaa 960
cagttcttat ccatattcaa cctggaccct gaaaccattt ttgacttgaa gcccctggat 1020
cccaccgtca aagtgccctt cccaacgcca actactattg gcgctgctat taaacactat 1080
ttggaaatta caggacctgt ctccagacaa ttgttttcat ctttgattca gttcgccccc 1140
aacgctgacg tcaaggaaaa attgactctg ctttcgaaag acaaggacca attcgccgtc 1200
gagataacct ccaaatattt caacatcgca gatgctctga aatatttgtc tgatggcgcc 1260
aaatgggaca ccgtacccat gcaattcttg gtcgaatcag ttccccaaat gactcctcgt 1320
tactactcta tctcttcctc ttctctgtct gaaaagcaaa ccgtccatgt cacctccatt 1380
gtggaaaact ttcctaaccc agaattgcct gatgctcctc cagttgttgg tgttacgact 1440
aacttgttaa gaaacattca attggctcaa aacaatgtta acattgccga aactaaccta 1500
cctgttcact acgatttaaa tggcccacgt aaactttttcg ccaattacaa attgcccgtc 1560
cacgttcgtc gttctaactt cagattgcct tccaaccctt ccaccccagt tatcatgatc 1620
ggtccaggta ccggtgttgc cccattccgt gggtttatca gagagcgtgt cgcgttcctc 1680
gaatcacaaa agaagggcgg taacaacgtt tcgctaggta agcatatact gttttatgga 1740
tcccgtaaca ctgatgattt cttgtaccag gacgaatggc cagaatacgc caaaaaattg 1800
gatggttcgt tcgaaatggt cgtggcccat tccaggttgc caaacaccaa aaaagtttat 1860
gttcaagata aattaaagga ttacgaggac caagtatttg aaatgattaa caacggtgca 1920
tttatctacg tctgtggtga tgcaaagggt atggccaagg gtgtgtcaac cgcattggtt 1980
ggcatcttat cccgtggtaa atccattacc actgatgaag caacagagct aatcaagatg 2040
ctcaagactt caggtagata ccaagaagat gtctggtaa 2079

<210> SEQ ID NO 27
<211> LENGTH: 658
<212> TYPE: PRT
<213> ORGANISM: artificial
<220> FEATURE:
<223> OTHER INFORMATION: chimeric cytochrome P450 reductase

<400> SEQUENCE: 27

Met Ser Pro Phe Gly Ile Asp Asn Thr Asp Phe Thr Val Leu Ala Gly
1 5 10 15

-continued

```
Leu Val Leu Ala Val Leu Leu Tyr Val Lys Arg Asn Ser Ile Lys Glu
            20                  25                  30

Leu Leu Met Ser Asp Asp Gly Asp Ile Thr Ala Val Ser Ser Gly Asn
        35                  40                  45

Arg Asp Ile Ala Gln Val Val Thr Glu Asn Asn Lys Asn Tyr Leu Val
    50                  55                  60

Leu Tyr Ala Ser Gln Thr Gly Thr Ala Glu Asp Tyr Ala Lys Lys Phe
65                  70                  75                  80

Ser Lys Glu Leu Val Ala Lys Phe Asn Leu Asn Val Met Cys Ala Asp
                85                  90                  95

Val Glu Asn Tyr Asp Phe Glu Ser Leu Asn Asp Val Pro Val Ile Val
            100                 105                 110

Ser Ile Phe Ile Ser Thr Tyr Gly Glu Gly Asp Phe Pro Asp Gly Ala
        115                 120                 125

Val Asn Phe Glu Asp Phe Ile Cys Asn Ala Glu Ala Gly Ala Leu Ser
    130                 135                 140

Asn Leu Arg Tyr Asn Met Phe Gly Leu Gly Asn Ser Thr Tyr Glu Phe
145                 150                 155                 160

Phe Asn Gly Ala Ala Lys Lys Ala Glu Lys His Leu Ser Ala Ala Gly
                165                 170                 175

Ala Ile Arg Leu Gly Lys Leu Gly Glu Ala Asp Asp Gly Ala Gly Thr
            180                 185                 190

Thr Asp Glu Asp Tyr Met Ala Trp Lys Asp Ser Ile Leu Glu Val Leu
        195                 200                 205

Lys Asp Glu Leu Gly Val Glu Ala Thr Gly Glu Glu Ser Ser Ile Arg
    210                 215                 220

Gln Tyr Glu Leu Val Val His Thr Asp Ile Asp Ala Ala Lys Val Tyr
225                 230                 235                 240

Met Gly Glu Met Gly Arg Leu Lys Ser Tyr Glu Asn Gln Lys Pro Pro
                245                 250                 255

Phe Asp Ala Lys Asn Pro Phe Leu Ala Ala Val Thr Thr Asn Arg Lys
            260                 265                 270

Leu Asn Gln Gly Thr Glu Arg His Leu Met His Leu Glu Leu Asp Ile
        275                 280                 285

Ser Asp Ser Lys Ile Arg Tyr Glu Ser Gly Asp His Val Ala Val Tyr
    290                 295                 300

Pro Ala Asn Asp Ser Ala Leu Val Asn Gln Leu Gly Lys Ile Leu Gly
305                 310                 315                 320

Ala Asp Leu Asp Val Val Met Ser Leu Asn Asn Leu Asp Glu Glu Ser
                325                 330                 335

Asn Lys Lys His Pro Phe Pro Cys Pro Thr Ser Tyr Arg Thr Ala Leu
            340                 345                 350

Thr Tyr Tyr Leu Asp Ile Thr Asn Pro Pro Arg Thr Asn Val Leu Tyr
        355                 360                 365

Glu Leu Ala Gln Tyr Ala Ser Glu Pro Ser Glu Gln Glu Leu Leu Arg
    370                 375                 380

Lys Met Ala Ser Ser Ser Gly Glu Gly Lys Glu Leu Tyr Leu Ser Trp
385                 390                 395                 400

Val Val Glu Ala Arg Arg His Ile Leu Ala Ile Leu Gln Asp Cys Pro
                405                 410                 415

Ser Leu Arg Pro Pro Ile Asp His Leu Cys Glu Leu Leu Pro Arg Leu
            420                 425                 430

Gln Ala Arg Tyr Tyr Ser Ile Ala Ser Ser Ser Lys Val His Pro Asn
```

-continued

```
        435                 440                 445

Ser Val His Ile Cys Ala Val Val Val Glu Tyr Glu Thr Lys Ala Gly
    450                 455                 460

Arg Ile Asn Lys Gly Val Ala Thr Asn Trp Leu Arg Ala Lys Glu Pro
465                 470                 475                 480

Ala Gly Glu Asn Gly Gly Arg Ala Leu Val Pro Met Phe Val Arg Lys
                485                 490                 495

Ser Gln Phe Arg Leu Pro Phe Lys Ala Thr Thr Pro Val Ile Met Val
            500                 505                 510

Gly Pro Gly Thr Gly Val Ala Pro Phe Ile Gly Phe Ile Gln Glu Arg
        515                 520                 525

Ala Trp Leu Arg Gln Gln Gly Lys Glu Val Gly Glu Thr Leu Leu Tyr
    530                 535                 540

Tyr Gly Cys Arg Arg Ser Asp Glu Asp Tyr Leu Tyr Arg Glu Glu Leu
545                 550                 555                 560

Ala Gln Phe His Arg Asp Gly Ala Leu Thr Gln Leu Asn Val Ala Phe
                565                 570                 575

Ser Arg Glu Gln Ser His Lys Val Tyr Val Gln His Leu Leu Lys Gln
            580                 585                 590

Asp Arg Glu His Leu Trp Lys Leu Ile Glu Gly Gly Ala His Ile Tyr
        595                 600                 605

Val Cys Gly Asp Ala Arg Asn Met Ala Arg Asp Val Gln Asn Thr Phe
    610                 615                 620

Tyr Asp Ile Val Ala Glu Leu Gly Ala Met Glu His Ala Gln Ala Val
625                 630                 635                 640

Asp Tyr Ile Lys Lys Leu Met Thr Lys Gly Arg Tyr Ser Leu Asp Val
                645                 650                 655

Trp Ser
```

<210> SEQ ID NO 28
<211> LENGTH: 1977
<212> TYPE: DNA
<213> ORGANISM: artificial
<220> FEATURE:
<223> OTHER INFORMATION: coding sequence for SEQ ID NO: 27

<400> SEQUENCE: 28

```
atgtccccat tcggtatcga caacaccgac ttcactgtct tggctggttt ggttttggcc     60

gttttgttgt acgttaagag aaactccatc aaggaattgt tgatgtccga tgacggtgat    120

atcactgctg tctcttctgg taacagagac attgctcaag ttgttaccga aaacaacaag    180

aactacttgg ttttgtacgc ttctcaaact ggtactgccg aagattacgc caagaagttc    240

tccaaggaat tggttgccaa gttcaacttg aacgttatgt gtgctgatgt tgaaaactac    300

gacttcgaat ctttgaacga tgttccagtc atcgtatcta ttttcatctc tacttacggt    360

gaaggtgact tcccagacgg tgctgtcaac ttcgaagatt tcatttgtaa cgctgaagct    420

ggtgctttgt ctaacttgag atacaacatg ttcggtttgg gtaactctac ttacgaattc    480

ttcaacggtg ccgccaagaa ggccgaaaag cacttgtccg ccgctggtgc tatcagattg    540

ggtaagttgg gtgaagctga tgatggtgct ggtactactg acgaagatta catggcctgg    600

aaggactcca tcttggaagt tttgaaggac gaattgggtg ttgaagccac tggtgaagaa    660

tcctctatta gacaatacga attggttgtc cacaccgaca tcgatgctgc caaggtttac    720

atgggtgaaa tgggtagatt gaagtcttac gaaaaccaaa agccaccatt cgatgccaag    780
```

-continued

```
aacccattct tggctgctgt caccaccaac agaaagttga accaaggtac cgaaagacac    840

ttgatgcact tggaattgga catctctgac tccaagatca gatacgaatc tggtgaccac    900

gttgctgttt acccagccaa cgactctgct ttggtcaacc aattgggtaa gatcttgggt    960

gccgacttgg acgtcgtcat gtccttgaac aacttggatg aagaatccaa caagaagcac   1020

ccattcccat gtccaacttc ctacagaact gccttgacct actacttgga catcaccaac   1080

ccaccaagaa ccaacgtttt gtacgaattg gctcaatacg cctctgaacc atctgaacaa   1140

gaattgttga gaaagatggc ctcctcctcc ggtgaaggta aggaattgta cttgtcttgg   1200

gttgttgaag ccaggagaca catcttggcc atcttgcaag actgtccatc cttaagacca   1260

ccaatcgacc acttgtgtga attgttgcca agattgcaag ccagatacta ctccatcgcc   1320

tcttcctcca aggtccaccc aaactctgtt cacatctgtg ctgttgttgt tgaatacgaa   1380

accaaggctg gtagaatcaa caagggtgtt gccaccaact ggttgagagc caaggaacca   1440

gccggtgaaa acggtggtag agctttggtt ccaatgttcg ttagaaagtc ccaattcaga   1500

ttgccattca aggccaccac tccagtcatc atggttggtc caggtaccgg tgttgctcca   1560

ttcatcggtt tcatccaaga aagagcctgg ttgagacaac aaggtaagga agttggtgaa   1620

actttgttgt actacggttg tagaagatct gatgaagatt acttgtacag agaagaattg   1680

gctcaattcc acagagatgg tgctttgacc caattgaacg ttgccttctc cagagaacaa   1740

tcccacaagg tctacgtcca acacttgttg aagcaagaca gagaacactt gtggaagttg   1800

atcgaaggtg gtgcccacat ctacgtctgt ggtgatgcta gaaacatggc cagagatgtt   1860

caaaacacct tctacgacat cgttgctgaa ttgggtgcca tggaacacgc tcaagctgtt   1920

gactacatca agaagttgat gaccaagggt agatactcct tggacgtttg gtcttaa      1977
```

<210> SEQ ID NO 29
<211> LENGTH: 693
<212> TYPE: PRT
<213> ORGANISM: Arabidopsis thaliana

<400> SEQUENCE: 29

```
Met Ser Thr Ser Ala Leu Tyr Ala Ser Asp Leu Phe Lys Gln Leu Lys
1               5                   10                  15

Ser Ile Met Gly Thr Asp Ser Leu Ser Asp Asp Val Val Leu Val Ile
            20                  25                  30

Ala Thr Thr Ser Leu Ala Leu Val Ala Gly Phe Val Val Leu Leu Trp
        35                  40                  45

Lys Lys Thr Thr Ala Asp Arg Ser Gly Glu Leu Lys Pro Leu Met Ile
    50                  55                  60

Pro Lys Ser Leu Met Ala Lys Asp Glu Asp Asp Asp Leu Asp Leu Gly
65                  70                  75                  80

Ser Gly Lys Thr Arg Val Ser Ile Phe Phe Gly Thr Gln Thr Gly Thr
                85                  90                  95

Ala Glu Gly Phe Ala Lys Ala Leu Ser Glu Glu Ile Lys Ala Arg Tyr
            100                 105                 110

Glu Lys Ala Ala Val Lys Val Ile Asp Leu Asp Asp Tyr Ala Ala Asp
        115                 120                 125

Asp Asp Gln Tyr Glu Glu Lys Leu Lys Lys Glu Thr Leu Ala Phe Phe
    130                 135                 140

Cys Val Ala Thr Tyr Gly Asp Gly Glu Pro Thr Asp Asn Ala Ala Arg
145                 150                 155                 160

Phe Tyr Lys Trp Phe Thr Glu Glu Asn Glu Arg Asp Ile Lys Leu Gln
```

```
                165                 170                 175

Gln Leu Ala Tyr Gly Val Phe Ala Leu Gly Asn Arg Gln Tyr Glu His
            180                 185                 190

Phe Asn Lys Ile Gly Ile Val Leu Asp Glu Glu Leu Cys Lys Lys Gly
        195                 200                 205

Ala Lys Arg Leu Ile Glu Val Gly Leu Gly Asp Asp Asp Gln Ser Ile
    210                 215                 220

Glu Asp Asp Phe Asn Ala Trp Lys Glu Ser Leu Trp Ser Glu Leu Asp
225                 230                 235                 240

Lys Leu Leu Lys Asp Glu Asp Asp Lys Ser Val Ala Thr Pro Tyr Thr
                245                 250                 255

Ala Val Ile Pro Glu Tyr Arg Val Val Thr His Asp Pro Arg Phe Thr
            260                 265                 270

Thr Gln Lys Ser Met Glu Ser Asn Val Ala Asn Gly Asn Thr Thr Ile
        275                 280                 285

Asp Ile His His Pro Cys Arg Val Asp Val Ala Val Gln Lys Glu Leu
    290                 295                 300

His Thr His Glu Ser Asp Arg Ser Cys Ile His Leu Glu Phe Asp Ile
305                 310                 315                 320

Ser Arg Thr Gly Ile Thr Tyr Glu Thr Gly Asp His Val Gly Val Tyr
                325                 330                 335

Ala Glu Asn His Val Glu Ile Val Glu Glu Ala Gly Lys Leu Leu Gly
            340                 345                 350

His Ser Leu Asp Leu Val Phe Ser Ile His Ala Asp Lys Glu Asp Gly
        355                 360                 365

Ser Pro Leu Glu Ser Ala Val Pro Pro Pro Phe Pro Gly Pro Cys Thr
    370                 375                 380

Leu Gly Thr Gly Leu Ala Arg Tyr Ala Asp Leu Leu Asn Pro Pro Arg
385                 390                 395                 400

Lys Ser Ala Leu Val Ala Leu Ala Ala Tyr Ala Thr Glu Pro Ser Glu
                405                 410                 415

Ala Glu Lys Leu Lys His Leu Thr Ser Pro Asp Gly Lys Asp Glu Tyr
            420                 425                 430

Ser Gln Trp Ile Val Ala Ser Gln Arg Ser Leu Leu Glu Val Met Ala
        435                 440                 445

Ala Phe Pro Ser Ala Lys Pro Pro Leu Gly Val Phe Phe Ala Ala Ile
    450                 455                 460

Ala Pro Arg Leu Gln Pro Arg Tyr Tyr Ser Ile Ser Ser Ser Pro Arg
465                 470                 475                 480

Leu Ala Pro Ser Arg Val His Val Thr Ser Ala Leu Val Tyr Gly Pro
                485                 490                 495

Thr Pro Thr Gly Arg Ile His Lys Gly Val Cys Ser Thr Trp Met Lys
            500                 505                 510

Asn Ala Val Pro Ala Glu Lys Ser His Glu Cys Ser Gly Ala Pro Ile
        515                 520                 525

Phe Ile Arg Ala Ser Asn Phe Lys Leu Pro Ser Asn Pro Ser Thr Pro
    530                 535                 540

Ile Val Met Val Gly Pro Gly Thr Gly Leu Ala Pro Phe Arg Gly Phe
545                 550                 555                 560

Leu Gln Glu Arg Met Ala Leu Lys Glu Asp Gly Glu Glu Leu Gly Ser
                565                 570                 575

Ser Leu Leu Phe Phe Gly Cys Arg Asn Arg Gln Met Asp Phe Ile Tyr
            580                 585                 590
```

```
Glu Asp Glu Leu Asn Asn Phe Val Asp Gln Gly Val Ile Ser Glu Leu
        595                 600                 605

Ile Met Ala Phe Ser Arg Glu Gly Ala Gln Lys Glu Tyr Val Gln His
    610                 615                 620

Lys Met Met Glu Lys Ala Ala Gln Val Trp Asp Leu Ile Lys Glu Glu
625                 630                 635                 640

Gly Tyr Leu Tyr Val Cys Gly Asp Ala Lys Gly Met Ala Arg Asp Val
                645                 650                 655

His Arg Thr Leu His Thr Ile Val Gln Glu Gln Glu Gly Val Ser Ser
            660                 665                 670

Ser Glu Ala Glu Ala Ile Val Lys Lys Leu Gln Thr Glu Gly Arg Tyr
        675                 680                 685

Leu Arg Asp Val Trp
    690


<210> SEQ ID NO 30
<211> LENGTH: 2082
<212> TYPE: DNA
<213> ORGANISM: artificial
<220> FEATURE:
<223> OTHER INFORMATION: coding sequence for SEQ ID NO: 29

<400> SEQUENCE: 30

atgtccactt ctgctttgta cgcttccgat ttgttcaagc aattgaagtc tattatgggt     60

actgattctt tgtccgacga tgttgttttg gttattgcta ctacttcttt ggctttggtt    120

gctggtttcg ttgttttgtt gtggaagaaa actactgctg atagatctgg tgaattgaag    180

ccattgatga tcccaaagtc tttgatggct aaggacgaag atgatgattt ggatttgggt    240

tccggtaaga ctagagtctc tatcttcttc ggtactcaaa ctggtactgc tgaaggtttc    300

gctaaggctt tgtccgaaga aatcaaggct agatacgaaa aggctgctgt caaggtcatt    360

gacttggatg actacgctgc cgatgatgac caatacgaag aaaagttgaa gaaggaaact    420

ttggctttct tctgtgttgc tacttacggt gatggtgaac caactgacaa cgctgccaga    480

ttctacaagt ggttcactga agaaaacgaa agagatatca agttgcaaca attggcttac    540

ggtgttttcg ctttgggtaa cagacaatac gaacacttca acaagatcgg tatcgttttg    600

gatgaagaat tgtgtaagaa gggtgctaag agattgattg aagtcggttt gggtgatgat    660

gatcaatcta ttgaagatga tttcaacgcc tggaaggaat ctttgtggtc tgaattggac    720

aagttgttga aggacgaaga tgataagtct gttgctactc catacactgc tgttattcca    780

gaatacagag ttgttactca cgatccaaga ttcactactc aaaagtctat ggaatctaac    840

gttgccaacg gtaacactac tattgacatt caccacccat gtagagttga tgttgctgtt    900

caaaaggaat tgcacactca cgaatctgat agatcttgta ttcacttgga attcgacatc    960

tccagaactg gtattactta cgaaactggt gaccacgttg gtgtttacgc tgaaaaccac   1020

gttgaaatcg ttgaagaagc tggtaagttg ttgggtcact ctttggattt ggtttttctcc   1080

atccacgctg acaaggaaga tggttcccca ttggaatctg ctgttccacc accattccca   1140

ggtccatgta ctttgggtac tggtttggct agatacgctg acttgttgaa cccaccaaga   1200

aagtctgctt tggttgcctt ggctgcctac gccactgaac catctgaagc cgaaaagttg   1260

aagcacttga cttctccaga tggtaaggat gaatactctc aatggattgt tgcttctcaa   1320

agatctttgt tggaagttat ggctgctttc ccatctgcta agccaccatt gggtgttttc   1380

ttcgctgcta tcgctccaag attgcaacca agatactact ccatctcttc ctctccaaga   1440
```

```
ttggctccat ctagagttca cgttacttcc gctttggttt acggtccaac tccaactggt   1500

agaatccaca agggtgtttg ttctacttgg atgaagaacg ctgttccagc tgaaaagtct   1560

cacgaatgtt ctggtgcccc aatcttcatt agagcttcta acttcaagtt gccatccaac   1620

ccatctactc caatcgttat ggttggtcca ggtactggtt tggctccatt cagaggtttc   1680

ttgcaagaaa gaatggcttt gaaggaagat ggtgaagaat tgggttcttc tttgttgttc   1740

ttcggttgta gaaacagaca aatggacttc atctacgaag atgaattgaa caacttcgtt   1800

gatcaaggtg ttatctctga attgatcatg gctttctcca gagaaggtgc tcaaaaggaa   1860

tacgttcaac acaagatgat ggaaaaggct gctcaagttt gggatttgat caaggaagaa   1920

ggttacttgt acgtttgtgg tgatgctaag ggtatggcta gagatgtcca cagaactttg   1980

cacaccattg ttcaagaaca agaaggtgtt tcttcttctg aagctgaagc tatcgttaag   2040

aagttgcaaa ccgaaggtag atacttgaga gatgtctggt aa                      2082
```

<210> SEQ ID NO 31
<211> LENGTH: 712
<212> TYPE: PRT
<213> ORGANISM: Arabidopsis thaliana

<400> SEQUENCE: 31

```
Met Ser Ser Ser Ser Ser Ser Ser Thr Ser Met Ile Asp Leu Met Ala
1               5                   10                  15

Ala Ile Ile Lys Gly Glu Pro Val Ile Val Ser Asp Pro Ala Asn Ala
            20                  25                  30

Ser Ala Tyr Glu Ser Val Ala Ala Glu Leu Ser Ser Met Leu Ile Glu
        35                  40                  45

Asn Arg Gln Phe Ala Met Ile Val Thr Thr Ser Ile Ala Val Leu Ile
    50                  55                  60

Gly Cys Ile Val Met Leu Val Trp Arg Arg Ser Gly Ser Gly Asn Ser
65                  70                  75                  80

Lys Arg Val Glu Pro Leu Lys Pro Leu Val Ile Lys Pro Arg Glu Glu
                85                  90                  95

Glu Ile Asp Asp Gly Arg Lys Lys Val Thr Ile Phe Phe Gly Thr Gln
            100                 105                 110

Thr Gly Thr Ala Glu Gly Phe Ala Lys Ala Leu Gly Glu Glu Ala Lys
        115                 120                 125

Ala Arg Tyr Glu Lys Thr Arg Phe Lys Ile Val Asp Leu Asp Asp Tyr
    130                 135                 140

Ala Ala Asp Asp Asp Glu Tyr Glu Glu Lys Leu Lys Lys Glu Asp Val
145                 150                 155                 160

Ala Phe Phe Phe Leu Ala Thr Tyr Gly Asp Gly Glu Pro Thr Asp Asn
                165                 170                 175

Ala Ala Arg Phe Tyr Lys Trp Phe Thr Glu Gly Asn Asp Arg Gly Glu
            180                 185                 190

Trp Leu Lys Asn Leu Lys Tyr Gly Val Phe Gly Leu Gly Asn Arg Gln
        195                 200                 205

Tyr Glu His Phe Asn Lys Val Ala Lys Val Val Asp Asp Ile Leu Val
    210                 215                 220

Glu Gln Gly Ala Gln Arg Leu Val Gln Val Gly Leu Gly Asp Asp Asp
225                 230                 235                 240

Gln Cys Ile Glu Asp Asp Phe Thr Ala Trp Arg Glu Ala Leu Trp Pro
                245                 250                 255
```

-continued

```
Glu Leu Asp Thr Ile Leu Arg Glu Glu Gly Asp Thr Ala Val Ala Thr
            260                 265                 270

Pro Tyr Thr Ala Ala Val Leu Glu Tyr Arg Val Ser Ile His Asp Ser
        275                 280                 285

Glu Asp Ala Lys Phe Asn Asp Ile Asn Met Ala Asn Gly Asn Gly Tyr
    290                 295                 300

Thr Val Phe Asp Ala Gln His Pro Tyr Lys Ala Asn Val Ala Val Lys
305                 310                 315                 320

Arg Glu Leu His Thr Pro Glu Ser Asp Arg Ser Cys Ile His Leu Glu
                325                 330                 335

Phe Asp Ile Ala Gly Ser Gly Leu Thr Tyr Glu Thr Gly Asp His Val
            340                 345                 350

Gly Val Leu Cys Asp Asn Leu Ser Glu Thr Val Asp Glu Ala Leu Arg
        355                 360                 365

Leu Leu Asp Met Ser Pro Asp Thr Tyr Phe Ser Leu His Ala Glu Lys
    370                 375                 380

Glu Asp Gly Thr Pro Ile Ser Ser Ser Leu Pro Pro Pro Phe Pro Pro
385                 390                 395                 400

Cys Asn Leu Arg Thr Ala Leu Thr Arg Tyr Ala Cys Leu Leu Ser Ser
                405                 410                 415

Pro Lys Lys Ser Ala Leu Val Ala Leu Ala Ala His Ala Ser Asp Pro
            420                 425                 430

Thr Glu Ala Glu Arg Leu Lys His Leu Ala Ser Pro Ala Gly Lys Val
        435                 440                 445

Asp Glu Tyr Ser Lys Trp Val Val Glu Ser Gln Arg Ser Leu Leu Glu
    450                 455                 460

Val Met Ala Glu Phe Pro Ser Ala Lys Pro Pro Leu Gly Val Phe Phe
465                 470                 475                 480

Ala Gly Val Ala Pro Arg Leu Gln Pro Arg Phe Tyr Ser Ile Ser Ser
                485                 490                 495

Ser Pro Lys Ile Ala Glu Thr Arg Ile His Val Thr Cys Ala Leu Val
            500                 505                 510

Tyr Glu Lys Met Pro Thr Gly Arg Ile His Lys Gly Val Cys Ser Thr
        515                 520                 525

Trp Met Lys Asn Ala Val Pro Tyr Glu Lys Ser Glu Asn Cys Ser Ser
    530                 535                 540

Ala Pro Ile Phe Val Arg Gln Ser Asn Phe Lys Leu Pro Ser Asp Ser
545                 550                 555                 560

Lys Val Pro Ile Ile Met Ile Gly Pro Gly Thr Gly Leu Ala Pro Phe
                565                 570                 575

Arg Gly Phe Leu Gln Glu Arg Leu Ala Leu Val Glu Ser Gly Val Glu
            580                 585                 590

Leu Gly Pro Ser Val Leu Phe Phe Gly Cys Arg Asn Arg Arg Met Asp
        595                 600                 605

Phe Ile Tyr Glu Glu Glu Leu Gln Arg Phe Val Glu Ser Gly Ala Leu
    610                 615                 620

Ala Glu Leu Ser Val Ala Phe Ser Arg Glu Gly Pro Thr Lys Glu Tyr
625                 630                 635                 640

Val Gln His Lys Met Met Asp Lys Ala Ser Asp Ile Trp Asn Met Ile
                645                 650                 655

Ser Gln Gly Ala Tyr Leu Tyr Val Cys Gly Asp Ala Lys Gly Met Ala
            660                 665                 670

Arg Asp Val His Arg Ser Leu His Thr Ile Ala Gln Glu Gln Gly Ser
```

```
        675                 680                 685

Met Asp Ser Thr Lys Ala Glu Gly Phe Val Lys Asn Leu Gln Thr Ser
    690                 695                 700

Gly Arg Tyr Leu Arg Asp Val Trp
705                 710
```

<210> SEQ ID NO 32
<211> LENGTH: 2139
<212> TYPE: DNA
<213> ORGANISM: artificial
<220> FEATURE:
<223> OTHER INFORMATION: coding sequence for SEQ ID NO: 31

<400> SEQUENCE: 32

```
atgtcctctt cttcttcttc ttctacctcc atgatcgatt tgatggctgc tatcatcaag     60
ggtgaaccag ttattgtctc cgacccagct aacgcctccg cttacgaatc cgttgctgct    120
gaattgtcct ctatgttgat cgaaaacaga caattcgcca tgattgttac cacttccatt    180
gctgttttga ttggttgtat cgttatgttg gtttggagaa gatccggttc tggtaactct    240
aagagagtcg aaccattgaa gccattggtt attaagccaa gagaagaaga aattgatgat    300
ggtagaaaga aggttaccat cttcttcggt actcaaactg gtactgctga aggtttcgct    360
aaggctttgg gtgaagaagc taaggctaga tacgaaaaga ccagattcaa gatcgttgat    420
ttggatgatt acgctgctga tgatgatgaa tacgaagaaa agttgaagaa ggaagatgtt    480
gctttcttct tcttggccac ttacggtgat ggtgaaccaa ccgacaacgc tgctagattc    540
tacaagtggt tcaccgaagg taacgacaga ggtgaatggt tgaagaactt gaagtacggt    600
gttttcggtt tgggtaacag acaatacgaa cacttcaaca aggttgccaa ggttgttgat    660
gacattttgg tcgaacaagg tgctcaaaga ttggttcaag ttggtttggg tgatgatgac    720
caatgtattg aagatgactt caccgcttgg agagaagctt tgtggccaga attggatact    780
atcttgagag aagaaggtga tactgctgtt gccactccat acactgctgc tgttttggaa    840
tacagagttt ctattcacga ctctgaagat gccaagttca acgatatcaa catggctaac    900
ggtaacggtt acactgtttt cgatgctcaa cacccataca aggctaacgt cgctgttaag    960
agagaattgc acactccaga atctgataga tcttgtatcc acttggaatt cgacattgct   1020
ggttctggtt tgacttacga aactggtgat cacgttggtg ttttgtgtga taacttgtct   1080
gaaactgttg atgaagcttt gagattgttg gatatgtctc cagatactta cttctctttg   1140
cacgctgaaa aggaagatgg tactccaatc tcttcttctt tgccaccacc attcccacca   1200
tgtaacttga gaactgcttt gactagatac gcttgtttgt tgtcatctcc aaagaagtct   1260
gctttggttg ctttggctgc tcacgcttct gatccaaccg aagctgaaag attgaagcac   1320
ttggcttctc cagctggtaa ggttgatgaa tactctaagt gggttgttga atctcaaaga   1380
tctttgttgg aagttatggc cgaattccca tctgccaagc caccattggg tgttttcttc   1440
gctggtgttg ctccaagatt gcaaccaaga ttctactcta tctcttcttc tccaaagatt   1500
gctgaaacta gaattcacgt cacttgtgct ttggtttacg aaaagatgcc aactggtaga   1560
attcacaagg gtgtttgttc cacttggatg aagaacgctg ttccatacga aaagtctgaa   1620
aactgttcct ctgctccaat cttcgttaga caatccaact tcaagttgcc atctgattct   1680
aaggttccaa tcatcatgat cggtccaggt actggtttgg ctccattcag aggtttcttg   1740
caagaaagat tggctttggt tgaatctggt gttgaattgg gtccatctgt tttgttcttc   1800
ggttgtagaa acagaagaat ggatttcatc tacgaagaag aattgcaaag attcgttgaa   1860
```

-continued

```
tctggtgctt tggctgaatt gtctgtcgcc ttctctagag aaggtccaac caaggaatac   1920

gttcaacaca agatgatgga caaggcttct gatatctgga acatgatctc tcaaggtgct   1980

tacttgtacg tttgtggtga cgccaagggt atggctagag atgttcacag atctttgcac   2040

actatcgctc aagaacaagg ttctatggat tctactaagg ctgaaggttt cgttaagaac   2100

ttgcaaactt ctggtagata cttgagagat gtttggtaa                          2139


<210> SEQ ID NO 33
<211> LENGTH: 522
<212> TYPE: PRT
<213> ORGANISM: Lonicera japonica

<400> SEQUENCE: 33

Met Ser Trp Ile Phe Asp Leu Thr Ile Ser Phe Thr Thr Leu Leu Phe
1               5                   10                  15

Leu Ile Phe Thr Thr Ala Leu Leu Leu Leu Leu Lys Val Phe Lys Lys
            20                  25                  30

Asn His Lys Leu Arg Pro Pro Pro Ser Pro Phe Thr Leu Pro Ile Ile
        35                  40                  45

Gly His Leu His Leu Leu Gly Pro Leu Ile His Gln Ser Phe His Arg
    50                  55                  60

Leu Ser Thr Leu Tyr Gly Pro Leu Ile Gln Leu Lys Ile Gly Tyr Ile
65                  70                  75                  80

Pro Cys Val Val Ala Ser Thr Pro Glu Leu Ala Lys Glu Phe Leu Lys
                85                  90                  95

Thr His Glu Leu Ala Phe Ser Ser Arg Lys His Ser Ala Ala Ile Lys
            100                 105                 110

Leu Leu Thr Tyr Asp Val Ser Phe Ala Phe Ser Pro Tyr Gly Pro Tyr
        115                 120                 125

Trp Lys Phe Ile Lys Lys Thr Cys Thr Phe Glu Leu Leu Gly Thr Arg
    130                 135                 140

Asn Met Asn His Phe Leu Pro Ile Arg Thr Asn Glu Ile Arg Arg Phe
145                 150                 155                 160

Leu Gln Val Met Leu Glu Lys Ala Lys Ala Ser Glu Gly Val Asn Val
                165                 170                 175

Thr Glu Glu Leu Ile Lys Leu Thr Asn Asn Val Ile Ser Gln Met Met
            180                 185                 190

Phe Ser Thr Arg Ser Ser Gly Thr Glu Gly Glu Ala Glu Glu Met Arg
        195                 200                 205

Thr Leu Val Arg Glu Val Thr Gln Ile Phe Gly Glu Phe Asn Val Ser
    210                 215                 220

Asp Phe Ile Lys Leu Cys Lys Asn Ile Asp Ile Gly Gly Phe Lys Lys
225                 230                 235                 240

Arg Ser Lys Asp Ile Gln Lys Arg Tyr Asp Ala Leu Leu Glu Lys Ile
                245                 250                 255

Ile Ser Glu Arg Glu Ser Glu Arg Ala Arg Arg Gly Lys Asn Arg Glu
            260                 265                 270

Thr Leu Gly Glu Glu Gly Gly Lys Asp Phe Leu Asp Met Met Leu Asp
        275                 280                 285

Thr Met Glu Asp Gly Lys Cys Glu Val Glu Ile Thr Arg Asp His Ile
    290                 295                 300

Lys Ala Leu Val Leu Asp Phe Leu Thr Ala Ala Thr Asp Thr Thr Ala
305                 310                 315                 320
```

```
Ile Ala Val Glu Trp Thr Leu Ala Glu Leu Ile Ser Asn Pro Glu Val
                325                 330                 335

Phe Asp Lys Ala Arg Glu Glu Ile Asp Lys Val Val Gly Lys His Arg
            340                 345                 350

Leu Val Thr Glu Leu Asp Thr Pro Asn Leu Pro Tyr Ile His Ala Ile
        355                 360                 365

Ile Lys Glu Ser Phe Arg Leu His Pro Pro Ile Pro Leu Leu Ile Arg
    370                 375                 380

Lys Ser Val Gln Asp Cys Thr Val Gly Gly Tyr His Ile Ser Ala Asn
385                 390                 395                 400

Thr Ile Leu Phe Val Asn Ile Trp Ala Ile Gly Arg Asn Pro Lys Tyr
                405                 410                 415

Trp Glu Ser Pro Met Lys Phe Trp Pro Glu Arg Phe Leu Glu Ser Asn
            420                 425                 430

Gly Pro Gly Pro Val Gly Ser Met Asp Ile Lys Gly His His Tyr Glu
        435                 440                 445

Leu Leu Pro Phe Gly Ser Gly Arg Arg Gly Cys Pro Gly Met Ala Leu
    450                 455                 460

Ala Met Gln Glu Leu Pro Val Val Leu Ala Ala Met Ile Gln Cys Phe
465                 470                 475                 480

Asn Trp Lys Pro Val Thr Leu Asp Gly Glu Glu Leu Asp Met Ser Glu
                485                 490                 495

Arg Pro Gly Leu Thr Ala Pro Arg Ala His Asp Leu Val Cys Val Pro
            500                 505                 510

Ser Ala Arg Ile Asn Ser Phe Asp Asn Phe
        515                 520
```

<210> SEQ ID NO 34
<211> LENGTH: 1569
<212> TYPE: DNA
<213> ORGANISM: artificial
<220> FEATURE:
<223> OTHER INFORMATION: coding sequence for SEQ ID NO: 33

<400> SEQUENCE: 34

```
atgtcctgga tcttcgactt gactatctct ttcaccactt tgttgttctt gatcttcacc     60

accgccttgt tgttgttgtt gaaggttttc aagaagaacc acaagttaag accaccacca    120

tctccattca ccttgccaat catcggtcac ttgcacttgt tgggtccatt gatccaccaa    180

tccttccaca gattgtccac cttgtacggt ccattgatcc aattgaagat cggttacatc    240

ccatgtgttg ttgcctctac tccagaattg gctaaggaat tcttaaagac tcacgaattg    300

gctttctcct ctagaaagca ctccgctgcc attaagttgt tgacctacga tgtttctttc    360

gctttctctc catacggtcc atactggaag ttcatcaaaa agacttgtac cttcgaattg    420

ttgggtacta gaaacatgaa ccacttcttg ccaattagaa ccaacgaaat tagaagattc    480

ttgcaagtta tgttggaaaa ggccaaggct tctgaaggtg ttaacgttac tgaagaattg    540

atcaagttga ctaacaacgt tatctctcaa atgatgttct ctactagatc ttctggtacc    600

gaaggtgaag ctgaagaaat gagaactttg gttagagaag ttactcaaat cttcggtgaa    660

ttcaacgttt ctgatttcat caagttgtgt aagaacattg atattggtgg tttcaagaag    720

agatctaagg atatccaaaa gagatacgat gctttgttgg aaaagatcat ctctgaaaga    780

gaatctgaaa gagctagaag aggtaagaac agagaaactt tgggtgaaga aggtggtaag    840

gatttcttgg atatgatgtt ggatactatg gaagatggta agtgtgaagt tgaaatcact    900
```

```
agagatcaca ttaaggcctt ggttttggat ttcttgactg ctgccactga tactactgct     960

attgctgttg aatggacttt ggccgaattg atctctaacc cagaagtttt cgataaggct    1020

agagaagaaa tcgataaggt cgttggtaag cacagattgg tcactgaatt ggacactcca    1080

aacttgccat acatccacgc tatcatcaag gaatctttca gattgcaccc accaattcca    1140

ttgttgatca gaaagtctgt ccaagattgt actgttggtg gttaccacat ctctgctaac    1200

accatcttgt tcgtcaacat ttgggccatc ggtagaaacc caaagtactg ggaatctcca    1260

atgaagttct ggccagaaag attcttggaa tccaacggtc caggtccagt tggttctatg    1320

gatattaagg gtcaccacta cgaattgttg ccattcggtt ctggtagaag aggttgtcca    1380

ggtatggctt tggccatgca agaattgcca gttgttttgg ccgccatgat ccaatgtttc    1440

aactggaagc cagttacttt ggacggtgaa gaattggata tgtctgaaag accaggtttg    1500

actgctccaa gagcccacga tttggtttgt gttccatccg ctagaattaa ctctttcgat    1560

aacttctaa                                                            1569
```

```
<210> SEQ ID NO 35
<211> LENGTH: 520
<212> TYPE: PRT
<213> ORGANISM: Lonicera macranthoides

<400> SEQUENCE: 35

Met Ser Leu Ile Phe Asp Leu Thr Ile Ser Phe Thr Thr Leu Leu Phe
1               5                   10                  15

Leu Ile Phe Thr Thr Ala Leu Leu Leu Lys Val Phe Lys Lys Asn His
            20                  25                  30

Lys Leu Gln Pro Pro Pro Ser Pro Phe Thr Leu Pro Ile Ile Gly His
        35                  40                  45

Leu His Leu Leu Gly Pro Leu Ile His Gln Ser Phe His Arg Leu Ser
    50                  55                  60

Thr Leu Tyr Gly Pro Leu Ile Gln Leu Lys Ile Gly Tyr Ile Pro Cys
65                  70                  75                  80

Val Val Ala Ser Thr Pro Glu Leu Ala Lys Glu Phe Leu Lys Thr His
                85                  90                  95

Glu Leu Ala Phe Ser Ser Arg Lys His Ser Ala Ala Ile Lys Leu Leu
            100                 105                 110

Thr Tyr Asp Val Ser Phe Ala Phe Ala Pro Tyr Gly Pro Tyr Trp Lys
        115                 120                 125

Phe Ile Lys Lys Thr Cys Thr Phe Glu Leu Leu Gly Thr Arg Asn Met
    130                 135                 140

Asn His Phe Leu Pro Ile Arg Thr Asn Glu Ile Arg Arg Phe Leu Gln
145                 150                 155                 160

Val Met Leu Glu Lys Ala Lys Ala Ser Glu Gly Val Asn Val Thr Glu
                165                 170                 175

Glu Leu Ile Lys Leu Thr Asn Asn Val Ile Ser Gln Met Met Phe Ser
            180                 185                 190

Thr Arg Ser Ser Gly Thr Glu Gly Glu Ala Glu Glu Val Arg Thr Leu
        195                 200                 205

Val Arg Glu Val Thr Gln Ile Phe Gly Glu Phe Asn Val Ser Asp Phe
    210                 215                 220

Ile Lys Leu Cys Lys Asn Ile Asp Ile Gly Gly Phe Lys Lys Arg Ser
225                 230                 235                 240

Glu Asp Ile Gln Lys Arg Tyr Asp Ala Leu Leu Glu Lys Ile Ile Ser
                245                 250                 255
```

```
Glu Arg Glu Ser Glu Arg Ala Arg Arg Gly Lys Asn Arg Glu Thr Leu
            260                 265                 270

Gly Glu Glu Gly Gly Lys Asp Phe Leu Asp Met Met Leu Asp Thr Met
        275                 280                 285

Glu Asp Gly Lys Cys Glu Val Glu Ile Thr Arg Asp His Ile Lys Ala
    290                 295                 300

Leu Val Leu Asp Phe Leu Thr Ala Ala Thr Asp Thr Thr Ala Ile Ala
305                 310                 315                 320

Val Glu Trp Thr Leu Ala Glu Leu Ile Ser Asn Pro Glu Val Phe Asp
                325                 330                 335

Lys Ala Arg Glu Glu Ile Asp Lys Val Val Gly Lys His Arg Leu Val
            340                 345                 350

Thr Glu Leu Asp Thr Pro Asn Leu Pro Tyr Ile His Ala Ile Ile Lys
        355                 360                 365

Glu Ser Phe Arg Leu His Pro Pro Ile Pro Leu Val Ile Arg Lys Ser
    370                 375                 380

Val Gln Asp Cys Thr Val Gly Gly Tyr His Ile Ser Ala Asn Thr Ile
385                 390                 395                 400

Leu Phe Ile Asn Ile Trp Ala Ile Gly Arg Asn Pro Lys Tyr Trp Glu
                405                 410                 415

Ser Pro Met Lys Phe Trp Pro Glu Arg Phe Leu Glu Ser Asn Glu Pro
            420                 425                 430

Gly Ser Val Gly Ser Thr Asp Ile Lys Gly His His Tyr Glu Leu Leu
        435                 440                 445

Pro Phe Gly Ser Gly Arg Arg Gly Cys Pro Gly Met Ala Leu Ala Met
    450                 455                 460

Gln Glu Leu Pro Val Val Leu Ala Ala Met Ile Gln Cys Phe Asn Trp
465                 470                 475                 480

Lys Pro Val Thr Leu Asp Gly Glu Glu Leu Asp Met Ser Glu Arg Pro
                485                 490                 495

Gly Leu Thr Ala Pro Arg Ala His Asp Leu Val Cys Val Pro Ser Ala
            500                 505                 510

Arg Ile Asn Ser Phe Asp Asn Phe
        515                 520


<210> SEQ ID NO 36
<211> LENGTH: 1563
<212> TYPE: DNA
<213> ORGANISM: artificial
<220> FEATURE:
<223> OTHER INFORMATION: coding sequence for SEQ ID NO: 35

<400> SEQUENCE: 36

atgtccttga tcttcgactt gactatctct ttcaccactt tgttgttctt gatcttcacc      60

accgccttgt tgttgaaggt tttcaagaag aaccacaagt tgcaaccacc accatctcca     120

ttcaccttgc caatcatcgg tcacttgcac ttgttgggtc cattgatcca ccaatccttc     180

cacagattgt ccaccttgta cggtccattg atccaattga agatcggtta catcccatgt     240

gttgttgctt ctactccaga attggctaag gaattcttaa agactcacga attggctttc     300

tcctctagaa agcactccgc tgccattaag ttgttgacct acgatgtttc tttcgctttc     360

gctccatacg gtccatactg gaagttcatc aaaaagactt gtaccttcga attgttgggt     420

actagaaaca tgaaccactt cttgccaatt agaaccaacg aaattagaag attcttgcaa     480

gttatgttgg aaaaggccaa ggcttctgaa ggtgttaacg ttactgaaga attgatcaag     540
```

```
ttgactaaca acgttatctc tcaaatgatg ttctctacta gatcttctgg taccgaaggt    600

gaagctgaag aagttagaac tttggttaga gaagttactc aaatcttcgg tgaattcaac    660

gtttctgatt tcatcaagtt gtgtaagaac attgatattg gtggtttcaa gaagagatct    720

gaagatatcc aaaagagata cgatgctttg ttggaaaaga tcatctctga aagagaatct    780

gaaagagcta gaagaggtaa gaacagagaa actttgggtg aagaaggtgg taaggatttc    840

ttggacatga tgttggatac tatggaagat ggtaagtgtg aagttgaaat cactagagat    900

cacattaagg ccttggtttt ggatttcttg actgctgcca ctgatactac tgctattgct    960

gttgaatgga ctttggctga attgatctct aacccagaag ttttcgataa ggctagagaa   1020

gaaatcgata aggtcgttgg taagcacaga ttggtcactg aattggacac tccaaacttg   1080

ccatacatcc acgctatcat caaggaatct ttcagattgc acccaccaat tccattggtc   1140

atcagaaagt ctgtccaaga ttgtactgtt ggtggttacc acatctctgc taacactatc   1200

ttgttcatca acatttgggc catcggtaga aacccaaagt actgggaatc tccaatgaag   1260

ttctggccag aaagattctt ggaatccaac gaaccaggtt ctgttggttc tactgatatt   1320

aagggtcacc actacgaatt gttgccattc ggttctggta gaagaggttg tccaggtatg   1380

gctttggcca tgcaagaatt gccagttgtt ttggccgcca tgatccaatg tttcaactgg   1440

aagccagtta ctttggacgg tgaagaattg gatatgtctg aaagaccagg tttgactgct   1500

ccaagagccc acgatttggt ttgtgttcca tccgctagaa ttaactcttt cgataacttc   1560

taa                                                                  1563
```

<210> SEQ ID NO 37
<211> LENGTH: 366
<212> TYPE: PRT
<213> ORGANISM: Petroselinum crispum

<400> SEQUENCE: 37

```
Met Ser Ala Pro Thr Thr Ile Thr Ala Leu Ala Lys Glu Lys Thr Leu
1               5                   10                  15

Asn Leu Asp Phe Val Arg Asp Glu Asp Glu Arg Pro Lys Val Ala Tyr
            20                  25                  30

Asn Gln Phe Ser Asn Glu Ile Pro Ile Ile Ser Leu Ala Gly Leu Asp
        35                  40                  45

Asp Asp Ser Asp Gly Arg Arg Pro Glu Ile Cys Arg Lys Ile Val Lys
    50                  55                  60

Ala Cys Glu Asp Trp Gly Ile Phe Gln Val Val Asp His Gly Ile Asp
65                  70                  75                  80

Ser Gly Leu Ile Ser Glu Met Thr Arg Leu Ser Arg Glu Phe Phe Ala
                85                  90                  95

Leu Pro Ala Glu Glu Lys Leu Glu Tyr Asp Thr Thr Gly Gly Lys Arg
            100                 105                 110

Gly Gly Phe Thr Ile Ser Thr Val Leu Gln Gly Asp Asp Ala Met Asp
        115                 120                 125

Trp Arg Glu Phe Val Thr Tyr Phe Ser Tyr Pro Ile Asn Ala Arg Asp
    130                 135                 140

Tyr Ser Arg Trp Pro Lys Lys Pro Glu Gly Trp Arg Ser Thr Thr Glu
145                 150                 155                 160

Val Tyr Ser Glu Lys Leu Met Val Leu Gly Ala Lys Leu Leu Glu Val
                165                 170                 175

Leu Ser Glu Ala Met Gly Leu Glu Lys Gly Asp Leu Thr Lys Ala Cys
```

```
            180                 185                 190

Val Asp Met Glu Gln Lys Val Leu Ile Asn Tyr Tyr Pro Thr Cys Pro
        195                 200                 205

Gln Pro Asp Leu Thr Leu Gly Val Arg Arg His Thr Asp Pro Gly Thr
    210                 215                 220

Ile Thr Ile Leu Leu Gln Asp Met Val Gly Gly Leu Gln Ala Thr Arg
225                 230                 235                 240

Asp Gly Gly Lys Thr Trp Ile Thr Val Gln Pro Val Glu Gly Ala Phe
                245                 250                 255

Val Val Asn Leu Gly Asp His Gly His Tyr Leu Ser Asn Gly Arg Phe
            260                 265                 270

Arg Asn Ala Asp His Gln Ala Val Val Asn Ser Thr Ser Ser Arg Leu
        275                 280                 285

Ser Ile Ala Thr Phe Gln Asn Pro Ala Gln Asn Ala Ile Val Tyr Pro
    290                 295                 300

Leu Lys Ile Arg Glu Gly Glu Lys Ala Ile Leu Asp Glu Ala Ile Thr
305                 310                 315                 320

Tyr Ala Glu Met Tyr Lys Lys Cys Met Thr Lys His Ile Glu Val Ala
                325                 330                 335

Thr Arg Lys Lys Leu Ala Lys Glu Lys Arg Leu Gln Asp Glu Lys Ala
            340                 345                 350

Lys Leu Glu Met Lys Ser Lys Ser Ala Asp Glu Asn Leu Ala
        355                 360                 365


<210> SEQ ID NO 38
<211> LENGTH: 1101
<212> TYPE: DNA
<213> ORGANISM: artificial
<220> FEATURE:
<223> OTHER INFORMATION: coding sequence for SEQ ID NO: 37

<400> SEQUENCE: 38

atgtccgctc caactactat caccgctttg gccaaggaaa agactttgaa cttggacttc     60

gttagagatg aagatgaaag accaaaggtt gcttacaacc aattctctaa cgaaattcca    120

attatttctt tggccggttt ggatgacgat tctgatggta gaaggccaga aatctgtaga    180

aagatcgtta aggcttgtga agattggggt attttccaag ttgttgatca cggtattgac    240

tctggtttga tttccgaaat gactagattg tctagagaat tcttcgcttt gccagctgaa    300

gaaaagttgg aatacgatac tactggtggt aagagaggtg gtttcactat ctccactgtt    360

ttgcaaggtg acgacgctat ggattggaga gaattcgtta cttacttctc ttacccaatc    420

aacgctagag actactctag atggccaaag aagccagaag gttggagatc taccactgaa    480

gtttactctg aaaagttgat ggttttgggt gccaagttgt tggaagtttt gtctgaagcc    540

atgggtttgg aaaagggtga tttgactaag gcttgtgttg atatggaaca aaaggttttg    600

attaactact acccaacttg tccacaacca gacttgactt tgggtgtcag gagacacact    660

gatccaggta ctattaccat tttgttgcaa gacatggttg gtggtttgca agccaccaga    720

gatggtggta agacttggat tactgttcaa ccagttgaag gtgctttcgt tgtcaacttg    780

ggtgatcacg gtcactactt gtctaacggt agattcagaa acgctgacca ccaagctgtt    840

gttaactcta cctcttctag attgtctatt gctactttcc aaaacccagc tcaaaacgct    900

atcgtttacc cattgaagat cagagaaggt gaaaaggcta ttttggatga agccatcacc    960

tacgctgaaa tgtacaagaa gtgtatgact aagcacattg aagttgctac tagaaagaag   1020
```

```
ttggccaagg aaaagagatt gcaagacgaa aaggccaagt tggaaatgaa gtccaagtct   1080

gctgatgaaa acttggctta a                                             1101


<210> SEQ ID NO 39
<211> LENGTH: 507
<212> TYPE: PRT
<213> ORGANISM: Flavobacterium johnsoniae

<400> SEQUENCE: 39

Met Ser Asn Thr Ile Asn Glu Tyr Leu Ser Leu Glu Glu Phe Glu Ala
1               5                   10                  15

Ile Ile Phe Gly Asn Gln Lys Val Thr Ile Ser Asp Val Val Val Asn
            20                  25                  30

Arg Val Asn Glu Ser Phe Asn Phe Leu Lys Glu Phe Ser Gly Asn Lys
        35                  40                  45

Val Ile Tyr Gly Val Asn Thr Gly Phe Gly Pro Met Ala Gln Tyr Arg
    50                  55                  60

Ile Lys Glu Ser Asp Gln Ile Gln Leu Gln Tyr Asn Leu Ile Arg Ser
65                  70                  75                  80

His Ser Ser Gly Thr Gly Lys Pro Leu Ser Pro Val Cys Ala Lys Ala
                85                  90                  95

Ala Ile Leu Ala Arg Leu Asn Thr Leu Ser Leu Gly Asn Ser Gly Val
            100                 105                 110

His Pro Ser Val Ile Asn Leu Met Ser Glu Leu Ile Asn Lys Asp Ile
        115                 120                 125

Thr Pro Leu Ile Phe Glu His Gly Gly Val Gly Ala Ser Gly Asp Leu
    130                 135                 140

Val Gln Leu Ser His Leu Ala Leu Val Leu Ile Gly Glu Gly Glu Val
145                 150                 155                 160

Phe Tyr Lys Gly Glu Arg Arg Pro Thr Pro Glu Val Phe Glu Ile Glu
                165                 170                 175

Gly Leu Lys Pro Ile Gln Val Glu Ile Arg Glu Gly Leu Ala Leu Ile
            180                 185                 190

Asn Gly Thr Ser Val Met Thr Gly Ile Gly Val Val Asn Val Tyr His
        195                 200                 205

Ala Lys Lys Leu Leu Asp Trp Ser Leu Lys Ser Ser Cys Ala Ile Asn
    210                 215                 220

Glu Leu Val Gln Ala Tyr Asp Asp His Phe Ser Ala Glu Leu Asn Gln
225                 230                 235                 240

Thr Lys Arg His Lys Gly Gln Gln Glu Ile Ala Leu Lys Met Arg Gln
                245                 250                 255

Asn Leu Ser Asp Ser Thr Leu Ile Arg Lys Arg Glu Asp His Leu Tyr
            260                 265                 270

Ser Gly Glu Asn Thr Glu Glu Ile Phe Lys Glu Lys Val Gln Glu Tyr
        275                 280                 285

Tyr Ser Leu Arg Cys Val Pro Gln Ile Leu Gly Pro Val Leu Glu Thr
    290                 295                 300

Ile Asn Asn Val Ala Ser Ile Leu Glu Asp Glu Phe Asn Ser Ala Asn
305                 310                 315                 320

Asp Asn Pro Ile Ile Asp Val Lys Asn Gln His Val Tyr His Gly Gly
                325                 330                 335

Asn Phe His Gly Asp Tyr Ile Ser Leu Glu Met Asp Lys Leu Lys Ile
            340                 345                 350

Val Ile Thr Lys Leu Thr Met Leu Ala Glu Arg Gln Leu Asn Tyr Leu
```

355 360 365

Leu Asn Ser Lys Ile Asn Glu Leu Leu Pro Pro Phe Val Asn Leu Gly
370 375 380

Thr Leu Gly Phe Asn Phe Gly Met Gln Gly Val Gln Phe Thr Ala Thr
385 390 395 400

Ser Thr Thr Ala Glu Ser Gln Met Leu Ser Asn Pro Met Tyr Val His
405 410 415

Ser Ile Pro Asn Asn Asn Asp Asn Gln Asp Ile Val Ser Met Gly Thr
420 425 430

Asn Ser Ala Val Ile Thr Ser Lys Val Ile Glu Asn Ala Phe Glu Val
435 440 445

Leu Ala Ile Glu Met Ile Thr Ile Val Gln Ala Ile Asp Tyr Leu Gly
450 455 460

Gln Lys Asp Lys Ile Ser Ser Val Ser Lys Lys Trp Tyr Asp Glu Ile
465 470 475 480

Arg Asn Ile Ile Pro Thr Phe Lys Glu Asp Gln Val Met Tyr Pro Phe
485 490 495

Val Gln Lys Val Lys Asp His Leu Ile Asn Asn
500 505

<210> SEQ ID NO 40
<211> LENGTH: 1524
<212> TYPE: DNA
<213> ORGANISM: artificial
<220> FEATURE:
<223> OTHER INFORMATION: coding sequence for SEQ ID NO: 39

<400> SEQUENCE: 40
atgtccaaca ctattaacga atacttgtct ttggaagaat tcgaagccat catcttcggt 60
aaccaaaagg ttactatttc tgacgttgtc gttaacagag ttaacgaatc tttcaacttc 120
ttgaaggaat tctctggtaa caaggttatt tacggtgtta acactggttt cggtccaatg 180
gctcaataca gaattaagga atctgatcaa attcaattgc aatacaactt gattagatct 240
cactcttctg gtaccggtaa gccattgtct ccagtttgtg ctaaggctgc tattttggct 300
agattgaaca ctttgtcttt gggtaactct ggtgttcacc catctgttat caacttgatg 360
tctgaattga tcaacaagga tattacccca ttgatcttcg aacacggtgg tgttggtgcc 420
tctggtgact tggttcaatt gtctcacttg gctttggttt tgattggtga aggtgaagtt 480
ttctacaagg gtgaaagaag gccaactcca gaagttttcg aaattgaagg tttgaagcca 540
attcaagttg aaattagaga aggtttggct ttgattaacg gtacttctgt tatgactggt 600
attggtgttg ttaacgttta ccacgctaag aagttgttgg actggtcttt gaaatcttct 660
tgtgctatta acgaattggt tcaagcttac gacgatcact tctctgctga attgaaccaa 720
actaagagac acaagggtca acaagaaatt gctttgaaga tgagacaaaa cttgtctgac 780
tctactttga tcagaaagag agaagatcac ttgtactctg gtgaaaacac cgaagaaatc 840
ttcaaggaaa aggttcaaga atactactct ttgagatgtg ttccacaaat tttgggtcca 900
gttttggaaa ctattaacaa cgttgcttct attttggaag atgaattcaa ctctgctaac 960
gataacccaa ttatcgatgt taagaaccaa cacgtttacc acggtggtaa cttccacggt 1020
gattacattt ctttggaaat ggataagttg aagattgtta ttaccaagtt gactatgttg 1080
gctgaaagac aattgaacta cttgttgaac tctaagatca acgaattgtt gccaccattc 1140
gttaacttgg gtactttggg tttcaacttc ggtatgcaag gtgttcaatt cactgctact 1200

-continued

```
tctactactg ctgaatctca aatgttgtct aacccaatgt acgttcactc tattccaaac   1260

aacaacgaca accaagatat cgtttctatg ggtactaact ctgctgttat tacctctaag   1320

gttatcgaaa acgctttcga agttttggct atcgaaatga ttactatcgt tcaagctatt   1380

gattacttgg gtcaaaagga caagatttct tctgtttcta agaagtggta cgatgaaatt   1440

agaaacatca ttccaacttt caaggaagat caagttatgt acccattcgt tcaaaaggtt   1500

aaggatcact tgatcaacaa ctaa                                          1524
```

```
<210> SEQ ID NO 41
<211> LENGTH: 694
<212> TYPE: PRT
<213> ORGANISM: Rhodotorula glutinis

<400> SEQUENCE: 41

Met Ser Ala Pro Arg Pro Thr Ser Gln Ser Gln Ala Arg Thr Cys Pro
1               5                   10                  15

Thr Thr Gln Val Thr Gln Val Asp Ile Val Glu Lys Met Leu Ala Ala
            20                  25                  30

Pro Thr Asp Ser Thr Leu Glu Leu Asp Gly Tyr Ser Leu Asn Leu Gly
        35                  40                  45

Asp Val Val Ser Ala Ala Arg Lys Gly Arg Pro Val Arg Val Lys Asp
    50                  55                  60

Ser Asp Glu Ile Arg Ser Lys Ile Asp Lys Ser Val Glu Phe Leu Arg
65                  70                  75                  80

Ser Gln Leu Ser Met Ser Val Tyr Gly Val Thr Thr Gly Phe Gly Gly
                85                  90                  95

Ser Ala Asp Thr Arg Thr Glu Asp Ala Ile Ser Leu Gln Lys Ala Leu
            100                 105                 110

Leu Glu His Gln Leu Cys Gly Val Leu Pro Ser Ser Phe Asp Ser Phe
        115                 120                 125

Arg Leu Gly Arg Gly Leu Glu Asn Ser Leu Pro Leu Glu Val Val Arg
    130                 135                 140

Gly Ala Met Thr Ile Arg Val Asn Ser Leu Thr Arg Gly His Ser Ala
145                 150                 155                 160

Val Arg Leu Val Val Leu Glu Ala Leu Thr Asn Phe Leu Asn His Gly
                165                 170                 175

Ile Thr Pro Ile Val Pro Leu Arg Gly Thr Ile Ser Ala Ser Gly Asp
            180                 185                 190

Leu Ser Pro Leu Ser Tyr Ile Ala Ala Ala Ile Ser Gly His Pro Asp
        195                 200                 205

Ser Lys Val His Val Val His Glu Gly Lys Glu Lys Ile Leu Tyr Ala
    210                 215                 220

Arg Glu Ala Met Ala Leu Phe Asn Leu Glu Pro Val Val Leu Gly Pro
225                 230                 235                 240

Lys Glu Gly Leu Gly Leu Val Asn Gly Thr Ala Val Ser Ala Ser Met
                245                 250                 255

Ala Thr Leu Ala Leu His Asp Ala His Met Leu Ser Leu Leu Ser Gln
            260                 265                 270

Ser Leu Thr Ala Met Thr Val Glu Ala Met Val Gly His Ala Gly Ser
        275                 280                 285

Phe His Pro Phe Leu His Asp Val Thr Arg Pro His Pro Thr Gln Ile
    290                 295                 300

Glu Val Ala Gly Asn Ile Arg Lys Leu Leu Glu Gly Ser Arg Phe Ala
305                 310                 315                 320
```

```
Val His His Glu Glu Glu Val Lys Val Lys Asp Asp Glu Gly Ile Leu
                325                 330                 335

Arg Gln Asp Arg Tyr Pro Leu Arg Thr Ser Pro Gln Trp Leu Gly Pro
            340                 345                 350

Leu Val Ser Asp Leu Ile His Ala His Ala Val Leu Thr Ile Glu Ala
        355                 360                 365

Gly Gln Ser Thr Thr Asp Asn Pro Leu Ile Asp Val Glu Asn Lys Thr
    370                 375                 380

Ser His His Gly Gly Asn Phe Gln Ala Ala Ala Val Ala Asn Thr Met
385                 390                 395                 400

Glu Lys Thr Arg Leu Gly Leu Ala Gln Ile Gly Lys Leu Asn Phe Thr
                405                 410                 415

Gln Leu Thr Glu Met Leu Asn Ala Gly Met Asn Arg Gly Leu Pro Ser
            420                 425                 430

Cys Leu Ala Ala Glu Asp Pro Ser Leu Ser Tyr His Cys Lys Gly Leu
        435                 440                 445

Asp Ile Ala Ala Ala Ala Tyr Thr Ser Glu Leu Gly His Leu Ala Asn
    450                 455                 460

Pro Val Thr Thr His Val Gln Pro Ala Glu Met Ala Asn Gln Ala Val
465                 470                 475                 480

Asn Ser Leu Ala Leu Ile Ser Ala Arg Arg Thr Thr Glu Ser Asn Asp
                485                 490                 495

Val Leu Ser Leu Leu Leu Ala Thr His Leu Tyr Cys Val Leu Gln Ala
            500                 505                 510

Ile Asp Leu Arg Ala Ile Glu Phe Glu Phe Lys Lys Gln Phe Gly Pro
        515                 520                 525

Ala Ile Val Ser Leu Ile Asp Gln His Phe Gly Ser Ala Met Thr Gly
    530                 535                 540

Ser Asn Leu Arg Asp Glu Leu Val Glu Lys Val Asn Lys Thr Leu Ala
545                 550                 555                 560

Lys Arg Leu Glu Gln Thr Asn Ser Tyr Asp Leu Val Pro Arg Trp His
                565                 570                 575

Asp Ala Phe Ser Phe Ala Ala Gly Thr Val Val Glu Val Leu Ser Ser
            580                 585                 590

Thr Ser Leu Ser Leu Ala Ala Val Asn Ala Trp Lys Val Ala Ala Ala
        595                 600                 605

Glu Ser Ala Ile Ser Leu Thr Arg Gln Val Arg Glu Thr Phe Trp Ser
    610                 615                 620

Ala Ala Ser Thr Ser Ser Pro Ala Leu Ser Tyr Leu Ser Pro Arg Thr
625                 630                 635                 640

Gln Ile Leu Tyr Ala Phe Val Arg Glu Glu Leu Gly Val Lys Ala Arg
                645                 650                 655

Arg Gly Asp Val Phe Leu Gly Lys Gln Glu Val Thr Ile Gly Ser Asn
            660                 665                 670

Val Ser Lys Ile Tyr Glu Ala Ile Lys Ser Gly Arg Ile Asn Asn Val
        675                 680                 685

Leu Leu Lys Met Leu Ala
    690
```

<210> SEQ ID NO 42
<211> LENGTH: 2085
<212> TYPE: DNA
<213> ORGANISM: artificial
<220> FEATURE:

-continued

<223> OTHER INFORMATION: coding sequence for SEQ ID NO: 41

<400> SEQUENCE: 42

```
atgtccgctc caagaccaac ttctcaatct caagccagaa cttgtccaac cacccaagtt     60
acccaagttg atatcgttga aaagatgttg gctgctccaa ctgattctac cttggaattg    120
gacggttact ctttgaactt gggtgatgtt gtttctgctg ctagaaaggg tagaccagtt    180
agagttaagg attctgatga aatcagatct aagatcgaca agtctgttga attcttgaga    240
tctcaattgt ctatgtctgt ttacggtgtt accaccggtt tcggtggttc cgctgacacc    300
agaaccgaag atgctatttc tttgcaaaag gctttgttgg aacaccaatt gtgtggtgtt    360
ttgccatctt ctttcgactc tttcagattg ggtagaggtt tggaaaactc tttgccattg    420
gaagttgtta gaggtgctat gaccattaga gttaactctt tgaccagagg tcactctgct    480
gttagattgg ttgttttgga agctttgacc aacttcttga accacggtat taccccaatt    540
gttccattga gaggtaccat ctccgcttct ggtgatttgt ctccattgtc ttacattgct    600
gctgctattt ctggtcaccc agattctaag gttcacgttg ttcacgaagg taaggaaaag    660
atcttgtacg ctagagaagc tatggctttg ttcaacttgg aaccagttgt tttgggtcca    720
aaggaaggtt tgggtttggt taacggtacc gctgtttccg cttctatggc taccttggct    780
ttgcacgacg ctcacatgtt gtctttgttg tctcaatctt tgaccgctat gaccgttgaa    840
gctatggttg gtcacgctgg ttctttccac ccattcttgc acgatgttac cagaccacac    900
ccaacccaaa tcgaagttgc tggtaacatt agaaagttgt tggaaggttc tagattcgct    960
gttcaccacg aagaagaagt taaggttaag gatgatgaag gtattttgag acaagataga   1020
tacccattga gaacctctcc acaatggttg ggtccattgg tttccgactt gattcacgct   1080
cacgccgttt tgaccatcga agctggtcaa tctaccaccg ataacccatt gatcgatgtt   1140
gaaaacaaga cctctcacca cggtggtaac ttccaagctg ctgctgttgc caacactatg   1200
gaaaagacca gattgggttt ggcccaaatc ggtaagttga acttcaccca attgaccgaa   1260
atgttgaacg ctggtatgaa cagaggtttg ccatcttgtt tggctgctga agatccatcc   1320
ttgtcttacc actgtaaggg tttggacatt gctgctgctg cttacacctc tgaattgggt   1380
cacttggcta acccagttac cacccacgtt caaccagctg aaatggctaa ccaagctgtt   1440
aactctttgg ctttgatttc tgctagaaga accaccgaat ctaacgacgt tttgtccttg   1500
ttgttggcta cccacttgta ctgtgttttg caagctatcg acttgagagc tattgaattc   1560
gaattcaaga agcaattcgg tccagccatt gtttctttga tcgaccaaca cttcggttct   1620
gctatgaccg gttctaactt gagagatgaa ttggttgaaa aggttaacaa gactttggcc   1680
aagagattgg aacaaaccaa ctcttacgat ttggttccaa gatggcacga cgctttctct   1740
ttcgctgctg gtactgttgt tgaagttttg tcctctacct ctttgtcttt ggctgccgtt   1800
aacgcttgga aggttgctgc tgccgaatct gctatctcct tgaccagaca agttagagaa   1860
accttctggt ccgctgcttc tacctcctct ccagctttgt cttacttgtc tccaagaacc   1920
caaatcttgt acgctttcgt tagagaagaa ttgggtgtta aggccagaag aggtgacgtt   1980
ttcttgggta agcaagaagt taccatcggt tctaacgttt ctaagattta cgaagccatc   2040
aagtctggta gaatcaacaa cgttttgttg aagatgttgg cttaa                   2085
```

<210> SEQ ID NO 43
<211> LENGTH: 562
<212> TYPE: PRT
<213> ORGANISM: Arabidopsis thaliana

<400> SEQUENCE: 43

Met Ser Ala Pro Gln Glu Gln Ala Val Ser Gln Val Met Glu Lys Gln
1 5 10 15

Ser Asn Asn Asn Asn Ser Asp Val Ile Phe Arg Ser Lys Leu Pro Asp
20 25 30

Ile Tyr Ile Pro Asn His Leu Ser Leu His Asp Tyr Ile Phe Gln Asn
35 40 45

Ile Ser Glu Phe Ala Thr Lys Pro Cys Leu Ile Asn Gly Pro Thr Gly
50 55 60

His Val Tyr Thr Tyr Ser Asp Val His Val Ile Ser Arg Gln Ile Ala
65 70 75 80

Ala Asn Phe His Lys Leu Gly Val Asn Gln Asn Asp Val Val Met Leu
85 90 95

Leu Leu Pro Asn Cys Pro Glu Phe Val Leu Ser Phe Leu Ala Ala Ser
100 105 110

Phe Arg Gly Ala Thr Ala Thr Ala Ala Asn Pro Phe Phe Thr Pro Ala
115 120 125

Glu Ile Ala Lys Gln Ala Lys Ala Ser Asn Thr Lys Leu Ile Ile Thr
130 135 140

Glu Ala Arg Tyr Val Asp Lys Ile Lys Pro Leu Gln Asn Asp Asp Gly
145 150 155 160

Val Val Ile Val Cys Ile Asp Asp Asn Glu Ser Val Pro Ile Pro Glu
165 170 175

Gly Cys Leu Arg Phe Thr Glu Leu Thr Gln Ser Thr Thr Glu Ala Ser
180 185 190

Glu Val Ile Asp Ser Val Glu Ile Ser Pro Asp Asp Val Val Ala Leu
195 200 205

Pro Tyr Ser Ser Gly Thr Thr Gly Leu Pro Lys Gly Val Met Leu Thr
210 215 220

His Lys Gly Leu Val Thr Ser Val Ala Gln Gln Val Asp Gly Glu Asn
225 230 235 240

Pro Asn Leu Tyr Phe His Ser Asp Asp Val Ile Leu Cys Val Leu Pro
245 250 255

Met Phe His Ile Tyr Ala Leu Asn Ser Ile Met Leu Cys Gly Leu Arg
260 265 270

Val Gly Ala Ala Ile Leu Ile Met Pro Lys Phe Glu Ile Asn Leu Leu
275 280 285

Leu Glu Leu Ile Gln Arg Cys Lys Val Thr Val Ala Pro Met Val Pro
290 295 300

Pro Ile Val Leu Ala Ile Ala Lys Ser Ser Glu Thr Glu Lys Tyr Asp
305 310 315 320

Leu Ser Ser Ile Arg Val Val Lys Ser Gly Ala Ala Pro Leu Gly Lys
325 330 335

Glu Leu Glu Asp Ala Val Asn Ala Lys Phe Pro Asn Ala Lys Leu Gly
340 345 350

Gln Gly Tyr Gly Met Thr Glu Ala Gly Pro Val Leu Ala Met Ser Leu
355 360 365

Gly Phe Ala Lys Glu Pro Phe Pro Val Lys Ser Gly Ala Cys Gly Thr
370 375 380

Val Val Arg Asn Ala Glu Met Lys Ile Val Asp Pro Asp Thr Gly Asp
385 390 395 400

Ser Leu Ser Arg Asn Gln Pro Gly Glu Ile Cys Ile Arg Gly His Gln

-continued

```
                405                 410                 415

Ile Met Lys Gly Tyr Leu Asn Asn Pro Ala Ala Thr Ala Glu Thr Ile
            420                 425                 430

Asp Lys Asp Gly Trp Leu His Thr Gly Asp Ile Gly Leu Ile Asp Asp
        435                 440                 445

Asp Asp Glu Leu Phe Ile Val Asp Arg Leu Lys Glu Leu Ile Lys Tyr
    450                 455                 460

Lys Gly Phe Gln Val Ala Pro Ala Glu Leu Glu Ala Leu Leu Ile Gly
465                 470                 475                 480

His Pro Asp Ile Thr Asp Val Ala Val Val Ala Met Lys Glu Glu Ala
                485                 490                 495

Ala Gly Glu Val Pro Val Ala Phe Val Val Lys Ser Lys Asp Ser Glu
            500                 505                 510

Leu Ser Glu Asp Asp Val Lys Gln Phe Val Ser Lys Gln Val Val Phe
        515                 520                 525

Tyr Lys Arg Ile Asn Lys Val Phe Phe Thr Glu Ser Ile Pro Lys Ala
    530                 535                 540

Pro Ser Gly Lys Ile Leu Arg Lys Asp Leu Arg Ala Lys Leu Ala Asn
545                 550                 555                 560

Gly Leu


<210> SEQ ID NO 44
<211> LENGTH: 1689
<212> TYPE: DNA
<213> ORGANISM: artificial
<220> FEATURE:
<223> OTHER INFORMATION: coding sequence for SEQ ID NO: 43

<400> SEQUENCE: 44

atgtccgctc cacaagaaca agctgtttct caagttatgg aaaagcaatc taacaacaac      60

aactctgacg tcattttcag atctaagttg ccagatattt acatcccaaa ccacttgtct     120

ttgcacgact acatcttcca aaacatctcc gaattcgcca ctaagccatg tttgatcaac     180

ggtccaaccg gtcacgttta cacttactcc gacgtccacg tcatctccag acaaatcgcc     240

gccaacttcc acaagttggg tgttaaccaa aacgacgtcg tcatgttgtt gttgccaaac     300

tgtccagaat tcgtcttgtc tttcttggcc gcctccttca gaggtgctac cgccaccgcc     360

gctaacccat tcttcactcc agctgaaatc gctaagcaag ccaaggcctc caacaccaag     420

ttgatcatca ccgaagctag atacgtcgac aagatcaagc cattgcaaaa cgacgacggt     480

gttgtcatcg tctgtatcga cgacaacgaa tccgttccaa tcccagaagg ttgtttgaga     540

ttcaccgaat tgactcaatc tactaccgaa gcttctgaag tcatcgactc tgttgaaatt     600

tctccagacg acgttgttgc tttgccatac tcctctggta ctactggttt gccaaagggt     660

gttatgttga ctcacaaggg tttggtcact tctgttgctc aacaagtcga cggtgaaaac     720

ccaaacttgt acttccactc tgatgacgtc atcttgtgtg ttttgccaat gttccacatc     780

tacgctttga actctatcat gttgtgtggt ttgagagttg gtgctgctat tttgatcatg     840

ccaaagttcg aaatcaactt gttgttggaa ttgatccaaa gatgtaaggt tactgttgct     900

ccaatggttc caccaattgt tttggccatt gctaaatctt ctgaaactga aaagtacgat     960

ttatcttcta tcagagttgt taagtctggt gctgctccat tgggtaagga attggaagat    1020

gccgttaacg ccaagttccc aaacgccaag ttgggtcaag gttacggtat gactgaagct    1080

ggtccagttt tggctatgtc tttgggtttc gctaaggaac cattcccagt taagtctggt    1140
```

-continued gcttgtggta ctgttgttag aaacgctgaa atgaagatcg ttgatccaga caccggtgat 1200
tctttgtcta gaaaccaacc aggtgaaatt tgtattagag gtcaccaaat catgaagggt 1260
tacttgaaca acccagctgc tactgctgaa accattgata aggacggttg gttgcacact 1320
ggtgatattg gtttgatcga tgacgatgac gaattgttca tcgttgatag attgaaggaa 1380
ttgatcaagt acaagggttt ccaagttgct ccagctgaat tggaagcttt gttgatcggt 1440
cacccagaca ttactgatgt tgctgttgtc gctatgaagg aagaagctgc tggtgaagtt 1500
ccagttgctt tcgttgttaa gtctaaggat tctgaattgt ctgaagatga tgttaagcaa 1560
ttcgtttcta agcaagttgt tttctacaag agaatcaaca aggttttctt cactgaatcc 1620
attccaaagg ctccatctgg taagatcttg agaaaggatt tgagagctaa gttggctaac 1680
ggtttgtaa 1689

<210> SEQ ID NO 45
<211> LENGTH: 545
<212> TYPE: PRT
<213> ORGANISM: Petroselinum crispum

<400> SEQUENCE: 45

Met Ser Gly Asp Cys Val Ala Pro Lys Glu Asp Leu Ile Phe Arg Ser
1 5 10 15

Lys Leu Pro Asp Ile Tyr Ile Pro Lys His Leu Pro Leu His Thr Tyr
20 25 30

Cys Phe Glu Asn Ile Ser Lys Val Gly Asp Lys Ser Cys Leu Ile Asn
35 40 45

Gly Ala Thr Gly Glu Thr Phe Thr Tyr Ser Gln Val Glu Leu Leu Ser
50 55 60

Arg Lys Val Ala Ser Gly Leu Asn Lys Leu Gly Ile Gln Gln Gly Asp
65 70 75 80

Thr Ile Met Leu Leu Leu Pro Asn Ser Pro Glu Tyr Phe Phe Ala Phe
85 90 95

Leu Gly Ala Ser Tyr Arg Gly Ala Ile Ser Thr Met Ala Asn Pro Phe
100 105 110

Phe Thr Ser Ala Glu Val Ile Lys Gln Leu Lys Ala Ser Gln Ala Lys
115 120 125

Leu Ile Ile Thr Gln Ala Cys Tyr Val Asp Lys Val Lys Asp Tyr Ala
130 135 140

Ala Glu Lys Asn Ile Gln Ile Ile Cys Ile Asp Asp Ala Pro Gln Asp
145 150 155 160

Cys Leu His Phe Ser Lys Leu Met Glu Ala Asp Glu Ser Glu Met Pro
165 170 175

Glu Val Val Ile Asn Ser Asp Asp Val Val Ala Leu Pro Tyr Ser Ser
180 185 190

Gly Thr Thr Gly Leu Pro Lys Gly Val Met Leu Thr His Lys Gly Leu
195 200 205

Val Thr Ser Val Ala Gln Gln Val Asp Gly Asp Asn Pro Asn Leu Tyr
210 215 220

Met His Ser Glu Asp Val Met Ile Cys Ile Leu Pro Leu Phe His Ile
225 230 235 240

Tyr Ser Leu Asn Ala Val Leu Cys Cys Gly Leu Arg Ala Gly Val Thr
245 250 255

Ile Leu Ile Met Gln Lys Phe Asp Ile Val Pro Phe Leu Glu Leu Ile
260 265 270

```
Gln Lys Tyr Lys Val Thr Ile Gly Pro Phe Val Pro Pro Ile Val Leu
        275                 280                 285

Ala Ile Ala Lys Ser Pro Val Val Asp Lys Tyr Asp Leu Ser Ser Val
    290                 295                 300

Arg Thr Val Met Ser Gly Ala Ala Pro Leu Gly Lys Glu Leu Glu Asp
305                 310                 315                 320

Ala Val Arg Ala Lys Phe Pro Asn Ala Lys Leu Gly Gln Gly Tyr Gly
                325                 330                 335

Met Thr Glu Ala Gly Pro Val Leu Ala Met Cys Leu Ala Phe Ala Lys
            340                 345                 350

Glu Pro Tyr Glu Ile Lys Ser Gly Ala Cys Gly Thr Val Val Arg Asn
        355                 360                 365

Ala Glu Met Lys Ile Val Asp Pro Glu Thr Asn Ala Ser Leu Pro Arg
    370                 375                 380

Asn Gln Arg Gly Glu Ile Cys Ile Arg Gly Asp Gln Ile Met Lys Gly
385                 390                 395                 400

Tyr Leu Asn Asp Pro Glu Ser Thr Arg Thr Thr Ile Asp Glu Glu Gly
                405                 410                 415

Trp Leu His Thr Gly Asp Ile Gly Phe Ile Asp Asp Asp Asp Glu Leu
            420                 425                 430

Phe Ile Val Asp Arg Leu Lys Glu Ile Ile Lys Tyr Lys Gly Phe Gln
        435                 440                 445

Val Ala Pro Ala Glu Leu Glu Ala Leu Leu Leu Thr His Pro Thr Ile
    450                 455                 460

Ser Asp Ala Ala Val Val Pro Met Ile Asp Glu Lys Ala Gly Glu Val
465                 470                 475                 480

Pro Val Ala Phe Val Val Arg Thr Asn Gly Phe Thr Thr Thr Glu Glu
                485                 490                 495

Glu Ile Lys Gln Phe Val Ser Lys Gln Val Val Phe Tyr Lys Arg Ile
            500                 505                 510

Phe Arg Val Phe Phe Val Asp Ala Ile Pro Lys Ser Pro Ser Gly Lys
        515                 520                 525

Ile Leu Arg Lys Asp Leu Arg Ala Arg Ile Ala Ser Gly Asp Leu Pro
    530                 535                 540

Lys
545
```

<210> SEQ ID NO 46
<211> LENGTH: 1638
<212> TYPE: DNA
<213> ORGANISM: artificial
<220> FEATURE:
<223> OTHER INFORMATION: coding sequence for SEQ ID NO: 45

<400> SEQUENCE: 46

```
atgtccggtg attgtgttgc tccaaaggaa gatttgattt tcagatctaa gttgccagat      60

atttacatcc caaagcactt gccattgcac acttactgtt tcgaaaacat ctctaaggtt     120

ggtgacaagt cctgtttgat caacggtgct actggtgaaa ctttcactta ctctcaagtt     180

gaattgttgt ccagaaaggt tgcttctggt ttgaacaagt tgggtattca acaaggtgat     240

accatcatgt tgttgttgcc aaactcccca gaatacttct tcgctttctt gggtgcttct     300

tacagaggtg ctatttctac tatggccaac ccattcttca cttctgctga agttatcaag     360

caattgaagg cttcccaagc taagttgatc attactcaag cttgttacgt tgacaaggtt     420

aaggactacg ctgctgaaaa gaacatccaa atcatttgta tcgatgatgc tccacaagat     480
```

```
tgtttgcact tctccaagtt gatggaagct gatgaatctg aaatgccaga agttgttatc    540

aactctgacg atgtcgtcgc tttgccatac tcttctggta ctactggttt gccaaagggt    600

gttatgttga ctcacaaggg tttggttact tctgttgctc aacaagttga tggtgacaac    660

ccaaacttgt acatgcactc tgaagatgtt atgatctgta tcttgccatt gttccacatt    720

tactctttga acgctgtttt gtgttgtggt ttgagagctg gtgttactat cttgattatg    780

caaaagttcg atattgttcc attcttggaa ttgatccaaa agtacaaggt tactattggt    840

ccattcgttc caccaattgt tttggctatt gctaagtctc cagttgttga taagtacgac    900

ttatcttctg ttagaactgt tatgtctggt gctgctccat tgggtaagga attggaagat    960

gctgttagag ctaagttccc aaacgccaag ttgggtcaag gttacggtat gactgaagct   1020

ggtccagttt tggctatgtg tttggctttc gctaaggaac catacgaaat caagtctggt   1080

gcctgtggta ctgttgttag aaacgctgaa atgaagattg ttgatccaga aaccaacgcc   1140

tctttgccaa gaaaccaaag aggtgaaatt tgtattagag gtgaccaaat tatgaagggt   1200

tacttgaacg atccagaatc tactagaact actatcgacg aagaaggttg gttgcacact   1260

ggtgatatcg gtttcattga cgacgatgat gaattgttca ttgttgatag attgaaggaa   1320

atcatcaagt acaagggttt ccaagttgcc ccagctgaat tggaagcttt gttgttgact   1380

cacccaacca tttccgatgc tgctgttgtt ccaatgatcg atgaaaaggc tggtgaagtt   1440

ccagttgctt tcgttgttag aactaacggt ttcaccacca ctgaagaaga aatcaagcaa   1500

ttcgtttcta agcaagttgt tttctacaag agaatcttca gagttttctt cgttgatgct   1560

attccaaagt ctccatctgg taagattttg agaaaggact tgagagctag aatcgcttcc   1620

ggtgatttgc caaagtaa                                                 1638
```

<210> SEQ ID NO 47
<211> LENGTH: 545
<212> TYPE: PRT
<213> ORGANISM: Petroselinum crispum

<400> SEQUENCE: 47

```
Met Ser Gly Asp Cys Val Ala Pro Lys Glu Asp Leu Ile Phe Arg Ser
1               5                   10                  15

Lys Leu Pro Asp Ile Tyr Ile Pro Lys His Leu Pro Leu His Thr Tyr
            20                  25                  30

Cys Phe Glu Asn Ile Ser Lys Val Gly Asp Lys Ser Cys Leu Ile Asn
        35                  40                  45

Gly Ala Thr Gly Glu Thr Phe Thr Tyr Ser Gln Val Glu Leu Leu Ser
    50                  55                  60

Arg Lys Val Ala Ser Gly Leu Asn Lys Leu Gly Ile Gln Gln Gly Asp
65                  70                  75                  80

Thr Ile Met Leu Leu Leu Pro Asn Ser Pro Glu Tyr Phe Phe Ala Phe
                85                  90                  95

Leu Gly Ala Ser Tyr Arg Gly Ala Ile Ser Thr Met Ala Asn Pro Phe
            100                 105                 110

Phe Thr Ser Ala Glu Val Ile Lys Gln Leu Lys Ala Ser Leu Ala Lys
        115                 120                 125

Leu Ile Ile Thr Gln Ala Cys Tyr Val Asp Lys Val Lys Asp Tyr Ala
    130                 135                 140

Ala Glu Lys Asn Ile Gln Ile Ile Cys Ile Asp Asp Ala Pro Gln Asp
145                 150                 155                 160
```

```
Cys Leu His Phe Ser Lys Leu Met Glu Ala Asp Glu Ser Glu Met Pro
                165                 170                 175

Glu Val Val Ile Asp Ser Asp Asp Val Val Ala Leu Pro Tyr Ser Ser
            180                 185                 190

Gly Thr Thr Gly Leu Pro Lys Gly Val Met Leu Thr His Lys Gly Leu
        195                 200                 205

Val Thr Ser Val Ala Gln Gln Val Asp Gly Asp Asn Pro Asn Leu Tyr
    210                 215                 220

Met His Ser Glu Asp Val Met Ile Cys Ile Leu Pro Leu Phe His Ile
225                 230                 235                 240

Tyr Ser Leu Asn Ala Val Leu Cys Cys Gly Leu Arg Ala Gly Val Thr
                245                 250                 255

Ile Leu Ile Met Gln Lys Phe Asp Ile Val Pro Phe Leu Glu Leu Ile
            260                 265                 270

Gln Lys Tyr Lys Val Thr Ile Gly Pro Phe Val Pro Pro Ile Val Leu
        275                 280                 285

Ala Ile Ala Lys Ser Pro Val Val Asp Lys Tyr Asp Leu Ser Ser Val
    290                 295                 300

Arg Thr Val Met Ser Gly Ala Ala Pro Leu Gly Lys Glu Leu Glu Asp
305                 310                 315                 320

Ala Val Arg Ala Lys Phe Pro Asn Ala Lys Leu Gly Gln Gly Tyr Gly
                325                 330                 335

Met Thr Glu Ala Gly Pro Val Leu Ala Met Cys Leu Ala Phe Ala Lys
            340                 345                 350

Glu Pro Tyr Glu Ile Lys Ser Gly Ala Cys Gly Thr Val Val Arg Asn
        355                 360                 365

Ala Glu Met Lys Ile Val Asp Pro Glu Thr Asn Ala Ser Leu Pro Arg
    370                 375                 380

Asn Gln Arg Gly Glu Ile Cys Ile Arg Gly Asp Gln Ile Met Lys Gly
385                 390                 395                 400

Tyr Leu Asn Asp Pro Glu Ser Thr Arg Thr Thr Ile Asp Glu Glu Gly
                405                 410                 415

Trp Leu His Thr Gly Asp Ile Gly Phe Ile Asp Asp Asp Asp Glu Leu
            420                 425                 430

Phe Ile Val Asp Arg Leu Lys Glu Ile Ile Lys Tyr Lys Gly Phe Gln
        435                 440                 445

Val Ala Pro Ala Glu Leu Glu Ala Leu Leu Leu Thr His Pro Thr Ile
    450                 455                 460

Ser Asp Ala Ala Val Val Pro Met Ile Asp Glu Lys Ala Gly Glu Val
465                 470                 475                 480

Pro Val Ala Phe Val Val Arg Thr Asn Gly Phe Thr Thr Thr Glu Glu
                485                 490                 495

Glu Ile Lys Gln Phe Val Ser Lys Gln Val Val Phe Tyr Lys Arg Ile
            500                 505                 510

Phe Arg Val Phe Phe Val Asp Ala Ile Pro Lys Ser Pro Ser Gly Lys
        515                 520                 525

Ile Leu Arg Lys Asp Leu Arg Ala Lys Ile Ala Ser Gly Asp Leu Pro
    530                 535                 540

Lys
545
```

<210> SEQ ID NO 48
<211> LENGTH: 1638
<212> TYPE: DNA

<213> ORGANISM: artificial
<220> FEATURE:
<223> OTHER INFORMATION: coding sequence for SEQ ID NO: 47

<400> SEQUENCE: 48
atgtccggtg actgtgttgc tccaaaggaa gatttgattt tcagatctaa gttgccagat 60
atttacatcc caaagcactt gccattgcac acttactgtt tcgaaaacat ctctaaggtt 120
ggtgacaagt cctgtttgat caacggtgct actggtgaaa ctttcactta ctctcaagtt 180
gaattgttgt ccagaaaggt tgcttctggt ttgaacaagt tgggtattca acaaggtgat 240
accatcatgt tgttgttgcc aaactcccca gaatacttct tcgctttctt gggtgcttct 300
tacagaggtg ctatttctac tatggccaac ccattcttca cttctgctga agttatcaag 360
caattgaagg cttccttggc taagttgatc attactcaag cttgttacgt tgacaaggtt 420
aaggactacg ctgctgaaaa gaacatccaa atcatttgta tcgatgatgc tccacaagat 480
tgtttgcact tctccaagtt gatggaagct gatgaatctg aaatgccaga agttgttatc 540
gattctgacg atgtcgtcgc tttgccatac tcttctggta ctactggttt gccaaagggt 600
gttatgttga cccacaaggg tttggttact tctgttgctc aacaagttga tggtgacaac 660
ccaaacttgt acatgcactc tgaagatgtt atgatctgta tcttgccatt gttccacatt 720
tactctttga acgctgtttt gtgttgtggt ttgagagctg gtgttactat cttgattatg 780
caaaagttcg atattgttcc attcttggaa ttgatccaaa agtacaaggt tactattggt 840
ccattcgttc caccaattgt tttggctatt gctaagtctc cagttgttga taagtacgac 900
ttatcttctg ttagaactgt tatgtctggt gctgctccat tgggtaagga attggaagat 960
gctgttagag ctaagttccc aaacgccaag ttgggtcaag gttacggtat gactgaagct 1020
ggtccagttt tggctatgtg tttggctttc gctaaggaac catacgaaat caagtctggt 1080
gcctgtggta ctgttgttag aaacgctgaa atgaagattg ttgatccaga aaccaacgcc 1140
tctttgccaa gaaaccaaag aggtgaaatt tgtattagag gtgaccaaat tatgaagggt 1200
tacttgaacg atccagaatc tactagaact actatcgacg aagaaggttg gttgcacact 1260
ggtgatatcg gtttcattga cgacgatgat gaattgttca ttgttgatag attgaaggaa 1320
atcatcaagt acaagggttt ccaagttgcc ccagctgaat tggaagcttt gttgttgact 1380
cacccaacca tttccgatgc tgctgttgtt ccaatgatcg atgaaaaggc tggtgaagtt 1440
ccagttgctt tcgttgttag aactaacggt ttcaccacca ctgaagaaga aatcaagcaa 1500
ttcgtttcta agcaagttgt tttctacaag agaatcttca gagttttctt cgttgatgct 1560
attccaaagt ctccatctgg taagattttg agaaaggact tgagagctaa gatcgcttcc 1620
ggtgatttgc caaagtaa 1638

<210> SEQ ID NO 49
<211> LENGTH: 579
<212> TYPE: PRT
<213> ORGANISM: Streptomyces clavuligerus

<400> SEQUENCE: 49

Met Ser Ala Ser Thr Pro Ser Pro Gly Pro Ser Gly Thr Pro Ser Gly
1               5                   10                  15

Thr Pro Pro Ser Gly Pro Ser Gly Thr Pro Ser Pro Gly Pro Ala Gly
            20                  25                  30

Ala Gly Thr Ala Pro Val Phe Arg Ser Arg Tyr Pro Asp Ile Glu Pro
        35                  40                  45

-continued

```
Val Ser Glu Pro Leu His Glu Ala Val Leu Gly Arg Ala Ala Gly Tyr
    50                  55                  60

Gly Ser Glu Pro Ala Leu Val Asp Gly Leu Thr Gly Ala Val Val Ser
65                  70                  75                  80

Tyr Ala Arg Leu Asp Arg Asp His Arg Arg Ile Ala Ala Ala Leu Ala
                85                  90                  95

Ala Ala Gly Val Arg Lys Gly Asp Val Val Ala Leu His Ser Pro Asn
            100                 105                 110

Ser Thr Gly Tyr Pro Ala Val Leu Tyr Gly Ala Leu Arg Ala Gly Ala
        115                 120                 125

Thr Val Thr Thr Ala His Pro Leu Ala Thr Ala Glu Glu Leu Ala Arg
    130                 135                 140

Gln Leu Arg Asp Ser Ala Ala Arg Trp Ile Val Thr Ala Ala Pro Cys
145                 150                 155                 160

Leu Glu Thr Ala Arg Arg Ala Ala Glu Leu Thr Pro Gly Ile Gly Glu
                165                 170                 175

Ile Phe Val Phe Asp Arg Ala Glu Gly His Thr Gly Val Ala Ala Met
            180                 185                 190

Leu Asp Ser Thr Ala Pro Glu Pro Ala Val Pro Val Asp Pro Asp Gln
        195                 200                 205

Asp Val Ala Leu Leu Pro Tyr Ser Ser Gly Thr Thr Gly Thr Pro Lys
    210                 215                 220

Gly Val Met Leu Thr His Arg Ser Leu Val Thr Asn Leu Val Gln Ala
225                 230                 235                 240

His Arg Leu Ile Pro Leu Arg Pro Gly Asp Arg Val Leu Ala Val Leu
                245                 250                 255

Pro Phe Phe His Ile Tyr Gly Leu Val Gly Leu Met Ser Ala Pro Leu
            260                 265                 270

Arg Asn Gly Ala Thr Val Val Val Leu Pro Arg Phe Asp Leu Glu Gly
        275                 280                 285

Phe Leu Ala Ala Val Glu Lys His Arg Val Thr Thr Leu Tyr Val Ala
    290                 295                 300

Pro Pro Ile Val Leu Ala Leu Ala Lys His Pro Ala Val Ala Arg Tyr
305                 310                 315                 320

Asp Leu Ser Ser Val Arg His Val Phe Ser Ala Ala Ala Pro Leu Asp
                325                 330                 335

Ala Glu Ile Ala Ala Ala Cys Ala Ala Arg Val Gly Val Pro Leu Val
            340                 345                 350

Arg Gln Ala Tyr Gly Met Thr Glu Leu Ser Pro Gly Cys Tyr Ala Val
        355                 360                 365

Pro Leu Asp Glu Pro Ala Pro Pro Pro Gly Thr Val Gly Leu Leu Phe
    370                 375                 380

Pro Ser Thr Glu Met Arg Leu Leu Arg Leu Asp Asp Pro Gly Arg Cys
385                 390                 395                 400

Val Gly Pro Gly Glu Asp Gly Glu Ile Ala Ile Arg Gly Pro Gln Val
                405                 410                 415

Met Lys Gly Tyr Leu Gly Arg Pro Glu Ala Thr Ala Glu Met Ile Asp
            420                 425                 430

Ala Asp Gly Trp Leu Arg Thr Gly Asp Val Gly Arg Val Asp Ala Asp
        435                 440                 445

Gly Trp Leu His Val Val Asp Arg Val Lys Glu Leu Ile Lys Tyr Lys
    450                 455                 460

Gly Phe Gln Val Ala Pro Ala Glu Leu Glu Ala Leu Leu Leu Thr His
```

-continued

```
465                 470                 475                 480

Gly Gly Ile Ala Asp Ala Ala Val Ile Gly Val Tyr Asp Glu Asp Glu
                485                 490                 495

Gly Thr Glu Ile Pro His Ala Phe Val Val Arg Arg Pro Gly Gly Ala
            500                 505                 510

Gly Asp Ser Leu Thr Ala Ala Asp Val Ala Ala His Val Ala Ala Arg
        515                 520                 525

Val Ser Pro Tyr Lys Lys Val Arg Arg Val Ser Phe Val Ser Gly Val
    530                 535                 540

Pro Arg Ala Ala Ser Gly Lys Ile Leu Arg Arg Glu Leu Arg Ala Ala
545                 550                 555                 560

Arg Arg Ser Pro Arg Gly Thr Asp Pro Gly Asp Glu Asp Arg Glu Gly
                565                 570                 575

Ala Thr Pro


<210> SEQ ID NO 50
<211> LENGTH: 1740
<212> TYPE: DNA
<213> ORGANISM: artificial
<220> FEATURE:
<223> OTHER INFORMATION: coding sequence for SEQ ID NO: 49

<400> SEQUENCE: 50

atgtccgctt ctactccatc tccaggtcca tctggtaccc catccggtac tccaccatcc      60

ggtccatctg gtactccatc cccaggtcca gctggtgccg gtaccgctcc agtattcaga     120

tctagatacc cagacatcga accagtttct gaaccattgc acgaagctgt tttgggtaga     180

gccgccggtt acggttccga accagccttg gtcgacggtt tgaccggtgc cgtcgtatct     240

tacgctagat tggacagaga tcacagaaga atcgccgccg ccttggccgc cgctggtgtc     300

agaaagggtg acgtcgtcgc cttgcactct ccaaactcta ccggttaccc agccgtcttg     360

tacggtgcct tgagagccgg tgccaccgtt accactgctc acccattggc tactgctgaa     420

gaattggcca gacaattgag agactctgcc gccagatgga tcgttaccgc cgccccatgt     480

ttggaaaccg ccagaagagc cgccgaattg accccaggta tcggtgaaat cttcgtattc     540

gacagagccg aaggtcacac cggtgttgcc gctatgttgg actccaccgc tccagaacca     600

gccgtcccag tcgacccaga ccaagacgtc gctttgttgc catactcctc tggtaccacc     660

ggtaccccaa agggtgttat gttgactcac agatccttgg tcaccaactt ggtccaagcc     720

cacagattga tcccattgag gccaggtgac agagtcttgg ccgttttgcc attcttccac     780

atctacggtt tggtcggttt gatgtctgcc ccattgagaa acggtgctac cgtcgtcgtc     840

ttgccaagat tcgacttgga aggtttcttg gctgccgtcg aaaagcacag agtcaccact     900

ttgtacgttg ccccaccaat cgttttggct ttggccaagc acccagctgt tgccagatac     960

gacttgtcct ctgtcagaca cgtattctct gccgccgccc cattggacgc tgaaatcgct    1020

gctgcctgtg ccgccagagt cggtgttcca ttggtcagac aagcttacgg tatgaccgaa    1080

ttgtctccag gttgttacgc cgtcccattg gacgaaccag ccccaccacc aggtactgtc    1140

ggtttgttgt tcccatccac cgaaatgaga ttgttgagat tggacgaccc aggtagatgt    1200

gtcggtccag gtgaggacgg tgaaatcgcc atcagaggtc cacaagtcat gaagggttac    1260

ttgggtagac cagaagccac cgccgaaatg atcgacgctg atggttggtt gagaaccggt    1320

gacgtcggta gagtcgacgc tgacggttgg ttgcacgtcg ttgacagagt taaggaattg    1380

atcaagtaca agggtttcca agtcgctcca gccgaattgg aagctttgtt gttgacccac    1440
```

```
ggtggtatcg ctgacgccgc cgttatcggt gtttacgacg aggacgaagg tactgaaatc   1500

ccacacgctt tcgttgtcag aaggccaggt ggtgctggtg actccttgac cgccgccgac   1560

gtcgccgccc acgtcgccgc tagagtctcc ccatacaaga aggtcagaag agtctctttc   1620

gtatccggtg ttccaagagc cgcttctggt aagatcttga gaagagaatt gagagccgct   1680

agaagatccc caagaggtac tgacccaggt gacgaggaca gagaaggtgc cactccataa   1740


<210> SEQ ID NO 51
<211> LENGTH: 400
<212> TYPE: PRT
<213> ORGANISM: Hordeum vulgare

<400> SEQUENCE: 51

Met Ser Ala Ala Val Arg Leu Lys Glu Val Arg Met Ala Gln Arg Ala
1               5                   10                  15

Glu Gly Leu Ala Thr Val Leu Ala Ile Gly Thr Ala Val Pro Ala Asn
            20                  25                  30

Cys Val Tyr Gln Ala Thr Tyr Pro Asp Tyr Tyr Phe Arg Val Thr Lys
        35                  40                  45

Ser Glu His Leu Ala Asp Leu Lys Glu Lys Phe Gln Arg Met Cys Asp
    50                  55                  60

Lys Ser Met Ile Arg Lys Arg His Met His Leu Thr Glu Glu Ile Leu
65                  70                  75                  80

Ile Lys Asn Pro Lys Ile Cys Ala His Met Glu Thr Ser Leu Asp Ala
                85                  90                  95

Arg His Ala Ile Ala Leu Val Glu Val Pro Lys Leu Gly Gln Gly Ala
            100                 105                 110

Ala Glu Lys Ala Ile Lys Glu Trp Gly Gln Pro Leu Ser Lys Ile Thr
        115                 120                 125

His Leu Val Phe Cys Thr Thr Ser Gly Val Asp Met Pro Gly Ala Asp
    130                 135                 140

Tyr Gln Leu Thr Lys Leu Leu Gly Leu Ser Pro Thr Val Lys Arg Leu
145                 150                 155                 160

Met Met Tyr Gln Gln Gly Cys Phe Gly Gly Ala Thr Val Leu Arg Leu
                165                 170                 175

Ala Lys Asp Ile Ala Glu Asn Asn Arg Gly Ala Arg Val Leu Val Val
            180                 185                 190

Cys Ser Glu Ile Thr Ala Met Ala Phe Arg Gly Pro Cys Lys Ser His
        195                 200                 205

Leu Asp Ser Leu Val Gly His Ala Leu Phe Gly Asp Gly Ala Ala Ala
    210                 215                 220

Ala Ile Ile Gly Ala Asp Pro Asp Gln Leu Asp Glu Gln Pro Val Phe
225                 230                 235                 240

Gln Leu Val Ser Ala Ser Gln Thr Ile Leu Pro Glu Ser Glu Gly Ala
                245                 250                 255

Ile Asp Gly His Leu Thr Glu Ala Gly Leu Thr Ile His Leu Leu Lys
            260                 265                 270

Asp Val Pro Gly Leu Ile Ser Glu Asn Ile Glu Gln Ala Leu Glu Asp
        275                 280                 285

Ala Phe Glu Pro Leu Gly Ile His Asn Trp Asn Ser Ile Phe Trp Ile
    290                 295                 300

Ala His Pro Gly Gly Pro Ala Ile Leu Asp Arg Val Glu Asp Arg Val
305                 310                 315                 320
```

-continued

```
Gly Leu Asp Lys Lys Arg Met Arg Ala Ser Arg Glu Val Leu Ser Glu
                325                 330                 335

Tyr Gly Asn Met Ser Ser Ala Ser Val Leu Phe Val Leu Asp Val Met
            340                 345                 350

Arg Lys Ser Ser Ala Lys Asp Gly Leu Ala Thr Thr Gly Glu Gly Lys
        355                 360                 365

Asp Trp Gly Val Leu Phe Gly Phe Gly Pro Gly Leu Thr Val Glu Thr
    370                 375                 380

Leu Val Leu His Ser Val Pro Val Pro Val Pro Thr Ala Ala Ser Ala
385                 390                 395                 400
```

<210> SEQ ID NO 52
<211> LENGTH: 1203
<212> TYPE: DNA
<213> ORGANISM: artificial
<220> FEATURE:
<223> OTHER INFORMATION: coding sequence for SEQ ID NO: 51

<400> SEQUENCE: 52

```
atgtccgctg ctgttagatt gaaggaagtt agaatggctc aaagagctga aggtttggct     60

actgttttgg ccattggtac cgccgttcca gccaactgtg tttaccaagc tacctaccca    120

gactactact tcagagtcac taagtctgaa cacttggctg acttgaagga aaagttccaa    180

agaatgtgtg acaagtccat gatcagaaag agacacatgc acttgaccga agaaatcttg    240

attaagaacc caaagatctg tgctcacatg gaaacctctt tggacgctag acacgccatt    300

gctttggtcg aagtcccaaa gttgggtcaa ggtgctgctg aaaaggctat caaggaatgg    360

ggtcaaccat tgtccaagat cacccacttg gttttctgta ctacctctgg tgtcgacatg    420

ccaggtgccg actaccaatt gaccaagttg ttgggtttgt ccccaactgt taagagattg    480

atgatgtacc aacaaggttg tttcggtggt gccactgttt tgagattggc caaggacatc    540

gctgaaaaca acagaggtgc tagagttttg gttgtctgtt ctgaaatcac cgccatggcc    600

ttcagaggtc catgtaagtc ccacttggac tctttggtcg gtcacgcttt gttcggtgat    660

ggtgctgctg ctgccatcat cggtgctgac ccagaccaat tggacgaaca accagttttc    720

caattggttt ctgcttctca aaccatcttg ccagaatctg aaggtgccat cgacggtcac    780

ttgactgaag ctggtttgac catccacttg ttgaaggacg ttccaggttt gatctctgaa    840

aacatcgaac aagctttgga agatgctttc gaaccattgg gtatccacaa ctggaactcc    900

atcttctgga ttgctcaccc aggtggtcca gccatcttgg acagagtcga agatagagtt    960

ggtttggaca agaagagaat gagagcttct agagaagttt tgtctgaata cggtaacatg   1020

tcctctgctt ctgttttgtt cgtcttggac gttatgagaa agtcatccgc caaggatggt   1080

ttggccacta ctggtgaagg taaggactgg ggtgtcttgt tcggtttcgg tccaggtttg   1140

accgtcgaaa ctttggtctt gcactctgtc ccagtcccag tcccaaccgc cgcttctgct   1200

taa                                                                 1203
```

<210> SEQ ID NO 53
<211> LENGTH: 392
<212> TYPE: PRT
<213> ORGANISM: Citrus sinensis

<400> SEQUENCE: 53

```
Met Ser Ala Thr Val Gln Glu Ile Arg Asn Ala Gln Arg Ala Asp Gly
1               5                   10                  15

Pro Ala Thr Val Leu Ala Ile Gly Thr Ala Thr Pro Ala His Ser Val
```

```
            20                  25                  30

Asn Gln Ala Asp Tyr Pro Asp Tyr Tyr Phe Arg Ile Thr Lys Ser Glu
        35                  40                  45

His Met Thr Glu Leu Lys Glu Lys Phe Lys Arg Met Cys Asp Lys Ser
    50                  55                  60

Met Ile Lys Lys Arg Tyr Met Tyr Leu Thr Glu Glu Ile Leu Lys Glu
65                  70                  75                  80

Asn Pro Asn Met Cys Ala Tyr Met Ala Pro Ser Leu Asp Ala Arg Gln
                85                  90                  95

Asp Ile Val Val Val Glu Val Pro Lys Leu Gly Lys Glu Ala Ala Thr
            100                 105                 110

Lys Ala Ile Lys Glu Trp Gly Gln Pro Lys Ser Lys Ile Thr His Leu
        115                 120                 125

Ile Phe Cys Thr Thr Ser Gly Val Asp Met Pro Gly Ala Asp Tyr Gln
    130                 135                 140

Leu Thr Lys Leu Ile Gly Leu Arg Pro Ser Val Lys Arg Phe Met Met
145                 150                 155                 160

Tyr Gln Gln Gly Cys Phe Ala Gly Gly Thr Val Leu Arg Leu Ala Lys
                165                 170                 175

Asp Leu Ala Glu Asn Asn Lys Gly Ala Arg Val Leu Val Val Cys Ser
            180                 185                 190

Glu Ile Thr Ala Val Thr Phe Arg Gly Pro Ala Asp Thr His Leu Asp
        195                 200                 205

Ser Leu Val Gly Gln Ala Leu Phe Gly Asp Gly Ala Ala Ala Val Ile
    210                 215                 220

Val Gly Ala Asp Pro Asp Thr Ser Val Glu Arg Pro Leu Tyr Gln Leu
225                 230                 235                 240

Val Ser Thr Ser Gln Thr Ile Leu Pro Asp Ser Asp Gly Ala Ile Asp
                245                 250                 255

Gly His Leu Arg Glu Val Gly Leu Thr Phe His Leu Leu Lys Asp Val
            260                 265                 270

Pro Gly Leu Ile Ser Lys Asn Ile Glu Lys Ser Leu Ser Glu Ala Phe
        275                 280                 285

Ala Pro Leu Gly Ile Ser Asp Trp Asn Ser Ile Phe Trp Ile Ala His
    290                 295                 300

Pro Gly Gly Pro Ala Ile Leu Asp Gln Val Glu Ser Lys Leu Gly Leu
305                 310                 315                 320

Lys Gly Glu Lys Leu Lys Ala Thr Arg Gln Val Leu Ser Glu Tyr Gly
                325                 330                 335

Asn Met Ser Ser Ala Cys Val Leu Phe Ile Leu Asp Glu Met Arg Lys
            340                 345                 350

Lys Ser Val Glu Glu Ala Lys Ala Thr Thr Gly Glu Gly Leu Asp Trp
        355                 360                 365

Gly Val Leu Phe Gly Phe Gly Pro Gly Leu Thr Val Glu Thr Val Val
    370                 375                 380

Leu His Ser Val Pro Ile Lys Ala
385                 390
```

<210> SEQ ID NO 54
<211> LENGTH: 1179
<212> TYPE: DNA
<213> ORGANISM: artificial
<220> FEATURE:
<223> OTHER INFORMATION: coding sequence for SEQ ID NO: 53

<400> SEQUENCE: 54
atgtccgcta ccgttcaaga aatcagaaac gctcaaagag ccgacggtcc agccaccgtc 60
ttggccatcg gtactgccac tccagcccac tctgtcaacc aagctgatta cccagactac 120
tacttcagaa tcactaagtc tgaacacatg actgaattga aggaaaagtt caagagaatg 180
tgtgacaagt ctatgattaa gaagagatac atgtacttga ctgaagaaat tttgaaggaa 240
aacccaaaca tgtgtgctta catggctcca tctttggacg ctagacaaga cattgttgtt 300
gtcgaagttc caaagttggg taaggaagct gctactaagg ccatcaagga atggggtcaa 360
ccaaagtcta agatcaccca cttgatcttc tgtaccacct ccggtgtcga catgccaggt 420
gccgactacc aattgaccaa gttgatcggt ttaagaccat ccgtcaagag attcatgatg 480
taccaacaag gttgtttcgc cggtggtact gttttgagat tggctaagga cttggctgaa 540
aacaacaagg gtgctagagt tttggttgtc tgttctgaaa tcactgctgt cactttcaga 600
ggtccagccg atactcactt ggattctttg gttggtcaag ctttgttcgg tgatggtgct 660
gctgctgtta tcgttggtgc cgatccagac acttctgtcg aaagaccatt gtaccaattg 720
gtttctactt ctcaaactat cttgccagac tctgacggtg ctattgacgg tcacttgaga 780
gaagtcggtt tgactttcca cttgttgaag gacgtcccag gtttgatctc taagaacatc 840
gaaaagtctt tgtctgaagc tttcgcccca ttgggtatct ctgactggaa ctctatcttc 900
tggatcgctc acccaggtgg tccagctatt ttggaccaag ttgaatctaa gttgggtttg 960
aagggtgaaa agttgaaggc cactagacaa gttttgtctg aatacggtaa catgtcatct 1020
gcttgtgtct tgttcatctt ggacgaaatg agaaagaagt ctgttgaaga agctaaggcc 1080
accaccggtg aaggtttgga ttggggtgtt ttgttcggtt tcggtccagg tttgaccgtc 1140
gaaaccgttg ttttgcactc tgtcccaatc aaggcttaa 1179

<210> SEQ ID NO 55
<211> LENGTH: 391
<212> TYPE: PRT
<213> ORGANISM: Citrus sinensis

<400> SEQUENCE: 55

Met Ser Leu Thr Val Asp Glu Val Arg Lys Ala Gln Arg Ala Glu Gly
1 5 10 15

Pro Ala Thr Ile Met Ala Ile Gly Thr Ala Thr Pro Pro Asn Cys Val
20 25 30

Asp Gln Ser Thr Tyr Pro Asp Tyr Tyr Phe Arg Ile Thr Asn Ser Glu
35 40 45

His Met Thr Asp Leu Lys Glu Lys Phe Lys Arg Met Cys Asp Lys Ser
50 55 60

Met Ile Lys Lys Arg Tyr Met Tyr Leu Thr Glu Glu Ile Leu Lys Glu
65 70 75 80

Asn Pro Asn Val Cys Ala Tyr Met Ala Pro Ser Leu Asp Thr Arg Gln
85 90 95

Asp Met Val Val Val Glu Val Pro Arg Leu Gly Lys Glu Ala Ala Thr
100 105 110

Lys Ala Ile Lys Glu Trp Gly Gln Pro Lys Ser Lys Ile Thr His Leu
115 120 125

Val Phe Cys Thr Thr Ser Gly Val Asp Met Pro Gly Ala Asp Tyr Arg
130 135 140

Leu Thr Lys Leu Leu Gly Leu Arg Pro Ser Val Lys Arg Leu Met Met
145 150 155 160

```
Tyr Gln Gln Gly Cys Phe Ala Gly Gly Thr Val Leu Arg Leu Ala Lys
                165                 170                 175

Asp Leu Ala Glu Asn Asn Lys Gly Ala Arg Val Leu Val Val Cys Ser
            180                 185                 190

Glu Ile Thr Ala Val Thr Phe Arg Gly Pro Ser Asp Thr His Leu Asp
        195                 200                 205

Ser Leu Val Gly Gln Ala Leu Phe Gly Asp Gly Ala Ala Ala Ile Ile
    210                 215                 220

Ile Gly Ala Asp Pro Ile Pro Glu Ile Glu Lys Pro Met Phe Glu Leu
225                 230                 235                 240

Val Ser Thr Ala Gln Thr Ile Leu Pro Asp Ser Asp Gly Ser Ile Asp
                245                 250                 255

Gly His Leu Arg Glu Val Gly Leu Thr Phe His Leu Leu Lys Asp Val
            260                 265                 270

Pro Gly Leu Ile Ser Lys Asn Ile Gln Lys Ser Leu Thr Glu Ala Phe
        275                 280                 285

Lys Pro Leu Gly Ile Ser Asp Trp Asn Ser Ile Phe Trp Ile Ala His
    290                 295                 300

Pro Gly Gly Pro Thr Ile Leu Asp Gln Val Glu Glu Lys Leu Gly Leu
305                 310                 315                 320

Lys Pro Glu Lys Leu Arg Ala Thr Arg His Val Leu Ser Glu Tyr Gly
                325                 330                 335

Asn Met Ser Ser Ala Cys Val Leu Phe Ile Leu Asp Glu Met Arg Lys
            340                 345                 350

Lys Ser Ala Glu Asp Gly Leu Glu Thr Ala Gly Glu Gly Leu Glu Trp
        355                 360                 365

Gly Val Leu Phe Gly Phe Gly Pro Gly Leu Thr Val Glu Thr Val Val
    370                 375                 380

Leu His Ser Val Ala Ala Ala
385                 390


<210> SEQ ID NO 56
<211> LENGTH: 1176
<212> TYPE: DNA
<213> ORGANISM: artificial
<220> FEATURE:
<223> OTHER INFORMATION: coding sequence for SEQ ID NO: 55

<400> SEQUENCE: 56

atgtccttga ccgtcgatga agttagaaag gctcaaagag ccgaaggtcc agccactatc      60

atggccattg gtactgctac cccaccaaac tgtgttgatc aatctactta cccagattac     120

tacttcagaa tcactaactc tgaacacatg actgatttga aggaaaagtt caagagaatg     180

tgtgacaagt ccatgatcaa gaagagatac atgtacttga ctgaagaaat cttgaaggaa     240

aacccaaacg tttgtgctta catggctcca tctttggata ctagacaaga tatggttgtt     300

gttgaagttc caagattggg taaggaagct gccaccaagg ccattaagga atggggtcaa     360

ccaaagtcca agatcaccca cttggtattc tgtaccactt ctggtgttga catgccaggt     420

gccgattaca gattgactaa gttgttgggt ttaagaccat ccgtcaagag attgatgatg     480

taccaacaag gttgtttcgc cggtggtact gttttgagat tggccaagga cttggccgaa     540

aacaacaagg gtgctagagt cttggttgtt tgttccgaaa tcaccgctgt tactttcaga     600

ggtccatctg acacccactt ggattctttg gttggtcaag ccttgttcgg tgatggtgct     660

gctgctatta tcattggtgc cgacccaatc ccagaaatcg aaaagccaat gttcgaattg     720
```

```
gtatctactg cccaaactat cttgccagat tctgatggtt ctatcgacgg tcacttgaga    780

gaagttggtt tgaccttcca cttgttgaag gatgttccag gtttgatttc taagaacatc    840

caaaagtctt tgaccgaagc tttcaagcca ttgggtatct ctgactggaa ctctattttc    900

tggatcgctc acccaggtgg tccaactatt ttggaccaag tcgaagaaaa gttgggtttg    960

aagccagaaa agttgagagc cactagacac gttttgtctg aatacggtaa catgtcatct   1020

gcttgtgttt tgttcatttt ggacgaaatg agaaagaagt ctgctgaaga tggtttggaa   1080

accgctggtg aaggtttgga atggggtgtc ttgttcggtt tcggtccagg tttgactgtt   1140

gaaaccgttg tcttgcactc tgttgccgct gcttaa                             1176


<210> SEQ ID NO 57
<211> LENGTH: 352
<212> TYPE: PRT
<213> ORGANISM: Streptomyces clavuligerus

<400> SEQUENCE: 57

Met Ser Ala Val Leu Cys Lys Pro Ala Ile Ala Val Pro Asp His Ile
1               5                   10                  15

Ile Thr Asn Glu Glu Thr Leu Glu Leu Ala Arg Arg Leu His Ser Asp
            20                  25                  30

His Pro Gln Leu Ala Leu Ala Cys Arg Leu Ile Glu His Thr Gly Val
        35                  40                  45

Arg Lys Arg His Leu Ile Gln Pro Ile Asp Glu Val Leu Lys His Pro
    50                  55                  60

Gly Leu Asp Ala Arg Ser Ala Thr Tyr Glu Thr Glu Ser Lys Ala Arg
65                  70                  75                  80

Val Pro Ser Val Val Arg Arg Ala Leu Asp Gln Ala Glu Leu Glu Pro
                85                  90                  95

Asp Gln Ile Asp Leu Ile Ile Tyr Val Ser Cys Thr Gly Phe Met Met
            100                 105                 110

Pro Ser Leu Ala Ser Trp Leu Val Asn Thr Met Gly Phe Arg Ala Asp
        115                 120                 125

Thr Arg Gln Leu Pro Ile Ala Gln Leu Gly Cys Ala Ala Gly Gly Ala
    130                 135                 140

Ala Val Asn Arg Ala His Asp Phe Cys Thr Ala Tyr Pro Gly Thr Asn
145                 150                 155                 160

Val Leu Ile Val Ala Cys Glu Phe Cys Ser Leu Cys Tyr Gln Pro Thr
                165                 170                 175

Asp Leu Gly Ile Gly Ser Leu Leu Ser Asn Gly Leu Phe Gly Asp Gly
            180                 185                 190

Ile Ala Ala Ala Val Val Arg Gly Glu Glu Gly Thr Gly Met Arg Leu
        195                 200                 205

Glu Arg Asn Gly Thr Tyr Leu Ile Pro His Thr Glu Glu Trp Ile Ser
    210                 215                 220

Tyr Ala Val Arg Ser Thr Gly Phe His Phe Gln Leu Asp Lys Arg Val
225                 230                 235                 240

Pro Gly Thr Met Glu Pro Leu Ser Pro Ala Leu Arg Ala Leu Ala Glu
                245                 250                 255

Gln His Gln Trp Asn Ala Gly Lys Leu Asp Phe Tyr Ile Ile His Ala
            260                 265                 270

Gly Gly Pro Arg Ile Leu Asp Asp Leu Ser Arg Phe Leu Asp Val Pro
        275                 280                 285
```

Pro Gly Ala Phe Arg His Ser Arg Ala Thr Leu Thr Glu Tyr Gly Asn
    290                 295                 300

Ile Ala Ser Ala Val Val Leu Asp Ala Leu Gly Arg Leu Phe Asp Glu
305                 310                 315                 320

Gln Ser Ala Leu Asp Gly His His Gly Met Leu Ala Gly Phe Gly Pro
                325                 330                 335

Gly Ile Ile Ala Glu Met Ser Leu Gly Thr Trp Val Ser Pro Glu Ser
            340                 345                 350

<210> SEQ ID NO 58
<211> LENGTH: 1059
<212> TYPE: DNA
<213> ORGANISM: artificial
<220> FEATURE:
<223> OTHER INFORMATION: coding sequence for SEQ ID NO: 57

<400> SEQUENCE: 58
atgtccgctg ttttgtgtaa gccagccatc gccgttccag accacatcat caccaacgaa      60
gaaaccttgg aattggctag aagattgcac tctgaccacc cacaattggc tttggcttgt     120
agattgatcg aacacactgg tgttagaaag agacacttga tccaaccaat cgacgaagtt     180
ttgaagcacc caggtttgga cgctagatct gccacctacg aaaccgaatc caaggctaga     240
gttccatctg ttgttagaag agctttggac caagctgaat tggaaccaga tcaaatcgac     300
ttgatcatct acgtatcctg taccggtttc atgatgccat ccttggcctc ctggttggtc     360
aacaccatgg gtttcagagc tgacaccaga caattgccaa tcgcccaatt gggttgtgct     420
gctggtggtg ctgccgtcaa cagagcccac gacttctgta ccgcctaccc aggtaccaac     480
gtcttgatcg ttgcctgtga attctgttct ttgtgttacc aaccaaccga tttgggtatc     540
ggttctttgt tgtccaacgg tttgttcggt gacggtatcg ccgccgctgt tgtcagaggt     600
gaagaaggta ccggtatgag attggaaaga aacggtacct acttgatccc acacaccgaa     660
gaatggatct cctacgctgt tagatccacc ggtttccact tccaattgga caagagagtc     720
ccaggtacca tggaaccatt gtctccagct ttgagagcct tggccgaaca acaccaatgg     780
aacgccggta agttggactt ctacatcatc cacgctggtg gtccaagaat cttggacgat     840
ttgtctagat tcttggacgt tccaccaggt gccttcagac actctagagc cactttgacc     900
gaatacggta acatcgcctc tgccgtcgtt ttggacgcct tgggtagatt gttcgacgaa     960
caatccgcct tggacggtca ccacggtatg ttggctggtt tcggtccagg tatcatcgcc    1020
gaaatgtcct tgggtacctg ggtttctcca gaatcctaa                           1059

<210> SEQ ID NO 59
<211> LENGTH: 401
<212> TYPE: PRT
<213> ORGANISM: Streptomyces clavuligerus

<400> SEQUENCE: 59

Met Ser Ser Thr Gly Ser Ser Ala His Tyr Cys Pro Phe Asp Tyr Ala
1               5                   10                  15

Glu Ala Leu Glu Phe Asp Pro Thr Leu Arg Arg Phe Met Arg Glu Glu
            20                  25                  30

Pro Val Ala Arg Ile Arg Leu Pro His Gly Ala Gly Glu Ala Trp Leu
        35                  40                  45

Val Thr Gly Tyr Asp Asp Val Arg Thr Val Thr Thr Asp Arg Arg Phe
    50                  55                  60

Ser Arg His Ala Val Val Gly Arg Asp Phe Pro Arg Met Thr Pro Glu

-continued

```
65                  70                  75                  80

Pro Ile Val Gln Asp Glu Ala Ile Asn Val Met Asp Pro Pro Ala Ser
                85                  90                  95

Ser Arg Leu Arg Ser Leu Val Ser Lys Gly Phe Ala Pro Glu Gln Ile
            100                 105                 110

Glu Arg Met Arg Pro Tyr Ile Gln Arg Ala Val Asp Asp Leu Leu Asp
        115                 120                 125

Arg Met Ala Glu Asp Ser Ser Ala Asp Leu Met Arg His Leu Ala Gly
    130                 135                 140

Pro Leu Pro Leu Ile Thr Ile Cys Glu Val Leu Glu Ile Pro Pro Ala
145                 150                 155                 160

Asp Gln Glu Thr Leu Arg Gly His Ala Arg Thr Met Met Asn Ile Ser
                165                 170                 175

Val Asp Asn Lys Ala Ala Ala Val Arg Ala Lys Ala Asp Leu Arg Ala
            180                 185                 190

Tyr Phe Ala Asp Leu Thr Ala Arg Arg Arg Ala Asp Pro Gly Glu Asp
        195                 200                 205

Leu Ile Ser Val Leu Ala Thr Ala Arg Asp Gly Asp Glu Leu Leu Asp
    210                 215                 220

Asp Gln Glu Leu Thr Val Met Ala Met Val Leu Leu Ile Thr Gly Gln
225                 230                 235                 240

Asp Thr Thr Thr Tyr Glu Leu Gly Asn Leu Ser Tyr Thr Leu Leu Thr
                245                 250                 255

Arg Pro Asp Val Arg Asp Leu Leu Arg Asp Arg Pro Glu Arg Leu Ala
            260                 265                 270

Gln Thr Ile Asn Glu Leu Leu Arg Phe Ile Pro Phe Arg Lys Gly Val
        275                 280                 285

Gly Ile Pro Arg Val Ala Thr Glu Asp Val Glu Leu Ser Gly Val Thr
    290                 295                 300

Ile Pro Ala Gly Asp Ile Val His Val Ser Tyr Leu Thr Ala Asn Arg
305                 310                 315                 320

Asp Gly Arg Lys Phe Asp Arg Pro Asp Glu Leu Asp Phe Asp Arg Thr
                325                 330                 335

Ala Pro Ser His Met Thr Phe Gly Trp Gly Ala His His Cys Leu Gly
            340                 345                 350

Ala Pro Leu Ala Gln Ala Glu Met Glu Thr Ala Phe Arg Thr Leu Leu
        355                 360                 365

Glu Arg Phe Pro Gly Ile Ala Leu Ala Lys Pro Ala Glu Asp Val Glu
    370                 375                 380

Trp Asn Thr Thr Ser Ile Trp Arg Tyr Pro Leu Ala Leu Pro Val Thr
385                 390                 395                 400

Trp
```

<210> SEQ ID NO 60
<211> LENGTH: 1206
<212> TYPE: DNA
<213> ORGANISM: artificial
<220> FEATURE:
<223> OTHER INFORMATION: coding sequence for SEQ ID NO: 59

<400> SEQUENCE: 60

```
atgtcctcca ccggttcctc tgctcactac tgtccattcg actacgccga agccttggaa     60

ttcgacccaa ctttgagaag attcatgaga gaagaaccag tcgctagaat cagattgcca    120

cacggtgctg gtgaagcttg gttggtcacc ggttacgacg atgttagaac cgttaccacc    180
```

gacagaagat tctctagaca cgccgttgtc ggtagagact tcccaagaat gactccagaa 240
ccaatcgtcc aagacgaagc catcaacgtc atggacccac cagcttcttc tagattgaga 300
tctttggttt ccaagggttt cgccccagaa caaatcgaaa gaatgaggcc atacatccaa 360
agagccgttg acgacttgtt ggacagaatg gctgaggact cctccgccga cttgatgaga 420
cacttggctg gtccattgcc attgatcacc atctgtgaag tcttggaaat cccaccagcc 480
gaccaagaaa ccttgagagg tcacgccaga actatgatga acatctctgt tgacaacaag 540
gccgccgccg ttagagccaa ggccgatttg agagcctact tcgctgactt gactgccaga 600
agaagagctg acccaggtga ggacttgatc tctgttttgg ccactgccag ggacggtgac 660
gaattgttgg acgaccaaga attgaccgtc atggctatgg tcttgttgat caccggtcaa 720
gacaccacca cctacgaatt gggtaacttg tcctacacct tgttgaccag accagacgtc 780
agagatttgt tgagagacag accagaaaga ttggctcaaa ctatcaacga attgttgaga 840
ttcatcccat tcagaaaggg tgtcggtatc ccaagagttg ccaccgagga cgttgaattg 900
tctggtgtta ctatcccagc cggtgacatc gtccacgtat cctacttgac cgccaacaga 960
gatggtagaa agttcgacag accagacgaa ttggacttcg acagaaccgc cccatcccac 1020
atgaccttcg gttggggtgc tcaccactgt ttgggtgccc cattggctca agccgaaatg 1080
gaaaccgcct tcagaacttt gttggaaaga ttcccaggta tcgctttggc taagccagcc 1140
gaggacgttg aatggaacac cacctctatc tggagatacc cattggcttt gccagtcacc 1200
tggtaa 1206

<210> SEQ ID NO 61
<211> LENGTH: 246
<212> TYPE: PRT
<213> ORGANISM: Arabidopsis thaliana

<400> SEQUENCE: 61

Met Ser Ser Ser Asn Ala Cys Ala Ser Pro Ser Pro Phe Pro Ala Val
1               5                   10                  15

Thr Lys Leu His Val Asp Ser Val Thr Phe Val Pro Ser Val Lys Ser
            20                  25                  30

Pro Ala Ser Ser Asn Pro Leu Phe Leu Gly Gly Ala Gly Val Arg Gly
        35                  40                  45

Leu Asp Ile Gln Gly Lys Phe Val Ile Phe Thr Val Ile Gly Val Tyr
    50                  55                  60

Leu Glu Gly Asn Ala Val Pro Ser Leu Ser Val Lys Trp Lys Gly Lys
65                  70                  75                  80

Thr Thr Glu Glu Leu Thr Glu Ser Ile Pro Phe Phe Arg Glu Ile Val
                85                  90                  95

Thr Gly Ala Phe Glu Lys Phe Ile Lys Val Thr Met Lys Leu Pro Leu
            100                 105                 110

Thr Gly Gln Gln Tyr Ser Glu Lys Val Thr Glu Asn Cys Val Ala Ile
        115                 120                 125

Trp Lys Gln Leu Gly Leu Tyr Thr Asp Cys Glu Ala Lys Ala Val Glu
    130                 135                 140

Lys Phe Leu Glu Ile Phe Lys Glu Glu Thr Phe Pro Pro Gly Ser Ser
145                 150                 155                 160

Ile Leu Phe Ala Leu Ser Pro Thr Gly Ser Leu Thr Val Ala Phe Ser
                165                 170                 175

Lys Asp Asp Ser Ile Pro Glu Thr Gly Ile Ala Val Ile Glu Asn Lys

```
            180                 185                 190

Leu Leu Ala Glu Ala Val Leu Glu Ser Ile Ile Gly Lys Asn Gly Val
        195                 200                 205

Ser Pro Gly Thr Arg Leu Ser Val Ala Glu Arg Leu Ser Gln Leu Met
    210                 215                 220

Met Lys Asn Lys Asp Glu Lys Glu Val Ser Asp His Ser Val Glu Glu
225                 230                 235                 240

Lys Leu Ala Lys Glu Asn
                245


<210> SEQ ID NO 62
<211> LENGTH: 741
<212> TYPE: DNA
<213> ORGANISM: artificial
<220> FEATURE:
<223> OTHER INFORMATION: coding sequence for SEQ ID NO: 61

<400> SEQUENCE: 62

atgtcctcta gcaatgcgtg tgcctccccg tccccgttcc cggctgttac gaagctgcat      60

gtcgattcag ttacctttgt cccgtccgtg aagtccccgg cgagcagcaa cccgctgttt     120

ctgggcggtg caggtgtccg tggtctggat attcagggca aatttgtgat tttcaccgtg     180

atcggcgttt atctggaagg caatgcggtc ccgtcactgt cggtgaaatg gaagggtaaa     240

accacggaag aactgaccga atctattccg tttttccgcg aaatcgttac gggcgcgttc     300

gaaaagttca tcaaggtcac catgaaactg ccgctgacgg gtcagcaata ttcagaaaag     360

gttaccgaaa actgcgtcgc catctggaaa caactgggcc tgtacacgga ctgtgaagcg     420

aaggccgtcg aaaagtttct ggaaattttc aaagaagaaa cctttccgcc gggcagttcc     480

atcctgttcg cactgagccc gaccggttct ctgacggttg ctttcagtaa agatgactcc     540

atcccggaaa ccggcattgc agtgatcgaa aacaagctgc tggcagaagc tgttctggaa     600

agcattatcg gcaaaaatgg tgtgtcaccg ggtacgcgtc tgtcggttgc ggaacgcctg     660

agccagctga tgatgaaaaa taaagatgaa aaggaagtgt cggaccacag cgttgaagaa     720

aaactggcaa aggaaaacta a                                               741


<210> SEQ ID NO 63
<211> LENGTH: 719
<212> TYPE: PRT
<213> ORGANISM: Citrus sinensis

<400> SEQUENCE: 63

Met Ser Glu Ile Gly Ala Thr Thr Glu Asn Gly His Gln Asn Gly Gly
1               5                   10                  15

Leu Glu Gly Leu Cys Lys Asn Asn Asn Tyr Asn Tyr Ser Ser Gly Asp
            20                  25                  30

Ala Leu Asn Trp Gly Val Met Ala Glu Thr Leu Lys Gly Ser His Leu
        35                  40                  45

Glu Glu Val Lys Arg Met Val Ala Glu Tyr Arg Lys Pro Val Val Asn
    50                  55                  60

Leu Gly Gly Glu Thr Leu Thr Val Ala Gln Val Ala Ala Ile Ala Thr
65                  70                  75                  80

Ser Ser Thr Asn Val Glu Leu Ser Glu Ser Ala Arg Glu Gly Val Lys
                85                  90                  95

Ala Ser Ser Asp Trp Val Met Glu Ser Met Asn Lys Gly Thr Asp Ser
            100                 105                 110
```

```
Tyr Gly Val Thr Thr Gly Phe Gly Ala Thr Ser His Arg Arg Thr Lys
        115                 120                 125

Asn Gly Gly Ala Leu Gln Lys Glu Leu Ile Arg Phe Leu Asn Ala Gly
    130                 135                 140

Ile Phe Gly Asn Gly Thr Glu Ser Ser His Thr Leu Pro His Ser Ala
145                 150                 155                 160

Thr Arg Ala Ala Met Leu Val Arg Val Asn Thr Leu Leu Gln Gly Tyr
                165                 170                 175

Ser Gly Ile Arg Phe Glu Ile Leu Glu Ala Ile Thr Lys Leu Leu Asn
            180                 185                 190

His Asn Ile Thr Pro Cys Leu Pro Leu Arg Gly Thr Ile Thr Ala Ser
        195                 200                 205

Gly Asp Leu Val Pro Leu Ser Tyr Ile Ala Gly Leu Leu Thr Gly Arg
    210                 215                 220

Pro Asn Ser Lys Ala Thr Gly Pro Asn Gly Glu Ile Ile Asp Ala Gln
225                 230                 235                 240

Glu Ala Ser Lys Gln Ala Gly Phe Gly Phe Phe Glu Leu Gln Pro Lys
                245                 250                 255

Glu Gly Leu Ala Leu Val Asn Gly Thr Ala Val Gly Ser Gly Leu Ala
            260                 265                 270

Ser Met Val Leu Phe Glu Ala Asn Asn Leu Ala Leu Leu Ser Glu Ile
        275                 280                 285

Leu Ser Ala Ile Phe Ala Glu Val Met Gln Gly Lys Pro Glu Phe Thr
    290                 295                 300

Asp His Leu Thr His Lys Leu Lys His His Pro Gly Gln Ile Glu Ala
305                 310                 315                 320

Ala Ala Ile Met Glu His Ile Leu Asp Gly Ser Ser Tyr Val Asn Val
                325                 330                 335

Ala Lys Lys Leu His Glu Ile Asp Pro Leu Gln Lys Pro Lys Gln Asp
            340                 345                 350

Arg Tyr Ala Leu Arg Thr Ser Pro Gln Trp Leu Gly Pro Gln Ile Glu
        355                 360                 365

Val Ile Arg Phe Ala Thr Lys Ser Ile Glu Arg Glu Ile Asn Ser Val
    370                 375                 380

Asn Asp Asn Pro Leu Ile Asp Val Ser Arg Asn Lys Ala Leu His Gly
385                 390                 395                 400

Gly Asn Phe Gln Gly Thr Pro Ile Gly Val Ser Met Asp Asn Thr Arg
                405                 410                 415

Leu Ala Ile Ala Ala Ile Gly Lys Leu Met Phe Ala Gln Phe Ser Glu
            420                 425                 430

Leu Val Asn Asp Phe Tyr Asn Asn Gly Leu Pro Ser Asn Leu Ser Gly
        435                 440                 445

Gly Arg Asn Pro Ser Leu Asp Tyr Gly Phe Lys Gly Ala Glu Ile Ala
    450                 455                 460

Met Ala Ser Tyr Cys Ser Glu Leu Gln Phe Leu Ala Asn Pro Val Thr
465                 470                 475                 480

Asn His Val Gln Ser Ala Glu Gln His Asn Gln Asp Val Asn Ser Leu
                485                 490                 495

Gly Leu Ile Ser Ser Arg Lys Thr Ala Glu Ala Val Asp Ile Leu Lys
            500                 505                 510

Leu Met Ser Ser Thr Phe Leu Val Ala Leu Cys Gln Ala Ile Asp Leu
        515                 520                 525

Arg His Leu Glu Glu Asn Leu Lys His Thr Val Lys Asn Thr Val Ser
```

530 535 540

Gln Val Ala Lys Lys Val Leu Thr Val Gly Ala Ser Gly Glu Leu His
545 550 555 560

Pro Ser Arg Phe Cys Glu Lys Asp Leu Leu Lys Ala Ala Asp Arg Glu
565 570 575

His Val Phe Ala Tyr Ile Asp Asp Pro Cys Ser Ala Thr Tyr Pro Leu
580 585 590

Met Gln Lys Leu Arg Gln Val Leu Val Glu His Ala Leu Asn Asn Gly
595 600 605

Glu Asn Glu Lys Thr Ala Asn Ser Ser Ile Phe Gln Lys Ile Ala Ala
610 615 620

Phe Glu Glu Glu Leu Lys Thr Val Leu Pro Lys Glu Val Glu Asn Ala
625 630 635 640

Arg Gln Thr Val Glu Asn Gly Ser Pro Thr Ile Pro Asn Arg Ile Lys
645 650 655

Glu Cys Arg Ser Tyr Pro Leu Tyr Arg Phe Val Arg Glu Gly Leu Gly
660 665 670

Ser Asn Phe Leu Thr Gly Glu Lys Val Thr Ser Pro Gly Glu Glu Phe
675 680 685

Asp Lys Val Phe Thr Ala Met Cys Gln Gly Lys Ile Ile Asp Pro Met
690 695 700

Leu Glu Cys Leu Arg Glu Trp Asn Gly Ala Pro Leu Pro Ile Cys
705 710 715

<210> SEQ ID NO 64
<211> LENGTH: 2160
<212> TYPE: DNA
<213> ORGANISM: artificial
<220> FEATURE:
<223> OTHER INFORMATION: coding sequence for SEQ ID NO: 63

<400> SEQUENCE: 64
atgtccgaaa tcggtgccac tactgaaaac ggtcaccaaa acggtggcct cgaaggcttg 60
tgtaagaaca ataactacaa ctactcttct ggtgatgctt tgaactgggg tgttatggct 120
gaaactttga agggttctca cttggaagaa gttaagagaa tggttgctga atacagaaag 180
ccagttgtca acttgggtgg tgaaactttg accgttgctc aagttgctgc cattgccact 240
tcctctacta acgttgaatt gtctgaatct gccagagaag gtgtcaaggc ctcttctgat 300
tgggttatgg aatctatgaa caagggtacc gactcttacg gtgttactac tggcttcggt 360
gccacttcgc acagaagaac caagaacggt ggtgctttgc aaaaggaatt gattagattc 420
ttgaacgctg gtatcttcgg taacggtact gaatcttctc acactttgcc acactctgct 480
actagagctg ccatgttggt tcgtgttaac acattgttgc aaggttactc cggtatcaga 540
ttcgaaatct tggaagctat cactaagttg ttgaaccaca acatcactcc atgtttgcca 600
ttgagaggta ctatcactgc ttctggtgat ttggttccat tgtcctacat agccggcttg 660
ttgaccggtc gtccaaactc taaggccacc ggtccaaacg gtgaaatcat tgatgcccaa 720
gaagcctcta agcaagctgg tttcggtttc ttcgaattgc aaccaaagga gggcttggct 780
ctcgtcaacg gtactgctgt tggttctggt ttggcttcta tggttttgtt cgaagctaac 840
aatctcgcgt tgttgtcgga aattttgtct gctattttcg ctgaagtcat gcaaggtaag 900
ccagaattca ccgatcactt gactcacaag ttgaagcacc acccaggtca aattgaagct 960
gctgctatca tggaacacat cttggatggt tcttcttacg ttaacgttgc taagaagttg 1020

```
cacgaaattg atccattgca aaagccaaag caagatagat acgccttgag aacttctcca   1080

caatggttgg gtccacaaat cgaagttatt agattcgcta ccaagtctat tgaaagagaa   1140

atcaactctg ttaacgacaa cccattgatc gacgtttcta gaaacaaggc cttgcacggt   1200

ggtaacttcc aaggtacccc aattggtgtc tctatggaca acaccagatt ggctattgct   1260

gctatcggta agttgatgtt cgcccaattc tctgaattgg tcaacgattt ctacaacaac   1320

ggtttgccat ctaacttgtc tggtggtaga aacccatctt tggattacgg tttcaagggt   1380

gctgaaattg ctatggcttc ctactgttct gaattgcaat tcttggccaa cccagttact   1440

aaccacgtcc aatctgctga acaacacaac caagatgtta actccttggg tttgatctct   1500

tccagaaaga ctgctgaagc tgtcgacatc ttgaagttga tgtcatccac tttcttggtt   1560

gctttgtgtc aagctattga tttgagacac ttggaagaaa acttgaagca cactgtcaag   1620

aacactgtct ctcaagttgc taagaaggtc ttgaccgtcg gtgcttctgg tgaattgcac   1680

ccatctagat tctgtgaaaa ggatttgttg aaggctgctg atagagaaca cgttttcgct   1740

tacattgatg acccatgttc tgctacctac ccattgatgc aaaagttgag acaagttttg   1800

gttgaacacg ctttgaacaa cggtgaaaac gaaaagactg ccaactcttc tatcttccaa   1860

aagattgctg ccttcgaaga agaattaaag accgttttgc caaaggaagt tgaaaacgcc   1920

agacaaactg ttgaaaacgg ttctccaact attccaaaca gaatcaagga atgtagatct   1980

tacccattgt acagattcgt tagagaaggt ttgggttcta acttcttgac tggtgaaaag   2040

gttacttctc caggtgaaga attcgacaag gttttcactg ctatgtgtca aggtaagatc   2100

attgatccaa tgttggaatg tttgagagaa tggaacggtg ccccattgcc aatttgttaa   2160
```

```
<210> SEQ ID NO 65
<211> LENGTH: 715
<212> TYPE: PRT
<213> ORGANISM: Citrus sinensis

<400> SEQUENCE: 65

Met Ser Glu Ala Ser His Glu Asn Gln Ser Gly Gly Asn Ile Pro Ser
1               5                   10                  15

Gly Lys Leu Cys Thr Asn Ile Asp Pro Leu Asn Trp Val Ser Ala Ser
            20                  25                  30

Glu Ser Leu Lys Gly Ser His Leu Asp Glu Val Lys Arg Met Val Ser
        35                  40                  45

Glu Tyr Arg Lys Gln Val Val Arg Leu Gly Gly Glu Thr Leu Thr Ile
    50                  55                  60

Ala Gln Val Ala Ala Val Ala Ser Arg Asp Gly Gly Val Thr Val Glu
65                  70                  75                  80

Leu Asn Glu Glu Ala Arg Ala Gly Val Lys Ala Ser Ser Asp Trp Val
                85                  90                  95

Met Glu Ser Met Asn Lys Gly Thr Asp Ser Tyr Gly Ile Thr Thr Gly
            100                 105                 110

Phe Gly Ala Thr Ser His Arg Arg Thr Lys Gln Gly Ala Ala Leu Gln
        115                 120                 125

Lys Glu Leu Ile Arg Phe Leu Asn Ala Gly Ile Phe Gly Lys Gly Thr
    130                 135                 140

Glu Ser Cys Gln Met Leu Pro His Thr Ala Thr Arg Ala Ala Met Leu
145                 150                 155                 160

Val Arg Ile Asn Thr Leu Leu Gln Gly Tyr Ser Gly Ile Arg Phe Glu
                165                 170                 175
```

```
Ile Leu Glu Ala Ile Thr Lys Phe Leu Asn Arg Asn Ile Thr Pro Cys
            180                 185                 190

Leu Pro Leu Arg Ala Ser Ile Thr Ala Ser Gly Asp Leu Ile Pro Phe
        195                 200                 205

Ser Tyr Ile Ala Gly Leu Leu Thr Gly Arg Leu Asn Ser Val Ala Val
    210                 215                 220

Gly Pro Asn Gly Glu Ser Leu Asn Ala Ala Glu Ala Phe Ser Gln Ala
225                 230                 235                 240

Gly Ile Asp Gly Gly Phe Phe Glu Leu Gln Pro Lys Glu Gly Leu Ala
                245                 250                 255

Leu Val Asn Gly Thr Gly Val Gly Ala Gly Leu Ala Ser Ile Val Leu
            260                 265                 270

Phe Glu Ala Asn Ile Leu Thr Val Leu Ser Glu Val Leu Ser Ala Ile
        275                 280                 285

Phe Ala Glu Ala Met Leu Gly Lys Pro Glu Phe Thr Asp His Leu Thr
    290                 295                 300

His Lys Leu Lys His His Pro Gly Gln Ile Glu Ala Ala Ala Ile Met
305                 310                 315                 320

Glu His Ile Leu Asp Gly Ser Ser Tyr Val Lys Ala Ala Gln Lys Leu
                325                 330                 335

His Glu Ile Asp Pro Leu Gln Lys Pro Lys Gln Asp Arg Tyr Ala Leu
            340                 345                 350

Arg Thr Ser Pro Gln Trp Leu Gly Pro Gln Ala Glu Val Ile Arg Ala
        355                 360                 365

Ser Thr Lys Ser Ile Glu Arg Glu Ile Asn Ser Val Asn Asp Asn Pro
    370                 375                 380

Leu Ile Asp Val Ser Arg Asn Lys Ala Leu His Gly Gly Asn Phe Gln
385                 390                 395                 400

Gly Thr Pro Ile Gly Val Ser Met Asp Asn Ser Arg Leu Ala Ile Ala
                405                 410                 415

Ser Ile Gly Lys Leu Met Phe Ala Gln Phe Ser Glu Leu Val Asn Asp
            420                 425                 430

Phe Tyr Ser Asn Gly Leu Pro Ser Asn Leu Ser Gly Gly Arg Asn Pro
        435                 440                 445

Ser Leu Asp Tyr Gly Phe Lys Gly Ala Glu Ile Ala Met Ala Ala Tyr
    450                 455                 460

Cys Ser Glu Leu Gln Phe Leu Ala Asn Pro Val Thr Asn His Val Gln
465                 470                 475                 480

Ser Ala Glu Gln His Asn Gln Asp Val Asn Ser Leu Gly Leu Ile Ser
                485                 490                 495

Ala Arg Lys Thr Ala Glu Ala Val Asp Ile Leu Lys Leu Met Ser Ser
            500                 505                 510

Thr Tyr Leu Ile Ala Leu Cys Gln Ala Ile Asp Leu Arg His Leu Glu
        515                 520                 525

Glu Asn Leu Lys Ser Thr Val Lys Asn Thr Ile Ser Gln Val Val Lys
    530                 535                 540

Lys Val Leu Thr Met Gly Val Asn Gly Glu Leu His Pro Ser Arg Phe
545                 550                 555                 560

Cys Glu Lys Asp Leu Leu Lys Val Val Asp Arg Glu Tyr Val Phe Ser
                565                 570                 575

Tyr Ala Asp Asp Pro Cys Ser Ala Thr Tyr Pro Leu Met Gln Lys Leu
            580                 585                 590

Arg Gln Val Leu Val Asp His Ala Leu Thr Asn Asn Glu Asp Leu Lys
```

```
        595                 600                 605

Asn Ala Asn Ala Ser Ile Phe Leu Lys Ile Gly Ala Phe Glu Glu Glu
    610                 615                 620

Leu Lys Thr Leu Leu Pro Lys Glu Val Glu Ser Ala Arg Ser Ala Phe
625                 630                 635                 640

Glu Ser Gly Asn Leu Glu Ile Pro Asn Arg Ile Lys Glu Cys Arg Ser
                645                 650                 655

Tyr Pro Leu Tyr Arg Phe Val Arg Glu Glu Leu Gly Ala Arg Tyr Leu
            660                 665                 670

Thr Gly Glu Lys Ala Ile Ser Pro Gly Glu Glu Cys Asp Lys Val Phe
        675                 680                 685

Thr Ala Ile Cys Gln Gly Lys Ile Ile Asp Pro Leu Leu Glu Cys Leu
    690                 695                 700

Lys Glu Trp Asp Gly Ser Pro Leu Pro Ile Cys
705                 710                 715


<210> SEQ ID NO 66
<211> LENGTH: 2148
<212> TYPE: DNA
<213> ORGANISM: artificial
<220> FEATURE:
<223> OTHER INFORMATION: coding sequence for SEQ ID NO: 65

<400> SEQUENCE: 66

atgtccgaag cttctcacga aaaccaatct ggtggtaaca ttccatctgg taagttgtgt      60

actaacattg atccattgaa ctgggtttct gcttctgaat ctttgaaggg ttctcacttg     120

gatgaagtta agagaatggt ttctgaatac agaaagcaag ttgttagatt gggtggtgaa     180

accttgacta tcgctcaagt tgctgctgtt gcttctagag atggtggtgt cactgttgaa     240

ttgaacgaag aagccagagc tggtgtcaag gcttcttctg attgggttat ggaatctatg     300

aacaagggta ctgattctta cggcatcact actggcttcg gtgctacttc gcacagaaga     360

accaagcaag gtgctgcctt gcaaaaggaa ttgattagat tcttgaacgc tggtatcttc     420

ggtaagggta ctgaatcctg tcaaatgttg ccacacactg ctactagagc tgctatgctc     480

gttcgtatca acacattgtt gcaaggttac tctggtatta gattcgaaat tttggaagct     540

atcactaagt tcttgaacag aaacattact ccatgtttgc cattgagagc ctccatcact     600

gcgtcgggtg atctcatccc attctcgtac atcgccggtt tgttgaccgg tagattgaac     660

tctgttgctg ttggtccaaa cggtgaatct ttgaacgctg ctgaagcttt ctctcaagct     720

ggtattgatg gtggtttctt cgaattgcaa ccaaaggagg gcttggcgtt ggttaacggt     780

actggtgttg gtgctggttt ggcttctatt gttttgttcg aagctaacat tttgactgtt     840

ttgtccgaag ttttgtctgc tattttcgct gaagctatgt tgggtaagcc agaattcact     900

gatcacttga ctcacaagtt gaagcaccac ccaggtcaaa ttgaagctgc tgctatcatg     960

gaacacatct tggatggttc ttcttacgtt aaggctgctc aaaagttgca cgaaattgac    1020

ccattgcaaa agccaaagca agatagatac gctttgagaa cttctccaca atggttgggt    1080

ccacaagctg aagttattag agcttctact aagtctattg aaagagaaat taactctgtt    1140

aacgataacc cattgattga tgtttctaga aacaaggctt tgcacggtgg taacttccaa    1200

ggtaccccaa ttggtgtctc tatggataac tctagattgg ctattgcttc tattggtaag    1260

ttgatgttcg ctcaattctc tgaattggtt aacgatttct actctaacgg tttgccatct    1320

aacttgtctg gtggtagaaa cccatctttg gattacggtt tcaagggtgc cgaaatcgct    1380
```

```
atggctgctt actgttccga attgcaattc ttggccaacc cagttactaa ccacgtccaa   1440

tctgctgaac aacacaacca agatgttaac tctttgggtt tgatctctgc cagaaagact   1500

gctgaagctg ttgatatctt gaagttgatg tcctctactt acttgattgc tttgtgtcaa   1560

gctatcgact tgagacactt ggaagaaaac ttgaagtcta ctgttaagaa cactatctct   1620

caagttgtta agaaggtctt gactatgggt gtcaacggtg aattgcaccc atctagattc   1680

tgtgaaaagg atttgttgaa ggttgttgat agagaatacg ttttctctta cgctgatgat   1740

ccatgttctg ctacttaccc attgatgcaa aagttgagac aagtcttggt tgatcacgct   1800

ttgactaaca acgaagattt gaagaacgct aacgcttcta tcttcttgaa aataggtgcg   1860

ttcgaagaag aactcaagac cttgttgcca aaggaagttg aatctgctag atctgctttc   1920

gaatctggta acttggaaat cccaaacaga attaaggaat gtagatccta cccattgtac   1980

agattcgtta gagaagaatt gggtgctaga tacttgactg gtgaaaaggc tatctctcca   2040

ggtgaagaat gtgataaggt tttcactgct atttgtcaag gtaagatcat tgatccattg   2100

ttggaatgtt tgaaggaatg ggatggttct ccattgccaa tttgttaa                2148
```

<210> SEQ ID NO 67
<211> LENGTH: 537
<212> TYPE: PRT
<213> ORGANISM: Citrus sinensis

<400> SEQUENCE: 67

```
Met Ser Ala Asn Leu Val Thr Ile Ser Phe Phe Ser Ile Leu Leu Thr
1               5                   10                  15

Ile Ser Leu Leu Ser Phe Asn Lys Ser Leu Asn Leu Ile Ser Ile Thr
            20                  25                  30

Leu Pro Leu Val Pro Leu Ile Ala Tyr Val Leu Lys Ser Phe Leu Lys
        35                  40                  45

Ser Ser Lys Ala Phe Tyr Pro Pro Thr Pro Ile Ser Ile Pro Ile Phe
    50                  55                  60

Gly Asn Trp Leu Gln Val Gly Asn Asp Leu Asn His Arg Leu Leu Ala
65                  70                  75                  80

Ser Met Ala Gln Ile Tyr Gly Pro Val Phe Arg Leu Lys Leu Gly Ser
                85                  90                  95

Lys Asn Leu Ile Val Val Ser Glu Pro Asp Leu Ala Thr Gln Val Leu
            100                 105                 110

His Thr Gln Gly Val Glu Phe Gly Ser Arg Pro Arg Asn Val Val Phe
        115                 120                 125

Asp Ile Phe Thr Gly Asn Gly Gln Asp Met Val Phe Thr Val Tyr Gly
    130                 135                 140

Glu His Trp Arg Lys Met Arg Arg Ile Met Thr Leu Pro Phe Phe Thr
145                 150                 155                 160

Asn Lys Val Val His Asn Tyr Ser Asp Met Trp Glu Gln Glu Met Asp
                165                 170                 175

Leu Val Val His Asp Leu Lys Asn Asp Tyr Glu Ser Val Ser Thr Lys
            180                 185                 190

Gly Ile Val Ile Arg Lys Arg Leu Gln Leu Met Leu Tyr Asn Ile Met
        195                 200                 205

Tyr Arg Met Met Phe Asp Ala Lys Phe Glu Ser Gln Glu Asp Pro Leu
    210                 215                 220

Phe Ile Glu Ala Thr Arg Phe Asn Ser Glu Arg Ser Arg Leu Ala Gln
225                 230                 235                 240
```

```
Ser Phe Glu Tyr Asn Tyr Gly Asp Phe Ile Pro Leu Leu Arg Pro Phe
                245                 250                 255

Leu Arg Gly Tyr Leu Asn Lys Cys Arg Asp Leu Gln Cys Arg Arg Leu
            260                 265                 270

Ala Phe Phe Asn Asn Asn Phe Val Glu Lys Arg Arg Lys Ile Met Ala
        275                 280                 285

Ala Asn Gly Glu Lys His Lys Ile Ser Cys Ala Ile Asp His Ile Ile
    290                 295                 300

Asp Ala Gln Met Lys Gly Glu Ile Thr Glu Glu Asn Val Ile Tyr Ile
305                 310                 315                 320

Val Glu Asn Ile Asn Val Ala Ala Ile Glu Thr Thr Leu Trp Ser Met
                325                 330                 335

Glu Trp Ala Ile Ala Glu Leu Val Asn His Pro Glu Val Gln Gln Lys
            340                 345                 350

Ile Arg Arg Glu Ile Ser Thr Val Leu Lys Gly Asn Pro Val Thr Glu
        355                 360                 365

Ser Asn Leu His Glu Leu Pro Tyr Leu Gln Ala Ala Val Lys Glu Val
    370                 375                 380

Leu Arg Leu His Thr Pro Ile Pro Leu Leu Val Pro His Met Asn Leu
385                 390                 395                 400

Glu Glu Ala Lys Leu Gly Gly Phe Thr Ile Pro Lys Glu Ser Lys Ile
                405                 410                 415

Val Val Asn Ala Trp Trp Leu Ala Asn Asn Pro Lys Trp Trp Glu Lys
            420                 425                 430

Pro Glu Glu Phe Arg Pro Glu Arg Phe Leu Glu Glu Glu Cys Asn Ile
        435                 440                 445

Asp Ala Val Ala Gly Gly Gly Lys Val Asp Phe Arg Tyr Leu Pro Phe
    450                 455                 460

Gly Val Gly Arg Arg Ser Cys Pro Gly Ile Ile Leu Ala Leu Pro Ile
465                 470                 475                 480

Leu Gly Leu Val Ile Ala Lys Leu Val Thr Ser Phe Glu Met Lys Ala
                485                 490                 495

Pro Gln Gly Ile Asp Lys Ile Asp Val Ser Glu Lys Gly Gly Gln Phe
            500                 505                 510

Ser Leu His Ile Ala Asn His Ser Thr Val Val Phe Asp Pro Ile Met
        515                 520                 525

Glu Ser Leu Ser Gln Pro Met Pro Gln
    530                 535
```

<210> SEQ ID NO 68
<211> LENGTH: 1614
<212> TYPE: DNA
<213> ORGANISM: artificial
<220> FEATURE:
<223> OTHER INFORMATION: coding sequence for SEQ ID NO: 67

<400> SEQUENCE: 68

```
atgtccgcta acttggttac tatttctttc ttctctatct tgttgactat ctctttgttg      60

tctttcaaca agtctttgaa cttgatctct atcactttgc cattggttcc attgattgct     120

tacgttttga agtccttctt gaagtcatct aaggccttct acccaccaac tccaatctct     180

atcccaatct tcggtaactg gttgcaagtt ggtaacgact tgaaccacag attgttggct     240

tctatggctc aaatttacgg tccagttttc agattgaagt tgggttctaa gaacttgatc     300

gttgtttctg aaccagacct cgctactcaa gtgctacaca ctcaaggtgt tgaattcggt     360
```

-continued

```
tccagaccaa gaaacgttgt tttcgatatt ttcactggta acggtcaaga catggtattt    420

actgtctacg gcgaacactg gagaaagatg agaagaatta tgactttgcc attcttcacc    480

aacaaggttg ttcacaacta ctctgacatg tgggaacaag aaatggactt ggttgttcac    540

gacttgaaga acgattacga gtctgtaagc actaagggta ttgttattag aaagagattg    600

caattgatgt tgtacaacat tatgtacaga atgatgttcg atgctaagtt cgaatctcaa    660

gaagatccat tgttcattga agctactaga ttcaactctg aaagatctag attggcgcag    720

agcttcgaat acaactacgg tgatttcatt ccattgttaa gaccattctt gagaggttac    780

ttgaacaagt gtagagactt gcaatgtaga agattggctt tcttcaacaa caacttcgtt    840

gaaaagagaa gaaagatcat ggctgccaac ggtgaaaagc acaagatctc ttgtgccatt    900

gatcacatca ttgatgctca aatgaagggt gaaatcactg aagaaaacgt tatttacatt    960

gttgaaaaca tcaacgttgc tgctatcgaa actactttgt ggtccatgga atgggctatc   1020

gctgaattgg tcaaccaccc agaagttcaa caaaagatca gaagagaaat ctctactgtc   1080

ttgaagggta acccagtcac tgaatctaac ttgcacgaat tgccatactt gcaagccgct   1140

gttaaggaag ttttgagatt gcacactcca attccattgt tggttccaca catgaacttg   1200

gaagaagcta agttgggtgg tttcactatt ccaaaggaat ccaagattgt tgttaacgct   1260

tggtggttgg ctaacaaccc aaagtggtgg gaaaagccag aagaattcag accagaaaga   1320

ttcttggaag aagaatgtaa cattgatgct gttgctggtg gtggtaaggt tgacttcaga   1380

tacttgccat tcggtgttgg tagaagatct tgtccaggta taatattggc tctcccaatc   1440

ttgggcttgg ttattgctaa gttggttact tctttcgaaa tgaaggctcc acaaggtatc   1500

gataagattg acgtttctga aaagggtggt caattctctt tgcacattgc taaccactct   1560

actgttgtct ttgatccaat catggaatct ttgtcccaac caatgccaca ataa         1614
```

```
<210> SEQ ID NO 69
<211> LENGTH: 520
<212> TYPE: PRT
<213> ORGANISM: Citrus sinensis

<400> SEQUENCE: 69

Met Ser Asp Leu Asn Gly Trp Cys Asn Ser Gly Asn Gln Asn Met Cys
1               5                   10                  15

Cys Cys Gln Ser Tyr Val Lys Arg Gly Tyr Asp Arg Val Leu Ser Phe
            20                  25                  30

Asn Gly Leu Ile Thr Val Ser Lys Leu Arg Gly Lys Arg Phe Lys Leu
        35                  40                  45

Pro Pro Gly Pro Leu Pro Val Pro Val Phe Gly Asn Trp Leu Gln Val
    50                  55                  60

Gly Asp Asp Leu Asn His Arg Asn Leu Ser Asp Leu Ala Lys Lys Tyr
65                  70                  75                  80

Gly Asp Val Leu Leu Leu Arg Met Gly Gln Arg Asn Leu Val Val Val
                85                  90                  95

Ser Ser Pro Asp His Ala Lys Glu Val Leu His Thr Gln Gly Val Glu
            100                 105                 110

Phe Gly Ser Arg Thr Arg Asn Val Val Phe Asp Ile Phe Thr Gly Lys
        115                 120                 125

Gly Gln Asp Met Val Phe Thr Val Tyr Gly Glu His Trp Arg Lys Met
    130                 135                 140

Arg Arg Ile Met Thr Val Pro Phe Phe Thr Asn Lys Val Val Gln Gln
145                 150                 155                 160
```

```
Gln Arg Phe Asn Trp Glu Asp Glu Ala Ala Arg Val Val Glu Asp Val
                165                 170                 175

Lys Lys Asp Pro Glu Ala Ala Thr Asn Gly Ile Val Leu Arg Arg Arg
            180                 185                 190

Leu Gln Leu Met Met Tyr Asn Asn Met Tyr Arg Ile Met Phe Asp Arg
        195                 200                 205

Arg Phe Glu Ser Gln Asp Asp Pro Leu Phe Asn Arg Leu Lys Ala Leu
    210                 215                 220

Asn Gly Glu Arg Ser Arg Leu Ala Gln Ser Phe Glu Tyr Asn Tyr Gly
225                 230                 235                 240

Asp Phe Ile Pro Ile Leu Arg Pro Phe Leu Arg Gly Tyr Leu Lys Ile
                245                 250                 255

Cys Lys Glu Val Lys Glu Arg Arg Leu Gln Leu Phe Lys Asp Tyr Phe
            260                 265                 270

Val Glu Glu Arg Lys Lys Leu Ala Ser Thr Lys Ser Met Ser Asn Glu
        275                 280                 285

Ser Leu Lys Cys Ala Ile Asp His Ile Leu Asp Ala Gln Thr Lys Gly
    290                 295                 300

Glu Ile Asn Glu Asp Asn Val Leu Tyr Ile Val Glu Asn Ile Asn Val
305                 310                 315                 320

Ala Ala Ile Glu Thr Thr Leu Trp Ser Ile Glu Trp Gly Ile Ala Glu
                325                 330                 335

Leu Val Asn His Pro Glu Ile Gln Lys Lys Leu Arg Asn Glu Leu Asp
            340                 345                 350

Thr Val Leu Gly Pro Gly His Gln Ile Thr Glu Pro Asp Thr His Lys
        355                 360                 365

Leu Pro Tyr Leu Gln Ala Val Ile Lys Glu Thr Leu Arg Leu Arg Met
    370                 375                 380

Ala Ile Pro Leu Leu Val Pro His Met Asn Leu His Asp Ala Lys Leu
385                 390                 395                 400

Gly Gly Tyr Asp Val Pro Ala Glu Ser Lys Ile Leu Val Asn Ala Trp
                405                 410                 415

Trp Leu Ala Asn Asn Pro Ala Gln Trp Lys Lys Pro Glu Glu Phe Arg
            420                 425                 430

Pro Glu Arg Phe Leu Glu Glu Glu Ser Lys Val Glu Ala Asn Gly Asn
        435                 440                 445

Asp Phe Arg Tyr Leu Pro Phe Gly Val Gly Arg Arg Ser Cys Pro Gly
    450                 455                 460

Ile Ile Leu Ala Leu Pro Ile Leu Gly Ile Thr Ile Gly Arg Leu Val
465                 470                 475                 480

Gln Asn Phe Glu Leu Leu Pro Pro Pro Gly Gln Ser Lys Ile Asp Thr
                485                 490                 495

Ala Glu Lys Gly Gly Gln Phe Ser Leu His Ile Leu Lys His Ser Thr
            500                 505                 510

Ile Val Ala Lys Pro Arg Ser Phe
        515                 520
```

<210> SEQ ID NO 70
<211> LENGTH: 1563
<212> TYPE: DNA
<213> ORGANISM: artificial
<220> FEATURE:
<223> OTHER INFORMATION: coding sequence for SEQ ID NO: 69

<400> SEQUENCE: 70

```
atgtccgact tgaacggttg gtgtaactct ggtaaccaaa acatgtgttg ttgtcaatct     60

tacgttaaga gaggttacga tagagttttg tctttcaacg gtttgattac cgtttctaag    120

ttgagaggta agagattcaa gttgccacca ggtccattgc cagtcccagt tttcggtaac    180

tggttgcaag tcggtgatga cttgaaccac agaaacttgt ccgacttggc caagaagtac    240

ggtgatgtct tgttgttgag aatgggtcaa agaaacttgg tcgtcgtttc ttctccagac    300

cacgccaagg aagtcttgca cactcaaggt gttgaattcg gttctagaac tcgtaatgtc    360

gtgttcgaca tcttcactgg taagggtcaa gatatggttt tcactgtcta cggcgaacac    420

tggagaaaga tgagaagaat catgaccgtc ccattcttca ctaacaaggt tgttcaacaa    480

caaagattca actgggaaga tgaagccgct agagtcgttg aagatgttaa gaaggaccca    540

gaagctgcta ccaacggtat cgtcttgaga agaagattgc aattgatgat gtacaacaac    600

atgtacagaa ttatgttcga tagaagattc gaatctcaag atgatccatt gttcaacaga    660

ttgaaggctt tgaacggtga aagatctaga ttggcgcaga gcttcgaata caactacggt    720

gatttcattc caattttaag accattcttg agaggttact tgaagatttg taaggaagtt    780

aaggaaagaa gattgcaatt gttcaaggac tacttcgttg aagaaagaaa gaagttggct    840

tctactaagt ctatgtctaa cgaatctttg aagtgtgcta tcgatcacat tttggacgct    900

caaactaagg gtgaaatcaa cgaagataac gttttgtaca tcgttgaaaa catcaacgtt    960

gccgctatcg aaactacttt gtggtctatc gaatggggta ttgctgaatt ggttaaccac   1020

ccagaaatcc aaaagaagtt gagaaacgaa ttggacaccg ttttgggtcc aggtcaccaa   1080

atcactgaac cagacaccca caagttgcca tacttgcaag ccgttatcaa ggaaactttg   1140

agattgagaa tggctattcc attgttggtt ccacacatga acttgcacga cgccaagttg   1200

ggtggttacg acgtcccagc tgaatctaag atcttggtta acgcttggtg gttggccaac   1260

aacccagccc aatggaagaa gccagaagaa ttcagaccag aaagattctt ggaagaagaa   1320

tccaaggttg aagctaacgg taacgacttc agatacttgc cattcggtgt tggtagaaga   1380

tcttgtccag gtataatatt ggctctccca attttgggca tcactattgg tagattggtt   1440

caaaacttcg aattgttgcc accaccaggt caatctaaga ttgacactgc tgaaaagggt   1500

ggtcaattct ctttgcacat tttgaagcac tctaccattg ttgccaagcc aagatctttc   1560

taa                                                                 1563
```

<210> SEQ ID NO 71
<211> LENGTH: 513
<212> TYPE: PRT
<213> ORGANISM: Saccharothrix espanaensis

<400> SEQUENCE: 71

```
Met Ser Thr Ile Thr Ser Pro Ala Pro Ala Gly Arg Leu Asn Asn Val
1               5                   10                  15

Arg Pro Met Thr Gly Glu Glu Tyr Leu Glu Ser Leu Arg Asp Gly Arg
            20                  25                  30

Glu Val Tyr Ile Tyr Gly Glu Arg Val Asp Asp Val Thr Thr His Leu
        35                  40                  45

Ala Phe Arg Asn Ser Val Arg Ser Ile Ala Arg Leu Tyr Asp Val Leu
    50                  55                  60

His Asp Pro Ala Ser Glu Gly Val Leu Arg Val Pro Thr Asp Thr Gly
65                  70                  75                  80

Asn Gly Gly Phe Thr His Pro Phe Phe Lys Thr Ala Arg Ser Ser Glu
```

```
                85                  90                  95

Asp Leu Val Ala Ala Arg Glu Ala Ile Val Gly Trp Gln Arg Leu Val
            100                 105                 110

Tyr Gly Trp Met Gly Arg Thr Pro Asp Tyr Lys Ala Ala Phe Phe Gly
        115                 120                 125

Thr Leu Asp Ala Asn Ala Glu Phe Tyr Gly Pro Phe Glu Ala Asn Ala
    130                 135                 140

Arg Arg Trp Tyr Arg Asp Ala Gln Glu Arg Val Leu Tyr Phe Asn His
145                 150                 155                 160

Ala Ile Val His Pro Pro Val Asp Arg Asp Arg Pro Ala Asp Arg Thr
                165                 170                 175

Ala Asp Ile Cys Val His Val Glu Glu Glu Thr Asp Ser Gly Leu Ile
            180                 185                 190

Val Ser Gly Ala Lys Val Val Ala Thr Gly Ser Ala Met Thr Asn Ala
        195                 200                 205

Asn Leu Ile Ala His Tyr Gly Leu Pro Val Arg Asp Lys Lys Phe Gly
    210                 215                 220

Leu Val Phe Thr Val Pro Met Asn Ser Pro Gly Leu Lys Leu Ile Cys
225                 230                 235                 240

Arg Thr Ser Tyr Glu Leu Met Val Ala Thr Gln Gly Ser Pro Phe Asp
                245                 250                 255

Tyr Pro Leu Ser Ser Arg Leu Asp Glu Asn Asp Ser Ile Met Ile Phe
            260                 265                 270

Asp Arg Val Leu Val Pro Trp Glu Asn Val Phe Met Tyr Asp Ala Gly
        275                 280                 285

Ala Ala Asn Ser Phe Ala Thr Gly Ser Gly Phe Leu Glu Arg Phe Thr
    290                 295                 300

Phe His Gly Cys Thr Arg Leu Ala Val Lys Leu Asp Phe Ile Ala Gly
305                 310                 315                 320

Cys Val Met Lys Ala Val Glu Val Thr Gly Thr Thr His Phe Arg Gly
                325                 330                 335

Val Gln Ala Gln Val Gly Glu Val Leu Asn Trp Arg Asp Val Phe Trp
            340                 345                 350

Gly Leu Ser Asp Ala Met Ala Lys Ser Pro Asn Ser Trp Val Gly Gly
        355                 360                 365

Ser Val Gln Pro Asn Leu Asn Tyr Gly Leu Ala Tyr Arg Thr Phe Met
    370                 375                 380

Gly Val Gly Tyr Pro Arg Ile Lys Glu Ile Ile Gln Gln Thr Leu Gly
385                 390                 395                 400

Ser Gly Leu Ile Tyr Leu Asn Ser Ser Ala Ala Asp Trp Lys Asn Pro
                405                 410                 415

Asp Val Arg Pro Tyr Leu Asp Arg Tyr Leu Arg Gly Ser Arg Gly Ile
            420                 425                 430

Gln Ala Ile Asp Arg Val Lys Leu Leu Lys Leu Leu Trp Asp Ala Val
        435                 440                 445

Gly Thr Glu Phe Ala Gly Arg His Glu Leu Tyr Glu Arg Asn Tyr Gly
    450                 455                 460

Gly Asp His Glu Gly Ile Arg Val Gln Thr Leu Gln Ala Tyr Gln Ala
465                 470                 475                 480

Asn Gly Gln Ala Ala Ala Leu Lys Gly Phe Ala Glu Gln Cys Met Ser
                485                 490                 495

Glu Tyr Asp Leu Asp Gly Trp Thr Arg Pro Asp Leu Ile Asn Pro Gly
            500                 505                 510
```

Thr

<210> SEQ ID NO 72
<211> LENGTH: 1542
<212> TYPE: DNA
<213> ORGANISM: artificial
<220> FEATURE:
<223> OTHER INFORMATION: coding sequence for SEQ ID NO: 71

<400> SEQUENCE: 72
atgtccacca tcacttctcc agctccagct ggtagattga acaacgtcag accaatgact 60
ggtgaagaat acttggaatc tttgagagat ggtagagaag tctacatcta cggtgaaaga 120
gtcgacgacg tcaccactca cttggccttc agaaactctg ttagatccat cgctagattg 180
tacgacgttt tgcacgaccc agcttcggag ggtgtactaa gagttccaac cgacactggt 240
aatggtggct tcactcatcc attcttcaag accgcccgtt cttctgaaga tttggtcgcc 300
gctagagaag ccatcgtcgg ttggcaaaga ttggtttacg gttggatggg tagaacccca 360
gattacaagg ctgcgttctt cggtactctc gacgccaacg ccgaattcta cggtccattc 420
gaagccaacg ccagaagatg gtacagagat gcccaagaaa gagttttgta cttcaaccac 480
gctatcgttc acccaccagt cgacagagac agaccagccg acagaaccgc cgacatctgt 540
gttcacgttg aagaagaaac cgactctggt ttgatcgttt ccggtgccaa ggttgtcgct 600
accggttccg ctatgaccaa cgctaacttg atcgctcact acggtttgcc agttagagac 660
aagaagttcg gtttggtttt cactgtccca atgaactctc caggtttgaa gttgatctgt 720
agaacctcct acgaattgat ggtcgctact caaggttctc cattcgacta cccattatct 780
tctagattgg acgaaaacga ctctatcatg atcttcgaca gagttttggt tccatgggaa 840
aacgttttca tgtacgacgc tggtgctgcc aactccttcg ccaccggttc tggtttcttg 900
gaaagattca ccttccacgg ttgtaccaga ttggctgtca agttggactt catcgccggt 960
tgtgtcatga aggctgttga agtcaccggt accactcact tcagaggtgt tcaagctcaa 1020
gtcggtgaag ttttgaactg gagagatgtt ttctggggtt tgtccgacgc tatggccaag 1080
tctccaaact cttgggtcgg tggttctgtt caaccaaact tgaactacgg tttggcttac 1140
agaaccttca tgggtgttgg ttacccaaga atcaaggaaa tcatccaaca aaccttgggt 1200
tctggtttga tctacttgaa ctcctctgcc gccgactgga agaacccaga cgtcagacca 1260
tacttggaca gatacttgag aggttctaga ggtatccaag ctatcgacag agtcaagttg 1320
ttgaagttgt tgtgggacgc tgtcggtacc gaattcgccg gtagacacga attgtacgaa 1380
agaaactacg gtggtgacca cgaaggtatc agagttcaaa ccttgcaagc ttaccaagct 1440
aacggtcagg cggccgctct caagggtttc gcggaacaat gtatgtccga atacgacttg 1500
gacggttgga ctagaccaga cttgatcaac ccaggtacct aa 1542

<210> SEQ ID NO 73
<211> LENGTH: 498
<212> TYPE: PRT
<213> ORGANISM: Beta vulgaris

<400> SEQUENCE: 73

Met Ser Asp His Ala Thr Leu Ala Met Ile Leu Ala Ile Leu Phe Ile
1 5 10 15

Ser Phe His Phe Ile Lys Leu Leu Phe Ser Gln Gln Thr Thr Lys Leu
20 25 30

-continued

```
Leu Pro Pro Gly Pro Lys Pro Leu Pro Ile Ile Gly Asn Ile Leu Glu
        35                  40                  45

Val Gly Lys Lys Pro His Arg Ser Phe Ala Asn Leu Ala Lys Ile His
    50                  55                  60

Gly Pro Leu Ile Ser Leu Arg Leu Gly Ser Val Thr Thr Ile Val Val
65                  70                  75                  80

Ser Ser Ala Asp Val Ala Lys Glu Met Phe Leu Lys Lys Asp His Pro
                85                  90                  95

Leu Ser Asn Arg Thr Ile Pro Asn Ser Val Thr Ala Gly Asp His His
            100                 105                 110

Lys Leu Thr Met Ser Trp Leu Pro Val Ser Pro Lys Trp Arg Asn Phe
        115                 120                 125

Arg Lys Ile Thr Ala Val His Leu Leu Ser Pro Gln Arg Leu Asp Ala
    130                 135                 140

Cys Gln Thr Phe Arg His Ala Lys Val Gln Gln Leu Tyr Glu Tyr Val
145                 150                 155                 160

Gln Glu Cys Ala Gln Lys Gly Gln Ala Val Asp Ile Gly Lys Ala Ala
                165                 170                 175

Phe Thr Thr Ser Leu Asn Leu Leu Ser Lys Leu Phe Phe Ser Val Glu
            180                 185                 190

Leu Ala His His Lys Ser His Thr Ser Gln Glu Phe Lys Glu Leu Ile
        195                 200                 205

Trp Asn Ile Met Glu Asp Ile Gly Lys Pro Asn Tyr Ala Asp Tyr Phe
    210                 215                 220

Pro Ile Leu Gly Cys Val Asp Pro Ser Gly Ile Arg Arg Arg Leu Ala
225                 230                 235                 240

Cys Ser Phe Asp Lys Leu Ile Ala Val Phe Gln Gly Ile Ile Cys Glu
                245                 250                 255

Arg Leu Ala Pro Asp Ser Ser Thr Thr Thr Thr Thr Thr Thr Asp Asp
            260                 265                 270

Val Leu Asp Val Leu Leu Gln Leu Phe Lys Gln Asn Glu Leu Thr Met
        275                 280                 285

Gly Glu Ile Asn His Leu Leu Val Asp Ile Phe Asp Ala Gly Thr Asp
    290                 295                 300

Thr Thr Ser Ser Thr Leu Glu Trp Val Met Thr Glu Leu Ile Arg Asn
305                 310                 315                 320

Pro Glu Met Met Glu Lys Ala Gln Glu Glu Ile Lys Gln Val Leu Gly
                325                 330                 335

Lys Asp Lys Gln Ile Gln Glu Ser Asp Ile Ile Asn Leu Pro Tyr Leu
            340                 345                 350

Gln Ala Ile Ile Lys Glu Thr Leu Arg Leu His Pro Pro Thr Val Phe
        355                 360                 365

Leu Leu Pro Arg Lys Ala Asp Thr Asp Val Glu Leu Tyr Gly Tyr Ile
    370                 375                 380

Val Pro Lys Asp Ala Gln Ile Leu Val Asn Leu Trp Ala Ile Gly Arg
385                 390                 395                 400

Asp Pro Asn Ala Trp Gln Asn Ala Asp Ile Phe Ser Pro Glu Arg Phe
                405                 410                 415

Ile Gly Cys Glu Ile Asp Val Lys Gly Arg Asp Phe Gly Leu Leu Pro
            420                 425                 430

Phe Gly Ala Gly Arg Arg Ile Cys Pro Gly Met Asn Leu Ala Ile Arg
        435                 440                 445

Met Leu Thr Leu Met Leu Ala Thr Leu Leu Gln Phe Phe Asn Trp Lys
```

```
    450                 455                 460

Leu Glu Gly Asp Ile Ser Pro Lys Asp Leu Asp Met Asp Glu Lys Phe
465                 470                 475                 480

Gly Ile Ala Leu Gln Lys Thr Lys Pro Leu Lys Leu Ile Pro Ile Pro
                485                 490                 495

Arg Tyr


<210> SEQ ID NO 74
<211> LENGTH: 1497
<212> TYPE: DNA
<213> ORGANISM: artificial
<220> FEATURE:
<223> OTHER INFORMATION: coding sequence for SEQ ID NO: 73

<400> SEQUENCE: 74

atgtccgatc acgctacttt ggcgatgata ttggccatcc tattcatttc tttccacttc      60

atcaagttgt tgttctctca acaaactacc aagttgttgc caccaggtcc aaagccattg     120

ccaatcattg gtaacatctt ggaagttggt aagaagccac acagatcttt cgctaacttg     180

gctaagattc acggtccatt gatctctttg agattgggtt ctgttactac tattgttgtt     240

tcttctgctg atgttgctaa ggaaatgttc ttgaagaagg accacccatt gtctaacaga     300

actattccaa actctgtcac tgccggtgac caccacaagt tgaccatgtc ttggttgcca     360

gtttctccaa agtggagaaa cttcagaaag attactgccg tccacttgtt gtctccacaa     420

agattggatg cttgtcaaac cttcagacac gccaaggttc aacaattgta cgaatacgtt     480

caagaatgtg ctcaaaaggg tcaagctgtt gatattggta aggctgcttt cactacctcc     540

ttgaacttgt tgtctaagtt gttcttctct gttgaattgg cccaccacaa gtctcacact     600

tctcaagaat tcaaggaatt gatctggaac attatggaag atattggtaa gccaaactac     660

gctgattact tcccaatttt gggttgtgtt gatccatctg gtattagaag aagattggct     720

tgttctttcg acaagttgat tgctgttttc caaggtatca tctgtgaaag attggctcca     780

gattcttcta ctacaaccac tactaccact gatgatgttt tggacgtttt gttgcaattg     840

ttcaagcaaa acgaattgac tatgggtgaa attaaccact tgttggtcga cattttcgat     900

gctggtactg acactacttc ttctactttg gaatgggtca tgactgaatt gattagaaac     960

ccagaaatga tggaaaaggc tcaagaagaa attaagcaag ttttgggtaa ggataagcaa    1020

attcaagaat ctgacattat taacttgcca tacttgcaag ccattatcaa ggaaactttg    1080

agattgcacc caccaactgt tttcttgttg ccaagaaagg ccgacactga tgttgaattg    1140

tacggttaca ttgttccaaa ggatgctcaa atcttggtta acttgtgggc tattggtaga    1200

gatccaaacg cttggcaaaa cgctgatatt ttctctccag aaagattcat cggttgtgaa    1260

attgatgtca agggtagaga tttcggtttg ttgccattcg gtgccggtag aagaatctgt    1320

ccaggtatga acttggccat tagaatgttg actttgatgt tggctacttt gttgcaattc    1380

ttcaactgga agttggaagg tgacatctct ccaaaggact tggacatgga tgaaaagttc    1440

ggtattgctt tgcaaaagac taagccattg aagttgattc caatcccaag atactaa       1497


<210> SEQ ID NO 75
<211> LENGTH: 413
<212> TYPE: PRT
<213> ORGANISM: Rhodopseudomonas palustris

<400> SEQUENCE: 75

Met Ser Thr Thr Ala Pro Ser Leu Val Pro Val Thr Thr Pro Ser Gln
```

-continued

```
1               5                   10                  15

His Gly Ala Gly Val Pro His Leu Gly Ile Asp Pro Phe Ala Leu Asp
            20                  25                  30

Tyr Phe Ala Asp Pro Tyr Pro Glu Gln Glu Thr Leu Arg Glu Ala Gly
        35                  40                  45

Pro Val Val Tyr Leu Asp Lys Trp Asn Val Tyr Gly Val Ala Arg Tyr
    50                  55                  60

Ala Glu Val Tyr Ala Val Leu Asn Asp Pro Leu Thr Phe Cys Ser Ser
65                  70                  75                  80

Arg Gly Val Gly Leu Ser Asp Phe Lys Lys Glu Lys Pro Trp Arg Pro
                85                  90                  95

Pro Ser Leu Ile Leu Glu Ala Asp Pro Pro Ala His Thr Arg Thr Arg
            100                 105                 110

Ala Val Leu Ser Lys Val Leu Ser Pro Ala Thr Met Lys Arg Leu Arg
        115                 120                 125

Asp Gly Phe Ala Ala Ala Ala Asp Ala Lys Ile Asp Glu Leu Leu Ala
    130                 135                 140

Arg Gly Gly Asn Ile Asp Ala Ile Ala Asp Leu Ala Glu Ala Tyr Pro
145                 150                 155                 160

Leu Ser Val Phe Pro Asp Ala Met Gly Leu Lys Gln Glu Gly Arg Glu
                165                 170                 175

Asn Leu Leu Pro Tyr Ala Gly Leu Val Leu Asn Ala Phe Gly Pro Pro
            180                 185                 190

Asn Glu Leu Arg Gln Ser Ala Ile Glu Arg Ser Ala Pro His Gln Ala
        195                 200                 205

Tyr Val Ala Glu Gln Cys Gln Arg Pro Asn Leu Ala Pro Gly Gly Phe
    210                 215                 220

Gly Ala Cys Ile His Ala Phe Ser Asp Thr Gly Glu Ile Thr Pro Glu
225                 230                 235                 240

Glu Ala Pro Leu Leu Val Arg Ser Leu Leu Ser Ala Gly Leu Asp Thr
                245                 250                 255

Thr Val Asn Gly Ile Ala Ala Ala Val Tyr Cys Leu Ala Arg Phe Pro
            260                 265                 270

Asp Glu Phe Ala Arg Leu Arg Ala Asp Pro Ser Leu Ala Arg Asn Ala
        275                 280                 285

Phe Glu Glu Ala Val Arg Phe Glu Ser Pro Val Gln Thr Phe Phe Arg
    290                 295                 300

Thr Thr Thr Arg Asp Val Glu Leu Ala Gly Ala Thr Ile Gly Glu Gly
305                 310                 315                 320

Glu Lys Val Leu Met Phe Leu Gly Ser Ala Asn Arg Asp Pro Arg Arg
                325                 330                 335

Trp Asp Asp Pro Asp Arg Tyr Asp Ile Thr Arg Lys Thr Ser Gly His
            340                 345                 350

Val Gly Phe Gly Ser Gly Val His Met Cys Val Gly Gln Leu Val Ala
        355                 360                 365

Arg Leu Glu Gly Glu Val Val Leu Ala Ala Leu Ala Arg Lys Val Ala
    370                 375                 380

Ala Ile Glu Ile Ala Gly Pro Leu Lys Arg Arg Phe Asn Asn Thr Leu
385                 390                 395                 400

Arg Gly Leu Glu Ser Leu Pro Ile Gln Leu Thr Pro Ala
                405                 410
```

<210> SEQ ID NO 76

<211> LENGTH: 1242
<212> TYPE: DNA
<213> ORGANISM: artificial
<220> FEATURE:
<223> OTHER INFORMATION: coding sequence for SEQ ID NO: 75

<400> SEQUENCE: 76

```
atgtccacca ctgctccatc tttggttcca gttaccactc catcccaaca cggtgctggt     60

gttccacact tgggtatcga tccattcgct ttggactact tcgccgatcc atacccagaa    120

caagaaactt tgagagaagc tggtccagtt gtctacttgg acaagtggaa cgtctacggt    180

gtcgccagat acgctgaagt atacgccgta ctcaacgatc cattgacctt ctgttcctct    240

agaggtgttg gtttgtctga tttcaagaag gaaaagccat ggaggccacc atctttgatc    300

ttggaagccg acccaccagc tcacaccaga accagagctg ttttgtctaa ggttttgtct    360

ccagctacta tgaagagatt gagagatggt ttcgctgctg ctgctgacgc caagatcgat    420

gaattgttgg ccagaggtgg taacatcgat gctatcgccg acttggccga agcctaccca    480

ttgtctgttt tcccagatgc gatgggtttg aagcaagaag gcagagaaaa cttgttgcca    540

tacgcgggct tggttttgaa cgcattcggt ccaccaaacg aattgagaca atctgctatc    600

gaaagatctg ctccacacca agcctacgtt gccgaacaat gtcaaagacc aaacttggct    660

ccaggtggtt tcggtgcctg tatccacgcc ttctctgaca ccggtgaaat cactccagaa    720

gaagccccat tgttggttag atctttgttg tctgctggtt tggacactac cgtcaacggt    780

attgctgctg ctgtttactg tttggctaga ttcccagacg aattcgctag attgagagcc    840

gatccatctt tggccagaaa cgccttcgaa gaagctgtta gattcgaatc tccagttcaa    900

accttcttca gaaccaccac tagagatgtc gaattggctg gtgccactat cggtgaaggt    960

gaaaaggttt tgatgttctt gggttccgcc aacagagatc caagaagatg ggacgatcca   1020

gacagatacg acatcaccag aaagacctct gggcatgtcg gcttcggttc tggtgttcac   1080

atgtgtgtcg gtcaattggt cgccagattg gaaggtgaag ttgttttggc cgctttggct   1140

agaaaggttg ctgctatcga aatcgccggt ccattgaaga gaagattcaa caacactttg   1200

agaggtttgg aatctttgcc aatccaattg actccagctt aa                      1242
```

<210> SEQ ID NO 77
<211> LENGTH: 718
<212> TYPE: PRT
<213> ORGANISM: Arabidopsis thaliana

<400> SEQUENCE: 77

```
Met Ser Asp Gln Ile Glu Ala Met Leu Cys Gly Gly Gly Glu Lys Thr
1               5                   10                  15

Lys Val Ala Val Thr Thr Lys Thr Leu Ala Asp Pro Leu Asn Trp Gly
            20                  25                  30

Leu Ala Ala Asp Gln Met Lys Gly Ser His Leu Asp Glu Val Lys Lys
        35                  40                  45

Met Val Glu Glu Tyr Arg Arg Pro Val Val Asn Leu Gly Gly Glu Thr
    50                  55                  60

Leu Thr Ile Gly Gln Val Ala Ala Ile Ser Thr Val Gly Gly Ser Val
65                  70                  75                  80

Lys Val Glu Leu Ala Glu Thr Ser Arg Ala Gly Val Lys Ala Ser Ser
                85                  90                  95

Asp Trp Val Met Glu Ser Met Asn Lys Gly Thr Asp Ser Tyr Gly Val
            100                 105                 110
```

-continued

```
Thr Thr Gly Phe Gly Ala Thr Ser His Arg Arg Thr Lys Asn Gly Thr
        115                 120                 125

Ala Leu Gln Thr Glu Leu Ile Arg Phe Leu Asn Ala Gly Ile Phe Gly
    130                 135                 140

Asn Thr Lys Glu Thr Cys His Thr Leu Pro Gln Ser Ala Thr Arg Ala
145                 150                 155                 160

Ala Met Leu Val Arg Val Asn Thr Leu Leu Gln Gly Tyr Ser Gly Ile
                165                 170                 175

Arg Phe Glu Ile Leu Glu Ala Ile Thr Ser Leu Leu Asn His Asn Ile
            180                 185                 190

Ser Pro Ser Leu Pro Leu Arg Gly Thr Ile Thr Ala Ser Gly Asp Leu
        195                 200                 205

Val Pro Leu Ser Tyr Ile Ala Gly Leu Leu Thr Gly Arg Pro Asn Ser
    210                 215                 220

Lys Ala Thr Gly Pro Asp Gly Glu Ser Leu Thr Ala Lys Glu Ala Phe
225                 230                 235                 240

Glu Lys Ala Gly Ile Ser Thr Gly Phe Phe Asp Leu Gln Pro Lys Glu
                245                 250                 255

Gly Leu Ala Leu Val Asn Gly Thr Ala Val Gly Ser Gly Met Ala Ser
            260                 265                 270

Met Val Leu Phe Glu Ala Asn Val Gln Ala Val Leu Ala Glu Val Leu
        275                 280                 285

Ser Ala Ile Phe Ala Glu Val Met Ser Gly Lys Pro Glu Phe Thr Asp
    290                 295                 300

His Leu Thr His Arg Leu Lys His His Pro Gly Gln Ile Glu Ala Ala
305                 310                 315                 320

Ala Ile Met Glu His Ile Leu Asp Gly Ser Ser Tyr Met Lys Leu Ala
                325                 330                 335

Gln Lys Val His Glu Met Asp Pro Leu Gln Lys Pro Lys Gln Asp Arg
            340                 345                 350

Tyr Ala Leu Arg Thr Ser Pro Gln Trp Leu Gly Pro Gln Ile Glu Val
        355                 360                 365

Ile Arg Gln Ala Thr Lys Ser Ile Glu Arg Glu Ile Asn Ser Val Asn
    370                 375                 380

Asp Asn Pro Leu Ile Asp Val Ser Arg Asn Lys Ala Ile His Gly Gly
385                 390                 395                 400

Asn Phe Gln Gly Thr Pro Ile Gly Val Ser Met Asp Asn Thr Arg Leu
                405                 410                 415

Ala Ile Ala Ala Ile Gly Lys Leu Met Phe Ala Gln Phe Ser Glu Leu
            420                 425                 430

Val Asn Asp Phe Tyr Asn Asn Gly Leu Pro Ser Asn Leu Thr Ala Ser
        435                 440                 445

Ser Asn Pro Ser Leu Asp Tyr Gly Phe Lys Gly Ala Glu Ile Ala Met
    450                 455                 460

Ala Ser Tyr Cys Ser Glu Leu Gln Tyr Leu Ala Asn Pro Val Thr Ser
465                 470                 475                 480

His Val Gln Ser Ala Glu Gln His Asn Gln Asp Val Asn Ser Leu Gly
                485                 490                 495

Leu Ile Ser Ser Arg Lys Thr Ser Glu Ala Val Asp Ile Leu Lys Leu
            500                 505                 510

Met Ser Thr Thr Phe Leu Val Gly Ile Cys Gln Ala Val Asp Leu Arg
        515                 520                 525

His Leu Glu Glu Asn Leu Arg Gln Thr Val Lys Asn Thr Val Ser Gln
```

530 535 540

Val Ala Lys Lys Val Leu Thr Thr Gly Ile Asn Gly Glu Leu His Pro
545 550 555 560

Ser Arg Phe Cys Glu Lys Asp Leu Leu Lys Val Val Asp Arg Glu Gln
565 570 575

Val Phe Thr Tyr Val Asp Asp Pro Cys Ser Ala Thr Tyr Pro Leu Met
580 585 590

Gln Arg Leu Arg Gln Val Ile Val Asp His Ala Leu Ser Asn Gly Glu
595 600 605

Thr Glu Lys Asn Ala Val Thr Ser Ile Phe Gln Lys Ile Gly Ala Phe
610 615 620

Glu Glu Glu Leu Lys Ala Val Leu Pro Lys Glu Val Glu Ala Ala Arg
625 630 635 640

Ala Ala Tyr Gly Asn Gly Thr Ala Pro Ile Pro Asn Arg Ile Lys Glu
645 650 655

Cys Arg Ser Tyr Pro Leu Tyr Arg Phe Val Arg Glu Glu Leu Gly Thr
660 665 670

Lys Leu Leu Thr Gly Glu Lys Val Val Ser Pro Gly Glu Glu Phe Asp
675 680 685

Lys Val Phe Thr Ala Met Cys Glu Gly Lys Leu Ile Asp Pro Leu Met
690 695 700

Asp Cys Leu Lys Glu Trp Asn Gly Ala Pro Ile Pro Ile Cys
705 710 715

<210> SEQ ID NO 78
<211> LENGTH: 2157
<212> TYPE: DNA
<213> ORGANISM: artificial
<220> FEATURE:
<223> OTHER INFORMATION: coding sequence for SEQ ID NO: 77

<400> SEQUENCE: 78
atgtccgatc aaatcgaagc tatgttgtgt ggtggtggtg aaaaaacaaa agttgctgtt 60
actactaaga ccttggccga tccattgaat tggggtttgg ctgctgatca aatgaagggt 120
tctcatttgg atgaagtcaa gaagatggtc gaagaataca gaaggccagt tgttaatttg 180
ggtggtgaaa ctttgactat tggtcaagtt gctgctattt ctactgttgg tggttctgtt 240
aaggttgaat tggctgaaac ttctagagct ggtgttaagg cttcttctga ttgggttatg 300
gaatctatga acaagggtac tgattcttac ggtgttacta caggttttgg tgctacttct 360
catagaagaa ctaagaatgg tactgccttg caaaccgaat tgatcagatt tttgaacgcc 420
ggtattttcg gtaacaccaa agaaacttgt catacettgc cacaatctgc tactagagct 480
gctatgttgg ttagagttaa cactttgttg caaggttact ccggtatcag attcgaaatt 540
ttggaagcta tcacctcctt gttgaaccat aacatttctc catctttgcc attgagaggt 600
actattactg cttctggtga tttggttcca ttgtcttata ttgctggttt gttgactggt 660
agaccaaact ctaaagctac tggtccagat ggtgaatcat tgactgctaa agaagctttt 720
gaaaaggctg gtatctctac tggttttttc gacttgcaac ctaaagaagg tttggctttg 780
gttaatggta cagctgttgg ttctggtatg gcttctatgg ttttgtttga agctaacgtt 840
caagctgttt tggccgaagt tttgtctgct atttttgctg aagttatgtc cggtaagcca 900
gaattcactg atcatttgac ccatagattg aaacatcacc caggtcaaat tgaagctgct 960
gcaattatgg aacatatctt ggatggttcc tcttacatga agttggctca aaaagttcac 1020

-continued

```
gaaatggacc cattgcaaaa gccaaaacaa gatagatacg ctttgagaac ttctccacaa   1080

tggttgggtc cacaaataga agttattaga caagccacca agtccatcga aagagaaatc   1140

aattctgtta acgacaaccc attgatcgac gtcagtagaa acaaagctat tcatggtggt   1200

aacttccaag gtactccaat tggtgtttct atggacaaca ctagattggc tattgctgcc   1260

attggtaaat tgatgttcgc tcaattctcc gaattggtca acgattttta caacaacggt   1320

ttgccttcta acttgaccgc ttcttctaat ccatcattgg attacggttt taagggtgct   1380

gaaattgcta tggcttcata ctgttctgaa ttgcaatact tggctaaccc agttacctct   1440

catgttcaat ctgctgaaca acacaatcaa gacgttaact ccttgggttt gatctcttct   1500

agaaagactt ctgaagccgt tgacatcttg aagttgatgt ctactacatt cttggtcggt   1560

atttgccaag ctgttgattt gagacatttg gaagaaaact tgagacaaac cgtcaagaac   1620

accgtttcac aagttgctaa gaaagttttg accaccggta ttaacggtga attgcatcca   1680

tctagattct gcgaaaagga tttgttgaag gtcgttgata gagaacaagt tttcacctac   1740

gttgatgatc catgttctgc tacttatcca ttgatgcaaa gattgagaca agtcatcgtt   1800

gatcatgctt tgtctaatgg tgaaaccgaa aagaacgctg ttacctccat tttccaaaag   1860

attggtgctt tcgaagaaga attgaaggcc gttttgccaa aagaagttga agcagctaga   1920

gcagcttacg gtaacggtac tgctccaatt ccaaatagaa tcaaagaatg cagatcctac   1980

ccattataca gattcgttag agaagaatta ggtactaagt tgttgaccgg tgaaaaggtt   2040

gtttctccag gtgaagaatt cgataaggtt ttcactgcta tgtgcgaagg taaattgatc   2100

gatccattga tggactgctt gaaagaatgg aatggtgctc ctattcctat ctgctaa      2157
```

<210> SEQ ID NO 79
<211> LENGTH: 506
<212> TYPE: PRT
<213> ORGANISM: Arabidopsis thaliana

<400> SEQUENCE: 79

```
Met Ser Asp Leu Leu Leu Leu Glu Lys Ser Leu Ile Ala Val Phe Val
1               5                   10                  15

Ala Val Ile Leu Ala Thr Val Ile Ser Lys Leu Arg Gly Lys Lys Leu
            20                  25                  30

Lys Leu Pro Pro Gly Pro Ile Pro Ile Pro Ile Phe Gly Asn Trp Leu
        35                  40                  45

Gln Val Gly Asp Asp Leu Asn His Arg Asn Leu Val Asp Tyr Ala Lys
    50                  55                  60

Lys Phe Gly Asp Leu Phe Leu Leu Arg Met Gly Gln Arg Asn Leu Val
65                  70                  75                  80

Val Val Ser Ser Pro Asp Leu Thr Lys Glu Val Leu Leu Thr Gln Gly
                85                  90                  95

Val Glu Phe Gly Ser Arg Thr Arg Asn Val Val Phe Asp Ile Phe Thr
            100                 105                 110

Gly Lys Gly Gln Asp Met Val Phe Thr Val Tyr Gly Glu His Trp Arg
        115                 120                 125

Lys Met Arg Arg Ile Met Thr Val Pro Phe Phe Thr Asn Lys Val Val
    130                 135                 140

Gln Gln Asn Arg Glu Gly Trp Glu Phe Glu Ala Ala Ser Val Val Glu
145                 150                 155                 160

Asp Val Lys Lys Asn Pro Asp Ser Ala Thr Lys Gly Ile Val Leu Arg
                165                 170                 175
```

```
Lys Arg Leu Gln Leu Met Met Tyr Asn Asn Met Phe Arg Ile Met Phe
            180                 185                 190

Asp Arg Arg Phe Glu Ser Glu Asp Asp Pro Leu Phe Leu Arg Leu Lys
        195                 200                 205

Ala Leu Asn Gly Glu Arg Ser Arg Leu Ala Gln Ser Phe Glu Tyr Asn
    210                 215                 220

Tyr Gly Asp Phe Ile Pro Ile Leu Arg Pro Phe Leu Arg Gly Tyr Leu
225                 230                 235                 240

Lys Ile Cys Gln Asp Val Lys Asp Arg Arg Ile Ala Leu Phe Lys Lys
                245                 250                 255

Tyr Phe Val Asp Glu Arg Lys Gln Ile Ala Ser Ser Lys Pro Thr Gly
            260                 265                 270

Ser Glu Gly Leu Lys Cys Ala Ile Asp His Ile Leu Glu Ala Glu Gln
        275                 280                 285

Lys Gly Glu Ile Asn Glu Asp Asn Val Leu Tyr Ile Val Glu Asn Ile
    290                 295                 300

Asn Val Ala Ala Ile Glu Thr Thr Leu Trp Ser Ile Glu Trp Gly Ile
305                 310                 315                 320

Ala Glu Leu Val Asn His Pro Glu Ile Gln Ser Lys Leu Arg Asn Glu
                325                 330                 335

Leu Asp Thr Val Leu Gly Pro Gly Val Gln Val Thr Glu Pro Asp Leu
            340                 345                 350

His Lys Leu Pro Tyr Leu Gln Ala Val Val Lys Glu Thr Leu Arg Leu
        355                 360                 365

Arg Met Ala Ile Pro Leu Leu Val Pro His Met Asn Leu His Asp Ala
    370                 375                 380

Lys Leu Ala Gly Tyr Asp Ile Pro Ala Glu Ser Lys Ile Leu Val Asn
385                 390                 395                 400

Ala Trp Trp Leu Ala Asn Asn Pro Asn Ser Trp Lys Lys Pro Glu Glu
                405                 410                 415

Phe Arg Pro Glu Arg Phe Phe Glu Glu Glu Ser His Val Glu Ala Asn
            420                 425                 430

Gly Asn Asp Phe Arg Tyr Val Pro Phe Gly Val Gly Arg Arg Ser Cys
        435                 440                 445

Pro Gly Ile Ile Leu Ala Leu Pro Ile Leu Gly Ile Thr Ile Gly Arg
    450                 455                 460

Met Val Gln Asn Phe Glu Leu Leu Pro Pro Pro Gly Gln Ser Lys Val
465                 470                 475                 480

Asp Thr Ser Glu Lys Gly Gly Gln Phe Ser Leu His Ile Leu Asn His
                485                 490                 495

Ser Ile Ile Val Met Lys Pro Arg Asn Cys
            500                 505
```

<210> SEQ ID NO 80
<211> LENGTH: 1521
<212> TYPE: DNA
<213> ORGANISM: artificial
<220> FEATURE:
<223> OTHER INFORMATION: coding sequence for SEQ ID NO: 79

<400> SEQUENCE: 80

```
atgtccgact tgttgttgtt ggaaaagtcc ttgattgctg ttttcgttgc tgttattttg      60

gccaccgtta tctctaaatt gagaggtaag aaattgaagt tgccaccagg tccaattcca     120

atcccaattt ttggtaattg gttgcaagtt ggtgatgact tgaaccacag aaacttggtt     180
```

-continued

```
gattacgcta aaaagttcgg tgatttgttc ttgttgagaa tgggtcaaag aaatttggtc    240

gttgtttcct caccagactt gaccaaagaa gttttgttga ctcaaggtgt cgaattcggt    300

tccagaacta gaaatgttgt tttcgatatc ttcaccggta agggtcaaga tatggttttt    360

actgtttacg gtgaacattg gagaaagatg agaagaatta tgaccgttcc attcttcacc    420

aacaaggttg tccaacaaaa cagagaaggt tgggaatttg aagctgcttc tgttgttgaa    480

gatgtcaaga agaatccaga ttctgctact aagggtatcg ttttgagaaa aagattgcaa    540

ttgatgatgt acaacaacat gttcagaatc atgttcgaca gaagatttga atccgaagat    600

gacccttttgt ttttgagatt gaaggctttg aacggtgaaa gatctagatt ggctcaatcc    660

ttcgaataca actacggtga tttcatccca atcttaagac cattcttgag aggttacttg    720

aagatctgcc aagatgttaa ggatagaaga atcgccttgt tcaaaaagta cttcgttgac    780

gaaagaaagc aaatcgcttc ttctaaacct actggttctg aaggtttgaa gtgcgccatt    840

gatcatattt tggaagctga acaaaagggt gaaatcaacg aagataacgt cttgtacatc    900

gtcgaaaaca ttaacgttgc tgctattgaa actaccttgt ggtctattga atggggtatt    960

gctgaattgg ttaatcaccc agaaatccaa tccaagttga gaaacgaatt ggatactgtt   1020

ttgggtccag gtgttcaagt tactgaacct gacttgcata agttgccata cttgcaagct   1080

gttgtaaaag aaaccttgag attaagaatg gccatccctt tgttggttcc acatatgaac   1140

ttgcatgatg ctaaattggc cggttatgat attccagccg aatccaagat tttggttaat   1200

gcttggtggt tggctaacaa tccaaattct tggaaaaagc cagaagaatt cagaccagaa   1260

agatttttcg aagaagaaag tcacgttgaa gccaacggta atgattttag atacgttcca   1320

tttggtgttg gtagaagatc ttgtccaggt attatcttgg ctttgccaat tttgggtatt   1380

accatcggta gaatggtcca aaacttcgaa ttattgccac cacctggtca atctaaggtt   1440

gatacttctg aaaagggtgg tcaattctcc ttgcatattt tgaaccactc catcatcgtt   1500

atgaagccaa gaaactgtta a                                             1521
```

```
<210> SEQ ID NO 81
<211> LENGTH: 384
<212> TYPE: PRT
<213> ORGANISM: Saccharomyces cerevisiae

<400> SEQUENCE: 81

Met Ser Lys Ser Lys Thr Phe Leu Phe Thr Ser Glu Ser Val Gly Glu
1               5                   10                  15

Gly His Pro Asp Lys Ile Cys Asp Gln Val Ser Asp Ala Ile Leu Asp
            20                  25                  30

Ala Cys Leu Glu Gln Asp Pro Phe Ser Lys Val Ala Cys Glu Thr Ala
        35                  40                  45

Ala Lys Thr Gly Met Ile Met Val Phe Gly Glu Ile Thr Thr Lys Ala
    50                  55                  60

Arg Leu Asp Tyr Gln Gln Ile Val Arg Asp Thr Ile Lys Lys Ile Gly
65                  70                  75                  80

Tyr Asp Asp Ser Ala Lys Gly Phe Asp Tyr Lys Thr Cys Asn Val Leu
                85                  90                  95

Val Ala Ile Glu Gln Gln Ser Pro Asp Ile Ala Gln Gly Leu His Tyr
            100                 105                 110

Glu Lys Ser Leu Glu Asp Leu Gly Ala Gly Asp Gln Gly Ile Met Phe
        115                 120                 125

Gly Tyr Ala Thr Asp Glu Thr Pro Glu Gly Leu Pro Leu Thr Ile Leu
```

```
    130                 135                 140

Leu Ala His Lys Leu Asn Met Ala Met Ala Asp Ala Arg Arg Asp Gly
145                 150                 155                 160

Ser Leu Pro Trp Leu Arg Pro Asp Thr Lys Thr Gln Val Thr Val Glu
                165                 170                 175

Tyr Glu Asp Asp Asn Gly Arg Trp Val Pro Lys Arg Ile Asp Thr Val
            180                 185                 190

Val Ile Ser Ala Gln His Ala Asp Glu Ile Ser Thr Ala Asp Leu Arg
        195                 200                 205

Thr Gln Leu Gln Lys Asp Ile Val Glu Lys Val Ile Pro Lys Asp Met
    210                 215                 220

Leu Asp Glu Asn Thr Lys Tyr Phe Ile Gln Pro Ser Gly Arg Phe Val
225                 230                 235                 240

Ile Gly Gly Pro Gln Gly Asp Ala Gly Leu Thr Gly Arg Lys Ile Ile
                245                 250                 255

Val Asp Ala Tyr Gly Gly Ala Ser Ser Val Gly Gly Gly Ala Phe Ser
            260                 265                 270

Gly Lys Asp Tyr Ser Lys Val Asp Arg Ser Ala Ala Tyr Ala Ala Arg
        275                 280                 285

Trp Val Ala Lys Ser Leu Val Ala Ala Gly Leu Cys Lys Arg Val Gln
    290                 295                 300

Val Gln Phe Ser Tyr Ala Ile Gly Ile Ala Glu Pro Leu Ser Leu His
305                 310                 315                 320

Val Asp Thr Tyr Gly Thr Ala Thr Lys Ser Asp Asp Glu Ile Ile Glu
                325                 330                 335

Ile Ile Lys Lys Asn Phe Asp Leu Arg Pro Gly Val Leu Val Lys Glu
            340                 345                 350

Leu Asp Leu Ala Arg Pro Ile Tyr Leu Pro Thr Ala Ser Tyr Gly His
        355                 360                 365

Phe Thr Asn Gln Glu Tyr Ser Trp Glu Lys Pro Lys Lys Leu Glu Phe
    370                 375                 380
```

<210> SEQ ID NO 82
<211> LENGTH: 1155
<212> TYPE: DNA
<213> ORGANISM: artificial
<220> FEATURE:
<223> OTHER INFORMATION: coding sequence for SEQ ID NO: 81

<400> SEQUENCE: 82

```
atgtccaaga gcaaaacttt cttatttacc tctgaatccg tcggtgaagg tcacccagac     60

aagatttgtg accaagtttc tgatgctatt ttggacgctt gtttagaaca agatccattc    120

tccaaggttg cctgtgaaac agctgccaaa actggtatga ttatggtttt cggtgaaatt    180

accaccaaag ctagacttga ctaccaacaa atagtaagag ataccatcaa gaagattggt    240

tatgacgatt ctgccaaggg tttcgactac aagacatgta atgttttagt agctatcgaa    300

caacaatctc cagatatcgc tcaaggtctg cactatgaaa agagcttaga agatttaggt    360

gctggtgacc aaggtataat gtttggttac gctacagacg aaactccaga agggttacca    420

ttgaccattc ttttggctca caaattgaac atggctatgg cagatgctag aagagatggt    480

tctctcccat ggttgaggcc agacacaaag actcaagtca ctgtcgaata cgaggacgac    540

aatggtagat gggttccaaa gaggatagat accgttgtta tttctgctca acatgctgat    600

gaaatttcca ccgctgactt gagaactcaa cttcaaaaag atattgttga aaaggtcata    660
```

```
ccaaaggata tgttagacga aaataccaaa tatttcatcc aaccatccgg tagattcgtc    720

atcggtggtc ctcaaggtga cgctggtttg accggtagaa agattattgt cgacgcttac    780

ggtggtgcct catccgtcgg tggtggtgcc ttctccggta aggactattc caaggtcgat    840

cgttccgctg cttacgctgc tagatgggtt gccaagtctc tagttgccgc tggtttgtgt    900

aagagagtcc aagtccaatt ttcatatgct attggtattg ctgaaccatt gtctttacat    960

gtggacacct atggtacagc tacaaaatca gatgacgaaa tcattgaaat tattaagaag   1020

aacttcgact tgaggccagg tgtgttagta aaggaattag atttggctag accaatttac   1080

ttaccaaccg cttcttatgg tcacttcact aatcaagagt actcatggga aaaaccaaag   1140

aaattggaat tttaa                                                     1155
```

```
<210> SEQ ID NO 83
<211> LENGTH: 521
<212> TYPE: PRT
<213> ORGANISM: Escherichia coli

<400> SEQUENCE: 83

Met Ser Lys Pro Glu Asp Phe Arg Ala Ser Thr Gln Arg Pro Phe Thr
1               5                   10                  15

Gly Glu Glu Tyr Leu Lys Ser Leu Gln Asp Gly Arg Glu Ile Tyr Ile
            20                  25                  30

Tyr Gly Glu Arg Val Lys Asp Val Thr Thr His Pro Ala Phe Arg Asn
        35                  40                  45

Ala Ala Ala Ser Val Ala Gln Leu Tyr Asp Ala Leu His Lys Pro Glu
    50                  55                  60

Met Gln Asp Ser Leu Cys Trp Asn Thr Asp Thr Gly Ser Gly Gly Tyr
65                  70                  75                  80

Thr His Lys Phe Phe Arg Val Ala Lys Ser Ala Asp Asp Leu Arg Gln
                85                  90                  95

Gln Arg Asp Ala Ile Ala Glu Trp Ser Arg Leu Ser Tyr Gly Trp Met
            100                 105                 110

Gly Arg Thr Pro Asp Tyr Lys Ala Ala Phe Gly Cys Ala Leu Gly Ala
        115                 120                 125

Asn Pro Gly Phe Tyr Gly Gln Phe Glu Gln Asn Ala Arg Asn Trp Tyr
    130                 135                 140

Thr Arg Ile Gln Glu Thr Gly Leu Tyr Phe Asn His Ala Ile Val Asn
145                 150                 155                 160

Pro Pro Ile Asp Arg His Leu Pro Thr Asp Lys Val Lys Asp Val Tyr
                165                 170                 175

Ile Lys Leu Glu Lys Glu Thr Asp Ala Gly Ile Ile Val Ser Gly Ala
            180                 185                 190

Lys Val Val Ala Thr Asn Ser Ala Leu Thr His Tyr Asn Met Ile Gly
        195                 200                 205

Phe Gly Ser Ala Gln Val Met Gly Glu Asn Pro Asp Phe Ala Leu Met
    210                 215                 220

Phe Val Ala Pro Met Asp Ala Asp Gly Val Lys Leu Ile Ser Arg Ala
225                 230                 235                 240

Ser Tyr Glu Met Val Ala Gly Ala Thr Gly Ser Pro Tyr Asp Tyr Pro
                245                 250                 255

Leu Ser Ser Arg Phe Asp Glu Asn Asp Ala Ile Leu Val Met Asp Asn
            260                 265                 270

Val Leu Ile Pro Trp Glu Asn Val Leu Ile Tyr Arg Asp Phe Asp Arg
        275                 280                 285
```

```
Cys Arg Arg Trp Thr Met Glu Gly Gly Phe Ala Arg Met Tyr Pro Leu
    290                 295                 300

Gln Ala Cys Val Arg Leu Ala Val Lys Leu Asp Phe Ile Thr Ala Leu
305                 310                 315                 320

Leu Lys Lys Ser Leu Glu Cys Thr Gly Thr Leu Glu Phe Arg Gly Val
                325                 330                 335

Gln Ala Asp Leu Gly Glu Val Val Ala Trp Arg Asn Thr Phe Trp Ala
            340                 345                 350

Leu Ser Asp Ser Met Cys Ser Glu Ala Thr Pro Trp Val Asn Gly Ala
        355                 360                 365

Tyr Leu Pro Asp His Ala Ala Leu Gln Thr Tyr Arg Val Leu Ala Pro
    370                 375                 380

Met Ala Tyr Ala Lys Ile Lys Asn Ile Ile Glu Arg Asn Val Thr Ser
385                 390                 395                 400

Gly Leu Ile Tyr Leu Pro Ser Ser Ala Arg Asp Leu Asn Asn Pro Gln
                405                 410                 415

Ile Asp Gln Tyr Leu Ala Lys Tyr Val Arg Gly Ser Asn Gly Met Asp
            420                 425                 430

His Val Gln Arg Ile Lys Ile Leu Lys Leu Met Trp Asp Ala Ile Gly
        435                 440                 445

Ser Glu Phe Gly Gly Arg His Glu Leu Tyr Glu Ile Asn Tyr Ser Gly
    450                 455                 460

Ser Gln Asp Glu Ile Arg Leu Gln Cys Leu Arg Gln Ala Gln Asn Ser
465                 470                 475                 480

Gly Asn Met Asp Lys Met Met Ala Met Val Asp Arg Cys Leu Ser Glu
                485                 490                 495

Tyr Asp Gln Asp Gly Trp Thr Val Pro His Leu His Asn Asn Asp Asp
            500                 505                 510

Ile Asn Met Leu Asp Lys Leu Leu Lys
        515                 520
```

<210> SEQ ID NO 84
<211> LENGTH: 1566
<212> TYPE: DNA
<213> ORGANISM: artificial
<220> FEATURE:
<223> OTHER INFORMATION: coding sequence for SEQ ID NO: 83

<400> SEQUENCE: 84

```
atgtccaaac cagaagattt ccgcgccagt acccaacgtc ctttcaccgg ggaagagtat     60

ctgaaaagcc tgcaggatgg tcgcgagatc tatatctatg gcgagcgagt gaaagacgtc    120

accactcatc cggcatttcg taatgcggca gcgtctgttg cccagctgta cgacgcactg    180

cacaaaccgg agatgcagga ctctctgtgt tggaacaccg acaccggcag cggcggctat    240

acccataaat tcttccgcgt ggcgaaaagt gccgacgacc tgcgccagca acgcgacgcc    300

atcgctgagt ggtcacgcct gagctatggc tggatgggcc gtaccccaga ctacaaagcc    360

gctttcggtt gcgcactggg cgcgaatccg ggcttttacg gtcagttcga gcagaacgcc    420

cgtaactggt acacccgtat tcaggaaact ggcctctact ttaaccacgc gattgttaac    480

ccaccgatcg atcgtcattt gccgaccgat aaagtgaaag acgtttacat caagctggaa    540

aaagagactg acgccgggat tatcgtcagc ggtgcgaaag tggttgccac caactcggcg    600

ctgactcact acaacatgat tggcttcggc tcggcacaag tgatgggcga aaacccggac    660

ttcgcactga tgttcgttgc gccaatggat gccgatggcg tgaaattaat ctcccgcgcc    720
```

```
tcttatgaga tggtcgcggg tgctaccggc tcgccatacg actacccgct ctccagccgc    780

ttcgatgaga acgatgcgat tctggtgatg gataacgtgc tgattccatg ggaaaacgtg    840

ctgatctacc gcgattttga tcgctgccgt cgctggacga tggaaggcgg ttttgcccgt    900

atgtatccgc tgcaagcctg tgtgcgcctg gcagtgaaat tagacttcat tacggcactg    960

ctgaaaaaat cactcgaatg taccggcacc ctggagttcc gtggtgtgca ggccgatctc   1020

ggtgaagtgg tagcgtggcg caacaccttc tgggcattga gtgactcgat gtgttcagaa   1080

gcaacgccgt gggtcaacgg ggcttattta ccggatcatg ccgcactgca aacctatcgc   1140

gtactggcac caatggccta cgcgaagatc aaaaacatta tcgaacgcaa cgttaccagt   1200

ggcctgatct atctcccttc cagtgcccgt gacctgaata atccgcagat cgaccagtat   1260

ctggcgaagt atgtgcgcgg ttcgaacggt atggatcacg tccagcgcat caagatcctc   1320

aaactgatgt gggatgctat tggcagcgaa tttggtggtc gtcacgaact gtatgaaatc   1380

aactactccg gtagccagga tgagattcgc ctgcagtgtc tgcgccaggc acaaaactcc   1440

ggcaatatgg acaagatgat ggcgatggtt gatcgctgcc tgtcggaata cgaccaggac   1500

ggctggactg tgccgcacct gcacaacaac gacgatatca acatgctgga taagctgctg   1560

aaataa                                                              1566
```

<210> SEQ ID NO 85
<211> LENGTH: 171
<212> TYPE: PRT
<213> ORGANISM: Escherichia coli

<400> SEQUENCE: 85

```
Met Ser Gln Leu Asp Glu Gln Arg Leu Arg Phe Arg Asp Ala Met Ala
1               5                   10                  15

Ser Leu Ser Ala Ala Val Asn Ile Ile Thr Thr Glu Gly Asp Ala Gly
            20                  25                  30

Gln Cys Gly Ile Thr Ala Thr Ala Val Cys Ser Val Thr Asp Thr Pro
        35                  40                  45

Pro Ser Leu Met Val Cys Ile Asn Ala Asn Ser Ala Met Asn Pro Val
    50                  55                  60

Phe Gln Gly Asn Gly Lys Leu Cys Val Asn Val Leu Asn His Glu Gln
65                  70                  75                  80

Glu Leu Met Ala Arg His Phe Ala Gly Met Thr Gly Met Ala Met Glu
                85                  90                  95

Glu Arg Phe Ser Leu Ser Cys Trp Gln Lys Gly Pro Leu Ala Gln Pro
            100                 105                 110

Val Leu Lys Gly Ser Leu Ala Ser Leu Glu Gly Glu Ile Arg Asp Val
        115                 120                 125

Gln Ala Ile Gly Thr His Leu Val Tyr Leu Val Glu Ile Lys Asn Ile
    130                 135                 140

Ile Leu Ser Ala Glu Gly His Gly Leu Ile Tyr Phe Lys Arg Arg Phe
145                 150                 155                 160

His Pro Val Met Leu Glu Met Glu Ala Ala Ile
                165                 170
```

<210> SEQ ID NO 86
<211> LENGTH: 516
<212> TYPE: DNA
<213> ORGANISM: artificial
<220> FEATURE:
<223> OTHER INFORMATION: coding sequence for SEQ ID NO: 85

<400> SEQUENCE: 86
atgtcccaat tagatgaaca acgcctgcgc tttcgtgacg cgatggccag cctgtcggca 60
gcggtaaata ttatcaccac cgagggcgac gccggacaat gcgggattac ggcaacggcc 120
gtctgctcgg tcacggatac accaccgtcg ctgatggtgt gcattaacgc caacagtgcg 180
atgaacccgg tttttcaggg caacggcaag ttgtgcgtca acgtcctcaa ccatgagcag 240
gaactgatgg cacgccactt cgcgggcatg acaggcatgg cgatggaaga gcgttttagc 300
ctctcatgct ggcaaaaagg tccgctggcg cagccggtgc taaaaggttc gctggccagt 360
cttgaaggtg agatccgcga tgtgcaggca attggcacac atctggtgta tctggtggag 420
attaaaaaca tcatcctcag tgcagaaggt catggactta tctactttaa acgccgtttc 480
catccggtga tgctggaaat ggaagctgcg atttaa 516

<210> SEQ ID NO 87
<211> LENGTH: 233
<212> TYPE: PRT
<213> ORGANISM: Arabidopsis thaliana

<400> SEQUENCE: 87

Met Ser Ala Lys Asp Glu Ala Lys Gly Leu Leu Lys Ser Glu Glu Leu
1 5 10 15

Tyr Lys Tyr Ile Leu Glu Thr Ser Val Tyr Pro Arg Glu Pro Glu Val
20 25 30

Leu Arg Glu Leu Arg Asn Ile Thr His Asn His Pro Gln Ala Gly Met
35 40 45

Ala Thr Ala Pro Asp Ala Gly Gln Leu Met Gly Met Leu Leu Asn Leu
50 55 60

Val Asn Ala Arg Lys Thr Ile Glu Val Gly Val Phe Thr Gly Tyr Ser
65 70 75 80

Leu Leu Leu Thr Ala Leu Thr Leu Pro Glu Asp Gly Lys Val Ile Ala
85 90 95

Ile Asp Met Asn Arg Asp Ser Tyr Glu Ile Gly Leu Pro Val Ile Lys
100 105 110

Lys Ala Gly Val Glu His Lys Ile Asp Phe Lys Glu Ser Glu Ala Leu
115 120 125

Pro Ala Leu Asp Glu Leu Leu Asn Asn Lys Val Asn Glu Gly Gly Phe
130 135 140

Asp Phe Ala Phe Val Asp Ala Asp Lys Leu Asn Tyr Trp Asn Tyr His
145 150 155 160

Glu Arg Leu Ile Arg Leu Ile Lys Val Gly Gly Ile Ile Val Tyr Asp
165 170 175

Asn Thr Leu Trp Gly Gly Ser Val Ala Glu Pro Asp Ser Ser Thr Pro
180 185 190

Glu Trp Arg Ile Glu Val Lys Lys Ala Thr Leu Glu Leu Asn Lys Lys
195 200 205

Leu Ser Ala Asp Gln Arg Val Gln Ile Ser Gln Ala Ala Leu Gly Asp
210 215 220

Gly Ile Thr Ile Cys Arg Arg Leu Tyr
225 230

<210> SEQ ID NO 88
<211> LENGTH: 702
<212> TYPE: DNA
<213> ORGANISM: artificial

<220> FEATURE:
<223> OTHER INFORMATION: coding sequence for SEQ ID NO: 87

<400> SEQUENCE: 88
atgtccgcta aggatgaagc caagggtttg ttgaagtctg aagaattgta caagtacatc 60
ttggaaactt ctgtttaccc aagagaacca gaagttttga gagaattgag aaacattact 120
cacaaccacc cacaagctgg tatggctact gctccagacg ctggtcaatt gatgggtatg 180
ttgttgaact tggttaacgc tagaaagact atcgaagttg gtgttttcac tggttactct 240
ttgttgttga ctgctttgac tttgccagaa gatggtaagg ttatcgccat tgacatgaac 300
agagactctt acgaaatcgg tttgccagtt atcaagaagg ctggtgttga acacaagatt 360
gatttcaagg aatctgaagc tttgccagcc ttggacgaat tgttgaacaa caaggttaac 420
gaaggtggtt tcgacttcgc tttcgttgat gctgacaagt tgaactactg gaactaccac 480
gaaagattga ttagattgat caaggttggt ggtatcatcg tttacgataa cactttgtgg 540
ggtggttctg ttgctgaacc agactcttcc actccagaat ggagaatcga agtcaagaag 600
gctaccttgg aattgaacaa gaagttgtct gctgatcaaa gagttcaaat ctctcaagct 660
gctttgggtg atggtatcac tatttgtaga agattgtact aa 702

<210> SEQ ID NO 89
<211> LENGTH: 222
<212> TYPE: PRT
<213> ORGANISM: Homo sapiens

<400> SEQUENCE: 89

Met Ser Gly Asp Thr Lys Glu Gln Arg Ile Leu Asn His Val Leu Gln
1 5 10 15

His Ala Glu Pro Gly Asn Ala Gln Ser Val Leu Glu Ala Ile Asp Thr
20 25 30

Tyr Cys Glu Gln Lys Glu Trp Ala Met Asn Val Gly Asp Lys Lys Gly
35 40 45

Lys Ile Val Asp Ala Val Ile Gln Glu His Gln Pro Ser Val Leu Leu
50 55 60

Glu Leu Gly Ala Tyr Cys Gly Tyr Ser Ala Val Arg Met Ala Arg Leu
65 70 75 80

Leu Ser Pro Gly Ala Arg Leu Ile Thr Ile Glu Ile Asn Pro Asp Cys
85 90 95

Ala Ala Ile Thr Gln Arg Met Val Asp Phe Ala Gly Val Lys Asp Lys
100 105 110

Val Thr Leu Val Val Gly Ala Ser Gln Asp Ile Ile Pro Gln Leu Lys
115 120 125

Lys Lys Tyr Asp Val Asp Thr Leu Asp Met Val Phe Leu Asp His Trp
130 135 140

Lys Asp Arg Tyr Leu Pro Asp Thr Leu Leu Leu Glu Glu Cys Gly Leu
145 150 155 160

Leu Arg Lys Gly Thr Val Leu Leu Ala Asp Asn Val Ile Cys Pro Gly
165 170 175

Ala Pro Asp Phe Leu Ala His Val Arg Gly Ser Ser Cys Phe Glu Cys
180 185 190

Thr His Tyr Gln Ser Phe Leu Glu Tyr Arg Glu Val Val Asp Gly Leu
195 200 205

Glu Lys Ala Ile Tyr Lys Gly Pro Gly Ser Glu Ala Gly Pro
210 215 220

<210> SEQ ID NO 90
<211> LENGTH: 669
<212> TYPE: DNA
<213> ORGANISM: artificial
<220> FEATURE:
<223> OTHER INFORMATION: coding sequence for SEQ ID NO: 89

<400> SEQUENCE: 90
atgtccggtg acaccaagga acaaagaatc ttgaaccacg ttttgcaaca cgctgaacca 60
ggtaacgctc aatctgtttt ggaagccatt gacacctact gtgaacaaaa ggaatgggcc 120
atgaacgttg gtgacaagaa gggtaagatc gttgacgccg ttattcaaga acaccaacca 180
tccgttttgt tggaattggg tgcctactgt ggttactctg ctgttagaat ggccagattg 240
ttgtctccag gtgctagatt gatcaccatc gaaatcaacc cagactgtgc cgccatcacc 300
caaagaatgg ttgatttcgc tggtgttaag gacaaggtca ccttggttgt tggtgcttcc 360
caagacatca tcccacaatt gaagaagaag tacgatgttg acactttgga catggttttc 420
ttggaccact ggaaggacag atacttgcca gacactttgt tgttggaaga atgtggtttg 480
ttgagaaagg gtactgtttt gttggctgac aacgttatct gtccaggtgc tccagacttc 540
ttggctcacg ttagaggttc ttcttgtttc gaatgtactc actaccaatc tttcttggaa 600
tacagagaag ttgttgacgg tttggaaaag gccatctaca agggtccagg ttctgaagct 660
ggtccataa 669

<210> SEQ ID NO 91
<211> LENGTH: 489
<212> TYPE: PRT
<213> ORGANISM: Arabidopsis thaliana

<400> SEQUENCE: 91

Met Ser Gly Thr Pro Val Glu Val Ser Lys Leu His Phe Leu Leu Phe
1 5 10 15

Pro Phe Met Ala His Gly His Met Ile Pro Thr Leu Asp Met Ala Lys
20 25 30

Leu Phe Ala Thr Lys Gly Ala Lys Ser Thr Ile Leu Thr Thr Pro Leu
35 40 45

Asn Ala Lys Leu Phe Phe Glu Lys Pro Ile Lys Ser Phe Asn Gln Asp
50 55 60

Asn Pro Gly Leu Glu Asp Ile Thr Ile Gln Ile Leu Asn Phe Pro Cys
65 70 75 80

Thr Glu Leu Gly Leu Pro Asp Gly Cys Glu Asn Thr Asp Phe Ile Phe
85 90 95

Ser Thr Pro Asp Leu Asn Val Gly Asp Leu Ser Gln Lys Phe Leu Leu
100 105 110

Ala Met Lys Tyr Phe Glu Glu Pro Leu Glu Glu Leu Leu Val Thr Met
115 120 125

Arg Pro Asp Cys Leu Val Gly Asn Met Phe Phe Pro Trp Ser Thr Lys
130 135 140

Val Ala Glu Lys Phe Gly Val Pro Arg Leu Val Phe His Gly Thr Gly
145 150 155 160

Tyr Phe Ser Leu Cys Ala Ser His Cys Ile Arg Leu Pro Lys Asn Val
165 170 175

Ala Thr Ser Ser Glu Pro Phe Val Ile Pro Asp Leu Pro Gly Asp Ile
180 185 190

Leu Ile Thr Glu Glu Gln Val Met Glu Thr Glu Glu Glu Ser Val Met

```
        195                 200                 205

Gly Arg Phe Met Lys Ala Ile Arg Asp Ser Glu Arg Asp Ser Phe Gly
    210                 215                 220

Val Leu Val Asn Ser Phe Tyr Glu Leu Glu Gln Ala Tyr Ser Asp Tyr
225                 230                 235                 240

Phe Lys Ser Phe Val Ala Lys Arg Ala Trp His Ile Gly Pro Leu Ser
                245                 250                 255

Leu Gly Asn Arg Lys Phe Glu Glu Lys Ala Glu Arg Gly Lys Lys Ala
            260                 265                 270

Ser Ile Asp Glu His Glu Cys Leu Lys Trp Leu Asp Ser Lys Lys Cys
        275                 280                 285

Asp Ser Val Ile Tyr Met Ala Phe Gly Thr Met Ser Ser Phe Lys Asn
    290                 295                 300

Glu Gln Leu Ile Glu Ile Ala Ala Gly Leu Asp Met Ser Gly His Asp
305                 310                 315                 320

Phe Val Trp Val Val Asn Arg Lys Gly Ser Gln Val Glu Lys Glu Asp
                325                 330                 335

Trp Leu Pro Glu Gly Phe Glu Glu Lys Thr Lys Gly Lys Gly Leu Ile
            340                 345                 350

Ile Arg Gly Trp Ala Pro Gln Val Leu Ile Leu Glu His Lys Ala Ile
        355                 360                 365

Gly Gly Phe Leu Thr His Cys Gly Trp Asn Ser Leu Leu Glu Gly Val
    370                 375                 380

Ala Ala Gly Leu Pro Met Val Thr Trp Pro Val Gly Ala Glu Gln Phe
385                 390                 395                 400

Tyr Asn Glu Lys Leu Val Thr Gln Val Leu Lys Thr Gly Val Ser Val
                405                 410                 415

Gly Val Lys Lys Met Met Gln Val Val Gly Asp Phe Ile Ser Arg Glu
            420                 425                 430

Lys Val Glu Gly Ala Val Arg Glu Val Met Val Gly Glu Glu Arg Arg
        435                 440                 445

Lys Arg Ala Lys Glu Leu Ala Glu Met Ala Lys Asn Ala Val Lys Glu
    450                 455                 460

Gly Gly Ser Ser Asp Leu Glu Val Asp Arg Leu Met Glu Glu Leu Thr
465                 470                 475                 480

Leu Val Lys Leu Gln Lys Glu Lys Val
                485
```

<210> SEQ ID NO 92
<211> LENGTH: 1470
<212> TYPE: DNA
<213> ORGANISM: artificial
<220> FEATURE:
<223> OTHER INFORMATION: coding sequence for SEQ ID NO: 91

<400> SEQUENCE: 92

```
atgtccggta ctccagtcga agtctctaag ttgcacttct tgttgttccc attcatggct      60

cacggtcaca tgatcccaac tttggacatg gctaagttgt tcgccaccaa gggtgctaag     120

tccactatct tgactactcc attgaacgcc aagttgttct tcgaaaagcc aatcaagtct     180

ttcaaccaag acaacccagg tttggaagat atcaccatcc aaatcttgaa cttcccatgt     240

actgaattgg gtttgccaga tggttgtgaa aacactgatt tcatcttctc cactccagac     300

ttgaacgttg gtgacttgtc tcaaaagttc ttgttggcta tgaagtactt cgaagaacca     360

ttggaagaat tgttggttac tatgaggcca gactgtttgg tcggtaacat gttcttccca     420
```

```
tggtccacta aggttgctga aaagttcggt gttccaagat tggttttcca cggtactggt    480

tacttctctt tgtgtgcttc tcactgtatc agattgccaa agaacgttgc tacttcttct    540

gaaccattcg ttattccaga tttgccaggt gacattttga ttactgaaga acaagtcatg    600

gaaactgaag aagaatctgt tatgggtaga ttcatgaagg ctatcagaga ctctgaaaga    660

gattctttcg gtgttttggt taactctttc tacgaattgg aacaagctta ctctgattac    720

ttcaagtctt tcgttgctaa gagagcttgg cacatcggtc cattgtcctt gggtaacaga    780

aagttcgaag aaaaggctga aagaggtaag aaggcttcta ttgatgaaca cgaatgtttg    840

aagtggttgg actccaagaa gtgtgattct gttatttaca tggccttcgg taccatgtcc    900

tctttcaaga acgaacaatt gatcgaaatt gctgctggtt tggatatgtc tggtcacgat    960

ttcgtctggg ttgttaacag aaagggttct caagttgaaa aggaagattg gttgccagaa   1020

ggtttcgaag aaaagaccaa gggtaagggt ttgatcatca gaggttgggc tccacaagtt   1080

ttgatcttgg aacacaaggc tattggtggt ttcttgactc actgtggttg gaactctttg   1140

ttggaaggtg ttgctgctgg tttgccaatg gttacttggc cagttggtgc cgaacaattc   1200

tacaacgaaa agttggttac tcaagtttta aagactggtg tttctgttgg tgttaagaag   1260

atgatgcaag ttgttggtga cttcatttct agagaaaagg ttgaaggtgc tgttagagaa   1320

gttatggttg gtgaagaaag aagaaagaga gccaaggaat tggctgaaat ggctaagaac   1380

gctgttaagg aaggtggttc ttctgatttg gaagttgata gattgatgga agaattgact   1440

ttggttaagt tgcaaaagga aaaggtttaa                                    1470
```

<210> SEQ ID NO 93
<211> LENGTH: 470
<212> TYPE: PRT
<213> ORGANISM: Scutellaria baicalensis

<400> SEQUENCE: 93

```
Met Ser Gly Gln Leu His Ile Val Leu Val Pro Met Ile Ala His Gly
1               5                   10                  15

His Met Ile Pro Met Leu Asp Met Ala Lys Leu Phe Ser Ser Arg Gly
            20                  25                  30

Val Arg Thr Thr Ile Ile Ala Thr Pro Ala Phe Ala Glu Pro Ile Arg
        35                  40                  45

Lys Ala Arg Glu Ser Gly His Asp Ile Gly Leu Thr Thr Thr Lys Phe
    50                  55                  60

Pro Pro Lys Gly Ser Ser Leu Pro Asp Asn Ile Leu Ser Leu Asp Gln
65                  70                  75                  80

Val Thr His Asp Leu Leu Pro His Phe Phe Arg Ala Leu Glu Leu Leu
                85                  90                  95

Gln Glu Pro Val Glu Glu Ile Met Glu Asp Leu Lys Pro Asn Cys Leu
            100                 105                 110

Val Ser Asp Met Phe Leu Pro Trp Thr Thr Asp Ser Ala Ala Lys Phe
        115                 120                 125

Gly Ile Pro Arg Leu Leu Phe His Gly Thr Ser Leu Phe Ala Arg Cys
    130                 135                 140

Phe Ala Glu Gln Met Ser Leu Gln Lys Pro Tyr Lys Asn Val Ser Ser
145                 150                 155                 160

Asp Ser Glu Pro Phe Val Leu Arg Gly Leu Pro His Glu Val Ser Phe
                165                 170                 175

Val Arg Thr Gln Ile Pro Gly Tyr Glu Leu Gln Glu Gly Gly Asp Asp
```

```
            180                 185                 190

Ala Phe Ser Lys Met Ala Lys Gln Met Arg Asp Ala Asp Lys Lys Ser
        195                 200                 205

Tyr Gly Asp Val Ile Asn Ser Phe Glu Glu Leu Glu Ser Glu Tyr Val
    210                 215                 220

Asp His Tyr Lys Asn Val Phe Gly Lys Lys Ala Trp His Ile Gly Pro
225                 230                 235                 240

Leu Ser Leu Cys Asn Asn Arg Ala Glu Gln Lys Ser Pro Ile Asp Asp
                245                 250                 255

His Glu Cys Leu Ala Trp Leu Asn Ser Lys Lys Pro Asn Ser Val Val
            260                 265                 270

Tyr Met Cys Phe Gly Ser Met Ala Thr Phe Ser Pro Ala Gln Leu His
        275                 280                 285

Glu Thr Ala Val Gly Leu Glu Ser Ser Gly Gln Asp Phe Ile Trp Val
    290                 295                 300

Val Arg Asn Gly Gly Glu Asn Glu Asp Trp Leu Pro Gln Gly Phe Glu
305                 310                 315                 320

Glu Arg Ile Lys Gly Lys Gly Leu Met Ile Arg Gly Trp Ala Pro Gln
                325                 330                 335

Val Val Ile Leu Asp His Pro Ser Thr Gly Ala Phe Val Thr His Cys
            340                 345                 350

Gly Trp Asn Ser Thr Leu Glu Gly Ile Cys Ala Gly Leu Pro Met Val
        355                 360                 365

Thr Trp Pro Val Phe Ala Glu Gln Phe Tyr Asn Glu Lys Leu Val Thr
    370                 375                 380

Glu Val Leu Lys Thr Gly Val Ser Val Gly Asn Lys Lys Trp Gln Arg
385                 390                 395                 400

Val Gly Glu Trp Val Gly Ser Glu Ala Val Lys Glu Ala Val Glu Trp
                405                 410                 415

Val Met Val Gly Asp Gly Ala Ala Glu Met Arg Ser Arg Ala Asn Tyr
            420                 425                 430

Tyr Lys Glu Met Ala Arg Lys Ala Val Glu Asp Gly Gly Ser Ser Tyr
        435                 440                 445

Asn Asn Leu Asn Ala Leu Ile Gln Glu Leu Ser Ala Tyr Val Pro Pro
    450                 455                 460

Met Lys Gln Gly Leu Asn
465                 470


<210> SEQ ID NO 94
<211> LENGTH: 1413
<212> TYPE: DNA
<213> ORGANISM: artificial
<220> FEATURE:
<223> OTHER INFORMATION: coding sequence for SEQ ID NO: 93

<400> SEQUENCE: 94

atgtccggtc aattgcacat cgtcttggtt ccaatgatcg ctcacggtca catgatccca      60

atgttggaca tggccaagtt gttctcttcc agaggtgtca gaaccaccat catcgccact     120

ccagccttcg ctgaaccaat cagaaaggcc agagaatctg gtcacgacat cggtttgacc     180

accaccaagt tcccaccaaa gggttcctct ttgccagaca acatcttgtc tttggatcaa     240

gttactcacg atttgttgcc acacttcttc agagccttgg aattgttgca agaaccagtt     300

gaagaaatca tggaagattt gaagccaaac tgtttggttt ctgacatgtt cttgccatgg     360

actaccgact ctgctgccaa gttcggtatt ccaagattgt tgttccacgg tacctctttg     420
```

ttcgctagat gtttcgctga acaaatgtct ttgcaaaagc catacaagaa cgtttcttct 480
gattccgaac cattcgtttt gagaggtttg ccacacgaag tttctttcgt tagaactcaa 540
atcccaggtt acgaattgca agaaggtggt gatgatgcct tctctaagat ggctaagcaa 600
atgagagatg ctgataagaa gtcttacggt gacgttatca actctttcga agaattggaa 660
tctgaatacg ttgatcacta caagaacgtt ttcggtaaga aggcttggca catcggtcca 720
ttgtctttgt gtaacaacag agctgaacaa aagtctccaa tcgacgatca cgaatgtttg 780
gcttggttga actctaagaa gccaaactct gttgtttaca tgtgtttcgg ttctatggcc 840
actttctctc cagcccaatt gcacgaaact gctgtcggtt tggaatcctc tggtcaagat 900
ttcatctggg ttgttagaaa cggtggtgaa aacgaagatt ggttgccaca aggtttcgaa 960
gaaagaatca agggtaaggg tttgatgatc agaggttggg ccccacaagt tgttattttg 1020
gatcacccat ctactggtgc tttcgttact cactgtggtt ggaactctac tttggaaggt 1080
atctgtgctg gtttgccaat ggttacttgg ccagttttcg ctgaacaatt ctacaacgaa 1140
aagttggtta ctgaagtttt aaagactggt gtttctgttg gtaacaagaa gtggcaaaga 1200
gttggtgaat gggttggttc tgaagccgtt aaggaagctg ttgaatgggt catggtcggt 1260
gacggtgctg ctgaaatgag atctagagct aactactaca aggaaatggc tagaaaggct 1320
gttgaagatg gtggttcttc ttacaacaac ttgaacgctt tgatccaaga attgtctgcc 1380
tacgtcccac caatgaagca aggtttgaac taa 1413

<210> SEQ ID NO 95
<211> LENGTH: 470
<212> TYPE: PRT
<213> ORGANISM: Scutellaria baicalensis

<400> SEQUENCE: 95

Met Ser Gly Gln Leu His Ile Val Leu Val Pro Met Ile Ala His Gly
1 5 10 15

His Met Ile Pro Met Leu Asp Met Ala Lys Leu Phe Ser Ser Arg Gly
20 25 30

Val Lys Thr Thr Ile Ile Ala Thr Pro Ala Phe Ala Glu Pro Ile Arg
35 40 45

Lys Ala Arg Glu Ser Gly His Asp Ile Gly Leu Thr Thr Thr Lys Phe
50 55 60

Pro Pro Lys Gly Ser Ser Leu Pro Asp Asn Ile Trp Ser Leu Asp Gln
65 70 75 80

Val Thr Asp Asp Leu Leu Pro His Phe Phe Arg Ala Leu Glu Leu Leu
85 90 95

Gln Glu Pro Val Glu Glu Ile Met Glu Asp Leu Lys Pro Asn Cys Leu
100 105 110

Val Ser Asp Met Phe Leu Pro Trp Thr Thr Asp Ser Ala Ala Lys Phe
115 120 125

Gly Ile Pro Arg Leu Leu Phe His Gly Thr Ser Leu Phe Ala Arg Cys
130 135 140

Phe Ala Glu Gln Met Ser Leu Gln Lys Pro Tyr Lys Asn Val Ser Ser
145 150 155 160

Asp Ser Glu Pro Phe Val Leu Arg Gly Leu Pro His Glu Val Ser Phe
165 170 175

Val Arg Thr Gln Ile Pro Gly Tyr Glu Leu Gln Glu Gly Gly Asp Asp
180 185 190

-continued

```
Ala Phe Ser Lys Met Ala Lys Gln Met Arg Asp Ala Asp Lys Lys Ser
        195                 200                 205

Tyr Gly Asp Val Ile Asn Asn Phe Glu Glu Leu Glu Ser Glu Tyr Val
    210                 215                 220

Asp His Tyr Lys Asn Val Phe Gly Lys Lys Ala Trp His Ile Gly Pro
225                 230                 235                 240

Leu Ser Leu Cys Asn Asn Arg Ala Glu Gln Lys Ser Pro Ile Asp Asp
                245                 250                 255

His Glu Cys Leu Ala Trp Leu Asn Ser Lys Lys Pro Asn Ser Val Val
            260                 265                 270

Tyr Met Cys Phe Gly Ser Met Ala Thr Phe Thr Pro Ala Gln Leu His
        275                 280                 285

Glu Thr Ala Val Gly Leu Glu Ser Ser Gly Gln Asp Phe Ile Trp Val
    290                 295                 300

Val Arg Asn Gly Gly Glu Asn Glu Asp Trp Leu Pro Gln Gly Phe Glu
305                 310                 315                 320

Glu Arg Ile Lys Gly Lys Gly Leu Met Ile Arg Gly Trp Ala Pro Gln
                325                 330                 335

Val Met Ile Leu Asp His Pro Ser Thr Gly Ala Phe Val Thr His Cys
            340                 345                 350

Gly Trp Asn Ser Thr Leu Glu Gly Ile Cys Ala Gly Leu Pro Met Val
        355                 360                 365

Thr Trp Pro Val Phe Ala Glu Gln Phe Tyr Asn Glu Lys Leu Val Thr
    370                 375                 380

Glu Val Leu Lys Thr Gly Val Ser Val Gly Asn Lys Lys Trp Gln Arg
385                 390                 395                 400

Val Gly Glu Gly Val Gly Ser Glu Ala Val Lys Glu Ala Val Glu Arg
                405                 410                 415

Val Met Val Gly Asp Gly Ala Ala Glu Met Arg Ser Arg Ala Ile Tyr
            420                 425                 430

Tyr Lys Glu Met Ala Arg Lys Ala Val Glu Glu Gly Gly Ser Ser Tyr
        435                 440                 445

Asn Asn Leu Asn Ala Leu Ile Glu Glu Leu Ser Ala Tyr Val Pro Pro
    450                 455                 460

Met Lys Gln Gly Leu Asn
465                 470
```

<210> SEQ ID NO 96
<211> LENGTH: 1413
<212> TYPE: DNA
<213> ORGANISM: artificial
<220> FEATURE:
<223> OTHER INFORMATION: coding sequence for SEQ ID NO: 95

<400> SEQUENCE: 96

```
atgtccggtc aattgcacat cgtcttggtt ccaatgatcg ctcacggtca catgatccca      60

atgttggaca tggccaagtt gttctcttcc agaggtgtca agaccaccat catcgccact     120

ccagccttcg ctgaaccaat cagaaaggcc agagaatctg gtcacgacat cggtttgacc     180

accaccaagt tcccaccaaa gggttcctct ttgccagaca acatctggtc tttggatcaa     240

gttactgatg atttgttgcc acacttcttc agagccttgg aattgttgca agaaccagtt     300

gaagaaatca tggaagattt gaagccaaac tgtttggttt ctgacatgtt cttgccatgg     360

actaccgact ctgctgccaa gttcggtatt ccaagattgt tgttccacgg tacctctttg     420

ttcgctagat gtttcgctga acaaatgtct ttgcaaaagc catacaagaa cgtttcttct     480
```

-continued

```
gattccgaac cattcgtttt gagaggtttg ccacacgaag tttctttcgt tagaactcaa    540
atcccaggtt acgaattgca agaaggtggt gatgatgcct tctctaagat ggctaagcaa    600
atgagagatg ctgataagaa gtcttacggt gacgttatca acaacttcga agaattggaa    660
tctgaatacg ttgatcacta caagaacgtt ttcggtaaga aggcttggca catcggtcca    720
ttgtctttgt gtaacaacag agctgaacaa aagtctccaa tcgacgatca cgaatgtttg    780
gcttggttga actctaagaa gccaaactct gttgtttaca tgtgtttcgg ttctatggcc    840
actttcactc cagcccaatt gcacgaaact gctgtcggtt tggaatcctc tggtcaagat    900
ttcatctggg ttgttagaaa cggtggtgaa aacgaagatt ggttgccaca aggtttcgaa    960
gaaagaatca agggtaaggg tttgatgatc agaggttggg ccccacaagt tatgattttg   1020
gatcacccat ctactggtgc tttcgttact cactgtggtt ggaactctac tttggaaggt   1080
atctgtgctg gtttgccaat ggttacttgg ccagttttcg ctgaacaatt ctacaacgaa   1140
aagttggtta ctgaagtttt aaagactggt gtttctgttg gtaacaagaa gtggcaaaga   1200
gttggtgaag gtgttggttc tgaagctgtt aaggaagctg ttgaaagagt catggtcggt   1260
gacggtgctg ctgaaatgag atctagagct atctactaca aggaaatggc tagaaaggct   1320
gttgaagaag gtggttcttc ttacaacaac ttgaacgctt tgatcgaaga attgtctgcc   1380
tacgtcccac caatgaagca aggtttgaac taa                                1413
```

<210> SEQ ID NO 97
<211> LENGTH: 477
<212> TYPE: PRT
<213> ORGANISM: Scutellaria baicalensis

<400> SEQUENCE: 97

```
Met Ser Gly Gln Leu His Ile Val Leu Val Pro Met Ile Ala His Gly
1               5                   10                  15

His Met Ile Pro Met Leu Asp Met Ala Lys Leu Phe Ser Ser Arg Gly
            20                  25                  30

Val Lys Thr Thr Ile Ile Ala Thr Pro Ala Phe Ala Glu Pro Ile Arg
        35                  40                  45

Lys Ala Arg Glu Ser Gly His Asp Ile Gly Leu Thr Thr Thr Lys Phe
    50                  55                  60

Pro Pro Lys Gly Ser Ser Leu Pro Asp Asn Ile Arg Ser Leu Asp Gln
65                  70                  75                  80

Val Thr Gly Asp Leu Leu Pro His Phe Phe Arg Ala Leu Glu Leu Leu
                85                  90                  95

Gln Glu Pro Val Glu Glu Ile Met Glu Asp Leu Lys Pro Asn Cys Leu
            100                 105                 110

Val Ser Asp Met Phe Leu Pro Trp Thr Thr Asp Ser Ala Ala Lys Phe
        115                 120                 125

Gly Ile Pro Arg Leu Val Phe His Gly Thr Ser Leu Phe Ala Arg Cys
    130                 135                 140

Phe Ser Glu Gln Met Ser Ile Gln Lys Pro Tyr Lys Asn Val Ser Ser
145                 150                 155                 160

Asp Ser Glu Pro Phe Val Leu Arg Gly Leu Pro His Glu Val Ser Phe
                165                 170                 175

Val Arg Thr Gln Ile Pro Asp Tyr Glu Leu Gln Glu Gly Gly Asp Asp
            180                 185                 190

Ala Phe Ser Lys Met Ala Lys Gln Met Arg Asp Ala Asp Lys Lys Ser
        195                 200                 205
```

```
Tyr Gly Asp Val Ile Asn Ser Phe Glu Glu Leu Glu Ser Glu Tyr Ala
    210                 215                 220

Asp Tyr Asn Lys Asn Val Phe Gly Lys Lys Ala Trp His Ile Gly Pro
225                 230                 235                 240

Leu Lys Leu Phe Asn Asn Arg Ala Glu Gln Lys Ser Ser Gln Arg Gly
                245                 250                 255

Lys Glu Ser Ala Ile Asp Asp His Glu Cys Leu Ala Trp Leu Asn Ser
            260                 265                 270

Lys Lys Pro Asn Ser Val Val Tyr Met Cys Phe Gly Ser Met Ala Thr
        275                 280                 285

Phe Thr Pro Ala Gln Leu His Glu Thr Ala Val Gly Leu Glu Ser Ser
    290                 295                 300

Gly Gln Asp Phe Ile Trp Val Val Arg Asn Gly Gly Lys Asn Glu Asp
305                 310                 315                 320

Trp Leu Pro Gln Gly Phe Glu Glu Arg Ile Lys Gly Lys Gly Leu Met
                325                 330                 335

Ile Arg Gly Trp Ala Pro Gln Val Met Ile Leu Asp His Pro Ser Thr
            340                 345                 350

Gly Ala Phe Val Thr His Cys Gly Trp Asn Ser Thr Leu Glu Gly Ile
        355                 360                 365

Cys Ala Gly Leu Pro Met Val Thr Trp Pro Val Phe Ala Glu Gln Phe
    370                 375                 380

Tyr Asn Glu Lys Leu Val Thr Glu Val Leu Lys Thr Gly Val Ser Val
385                 390                 395                 400

Gly Asn Lys Lys Trp Gln Arg Val Gly Glu Gly Val Gly Ser Glu Ala
                405                 410                 415

Val Lys Glu Ala Val Glu Arg Val Met Val Gly Asp Gly Ala Ala Glu
            420                 425                 430

Met Arg Ser Arg Ala Val Tyr Tyr Lys Glu Met Ala Arg Lys Ala Val
        435                 440                 445

Glu Glu Gly Gly Ser Ser Tyr Asn Asn Leu Asn Ala Leu Ile Gln Glu
    450                 455                 460

Leu Ser Ala Tyr Val Pro Pro Met Lys Gln Gly Leu Asn
465                 470                 475
```

<210> SEQ ID NO 98
<211> LENGTH: 1434
<212> TYPE: DNA
<213> ORGANISM: artificial
<220> FEATURE:
<223> OTHER INFORMATION: coding sequence for SEQ ID NO:97

<400> SEQUENCE: 98

```
atgtccggtc aattgcacat cgtcttggtt ccaatgatcg ctcacggtca catgatccca     60

atgttggaca tggccaagtt gttctcttcc agaggtgtca agaccaccat catcgccact    120

ccagccttcg ctgaaccaat cagaaaggcc agagaatctg gtcacgacat cggtttgacc    180

accaccaagt tcccaccaaa gggttcctct ttgccagaca acatcagatc tttggatcaa    240

gttactggtg atttgttgcc acacttcttc agagccttgg aattgttgca agaaccagtt    300

gaagaaatca tggaagattt gaagccaaac tgtttggttt ctgacatgtt cttgccatgg    360

actaccgact ctgctgccaa gttcggtatt ccaagattgg ttttccacgg tacctctttg    420

ttcgctagat gtttctctga acaaatgtct atccaaaagc catacaagaa cgtttcttct    480

gattccgaac cattcgtttt gagaggtttg ccacacgaag tttctttcgt tagaactcaa    540
```

```
atcccagatt acgaattgca agaaggtggt gatgatgcct tctctaagat ggctaagcaa    600

atgagagatg ctgataagaa gtcttacggt gacgttatca actctttcga agaattggaa    660

tctgaatacg ctgattacaa caagaacgtt ttcggtaaga aggcttggca catcggtcca    720

ttgaagttgt tcaacaacag agctgaacaa aagtcatctc aaagaggtaa ggaatctgcc    780

atcgacgatc acgaatgttt ggcttggttg aactctaaga agccaaactc tgttgtttac    840

atgtgtttcg gttctatggc cactttcact ccagcccaat tgcacgaaac tgctgtcggt    900

ttggaatcct ctggtcaaga tttcatctgg gttgttagaa acggtggtaa gaacgaagat    960

tggttgccac aaggtttcga agaaagaatc aagggtaagg gtttgatgat cagaggttgg   1020

gccccacaag ttatgatttt ggatcaccca tctactggtg ctttcgttac tcactgtggt   1080

tggaactcta ctttggaagg tatctgtgcc ggtttgccaa tggttacttg gccagttttc   1140

gctgaacaat tctacaacga aaagttggtt actgaagttt taaagactgg tgtttctgtt   1200

ggtaacaaga agtggcaaag agttggtgaa ggtgttggtt ctgaagctgt taaggaagct   1260

gttgaaagag tcatggtcgg tgacggtgct gctgaaatga gatctagagc tgtctactac   1320

aaggaaatgg ctagaaaggc tgttgaagaa ggtggttctt cttacaacaa cttgaacgct   1380

ttgatccaag aattgtctgc ctacgttcca ccaatgaagc aaggtttgaa ctaa         1434
```

<210> SEQ ID NO 99
<211> LENGTH: 533
<212> TYPE: PRT
<213> ORGANISM: Homo sapiens

<400> SEQUENCE: 99

```
Met Ser Ala Cys Leu Leu Arg Ser Phe Gln Arg Ile Ser Ala Gly Val
1               5                   10                  15

Phe Phe Leu Ala Leu Trp Gly Met Val Val Gly Asp Lys Leu Leu Val
            20                  25                  30

Val Pro Gln Asp Gly Ser His Trp Leu Ser Met Lys Asp Ile Val Glu
        35                  40                  45

Val Leu Ser Asp Arg Gly His Glu Ile Val Val Val Val Pro Glu Val
    50                  55                  60

Asn Leu Leu Leu Lys Glu Ser Lys Tyr Tyr Thr Arg Lys Ile Tyr Pro
65                  70                  75                  80

Val Pro Tyr Asp Gln Glu Glu Leu Lys Asn Arg Tyr Gln Ser Phe Gly
                85                  90                  95

Asn Asn His Phe Ala Glu Arg Ser Phe Leu Thr Ala Pro Gln Thr Glu
            100                 105                 110

Tyr Arg Asn Asn Met Ile Val Ile Gly Leu Tyr Phe Ile Asn Cys Gln
        115                 120                 125

Ser Leu Leu Gln Asp Arg Asp Thr Leu Asn Phe Phe Lys Glu Ser Lys
    130                 135                 140

Phe Asp Ala Leu Phe Thr Asp Pro Ala Leu Pro Cys Gly Val Ile Leu
145                 150                 155                 160

Ala Glu Tyr Leu Gly Leu Pro Ser Val Tyr Leu Phe Arg Gly Phe Pro
                165                 170                 175

Cys Ser Leu Glu His Thr Phe Ser Arg Ser Pro Asp Pro Val Ser Tyr
            180                 185                 190

Ile Pro Arg Cys Tyr Thr Lys Phe Ser Asp His Met Thr Phe Ser Gln
        195                 200                 205

Arg Val Ala Asn Phe Leu Val Asn Leu Leu Glu Pro Tyr Leu Phe Tyr
```

```
    210                 215                 220

Cys Leu Phe Ser Lys Tyr Glu Glu Leu Ala Ser Ala Val Leu Lys Arg
225                 230                 235                 240

Asp Val Asp Ile Ile Thr Leu Tyr Gln Lys Val Ser Val Trp Leu Leu
                245                 250                 255

Arg Tyr Asp Phe Val Leu Glu Tyr Pro Arg Pro Val Met Pro Asn Met
            260                 265                 270

Val Phe Ile Gly Gly Ile Asn Cys Lys Lys Arg Lys Asp Leu Ser Gln
        275                 280                 285

Glu Phe Glu Ala Tyr Ile Asn Ala Ser Gly Glu His Gly Ile Val Val
    290                 295                 300

Phe Ser Leu Gly Ser Met Val Ser Glu Ile Pro Glu Lys Lys Ala Met
305                 310                 315                 320

Ala Ile Ala Asp Ala Leu Gly Lys Ile Pro Gln Thr Val Leu Trp Arg
                325                 330                 335

Tyr Thr Gly Thr Arg Pro Ser Asn Leu Ala Asn Asn Thr Ile Leu Val
            340                 345                 350

Lys Trp Leu Pro Gln Asn Asp Leu Leu Gly His Pro Met Thr Arg Ala
        355                 360                 365

Phe Ile Thr His Ala Gly Ser His Gly Val Tyr Glu Ser Ile Cys Asn
    370                 375                 380

Gly Val Pro Met Val Met Met Pro Leu Phe Gly Asp Gln Met Asp Asn
385                 390                 395                 400

Ala Lys Arg Met Glu Thr Lys Gly Ala Gly Val Thr Leu Asn Val Leu
                405                 410                 415

Glu Met Thr Ser Glu Asp Leu Glu Asn Ala Leu Lys Ala Val Ile Asn
            420                 425                 430

Asp Lys Ser Tyr Lys Glu Asn Ile Met Arg Leu Ser Ser Leu His Lys
        435                 440                 445

Asp Arg Pro Val Glu Pro Leu Asp Leu Ala Val Phe Trp Val Glu Phe
    450                 455                 460

Val Met Arg His Lys Gly Ala Pro His Leu Arg Pro Ala Ala His Asp
465                 470                 475                 480

Leu Thr Trp Tyr Gln Tyr His Ser Leu Asp Val Ile Gly Phe Leu Leu
                485                 490                 495

Ala Val Val Leu Thr Val Ala Phe Ile Thr Phe Lys Cys Cys Ala Tyr
            500                 505                 510

Gly Tyr Arg Lys Cys Leu Gly Lys Lys Gly Arg Val Lys Lys Ala His
        515                 520                 525

Lys Ser Lys Thr His
    530


<210> SEQ ID NO 100
<211> LENGTH: 1602
<212> TYPE: DNA
<213> ORGANISM: artificial
<220> FEATURE:
<223> OTHER INFORMATION: coding sequence for SEQ ID NO: 99

<400> SEQUENCE: 100

atgtccgcct gtttgttgag atctttccaa agaatttctg ctggtgtttt cttcttggct      60

ttgtggggta tggttgttgg tgacaagttg ttggttgtcc cacaagacgg ttctcactgg     120

ttgtctatga aggatatcgt tgaagttttg tctgacagag gtcacgaaat tgttgttgtt     180

gttccagaag ttaacttgtt gttgaaggaa tccaagtact acactagaaa gatctaccca     240
```

```
gttccatacg accaagaaga attgaagaac agataccaat ctttcggtaa caaccacttc    300

gctgaaagat ctttcttgac tgctccacaa actgaataca gaaacaacat gattgttatt    360

ggtttgtact tcatcaactg tcaatctttg ttgcaagaca gagacacctt gaacttcttc    420

aaggaatcta agttcgatgc tttgttcact gacccagcct tgccatgtgg tgttatcttg    480

gctgaatact tgggtttgcc atctgtttac ttgttcagag gtttcccatg ttccttggaa    540

cacactttct ctagatctcc agacccagtt tcctacattc caagatgtta cactaagttc    600

tctgaccaca tgactttctc ccaaagagtt gccaacttct tggttaactt gttggaacca    660

tacttgttct actgtttgtt ctctaagtac gaagaattgg cttctgctgt cttgaagaga    720

gatgttgata tcatcacctt gtaccaaaag gtatctgttt ggttgttgag atacgacttc    780

gttttggaat acccaagacc agtcatgcca aacatggtat tcattggtgg tatcaactgt    840

aagaagagaa aggacttgtc tcaagaattc gaagcctaca ttaacgcttc tggtgaacac    900

ggtattgttg ttttctcttt gggttctatg gtatctgaaa ttccagaaaa gaaggctatg    960

gctattgctg atgctttggg taagatccca caaactgtct tgtggagata cactggtacc   1020

agaccatcta acttggctaa caacactatc ttggttaagt ggttgccaca aaacgatttg   1080

ttgggtcacc caatgaccag agccttcatc acccacgctg gttcccacgg tgtttacgaa   1140

tctatctgta acggtgttcc aatggttatg atgccattgt tcggtgatca aatggacaac   1200

gctaagagaa tggaaactaa gggtgctggt gttaccttga acgttttgga aatgacttct   1260

gaagatttgg aaaacgcttt gaaggctgtc atcaacgaca agtcttacaa ggaaaacatc   1320

atgagattgt cctctttgca caaggacaga ccagttgaac cattggactt ggccgttttc   1380

tgggttgaat tcgttatgag acacaagggt gctccacact taagaccagc tgcccacgac   1440

ttgacctggt accaatacca ctccttggac gttattggtt tcttgttggc cgtcgttttg   1500

actgttgcct tcatcacctt caagtgttgt gcttacggtt acagaaagtg tttgggtaag   1560

aagggtagag ttaagaaggc ccacaagtcc aagacccact aa                       1602
```

<210> SEQ ID NO 101
<211> LENGTH: 531
<212> TYPE: PRT
<213> ORGANISM: Homo sapiens

<400> SEQUENCE: 101

```
Met Val Ala Arg Ala Gly Trp Thr Gly Leu Leu Pro Leu Tyr Val Cys
1               5                   10                  15

Leu Leu Leu Thr Cys Gly Phe Ala Lys Ala Gly Lys Leu Leu Val Val
            20                  25                  30

Pro Met Asp Gly Ser His Trp Phe Thr Met Gln Ser Val Val Glu Lys
        35                  40                  45

Leu Ile Leu Arg Gly His Glu Val Val Val Val Met Pro Glu Val Ser
    50                  55                  60

Trp Gln Leu Gly Arg Ser Leu Asn Cys Thr Val Lys Thr Tyr Ser Thr
65                  70                  75                  80

Ser Tyr Thr Leu Glu Asp Gln Asp Arg Glu Phe Met Val Phe Ala Asp
                85                  90                  95

Ala Arg Trp Thr Ala Pro Leu Arg Ser Ala Phe Ser Leu Leu Thr Ser
            100                 105                 110

Ser Ser Asn Gly Ile Phe Asp Leu Phe Phe Ser Asn Cys Arg Ser Leu
        115                 120                 125
```

-continued

```
Phe Asn Asp Arg Lys Leu Val Glu Tyr Leu Lys Glu Ser Cys Phe Asp
    130                 135                 140

Ala Val Phe Leu Asp Pro Phe Asp Ala Cys Gly Leu Ile Val Ala Lys
145                 150                 155                 160

Tyr Phe Ser Leu Pro Ser Val Val Phe Ala Arg Gly Ile Phe Cys His
                165                 170                 175

Tyr Leu Glu Glu Gly Ala Gln Cys Pro Ala Pro Leu Ser Tyr Val Pro
            180                 185                 190

Arg Leu Leu Leu Gly Phe Ser Asp Ala Met Thr Phe Lys Glu Arg Val
        195                 200                 205

Trp Asn His Ile Met His Leu Glu Glu His Leu Phe Cys Pro Tyr Phe
    210                 215                 220

Phe Lys Asn Val Leu Glu Ile Ala Ser Glu Ile Leu Gln Thr Pro Val
225                 230                 235                 240

Thr Ala Tyr Asp Leu Tyr Ser His Thr Ser Ile Trp Leu Leu Arg Thr
                245                 250                 255

Asp Phe Val Leu Glu Tyr Pro Lys Pro Val Met Pro Asn Met Ile Phe
            260                 265                 270

Ile Gly Gly Ile Asn Cys His Gln Gly Lys Pro Val Pro Met Glu Phe
        275                 280                 285

Glu Ala Tyr Ile Asn Ala Ser Gly Glu His Gly Ile Val Val Phe Ser
    290                 295                 300

Leu Gly Ser Met Val Ser Glu Ile Pro Glu Lys Lys Ala Met Ala Ile
305                 310                 315                 320

Ala Asp Ala Leu Gly Lys Ile Pro Gln Thr Val Leu Trp Arg Tyr Thr
                325                 330                 335

Gly Thr Arg Pro Ser Asn Leu Ala Asn Asn Thr Ile Leu Val Lys Trp
            340                 345                 350

Leu Pro Gln Asn Asp Leu Leu Gly His Pro Met Thr Arg Ala Phe Ile
        355                 360                 365

Thr His Ala Gly Ser His Gly Val Tyr Glu Ser Ile Cys Asn Gly Val
    370                 375                 380

Pro Met Val Met Met Pro Leu Phe Gly Asp Gln Met Asp Asn Ala Lys
385                 390                 395                 400

Arg Met Glu Thr Lys Gly Ala Gly Val Thr Leu Asn Val Leu Glu Met
                405                 410                 415

Thr Ser Glu Asp Leu Glu Asn Ala Leu Lys Ala Val Ile Asn Asp Lys
            420                 425                 430

Ser Tyr Lys Glu Asn Ile Met Arg Leu Ser Ser Leu His Lys Asp Arg
        435                 440                 445

Pro Val Glu Pro Leu Asp Leu Ala Val Phe Trp Val Glu Phe Val Met
    450                 455                 460

Arg His Lys Gly Ala Pro His Leu Arg Pro Ala Ala His Asp Leu Thr
465                 470                 475                 480

Trp Tyr Gln Tyr His Ser Leu Asp Val Ile Gly Phe Leu Leu Ala Val
                485                 490                 495

Val Leu Thr Val Ala Phe Ile Thr Phe Lys Cys Cys Ala Tyr Gly Tyr
            500                 505                 510

Arg Lys Cys Leu Gly Lys Lys Gly Arg Val Lys Lys Ala His Lys Ser
        515                 520                 525

Lys Thr His
    530
```

<210> SEQ ID NO 102
<211> LENGTH: 1596
<212> TYPE: DNA
<213> ORGANISM: artificial
<220> FEATURE:
<223> OTHER INFORMATION: coding sequence for SEQ ID NO: 101

<400> SEQUENCE: 102
atgtccgcta gagctggttg gactggtttg ttgccattgt acgtttgttt gttgttgacc 60
tgtggtttcg ccaaggctgg taagttgttg gttgttccaa tggatggttc tcactggttc 120
accatgcaat ctgttgttga aaagttgatc ttgagaggtc acgaagttgt cgttgtcatg 180
ccagaagttt cttggcaatt gggtagatct ttgaactgta ctgttaagac ttactctacc 240
tcttacactt tggaagatca agacagagaa ttcatggttt tcgccgatgc tagatggact 300
gctccattga gatctgcttt ctctttgttg acttcttctt ccaacggtat tttcgacttg 360
ttcttctcta actgtagatc tttgttcaac gacagaaagt tggttgaata cttgaaggaa 420
tcttgtttcg atgctgtttt cttggatcca ttcgatgcct gtggtttgat tgttgccaag 480
tacttctcct tgccatctgt tgtattcgcc agaggtatct tctgtcacta cttggaagaa 540
ggtgctcaat gtccagctcc attgtcctac gtcccaagat tgttgttggg tttctctgac 600
gccatgactt tcaaggaaag agtttggaac cacatcatgc acttggaaga acacttgttc 660
tgtccatact tcttcaagaa cgtcttggaa atcgcctctg aaattttgca aaccccagtc 720
actgcttacg atttgtactc tcacacttct atttggttgt tgagaactga cttcgttttg 780
gaatacccaa agccagttat gccaaacatg atcttcattg gtggtatcaa ctgtcaccaa 840
ggtaagccag ttccaatgga attcgaagcc tacattaacg cttctggtga acacggtatt 900
gttgttttct ctttgggttc tatggtatct gaaattccag aaaagaaggc tatggctatt 960
gctgatgctt tgggtaagat cccacaaact gtcttgtgga gatacactgg taccagacca 1020
tctaacttgg ctaacaacac tatcttggtt aagtggttgc cacaaaacga tttgttgggt 1080
cacccaatga ccagagcctt catcacccac gctggttccc acggtgttta cgaatctatc 1140
tgtaacggtg ttccaatggt tatgatgcca ttgttcggtg atcaaatgga caacgctaag 1200
agaatggaaa ctaagggtgc tggtgttacc ttgaacgttt tggaaatgac ttctgaagat 1260
ttggaaaacg ctttgaaggc tgtcatcaac gacaagtctt acaaggaaaa catcatgaga 1320
ttgtcctctt tgcacaagga cagaccagtt gaaccattgg acttggccgt tttctgggtt 1380
gaattcgtta tgagacacaa gggtgctcca cacttaagac cagctgccca cgacttgacc 1440
tggtaccaat accactcctt ggacgttatt ggtttcttgt tggccgtcgt tttgactgtt 1500
gccttcatca ccttcaagtg ttgtgcttac ggttacagaa agtgtttggg taagaagggt 1560
agagttaaga aggcccacaa gtccaagacc cactaa 1596

<210> SEQ ID NO 103
<211> LENGTH: 482
<212> TYPE: PRT
<213> ORGANISM: Citrus clementina

<400> SEQUENCE: 103

Met Ser His Ala Ser Ser Asn Met His Ala Pro Ser Asn Gln His His
1 5 10 15

Lys Met Gly Thr Glu Ser Ala Glu Ala Asp Gln Leu His Val Val Met
20 25 30

Phe Pro Trp Phe Ala Phe Gly His Ile Ser Pro Phe Val Gln Leu Ser
35 40 45

```
Asn Lys Leu Ser Leu His Gly Val Lys Val Ser Phe Phe Ser Ala Pro
    50                  55                  60

Gly Asn Ile Pro Arg Ile Lys Ser Ser Leu Asn Leu Thr Pro Met Ala
65                  70                  75                  80

Asp Ile Ile Pro Leu Gln Ile Pro His Val Asp Gly Leu Pro Pro Gly
                85                  90                  95

Leu Asp Ser Thr Ser Glu Met Thr Pro His Met Ala Glu Leu Leu Lys
            100                 105                 110

Gln Ala Leu Asp Leu Met Gln Pro Gln Ile Lys Thr Leu Leu Ser Gln
        115                 120                 125

Leu Lys Pro His Phe Val Phe Phe Asp Phe Thr His Tyr Trp Leu Pro
    130                 135                 140

Gly Leu Val Gly Ser Gln Leu Gly Ile Lys Thr Val Asn Phe Ser Val
145                 150                 155                 160

Phe Ser Ala Ile Ser Gln Ala Tyr Leu Val Val Pro Ala Arg Lys Leu
                165                 170                 175

Asn Asn Ser Leu Ala Asp Leu Met Lys Ser Pro Asp Gly Phe Pro Ala
            180                 185                 190

Thr Ser Ile Thr Ser Leu Asp Glu Phe Val Ala Arg Asp Tyr Leu Tyr
        195                 200                 205

Val Tyr Thr Lys Phe Asn Gly Gly Pro Ser Val Tyr Glu Arg Gly Ile
    210                 215                 220

Gln Gly Val Asp Gly Cys Asp Val Leu Ala Ile Lys Thr Cys Asn Glu
225                 230                 235                 240

Met Glu Gly Pro Tyr Leu Asp Phe Val Arg Thr Gln Phe Lys Lys Pro
                245                 250                 255

Val Leu Leu Thr Gly Pro Leu Val Asn Pro Glu Pro Pro Ser Gly Glu
            260                 265                 270

Leu Glu Glu Arg Trp Ala Lys Trp Leu Cys Lys Tyr Pro Pro Lys Ser
        275                 280                 285

Val Ile Tyr Cys Ser Phe Gly Ser Glu Thr Phe Leu Thr Val Asp Gln
    290                 295                 300

Ile Lys Glu Leu Ala Ile Gly Leu Glu Ile Thr Gly Leu Pro Phe Phe
305                 310                 315                 320

Leu Val Leu Asn Phe Pro Pro Asn Val Asp Ala Gln Ser Glu Leu Val
                325                 330                 335

Arg Thr Leu Pro Pro Gly Phe Met Asp Arg Val Lys Asp Arg Gly Val
            340                 345                 350

Val His Thr Gly Trp Val Gln Gln Gln Leu Ile Leu Arg His Glu Ser
        355                 360                 365

Val Gly Cys Tyr Val Cys His Ser Gly Phe Ser Ser Val Thr Glu Ala
    370                 375                 380

Val Ile Ser Asp Cys Gln Leu Val Leu Leu Pro Leu Lys Gly Asp Gln
385                 390                 395                 400

Phe Leu Asn Ser Lys Leu Val Ala Gly Asp Leu Lys Ala Gly Val Glu
                405                 410                 415

Val Asn Arg Arg Asp His Asp Gly His Phe Gly Lys Glu Asp Ile Phe
            420                 425                 430

Lys Ala Val Lys Thr Val Met Val Asp Val Asn Lys Glu Pro Gly Ala
        435                 440                 445

Ser Ile Arg Ala Asn Gln Lys Trp Trp Arg Glu Phe Leu Leu Asn Gly
    450                 455                 460
```

Gln Ile Gln Asp Lys Phe Ile Ala Asp Phe Val Lys Asp Leu Lys Thr
465 470 475 480

Leu Ala

<210> SEQ ID NO 104
<211> LENGTH: 1449
<212> TYPE: DNA
<213> ORGANISM: artificial
<220> FEATURE:
<223> OTHER INFORMATION: coding sequence for SEQ ID NO: 103

<400> SEQUENCE: 104
atgtcccacg cctcttctaa catgcacgcc ccatctaacc aacaccacaa gatgggtact 60
gaatctgctg aagctgatca attgcacgtt gttatgttcc catggttcgc tttcggtcac 120
atctctccat tcgttcaatt gtccaacaag ttgtctttgc acggtgtcaa ggtatctttc 180
ttctctgctc caggtaacat tccaagaatc aagtcatctt tgaacttgac tccaatggcc 240
gacattatcc cattgcaaat cccacacgtc gatggtttgc caccaggttt ggattctacc 300
tctgaaatga ctccacacat ggctgaattg ttgaagcaag ccttggactt gatgcaacca 360
caaatcaaga ctttgttgtc tcaattgaag ccacacttcg ttttcttcga tttcacccac 420
tactggttgc caggtttggt tggttctcaa ttgggtatca agactgttaa cttctctgtt 480
ttctctgcca tttctcaagc ctacttggtt gttccagcca gaaagttgaa caactctttg 540
gctgatttga tgaagtctcc agatggtttc ccagctactt ccattacctc tttggatgaa 600
ttcgttgcta gagattactt gtacgtttac actaagttca acggtggtcc atctgtttac 660
gaaagaggta ttcaaggtgt tgatggttgt gatgttttgg ccatcaagac ttgtaacgaa 720
atggaaggtc catacttgga tttcgttaga acccaattca agaagccagt tttgttgacc 780
ggtccattgg ttaacccaga accaccatcc ggtgaattgg aagaaagatg ggctaagtgg 840
ttgtgtaagt acccaccaaa gtctgttatt tactgttcct tcggttctga aactttcttg 900
accgttgatc aaatcaagga attggccatt ggtttggaaa ttactggttt gccattcttc 960
ttggtcttga acttcccacc aaacgtcgat gctcaatctg aattggtcag aactttgcca 1020
ccaggtttca tggacagagt taaggacaga ggtgttgttc acactggttg ggttcaacaa 1080
caattgattt tgagacacga atctgttggt tgttacgttt gtcactctgg tttctcttct 1140
gttactgaag ctgttatttc tgattgtcaa ttggttttgt tgccattgaa gggtgaccaa 1200
ttcttgaact ccaagttggt tgctggtgac ttgaaggctg gtgttgaagt taacagaaga 1260
gatcacgatg gtcacttcgg taaggaagat attttcaagg ctgttaagac tgttatggtt 1320
gatgttaaca aggaaccagg tgcttctatc agagctaacc aaaagtggtg gagagaattc 1380
ttgttgaacg gtcaaattca agataagttc attgctgatt tcgtcaagga tttaaagacc 1440
ttggcttaa 1449

<210> SEQ ID NO 105
<211> LENGTH: 476
<212> TYPE: PRT
<213> ORGANISM: Citrus sinensis

<400> SEQUENCE: 105

Met Ser His Ala Pro Ser Asn Gln His His Lys Met Gly Thr Glu Ser
1 5 10 15

Ala Glu Ala Asp Gln Leu His Val Val Met Phe Pro Trp Phe Ala Ser
20 25 30

-continued

```
Gly His Ile Ser Pro Phe Val Gln Leu Ser Asn Lys Leu Ser Leu His
        35                  40                  45

Gly Val Lys Val Ser Phe Phe Ser Ala Pro Gly Asn Ile Pro Arg Ile
    50                  55                  60

Lys Ser Ser Leu Asn Leu Thr Pro Met Ala Asp Ile Ile Pro Leu Gln
65                  70                  75                  80

Ile Pro His Val Asp Gly Leu Pro Pro Gly Leu Asp Ser Thr Ser Glu
                85                  90                  95

Met Thr Pro His Met Ala Glu Leu Leu Lys Gln Ala Leu Asp Leu Met
            100                 105                 110

Gln Pro Gln Ile Lys Thr Leu Leu Ser Gln Leu Lys Pro His Phe Val
        115                 120                 125

Phe Phe Asp Phe Thr His Tyr Trp Leu Pro Gly Leu Val Gly Ser Gln
    130                 135                 140

Leu Gly Ile Lys Thr Val Asn Phe Ser Val Phe Ser Ala Ile Ser Gln
145                 150                 155                 160

Ala Tyr Leu Val Val Pro Ala Arg Lys Leu Asn Asn Ser Leu Ala Asp
                165                 170                 175

Leu Met Lys Ser Pro Asp Gly Phe Pro Ala Thr Ser Ile Thr Ser Leu
            180                 185                 190

Asp Glu Phe Val Ala Arg Asp Tyr Leu Tyr Val Tyr Thr Lys Phe Asn
        195                 200                 205

Gly Gly Pro Ser Val Tyr Glu Arg Gly Ile Gln Gly Val Asp Gly Cys
    210                 215                 220

Asp Val Leu Ala Ile Lys Thr Cys Asn Glu Met Glu Gly Pro Tyr Leu
225                 230                 235                 240

Asp Phe Val Arg Thr Gln Phe Lys Lys Pro Val Leu Leu Thr Gly Pro
                245                 250                 255

Leu Val Asn Pro Glu Pro Pro Ser Gly Glu Leu Glu Glu Arg Trp Ala
            260                 265                 270

Asn Trp Leu Gly Lys Phe Pro Pro Lys Ser Val Ile Tyr Cys Ser Phe
        275                 280                 285

Gly Ser Glu Thr Phe Leu Thr Val Asp Gln Ile Lys Glu Leu Ala Ile
    290                 295                 300

Gly Leu Glu Ile Thr Gly Leu Pro Phe Phe Leu Val Leu Asn Phe Pro
305                 310                 315                 320

Pro Asn Val Asp Gly Gln Ser Glu Leu Val Arg Thr Leu Pro Pro Gly
                325                 330                 335

Phe Met Asp Arg Val Lys Asp Arg Gly Val Val His Thr Gly Trp Val
            340                 345                 350

Gln Gln Gln Leu Ile Leu Arg His Glu Ser Val Gly Cys Tyr Val Cys
        355                 360                 365

His Ser Gly Phe Ser Ser Val Thr Glu Ala Val Ile Ser Asp Cys Gln
    370                 375                 380

Leu Val Leu Leu Pro Leu Lys Gly Asp Gln Phe Leu Asn Ser Lys Leu
385                 390                 395                 400

Val Ala Gly Asp Leu Lys Ala Gly Val Glu Val Asn Arg Arg Asp His
                405                 410                 415

Asp Gly His Phe Gly Lys Glu Asp Ile Phe Lys Ala Val Lys Thr Val
            420                 425                 430

Met Val Asp Val Asn Lys Glu Pro Gly Ala Ser Ile Arg Ala Asn Gln
        435                 440                 445

Lys Trp Trp Arg Glu Phe Leu Leu Asn Gly Gln Ile Gln Asp Lys Phe
```

```
    450                 455                 460

Ile Ala Asp Phe Val Lys Asp Leu Lys Ala Leu Ala
465                 470                 475


<210> SEQ ID NO 106
<211> LENGTH: 1431
<212> TYPE: DNA
<213> ORGANISM: artificial
<220> FEATURE:
<223> OTHER INFORMATION: coding sequence for SEQ ID NO: 105

<400> SEQUENCE: 106

atgtcccacg ccccatctaa ccaacaccac aagatgggta ctgaatctgc tgaagctgat      60

caattgcacg ttgttatgtt cccatggttc gcttctggtc acatctctcc attcgttcaa     120

ttgtccaaca agttgtcttt gcacggtgtc aaggtatctt tcttctctgc tccaggtaac     180

attccaagaa tcaagtcatc tttgaacttg actccaatgg ccgacattat cccattgcaa     240

atcccacacg tcgatggttt gccaccaggt ttggattcta cctctgaaat gactccacac     300

atggctgaat tgttgaagca agccttggac ttgatgcaac cacaaatcaa gactttgttg     360

tctcaattga agccacactt cgttttcttc gatttcaccc actactggtt gccaggtttg     420

gttggttctc aattgggtat caagaccgtt aacttctctg ttttctctgc catttctcaa     480

gcctacttgg ttgtcccagc cagaaagttg aacaactctt tggctgattt gatgaagtct     540

ccagatggtt tcccagctac ttccattacc tctttggatg aattcgttgc tagagattac     600

ttgtacgttt acactaagtt caacggtggt ccatctgttt acgaaagagg tattcaaggt     660

gttgatggtt gtgatgtttt ggccatcaag acttgtaacg aaatggaagg tccatacttg     720

gatttcgtta gaacccaatt caagaagcca gttttgttga ccggtccatt ggttaaccca     780

gaaccaccat ccggtgaatt ggaagaaaga tgggctaact ggttgggtaa gttcccacca     840

aagtctgtca tttactgttc tttcggttct gaaactttct tgaccgttga tcaaatcaag     900

gaattggcca ttggtttgga aattactggt ttgccattct tcttggtctt gaacttccca     960

ccaaacgttg atggtcaatc tgaattggtc agaactttgc caccaggttt catggacaga    1020

gttaaggaca gaggtgttgt tcacactggt tgggttcaac aacaattgat tttgagacac    1080

gaatctgttg gttgttacgt ttgtcactct ggtttctctt ctgttactga agctgttatt    1140

tctgattgtc aattggtttt gttgccattg aagggtgacc aattcttgaa ctccaagttg    1200

gttgctggtg acttgaaggc tggtgttgaa gttaacagaa gagatcacga tggtcacttc    1260

ggtaaggaag atattttcaa ggctgttaag actgttatgg ttgatgttaa caaggaacca    1320

ggtgcttcta tcagagctaa ccaaaagtgg tggagagaat tcttgttgaa cggtcaaatt    1380

caagataagt tcattgctga tttcgtcaag gatttgaagg ccttggctta a             1431


<210> SEQ ID NO 107
<211> LENGTH: 669
<212> TYPE: PRT
<213> ORGANISM: Citrus sinensis

<400> SEQUENCE: 107

Met Ser Ala Thr Tyr Thr Pro Lys Asn Ile Leu Ile Thr Gly Ala Ala
1               5                   10                  15

Gly Phe Ile Ala Ser His Val Cys Asn Arg Leu Ile Arg Asn Tyr Pro
            20                  25                  30

Glu Tyr Lys Ile Val Val Leu Asp Lys Leu Asp Tyr Cys Ser Asn Leu
        35                  40                  45
```

```
Lys Asn Leu Ile Pro Ser Lys Ala Ser Ser Asn Phe Lys Phe Val Lys
    50                  55                  60

Gly Asp Ile Ala Ser Ala Asp Leu Val Asn Phe Leu Leu Ile Thr Glu
65                  70                  75                  80

Ser Ile Asp Thr Ile Met His Phe Ala Ala Gln Thr His Val Asp Asn
                85                  90                  95

Ser Phe Gly Asn Ser Phe Glu Phe Thr Lys Asn Asn Ile Tyr Gly Thr
            100                 105                 110

His Val Leu Leu Glu Ala Cys Lys Val Thr Gly Gln Ile Arg Arg Phe
        115                 120                 125

Ile His Val Ser Thr Asp Glu Val Tyr Gly Glu Thr Asp Glu Asp Ala
    130                 135                 140

Val Val Gly Asn His Glu Ala Ser Gln Leu Leu Pro Thr Asn Pro Tyr
145                 150                 155                 160

Ser Ala Thr Lys Ala Gly Ala Glu Met Leu Val Met Ala Tyr Gly Arg
                165                 170                 175

Ser Tyr Gly Leu Pro Val Ile Thr Thr Arg Gly Asn Asn Val Tyr Gly
            180                 185                 190

Pro Asn Gln Phe Pro Glu Lys Leu Ile Pro Lys Phe Ile Leu Leu Ala
        195                 200                 205

Met Arg Gly Leu Pro Leu Pro Ile His Gly Asp Gly Ser Asn Val Arg
    210                 215                 220

Ser Tyr Leu Tyr Cys Glu Asp Val Ala Glu Ala Phe Glu Cys Ile Leu
225                 230                 235                 240

His Lys Gly Glu Val Gly His Val Tyr Asn Val Gly Thr Lys Lys Glu
                245                 250                 255

Arg Arg Val Ile Asp Val Ala Lys Asp Ile Cys Lys Leu Phe Ser Met
            260                 265                 270

Asp Pro Glu Thr Ser Ile Lys Phe Val Glu Asn Arg Pro Phe Asn Asp
        275                 280                 285

Gln Arg Tyr Phe Leu Asp Asp Gln Lys Leu Thr Ser Leu Gly Trp Ser
    290                 295                 300

Glu Arg Thr Ile Trp Glu Glu Gly Leu Arg Lys Thr Ile Glu Trp Tyr
305                 310                 315                 320

Thr Gln Asn Pro Asp Trp Trp Gly Asp Val Ser Gly Ala Leu Leu Pro
                325                 330                 335

His Pro Arg Met Leu Met Met Pro Gly Gly Arg His Phe Asp Gly Ser
            340                 345                 350

Glu Glu Asn Lys Ala Val Ser Ser Val Ser Thr Asn Asn Ile Gln Ser
        355                 360                 365

Arg Met Val Val Pro Val Ser Lys Cys Ser Ser Pro Arg Lys Pro Ser
    370                 375                 380

Met Lys Phe Leu Ile Tyr Gly Arg Thr Gly Trp Ile Gly Gly Leu Leu
385                 390                 395                 400

Gly Lys Leu Cys Glu Lys Glu Gly Ile Pro Phe Glu Tyr Gly Lys Gly
                405                 410                 415

Arg Leu Glu Asp Arg Ser Ser Leu Ile Ala Asp Val Gln Ser Val Lys
            420                 425                 430

Pro Thr His Val Phe Asn Ala Ala Gly Val Thr Gly Arg Pro Asn Val
        435                 440                 445

Asp Trp Cys Glu Ser His Lys Thr Asp Thr Ile Arg Thr Asn Val Ala
    450                 455                 460
```

```
Gly Thr Leu Thr Leu Ala Asp Val Cys Arg Asp His Gly Ile Leu Met
465                 470                 475                 480

Met Asn Tyr Ala Thr Gly Cys Ile Phe Glu Tyr Asp Ala Ala His Pro
                485                 490                 495

Glu Gly Ser Gly Ile Gly Tyr Lys Glu Glu Asp Thr Pro Asn Phe Thr
            500                 505                 510

Gly Ser Phe Tyr Ser Lys Thr Lys Ala Met Val Glu Glu Leu Leu Lys
        515                 520                 525

Glu Tyr Asp Asn Val Cys Thr Leu Arg Val Arg Met Pro Ile Ser Ser
    530                 535                 540

Asp Leu Asn Asn Pro Arg Asn Phe Ile Thr Lys Ile Ser Arg Tyr Asn
545                 550                 555                 560

Lys Val Val Asn Ile Pro Asn Ser Met Thr Val Leu Asp Glu Leu Leu
                565                 570                 575

Pro Ile Ser Ile Glu Met Ala Lys Arg Asn Leu Arg Gly Ile Trp Asn
            580                 585                 590

Phe Thr Asn Pro Gly Val Val Ser His Asn Glu Ile Leu Glu Met Tyr
        595                 600                 605

Lys Lys Tyr Ile Asn Pro Glu Phe Lys Trp Val Asn Phe Thr Leu Asp
    610                 615                 620

Glu Gln Ala Lys Val Ile Val Ala Pro Arg Ser Asn Asn Glu Met Asp
625                 630                 635                 640

Ala Ser Lys Leu Lys Lys Glu Phe Pro Glu Leu Leu Ser Ile Lys Asp
                645                 650                 655

Ser Leu Ile Lys Tyr Val Phe Glu Pro Asn Lys Lys Thr
            660                 665
```

<210> SEQ ID NO 108
<211> LENGTH: 2010
<212> TYPE: DNA
<213> ORGANISM: artificial
<220> FEATURE:
<223> OTHER INFORMATION: coding sequence for SEQ ID NO: 107

<400> SEQUENCE: 108

```
atgtccgcta cttacacccc aaagaacatc ttgatcactg gtgctgctgg tttcattgct     60

tcccacgttt gtaacagatt gattagaaac tacccagaat acaagattgt tgttttggac    120

aagttggatt actgttctaa cttgaagaac ttgatcccat ccaaggcttc ctccaacttc    180

aagttcgtta agggtgacat tgcctctgct gacttggtca acttcttgtt gatcaccgaa    240

tccattgaca ctattatgca cttcgctgct caaactcacg ttgacaactc tttcggtaac    300

tctttcgaat tcaccaagaa caacatctac ggtactcacg tcttgttgga agcctgtaag    360

gttactggtc aaatcagaag attcatccac gtatctactg atgaagtcta cggtgaaact    420

gatgaagatg ctgttgttgg taaccacgaa gcttcccaat tgttgccaac taacccatac    480

tctgctacta aggctggtgc tgaaatgttg gttatggctt acggtagatc ttacggtttg    540

ccagttatta ctaccagagg taacaacgtt tacggtccaa accaattccc agaaaagttg    600

attccaaagt tcatcttgtt ggccatgaga ggtttgccat tgccaattca cggtgatggt    660

tctaacgtta gatcttactt gtactgtgaa gatgttgctg aagctttcga atgtattttg    720

cacaagggtg aagttggtca cgtttacaac gttggtacta agaaggaaag aagagttatt    780

gatgttgcta aggatatttg taagttgttc tctatggacc cagaaacttc tatcaagttc    840

gttgaaaaca gaccattcaa cgatcaaaga tacttcttgg atgatcaaaa gttgacttct    900
```

-continued

```
ttgggttggt ctgaaagaac catctgggaa gaaggtttga gaaagactat tgaatggtac     960

actcaaaacc cagattggtg gggtgatgtc tctggtgctt tgttgccaca cccaagaatg    1020

ttgatgatgc caggtggtag acacttcgat ggttctgaag aaaacaaggc tgtttcctct    1080

gtctctacta acaacattca atccagaatg gttgttccag tttccaagtg ttcttctcca    1140

agaaagccat ccatgaagtt cttgatctac ggtagaactg gttggattgg tggtttgttg    1200

ggtaagttgt gtgaaaagga aggtattcca ttcgaatacg gtaagggtag attggaagat    1260

agatcttctt tgattgctga tgttcaatct gttaagccaa ctcacgtttt caacgctgct    1320

ggtgttactg gtagaccaaa cgttgattgg tgtgaatctc acaagactga caccattaga    1380

accaacgttg ctggtacctt gaccttggct gatgtttgta gagatcacgg tatcttgatg    1440

atgaactacg ctaccggttg tatcttcgaa tacgatgctg ctcacccaga aggttctggt    1500

attggttaca aggaagaaga tactccaaac ttcactggtt ctttctactc taagaccaag    1560

gccatggttg aagaattgtt gaaggaatac gacaacgttt gtactttgag agtcagaatg    1620

ccaatctctt ctgacttgaa caacccaaga aacttcatta ccaagatttc tagatacaac    1680

aaggttgtca acattccaaa ctctatgact gttttggatg aattgttgcc aatttctatt    1740

gaaatggcta agagaaactt gagaggtatt tggaacttca ctaacccagg tgttgtttct    1800

cacaacgaaa ttttggaaat gtacaagaag tacattaacc cagaattcaa gtgggttaac    1860

ttcactttgg atgaacaagc taaggttatc gtcgccccaa gatctaacaa cgaaatggat    1920

gcttctaagt tgaagaagga attcccagaa ttgttgtcca tcaaggattc tttgatcaag    1980

tacgtattcg aaccaaacaa gaaaacctaa                                     2010
```

```
<210> SEQ ID NO 109
<211> LENGTH: 670
<212> TYPE: PRT
<213> ORGANISM: Arabidopsis thaliana

<400> SEQUENCE: 109

Met Ser Ala Ser Tyr Thr Pro Lys Asn Ile Leu Ile Thr Gly Ala Ala
1               5                   10                  15

Gly Phe Ile Ala Ser His Val Ala Asn Arg Leu Ile Arg Ser Tyr Pro
            20                  25                  30

Asp Tyr Lys Ile Val Val Leu Asp Lys Leu Asp Tyr Cys Ser Asn Leu
        35                  40                  45

Lys Asn Leu Asn Pro Ser Lys His Ser Pro Asn Phe Lys Phe Val Lys
    50                  55                  60

Gly Asp Ile Ala Ser Ala Asp Leu Val Asn His Leu Leu Ile Thr Glu
65                  70                  75                  80

Gly Ile Asp Thr Ile Met His Phe Ala Ala Gln Thr His Val Asp Asn
                85                  90                  95

Ser Phe Gly Asn Ser Phe Glu Phe Thr Lys Asn Asn Ile Tyr Gly Thr
            100                 105                 110

His Val Leu Leu Glu Ala Cys Lys Val Thr Gly Gln Ile Arg Arg Phe
        115                 120                 125

Ile His Val Ser Thr Asp Glu Val Tyr Gly Glu Thr Asp Glu Asp Ala
    130                 135                 140

Leu Val Gly Asn His Glu Ala Ser Gln Leu Leu Pro Thr Asn Pro Tyr
145                 150                 155                 160

Ser Ala Thr Lys Ala Gly Ala Glu Met Leu Val Met Ala Tyr Gly Arg
                165                 170                 175
```

```
Ser Tyr Gly Leu Pro Val Ile Thr Thr Arg Gly Asn Asn Val Tyr Gly
            180                 185                 190

Pro Asn Gln Phe Pro Glu Lys Leu Ile Pro Lys Phe Ile Leu Leu Ala
        195                 200                 205

Met Arg Gly Gln Val Leu Pro Ile His Gly Asp Gly Ser Asn Val Arg
    210                 215                 220

Ser Tyr Leu Tyr Cys Glu Asp Val Ala Glu Ala Phe Glu Val Val Leu
225                 230                 235                 240

His Lys Gly Glu Val Gly His Val Tyr Asn Ile Gly Thr Lys Lys Glu
                245                 250                 255

Arg Arg Val Asn Asp Val Ala Lys Asp Ile Cys Lys Leu Phe Asn Met
            260                 265                 270

Asp Pro Glu Ala Asn Ile Lys Phe Val Asp Asn Arg Pro Phe Asn Asp
        275                 280                 285

Gln Arg Tyr Phe Leu Asp Asp Gln Lys Leu Lys Lys Leu Gly Trp Ser
    290                 295                 300

Glu Arg Thr Thr Trp Glu Glu Gly Leu Lys Lys Thr Met Asp Trp Tyr
305                 310                 315                 320

Thr Gln Asn Pro Glu Trp Trp Gly Asp Val Ser Gly Ala Leu Leu Pro
                325                 330                 335

His Pro Arg Met Leu Met Met Pro Gly Gly Arg His Phe Asp Gly Ser
            340                 345                 350

Glu Asp Asn Ser Leu Ala Ala Thr Leu Ser Glu Lys Pro Ser Gln Thr
        355                 360                 365

His Met Val Val Pro Ser Gln Arg Ser Asn Gly Thr Pro Gln Lys Pro
    370                 375                 380

Ser Leu Lys Phe Leu Ile Tyr Gly Lys Thr Gly Trp Ile Gly Gly Leu
385                 390                 395                 400

Leu Gly Lys Ile Cys Asp Lys Gln Gly Ile Ala Tyr Glu Tyr Gly Lys
                405                 410                 415

Gly Arg Leu Glu Asp Arg Ser Ser Leu Leu Gln Asp Ile Gln Ser Val
            420                 425                 430

Lys Pro Thr His Val Phe Asn Ser Ala Gly Val Thr Gly Arg Pro Asn
        435                 440                 445

Val Asp Trp Cys Glu Ser His Lys Thr Glu Thr Ile Arg Ala Asn Val
    450                 455                 460

Ala Gly Thr Leu Thr Leu Ala Asp Val Cys Arg Glu His Gly Leu Leu
465                 470                 475                 480

Met Met Asn Phe Ala Thr Gly Cys Ile Phe Glu Tyr Asp Asp Lys His
                485                 490                 495

Pro Glu Gly Ser Gly Ile Gly Phe Lys Glu Glu Asp Thr Pro Asn Phe
            500                 505                 510

Thr Gly Ser Phe Tyr Ser Lys Thr Lys Ala Met Val Glu Glu Leu Leu
        515                 520                 525

Lys Glu Tyr Asp Asn Val Cys Thr Leu Arg Val Arg Met Pro Ile Ser
    530                 535                 540

Ser Asp Leu Asn Asn Pro Arg Asn Phe Ile Thr Lys Ile Ser Arg Tyr
545                 550                 555                 560

Asn Lys Val Val Asn Ile Pro Asn Ser Met Thr Val Leu Asp Glu Leu
                565                 570                 575

Leu Pro Ile Ser Ile Glu Met Ala Lys Arg Asn Leu Lys Gly Ile Trp
            580                 585                 590

Asn Phe Thr Asn Pro Gly Val Val Ser His Asn Glu Ile Leu Glu Met
```

```
        595                 600                 605

Tyr Arg Asp Tyr Ile Asn Pro Glu Phe Lys Trp Ala Asn Phe Thr Leu
    610                 615                 620

Glu Glu Gln Ala Lys Val Ile Val Ala Pro Arg Ser Asn Asn Glu Met
625                 630                 635                 640

Asp Ala Ser Lys Leu Lys Lys Glu Phe Pro Glu Leu Leu Ser Ile Lys
                645                 650                 655

Glu Ser Leu Ile Lys Tyr Ala Tyr Gly Pro Asn Lys Lys Thr
            660                 665                 670
```

<210> SEQ ID NO 110
<211> LENGTH: 2013
<212> TYPE: DNA
<213> ORGANISM: artificial
<220> FEATURE:
<223> OTHER INFORMATION: coding sequence for SEQ ID NO: 109

<400> SEQUENCE: 110

```
atgtccgctt cttacactcc aaagaacatt ttgatcaccg gtgctgctgg tttcattgct     60

tctcacgtcg ccaacagatt gatcagatct tacccagatt acaagatcgt tgttttggac    120

aagttggatt actgttctaa cttgaagaac ttgaacccat ctaagcactc tccaaacttc    180

aagttcgtca agggtgatat cgcttctgct gacttggtta accacttgtt gatcactgaa    240

ggtattgaca ccatcatgca cttcgctgct caaactcacg tcgacaactc cttcggtaac    300

tctttcgaat tcactaagaa caacatctac ggtactcacg tcttgttgga agcttgtaag    360

gttactggtc aaattagaag attcattcac gtttctactg atgaagttta cggtgaaact    420

gatgaagatg ctttggttgg taaccacgaa gcttctcaat tgttgccaac taacccatac    480

tctgccacta aggctggtgc tgaaatgttg gttatggctt acggtagatc ttacggtttg    540

ccagttatta ccactagagg taacaacgtc tacggtccaa accaattccc agaaaagttg    600

attccaaagt tcattttgtt ggctatgaga ggtcaagttt tgccaattca cggtgatggt    660

tctaacgtca gatcttactt gtactgtgag gacgttgctg aagctttcga agttgttttg    720

cacaagggtg aagttggtca cgtttacaac attggtacta agaaggaaag aagagttaac    780

gatgttgcca aggacatctg taagttgttc aacatggacc cagaagctaa catcaagttc    840

gtcgacaaca gaccattcaa cgatcaaaga tacttcttgg acgatcaaaa gttgaagaag    900

ttgggttggt ctgaaagaac cacttgggaa gaaggtttga agaaaactat ggattggtac    960

actcaaaacc cagaatggtg gggtgatgtt tctggtgctt tgttgccaca cccaagaatg   1020

ttgatgatgc caggtggtag acacttcgat ggttccgaag ataactcttt ggctgctact   1080

ttgtctgaaa agccatctca aacccacatg gttgttccat ctcaaagatc taacggtact   1140

ccacaaaagc catctttgaa gttcttgatc tacggtaaga ccggttggat cggtggtttg   1200

ttgggtaaga tctgtgataa gcaaggtatt gcttacgaat acggtaaggg tagattggaa   1260

gatagatctt ctttgttgca agatattcaa tctgttaagc caacccacgt tttcaactcc   1320

gctggtgtta ctggtagacc aaacgttgac tggtgtgaat ctcacaagac cgaaactatc   1380

agagccaacg ttgctggtac tttgactttg gctgatgtct gtagagaaca cggtttgttg   1440

atgatgaact tcgctactgg ttgtatcttc gaatacgacg acaagcaccc agaaggttct   1500

ggtattggtt tcaaggaaga agatactcca aacttcactg gttctttcta ctctaagacc   1560

aaggccatgg tcgaagaatt gttgaaggaa tacgacaacg tttgtacttt gagagttaga   1620

atgccaatct cctctgattt gaacaaccca agaaacttca tcaccaagat ctccagatac   1680
```

aacaaggttg ttaacatccc aaactctatg actgttttgg acgaattgtt gccaatctcc 1740
atcgaaatgg ctaagagaaa cttgaagggt atctggaact tcactaaccc aggtgttgtt 1800
tctcacaacg aaatcttgga aatgtacaga gactacatca acccagaatt caagtgggct 1860
aacttcactt tggaagaaca agctaaggtc attgttgctc caagatctaa caacgaaatg 1920
gatgcttcca agttgaagaa ggaattccca gaattgttgt ctatcaagga atctttgatt 1980
aagtacgctt acggtccaaa caagaaaacc taa 2013

<210> SEQ ID NO 111
<211> LENGTH: 668
<212> TYPE: PRT
<213> ORGANISM: Arabidopsis thaliana

<400> SEQUENCE: 111

Met Ser Asp Asp Thr Thr Tyr Lys Pro Lys Asn Ile Leu Ile Thr Gly
1 5 10 15

Ala Ala Gly Phe Ile Ala Ser His Val Ala Asn Arg Leu Ile Arg Asn
20 25 30

Tyr Pro Asp Tyr Lys Ile Val Val Leu Asp Lys Leu Asp Tyr Cys Ser
35 40 45

Asp Leu Lys Asn Leu Asp Pro Ser Phe Ser Ser Pro Asn Phe Lys Phe
50 55 60

Val Lys Gly Asp Ile Ala Ser Asp Asp Leu Val Asn Tyr Leu Leu Ile
65 70 75 80

Thr Glu Asn Ile Asp Thr Ile Met His Phe Ala Ala Gln Thr His Val
85 90 95

Asp Asn Ser Phe Gly Asn Ser Phe Glu Phe Thr Lys Asn Asn Ile Tyr
100 105 110

Gly Thr His Val Leu Leu Glu Ala Cys Lys Val Thr Gly Gln Ile Arg
115 120 125

Arg Phe Ile His Val Ser Thr Asp Glu Val Tyr Gly Glu Thr Asp Glu
130 135 140

Asp Ala Ala Val Gly Asn His Glu Ala Ser Gln Leu Leu Pro Thr Asn
145 150 155 160

Pro Tyr Ser Ala Thr Lys Ala Gly Ala Glu Met Leu Val Met Ala Tyr
165 170 175

Gly Arg Ser Tyr Gly Leu Pro Val Ile Thr Thr Arg Gly Asn Asn Val
180 185 190

Tyr Gly Pro Asn Gln Phe Pro Glu Lys Met Ile Pro Lys Phe Ile Leu
195 200 205

Leu Ala Met Ser Gly Lys Pro Leu Pro Ile His Gly Asp Gly Ser Asn
210 215 220

Val Arg Ser Tyr Leu Tyr Cys Glu Asp Val Ala Glu Ala Phe Glu Val
225 230 235 240

Val Leu His Lys Gly Glu Ile Gly His Val Tyr Asn Val Gly Thr Lys
245 250 255

Arg Glu Arg Arg Val Ile Asp Val Ala Arg Asp Ile Cys Lys Leu Phe
260 265 270

Gly Lys Asp Pro Glu Ser Ser Ile Gln Phe Val Glu Asn Arg Pro Phe
275 280 285

Asn Asp Gln Arg Tyr Phe Leu Asp Asp Gln Lys Leu Lys Lys Leu Gly
290 295 300

Trp Gln Glu Arg Thr Asn Trp Glu Asp Gly Leu Lys Lys Thr Met Asp

```
305                 310                 315                 320

Trp Tyr Thr Gln Asn Pro Glu Trp Trp Gly Asp Val Ser Gly Ala Leu
                325                 330                 335

Leu Pro His Pro Arg Met Leu Met Met Pro Gly Gly Arg Leu Ser Asp
            340                 345                 350

Gly Ser Ser Glu Lys Lys Asp Val Ser Ser Asn Thr Val Gln Thr Phe
        355                 360                 365

Thr Val Val Thr Pro Lys Asn Gly Asp Ser Gly Asp Lys Ala Ser Leu
    370                 375                 380

Lys Phe Leu Ile Tyr Gly Lys Thr Gly Trp Leu Gly Gly Leu Leu Gly
385                 390                 395                 400

Lys Leu Cys Glu Lys Gln Gly Ile Thr Tyr Glu Tyr Gly Lys Gly Arg
                405                 410                 415

Leu Glu Asp Arg Ala Ser Leu Val Ala Asp Ile Arg Ser Ile Lys Pro
            420                 425                 430

Thr His Val Phe Asn Ala Ala Gly Leu Thr Gly Arg Pro Asn Val Asp
        435                 440                 445

Trp Cys Glu Ser His Lys Pro Glu Thr Ile Arg Val Asn Val Ala Gly
    450                 455                 460

Thr Leu Thr Leu Ala Asp Val Cys Arg Glu Asn Asp Leu Leu Met Met
465                 470                 475                 480

Asn Phe Ala Thr Gly Cys Ile Phe Glu Tyr Asp Ala Thr His Pro Glu
                485                 490                 495

Gly Ser Gly Ile Gly Phe Lys Glu Glu Asp Lys Pro Asn Phe Phe Gly
            500                 505                 510

Ser Phe Tyr Ser Lys Thr Lys Ala Met Val Glu Glu Leu Leu Arg Glu
        515                 520                 525

Phe Asp Asn Val Cys Thr Leu Arg Val Arg Met Pro Ile Ser Ser Asp
    530                 535                 540

Leu Asn Asn Pro Arg Asn Phe Ile Thr Lys Ile Ser Arg Tyr Asn Lys
545                 550                 555                 560

Val Val Asp Ile Pro Asn Ser Met Thr Val Leu Asp Glu Leu Leu Pro
                565                 570                 575

Ile Ser Ile Glu Met Ala Lys Arg Asn Leu Arg Gly Ile Trp Asn Phe
            580                 585                 590

Thr Asn Pro Gly Val Val Ser His Asn Glu Ile Leu Glu Met Tyr Lys
        595                 600                 605

Asn Tyr Ile Glu Pro Gly Phe Lys Trp Ser Asn Phe Thr Val Glu Glu
    610                 615                 620

Gln Ala Lys Val Ile Val Ala Ala Arg Ser Asn Asn Glu Met Asp Gly
625                 630                 635                 640

Ser Lys Leu Ser Lys Glu Phe Pro Glu Met Leu Ser Ile Lys Glu Ser
                645                 650                 655

Leu Leu Lys Tyr Val Phe Glu Pro Asn Lys Arg Thr
            660                 665
```

<210> SEQ ID NO 112
<211> LENGTH: 2007
<212> TYPE: DNA
<213> ORGANISM: artificial
<220> FEATURE:
<223> OTHER INFORMATION: coding sequence for SEQ ID NO: 111

<400> SEQUENCE: 112

```
atgtccgatg atactactta caagccaaag aacattttga ttactggtgc tgctggtttc     60
```

```
attgcttctc acgttgccaa cagattgatc agaaactacc cagattacaa gatcgttgtt    120
ttggacaagt tggattactg ttctgatttg aagaacttgg atccatcttt ctcttctcca    180
aacttcaagt tcgtcaaggg tgatatcgct tctgatgatt tggttaacta cttgttgatc    240
actgaaaaca ttgatactat catgcacttc gctgctcaaa ctcacgttga taactctttc    300
ggtaactctt tcgaattcac caagaacaac atttacggta ctcacgtttt gttggaagcc    360
tgtaaggtta ctggtcaaat cagaagattc atccacgttt ctaccgatga agtctacggt    420
gaaaccgatg aagatgctgc tgttggtaac cacgaagctt ctcaattgtt gccaactaac    480
ccatactctg ctactaaggc tggtgctgaa atgttggtta tggcttacgg tagatcttac    540
ggtttgccag ttattactac tagaggtaac aacgtttacg gtccaaacca attcccagaa    600
aagatgattc caaagttcat cttgttggct atgtctggta agccattgcc aatccacggt    660
gatggttcta acgtcagatc ttacttgtac tgtgaggacg ttgctgaagc tttcgaagtt    720
gttttgcaca agggtgaaat cggtcacgtc tacaacgtcg gtactaagag agaaagaaga    780
gttatcgatg ttgctagaga catctgtaag ttgttcggta aggacccaga atcttctatt    840
caattcgttg aaaacagacc attcaacgat caaagatact tcttggatga tcaaaagttg    900
aagaagttgg gttggcaaga aagaactaac tgggaagatg gtttgaagaa aactatggac    960
tggtacactc aaaacccaga atggtggggt gatgtttctg gtgctttgtt gccacaccca   1020
agaatgttga tgatgccagg tggtagattg tctgatggtt cttctgaaaa gaaggacgtt   1080
tcttctaaca ctgtccaaac tttcactgtt gttactccaa agaacggtga ttctggtgac   1140
aaggcttctt tgaagttctt gatctacggt aagactggtt ggttgggtgg tttgttgggt   1200
aagttgtgtg aaaagcaagg tattacttac gaatacggta agggtagatt ggaagataga   1260
gcttctttgg ttgctgatat tagatctatc aagccaactc acgttttcaa cgctgctggt   1320
ttgactggta gaccaaacgt tgactggtgt gaatctcaca agccagaaac cattagagtt   1380
aacgtcgctg gtactttgac tttggctgat gtttgtagag aaaacgattt gttgatgatg   1440
aacttcgcca ccggttgtat cttcgaatac gacgctactc acccagaagg ttctggtatc   1500
ggtttcaagg aagaagataa gccaaacttc ttcggttctt tctactctaa gaccaaggcc   1560
atggttgaag aattgttgag agaattcgac aacgtttgta ccttgagagt cagaatgcca   1620
atctcctctg acttgaacaa cccaagaaac ttcatcacta agatctctag atacaacaag   1680
gttgttgaca tcccaaactc tatgaccgtt ttggacgaat tgttgccaat ctctatcgaa   1740
atggctaaga gaaacttgag aggtatctgg aacttcacca acccaggtgt tgtttctcac   1800
aacgaaatct tggaaatgta caagaactac atcgaaccag gtttcaagtg gtccaacttc   1860
actgttgaag aacaagctaa ggtcattgtt gctgctagat ctaacaacga aatggatggt   1920
tctaagttgt ctaaggaatt cccagaaatg ttgtccatca aggaatcttt gttgaagtac   1980
gtattcgaac caaacaagag aacctaa                                       2007
```

<210> SEQ ID NO 113
<211> LENGTH: 482
<212> TYPE: PRT
<213> ORGANISM: Citrus sinensis

<400> SEQUENCE: 113

```
Met Ser Lys Asp Thr Ile Val Phe Tyr Thr Ser Pro Gly Arg Gly His
1               5                   10                  15

Leu Asn Ser Met Val Glu Leu Gly Lys Leu Ile Leu Thr Tyr His Pro
```

```
            20                  25                  30

Cys Phe Ser Ile Asp Ile Ile Ile Pro Thr Ala Pro Phe Val Ser Ser
        35                  40                  45

Ala Gly Thr Asp Asp Tyr Ile Ala Ser Val Ser Ala Thr Ala Pro Ser
    50                  55                  60

Val Thr Phe His Gln Leu Pro Pro Pro Val Ser Gly Leu Pro Asp Thr
65                  70                  75                  80

Leu Arg Ser Pro Ala Asp Phe Pro Ala Leu Val Tyr Glu Leu Gly Glu
                85                  90                  95

Leu Asn Asn Pro Asn Leu His Glu Thr Leu Ile Thr Ile Ser Lys Arg
            100                 105                 110

Ser Asn Leu Lys Ala Phe Val Ile Asp Phe Leu Cys Asn Pro Ala Phe
        115                 120                 125

Gln Val Ser Ser Ser Thr Leu Ser Ile Pro Thr Tyr Tyr Tyr Phe Thr
    130                 135                 140

Thr Ala Gly Ser Val Leu Ala Ala Asn Leu Tyr Leu Pro Thr Leu His
145                 150                 155                 160

Lys Asn Thr Thr Lys Ser Phe Arg Glu Leu Gly Ser Ala Leu Leu Asn
                165                 170                 175

Phe Pro Gly Phe Pro Pro Phe Pro Ala Arg Asp Met Ala Leu Pro Met
            180                 185                 190

His Asp Arg Glu Gly Lys Val Tyr Lys Gly Leu Val Asp Thr Gly Ile
        195                 200                 205

Gln Met Ala Lys Ser Ala Gly Val Ile Val Asn Thr Phe Glu Leu Leu
    210                 215                 220

Glu Glu Arg Ala Ile Lys Ala Met Leu Glu Gly Gln Cys Thr Pro Gly
225                 230                 235                 240

Asp Thr Ser Pro Pro Leu Tyr Cys Ile Gly Pro Val Val Gly Arg Gly
                245                 250                 255

Asn Gly Glu Asn Arg Gly Arg Asp Arg His Glu Cys Leu Ser Trp Leu
            260                 265                 270

Asp Ser Lys Pro Ser Arg Ser Val Leu Phe Leu Cys Phe Gly Ser Leu
        275                 280                 285

Gly Ser Phe Ser Cys Lys Gln Leu Lys Glu Met Ala Ile Gly Leu Glu
    290                 295                 300

Arg Ser Gly Val Lys Phe Leu Trp Val Val Arg Ala Pro Ala Pro Asp
305                 310                 315                 320

Ser Val Glu Asn Arg Ser Ser Leu Glu Ser Leu Leu Pro Glu Gly Phe
                325                 330                 335

Leu Asp Arg Thr Lys Asp Arg Gly Leu Val Val Glu Ser Trp Ala Pro
            340                 345                 350

Gln Val Glu Val Leu Asn His Glu Ser Val Gly Gly Phe Val Thr His
        355                 360                 365

Cys Gly Trp Asn Ser Val Leu Glu Gly Val Cys Ala Gly Val Pro Met
    370                 375                 380

Leu Ala Trp Pro Leu Tyr Ala Glu Gln Lys Met Ile Arg Ala Val Val
385                 390                 395                 400

Val Glu Glu Met Lys Val Gly Leu Ala Val Thr Arg Ser Glu Glu Gly
                405                 410                 415

Asp Gly Leu Val Ser Ser Ala Glu Leu Glu Gln Arg Val Ser Glu Leu
            420                 425                 430

Met Asp Ser Glu Lys Gly Arg Ala Val Lys Glu Arg Ala Val Ala Met
        435                 440                 445
```

```
Lys Glu Ala Ala Ala Ala Ala Met Arg Asp Gly Gly Ser Ser Arg Val
    450                 455                 460

Ala Leu Asp Asn Leu Val Glu Ser Phe Lys Arg Gly Cys Ile Ala Pro
465                 470                 475                 480

Phe Gly


<210> SEQ ID NO 114
<211> LENGTH: 1449
<212> TYPE: DNA
<213> ORGANISM: Artificial Sequence
<220> FEATURE:
<223> OTHER INFORMATION: coding sequence for SEQ ID NO: 113

<400> SEQUENCE: 114

atgtccaagg atactattgt tttctacact tctccaggta gaggtcactt gaactccatg      60

gttgaattgg gtaagttgat cttgacttac cacccatgtt tctccattga catcatcatc     120

ccaaccgccc cattcgtttc ttctgccggt accgatgatt acatcgcctc cgtttccgcc     180

actgctccat ccgttacctt ccaccaattg ccaccaccag ttagtggttt gccagacact     240

ctcagatctc cagctgactt cccagccttg gtttacgaat tgggtgaatt gaacaaccca     300

aacttgcacg aaaccttgat cactatttcc aagagatcta acttgaaggc cttcgttatc     360

gatttcttgt gtaacccagc tttccaagtt tcctcttcta ctttgtctat cccaacttac     420

tactacttca ccaccgctgg ttctgttttg gctgctaact tgtacttgcc aactttgcac     480

aagaacacca ctaagtcttt cagagaattg ggttctgctt tgttgaactt cccaggtttc     540

ccaccattcc cagctagaga catggctttg ccaatgcacg atagagaagg taaggtttac     600

aagggtttgg tcgacaccgg tatccaaatg gctaagtctg ctggtgtaat tgttaacaca     660

ttcgaattgt tggaggaaag agctatcaag gctatgttgg aaggtcaatg tactccaggt     720

gatacttctc caccattgta ctgtatcggt ccagttgttg gtagaggtaa cggtgaaaac     780

agaggtagag atagacacga atgtttgtct tggttggact ctaagccatc tagatctgtc     840

ttgttcttgt gtttcggttc tttgggttct ttctcttgta agcaattgaa ggaaatggcc     900

attggtttgg aaagatctgg tgttaagttc ttgtgggtcg ttagagctcc agctccagac     960

tctgtcgaaa acagatcttc tttggaatct ttgttgccag aaggtttctt ggatagaact    1020

aaggatagag gtttggttgt tgaatcttgg gctccacaag ttgaagtttt gaaccacgaa    1080

tctgttggcg gcttcgttac tcactgcggt tggaactctg ttttggaagg tgtttgtgcc    1140

ggtgttccaa tgttggcttg gccattgtac gccgaacaaa agatgattag agctgtcgtt    1200

gttgaagaaa tgaaggttgg tttggctgtt actagatctg aagaaggtga cggtttggtt    1260

tcttctgccg aattggaaca aagagtttct gaattgatgg actctgaaaa gggtagagct    1320

gttaaggaaa gagctgttgc tatgaaggaa gctgctgctg ctgctatgag agatggtggt    1380

tcttctagag ttgcgctcga caacttggtt gaaagcttta agagaggttg catcgctcca    1440

ttcggttaa                                                             1449


<210> SEQ ID NO 115
<211> LENGTH: 477
<212> TYPE: PRT
<213> ORGANISM: Citrus clementina

<400> SEQUENCE: 115

Met Ser Glu Lys Gln Asp His Val His Val Ala Ile Leu Pro Leu Pro
1               5                   10                  15
```

```
Ala Val Gly His Val Asn Ser Met Leu Asn Leu Ala Glu Leu Leu Gly
            20                  25                  30

His Ala Gly Ile Lys Ile Thr Phe Leu Asn Thr Glu His Tyr Tyr Asp
        35                  40                  45

Arg Val Ile Arg His Ser Ser Asp Ala Phe Ser Arg Tyr Met Gln Ile
    50                  55                  60

Pro Gly Phe Gln Phe Lys Thr Leu Thr Asp Gly Leu Pro Arg Asp His
65                  70                  75                  80

Pro Arg Thr Pro Asp Lys Phe Pro Glu Leu Val Asp Ser Leu Asn Cys
                85                  90                  95

Ala Thr Pro Pro Leu Leu Lys Glu Met Val Ser Asp Ser Lys Ser Pro
            100                 105                 110

Val Asn Cys Ile Ile Thr Asp Gly Tyr Met Ser Arg Ala Ile Asp Ala
        115                 120                 125

Ala Arg Glu Val Gly Val Ser Ile Ile Tyr Phe Arg Thr Ile Ser Ala
    130                 135                 140

Cys Ala Phe Trp Ser Phe His Cys Ile Pro Asp Ile Ile Asp Ala Gly
145                 150                 155                 160

Glu Leu Pro Ile Lys Gly Thr Glu Asp Met Asp Arg Leu Ile Thr Thr
                165                 170                 175

Val Pro Gly Met Glu Gly Phe Leu Arg Cys Arg Asp Leu Pro Ser Phe
            180                 185                 190

Cys Arg Val Asn Asp Pro Met Asp Pro His Leu Leu Leu Phe Ala Arg
        195                 200                 205

Glu Thr Arg Leu Ser Ala His Ala Asp Gly Leu Ile Leu Asn Thr Phe
    210                 215                 220

Glu Asp Leu Glu Gly Pro Ile Leu Ser Gln Ile Arg Asn His Ser Cys
225                 230                 235                 240

Pro Asn Ile Tyr Ser Ile Gly Pro Leu Asn Ala His Leu Lys Val Arg
                245                 250                 255

Ile Pro Glu Lys Thr Tyr Ser Ser Ser Ser Leu Trp Lys Ile Asp Arg
            260                 265                 270

Ser Cys Met Ala Trp Leu Asp Lys Gln Pro Lys Gln Ser Val Ile Tyr
        275                 280                 285

Val Ser Phe Gly Ser Ile Ala Val Met Ser Arg Asp Gln Leu Ile Glu
    290                 295                 300

Phe Tyr Tyr Gly Leu Val His Ser Lys Lys Asn Phe Leu Trp Val Ile
305                 310                 315                 320

Arg Pro Asp Leu Ile Ser Gly Lys Asp Gly Glu Asn Gln Ile Pro Glu
                325                 330                 335

Glu Leu Leu Glu Ala Thr Lys Glu Arg Gly Cys Ile Ala Gly Trp Val
            340                 345                 350

Pro Gln Glu Glu Val Leu Ala His Ser Ala Val Gly Gly Phe Leu Thr
        355                 360                 365

His Cys Gly Trp Asn Ser Thr Leu Glu Ser Ile Val Ala Gly Met Pro
    370                 375                 380

Met Ile Cys Trp Pro Ser Phe Ala Asp Gln Gln Ile Asn Ser Arg Phe
385                 390                 395                 400

Val Gly Glu Val Trp Lys Leu Gly Leu Asp Ile Lys Asp Leu Cys Asp
                405                 410                 415

Arg Asn Ile Val Glu Lys Thr Val Asn Asp Leu Met Val Glu Arg Lys
            420                 425                 430
```

```
Glu Glu Phe Met Glu Ser Ala Asp Arg Met Ala Asn Leu Ala Lys Lys
        435                 440                 445

Ser Val Asn Lys Gly Gly Ser Ser Tyr Cys Asn Leu Asp Arg Leu Val
    450                 455                 460

Asn Asp Ile Lys Met Met Ser Ser Gln Pro Gln Asn Cys
465                 470                 475
```

<210> SEQ ID NO 116
<211> LENGTH: 1434
<212> TYPE: DNA
<213> ORGANISM: Artificial Sequence
<220> FEATURE:
<223> OTHER INFORMATION: coding sequence for SEQ ID NO: 115

<400> SEQUENCE: 116

```
atgtccgaaa agcaagatca cgttcacgtt gctatcttgc cattgccagc cgttggtcac     60

gtcaactcca tgttgaactt ggctgaattg ttgggtcacg ccggtatcaa gattactttc    120

ttgaacaccg aacactacta cgatagagtc atcagacact cttctgatgc cttctctaga    180

tacatgcaaa ttccaggttt ccaattcaag accttgactg atggtttgcc aagagatcac    240

ccaagaactc cagataagtt cccagaattg gttgattctt tgaactgtgc cactccacca    300

ttgttgaagg aaatggtatc tgattctaag tctccagtta actgtattat cactgatggt    360

tacatgtcta gagctattga cgctgccaga gaagttggtg tttccattat ttacttcaga    420

actatttctg cttgtgcttt ctggtctttc cactgtatcc cagatatcat tgatgctggt    480

gaattgccaa tcaagggtac tgaagatatg gatagattga tcaccactgt tccaggtatg    540

gaaggtttct tgagatgtag agatttgcca tctttctgta gagttaacga cccaatggat    600

ccacacttgt tgttgttcgc tagagaaacc agattgagtg ctcatgctga cggcttgatc    660

ttgaacactt tcgaagattt ggaaggtcca atcttgtccc aaatcagaaa ccactcttgt    720

ccaaacatct actctattgg tccattgaac gctcacttga aggttagaat cccagaaaag    780

acttactcct cttcttcttt gtggaagatt gacagatctt gtatggcttg gttggacaag    840

caaccaaagc aatctgttat ctacgtatct ttcggttcta ttgctgttat gtctagagat    900

caattgatcg aattctacta cggtttggtt cactctaaga agaacttctt gtgggtcatc    960

agaccagact tgatttctgg taaggatggt gaaaaccaaa ttccagaaga attgttggaa   1020

gctaccaagg aaagaggttg tattgctggt tgggttccac aagaagaagt tttggcccac   1080

tctgctgttg gtggtttctt gacccactgt ggttggaact ctaccttgga atctatcgtt   1140

gctggtatgc caatgatttg ctggccaagc ttcgctgatc aacagatcaa ctctagattc   1200

gttggtgaag tttggaagtt gggtttggat atcaaggatt tgtgtgatag aaacattgtt   1260

gaaaagactg ttaacgattt gatggttgaa agaaaggaag aattcatgga atctgctgat   1320

agaatggcta acttggctaa gaagtctgtt aacaagggtg gttcctctta ctgtaacttg   1380

gacagattgg ttaacgatat caagatgatg tcctctcaac cacaaaactg ttaa          1434
```

<210> SEQ ID NO 117
<211> LENGTH: 354
<212> TYPE: PRT
<213> ORGANISM: Citrus clementina

<400> SEQUENCE: 117

```
Met Ser Gly Ser Ile Val Asp Gly Glu Arg Asp Gln Ser Phe Ala Tyr
1               5                   10                  15

Ala Asn Gln Leu Ala Met Gly Thr Val Leu Pro Met Ala Met Gln Ala
```

```
            20                  25                  30

Val Tyr Glu Leu Gly Ile Phe Gln Ile Ile Asp Lys Ala Gly Pro Gly
        35                  40                  45

Ala Lys Leu Ser Ala Ser Asp Ile Ala Ala Gln Leu Pro Thr Lys Asn
    50                  55                  60

Lys Asp Ala Pro Thr Met Leu Asp Arg Ile Leu Arg Leu Leu Ala Ser
65                  70                  75                  80

Tyr Ser Val Val Glu Cys Ser Leu Asp Gly Ser Gly Ala Arg Arg Arg
                85                  90                  95

Tyr Ser Leu Asn Ser Val Ser Lys Tyr Tyr Val Pro Asn Lys Asp Gly
            100                 105                 110

Val Ser Leu Gly Pro Ala Leu Gln Met Ile Gln Asp Lys Val Phe Leu
        115                 120                 125

Glu Ser Trp Ser His Leu Lys Asp Ala Ile Leu Glu Gly Gly Ile Pro
    130                 135                 140

Phe Asn Arg Ala His Gly Met His Ala Phe Glu Tyr Gly Arg Val Asp
145                 150                 155                 160

Pro Arg Phe Asn Lys His Phe Asn Thr Ala Met Tyr Asn His Thr Ser
                165                 170                 175

Leu Ile Met Ser Asn Ile Leu Glu Ser Tyr Lys Gly Phe Ala Asn Ile
            180                 185                 190

Lys Gln Leu Val Asp Val Gly Gly Asn Leu Gly Val Thr Leu Gln Ala
        195                 200                 205

Ile Thr Ser Lys Tyr Pro Tyr Ile Lys Gly Ile Asn Phe Asp Gln Pro
    210                 215                 220

His Val Ile Glu His Ala Pro Leu His Pro His Ile Glu His Val Ala
225                 230                 235                 240

Gly Asp Met Phe Gln Ser Val Pro Lys Gly Asp Ala Ile Phe Leu Lys
                245                 250                 255

Trp Ile Leu His Asp Trp Asp Asp Glu His Cys Leu Lys Leu Leu Lys
            260                 265                 270

Asn Cys Tyr Lys Ser Val Pro Glu Asp Gly Lys Val Ile Val Val Glu
        275                 280                 285

Leu Met Leu Pro Glu Val Pro Asn Thr Ser Ile Glu Ser Lys Ser Asn
    290                 295                 300

Ser His Ile Asp Val Leu Met Met Thr Gln Asn Pro Gly Gly Lys Glu
305                 310                 315                 320

Arg Thr Lys His Glu Phe Met Thr Leu Ala Thr Gly Ala Gly Phe Ser
                325                 330                 335

Gly Ile Arg Phe Asp Leu Val Thr Gly Asn Phe Trp Val Met Glu Phe
            340                 345                 350

Tyr Lys
```

<210> SEQ ID NO 118
<211> LENGTH: 1065
<212> TYPE: DNA
<213> ORGANISM: Artificial Sequence
<220> FEATURE:
<223> OTHER INFORMATION: coding sequence for SEQ ID NO:117

<400> SEQUENCE: 118

```
atgtccggtt ctatcgttga tggtgaaaga gatcaatctt tcgcttacgc taaccaattg      60

gctatgggta ctgttttgcc aatggccatg caagctgttt acgaattggg tattttccaa     120

atcatcgaca aggctggtcc aggtgctaag ttgtctgctt ctgatattgc tgcccaattg     180
```

```
ccaaccaaga acaaggacgc tccaactatg ctcgacagaa tactaagatt gttggcttct    240

tactctgttg ttgaatgttc tttggatggt tctggtgcca gaagaagata ctctttgaac    300

tctgtctcca agtactacgt tccaaacaag gatggtgtct ctttgggtcc agctttgcaa    360

atgattcaag acaaggtttt cttggaatct tggtcccact tgaaggatgc tattttggaa    420

ggtggtattc cattcaacag agcccacggt atgcacgctt tcgaatacgg tagagttgac    480

ccaagattca acaagcactt caacactgct atgtacaacc acacctcttt gattatgtct    540

aacattttgg aatcttacaa gggtttcgcc aacatcaagc aattggtcga tgttggtggt    600

aacttgggcg taactctcca agccatcact tccaagtacc catacattaa gggtatcaac    660

ttcgaccaac cacacgttat tgaacacgcc ccattgcacc cacacattga acacgttgct    720

ggtgatatgt tccaatctgt tccaaagggt gacgccattt tcttgaagtg gatcttgcac    780

gattgggacg atgaacactg tttgaagttg ttgaagaact gttacaagtc tgttccagaa    840

gatggtaagg ttatcgttgt tgaattgatg ttgccagaag ttccaaacac ttctattgaa    900

tctaagtcta actcccacat tgacgttttg atgatgactc aaaacccagg tggtaaggaa    960

agaactaagc acgaattcat gaccttggct actggtgctg gtttctctgg tatcagattc   1020

gatttggtta ctggtaactt ctgggttatg gaattctaca agtaa                   1065
```

<210> SEQ ID NO 119
<211> LENGTH: 250
<212> TYPE: PRT
<213> ORGANISM: Citrus sinensis

<400> SEQUENCE: 119

```
Met Ser Ala Ala Asn Arg Glu Asp Gln Glu Glu Asn Lys Asp Arg Tyr
1               5                   10                  15

Phe Lys Ala Val His Gly Asn Lys Thr Leu Leu Gln Ser Glu Lys Leu
            20                  25                  30

Tyr Glu Tyr Ile Leu Glu Thr Ser Val Tyr Pro Arg Glu Pro Gln Cys
        35                  40                  45

Leu Lys Glu Ile Arg Glu Leu Thr Tyr Lys His Pro Leu Ser Pro Met
    50                  55                  60

Met Thr Ser Pro Asp Glu Ala Gln Phe Phe Ser Met Leu Leu Lys Leu
65                  70                  75                  80

Ile Asn Ala Lys Asn Thr Met Glu Ile Gly Val Phe Thr Gly Tyr Ser
                85                  90                  95

Leu Leu Ala Thr Ala Leu Ala Ile Pro Asp Asp Gly Lys Ile Leu Ala
            100                 105                 110

Leu Asp Ile Thr Lys Glu His Tyr Glu Lys Gly Leu Pro Ile Ile Gln
        115                 120                 125

Lys Ala Gly Val Ala His Lys Ile Asp Phe Arg Glu Gly Pro Ala Leu
    130                 135                 140

Pro Leu Leu Asp Gln Leu Ile Gln His Glu Lys Tyr His Gly Thr Phe
145                 150                 155                 160

Asp Phe Val Phe Val Asp Ala Asp Lys Asp Asn Tyr Val Asn Tyr His
                165                 170                 175

Lys Arg Leu Ile Glu Leu Val Lys Val Gly Gly Val Ile Gly Tyr Asp
            180                 185                 190

Asn Thr Leu Trp Gly Gly Ser Val Val Ala Pro Pro Asp Ala Asp Leu
        195                 200                 205

Asp Glu His Ile Leu Tyr Leu Arg Asp Phe Val Gln Glu Leu Asn Lys
```

```
    210                 215                 220

Ala Leu Ala Val Asp Pro Arg Ile Glu Ile Cys Gln Leu Ser Ile Ala
225                 230                 235                 240

Asp Gly Val Thr Leu Cys Arg Arg Ile Gly
                245                 250
```

<210> SEQ ID NO 120
<211> LENGTH: 753
<212> TYPE: DNA
<213> ORGANISM: Artificial Sequence
<220> FEATURE:
<223> OTHER INFORMATION: coding sequence for SEQ ID NO:119

<400> SEQUENCE: 120

```
atgtccgctg ctaacagaga agatcaagaa gaaaacaagg atagatactt caaggctgtt      60

cacggtaaca agaccttgtt gcaatctgaa aagttgtacg aatacatctt ggaaacctct     120

gtttacccaa gagaaccaca atgtttgaag gaaatcagag aattgactta caagcaccca     180

ttgtctccaa tgatgacttc tccagatgaa gctcaattct tctctatgtt gttgaagttg     240

atcaacgcca agaacaccat ggagataggt gtattcaccg gttactcttt gttggccact     300

gccttggcca ttccagacga tggtaagatt ttggccttgg acatcaccaa ggaacactac     360

gaaaagggtt tgccaatcat tcaaaaggct ggtgttgctc acaagattga cttcagagaa     420

ggtccagctt tgccattatt ggatcaatta atccaacacg aaaagtacca tggcacattc     480

gacttcgtct ttgttgatgc tgacaaggat aactacgtta actaccacaa gagattgatt     540

gaattggtta aggttggtgg tgttattggt tacgacaaca ccttgtgggg tggttctgtt     600

gttgctccac cagatgccga cttggatgaa cacatcttgt acttgagaga tttcgttcaa     660

gaattgaaca aggccttggc cgttgatcca agaatagaaa tttgtcaatt gtccattgct     720

gatggtgtta ctttgtgtag aagaattggt taa                                  753
```

<210> SEQ ID NO 121
<211> LENGTH: 514
<212> TYPE: PRT
<213> ORGANISM: Arabidopsis thaliana

<400> SEQUENCE: 121

```
Met Ser Ala Thr Leu Phe Leu Thr Ile Leu Leu Ala Thr Val Leu Phe
1               5                   10                  15

Leu Ile Leu Arg Ile Phe Ser His Arg Arg Asn Arg Ser His Asn Asn
            20                  25                  30

Arg Leu Pro Pro Gly Pro Asn Pro Trp Pro Ile Ile Gly Asn Leu Pro
        35                  40                  45

His Met Gly Thr Lys Pro His Arg Thr Leu Ser Ala Met Val Thr Thr
    50                  55                  60

Tyr Gly Pro Ile Leu His Leu Arg Leu Gly Phe Val Asp Val Val Val
65                  70                  75                  80

Ala Ala Ser Lys Ser Val Ala Glu Gln Phe Leu Lys Ile His Asp Ala
                85                  90                  95

Asn Phe Ala Ser Arg Pro Pro Asn Ser Gly Ala Lys His Met Ala Tyr
            100                 105                 110

Asn Tyr Gln Asp Leu Val Phe Ala Pro Tyr Gly His Arg Trp Arg Leu
        115                 120                 125

Leu Arg Lys Ile Ser Ser Val His Leu Phe Ser Ala Lys Ala Leu Glu
    130                 135                 140
```

-continued

```
Asp Phe Lys His Val Arg Gln Glu Glu Val Gly Thr Leu Thr Arg Glu
145                 150                 155                 160

Leu Val Arg Val Gly Thr Lys Pro Val Asn Leu Gly Gln Leu Val Asn
                165                 170                 175

Met Cys Val Val Asn Ala Leu Gly Arg Glu Met Ile Gly Arg Arg Leu
            180                 185                 190

Phe Gly Ala Asp Ala Asp His Lys Ala Asp Glu Phe Arg Ser Met Val
        195                 200                 205

Thr Glu Met Met Ala Leu Ala Gly Val Phe Asn Ile Gly Asp Phe Val
    210                 215                 220

Pro Ser Leu Asp Trp Leu Asp Leu Gln Gly Val Ala Gly Lys Met Lys
225                 230                 235                 240

Arg Leu His Lys Arg Phe Asp Ala Phe Leu Ser Ser Ile Leu Lys Glu
                245                 250                 255

His Glu Met Asn Gly Gln Asp Gln Lys His Thr Asp Met Leu Ser Thr
            260                 265                 270

Leu Ile Ser Leu Lys Gly Thr Asp Leu Asp Gly Asp Gly Gly Ser Leu
        275                 280                 285

Thr Asp Thr Glu Ile Lys Ala Leu Leu Leu Asn Met Phe Thr Ala Gly
    290                 295                 300

Thr Asp Thr Ser Ala Ser Thr Val Asp Trp Ala Ile Ala Glu Leu Ile
305                 310                 315                 320

Arg His Pro Asp Ile Met Val Lys Ala Gln Glu Glu Leu Asp Ile Val
                325                 330                 335

Val Gly Arg Asp Arg Pro Val Asn Glu Ser Asp Ile Ala Gln Leu Pro
            340                 345                 350

Tyr Leu Gln Ala Val Ile Lys Glu Asn Phe Arg Leu His Pro Pro Thr
        355                 360                 365

Pro Leu Ser Leu Pro His Ile Ala Ser Glu Ser Cys Glu Ile Asn Gly
    370                 375                 380

Tyr His Ile Pro Lys Gly Ser Thr Leu Leu Thr Asn Ile Trp Ala Ile
385                 390                 395                 400

Ala Arg Asp Pro Asp Gln Trp Ser Asp Pro Leu Ala Phe Lys Pro Glu
                405                 410                 415

Arg Phe Leu Pro Gly Gly Glu Lys Ser Gly Val Asp Val Lys Gly Ser
            420                 425                 430

Asp Phe Glu Leu Ile Pro Phe Gly Ala Gly Arg Arg Ile Cys Ala Gly
        435                 440                 445

Leu Ser Leu Gly Leu Arg Thr Ile Gln Phe Leu Thr Ala Thr Leu Val
    450                 455                 460

Gln Gly Phe Asp Trp Glu Leu Ala Gly Gly Val Thr Pro Glu Lys Leu
465                 470                 475                 480

Asn Met Glu Glu Ser Tyr Gly Leu Thr Leu Gln Arg Ala Val Pro Leu
                485                 490                 495

Val Val His Pro Lys Pro Arg Leu Ala Pro Asn Val Tyr Gly Leu Gly
            500                 505                 510

Ser Gly
```

<210> SEQ ID NO 122
<211> LENGTH: 1545
<212> TYPE: DNA
<213> ORGANISM: Artificial Sequence
<220> FEATURE:
<223> OTHER INFORMATION: coding sequence for SEQ ID NO:121

<400> SEQUENCE: 122

```
atgtccgcta ctttgttctt gactatcttg ttggctactg ttttgttctt gatcttgaga     60
atcttctctc acagaagaaa cagatctcac aacaacagat tgccaccagg tccaaaccca    120
tggccaatca tcggtaactt gccacacatg ggtactaagc cacacagaac tttgtctgct    180
atggttacta cttacggtcc aatcttgcac ttgagattgg gtttcgttga cgttgttgtt    240
gctgcttcta agtctgttgc tgaacaattc ttgaagatcc acgacgctaa cttcgcttct    300
agaccaccaa actctggtgc taagcacatg gcttacaact accaagactt ggttttcgct    360
ccatacggtc acagatggag attgttgaga aagatctctt ctgttcactt gttctctgct    420
aaggctttgg aagatttcaa gcacgttaga caagaagaag ttggtacttt gactagagaa    480
ttggttagag ttggtactaa gccagttaac ttgggtcaat tggttaacat gtgtgttgtt    540
aacgctttgg gtagagaaat gatcggtaga agattgttcg gtgctgacgc tgaccacaag    600
gctgacgaat tcagatctat ggttactgaa atgatggctt tggctggtgt tttcaacatc    660
ggtgacttcg ttccatcttt ggactggttg gacttgcaag gtgttgctgg taagatgaag    720
agattgcaca agagattcga cgctttcttg tcatctatct tgaaggaaca cgaaatgaac    780
ggtcaagacc aaaagcacac tgacatgttg tctactttga tctctttgaa gggtactgac    840
ttggacggtg acggtggttc tttgactgac actgaaatca aggctttgtt gttgaacatg    900
ttcactgctg gtactgacac ttctgcttct actgttgact gggctatcgc tgaattgatc    960
agacacccag acatcatggt taaggctcaa gaagaattgg acatcgttgt tggtagagac   1020
agaccagtta acgaatctga catcgctcaa ttgccatact tgcaagctgt tatcaaggaa   1080
aacttcagat tgcacccacc aactccattg tctttgccac acatcgcttc tgaatcttgt   1140
gaaatcaacg gttaccacat cccaaagggt tctactttgt tgactaacat ctgggctatc   1200
gctagggacc cagaccaatg gtctgaccca ttggctttca agccagaaag attcttgcca   1260
ggtggtgaaa agtctggtgt tgacgttaag ggttctgact tcgaattgat cccattcggt   1320
gctggtagaa gaatctgtgc tggtttgtct ttgggtttga gaactatcca attcttgact   1380
gctactttgg ttcaaggttt cgactgggaa ttggctggtg gtgttactcc agaaaagttg   1440
aacatggaag aatcttacgg tttgactttg caaagagctg ttccattggt tgttcaccca   1500
aagccaagat tggctccaaa cgtttacggt ttgggttctg gttaa                   1545
```

<210> SEQ ID NO 123
<211> LENGTH: 571
<212> TYPE: PRT
<213> ORGANISM: Arabidopsis thaliana

<400> SEQUENCE: 123

```
Met Ser Val Leu Gln Gln Gln Thr His Phe Leu Thr Lys Lys Ile Asp
1               5                   10                  15

Gln Glu Asp Glu Glu Glu Glu Pro Ser His Asp Phe Ile Phe Arg Ser
            20                  25                  30

Lys Leu Pro Asp Ile Phe Ile Pro Asn His Leu Pro Leu Thr Asp Tyr
        35                  40                  45

Val Phe Gln Arg Phe Ser Gly Asp Gly Asp Gly Asp Ser Ser Thr Thr
    50                  55                  60

Cys Ile Ile Asp Gly Ala Thr Gly Arg Ile Leu Thr Tyr Ala Asp Val
65                  70                  75                  80

Gln Ile Asn Met Arg Arg Ile Ala Thr Gly Ile His Arg Leu Gly Ile
                85                  90                  95
```

-continued

```
Arg His Gly Asp Val Val Met Leu Leu Leu Pro Asn Ser Pro Glu Phe
            100                 105                 110

Ala Leu Ser Phe Leu Ala Val Ala Tyr Leu Gly Ala Val Ser Thr Thr
        115                 120                 125

Ala Asn Pro Phe Tyr Thr Gln Pro Glu Ile Ala Lys Gln Ala Lys Ala
    130                 135                 140

Ser Ala Ala Lys Met Ile Ile Thr Lys Lys Cys Leu Val Asp Lys Leu
145                 150                 155                 160

Thr Asn Leu Lys Asn Asp Gly Val Leu Ile Val Cys Leu Asp Asp Asp
                165                 170                 175

Gly Asp Asn Gly Val Val Ser Ser Ser Asp Asp Gly Cys Val Ser Phe
            180                 185                 190

Thr Glu Leu Thr Gln Ala Asp Glu Thr Glu Leu Leu Lys Pro Lys Ile
        195                 200                 205

Ser Pro Glu Asp Thr Val Ala Met Pro Tyr Ser Ser Gly Thr Thr Gly
    210                 215                 220

Leu Pro Lys Gly Val Met Ile Thr His Lys Gly Leu Val Thr Ser Ile
225                 230                 235                 240

Ala Gln Lys Val Asp Gly Glu Asn Pro Asn Leu Asn Phe Thr Ala Asn
                245                 250                 255

Asp Val Ile Leu Cys Phe Leu Pro Met Phe His Ile Tyr Ala Leu Asp
            260                 265                 270

Ala Leu Met Leu Ser Ala Met Arg Thr Gly Ala Ala Leu Leu Ile Val
        275                 280                 285

Pro Arg Phe Glu Leu Asn Leu Val Met Glu Leu Ile Gln Arg Tyr Lys
    290                 295                 300

Val Thr Val Val Pro Val Ala Pro Pro Val Val Leu Ala Phe Ile Lys
305                 310                 315                 320

Ser Pro Glu Thr Glu Arg Tyr Asp Leu Ser Ser Val Arg Ile Met Leu
                325                 330                 335

Ser Gly Ala Ala Thr Leu Lys Lys Glu Leu Glu Asp Ala Val Arg Leu
            340                 345                 350

Lys Phe Pro Asn Ala Ile Phe Gly Gln Gly Tyr Gly Met Thr Glu Ser
        355                 360                 365

Gly Thr Val Ala Lys Ser Leu Ala Phe Ala Lys Asn Pro Phe Lys Thr
    370                 375                 380

Lys Ser Gly Ala Cys Gly Thr Val Ile Arg Asn Ala Glu Met Lys Val
385                 390                 395                 400

Val Asp Thr Glu Thr Gly Ile Ser Leu Pro Arg Asn Lys Ser Gly Glu
                405                 410                 415

Ile Cys Val Arg Gly His Gln Leu Met Lys Gly Tyr Leu Asn Asp Pro
            420                 425                 430

Glu Ala Thr Ala Arg Thr Ile Asp Lys Asp Gly Trp Leu His Thr Gly
        435                 440                 445

Asp Ile Gly Phe Val Asp Asp Asp Asp Glu Ile Phe Ile Val Asp Arg
    450                 455                 460

Leu Lys Glu Leu Ile Lys Phe Lys Gly Tyr Gln Val Ala Pro Ala Glu
465                 470                 475                 480

Leu Glu Ala Leu Leu Ile Ser His Pro Ser Ile Asp Asp Ala Ala Val
                485                 490                 495

Val Ala Met Lys Asp Glu Val Ala Asp Glu Val Pro Val Ala Phe Val
            500                 505                 510
```

```
Ala Arg Ser Gln Gly Ser Gln Leu Thr Glu Asp Asp Val Lys Ser Tyr
        515                 520                 525

Val Asn Lys Gln Val Val His Tyr Lys Arg Ile Lys Met Val Phe Phe
    530                 535                 540

Ile Glu Val Ile Pro Lys Ala Val Ser Gly Lys Ile Leu Arg Lys Asp
545                 550                 555                 560

Leu Arg Ala Lys Leu Glu Thr Met Cys Ser Lys
                565                 570
```

```
<210> SEQ ID NO 124
<211> LENGTH: 1716
<212> TYPE: DNA
<213> ORGANISM: Artificial Sequence
<220> FEATURE:
<223> OTHER INFORMATION: coding sequence for SEQ ID NO:123

<400> SEQUENCE: 124

atgtccgttt tgcaacaaca aactcacttc ttgactaaga agatcgatca agaagatgaa     60

gaagaagaac catctcacga tttcattttc agatctaagt tgccagatat cttcatccca    120

aaccacttgc cattgaccga ttacgtattc caaagattct ccggtgatgg tgacggtgat    180

tcctctacta cctgtatcat cgacggtgcc actggccgta tcctcaccta cgccgatgtt    240

caaatcaaca tgagaagaat cgctaccggt atccacagat tgggtatcag acacggtgac    300

gtcgttatgt tgttgttgcc aaactctcca gaattcgctt tgtctttctt ggccgttgct    360

tacttgggtg ccgtttccac taccgctaac ccattctaca ctcaaccaga aatcgctaag    420

caagctaagg cctccgccgc taagatgatc atcactaaga aatgcctggt cgataagttg    480

actaacttga agaacgacgg tgttttgatc gtttgtttgg acgatgacgg tgacaatggc    540

gttgtgagct cttctgatga tggttgtgtt tctttcactg aattgactca agctgacgaa    600

actgaattgt tgaagccaaa gatctctcca gaagatactg ttgctatgcc atactcttcc    660

ggcactactg gtttaccaaa gggtgttatg attactcaca agggtttggt tacttctatc    720

gctcaaaagg tcgacggtga aaacccaaac ttgaacttca ctgccaacga cgtcatcttg    780

tgtttcttgc caatgttcca catttacgct ttggacgctt tgatgttgtc tgctatgaga    840

accggtgctg ctttgttgat cgttccaaga ttcgaattga acttggttat ggaattgatt    900

caaagataca aggtcactgt tgttccagtt gctccaccag ttgttttggc tttcattaag    960

tccccagaaa ctgaaagata cgacttatct tctgttagaa ttatgttgtc tggtgctgct   1020

actttgaaga aggaattgga agatgccgtt agattgaagt tcccaaacgc cattttcggt   1080

caaggttacg gtatgaccga atccggtact gttgctaagt cgctcgcgtt cgctaagaac   1140

ccattcaaga ccaagtccgg tgcttgtggt actgttatca gaaacgccga aatgaaggtt   1200

gtcgataccg aaaccggtat ctccttgcca agaaacaagt ctggtgaaat ctgtgtcaga   1260

ggtcaccaat tgatgaaggg ttacttgaac gatccagaag ctactgctag aaccatcgac   1320

aaggacggtt ggttgcacac tggtgatatt ggtttcgttg atgatgatga tgaaatcttc   1380

attgttgata gattgaagga attgatcaag ttcaagggtt accaagttgc tccagctgaa   1440

ttggaagctt tgttgatttc tcacccatct atcgatgatg ccgctgttgt tgctatgaag   1500

gatgaagttg ctgatgaagt tccagttgct ttcgttgcta gatctcaagg ttctcaattg   1560

actgaagatg atgtcaagtc ttacgttaac aagcaagttg ttcactacaa gagaattaag   1620

atggttttct tcatcgaagt tatcccaaag gctgtttctg gtaagatttt gagaaaggat   1680

ttgagagcta agttggaaac catgtgttct aagtaa                             1716
```

<210> SEQ ID NO 125
<211> LENGTH: 561
<212> TYPE: PRT
<213> ORGANISM: Citrus clementina

<400> SEQUENCE: 125

```
Met Ser Ile Ser Ile Ala Thr Lys Lys Pro Glu Leu Ser Leu Asp Ile
1               5                   10                  15

Ser Ser Pro Ala Pro Pro Ala Pro Ser Asn Glu Lys Ile Ala Thr His
            20                  25                  30

Ile Phe Lys Ser Lys Leu Pro Asp Ile Pro Ile Ser Asn His Leu Pro
        35                  40                  45

Leu His Thr Tyr Cys Phe Gln Asp Arg Leu Ser Asp Asp Pro Cys Leu
    50                  55                  60

Ile Val Gly Leu Thr Gly Lys Thr Tyr Ser Tyr Ala Glu Thr His Leu
65                  70                  75                  80

Ile Cys Arg Lys Thr Ala Ala Gly Leu Ser Asn Leu Gly Ile Lys Lys
                85                  90                  95

Gly Asp Val Ile Met Ile Leu Leu Gln Asn Cys Ala Glu Phe Val Phe
            100                 105                 110

Ser Phe Met Gly Ala Ser Met Ile Gly Ala Val Thr Thr Thr Ala Asn
        115                 120                 125

Pro Phe Tyr Thr Ser Ala Glu Ile Leu Lys Gln Phe Arg Thr Ser Gly
    130                 135                 140

Ala Lys Leu Ile Ile Thr Met Ser Gln Tyr Val Asp Arg Leu Pro Lys
145                 150                 155                 160

Thr Asp Lys Asp Phe Thr Val Ile Thr Ile Asp Ala Pro Pro Glu Asn
                165                 170                 175

Cys Leu His Phe Thr Val Leu Ser Glu Ala Asp Glu Asp Gln Ile Pro
            180                 185                 190

Glu Val Ala Ile Glu Pro Asp Asp Pro Val Ala Leu Pro Phe Ser Ser
        195                 200                 205

Gly Thr Thr Gly Leu Pro Lys Gly Val Val Leu Thr His Lys Ser Leu
    210                 215                 220

Ile Thr Ser Val Ala Gln Gln Val Asp Gly Glu Asn Pro Asn Leu Tyr
225                 230                 235                 240

Leu Thr Asn Gly Asp Val Val Leu Cys Val Leu Pro Leu Phe His Ile
                245                 250                 255

Tyr Ser Leu Asn Ser Val Leu Leu Cys Ser Leu Arg Ala Gly Ala Gly
            260                 265                 270

Val Leu Leu Met Gln Lys Phe Glu Ile Gly Ala Leu Leu Glu Leu Ile
        275                 280                 285

Gln Arg His Arg Val Ser Val Ala Ala Val Val Pro Pro Leu Val Leu
    290                 295                 300

Ala Leu Ala Lys Asn Pro Met Val Ala Asp Tyr Asp Leu Ser Ser Ile
305                 310                 315                 320

Arg Val Val Leu Ser Gly Ala Ala Pro Leu Gly Lys Glu Leu Glu Asp
                325                 330                 335

Ala Leu Arg Ser Arg Val Pro Gln Ala Ile Leu Gly Gln Gly Tyr Gly
            340                 345                 350

Met Thr Glu Ala Gly Pro Val Leu Ser Met Cys Leu Gly Phe Ala Lys
        355                 360                 365

Gln Pro Phe Pro Thr Lys Ser Gly Ser Cys Gly Thr Val Val Arg Asn
```

```
    370                 375                 380

Ala Glu Leu Lys Val Ile Asp Pro Glu Ile Gly Ala Ser Leu Pro His
385                 390                 395                 400

Asn Gln Pro Gly Glu Ile Cys Ile Arg Gly Pro Gln Ile Met Lys Gly
                405                 410                 415

Tyr Leu Asn Asp Pro Glu Ala Thr Ala Ala Thr Ile Asp Val Glu Gly
            420                 425                 430

Trp Leu His Thr Gly Asp Ile Gly Tyr Val Asp Asp Asp Glu Val
        435                 440                 445

Phe Ile Val Asp Arg Val Lys Glu Ile Ile Lys Phe Lys Gly Phe Gln
    450                 455                 460

Val Pro Pro Ala Glu Ile Glu Ala Leu Leu Leu Ser His Pro Ser Ile
465                 470                 475                 480

Gly Asp Ala Ala Val Val Pro Gln Lys Asp Glu Val Ala Gly Glu Val
                485                 490                 495

Pro Val Ala Phe Val Val Arg Ser Asn Gly Phe Glu Leu Thr Glu Glu
            500                 505                 510

Ala Ile Lys Glu Tyr Ile Ala Lys Gln Val Val Phe Tyr Lys Arg Leu
        515                 520                 525

His Lys Ile Tyr Phe Val His Ala Ile Pro Lys Ser Pro Ser Gly Lys
    530                 535                 540

Ile Leu Arg Lys Asp Leu Arg Ala Lys Leu Ala Ser Ser Met Pro Leu
545                 550                 555                 560

Asn


<210> SEQ ID NO 126
<211> LENGTH: 1686
<212> TYPE: DNA
<213> ORGANISM: Artificial Sequence
<220> FEATURE:
<223> OTHER INFORMATION: coding sequence for SEQ ID NO:125

<400> SEQUENCE: 126

atgtccatct ctatcgccac taagaagcca gaattgtctt tggatatctc ttctccagct     60

ccaccagctc catccaacga aaagatcgcc acccacattt tcaagtctaa gttgccagat    120

atcccaatct ccaaccactt gccattgcac acttactgtt tccaagatag attgtctgac    180

gacccatgtt tgatcgttgg tttgactggt aagacttact cttacgccga aactcacttg    240

atctgtagaa agaccgctgc cggtttgtct aacttgggta tcaagaaggg tgacgttatc    300

atgatcttgt tgcaaaactg tgccgaattc gttttctctt tcatgggtgc ttccatgatc    360

ggtgctgtca ctactactgc caacccattc tacacttctg ctgaaatctt gaagcaattc    420

agaacctctg gtgccaagtt gattatcact atgtctcaat acgtcgacag attgccaaag    480

actgacaagg atttcactgt tatcactatc gatgccccac cagaaaactg tttgcacttc    540

actgttttgt ctgaagctga tgaagatcaa atcccagaag ttgccatcga accagacgat    600

ccagttgctt tgccattctc ttctggtacc actggtttgc caaagggtgt tgttttgact    660

cataagagct tgatcacctc tgttgctcaa caagttgacg gtgaaaaccc aaacttgtac    720

ttgactaacg gtgacgttgt tttgtgtgtt ttgccattgt tccacattta ctctttgaac    780

tctgttttgt tgtgttcttt gagagctggt gctggtgttt tgttgatgca aaagttcgaa    840

atcggtgctt tgttggaatt gatccaaaga cacagagttt ctgttgctgc tgttgttcca    900

ccattggttt tggctttggc caagaaccca atggttgctg attacgactt gtcatctatc    960
```

agagttgttt tgtccggtgc tgctccattg ggtaaggaat tggaagatgc tttgagatct 1020
agagtcccac aagctatctt gggtcaaggt tacggtatga ctgaagctgg tccagttttg 1080
tctatgtgtt tgggtttcgc taagcaacca ttcccaacta agtctggttc ttgtggtacc 1140
gttgttagaa acgctgaatt gaaggttatt gacccagaaa ttggtgcctc cttgccacac 1200
aaccaaccag gtgaaatttg tatcagaggt ccacaaatta tgaagggtta cttgaacgat 1260
ccagaagcta ctgctgctac tatcgacgtt gaaggttggt tgcacactgg tgacatcggt 1320
tacgttgatg atgatgatga agttttcatc gtcgatagag tcaaggaaat catcaagttc 1380
aagggtttcc aagttccacc agctgaaatt gaagccttgt tgttgtctca cccatctatt 1440
ggtgatgctg ctgttgttcc acaaaaggat gaagttgcgg gtgaagttcc agttgcgttc 1500
gttgttcgtt cgaacggctt cgaattgacc gaggaagcca ttaaggaata catcgctaag 1560
caagttgttt tctacaagag attgcacaag atttacttcg ttcacgctat tccaaagtct 1620
ccatccggta agattttgag aaaggatttg agagccaagt tggcctcttc tatgccattg 1680
aactaa 1686

<210> SEQ ID NO 127
<211> LENGTH: 365
<212> TYPE: PRT
<213> ORGANISM: Angelica archangelica

<400> SEQUENCE: 127

Met Ser Ala Pro Thr Thr Ile Thr Ala Leu Ala Gln Glu Lys Thr Leu
1 5 10 15

Asn Leu Ala Phe Val Arg Asp Glu Asp Glu Arg Pro Lys Val Ala Tyr
20 25 30

Asn Gln Phe Ser Asn Glu Ile Pro Ile Ile Ser Leu Ala Gly Met Asp
35 40 45

Asp Asp Thr Gly Arg Arg Pro Gln Ile Cys Arg Lys Ile Val Glu Ala
50 55 60

Phe Glu Asp Trp Gly Ile Phe Gln Val Val Asp His Gly Ile Asp Gly
65 70 75 80

Thr Leu Ile Ser Glu Met Thr Arg Leu Ser Arg Glu Phe Phe Ala Leu
85 90 95

Pro Ala Glu Glu Lys Leu Arg Tyr Asp Thr Thr Gly Gly Lys Arg Gly
100 105 110

Gly Phe Thr Ile Ser Thr His Leu Gln Gly Asp Asp Val Lys Asp Trp
115 120 125

Arg Glu Phe Val Thr Tyr Phe Ser Tyr Pro Ile Asp Asp Arg Asp Tyr
130 135 140

Ser Arg Trp Pro Asp Lys Pro Gln Gly Trp Arg Ser Thr Thr Glu Val
145 150 155 160

Tyr Ser Glu Lys Leu Met Val Leu Gly Ala Lys Leu Leu Glu Val Leu
165 170 175

Ser Glu Ala Met Gly Leu Glu Lys Glu Ala Leu Thr Lys Ala Cys Val
180 185 190

Asn Met Glu Gln Lys Val Leu Ile Asn Tyr Tyr Pro Thr Cys Pro Glu
195 200 205

Pro Asp Leu Thr Leu Gly Val Arg Arg His Thr Asp Pro Gly Thr Ile
210 215 220

Thr Ile Leu Leu Gln Asp Met Val Gly Gly Leu Gln Ala Thr Arg Asp
225 230 235 240

```
Gly Gly Lys Thr Trp Ile Thr Val Gln Pro Val Glu Gly Ala Phe Val
                245                 250                 255

Val Asn Leu Gly Asp His Gly His Tyr Leu Ser Asn Gly Arg Phe Lys
            260                 265                 270

Asn Ala Asp His Gln Ala Val Val Asn Ser Thr Ser Ser Arg Leu Ser
        275                 280                 285

Ile Ala Thr Phe Gln Asn Pro Ala Gln Asn Ala Ile Val Tyr Pro Leu
    290                 295                 300

Arg Ile Arg Glu Gly Glu Lys Ala Val Leu Asp Glu Ala Ile Thr Tyr
305                 310                 315                 320

Ala Glu Met Tyr Lys Lys Asn Met Thr Lys His Ile Glu Val Ala Thr
                325                 330                 335

Leu Lys Lys Leu Ala Lys Glu Lys Arg Leu Gln Glu Glu Lys Ala Lys
            340                 345                 350

Leu Glu Thr Glu Ser Lys Ser Ala Asp Gly Ile Ser Ala
        355                 360                 365


<210> SEQ ID NO 128
<211> LENGTH: 1098
<212> TYPE: DNA
<213> ORGANISM: Artificial Sequence
<220> FEATURE:
<223> OTHER INFORMATION: coding sequence for SEQ ID NO:127

<400> SEQUENCE: 128

atgtccgctc caactactat cactgctttg gctcaagaaa agactttgaa cttggctttc      60

gttagagatg aagatgaaag accaaaggtt gcttacaacc aattctctaa cgaaatccca     120

atcatctctt tggctggtat ggacgacgac actggtagga ggccacaaat ctgtagaaag     180

atcgttgaag ctttcgaaga ttggggtatc ttccaagttg ttgaccacgg tatcgacggt     240

actttgatct ctgaaatgac tagattgtct agagaattct tcgctttgcc agctgaagaa     300

aagttgagat acgacactac tggtggtaag agaggtggtt tcactatctc tactcacttg     360

caaggtgacg acgttaagga ctggagagaa ttcgttactt acttctctta cccaatcgac     420

gacagagact actctagatg gccagacaag ccacaaggtt ggagatctac tactgaagtt     480

tactctgaaa agttgatggt tttgggtgct aagttgttgg aagttttgtc tgaagctatg     540

ggtttggaaa aggaagcttt gactaaggct tgtgttaaca tggaacaaaa ggttttgatc     600

aactactacc caacttgtcc agaaccagac ttgactttgg gtgttaggag acacactgac     660

ccaggtacta tcactatctt gttgcaagac atggttggtg gtttgcaagc tactagagat     720

ggtggtaaga cttggatcac tgttcaacca gttgaaggtg ctttcgttgt taacttgggt     780

gaccacggtc actacttgtc taacggtaga ttcaagaacg ctgaccacca agctgttgtt     840

aactctactt cttctagatt gtctatcgct actttccaaa acccagctca aaacgctatc     900

gtttacccat tgagaatcag agaaggtgaa aaggctgttt tggacgaagc tatcacttac     960

gctgaaatgt acaagaagaa catgactaag cacatcgaag ttgctacttt gaagaagttg    1020

gctaaggaaa agagattgca agaagaaaag gctaagttgg aaactgaatc taagtctgct    1080

gacggtatct ctgcttaa                                                  1098


<210> SEQ ID NO 129
<211> LENGTH: 514
<212> TYPE: PRT
<213> ORGANISM: Cynara cardunculus var. scolymus

<400> SEQUENCE: 129
```

```
Met Ser Gln Val His Glu Thr Leu Thr Pro Ala Val Ile Ala Ala Val
1               5                   10                  15

Val Leu Ser Ser Val Phe Leu Tyr Leu Leu Phe Lys Lys Lys Gln Asn
            20                  25                  30

His Arg Leu Pro Pro Ser Pro Pro Ser Leu Pro Ile Ile Gly His Leu
        35                  40                  45

His His Leu Gly Pro Leu Ile His Gln Ser Phe His His Leu Ser Thr
    50                  55                  60

Arg Tyr Gly Pro Leu Ile His Leu Arg Leu Gly Ser Val Pro Cys Ile
65                  70                  75                  80

Val Ala Ser Thr Pro Asp Leu Ala Arg Asp Phe Leu Lys Thr Asn Glu
                85                  90                  95

Leu Ala Phe Ser Ser Arg Lys His Ser Leu Ala Ile Asp His Ile Thr
            100                 105                 110

Tyr Gly Val Ala Phe Ala Phe Ala Pro Tyr Gly Pro Tyr Trp Lys Phe
        115                 120                 125

Ile Lys Lys Met Ser Thr Val Glu Leu Leu Gly Asn Gln Asn Leu Gly
    130                 135                 140

His Phe Leu Pro Ile Arg Thr His Glu Ile Gln Glu Leu Leu Gln Thr
145                 150                 155                 160

Leu Thr Glu Lys Ala Lys Arg Arg Glu Ser Val Asn Leu Thr Glu Glu
                165                 170                 175

Leu Leu Lys Leu Thr Asn Asn Val Ile Cys Gln Met Met Met Ser Ile
            180                 185                 190

Arg Cys Ser Gly Thr Asn Ser Glu Ala Asp Glu Ala Lys Asn Leu Val
        195                 200                 205

Arg Glu Val Thr Gln Ile Phe Gly Glu Phe Asn Val Ser Asp Phe Ile
    210                 215                 220

Trp Phe Cys Lys Asn Ile Asp Leu Gln Gly Phe Lys Lys Arg Tyr Thr
225                 230                 235                 240

Asp Thr His Lys Arg Tyr Asp Ala Leu Leu Glu Lys Ile Ile Phe Glu
                245                 250                 255

Arg Glu Glu Lys Arg Arg Lys Glu Gly Lys Arg Glu Asp Gly Lys Gly
            260                 265                 270

Lys Asp Phe Leu Asp Met Leu Leu Asp Val Leu Glu Asp Ala Lys Ala
        275                 280                 285

Glu Ile Lys Ile Thr Arg Asp His Ile Lys Ala Leu Ile Leu Asp Phe
    290                 295                 300

Phe Thr Ala Ala Thr Asp Thr Thr Ala Ile Ala Leu Glu Trp Met Leu
305                 310                 315                 320

Val Glu Leu Ile Ser Asn Pro Lys Val Leu Glu Ile Ala Arg Glu Glu
                325                 330                 335

Ile Asp Gln Val Val Gly Asn Glu Arg Leu Val Gln Glu Ser Asp Ala
            340                 345                 350

Pro Asn Leu Pro Tyr Ile Gln Ala Ile Ile Lys Glu Ala Leu Arg Leu
        355                 360                 365

His Pro Pro Ile Pro Met Leu Ile Arg Lys Ser Ile Glu Asp Val Ser
    370                 375                 380

Val Gln Gly Tyr Asp Ile Pro Ala Gly Thr Met Leu Phe Val Asn Ile
385                 390                 395                 400

Trp Ser Ile Gly Arg Asn Pro Lys Tyr Trp Glu Ser Pro Leu Glu Phe
                405                 410                 415
```

```
Lys Pro His Arg Phe Leu Glu Asp Asp Pro Val Lys Lys Ser Leu Asp
            420                 425                 430

Ile Lys Gly Gln Ser Phe Gln Leu Leu Pro Phe Gly Thr Gly Arg Arg
        435                 440                 445

Gly Cys Pro Gly Ile Asn Leu Ala Met Arg Glu Leu Pro Val Val Ile
    450                 455                 460

Ala Gly Leu Ile Gln Cys Phe Glu Trp Asn Val Asn Gly Lys Gln Val
465                 470                 475                 480

Leu Asp Met Asp Glu Arg Ala Gly Leu Thr Ala Pro Arg Ala Ala Asp
                485                 490                 495

Phe Val Cys Val Pro Ser Val Arg Glu Asn Ser Pro Met Met Phe Thr
            500                 505                 510

Ser Thr


<210> SEQ ID NO 130
<211> LENGTH: 1545
<212> TYPE: DNA
<213> ORGANISM: Artificial Sequence
<220> FEATURE:
<223> OTHER INFORMATION: coding sequence for SEQ ID NO:129

<400> SEQUENCE: 130

atgtcccaag ttcacgaaac tttgactcca gctgttatcg ctgctgttgt tttgtcatct     60

gttttcttgt acttgttgtt caagaagaag caaaaccaca gattgccacc atctccacca    120

tctttgccaa tcatcggtca cttgcaccac ttgggtccat tgatccacca atctttccac    180

cacttgtcta ctagatacgg tccattgatc cacttgagat tgggttctgt tccatgtatc    240

gttgcttcta ctccagactt ggctagagac ttcttgaaaa ctaacgaatt ggctttctct    300

tctagaaagc actctttggc tatcgaccac atcacttacg gtgttgcttt cgctttcgct    360

ccatacggtc catactggaa gttcatcaag aagatgtcta ctgttgaatt gttgggtaac    420

caaaacttgg gtcacttctt gccaatcaga actcacgaaa tccaagaatt gttgcaaact    480

ttgactgaaa aggctaagag aagagaatct gttaacttga ctgaagaatt gttgaagttg    540

actaacaacg ttatctgtca aatgatgatg tctatcagat gttctggtac taactctgaa    600

gctgacgaag ctaagaactt ggttagagaa gttactcaaa tcttcggtga attcaacgtt    660

tctgacttca tctggttctg taagaacatc gacttgcaag gtttcaagaa gagatacact    720

gacactcaca agagatacga cgctttgttg gaaaagatca tcttcgaaag agaagaaaag    780

agaagaaagg aaggtaagag agaagatggt aagggtaagg acttcttgga catgttgttg    840

gacgttttgg aagatgctaa ggctgaaatc aagatcacta gagatcacat caaggctttg    900

atcttggact tcttcactgc tgctactgac actactgcta tcgctttgga atggatgttg    960

gttgaattga tctctaaccc aaaggttttg gaaatcgcta gagaagaaat cgaccaagtt   1020

gttggtaacg aaagattggt tcaagaatct gacgctccaa acttgccata catccaagct   1080

atcatcaagg aagctttgag attgcaccca ccaatcccaa tgttgatcag aaagtctatc   1140

gaagatgttt ctgttcaagg ttacgacatc ccagctggta ctatgttgtt cgttaacatc   1200

tggtctatcg gtagaaaccc aaagtactgg gaatctccat tggaattcaa gccacacaga   1260

ttcttggaag atgacccagt taagaagtct ttggacatca agggtcaatc tttccaattg   1320

ttgccattcg gtactggtag aagaggttgt ccaggtatca acttggctat gagagaattg   1380

ccagttgtta tcgctggttt gatccaatgt ttcgaatgga acgttaacgg taagcaagtt   1440

ttggacatgg acgaaagagc tggtttgact gctccaagag ctgctgactt cgtttgtgtt   1500
```

ccatctgtta gagaaaactc tccaatgatg ttcacttcta cttaa 1545

<210> SEQ ID NO 131
<211> LENGTH: 507
<212> TYPE: PRT
<213> ORGANISM: Perilla frutescens var. crispa

<400> SEQUENCE: 131

Met Ser Ala Leu Tyr Ala Ala Leu Phe Leu Leu Ser Ala Ala Val Val
1 5 10 15

Arg Ser Val Leu Asp Arg Lys Arg Gly Arg Pro Pro Tyr Pro Pro Gly
20 25 30

Pro Phe Pro Leu Pro Ile Ile Gly His Leu His Leu Leu Gly Pro Arg
35 40 45

Leu His Gln Thr Phe His Asp Leu Ser Gln Arg Tyr Gly Pro Leu Met
50 55 60

Gln Leu Arg Leu Gly Ser Ile Arg Cys Val Ile Ala Ala Ser Pro Glu
65 70 75 80

Leu Ala Lys Glu Cys Leu Lys Thr His Glu Leu Val Phe Ser Ser Arg
85 90 95

Lys His Ser Thr Ala Ile Asp Ile Val Thr Tyr Asp Ser Ser Phe Ala
100 105 110

Phe Ser Pro Tyr Gly Pro Tyr Trp Lys Phe Ile Lys Lys Leu Cys Thr
115 120 125

Tyr Glu Leu Leu Gly Ala Arg Asn Leu Ala His Phe Gln Pro Ile Arg
130 135 140

Thr Leu Glu Val Lys Ser Phe Leu Gln Ile Leu Met Arg Lys Gly Glu
145 150 155 160

Ser Gly Glu Ser Phe Asn Val Thr Glu Glu Leu Val Lys Leu Thr Ser
165 170 175

Asn Val Ile Ser His Met Met Leu Ser Ile Arg Cys Ser Glu Thr Glu
180 185 190

Ser Glu Ala Glu Ala Ala Arg Thr Val Ile Arg Glu Val Thr Gln Ile
195 200 205

Phe Gly Glu Phe Asp Val Ser Asp Ile Ile Trp Leu Cys Lys Asn Phe
210 215 220

Asp Phe Gln Gly Ile Arg Lys Arg Ser Glu Asp Ile Gln Arg Arg Tyr
225 230 235 240

Asp Ala Leu Leu Glu Lys Ile Ile Thr Asp Arg Glu Lys Gln Arg Arg
245 250 255

Thr His Gly Gly Gly Gly Gly Gly Gly Glu Ala Lys Asp Phe Leu Asp
260 265 270

Met Phe Leu Asp Ile Met Glu Ser Gly Lys Ala Glu Val Lys Phe Thr
275 280 285

Arg Glu His Leu Lys Ala Leu Ile Leu Asp Phe Phe Thr Ala Gly Thr
290 295 300

Asp Thr Thr Ala Ile Val Cys Glu Trp Ala Ile Ala Glu Val Ile Asn
305 310 315 320

Asn Pro Asn Val Leu Lys Lys Ala Gln Glu Glu Ile Ala Asn Ile Val
325 330 335

Gly Phe Asp Arg Ile Leu Gln Glu Ser Asp Ala Pro Asn Leu Pro Tyr
340 345 350

Leu Gln Ala Leu Ile Lys Glu Thr Phe Arg Leu His Pro Pro Ile Pro
355 360 365

```
Met Leu Ala Arg Lys Ser Ile Ser Asp Cys Val Ile Asp Gly Tyr Met
    370                 375                 380

Ile Pro Ala Asn Thr Leu Leu Phe Val Asn Leu Trp Ser Met Gly Arg
385                 390                 395                 400

Asn Pro Lys Ile Trp Asp Tyr Pro Thr Ala Phe Gln Pro Glu Arg Phe
                405                 410                 415

Leu Glu Lys Glu Lys Ala Ala Ile Asp Val Lys Gly Gln His Phe Glu
            420                 425                 430

Leu Leu Pro Phe Gly Thr Gly Arg Arg Gly Cys Pro Gly Met Leu Leu
        435                 440                 445

Ala Ile Gln Glu Val Val Ile Ile Ile Gly Thr Met Ile Gln Cys Phe
    450                 455                 460

Asp Trp Lys Leu Pro Asp Gly Ser Gly His Val Asp Met Ala Glu Arg
465                 470                 475                 480

Pro Gly Leu Thr Ala Pro Arg Glu Thr Asp Leu Phe Cys Arg Val Val
                485                 490                 495

Pro Arg Val Asp Pro Leu Val Val Ser Thr Gln
            500                 505


<210> SEQ ID NO 132
<211> LENGTH: 1524
<212> TYPE: DNA
<213> ORGANISM: Artificial Sequence
<220> FEATURE:
<223> OTHER INFORMATION: coding sequence for SEQ ID NO:131

<400> SEQUENCE: 132

atgtccgctt tgtacgctgc tttgttcttg ttgtctgctg ctgttgttag atctgttttg      60

gacagaaaga gaggtagacc accataccca ccaggtccat tcccattgcc aatcatcggt     120

cacttgcact tgttgggtcc aagattgcac caaactttcc acgacttgtc tcaaagatac     180

ggtccattga tgcaattgag attgggttct atcagatgtg ttatcgctgc ttctccagaa     240

ttggctaagg aatgtttgaa aactcacgaa ttggtttttct cttctagaaa gcactctact     300

gctatcgaca tcgttactta cgactcttct ttcgctttct ctccatacgg tccatactgg     360

aagttcatca agaagttgtg tacttacgaa ttgttgggtg ctagaaactt ggctcacttc     420

caaccaatca gaactttgga agttaagtct ttcttgcaaa tcttgatgag aaagggtgaa     480

tctggtgaat ctttcaacgt tactgaagaa ttggttaagt tgacttctaa cgttatctct     540

cacatgatgt tgtctatcag atgttctgaa actgaatctg aagctgaagc tgctagaact     600

gttatcagag aagttactca aatcttcggt gaattcgacg tttctgacat catctggttg     660

tgtaagaact tcgacttcca aggtatcaga aagagatctg aagatatcca aagaagatac     720

gacgctttgt tggaaaagat catcactgac agagaaaagc aaagaagaac tcacggtggt     780

ggtggtggtg gtggtgaagc taaggacttc ttggacatgt tcttggacat catggaatct     840

ggtaaggctg aagttaagtt cactagagaa cacttgaagg ctttgatctt ggacttcttc     900

actgctggta ctgacactac tgctatcgtt tgtgaatggg ctatcgctga agttatcaac     960

aacccaaacg ttttgaagaa ggctcaagaa gaaatcgcta acatcgttgg tttcgacaga    1020

atcttgcaag aatctgacgc tccaaacttg ccatacttgc aagctttgat caaggaaact    1080

ttcagattgc acccaccaat cccaatgttg gctagaaagt ctatctctga ctgtgttatc    1140

gacggttaca tgatcccagc taacactttg ttgttcgtta acttgtggtc tatgggtaga    1200

aacccaaaga tctgggacta cccaactgct ttccaaccag aaagattctt ggaaaaggaa    1260
```

```
aaggctgcta tcgacgttaa gggtcaacac ttcgaattgt tgccattcgg tactggtaga   1320

agaggttgtc caggtatgtt gttggctatc caagaagttg ttatcatcat cggtactatg   1380

atccaatgtt tcgactggaa gttgccagac ggttctggtc acgttgacat ggctgaaaga   1440

ccaggtttga ctgctccaag agaaactgac ttgttctgta gagttgttcc aagagttgac   1500

ccattggttg tttctactca ataa                                           1524


<210> SEQ ID NO 133
<211> LENGTH: 515
<212> TYPE: PRT
<213> ORGANISM: Dahlia pinnata

<400> SEQUENCE: 133

Met Ser Asn Thr Leu Leu Val Leu Gln Met Val Ile Pro Ala Ile Ile
1               5                   10                  15

Ala Phe Val Ile Phe His Leu Leu Phe Phe Lys Ser Lys Pro Asn Arg
            20                  25                  30

Arg Leu Pro Pro Ser Pro Pro Ser Leu Pro Ile Ile Gly His Leu His
        35                  40                  45

His Leu Gly Pro Leu Ile His Gln Ser Phe Asn Arg Leu Ser Ala Arg
    50                  55                  60

Tyr Gly Pro Leu Ile His Leu Arg Leu Gly Ser Val Ser Cys Val Val
65                  70                  75                  80

Ala Asp Ala Pro Asp Leu Ala Gln Glu Leu Leu Gln Lys Asn Asp Leu
                85                  90                  95

Ala Phe Ala Asn Arg Lys His Thr Leu Ala Ile Asp His Val Thr Tyr
            100                 105                 110

Gly Val Ala Phe Ala Phe Ala Pro Tyr Gly Pro Tyr Trp Arg Phe Ile
        115                 120                 125

Lys Lys Met Ser Thr Val Glu Leu Leu Gly Ile Gln Asn Leu Gly His
    130                 135                 140

Phe Leu Pro Ile Arg Thr Gln Glu Ile His Gly Leu Leu Leu Thr Leu
145                 150                 155                 160

Thr Glu Lys Ser Lys Gln Asn Glu Ser Val Asn Met Thr Asn Glu Leu
                165                 170                 175

Leu Lys Leu Ser Asn Asn Ile Ile Cys Gln Met Met Met Gly Ile Arg
            180                 185                 190

Cys Ser Gly Asn Lys Thr Glu Ala Glu Glu Ala Lys Asn Leu Val Arg
        195                 200                 205

Glu Val Thr Thr Ile Phe Gly Glu Phe Asn Val Ser Asp Phe Ile Trp
    210                 215                 220

Phe Cys Lys Lys Leu Asp Leu Gln Gly Phe Lys Lys Arg Tyr Glu Asp
225                 230                 235                 240

Ile Arg Thr Arg Tyr Asp Ala Leu Leu Glu Arg Ile Ile Phe Ala Arg
                245                 250                 255

Glu Glu Met Arg Lys Glu Gly Lys Gly Met Glu Asp Gly Lys Gly Lys
            260                 265                 270

Asp Phe Leu Asp Met Leu Leu Asp Val Leu Glu Asp Asp Lys Ala Glu
        275                 280                 285

Ile Lys Ile Thr Arg Asn His Ile Lys Ala Leu Ile Leu Asp Phe Val
    290                 295                 300

Thr Ala Gly Thr Asp Thr Thr Ala Val Ile Ile Glu Trp Thr Leu Val
305                 310                 315                 320
```

-continued

```
Glu Leu Ile Lys Asn Pro Met Val Met Glu Lys Ala Lys Gln Glu Leu
                325                 330                 335

Asp Glu Val Val Gly Asn Thr Arg Leu Val Glu Glu Ser Asp Ala Pro
            340                 345                 350

Lys Leu Pro Tyr Ile Gln Ala Ile Ile Lys Glu Ala Phe Arg Leu His
        355                 360                 365

Pro Pro Ile Pro Met Ile Ile Arg Lys Ser Asn Glu Asn Val Ser Val
    370                 375                 380

Lys Ser Gly Tyr Glu Ile Pro Ala Gly Ser Ile Leu Phe Val Asn Asn
385                 390                 395                 400

Trp Ser Ile Gly Arg Asn Pro Lys Tyr Trp Glu Ser Pro Leu Glu Phe
                405                 410                 415

Lys Pro Asp Arg Phe Leu Lys Glu Gly Val Leu Lys Pro Ser Leu Asp
            420                 425                 430

Ile Arg Gly Gln Asn Phe Gln Ile Leu Pro Phe Gly Thr Gly Arg Arg
        435                 440                 445

Ser Cys Pro Gly Ile Asn Met Ala Met Arg Gln Leu Pro Val Val Val
    450                 455                 460

Ala Ile Leu Ile Gln Cys Phe Glu Trp Thr Val Asn Asp Lys Gln Val
465                 470                 475                 480

Leu Asn Met Asp Glu Arg Gly Gly Leu Thr Thr Pro Arg Ala Thr Asp
                485                 490                 495

Leu Val Cys Phe Pro Leu Leu Arg Lys Asn Ser Pro His Ser Met Phe
            500                 505                 510

Thr Ser Val
        515
```

<210> SEQ ID NO 134
<211> LENGTH: 1548
<212> TYPE: DNA
<213> ORGANISM: Artificial Sequence
<220> FEATURE:
<223> OTHER INFORMATION: coding sequence for SEQ ID NO:133

<400> SEQUENCE: 134

```
atgtccaaca ctttgttggt tttgcaaatg gttatcccag ctatcatcgc tttcgttatc     60

ttccacttgt tgttcttcaa gtctaagcca aacagaagat tgccaccatc tccaccatct    120

ttgccaatca tcggtcactt gcaccacttg ggtccattga tccaccaatc tttcaacaga    180

ttgtctgcta gatacggtcc attgatccac ttgagattgg gttctgtttc ttgtgttgtt    240

gctgacgctc cagacttggc tcaagaattg ttgcaaaaga acgacttggc tttcgctaac    300

agaaagcaca ctttggctat cgaccacgtt acttacggtg ttgctttcgc tttcgctcca    360

tacggtccat actggagatt catcaagaag atgtctactg ttgaattgtt gggtatccaa    420

aacttgggtc acttcttgcc aatcagaact caagaaatcc acggtttgtt gttgactttg    480

actgaaaagt ctaagcaaaa cgaatctgtt aacatgacta acgaattgtt gaagttgtct    540

aacaacatca tctgtcaaat gatgatgggt atcagatgtt ctggtaacaa gactgaagct    600

gaagaagcta agaacttggt tagagaagtt actactatct tcggtgaatt caacgtttct    660

gacttcatct ggttctgtaa gaagttggac ttgcaaggtt tcaagaagag atacgaagat    720

atcagaacta gatacgacgc tttgttggaa agaatcatct tcgctagaga agaaatgaga    780

aaggaaggta agggtatgga agatggtaag ggtaaggact tcttggacat gttgttggac    840

gttttggaag atgacaaggc tgaaatcaag atcactagaa accacatcaa ggctttgatc    900
```

```
ttggacttcg ttactgctgg tactgacact actgctgtta tcatcgaatg gactttggtt    960

gaattgatca agaacccaat ggttatggaa aaggctaagc aagaattgga cgaagttgtt   1020

ggtaacacta gattggttga agaatctgac gctccaaagt tgccatacat ccaagctatc   1080

atcaaggaag ctttcagatt gcacccacca atcccaatga tcatcagaaa gtctaacgaa   1140

aacgtttctg ttaagtctgg ttacgaaatc ccagctggtt ctatcttgtt cgttaacaac   1200

tggtctatcg gtagaaaccc aaagtactgg gaatctccat tggaattcaa gccagacaga   1260

ttcttgaagg aaggtgtttt gaagccatct ttggacatca gaggtcaaaa cttccaaatc   1320

ttgccattcg gtactggtag aagatcttgt ccaggtatca acatggctat gagacaattg   1380

ccagttgttg ttgctatctt gatccaatgt ttcgaatgga ctgttaacga caagcaagtt   1440

ttgaacatgg acgaaagagg tggtttgact actccaagag ctactgactt ggtttgtttc   1500

ccattgttga gaaagaactc tccacactct atgttcactt ctgtttaa                1548


<210> SEQ ID NO 135
<211> LENGTH: 515
<212> TYPE: PRT
<213> ORGANISM: Callistephus chinensis

<400> SEQUENCE: 135

Met Ser Asn Ile Phe Glu Val Phe Gln Ser Val Ser Pro Ala Ile Ile
1               5                   10                  15

Ala Ile Phe Phe Ile Ser Ser Leu Phe Ile Tyr Leu Val Leu Ile Arg
            20                  25                  30

Asn Gln Lys Ser Leu Ser Leu Pro Pro Ser Pro Pro Ala Leu Pro Ile
        35                  40                  45

Ile Gly His Leu His His Leu Gly Pro Leu Ile His His Ser Phe His
    50                  55                  60

Asp Leu Ser Thr Arg Tyr Gly Pro Leu Ile His Leu Arg Leu Gly Ser
65                  70                  75                  80

Val Pro Cys Val Val Ala Ser Thr Pro Asp Leu Ala Arg Asp Phe Leu
                85                  90                  95

Lys Thr Asn Glu Leu Ala Phe Ser Ser Arg Lys His Ser Leu Ala Ile
            100                 105                 110

Asp His Val Thr Tyr Gly Val Ser Phe Ala Phe Ala Pro Tyr Gly Pro
        115                 120                 125

Tyr Trp Lys Phe Ile Lys Lys Thr Ser Ile Val Glu Leu Leu Gly Asn
    130                 135                 140

Gln Asn Leu Ser Asn Phe Leu Pro Ile Arg Thr Gln Glu Val His Glu
145                 150                 155                 160

Leu Leu Gln Thr Leu Met Val Lys Ser Lys Lys Asn Glu Ser Val Asn
                165                 170                 175

Leu Ser Glu Glu Leu Leu Lys Leu Thr Asn Asn Val Ile Cys Gln Met
            180                 185                 190

Met Met Ser Ile Arg Cys Ser Gly Thr Asn Asn Glu Ala Asp Glu Ala
        195                 200                 205

Lys Asn Leu Val Arg Glu Val Thr Lys Ile Phe Gly Glu Phe Asn Ile
    210                 215                 220

Ser Asp Phe Ile Cys Leu Phe Lys Asn Ile Asp Leu Gln Gly Phe Lys
225                 230                 235                 240

Lys Arg Tyr Val Asp Thr His Thr Arg Tyr Asn Ala Leu Leu Glu Lys
                245                 250                 255

Met Ile Phe Glu Arg Glu Glu Lys Arg Lys Gln Lys Lys Ser Glu Asp
```

```
            260                 265                 270

Gly Lys Gly Lys Asp Phe Leu Asp Ile Leu Leu Asp Val Leu Glu Asp
        275                 280                 285

Glu Asn Ala Glu Ile Lys Ile Thr Arg Asp His Ile Lys Ala Leu Ile
    290                 295                 300

Leu Asp Phe Phe Thr Ala Ala Thr Asp Thr Thr Ala Ile Ser Ile Glu
305                 310                 315                 320

Trp Thr Leu Val Glu Leu Thr Asn Asn Pro Lys Val Leu Glu Asn Ala
                325                 330                 335

Arg Lys Glu Ile Ala Glu Val Val Gly Asp Glu Arg Leu Val Gln Glu
            340                 345                 350

Ser Asp Ile Pro Asn Leu Pro Tyr Ile Gln Ala Ile Ile Lys Glu Thr
        355                 360                 365

Leu Arg Met His Pro Pro Ile Pro Met Val Ile Arg Lys Ser Ile Asp
    370                 375                 380

Asn Val Thr Val Gln Gly Tyr Asp Ile Arg Ala Gly Thr Met Leu Phe
385                 390                 395                 400

Val Asn Ile Trp Ser Ile Gly Arg Asn Pro Leu Tyr Trp Glu Ser Pro
                405                 410                 415

Leu Glu Phe Lys Pro His Arg Phe Leu Asp Gly His Ala Arg Asn Leu
            420                 425                 430

Asp Val Lys Gly Gln Cys Phe Gln Leu Leu Pro Phe Gly Thr Gly Arg
        435                 440                 445

Arg Gly Cys Pro Gly Ile Ser Leu Ala Met Arg Glu Leu Pro Val Val
    450                 455                 460

Ile Ala Gly Leu Ile Gln Cys Phe Glu Trp Asn Ala Asn Asp Lys Glu
465                 470                 475                 480

Val Leu Ser Met Asp Glu Arg Ala Gly Leu Thr Ala Pro Arg Ala Val
                485                 490                 495

Asp Leu Glu Phe Val Pro Leu Met Arg Gln Asn Cys Pro Asn Ile Phe
            500                 505                 510

Val Ser Ala
        515
```

<210> SEQ ID NO 136
<211> LENGTH: 1548
<212> TYPE: DNA
<213> ORGANISM: artificial
<220> FEATURE:
<223> OTHER INFORMATION: coding sequence for SEQ D NO 135

<400> SEQUENCE: 136

```
atgtccaaca tcttcgaagt tttccaatct gtttctccag ctatcatcgc tatcttcttc      60

atctcttctt tgttcatcta cttggttttg atcagaaacc aaaagtcttt gtctttgcca     120

ccatctccac cagctttgcc aatcatcggt cacttgcacc acttgggtcc attgatccac     180

cactctttcc acgacttgtc tactagatac ggtccattga tccacttgag attgggttct     240

gttccatgtg ttgttgcttc tactccagac ttggctagag acttcttgaa aactaacgaa     300

ttggctttct cttctagaaa gcactctttg gctatcgacc acgttactta cggtgtttct     360

ttcgctttcg ctccatacgg tccatactgg aagttcatca agaaaacttc tatcgttgaa     420

ttgttgggta accaaaactt gtctaacttc ttgccaatca gaactcaaga agttcacgaa     480

ttgttgcaaa ctttgatggt taagtctaag aagaacgaat ctgttaactt gtctgaagaa     540

ttgttgaagt tgactaacaa cgttatctgt caaatgatga tgtctatcag atgttctggt     600
```

```
actaacaacg aagctgacga agctaagaac ttggttagag aagttactaa gatcttcggt    660

gaattcaaca tctctgactt catctgtttg ttcaagaaca tcgacttgca aggtttcaag    720

aagagatacg ttgacactca cactagatac aacgctttgt tggaaaagat gatcttcgaa    780

agagaagaaa agagaaagca aaagaagtct gaagatggta agggtaagga cttcttggac    840

atcttgttgg acgttttgga agatgaaaac gctgaaatca agatcactag agatcacatc    900

aaggctttga tcttggactt cttcactgct gctactgaca ctactgctat ctctatcgaa    960

tggactttgg ttgaattgac taacaaccca aaggttttgg aaaacgctag aaaggaaatc   1020

gctgaagttg ttggtgacga aagattggtt caagaatctg acatcccaaa cttgccatac   1080

atccaagcta tcatcaagga aactttgaga atgcacccac caatcccaat ggttatcaga   1140

aagtctatcg acaacgttac tgttcaaggt tacgacatca gagctggtac tatgttgttc   1200

gttaacatct ggtctatcgg tagaaaccca ttgtactggg aatctccatt ggaattcaag   1260

ccacacagat tcttggacgg tcacgctaga aacttggacg ttaagggtca atgtttccaa   1320

ttgttgccat tcggtactgg tagaagaggt tgtccaggta tctctttggc tatgagagaa   1380

ttgccagttg ttatcgctgg tttgatccaa tgtttcgaat ggaacgctaa cgacaaggaa   1440

gttttgtcta tggacgaaag agctggtttg actgctccaa gagctgttga cttggaattc   1500

gttccattga tgagacaaaa ctgtccaaac atcttcgttt ctgcttaa                1548
```

<210> SEQ ID NO 137
<211> LENGTH: 356
<212> TYPE: PRT
<213> ORGANISM: Apium graveolens

<400> SEQUENCE: 137

```
Met Ser Ala Pro Ser Thr Ile Thr Ala Leu Ser Gln Glu Lys Thr Leu
1               5                   10                  15

Asn Leu Asp Phe Val Arg Asp Glu Asp Glu Arg Pro Lys Val Ala Tyr
            20                  25                  30

Asn Gln Phe Ser Asn Glu Val Pro Ile Ile Ser Leu Ala Gly Leu Asp
        35                  40                  45

Asp Asp Ser Asn Gly Arg Arg Ala Glu Ile Cys Arg Lys Ile Val Glu
    50                  55                  60

Ala Phe Glu Glu Trp Gly Ile Phe Gln Val Val Asp His Gly Ile Asp
65                  70                  75                  80

Ser Gly Leu Ile Ser Glu Met Ser Arg Leu Ser Arg Glu Phe Phe Ala
                85                  90                  95

Leu Pro Ala Glu Glu Lys Leu Val Tyr Asp Thr Thr Gly Glu Lys Lys
            100                 105                 110

Gly Gly Phe Thr Ile Ser Thr His Leu Gln Gly Asp Asp Val Arg Asp
        115                 120                 125

Trp Arg Glu Phe Val Thr Tyr Phe Ser Tyr Pro Ile Ser Ala Arg Asp
    130                 135                 140

Tyr Ser Arg Trp Pro Lys Lys Pro Glu Gly Trp Arg Ser Thr Thr Glu
145                 150                 155                 160

Val Tyr Ser Glu Lys Leu Met Val Leu Gly Ala Lys Leu Leu Glu Val
                165                 170                 175

Leu Ser Glu Ala Met Gly Leu Glu Lys Glu Ala Leu Thr Lys Ala Cys
            180                 185                 190

Val Glu Met Glu Gln Lys Val Leu Ile Asn Tyr Tyr Pro Thr Cys Pro
        195                 200                 205
```

```
Glu Pro Asp Leu Thr Leu Gly Val Arg Arg His Thr Asp Pro Gly Thr
    210                 215                 220

Ile Thr Ile Leu Leu Gln Asp Met Val Gly Gly Leu Gln Ala Thr Arg
225                 230                 235                 240

Asp Gly Gly Lys Thr Trp Ile Thr Val Gln Pro Val Glu Gly Ala Phe
                245                 250                 255

Val Val Asn Leu Gly Asp His Gly His Tyr Leu Ser Asn Gly Arg Phe
            260                 265                 270

Arg Asn Ala Asp His Gln Ala Val Val Asn Ser Thr Ser Thr Arg Leu
        275                 280                 285

Ser Ile Ala Thr Phe Gln Asn Pro Ala Gln Asn Ala Ile Val Tyr Pro
    290                 295                 300

Leu Lys Ile Arg Glu Gly Glu Lys Ala Ile Leu Asp Glu Ala Ile Thr
305                 310                 315                 320

Tyr Ala Glu Met Tyr Lys Lys Asn Met Thr Lys His Ile Ala Val Ala
                325                 330                 335

Thr Gln Lys Lys Leu Ala Lys Glu Lys Arg Leu Gln Asp Glu Lys Ala
            340                 345                 350

Lys Met Lys Ile
        355
```

<210> SEQ ID NO 138
<211> LENGTH: 1071
<212> TYPE: DNA
<213> ORGANISM: artificial
<220> FEATURE:
<223> OTHER INFORMATION: coding sequence for SEQ ID NO: 137

<400> SEQUENCE: 138

```
atgtccgctc catctactat cactgctttg tctcaagaaa agactttgaa cttggacttc      60

gttagagatg aagatgaaag accaaaggtt gcttacaacc aattctctaa cgaagttcca     120

atcatctctt tggctggttt ggacgacgac tctaacggta gaagagctga aatctgtaga     180

aagatcgttg aagctttcga agaatggggt atcttccaag ttgttgacca cggtatcgac     240

tctggtttga tctctgaaat gtctagattg tctagagaat tcttcgcttt gccagctgaa     300

gaaaagttgg tttacgacac tactggtgaa aagaagggtg gtttcactat ctctactcac     360

ttgcaaggtg acgacgttag agactggaga gaattcgtta cttacttctc ttacccaatc     420

tctgctagag actactctag atggccaaag aagccagaag gttggagatc tactactgaa     480

gtttactctg aaaagttgat ggttttgggt gctaagttgt tggaagtttt gtctgaagct     540

atgggtttgg aaaaggaagc tttgactaag gcttgtgttg aaatggaaca aaaggttttg     600

atcaactact acccaacttg tccagaacca gacttgactt tgggtgttag gagacacact     660

gacccaggta ctatcactat cttgttgcaa gacatggttg gtggtttgca agctactaga     720

gatggtggta agacttggat cactgttcaa ccagttgaag gtgctttcgt tgttaacttg     780

ggtgaccacg gtcactactt gtctaacggt agattcagaa acgctgacca ccaagctgtt     840

gttaactcta cttctactag attgtctatc gctactttcc aaaacccagc tcaaaacgct     900

atcgtttacc cattgaagat cagagaaggt gaaaaggcta tcttggacga agctatcact     960

tacgctgaaa tgtacaagaa gaacatgact aagcacatcg ctgttgctac tcaaaagaag    1020

ttggctaagg aaaagagatt gcaagacgaa aaggctaaga tgaagatcta a             1071
```

<210> SEQ ID NO 139

<211> LENGTH: 521
<212> TYPE: PRT
<213> ORGANISM: Medicago truncatula

<400> SEQUENCE: 139

```
Met Ser Glu Pro Leu Leu Leu Ala Phe Thr Leu Phe Leu Ser Ser Leu
1               5                   10                  15

Ile Cys Tyr Ile Ile Phe Gln Pro Ile Leu Asn Arg His Lys Asn Leu
            20                  25                  30

Pro Pro Ser Pro Leu Phe Lys Leu Pro Ile Ile Gly His Met His Met
        35                  40                  45

Leu Gly Pro Leu Leu His His Ser Phe Asp Arg Leu Ser Gln Lys Tyr
    50                  55                  60

Gly Pro Ile Phe Ser Leu Asn Phe Gly Ser Val Leu Cys Val Val Ala
65                  70                  75                  80

Ser Thr Pro His Tyr Ala Lys Gln Ile Leu Gln Ile Asn Glu His Ala
                85                  90                  95

Phe Asn Cys Arg Asn Glu Ser Thr Ala Ile Lys Arg Leu Thr Tyr Glu
            100                 105                 110

Ala Ser Leu Ala Phe Ala Pro Tyr Gly Glu Tyr Trp Arg Phe Ile Lys
        115                 120                 125

Lys Leu Ser Met Asn Glu Leu Leu Gly Ser Arg Ser Ile Ser Ser Phe
    130                 135                 140

Gln His Leu Arg Leu Gln Glu Thr His Asn Leu Leu Lys Leu Phe Ala
145                 150                 155                 160

Asp Lys Ala Lys Asn Tyr Glu Ala Val Asn Val Thr Gln Glu Leu Leu
                165                 170                 175

Lys Leu Ser Asn Asn Val Ile Ser Lys Met Met Leu Gly Glu Ala Glu
            180                 185                 190

Glu Ala Arg Asp Val Val Arg Asp Val Thr Glu Ile Phe Gly Glu Phe
        195                 200                 205

Asn Val Ser Asp Phe Ile Trp Leu Phe Lys Lys Leu Asp Leu Gln Gly
    210                 215                 220

Phe Gly Lys Arg Ile Glu Asp Leu Phe Met Arg Phe Asp Thr Leu Val
225                 230                 235                 240

Glu Arg Ile Ile Ser Lys Arg Glu Glu Leu Arg Lys Asn Lys Gly Arg
                245                 250                 255

Lys Glu Asn Lys Gly Glu Gln Gly Ala Glu Phe Arg Asp Phe Leu Asp
            260                 265                 270

Ile Leu Leu Asp Cys Ala Glu Asp Gln Asn Ser Glu Ile Lys Val Gln
        275                 280                 285

Arg Val His Ile Lys Ala Leu Ile Met Asp Phe Phe Thr Ala Gly Thr
    290                 295                 300

Asp Thr Thr Ser Ile Ser Thr Glu Trp Ala Leu Val Glu Leu Met Asn
305                 310                 315                 320

Asn Pro Ser Leu Leu Gln Lys Ala Arg Glu Glu Ile Asp Asn Val Val
                325                 330                 335

Gly Lys Asn Arg Leu Val Asp Glu Ser Asp Gly Pro Asn Leu Pro Tyr
            340                 345                 350

Ile Gln Ala Ile Ile Lys Glu Thr Phe Arg Leu His Pro Pro Val Pro
        355                 360                 365

Met Val Thr Arg Arg Cys Val Thr Gln Cys Lys Ile Glu Asn Tyr Val
    370                 375                 380

Ile Pro Glu Asn Ser Leu Ile Phe Val Asn Asn Trp Ala Met Gly Arg
```

-continued

```
385                 390                 395                 400

Asn Ser Ala Tyr Trp Asp Lys Pro Leu Glu Phe Asn Pro Glu Arg Phe
                405                 410                 415

Leu Lys Asn Ser Thr Asn Ser Asn Gly Val Ile Asp Val Arg Gly Gln
            420                 425                 430

Asn Phe Gln Ile Leu Pro Phe Gly Ser Gly Arg Arg Met Cys Pro Gly
        435                 440                 445

Val Thr Leu Ala Met Gln Glu Val Pro Ala Leu Leu Gly Ala Ile Ile
    450                 455                 460

Gln Cys Phe Asp Phe Asn Phe Val Gly Pro Lys Gly Glu Ile Leu Lys
465                 470                 475                 480

Gly Gly Asp Ile Val Ile Asp Val Asn Glu Arg Pro Gly Leu Thr Ala
                485                 490                 495

Pro Arg Val His Asp Leu Val Cys Val Pro Val Glu Arg Phe Ala Cys
            500                 505                 510

Gly Gly Pro Leu Gln Ser Leu Gly Cys
        515                 520


<210> SEQ ID NO 140
<211> LENGTH: 1566
<212> TYPE: DNA
<213> ORGANISM: artificial
<220> FEATURE:
<223> OTHER INFORMATION: coding sequence for SEQ ID NO: 139

<400> SEQUENCE: 140

atgtccgaac cattgttgtt ggctttcact ttgttcttgt catctttgat ctgttacatc     60

atcttccaac caatcttgaa cagacacaag aacttgccac catctccatt gttcaagttg    120

ccaatcatcg gtcacatgca catgttgggt ccattgttgc accactcttt cgacagattg    180

tctcaaaagt acggtccaat cttctctttg aacttcggtt ctgttttgtg tgttgttgct    240

tctactccac actacgctaa gcaaatcttg caaatcaacg aacacgcttt caactgtaga    300

aacgaatcta ctgctatcaa gagattgact tacgaagctt ctttggcttt cgctccatac    360

ggtgaatact ggagattcat caagaagttg tctatgaacg aattgttggg ttctagatct    420

atctcttctt tccaacactt gagattgcaa gaaactcaca acttgttgaa gttgttcgct    480

gacaaggcta agaactacga agctgttaac gttactcaag aattgttgaa gttgtctaac    540

aacgttatct ctaagatgat gttgggtgaa gctgaagaag ctagagatgt tgttagagat    600

gttactgaaa tcttcggtga attcaacgtt tctgacttca tctggttgtt caagaagttg    660

gacttgcaag gtttcggtaa gagaatcgaa gatttgttca tgagattcga cactttggtt    720

gaaagaatca tctctaagag agaagaattg agaaagaaca agggtagaaa ggaaaacaag    780

ggtgaacaag gtgctgaatt cagagacttc ttggacatct tgttggactg tgctgaagat    840

caaaactctg aaatcaaggt tcaaagagtt cacatcaagg ctttgatcat ggacttcttc    900

actgctggta ctgacactac ttctatctct actgaatggg ctttggttga attgatgaac    960

aacccatctt tgttgcaaaa ggctagagaa gaaatcgaca acgttgttgg taagaacaga   1020

ttggttgacg aatctgacgg tccaaacttg ccatacatcc aagctatcat caaggaaact   1080

ttcagattgc acccaccagt tccaatggtt actagaagat gtgttactca atgtaagatc   1140

gaaaactacg ttatcccaga aaactctttg atcttcgtta acaactgggc tatgggtaga   1200

aactctgctt actgggacaa gccattggaa ttcaacccag aaagattctt gaagaactct   1260

actaactcta acggtgttat cgacgttaga ggtcaaaact tccaaatctt gccattcggt   1320
```

```
tctggtagaa gaatgtgtcc aggtgttact ttggctatgc aagaagttcc agctttgttg   1380

ggtgctatca tccaatgttt cgacttcaac ttcgttggtc caaagggtga aatcttgaag   1440

ggtggtgaca tcgttatcga cgttaacgaa agaccaggtt tgactgctcc aagagttcac   1500

gacttggttt gtgttccagt tgaaagattc gcttgtggtg gtccattgca atctttgggt   1560

tgttaa                                                              1566


<210> SEQ ID NO 141
<211> LENGTH: 366
<212> TYPE: PRT
<213> ORGANISM: Cuminum cyminum

<400> SEQUENCE: 141

Met Ser Ala Pro Thr Thr Ile Thr Ala Leu Ala Gln Glu Lys Thr Leu
1               5                   10                  15

Asn Ser Asp Phe Val Arg Asp Glu Asp Glu Arg Pro Lys Val Ala Tyr
            20                  25                  30

Asn Gln Phe Ser Thr Glu Ile Pro Ile Ile Ser Leu Ala Gly Ile Asp
        35                  40                  45

Asp Asp Ser Lys Gly Arg Arg Pro Glu Val Cys Arg Lys Ile Val Glu
    50                  55                  60

Ala Phe Glu Asp Trp Gly Ile Phe Gln Val Val Asp His Gly Val Asp
65                  70                  75                  80

Ser Ala Leu Ile Ser Glu Met Ser Arg Leu Ser Arg Glu Phe Phe Ala
                85                  90                  95

Leu Pro Ala Glu Glu Lys Leu Arg Tyr Asp Thr Thr Gly Gly Lys Arg
            100                 105                 110

Gly Gly Phe Thr Ile Ser Thr His Gln Gln Gly Asp Asp Val Arg Asp
        115                 120                 125

Trp Arg Glu Phe Val Thr Tyr Phe Ser Tyr Pro Val Asp Ala Arg Asp
    130                 135                 140

Tyr Ser Arg Trp Pro Glu Lys Pro Glu Gly Trp Arg Ser Val Thr Glu
145                 150                 155                 160

Val Tyr Ser Glu Lys Leu Met Val Leu Gly Ala Lys Leu Leu Glu Val
                165                 170                 175

Leu Ser Glu Ala Met Gly Leu Asp Lys Gly Ala Leu Thr Lys Ala Cys
            180                 185                 190

Val Asn Met Glu Gln Lys Val Leu Ile Asn Tyr Tyr Pro Thr Cys Pro
        195                 200                 205

Glu Pro Asp Leu Thr Leu Gly Val Arg Arg His Thr Asp Pro Gly Thr
    210                 215                 220

Ile Thr Ile Leu Leu Gln Asp Met Val Gly Gly Leu Gln Ala Thr Arg
225                 230                 235                 240

Asp Gly Gly Lys Thr Trp Ile Thr Val Gln Pro Val Glu Gly Val Phe
                245                 250                 255

Val Val Asn Leu Gly Asp His Gly His Tyr Leu Ser Asn Gly Arg Phe
            260                 265                 270

Lys Asn Ala Asp His Gln Ala Val Val Asn Ser Thr Ser Ser Arg Leu
        275                 280                 285

Ser Ile Ala Thr Phe Gln Asn Pro Ala Gln Asn Ala Ile Val Tyr Pro
    290                 295                 300

Leu Lys Ile Arg Glu Gly Glu Lys Pro Ile Leu Glu Glu Ala Ile Thr
305                 310                 315                 320
```

```
Tyr Ala Glu Met Tyr Lys Lys Asn Met Thr Lys His Ile Glu Val Ala
                325                 330                 335

Thr Gln Lys Lys Leu Ala Lys Glu Lys Arg Leu Gln Glu Glu Lys Ala
            340                 345                 350

Lys Leu Glu Thr Lys Thr Lys Ser Ala Asp Gly Ile Leu Ala
        355                 360                 365


<210> SEQ ID NO 142
<211> LENGTH: 1101
<212> TYPE: DNA
<213> ORGANISM: artificial
<220> FEATURE:
<223> OTHER INFORMATION: coding sequence for SEQ ID NO: 141

<400> SEQUENCE: 142

atgtccgctc caactactat cactgctttg gctcaagaaa agactttgaa ctctgacttc     60

gttagagatg aagatgaaag accaaaggtt gcttacaacc aattctctac tgaaatccca    120

atcatctctt tggctggtat cgacgacgac tctaagggta ggaggccaga agtttgtaga    180

aagatcgttg aagctttcga agattggggt atcttccaag ttgttgacca cggtgttgac    240

tctgctttga tctctgaaat gtctagattg tctagagaat tcttcgcttt gccagctgaa    300

gaaaagttga gatacgacac tactggtggt aagagaggtg gtttcactat ctctactcac    360

caacaaggtg acgacgttag agactggaga gaattcgtta cttacttctc ttacccagtt    420

gacgctagag actactctag atggccagaa aagccagaag gttggagatc tgttactgaa    480

gtttactctg aaaagttgat ggttttgggt gctaagttgt tggaagtttt gtctgaagct    540

atgggtttgg acaagggtgc tttgactaag gcttgtgtta acatggaaca aaaggttttg    600

atcaactact acccaacttg tccagaacca gacttgactt tgggtgttag gagacacact    660

gacccaggta ctatcactat cttgttgcaa gacatggttg gtggtttgca agctactagg    720

gacggtggta agacttggat cactgttcaa ccagttgaag gtgttttcgt tgttaacttg    780

ggtgaccacg gtcactactt gtctaacggt agattcaaga acgctgacca ccaagctgtt    840

gttaactcta cttcttctag attgtctatc gctactttcc aaaacccagc tcaaaacgct    900

atcgtttacc cattgaagat cagagaaggt gaaaagccaa tcttggaaga agctatcact    960

tacgctgaaa tgtacaagaa gaacatgact aagcacatcg aagttgctac tcaaaagaag   1020

ttggctaagg aaaagagatt gcaagaagaa aaggctaagt tggaaactaa gactaagtct   1080

gctgacggta tcttggctta a                                              1101


<210> SEQ ID NO 143
<211> LENGTH: 356
<212> TYPE: PRT
<213> ORGANISM: Aethusa cynapium

<400> SEQUENCE: 143

Met Ser Ala Pro Thr Thr Ile Thr Ala Leu Ser Gln Glu Lys Ser Leu
1               5                   10                  15

Asn Leu Asp Phe Val Arg Asp Glu Asp Glu Arg Pro Lys Val Ala Tyr
            20                  25                  30

Asn Gln Phe Ser Asn Glu Ile Pro Ile Ile Ser Leu Ala Gly Met Asp
        35                  40                  45

Asp Asp Ser Asn Gly Arg Arg Pro Glu Ile Cys Arg Lys Ile Val Glu
    50                  55                  60

Ala Phe Glu Asp Trp Gly Ile Phe Gln Val Val Asp His Gly Ile Asp
65                  70                  75                  80
```

```
Lys Gly Leu Ile Ser Gln Met Ser Arg Leu Ser Arg Glu Phe Phe Ala
                85                  90                  95

Leu Pro Ala Glu Glu Lys Leu Arg Tyr Asp Thr Thr Gly Gly Lys Arg
            100                 105                 110

Gly Gly Phe Thr Ile Ser Thr His Leu Gln Gly Asp Asp Val Lys Asp
        115                 120                 125

Trp Arg Glu Phe Val Thr Tyr Phe Ser Tyr Pro Ile Glu Asp Arg Asp
    130                 135                 140

Tyr Ser Arg Trp Pro Glu Lys Pro Glu Gly Trp Arg Ser Thr Thr Glu
145                 150                 155                 160

Val Tyr Ser Glu Lys Leu Met Val Leu Gly Ala Lys Leu Leu Glu Val
                165                 170                 175

Leu Ser Glu Ala Met Gly Leu Glu Lys Glu Ala Leu Thr Lys Ala Cys
            180                 185                 190

Val Asn Met Glu Gln Lys Val Leu Ile Asn Tyr Tyr Pro Thr Cys Pro
        195                 200                 205

Glu Pro Asp Leu Thr Leu Gly Val Arg Arg His Thr Asp Pro Gly Thr
    210                 215                 220

Ile Thr Ile Leu Leu Gln Asp Met Val Gly Gly Leu Gln Ala Thr Arg
225                 230                 235                 240

Asp Gly Gly Lys Thr Trp Ile Thr Val Gln Pro Val Glu Gly Ala Phe
                245                 250                 255

Val Val Asn Leu Gly Asp His Gly His Tyr Leu Ser Asn Gly Arg Phe
            260                 265                 270

Lys Asn Ala Asp His Gln Ala Val Val Asn Ser Thr Ser Ser Arg Leu
        275                 280                 285

Ser Ile Ala Thr Phe Gln Asn Pro Ala Gln Asn Ala Ile Val Tyr Pro
    290                 295                 300

Leu Lys Ile Arg Glu Gly Glu Lys Ala Ile Leu Asp Glu Ala Ile Thr
305                 310                 315                 320

Tyr Ala Glu Met Tyr Lys Lys Asn Met Thr Lys His Ile Glu Val Ala
                325                 330                 335

Ala Leu Lys Lys Leu Ala Lys Glu Lys Arg Leu Gln Asp Glu Lys Ala
            340                 345                 350

Lys Leu Glu Met
        355
```

<210> SEQ ID NO 144
<211> LENGTH: 1071
<212> TYPE: DNA
<213> ORGANISM: artificial
<220> FEATURE:
<223> OTHER INFORMATION: coding sequence for SEQ ID NO: 143

<400> SEQUENCE: 144

```
atgtccgctc caactactat cactgctttg tctcaagaaa agtctttgaa cttggacttc      60

gttagagatg aagatgaaag accaaaggtt gcttacaacc aattctctaa cgaaatccca     120

atcatctctt tggctggtat ggacgacgac tctaacggta ggaggccaga aatctgtaga     180

aagatcgttg aagctttcga agattggggt atcttccaag ttgttgacca cggtatcgac     240

aagggtttga tctctcaaat gtctagattg tctagagaat tcttcgcttt gccagctgaa     300

gaaaagttga gatacgacac tactggtggt aagagaggtg gtttcactat ctctactcac     360

ttgcaaggtg acgacgttaa ggactggaga gaattcgtta cttacttctc ttacccaatc     420
```

```
gaagatagag actactctag atggccagaa aagccagaag gttggagatc tactactgaa    480
gtttactctg aaaagttgat ggttttgggt gctaagttgt tggaagtttt gtctgaagct    540
atgggtttgg aaaaggaagc tttgactaag gcttgtgtta acatggaaca aaaggttttg    600
atcaactact acccaacttg tccagaacca gacttgactt tgggtgttag gagacacact    660
gacccaggta ctatcactat cttgttgcaa gacatggttg gtggtttgca agctactagg    720
gacggtggta agacttggat cactgttcaa ccagttgaag gtgctttcgt tgttaacttg    780
ggtgaccacg gtcactactt gtctaacggt agattcaaga acgctgacca ccaagctgtt    840
gttaactcta cttcttctag attgtctatc gctactttcc aaaacccagc tcaaaacgct    900
atcgtttacc cattgaagat cagagaaggt gaaaaggcta tcttggacga agctatcact    960
tacgctgaaa tgtacaagaa gaacatgact aagcacatcg aagttgctgc tttgaagaag   1020
ttggctaagg aaaagagatt gcaagacgaa aaggctaagt tggaaatgta a            1071
```

<210> SEQ ID NO 145
<211> LENGTH: 366
<212> TYPE: PRT
<213> ORGANISM: Conium maculatum

<400> SEQUENCE: 145

```
Met Ser Ala Pro Thr Thr Ile Thr Ala Leu Ala Gln Glu Lys Thr Leu
1               5                   10                  15

Asn Leu Ala Phe Val Arg Asp Glu Asp Glu Arg Pro Lys Val Ala Tyr
            20                  25                  30

Asn Glu Phe Ser Asn Glu Ile Pro Ile Ile Ser Leu Ala Gly Leu Glu
        35                  40                  45

Asn Asp Ser Asp Gly Arg Arg Pro Glu Ile Cys Arg Lys Ile Val Glu
    50                  55                  60

Ala Phe Glu Asn Trp Gly Ile Phe Gln Val Val Asp His Gly Ile Asp
65                  70                  75                  80

Ser Ala Leu Ile Ser Glu Met Ser Arg Leu Ser Arg Glu Phe Phe Ala
                85                  90                  95

Leu Pro Ala Glu Glu Lys Leu Arg Tyr Asp Thr Thr Gly Gly Lys Arg
            100                 105                 110

Gly Gly Phe Thr Ile Ser Thr His Leu Gln Gly Asp Asp Val Arg Asp
        115                 120                 125

Trp Arg Glu Phe Val Thr Tyr Phe Ser Tyr Pro Ile Asp Ala Arg Asp
    130                 135                 140

Tyr Ser Arg Trp Pro Asp Lys Pro Glu Gly Trp Arg Ser Ile Thr Glu
145                 150                 155                 160

Val Tyr Ser Glu Arg Leu Met Val Leu Gly Ala Lys Leu Leu Glu Val
                165                 170                 175

Leu Ser Glu Ala Met Gly Leu Glu Lys Glu Ala Leu Thr Lys Ala Cys
            180                 185                 190

Val Asn Met Glu Gln Lys Val Leu Ile Asn Tyr Tyr Pro Thr Cys Pro
        195                 200                 205

Glu Pro Asp Leu Thr Leu Gly Val Arg Arg His Thr Asp Pro Gly Thr
    210                 215                 220

Ile Thr Val Leu Leu Gln Asp Met Val Gly Gly Leu Gln Ala Thr Arg
225                 230                 235                 240

Asp Gly Gly Lys Thr Trp Ile Thr Val Gln Pro Val Glu Gly Ala Phe
                245                 250                 255

Val Val Asn Leu Gly Asp His Gly His Tyr Leu Ser Asn Gly Arg Phe
```

-continued

```
            260                 265                 270

Lys Asn Ala Asp His Gln Ala Val Val Asn Ser Ser Ser Ser Arg Leu
        275                 280                 285

Ser Ile Ala Thr Phe Gln Asn Pro Ala Gln Asn Ala Ile Val Tyr Pro
    290                 295                 300

Leu Lys Ile Arg Glu Gly Glu Lys Ala Ile Leu Asp Glu Ala Ile Thr
305                 310                 315                 320

Tyr Ala Glu Met Tyr Lys Lys Asn Met Thr Lys His Ile Glu Val Ala
                325                 330                 335

Thr Leu Lys Lys Leu Ala Lys Glu Lys Arg Leu Gln Asp Glu Lys Ala
            340                 345                 350

Asn Met Glu Lys Lys Ser Lys Ser Ala His Gly Ile Ser Ala
        355                 360                 365


<210> SEQ ID NO 146
<211> LENGTH: 1101
<212> TYPE: DNA
<213> ORGANISM: artificial
<220> FEATURE:
<223> OTHER INFORMATION: coding sequence for SEQ ID NO: 145

<400> SEQUENCE: 146

atgtccgctc caactactat cactgctttg gctcaagaaa agactttgaa cttggctttc      60

gttagagatg aagatgaaag accaaaggtt gcttacaacg aattctctaa cgaaatccca     120

atcatctctt tggctggttt ggaaaacgac tctgacggta gaaggccaga aatctgtaga     180

aagatcgttg aagctttcga aaactggggt atcttccaag ttgttgacca cggtatcgac     240

tctgctttga tctctgaaat gtctagattg tctagagaat tcttcgcttt gccagctgaa     300

gaaaagttga gatacgacac tactggtggt aagagaggtg gtttcactat ctctactcac     360

ttgcaaggtg acgacgttag agactggaga gaattcgtta cttacttctc ttacccaatc     420

gacgctagag actactctag atggccagac aagccagaag gttggagatc tatcactgaa     480

gtttactctg aaagattgat ggttttgggt gctaagttgt tggaagtttt gtctgaagct     540

atgggtttgg aaaaggaagc tttgactaag gcttgtgtta acatggaaca aaaggttttg     600

atcaactact acccaacttg tccagaacca gacttgactt tgggtgttag aaggcacact     660

gacccaggta ctatcactgt tttgttgcaa gacatggttg gtggtttgca agctactaga     720

gatggtggta agacttggat cactgttcaa ccagttgaag gtgctttcgt tgttaacttg     780

ggtgaccacg gtcactactt gtctaacggt agattcaaga acgctgacca ccaagctgtt     840

gttaactctt cttcttctag attgtctatc gctactttcc aaaacccagc tcaaaacgct     900

atcgtttacc cattgaagat cagagaaggt gaaaaggcta tcttggacga agctatcact     960

tacgctgaaa tgtacaagaa gaacatgact aagcacatcg aagttgctac tttgaagaag    1020

ttggctaagg aaaagagatt gcaagacgaa aaggctaaca tggaaaagaa gtctaagtct    1080

gctcacggta tctctgctta a                                              1101


<210> SEQ ID NO 147
<211> LENGTH: 535
<212> TYPE: PRT
<213> ORGANISM: Camellia sinensis

<400> SEQUENCE: 147

Met Ser Phe Asp Leu Ile Ser Ile Ala Thr Leu Phe Phe Val Ile Ile
1               5                   10                  15
```

-continued

```
Ser Thr Thr Ile Leu Leu Leu Ser Ile Asn His Phe Lys Lys Pro Pro
            20                  25                  30

His Leu Arg Arg Arg Leu Ser Leu Pro Pro Thr Pro Phe Ala Leu Pro
        35                  40                  45

Ile Ile Gly His Leu His Leu Leu Gly Pro Ile Ile His Arg Ser Phe
    50                  55                  60

His Asp Leu Ser Ser Arg Tyr Gly Pro Leu Phe His Leu Arg Leu Gly
65                  70                  75                  80

Ser Val Pro Cys Phe Val Val Ser Thr Pro Glu Leu Ala Lys Glu Phe
                85                  90                  95

Leu Leu Thr His Glu Leu Lys Phe Ser Ser Arg Arg Asp Ser Ile Ala
            100                 105                 110

Ile Gln Arg Leu Thr Tyr Asp Ser Ala Phe Ala Phe Ala Pro Tyr Gly
        115                 120                 125

Pro Tyr Trp Lys Phe Leu Lys Lys Leu Cys Thr Cys Asp Leu Leu Gly
    130                 135                 140

Ala Arg Ser Ile Asn His Phe Leu Pro Thr Arg Thr Arg Glu Leu His
145                 150                 155                 160

Cys Phe Val Arg Leu Leu Ile Asp Lys Ala Val Ala Cys Glu Pro Val
                165                 170                 175

Asn Ile Thr Lys Glu Leu Ser Thr Leu Ala Asn Asn Ile Ile Ser Gln
            180                 185                 190

Met Met Ile Gly Val Arg Cys Ser Gly Thr Thr Gly Glu Ala Glu Glu
        195                 200                 205

Ala Thr Thr Leu Ala Arg Glu Val Thr Lys Ile Phe Gly Glu Phe Asn
    210                 215                 220

Val Ser Asp Phe Met Trp Val Ile Arg Asn Phe Asp Leu Gln Gly Phe
225                 230                 235                 240

Arg Lys Arg Val Glu Asp Ile Tyr Thr Arg Tyr Asp Ala Leu Leu Glu
                245                 250                 255

Arg Ile Ile Thr Asn Arg Glu Glu Val Arg Glu Lys Asn Val Gln Glu
            260                 265                 270

Arg Lys Leu Gly Val Gly Glu Gly His His Val Lys Asp Phe Leu Asp
        275                 280                 285

Leu Leu Leu Asp Val Leu Glu Glu Asp His Ser Glu Ile Asn Phe Ser
    290                 295                 300

Arg Asp Asn Ile Lys Gly Leu Ile Leu Asp Phe Phe Thr Ala Gly Thr
305                 310                 315                 320

Asp Thr Ser Ser Ile Ala Ile Glu Trp Ala Leu Ala Glu Leu Ile Asn
                325                 330                 335

Asn Pro Arg Val Leu Gln Lys Ala Gln Glu Glu Ile Asp Asn Val Val
            340                 345                 350

Gly Lys His Arg Leu Val Ser Glu Ser Asp Gly Pro Asn Leu Pro Tyr
        355                 360                 365

Ile Gln Ala Ile Ile Arg Glu Ala Leu Arg Leu His Pro Pro Val Pro
    370                 375                 380

Leu Ile Thr Arg Lys Ser Ile Glu Asp Cys Met Ile Gln Gly Tyr Asn
385                 390                 395                 400

Ile Pro Ala Asn Ser Met Leu Phe Val Asn Val Trp Ser Leu Ala Arg
                405                 410                 415

Asn Pro Lys Tyr Trp Asp Ser Pro Leu Asp Phe Leu Pro Glu Arg Phe
            420                 425                 430

Leu Arg Pro Glu Lys Gly Gly Pro Val Gly Pro Thr Asp Val Lys Gly
```

-continued

```
        435                 440                 445

Gln His Phe Gln Leu Leu Pro Phe Gly Thr Gly Arg Arg Gly Cys Pro
    450                 455                 460

Gly Thr Ser Leu Ala Met Gln Glu Leu Pro Ala Met Leu Ala Ala Met
465                 470                 475                 480

Ile Gln Cys Phe Glu Trp Lys Val Val Asn Gln Ser Gly Asp Val Met
                485                 490                 495

Asn Gly Asp Gly Ala Leu Asp Met Thr Glu Gln Pro Gly Met Thr Ala
            500                 505                 510

Pro Arg Ala His Asp Leu Val Cys Met Pro Ile Pro Arg Ile Asp Gln
        515                 520                 525

Leu Tyr Ala Leu Leu Asp Pro
    530                 535


<210> SEQ ID NO 148
<211> LENGTH: 1608
<212> TYPE: DNA
<213> ORGANISM: artificial
<220> FEATURE:
<223> OTHER INFORMATION: coding sequence for SEQ ID NO:147

<400> SEQUENCE: 148

atgtccttcg acttgatctc tatcgctact ttgttcttcg ttatcatctc tactactatc     60

ttgttgttgt ctatcaacca cttcaagaag ccaccacact tgagaagaag attgtctttg    120

ccaccaactc cattcgcttt gccaatcatc ggtcacttgc acttgttggg tccaatcatc    180

cacagatctt tccacgactt gtcatctaga tacggtccat tgttccactt gagattgggt    240

tctgttccat gtttcgttgt ttctactcca gaattggcta aggaattctt gttgactcac    300

gaattgaagt tctcttctag aagagactct atcgctatcc aaagattgac ttacgactct    360

gctttcgctt tcgctccata cggtccatac tggaagttct tgaagaagtt gtgtacttgt    420

gacttgttgg gtgctagatc tatcaaccac ttcttgccaa ctagaactag agaattgcac    480

tgtttcgtta gattgttgat cgacaaggct gttgcttgtg aaccagttaa catcactaag    540

gaattgtcta ctttggctaa caacatcatc tctcaaatga tgatcggtgt tagatgttct    600

ggtactactg gtgaagctga agaagctact actttggcta gagaagttac taagatcttc    660

ggtgaattca acgtttctga cttcatgtgg gttatcagaa acttcgactt gcaaggtttc    720

agaaagagag ttgaagatat ctacactaga tacgacgctt tgttggaaag aatcatcact    780

aacagagaag aagttagaga aaagaacgtt caagaaagaa agttgggtgt tggtgaaggt    840

caccacgtta aggacttctt ggacttgttg ttggacgttt tggaagaaga tcactctgaa    900

atcaacttct ctagagacaa catcaagggt ttgatcttgg acttcttcac tgctggtact    960

gacacttctt ctatcgctat cgaatgggct ttggctgaat tgatcaacaa cccaagagtt   1020

ttgcaaaagg ctcaagaaga aatcgacaac gttgttggta agcacagatt ggtttctgaa   1080

tctgacggtc caaacttgcc atacatccaa gctatcatca gagaagcttt gagattgcac   1140

ccaccagttc cattgatcac tagaaagtct atcgaagatt gtatgatcca aggttacaac   1200

atcccagcta actctatgtt gttcgttaac gtttggtctt tggctagaaa cccaaagtac   1260

tgggactctc cattggactt cttgccagaa agattcttga ggccagaaaa gggtggtcca   1320

gttggtccaa ctgacgttaa gggtcaacac ttccaattgt tgccattcgg tactggtaga   1380

agaggttgtc caggtacttc tttggctatg caagaattgc cagctatgtt ggctgctatg   1440

atccaatgtt tcgaatggaa ggttgttaac caatctggtg acgttatgaa cggtgacggt   1500
```

gctttggaca tgactgaaca accaggtatg actgctccaa gagctcacga cttggtttgt 1560
atgccaatcc caagaatcga ccaattgtac gctttgttgg acccataa 1608

<210> SEQ ID NO 149
<211> LENGTH: 517
<212> TYPE: PRT
<213> ORGANISM: Saussurea medusa

<400> SEQUENCE: 149

Met Ser Gln Val Leu Gln Thr Leu Thr Pro Ala Val Ile Ala Ala Val
1 5 10 15

Leu Leu Ser Ser Leu Phe Leu Tyr Leu Leu Ile Lys Lys Asn Gln Asn
20 25 30

His Arg Leu Pro Pro Ser Pro Pro Ser Leu Pro Ile Ile Gly His Leu
35 40 45

His His Leu Gly Pro Leu Ile His Gln Ser Phe His His Leu Ser Thr
50 55 60

Lys Tyr Gly Pro Leu Ile His Leu Arg Leu Gly Ser Val Thr Cys Val
65 70 75 80

Val Ala Ser Thr Pro Asp Leu Ala Arg Asp Phe Leu Lys Thr Asn Glu
85 90 95

Leu Ala Phe Ser Ser Arg Lys His Ser Leu Ala Ile Asp His Ile Thr
100 105 110

Tyr Gly Val Ala Phe Ala Phe Ala Pro Tyr Gly Pro Tyr Trp Lys Phe
115 120 125

Ile Lys Lys Met Ser Thr Val Glu Leu Leu Gly Asn Gln Asn Leu Gly
130 135 140

His Phe Leu Pro Ile Arg Thr Gln Glu Ile His Glu Leu Leu His Thr
145 150 155 160

Leu Met Asn Lys Ala Lys Lys Arg Glu Ser Val Asn Leu Thr Glu Glu
165 170 175

Leu Leu Lys Leu Thr Asn Asn Val Ile Cys Gln Met Met Met Ser Ile
180 185 190

Arg Cys Ser Gly Thr Asn Ser Glu Ala Asp Glu Ala Lys Asn Leu Val
195 200 205

Arg Glu Val Thr Gln Ile Phe Gly Glu Phe Asn Val Ser Asp Phe Ile
210 215 220

Trp Phe Cys Lys Asn Ile Asp Leu Gln Gly Phe Lys Lys Arg Tyr Glu
225 230 235 240

Asp Thr His Arg Arg Tyr Asp Val Leu Leu Glu Lys Ile Ile Leu Glu
245 250 255

Arg Glu Glu Glu Arg Arg Lys Glu Gly Lys Arg Glu Asp Gly Asn Lys
260 265 270

Gly Lys Asp Phe Leu Asp Met Leu Leu Asp Val Leu Glu Asp Gly Lys
275 280 285

Ala Glu Ile Gln Ile Thr Arg Asp His Ile Lys Ala Leu Ile Leu Asp
290 295 300

Phe Phe Thr Ala Ala Thr Asp Thr Thr Ala Ile Ala Leu Glu Trp Met
305 310 315 320

Leu Val Glu Leu Ile Arg Asn Pro Lys Val Leu Glu Ile Ala Arg Glu
325 330 335

Glu Ile Asp His Ile Ile Gly Asn Glu Arg Leu Val Gln Glu Ser Asp
340 345 350

```
Ile Pro Asn Leu Pro Tyr Ile Gln Ala Ile Ile Lys Glu Thr Leu Arg
        355                 360                 365

Leu His Pro Pro Ile Pro Met Leu Ile Arg Lys Ser Ile Glu Asn Val
    370                 375                 380

Ser Val Gln Gly Tyr Asp Ile Pro Ala Gly Thr Met Leu Phe Val Asn
385                 390                 395                 400

Ile Trp Ser Ile Gly Arg Asn Pro Lys Tyr Trp Glu Ser Pro Leu Glu
                405                 410                 415

Phe Lys Pro His Arg Phe Leu Glu Glu Asp Asn Ala Leu Lys Ser Ser
            420                 425                 430

Phe Asp Ile Lys Gly Gln Asn Phe Gln Leu Leu Pro Phe Gly Thr Gly
        435                 440                 445

Arg Arg Gly Cys Pro Gly Ile Asn Leu Ala Met Lys Glu Leu Pro Val
    450                 455                 460

Val Ile Ala Gly Leu Ile Gln Cys Phe Glu Trp Asn Ile Asn Glu Lys
465                 470                 475                 480

Gln Val Leu Asp Met Asp Glu Arg Ala Gly Leu Thr Ala Pro Arg Ala
                485                 490                 495

Ala Asp Phe Val Cys Val Pro Ser Ile Arg Glu Asp Ser Pro Lys Ser
            500                 505                 510

Phe Ile Thr Ser Thr
        515


<210> SEQ ID NO 150
<211> LENGTH: 1554
<212> TYPE: DNA
<213> ORGANISM: artificial
<220> FEATURE:
<223> OTHER INFORMATION: coding sequence for SEQ ID NO: 149

<400> SEQUENCE: 150

atgtcccaag ttttgcaaac tttgactcca gctgttatcg ctgctgtttt gttgtcatct     60

ttgttcttgt acttgttgat caagaagaac caaaaccaca gattgccacc atctccacca    120

tctttgccaa tcatcggtca cttgcaccac ttgggtccat tgatccacca atctttccac    180

cacttgtcta ctaagtacgg tccattgatc cacttgagat tgggttctgt tacttgtgtt    240

gttgcttcta ctccagactt ggctagagac ttcttgaaaa ctaacgaatt ggctttctct    300

tctagaaagc actctttggc tatcgaccac atcacttacg gtgttgcttt cgctttcgct    360

ccatacggtc catactggaa gttcatcaag aagatgtcta ctgttgaatt gttgggtaac    420

caaaacttgg gtcacttctt gccaatcaga actcaagaaa tccacgaatt gttgcacact    480

ttgatgaaca aggctaagaa gagagaatct gttaacttga ctgaagaatt gttgaagttg    540

actaacaacg ttatctgtca aatgatgatg tctatcagat gttctggtac taactctgaa    600

gctgacgaag ctaagaactt ggttagagaa gttactcaaa tcttcggtga attcaacgtt    660

tctgacttca tctggttctg taagaacatc gacttgcaag gtttcaagaa gagatacgaa    720

gatactcaca gaagatacga cgttttgttg gaaaagatca tcttggaaag agaagaagaa    780

agaagaaagg aaggtaagag agaagatggt aacaagggta aggacttctt ggacatgttg    840

ttggacgttt tggaagatgg taaggctgaa atccaaatca ctagagatca catcaaggct    900

ttgatcttgg acttcttcac tgctgctact gacactactg ctatcgcttt ggaatggatg    960

ttggttgaat tgatcagaaa cccaaaggtt ttggaaatcg ctagagaaga aatcgaccac   1020

atcatcggta acgaaagatt ggttcaagaa tctgacatcc caaacttgcc atacatccaa   1080
```

```
gctatcatca aggaaacttt gagattgcac ccaccaatcc caatgttgat cagaaagtct   1140

atcgaaaacg tttctgttca aggttacgac atcccagctg gtactatgtt gttcgttaac   1200

atctggtcta tcggtagaaa cccaaagtac tgggaatctc cattggaatt caagccacac   1260

agattcttgg aagaagataa cgctttgaag tcatctttcg acatcaaggg tcaaaacttc   1320

caattgttgc cattcggtac tggtagaaga ggttgtccag gtatcaactt ggctatgaag   1380

gaattgccag ttgttatcgc tggtttgatc caatgtttcg aatggaacat caacgaaaag   1440

caagttttgg acatggacga aagagctggt ttgactgctc caagagctgc tgacttcgtt   1500

tgtgttccat ctatcagaga agattctcca aagtctttca tcacttctac ttaa         1554


<210> SEQ ID NO 151
<211> LENGTH: 510
<212> TYPE: PRT
<213> ORGANISM: Plectranthus barbatus

<400> SEQUENCE: 151

Met Ser Asp His Val Glu Ala Ala Leu Phe Ala Ala Ile Phe Leu Leu
1               5                   10                  15

Ser Ala Ala Leu Leu Asn His Leu Leu Thr Gly Lys Arg Arg Gln Asn
            20                  25                  30

Ala Tyr Pro Pro Gly Pro Phe Pro Leu Pro Ile Ile Gly His Leu His
        35                  40                  45

Leu Leu Gly Pro Arg Leu His His Thr Phe His Asp Leu Thr Gln Arg
    50                  55                  60

Tyr Gly Pro Leu Met Gln Val Arg Leu Gly Ser Ile Arg Cys Val Ile
65                  70                  75                  80

Ala Ala Thr Pro Glu Leu Ala Lys Glu Phe Leu Lys Thr Ser Glu Leu
                85                  90                  95

Val Phe Ser Ala Arg Lys His Ser Thr Ala Ile Asp Ile Val Thr Tyr
            100                 105                 110

Glu Ser Ser Phe Ala Phe Ser Pro Tyr Gly Pro Tyr Trp Lys Tyr Ile
        115                 120                 125

Lys Lys Leu Cys Thr Tyr Glu Leu Leu Gly Ala Arg Asn Leu Asn His
    130                 135                 140

Phe Leu Pro Ile Arg Thr Ile Glu Val Lys Thr Phe Leu Glu Ala Leu
145                 150                 155                 160

Met Gln Lys Gly Lys Thr Gly Glu Arg Leu Asn Val Thr Glu Glu Leu
                165                 170                 175

Val Lys Leu Thr Ser Asn Val Ile Ser Gln Met Met Leu Ser Ile Arg
            180                 185                 190

Cys Ser Gly Thr Glu Gly Glu Thr Glu Ala Val Arg Thr Val Ile Arg
        195                 200                 205

Glu Val Thr Gln Ile Phe Gly Glu Phe Asp Val Ala Asp Ile Ile Trp
    210                 215                 220

Phe Cys Lys Asn Phe Asp Phe Gln Gly Ile Arg Lys Arg Ser Glu Asp
225                 230                 235                 240

Ile Gln Arg Arg Tyr Asp Ala Leu Leu Glu Lys Ile Ile Thr Asp Arg
                245                 250                 255

Glu Lys Gln Arg Arg Thr Gln His Gly Gly Glu Ala Lys Asp Phe Leu
            260                 265                 270

Asp Met Phe Leu Asp Ile Met Lys Ser Gly Lys Ala Glu Val Asn Phe
        275                 280                 285

Thr Arg Asp His Leu Lys Ala Leu Ile Leu Asp Phe Phe Thr Ala Gly
```

```
    290                 295                 300

Thr Asp Thr Thr Ala Ile Val Val Gly Trp Ala Ile Ala Glu Leu Ile
305                 310                 315                 320

Asn Asn Pro Asn Val Leu Lys Lys Ala Gln Ala Glu Ile Asp Lys Val
                325                 330                 335

Val Gly Leu His Arg Ile Leu Gln Glu Ser Asp Gly Pro Asn Leu Pro
            340                 345                 350

Tyr Leu Asn Ala Val Ile Lys Glu Thr Phe Arg Leu His Pro Pro Ile
        355                 360                 365

Pro Met Leu Ser Arg Lys Ser Ile Ser Asp Cys Val Ile Asp Gly Tyr
    370                 375                 380

Thr Ile Pro Ala Asn Thr Leu Leu Phe Val Asn Ile Trp Ser Met Gly
385                 390                 395                 400

Arg Asn Pro Lys Ile Trp Asp Asn Pro Met Ala Phe Arg Pro Glu Arg
                405                 410                 415

Phe Leu Glu Lys Glu Lys Thr Gly Ile Asp Ile Lys Gly Gln His Phe
            420                 425                 430

Glu Leu Leu Pro Phe Gly Thr Gly Arg Arg Gly Cys Pro Gly Met Leu
        435                 440                 445

Leu Ala Ile Arg Glu Val Val Val Ile Ile Gly Thr Val Ile Gln Cys
    450                 455                 460

Phe Asp Trp Lys Leu Pro Val Asp Asp Val Ser Gly Leu Val Asp Met
465                 470                 475                 480

Thr Glu Arg Pro Gly Leu Thr Ala Pro Arg Ala Asp Asp Leu Ile Cys
                485                 490                 495

Arg Val Val Pro Arg Val Asp Pro Leu Val Val Ser Gly His
            500                 505                 510


<210> SEQ ID NO 152
<211> LENGTH: 1533
<212> TYPE: DNA
<213> ORGANISM: artificial
<220> FEATURE:
<223> OTHER INFORMATION: coding sequence for SEQ ID NO: 151

<400> SEQUENCE: 152

atgtccgacc acgttgaagc tgctttgttc gctgctatct tcttgttgtc tgctgctttg      60

ttgaaccact tgttgactgg taagagaagg caaaacgctt acccaccagg tccattccca     120

ttgccaatca tcggtcactt gcacttgttg ggtccaagat tgcaccacac tttccacgac     180

ttgactcaaa gatacggtcc attgatgcaa gttagattgg gttctatcag atgtgttatc     240

gctgctactc cagaattggc taaggaattc ttgaaaactt ctgaattggt tttctctgct     300

agaaagcact ctactgctat cgacatcgtt acttacgaat cttctttcgc tttctctcca     360

tacggtccat actggaagta catcaagaag ttgtgtactt acgaattgtt gggtgctaga     420

aacttgaacc acttcttgcc aatcagaact atcgaagtta agactttctt ggaagctttg     480

atgcaaaagg gtaagactgg tgaaagattg aacgttactg aagaattggt taagttgact     540

tctaacgtta tctctcaaat gatgttgtct atcagatgtt ctggtactga aggtgaaact     600

gaagctgtta gaactgttat cagagaagtt actcaaatct tcggtgaatt cgacgttgct     660

gacatcatct ggttctgtaa gaacttcgac ttccaaggta tcagaaagag atctgaagat     720

atccaaagaa gatacgacgc tttgttggaa aagatcatca ctgacagaga aaagcaaaga     780

agaactcaac acggtggtga agctaaggac ttcttggaca tgttcttgga catcatgaag     840
```

```
tctggtaagg ctgaagttaa cttcactaga gatcacttga aggctttgat cttggacttc    900

ttcactgctg gtactgacac tactgctatc gttgttggtt gggctatcgc tgaattgatc    960

aacaacccaa acgttttgaa gaaggctcaa gctgaaatcg acaaggttgt tggtttgcac   1020

agaatcttgc aagaatctga cggtccaaac ttgccatact tgaacgctgt tatcaaggaa   1080

actttcagat tgcacccacc aatcccaatg ttgtctagaa agtctatctc tgactgtgtt   1140

atcgacggtt acactatccc agctaacact ttgttgttcg ttaacatctg gtctatgggt   1200

agaaacccaa agatctggga caacccaatg gctttcagac cagaaagatt cttggaaaag   1260

gaaaagactg gtatcgacat caagggtcaa cacttcgaat tgttgccatt cggtactggt   1320

agaagaggtt gtccaggtat gttgttggct atcagagaag ttgttgttat catcggtact   1380

gttatccaat gtttcgactg gaagttgcca gttgacgacg tttctggttt ggttgacatg   1440

actgaaagac caggtttgac tgctccaaga gctgacgact tgatctgtag agttgttcca   1500

agagttgacc cattggttgt ttctggtcac taa                                1533
```

<210> SEQ ID NO 153
<211> LENGTH: 506
<212> TYPE: PRT
<213> ORGANISM: Scutellaria baicalensis

<400> SEQUENCE: 153

```
Met Ser Glu Val Thr Leu Asn Val Ala Leu Leu Leu Leu Ser Ala Ala
1               5                   10                  15

Val Cys Leu Met Val Phe Thr Gly Lys Arg Arg Arg Arg Leu Pro Asn
            20                  25                  30

Pro Pro Gly Pro Phe Pro Leu Pro Leu Ile Gly Asn Leu Asn Leu Val
        35                  40                  45

Ser Pro Arg Leu His His Thr Phe His Met Leu Ala Gln Arg Tyr Gly
    50                  55                  60

Pro Ile Met Lys Phe Arg Leu Gly Ser Ile Pro Cys Leu Val Val Ser
65                  70                  75                  80

Thr Pro Glu Leu Ala Lys Asp Ile Leu Lys Thr His Glu Leu Ile Phe
                85                  90                  95

Ser Ser Arg Val Lys Ser Thr Ala Ile Asp Ile Val Thr Tyr Gly Val
            100                 105                 110

Ser Phe Ala Phe Ser Pro Tyr Gly Pro Tyr Trp Lys Tyr Ile Lys Lys
        115                 120                 125

Leu Cys Thr Tyr Glu Leu Leu Gly Ser Arg Met Leu Asn His Phe Glu
    130                 135                 140

Pro Leu Arg Ala Leu Glu Val Arg Glu Phe Leu Lys Asp Val Met Ala
145                 150                 155                 160

Met Gly Lys Ala Gly Lys Ser Phe Asn Val Thr Glu Glu Leu Met Lys
                165                 170                 175

Leu Thr Ser Asn Val Met Ser Asn Met Met Leu Ser Ile Arg Ala Ala
            180                 185                 190

Glu Ser Glu Glu Gln Ala Glu Val Ala Arg Thr Leu Ile Arg Glu Val
        195                 200                 205

Ser Gln Leu Phe Gly Glu Phe Asp Phe Gly Asp Met Leu Trp Phe Cys
    210                 215                 220

Lys Ser Phe Asp Phe Gln Gly Ile Lys Lys Arg Ser Lys Asp Ile Lys
225                 230                 235                 240

Val Arg Tyr Asp Ala Leu Leu Glu Lys Ile Leu Thr Asp Arg Glu Asn
                245                 250                 255
```

Val Arg Arg Gln Asn Gly Val Val Glu Pro Lys Asp Met Leu Asp Met
260 265 270

Phe Leu Asp Ile Met Glu Gly Gly Lys Thr Asp Val Glu Phe Thr Arg
275 280 285

Glu His Leu Lys Ala Val Ile Leu Asp Phe Leu Thr Ala Gly Thr Asp
290 295 300

Thr Thr Ala Ile Thr Val Glu Trp Val Leu Ala Glu Leu Met Asn Ser
305 310 315 320

Pro Lys Ala Met Lys Lys Ala Gln Asp Glu Met Asp Arg Val Val Gly
325 330 335

Arg Glu Arg Met Met Ala Glu Ser Asp Ala Pro Asn Leu Pro Tyr Phe
340 345 350

Leu Ala Ile Ile Lys Glu Thr Phe Arg Leu His Pro Pro Ile Pro Leu
355 360 365

Ile Ile Arg Arg Ser Ile Glu Asp Cys Val Ile Asp Gly Tyr His Ile
370 375 380

Pro Ala Asp Thr Leu Ala Phe Ile Asn Val Trp Ser Met Gly Arg Asn
385 390 395 400

Glu Lys Tyr Trp Asp Ser Pro Leu Ser Phe Arg Pro Glu Arg Phe Leu
405 410 415

Glu Gly Asp Asn Ala Ala Ile Asp Ile Lys Gly Met His Phe Glu Leu
420 425 430

Leu Pro Phe Gly Ser Gly Arg Arg Gly Cys Pro Gly Met Leu Ser Ala
435 440 445

Ile Gln Glu Val Leu Ile Ile Ala Gly Thr Val Ile Gln Cys Phe Asp
450 455 460

Trp Glu Gln Ala Asp Gly Ser Gly Arg Val Asp Met Ser Glu Arg Pro
465 470 475 480

Gly Leu Thr Thr Pro Arg Glu Ile Asp Leu Val Cys Arg Val Val Pro
485 490 495

Arg Val Asp Glu Arg Val Ile Ser Gly His
500 505

<210> SEQ ID NO 154
<211> LENGTH: 1521
<212> TYPE: DNA
<213> ORGANISM: artificial
<220> FEATURE:
<223> OTHER INFORMATION: coding sequence for SEQ ID NO:153

<400> SEQUENCE: 154
atgtccgaag ttactttgaa cgttgctttg ttgttgttgt ctgctgctgt ttgtttgatg 60
gttttcactg gtaagagaag aagaagattg ccaaacccac caggtccatt cccattgcca 120
ttgatcggta acttgaactt ggtttctcca agattgcacc acactttcca catgttggct 180
caaagatacg gtccaatcat gaagttcaga ttgggttcta tcccatgttt ggttgtttct 240
actccagaat tggctaagga catcttgaaa actcacgaat tgatcttctc ttctagagtt 300
aagtctactg ctatcgacat cgttacttac ggtgtttctt tcgctttctc tccatacggt 360
ccatactgga agtacatcaa gaagttgtgt acttacgaat tgttgggttc tagaatgttg 420
aaccacttcg aaccattgag agctttggaa gttagagaat tcttgaagga cgttatggct 480
atgggtaagg ctggtaagtc tttcaacgtt actgaagaat tgatgaagtt gacttctaac 540
gttatgtcta acatgatgtt gtctatcaga gctgctgaat ctgaagaaca agctgaagtt 600

```
gctagaactt tgatcagaga agtttctcaa ttgttcggtg aattcgactt cggtgacatg    660

ttgtggttct gtaagtcttt cgacttccaa ggtatcaaga agagatctaa ggacatcaag    720

gttagatacg acgctttgtt ggaaaagatc ttgactgaca gagaaaacgt taggagacaa    780

aacggtgttg ttgaaccaaa ggacatgttg gacatgttct tggacatcat ggaaggtggt    840

aagactgacg ttgaattcac tagagaacac ttgaaggctg ttatcttgga cttcttgact    900

gctggtactg acactactgc tatcactgtt gaatgggttt tggctgaatt gatgaactct    960

ccaaaggcta tgaagaaggc tcaagacgaa atggacagag ttgttggtag agaaagaatg   1020

atggctgaat ctgacgctcc aaacttgcca tacttcttgg ctatcatcaa ggaaactttc   1080

agattgcacc caccaatccc attgatcatc agaagatcta tcgaagattg tgttatcgac   1140

ggttaccaca tcccagctga cactttggct ttcatcaacg tttggtctat gggtagaaac   1200

gaaaagtact gggactctcc attgtctttc agaccagaaa gattcttgga aggtgacaac   1260

gctgctatcg acatcaaggg tatgcacttc gaattgttgc cattcggttc tggtagaaga   1320

ggttgtccag gtatgttgtc tgctatccaa gaagttttga tcatcgctgg tactgttatc   1380

caatgtttcg actgggaaca agctgacggt tctggtagag ttgacatgtc tgaaagacca   1440

ggtttgacta ctccaagaga aatcgacttg gtttgtagag ttgttccaag agttgacgaa   1500

agagttatct ctggtcacta a                                             1521
```

```
<210> SEQ ID NO 155
<211> LENGTH: 510
<212> TYPE: PRT
<213> ORGANISM: Dorcoceras hygrometricum

<400> SEQUENCE: 155

Met Ser Asp Leu Val Gln Ile Thr Leu Ser Ala Ala Leu Leu Leu Leu
1               5                   10                  15

Ser Ala Ala Phe Leu His Thr Ile Phe Ala Thr Lys Arg Arg Arg Leu
            20                  25                  30

Ser Pro Pro Pro Gly Pro Leu Ala Leu Pro Ile Ile Gly His Leu His
        35                  40                  45

Leu Leu Gly Pro Arg Leu His Gln Thr Phe His Asp Leu Ser Leu Arg
    50                  55                  60

His Gly Pro Ile Phe Asn Leu Arg Leu Gly Ser Val Ala Cys Ala Val
65                  70                  75                  80

Val Ser Thr Pro Glu Leu Ala Lys Glu Cys Leu Lys Thr His Glu Leu
                85                  90                  95

Val Phe Ser Ser Arg Lys His Ser Thr Ala Ile Asp Ile Val Thr Tyr
            100                 105                 110

Asp Ser Ser Phe Ala Phe Ser Pro Tyr Gly Pro Tyr Trp Lys Tyr Ile
        115                 120                 125

Lys Lys Leu Cys Thr Tyr Glu Leu Leu Gly Ala Arg Asn Leu Leu His
    130                 135                 140

Phe Gln Pro Ile Arg Thr Leu Glu Val Asn Ser Phe Val Gly Thr Leu
145                 150                 155                 160

Met Asn Lys Ala Glu Ser Gly Glu Ser Phe Asn Val Thr Glu Glu Leu
                165                 170                 175

Val Lys Leu Thr Ser Asn Val Ile Ser His Met Met Leu Gly Ile Arg
            180                 185                 190

Cys Ser Gly Thr Glu Gly Glu Ala Glu Ala Ala Arg Thr Val Ile Arg
        195                 200                 205
```

```
Glu Val Thr Gln Ile Phe Gly Glu Phe Asp Val Ala Asp Ile Ile Trp
    210                 215                 220

Phe Cys Lys Asn Phe Asp Phe Gln Gly Ile Arg Lys Arg Ser Glu Asp
225                 230                 235                 240

Ile Gln Arg Arg Tyr Asp Ala Leu Leu Glu Lys Ile Ile Thr Asp Arg
                245                 250                 255

Glu Glu Leu Arg Arg Ser His Gly Gly Ala Ala Gly Glu Ala Arg Asp
            260                 265                 270

Phe Leu Asp Met Phe Leu Asp Ile Met Glu Gly Gly Lys Ser Glu Val
        275                 280                 285

Thr Phe Thr Arg Glu His Leu Lys Ala Leu Ile Leu Asp Phe Phe Thr
    290                 295                 300

Ala Gly Thr Asp Thr Thr Ala Ile Val Thr Glu Trp Ala Ile Ser Glu
305                 310                 315                 320

Leu Ile Asn Asn Pro Lys Val Leu Glu Lys Ala Gln Gln Glu Ile Asp
                325                 330                 335

Lys Val Ile Gly Ser Gly Arg Leu Val Gln Glu Ser Asp Ala Pro Asn
            340                 345                 350

Leu Pro Tyr Leu Met Ala Val Ile Lys Glu Thr Phe Arg Leu His Pro
        355                 360                 365

Pro Ile Pro Met Leu Ser Arg Lys Ser Ile Ser Asp Cys Val Ile Asp
    370                 375                 380

Gly Tyr Asp Val Pro Ala Lys Ser Leu Leu Phe Val Asn Ile Trp Ser
385                 390                 395                 400

Met Gly Arg Asn Pro Lys Ile Trp Glu Ser Pro Leu Glu Phe Arg Pro
                405                 410                 415

Glu Arg Phe Leu Glu Arg Glu Lys Ser Ser Ile Asp Ile Lys Gly Gln
            420                 425                 430

His Phe Glu Leu Leu Pro Phe Gly Thr Gly Arg Arg Gly Cys Pro Gly
        435                 440                 445

Met Leu Leu Gly Ile Gln Glu Val Val Ile Ile Ile Gly Thr Met Val
    450                 455                 460

Gln Cys Phe Asp Trp Lys Leu Ser Asp Gly Ser Gly Gln Val Asp Met
465                 470                 475                 480

Thr Glu Arg Pro Gly Leu Thr Ala Pro Arg Ala His Asp Leu Phe Cys
                485                 490                 495

Arg Val Val Pro Arg Ile Asn Pro Val Val Val Ser Gly Asn
            500                 505                 510
```

<210> SEQ ID NO 156
<211> LENGTH: 1533
<212> TYPE: DNA
<213> ORGANISM: artificial
<220> FEATURE:
<223> OTHER INFORMATION: coding sequence for SEQ ID NO: 155

<400> SEQUENCE: 156

```
atgtccgact tggttcaaat cactttgtct gctgctttgt tgttgttgtc tgctgctttc      60

ttgcacacta tcttcgctac taagagaaga agattgtctc caccaccagg tccattggct     120

ttgccaatca tcggtcactt gcacttgttg ggtccaagat tgcaccaaac tttccacgac     180

ttgtctttga gacacggtcc aatcttcaac ttgagattgg gttctgttgc ttgtgctgtt     240

gtttctactc cagaattggc taaggaatgt ttgaaaactc acgaattggt tttctcttct     300

agaaagcact ctactgctat cgacatcgtt acttacgact cttctttcgc tttctctcca     360
```

-continued

```
tacggtccat actggaagta catcaagaag ttgtgtactt acgaattgtt gggtgctaga    420

aacttgttgc acttccaacc aatcagaact ttggaagtta actctttcgt tggtactttg    480

atgaacaagg ctgaatctgg tgaatctttc aacgttactg aagaattggt taagttgact    540

tctaacgtta tctctcacat gatgttgggt atcagatgtt ctggtactga aggtgaagct    600

gaagctgcta gaactgttat cagagaagtt actcaaatct tcggtgaatt cgacgttgct    660

gacatcatct ggttctgtaa gaacttcgac ttccaaggta tcagaaagag atctgaagat    720

atccaaagaa gatacgacgc tttgttggaa aagatcatca ctgacagaga agaattgaga    780

agatctcacg gtggtgctgc tggtgaagct agagacttct tggacatgtt cttggacatc    840

atggaaggtg gtaagtctga agttactttc actagagaac acttgaaggc tttgatcttg    900

gacttcttca ctgctggtac tgacactact gctatcgtta ctgaatgggc tatctctgaa    960

ttgatcaaca acccaaaggt tttggaaaag gctcaacaag aaatcgacaa ggttatcggt   1020

tctggtagat tggttcaaga atctgacgct ccaaacttgc catacttgat ggctgttatc   1080

aaggaaactt tcagattgca cccaccaatc ccaatgttgt ctagaaagtc tatctctgac   1140

tgtgttatcg acggttacga cgttccagct aagtctttgt tgttcgttaa catctggtct   1200

atgggtagaa acccaaagat ctgggaatct ccattggaat tcagaccaga aagattcttg   1260

gaaagagaaa agtcatctat cgacatcaag ggtcaacact tcgaattgtt gccattcggt   1320

actggtagaa gaggttgtcc aggtatgttg ttgggtatcc aagaagttgt tatcatcatc   1380

ggtactatgg ttcaatgttt cgactggaag ttgtctgacg gttctggtca agttgacatg   1440

actgaaagac caggtttgac tgctccaaga gctcacgact tgttctgtag agttgttcca   1500

agaatcaacc cagttgttgt ttctggtaac taa                                1533
```

<210> SEQ ID NO 157
<211> LENGTH: 507
<212> TYPE: PRT
<213> ORGANISM: Antirrhinum majus

<400> SEQUENCE: 157

```
Met Ser Ser Thr Leu Val Tyr Ser Thr Leu Phe Ile Leu Ser Thr Leu
1               5                   10                  15

Leu Leu Thr Leu Leu Thr Arg Thr Arg Arg Lys Thr Arg Pro Pro Gly
            20                  25                  30

Pro Leu Ala Leu Pro Leu Ile Gly His Leu His Leu Leu Gly Pro Lys
        35                  40                  45

Leu His His Thr Phe His Gln Phe Ser Gln Arg Tyr Gly Pro Leu Ile
    50                  55                  60

Gln Leu Tyr Leu Gly Ser Val Pro Cys Val Val Ala Ser Thr Pro Glu
65                  70                  75                  80

Leu Ala Arg Glu Phe Leu Lys Thr His Glu Leu Asp Phe Ser Ser Arg
                85                  90                  95

Lys His Ser Thr Ala Ile Asp Ile Val Thr Tyr Asp Ser Ser Phe Ala
            100                 105                 110

Phe Ala Pro Tyr Gly Pro Tyr Trp Lys Phe Ile Lys Lys Leu Cys Thr
        115                 120                 125

Tyr Glu Leu Leu Gly Ala Arg Asn Leu Ser His Phe Gln Pro Ile Arg
    130                 135                 140

Ala Leu Glu Val Asn Ser Phe Leu Arg Ile Leu Tyr Glu Lys Thr Glu
145                 150                 155                 160

Gln Lys Gln Ser Val Asn Val Thr Glu Glu Leu Val Lys Leu Thr Ser
```

```
                165                 170                 175

Asn Val Ile Ser Asn Met Met Leu Gly Ile Arg Cys Ser Gly Thr Glu
            180                 185                 190

Gly Glu Ala Glu Val Ala Arg Thr Val Ile Arg Glu Val Thr Gln Ile
        195                 200                 205

Phe Gly Glu Phe Asp Val Ser Glu Ile Val Trp Phe Cys Lys Asn Leu
    210                 215                 220

Asp Leu Gln Gly Ile Arg Lys Arg Ser Glu Asp Ile Arg Arg Arg Tyr
225                 230                 235                 240

Asp Ala Leu Leu Glu Lys Ile Ile Ser Asp Arg Glu Arg Leu Arg Leu
                245                 250                 255

Arg Gly Gly Gly Gly Gly Gly Gly Gly Glu Val Lys Asp Phe Leu Asp
            260                 265                 270

Met Leu Leu Asp Val Met Glu Ser Glu Lys Ser Glu Val Glu Phe Thr
        275                 280                 285

Arg Glu His Leu Lys Ala Leu Ile Leu Asp Phe Phe Thr Ala Gly Thr
    290                 295                 300

Asp Thr Thr Ala Ile Thr Thr Glu Trp Ala Ile Ala Glu Leu Ile Ser
305                 310                 315                 320

Asn Pro Asn Val Leu Lys Lys Ala Gln Glu Glu Met Asp Lys Val Ile
                325                 330                 335

Gly Ser Gln Arg Leu Leu Gln Glu Ser Asp Ala Pro Asn Leu Pro Tyr
            340                 345                 350

Leu Asn Ala Ile Ile Lys Glu Thr Phe Arg Leu His Pro Pro Ile Pro
        355                 360                 365

Met Leu Thr Arg Lys Ser Ile Ser Asp Val Val Val Asn Gly Tyr Thr
    370                 375                 380

Ile Pro Ala Lys Thr Leu Leu Phe Val Asn Leu Trp Ser Met Gly Arg
385                 390                 395                 400

Asn Pro Asn Tyr Trp Glu Asn Pro Met Glu Phe Arg Pro Glu Arg Phe
                405                 410                 415

Leu Glu Lys Gly Thr Gly Ser Ile Asp Val Lys Gly Gln His Phe Glu
            420                 425                 430

Leu Leu Pro Phe Gly Thr Gly Arg Arg Gly Cys Pro Gly Met Leu Leu
        435                 440                 445

Gly Met Gln Glu Leu Phe Ser Ile Ile Gly Ala Met Val Gln Cys Phe
    450                 455                 460

Asp Trp Lys Leu Pro Asp Gly Val Lys Ser Val Asp Met Thr Glu Arg
465                 470                 475                 480

Pro Gly Leu Thr Ala Pro Arg Ala Asn Asp Leu Val Cys Gln Leu Val
                485                 490                 495

Pro Arg Ile Asp Pro Val Val Val Ser Gly Pro
            500                 505
```

<210> SEQ ID NO 158
<211> LENGTH: 1524
<212> TYPE: DNA
<213> ORGANISM: artificial
<220> FEATURE:
<223> OTHER INFORMATION: coding sequence for SEQ ID NO: 157

<400> SEQUENCE: 158

```
atgtcctcta ctttggttta ctctactttg ttcatcttgt ctactttgtt gttgactttg      60

ttgactagaa ctagaagaaa gactagacca ccaggtccat tggctttgcc attgatcggt     120
```

```
cacttgcact tgttgggtcc aaagttgcac cacactttcc accaattctc tcaaagatac    180

ggtccattga tccaattgta cttgggttct gttccatgtg ttgttgcttc tactccagaa    240

ttggctagag aattcttgaa aactcacgaa ttggacttct cttctagaaa gcactctact    300

gctatcgaca tcgttactta cgactcttct ttcgctttcg ctccatacgg tccatactgg    360

aagttcatca agaagttgtg tacttacgaa ttgttgggtg ctagaaactt gtctcacttc    420

caaccaatca gagctttgga agttaactct ttcttgagaa tcttgtacga aaagactgaa    480

caaaagcaat ctgttaacgt tactgaagaa ttggttaagt tgacttctaa cgttatctct    540

aacatgatgt tgggtatcag atgttctggt actgaaggtg aagctgaagt tgctagaact    600

gttatcagag aagttactca aatcttcggt gaattcgacg tttctgaaat cgtttggttc    660

tgtaagaact tggacttgca aggtatcaga aagagatctg aagatatcag aagaagatac    720

gacgctttgt tggaaaagat catctctgac agagaaagat tgagattgag aggtggtggt    780

ggtggtggtg gtggtgaagt taaggacttc ttggacatgt tgttggacgt tatggaatct    840

gaaaagtctg aagttgaatt cactagagaa cacttgaagg ctttgatctt ggacttcttc    900

actgctggta ctgacactac tgctatcact actgaatggg ctatcgctga attgatctct    960

aacccaaacg ttttgaagaa ggctcaagaa gaaatggaca aggttatcgg ttctcaaaga   1020

ttgttgcaag aatctgacgc tccaaacttg ccatacttga acgctatcat caaggaaact   1080

ttcagattgc acccaccaat cccaatgttg actagaaagt ctatctctga cgttgttgtt   1140

aacggttaca ctatcccagc taagactttg ttgttcgtta acttgtggtc tatgggtaga   1200

aacccaaact actgggaaaa cccaatggaa ttcagaccag aaagattctt ggaaaagggt   1260

actggttcta tcgacgttaa gggtcaacac ttcgaattgt tgccattcgg tactggtaga   1320

agaggttgtc caggtatgtt gttgggtatg caagaattgt tctctatcat cggtgctatg   1380

gttcaatgtt tcgactggaa gttgccagac ggtgttaagt ctgttgacat gactgaaaga   1440

ccaggtttga ctgctccaag agctaacgac ttggtttgtc aattggttcc aagaatcgac   1500

ccagttgttg tttctggtcc ataa                                           1524
```

<210> SEQ ID NO 159
<211> LENGTH: 511
<212> TYPE: PRT
<213> ORGANISM: Erythranthe lewisii

<400> SEQUENCE: 159

```
Met Ser Asn Gln Thr Met Asp Leu Pro Glu Ile Cys Leu Tyr Ala Val
1               5                   10                  15

Ile Leu Phe Val Ser Thr Leu Leu Ile Leu Gly Ile Tyr Lys Arg Lys
            20                  25                  30

Arg Ser His Ile Pro Ser Pro Pro Gly Pro Phe Ala Leu Pro Val Ile
        35                  40                  45

Gly His Leu His Leu Leu Gly Pro Arg Ile His His Thr Phe His Asp
    50                  55                  60

Leu Ser Gln Arg Tyr Gly Pro Leu Phe Gln Leu Ser Leu Gly Ser Val
65                  70                  75                  80

Arg Cys Val Val Val Ser Thr Pro Glu Leu Ala Arg Glu Phe Leu Lys
                85                  90                  95

Thr His Glu Leu Val Phe Ser Ser Arg Lys His Thr Thr Ala Ile Asp
            100                 105                 110

Ile Val Thr Tyr Glu Ser Ser Phe Ala Phe Ser Pro Tyr Gly Pro Tyr
        115                 120                 125
```

```
Trp Lys Tyr Ile Lys Lys Leu Cys Thr Tyr Glu Leu Leu Gly Ala Arg
    130                 135                 140

Asn Leu Ala Asn Phe Glu Pro Val Arg Asn Val Glu Ile Lys Asp Phe
145                 150                 155                 160

Leu Lys Val Met Ser Asn Lys Ala Asn Thr Gly Glu Ile Val Asn Val
                165                 170                 175

Thr Glu Glu Leu Val Lys Leu Thr Ser Asn Val Ile Ser His Met Met
            180                 185                 190

Leu Gly Ile Arg Cys Ser Gly Thr Glu Gly Glu Ala Glu Ala Ala Arg
        195                 200                 205

Asn Val Ile Arg Asp Val Thr Gln Ile Phe Gly Glu Phe Asp Val Ser
    210                 215                 220

Asp Ile Ile Trp Phe Cys Lys Asn Phe Asp Leu Gln Gly Ile Arg Arg
225                 230                 235                 240

Arg Ser Glu Asp Ile Gln Lys Arg Tyr Asp Gly Leu Leu Glu Lys Ile
                245                 250                 255

Ile Thr Asp Arg Glu Lys Thr Arg Gly Gly Gly Gly Gly Gly Val Lys
            260                 265                 270

Asp Phe Leu Asp Met Leu Leu Asp Val Met Asp Ser Lys Asn Ser Asp
        275                 280                 285

Val Lys Phe Thr Arg Glu His Leu Lys Ala Leu Ile Leu Asp Phe Phe
    290                 295                 300

Thr Ala Gly Thr Asp Thr Thr Ala Ile Ala Val Glu Trp Ser Ile Ala
305                 310                 315                 320

Glu Leu Leu Arg Asn Pro Lys Val Ile Lys Lys Ala Gln Gln Glu Ile
                325                 330                 335

Asp Asn Val Val Gly Ser Gln Arg Leu Leu Gln Glu Ser Asp Ala Pro
            340                 345                 350

Lys Leu Pro Tyr Ile Met Ala Ile Ile Lys Glu Thr Phe Arg Leu His
        355                 360                 365

Pro Pro Ile Pro Met Ile Ser Arg Lys Ser Val Ser Asp Cys Ala Ile
    370                 375                 380

Asn Gly Cys Met Ile Arg Ala Asn Thr Leu Leu Phe Val Asn Ile Trp
385                 390                 395                 400

Ser Ile Gly Arg Asn Pro Met Tyr Trp Glu Arg Pro Met Glu Phe Arg
                405                 410                 415

Pro Glu Arg Phe Leu Asp Pro Gly Cys Gly Ser Ile Asp Val Lys Gly
            420                 425                 430

Gln Asn Phe Glu Leu Met Pro Phe Gly Thr Gly Arg Arg Gly Cys Pro
        435                 440                 445

Gly Met Leu Leu Ala Met Gln Glu Leu Val Ala Ile Ile Gly Ala Met
    450                 455                 460

Val Gln Cys Phe Glu Trp Gln Leu Pro Asp Asp Ser Gln Asp Val Asp
465                 470                 475                 480

Met Thr Glu Arg Pro Gly Leu Thr Ala Pro Arg Ala Asn Asp Leu Phe
                485                 490                 495

Cys Arg Val Val Pro Arg Val Asp Val Ala Val Val Ser Gly Asn
            500                 505                 510
```

<210> SEQ ID NO 160
<211> LENGTH: 1536
<212> TYPE: DNA
<213> ORGANISM: artificial
<220> FEATURE:

-continued

```
<223> OTHER INFORMATION: coding sequence for SEQ ID NO: 159

<400> SEQUENCE: 160

atgtccaacc aaactatgga cttgccagaa atctgtttgt acgctgttat cttgttcgtt     60
tctactttgt tgatcttggg tatctacaag agaaagagat ctcacatccc atctccacca    120
ggtccattcg ctttgccagt tatcggtcac ttgcacttgt tgggtccaag aatccaccac    180
actttccacg acttgtctca aagatacggt ccattgttcc aattgtcttt gggttctgtt    240
agatgtgttg ttgtttctac tccagaattg gctagagaat tcttgaaaac tcacgaattg    300
gttttctctt ctagaaagca cactactgct atcgacatcg ttacttacga atcttctttc    360
gctttctctc catacggtcc atactggaag tacatcaaga agttgtgtac ttacgaattg    420
ttgggtgcta gaaacttggc taacttcgaa ccagttagaa acgttgaaat caaggacttc    480
ttgaaggtta tgtctaacaa ggctaacact ggtgaaatcg ttaacgttac tgaagaattg    540
gttaagttga cttctaacgt tatctctcac atgatgttgg gtatcagatg ttctggtact    600
gaaggtgaag ctgaagctgc tagaaacgtt atcagagatg ttactcaaat cttcggtgaa    660
ttcgacgttt ctgacatcat ctggttctgt aagaacttcg acttgcaagg tatcagaaga    720
agatctgaag atatccaaaa gagatacgac ggtttgttgg aaaagatcat cactgacaga    780
gaaaagacta gaggtggtgg tggtggtggt gttaaggact tcttggacat gttgttggac    840
gttatggact ctaagaactc tgacgttaag ttcactagag aacacttgaa ggctttgatc    900
ttggacttct tcactgctgg tactgacact actgctatcg ctgttgaatg gtctatcgct    960
gaattgttga gaaacccaaa ggttatcaag aaggctcaac aagaaatcga caacgttgtt   1020
ggttctcaaa gattgttgca agaatctgac gctccaaagt tgccatacat catggctatc   1080
atcaaggaaa ctttcagatt gcacccacca atcccaatga tctctagaaa gtctgtttct   1140
gactgtgcta tcaacggttg tatgatcaga gctaacactt tgttgttcgt taacatctgg   1200
tctatcggta gaaacccaat gtactgggaa agaccaatgg aattcagacc agaaagattc   1260
ttggacccag gttgtggttc tatcgacgtt aagggtcaaa acttcgaatt gatgccattc   1320
ggtactggta gaagaggttg tccaggtatg ttgttggcta tgcaagaatt ggttgctatc   1380
atcggtgcta tggttcaatg tttcgaatgg caattgccag acgactctca agacgttgac   1440
atgactgaaa gaccaggttt gactgctcca agagctaacg acttgttctg tagagttgtt   1500
ccaagagttg acgttgctgt tgtttctggt aactaa                             1536
```

METHOD FOR THE BIOSYNTHESIS OF DIOSMIN AND/OR HESPERIDIN IN A MICROORGANISM

CROSS-REFERENCE TO RELATED APPLICATION

This application is the U.S. national stage application of International Patent Application No. PCT/EP2020/053503, filed Feb. 11, 2020.

The Sequence Listing for this application is labeled "Seq-List.txt" which was created on Aug. 4, 2021 and is 504 KB. The entire content of the sequence listing is incorporated herein by reference in its entirety.

FIELD OF THE INVENTION

The present invention relates to a method for producing diosmin and hesperidin.

TECHNOLOGICAL BACKGROUND

Daflon is a mixture of flavonoids with vasotonic and vascular-protective effects. This mixture is mainly composed of ~85% diosmin, ~8% hesperidin and traces of various flavones and the respective oxidized forms thereof.

The current method for producing the medicament is acid/base extraction, from the peel of small oranges, of a mixture of flavonoids mainly containing hesperidin (94%) and a mixture of isonaringin (~3%), neoponcirin (~2%) and hesperetin (<1%). This mixture then undergoes controlled oxidation via a chemical process, transforming about 90% of the hesperidin into diosmin, and minor flavonoids in their oxidized form.

Thus, the production of Daflon is associated with the supply of purified extract of orange flavonoids, which may vary as a result of climatic variations, fluctuations in currency movements and the difficulty of being supplied from dozens of sites in several countries (mainly Mexico, the countries of the Mediterranean basin and China).

It would thus be valuable to have available an alternative method for producing Daflon which is not dependent on the vagaries of being supplied with purified extract of orange flavonoids. Thus, there is an unsatisfied need for a process for the biosynthesis of diosmin and hesperidin.

SUMMARY OF THE INVENTION

The inventors have developed a method for the biosynthesis of diosmin and hesperidin in a recombinant microorganism.

Thus, the present invention relates to a recombinant microorganism comprising:

- a heterologous nucleic acid sequence coding for a flavanone 7-O-beta-D-glucosyltransferase (UGT) which is capable of adding a glucose in position 7 of hesperetin and/or diosmetin; and
- a heterologous nucleic acid sequence coding for a 6"-O-rhamnosyltransferase (RhaT) which is capable of transferring a rhamnose into position 6 of the glucose of hesperetin-7-O-glucoside and/or of diosmetin-7-O-glucoside; and
- a heterologous nucleic acid sequence coding for a UDP-glucose 4,6-dehydratase/UDP-4-keto-6-deoxy-D-glucose 3,5-epimerase/UDP-4-keto-L-rhamnose-reductase (RHM) which is capable of producing UDP-rhamnose.

Preferably, the flavanone 7-O-beta-D-glucosyltransferase (UGT) is an enzyme from *Citrus sinensis, Citrus clementina, Arabidopsis thaliana, Scutellaria baicalensis* or *Homo sapiens. In particular, the flavanone* 7-O-beta-D-glucosyltransferase (UGT) may be an enzyme from *Arabidopsis thaliana, Scutellaria baicalensis* or *Homo sapiens*, preferably from *Arabidopsis thaliana* or *Scutellaria baicalensis*. Preferably, the flavanone 7-O-beta-D-glucosyltransferase (UGT) is from *Citrus sinensis* or *Scutellaria baicalensis.*

The flavanone 7-O-beta-D-glucosyltransferase may be selected from enzymes comprising a sequence chosen from SEQ ID NOs: 113, 115, 91, 93, 95, 97, 99 and 101 and polypeptides comprising a sequence having at least 60, 70, 80, 85, 90 or 95% sequence identity with one of these sequences and having flavanone 7-O-beta-D-glucosyltransferase activity, preferably selected from enzymes comprising a sequence chosen from SEQ ID NOs: 113, 115, 91, 93, 95 and 97 and polypeptides comprising a sequence having at least 60, 70, 80, 85, 90 or 95% sequence identity with one of these sequences and having flavanone 7-O-beta-D-glucosyltransferase activity. In particular, it may be selected from enzymes comprising a sequence chosen from SEQ ID NOs: 91, 93, 95, 97, 99 and 101 and polypeptides comprising a sequence having at least 60, 70, 80, 85, 90 or 95% sequence identity with one of these sequences and having flavanone 7-O-beta-D-glucosyltransferase activity, preferably selected from enzymes comprising a sequence chosen from SEQ ID NOs: 91, 93, 95 and 97 and polypeptides comprising a sequence having at least 60, 70, 80, 85, 90 or 95% sequence identity with one of these sequences and having flavanone 7-O-beta-D-glucosyltransferase activity. Preferably, the flavanone 7-O-beta-D-glucosyltransferase is selected from enzymes comprising a sequence chosen from SEQ ID NOs: 113 and 95 and polypeptides comprising a sequence having at least 60, 70, 80, 85, 90 or 95% sequence identity with one of these sequences and having flavanone 7-O-beta-D-glucosyltransferase activity, preferably selected from enzymes comprising a sequence chosen from SEQ ID NO: 113 and polypeptides comprising a sequence having at least 60, 70, 80, 85, 90 or 95% sequence identity with this sequence and having flavanone 7-O-beta-D-glucosyltransferase activity.

Preferably, 6"-O-rhamnosyltransferase (RhaT) is a plant enzyme, preferably of the genus *Citrus* or *Petunia hybrida*, preferably *Citrus sinensis, Citrus maxima*, or *Citrus clementina*, more preferably *Citrus sinensis* or *Citrus clementina*. Preferably, 6"-O-rhamnosyltransferase is selected from enzymes comprising a sequence chosen from SEQ ID NOs: 103, 105 and polypeptides comprising a sequence having at least 60, 70, 80, 85, 90 or 95% sequence identity with one of these sequences and having 6"-O-rhamnosyltransferase activity. More particularly preferably, 6"-O-rhamnosyltransferase is selected from enzymes comprising a sequence chosen from SEQ ID NO: 103 and polypeptides comprising a sequence having at least 60, 70, 80, 85, 90 or 95% sequence identity with this sequence and having 6"-O-rhamnosyltransferase activity.

Preferably, UDP-glucose 4,6-dehydratase/UDP-4-keto-6-deoxy-D-glucose 3,5-epimerase/UDP-4-keto-L-rhamnose-reductase (RHM) is a plant enzyme, preferably from *Citrus sinensis* or *Arabidopsis thaliana*. Preferably, UDP-glucose 4,6-dehydratase/UDP-4-keto-6-deoxy-D-glucose 3,5-epimerase/UDP-4-keto-L-rhamnose-reductase is selected from enzymes comprising a sequence chosen from SEQ ID NOs: 107, 109 and 111 and polypeptides comprising a sequence having at least 60, 70, 80, 85, 90 or 95% sequence identity with one of these sequences and having UDP-glucose 4,6- dehydratase/UDP-4-keto-6-deoxy-D-glucose 3,5-epimerase/UDP-4-keto-L-rhamnose-reductase activity. More particularly preferably, UDP-glucose 4,6-dehydratase/UDP-4-keto-6-deoxy-D-glucose 3,5-epimerase/UDP-4-keto-L-rhamnose-reductase is selected from enzymes comprising a sequence chosen from SEQ ID NO: 107 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity.

In one embodiment, the microorganism according to the invention also comprises:

- a heterologous nucleic acid sequence coding for a tyrosine ammonia lyase (TAL); and/or a heterologous nucleic acid sequence coding for a phenylalanine ammonia lyase (PAL) and a heterologous nucleic acid sequence coding for a cinnamate 4-hydroxylase (C4H);
- a heterologous nucleic acid sequence coding for a 4-coumaroyl-CoA ligase (4CL);
- a heterologous nucleic acid sequence coding for a naringenin-chalcone synthase (CHS);
- a heterologous nucleic acid sequence coding for a chalcone isomerase (CHI);
- a heterologous nucleic acid sequence coding for a flavonoid 3'-monooxygenase (F3'H);
- a heterologous nucleic acid sequence coding for an O-methyl-transferase (OMT), and
- optionally, a heterologous nucleic acid sequence coding for a 4-methoxybenzoate O-demethylase which is capable of converting tyrosine into L-DOPA and also p-coumaric acid into caffeic acid; or a heterologous nucleic acid sequence coding for a p-coumarate 3-hydroxylase which is capable of converting p-coumaric acid into caffeic acid.

Preferably, the microorganism comprises:

- a heterologous nucleic acid sequence coding for a tyrosine ammonia lyase (TAL) comprising a sequence chosen from SEQ ID NOs: 41 and 39 and polypeptides comprising a sequence having at least 60, 70, 80, 85, 90 or 95% sequence identity with one of these sequences and having tyrosine ammonia lyase activity, and preferably a tyrosine ammonia lyase (TAL) comprising a sequence chosen from SEQ ID NO: 41 and polypeptides comprising a sequence having at least 60, 70, 80, 85, 90 or 95% sequence identity with this sequence and having tyrosine ammonia lyase activity; and
- a heterologous nucleic acid sequence coding for a 4-coumaroyl-CoA ligase (4CL) comprising a sequence chosen from SEQ ID NOs: 123, 125, 43, 45, 47 and 49 and polypeptides comprising a sequence having at least 60, 70, 80, 85, 90 or 95% sequence identity with one of these sequences and having 4-coumarate-CoA ligase activity, preferably a 4CL comprising a sequence selected from SEQ ID NOs: 123, 125 and 45 and polypeptides comprising a sequence having at least 60, 70, 80, 85, 90 or 95% sequence identity with one of these sequences and having 4-coumarate-CoA ligase activity, and in particular a heterologous nucleic acid sequence coding for a 4-coumaroyl-CoA ligase (4CL) comprising a sequence selected from SEQ ID NO: 45 and polypeptides comprising a sequence having at least 60, 70, 80, 85, 90 or 95% sequence identity with this sequence and having 4-coumarate-CoA ligase activity; and
- a heterologous nucleic acid sequence coding for a chalcone synthase (CHS) comprising a sequence chosen from SEQ ID NOs: 53, 51, 55 and 57 and polypeptides comprising a sequence having at least 60, 70, 80, 85, 90 or 95% sequence identity with one of these sequences and having chalcone synthase activity, preferably a CHS comprising a sequence chosen from SEQ ID NO: 53 and polypeptides comprising a sequence having at least 60, 70, 80, 85, 90 or 95% sequence identity with this sequence and having chalcone synthase activity; and
- a heterologous nucleic acid sequence coding for a chalcone isomerase (CHI) comprising a sequence chosen from SEQ ID NOs: 61 and 59 and polypeptides comprising a sequence having at least 60, 70, 80, 85, 90 or 95% sequence identity with one of these sequences and having chalcone isomerase activity, and preferably a CHI comprising a sequence chosen from SEQ ID NO: 61 and polypeptides comprising a sequence having at least 60, 70, 80, 85, 90 or 95% sequence identity with this sequence and having chalcone isomerase activity.

Preferably, the microorganism comprises a heterologous nucleic acid sequence coding for a flavonoid 3'-monooxygenase (F3'H) from *Callistephus chinensis, Perilla frutescens* var. *crispa, Petunia* x *hybrida, Gerbera hybrida, Citrus sinensis, Arabidopsis thaliana, Pilosella officinarum*, Osteospermurn hybrid cultivar, *Phanerochaete chrysosporium, Citrus clementina* or *Streptomyces avermitilis*, in particular from *Callistephus chinensis, Perilla frutescens* var. *crispa, Petunia* x *hybrida, Gerbera hybrida, Citrus sinensis, Arabidopsis thaliana* or *Pilosella officinarum*, preferably an enzyme comprising a sequence chosen from SEQ ID NOs: 7, 1, 3, 5, 9, 11, 13, 15, 17, 19, 21 and 121 and polypeptides comprising a sequence having at least 60, 70, 80, 85, 90 or 95% sequence identity with one of these sequences and having flavonoid 3'-monooxygenase activity, preferably selected from enzymes having the SEQ ID NOs: 7, 11, 17 and 121 and polypeptides having at least 60, 70, 80, 85, 90 or 95% identity with one of these sequences and having flavonoid 3'-monooxygenase activity.

More particularly preferably, the microorganism comprises a heterologous nucleic acid sequence coding for a flavonoid 3'-monooxygenase (F3'H) comprising a sequence chosen from SEQ ID NOs: 7, 17 and 121 and polypeptides having at least 60, 70, 80, 85, 90 or 95% identity with one of these sequences and having flavonoid 3'-monooxygenase activity, preferably a flavonoid 3'-monooxygenase (F3'H) comprising a sequence chosen from SEQ ID NO: 7 and polypeptides having at least 60, 70, 80, 85, 90 or 95% identity with this sequence and having flavonoid 3'-monooxygenase activity.

Preferably, the microorganism comprises a heterologous nucleic acid sequence coding for an O-methyl-transferase (OMT) from *Citrus*, in particular *Citrus clementina* or *Citrus sinensis*, from *Homo sapiens* or from *Arabidopsis thaliana*, preferably an enzyme comprising a sequence chosen from SEQ ID NOs: 119, 117, 87 and 89 and polypeptides comprising a sequence having at least 60, 70, 80, 85, 90 or 95% sequence identity with one of these sequences and having O-methyltransferase activity. More particularly preferably, it comprises a heterologous nucleic acid sequence coding for an O-methyltransferase (OMT) comprising a sequence chosen from SEQ ID NOs: 119, 117 and 89 and polypeptides comprising a sequence having at least 60, 70, 80, 85, 90 or 95% sequence identity with one of these sequences and having O-methyltransferase activity, preferably a sequence chosen from SEQ ID NOs: 119 and 117 and polypeptides comprising a sequence having at least 60, 70, 80, 85, 90 or 95% sequence identity with one of these sequences and having O-methyltransferase activity.

Preferably, the microorganism comprises:

- a heterologous nucleic acid sequence coding for a phenylalanine ammonia lyase (PAL), in particular a PAL comprising a sequence chosen from SEQ ID NOs: 63, 65 and 77, preferably SEQ ID NOs: 65 and 77, and polypeptides comprising a sequence having at least 60, 70, 80, 85, 90 or 95% sequence identity with one of these sequences and having phenylalanine ammonia lyase activity, and more particularly preferably a phenylalanine ammonia lyase (PAL) comprising a sequence chosen from SEQ ID NO: 65 and polypeptides comprising a sequence having at least 60, 70, 80, 85, 90 or 95% sequence identity with this sequence and having phenylalanine ammonia lyase activity; and
- a heterologous nucleic acid sequence coding for a cinnamate 4-hydroxylase (C4H), in particular a C4H comprising a sequence chosen from SEQ ID NOs: 67, 69 and 79 and polypeptides comprising a sequence having at least 60, 70, 80, 85, 90 or 95% sequence identity with one of these sequences and having cinnamate 4-hydroxylase activity; and most particularly preferably a cinnamate 4-hydroxylase (C4H) comprising a sequence chosen from SEQ ID NO: 79 and polypeptides comprising a sequence having at least 60, 70, 80, 85, 90 or 95% sequence identity with this sequence and having cinnamate 4-hydroxylase activity.

The microorganism may also comprise a heterologous nucleic acid sequence coding for a flavone synthase (FNS), in particular a flavone synthase which is capable of producing luteolin from eriodictyol, preferably from *Arabidopsis thaliana, Petroselinum crispum, Zea mays, Lonicera japonica, Lonicera macranthoides, Callistephus chinensis, Apium graveolens, Medicago truncatula, Cuminurn cyminum, Aethusa cynapium, Angelica archangelica, Conium maculaturn, Camellia sinensis, Cynara cardunculus* var *scolymus, Saussurea medusa, Plectranthus barbatus, Scutellaria baicalensis, Dorcoceras hygrometricum, Antirrhinum majus, Perilla frutescens* var *crispa, Dahlia pinnata* or *Erythranthe lewisii*. The flavone synthase (FNS) may be selected from enzymes comprising a sequence chosen from SEQ ID NOs: 33, 35, 37, 127, 129, 131, 133, 135, 137, 139, 141, 143, 145, 147, 149, 151, 153, 155, 157 and 159 and polypeptides comprising a sequence having at least 60, 70, 80, 85, 90 or 95% sequence identity with one of these sequences and having flavone synthase activity. In particular, the FNS may be an FNS comprising a sequence chosen from SEQ ID NOs: 33, 35 and 37 and polypeptides comprising a sequence having at least 60, 70, 80, 85, 90 or 95% sequence identity with one of these sequences and having flavone synthase activity, and preferably a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity.

Moreover, it may also comprise:

- a heterologous nucleic acid sequence coding for a cytochrome P450 reductase (CPR); and/or
- a heterologous or endogenous nucleic acid sequence coding for an S-adenosylmethionine synthetase (SAMT).

Preferably, the CPR comprises a sequence chosen from SEQ ID NOs: 25, 23, 27, 29 and 31 and polypeptides comprising a sequence having at least 60, 70, 80, 85, 90 or 95% sequence identity with one of these sequences and having cytochrome P450 reductase activity, preferably a sequence chosen from SEQ ID NOs: 23, 25 and 29 and polypeptides comprising a sequence having at least 60, 70, 80, 85, 90 or 95% sequence identity with one of these sequences and having cytochrome P450 reductase activity, and particularly a sequence chosen from SEQ ID NO: 25 and polypeptides comprising a sequence having at least 60, 70, 80, 85, 90 or 95% sequence identity with this sequence and having cytochrome P450 reductase activity.

Preferably, the microorganism is a yeast or a bacterium, preferably a yeast of the genus *Saccharomyces*, in particular *Saccharomyces cerevisiae*, or a bacterium such as *Escherichia coli.*

The present invention also relates to the use of a microorganism as described in the present document for producing diosmin and/or hesperidin.

In addition, the invention relates to a method for producing diosmin and/or hesperidin comprising the cultivation of a microorganism as described in the present document, and optionally the harvesting of diosmin and/or hesperidin.

Preferably, during the use of the microorganism according to the invention for producing diosmin and/or hesperidin there is no naringenin, apigenin, eriodictyol, luteolin, hesperetin and/or diosmetin supplied to the culture medium.

DETAILED DESCRIPTION OF THE INVENTION

The pathways for the biosynthesis of hesperetin in the peel of small oranges are poorly understood. The inventors thus explored several biosynthetic pathways and succeeded in developing the biosynthesis of diosmin and of hesperidin in a recombinant microorganism.

Definition

The term "microorganism" refers to a unicellular organism. Preferably, the microorganism is a bacterium or a yeast.

The term "recombinant microorganism" refers to a microorganism which is not found in nature and which contains a genome modified following insertion, modification or deletion of one or more heterologous genetic elements.

The term "recombinant nucleic acid" refers to a nucleic acid which has been modified and does not exist in a natural microorganism. For example, this term may denote a coding sequence or gene which is operatively linked to a promoter which is not the natural promoter. This may also denote a coding sequence in which the introns have been deleted for genes comprising exons and introns.

The term "heterologous" means that the gene has been introduced by genetic engineering into the cell. It may be present therein in episomal or chromosomal form. The origin of the gene may be different from that of the cell into which it is introduced. However, the gene may also originate from the same species as the cell into which it is introduced, but it is considered as heterologous on account of its unnatural environment. For example, the gene or the nucleic acid sequence is heterologous since it is under the control of a promoter other than its natural promoter, it is introduced into a position different from that in which it is naturally located. The host cell may contain a copy of the endogenous gene prior to the introduction of the heterologous gene or it may not contain an endogenous copy. Moreover, the nucleic acid sequence may be heterologous in the sense that the coding sequence has been optimized for expression in the host microorganism. Preferably, in the present document, a heterologous nucleic acid sequence codes for a protein which is heterologous to the host cell, i.e. which is not naturally present in the yeast.

As used herein, the term "native" or "endogenous", relative to the host microorganism, refers to a genetic element or to a protein that is naturally present in said microorganism. The term "gene" denotes any nucleic acid coding for a protein. The term "gene" covers DNA, such as cDNA or gDNA, and also RNA. The gene may first be prepared via recombinant, enzymatic and/or chemical techniques, and subsequently replicated in a host cell or a system in vitro. The gene typically comprises an open reading frame coding for a desired protein. The gene may contain additional sequences such as a transcription terminator or a signal peptide.

As a result of degeneracy of the genetic code, several nucleic acids may code for a particular polypeptide. Thus, the codons in the coding sequence for a given polypeptide may be modified such that optimum expression in a particular microorganism is obtained, for example by using suitable codon translation tables for this microorganism. The nucleic acids may also be optimized according to a preferable GC content for the particular yeast and/or to reduce the number of repeat sequences. In certain embodiments, the heterologous nucleic acids were codon-optimized for expression in the microorganism concerned. Codon optimization may be performed via routine processes known in the art (see, for example, Welch, M., et al. (2011), Methods in Enzymology 498: 43-66).

The term "operatively linked" denotes a configuration in which a control sequence is placed in a suitable position relative to a coding sequence, such that the control sequence controls the expression of the coding sequence.

The term "control sequences" denotes the nucleic acid sequences required for the expression of a gene. The control sequences may be native or heterologous. Control sequences that are well known and currently used by those skilled in the art will be preferred. Such control sequences comprise, but without being limited thereto, a leader, a polyadenylation sequence, a propeptide sequence, a promoter, a signal peptide sequence and a transcription terminator. Preferably, the control sequences comprise a promoter and a transcription terminator.

The term "expression cassette" denotes a nucleic acid construct comprising a coding region, i.e. a gene, and a regulating region, i.e. a region comprising one or more control sequences, which are operatively linked. Preferably, the control sequences are suitable for use in the host microorganism.

As used herein, the term "expression vector" denotes a DNA or RNA molecule which comprises an expression cassette. Preferably, the expression vector is a linear or circular double-stranded DNA molecule. The vector may also comprise an origin of replication, a selection marker, etc.

For the purposes of the present invention, the term "percentage of identity" between two nucleic acid sequences or amino acid sequences is intended to denote a percentage of nucleotides or of amino acid residues that are identical between the two sequences to be compared, obtained after the best alignment, this percentage being purely statistical and the differences between the two sequences being distributed randomly and over their entire length. The best alignment or optimum alignment is the alignment for which the percentage of identity between the two sequences to be compared, as calculated below, is the highest. Sequence comparisons between two nucleic acid or amino acid sequences are conventionally performed by comparing these sequences after they have been optimally aligned, said comparison being performed by segment or by comparison window to identify and compare the local regions with sequence similarity. The alignment for the purposes of determining the percentage of amino acid sequence identity may be performed in various ways that are well known in the field, for example by using computer software available on the Internet, such as blast.ncbi.nlm. Nih.gov/ or www.ebi-.ac.uk/Tools/emboss/). A person skilled in the art can determine the appropriate parameters for measuring the alignment, including any algorithm necessary to obtain a maximum alignment over the entire length of the sequences compared. For the purposes of the present invention, the values of the percentage of amino acid sequence identity refer to values generated using the EMBOSS Needle pair sequence alignment program which creates an optimum global alignment of two sequences by means of the Needleman-Wunsch algorithm, in which all the search parameters are defined by default Notation matrix=BLOSUM62, Open gap=10, Extended gap=0.5, end gap penalty=false, open end gap=10 and extended end gap=0.5. In certain embodiments, all the percentages of identity mentioned in the present patent application may be set at at least 60%, at least 70%, at least 80%, at least 85%, preferably at at least 90% identity, more preferably at at least 95% identity. In particular, the embodiments in which all the percentages of sequence identity of the enzymes are at least 80% or at least 85%, preferably at least 90% or at least 95% sequence identity are considered as described.

In one embodiment, the polypeptides may contain 1, 2, 3, 4, 5, 6, 7, 8, 9 or 10 additions, substitutions or deletions relative to the sequences described in the SEQ ID NOs. In particular, these additions, substitutions or deletions are introduced at the N-terminal end, the C-terminal end or at both ends.

The polypeptides may optionally be in the form of a fusion protein.

The terms "overexpression" and "increased expression" as used herein are used interchangeably and mean that the expression of a gene or of an enzyme is increased relative to an unmodified microorganism, for example a wild-type microorganism or a microorganism not comprising the genetic modifications described herein. The term "wild-type" refers to an unmodified microorganism existing in nature. The increased expression of an enzyme is usually obtained by increasing the expression of the gene coding for said enzyme. In embodiments in which the gene or the enzyme is not naturally present in the microorganism of the invention, i.e. a heterologous gene or enzyme, the terms "overexpression" and "expression" may be used interchangeably. To increase the expression of a gene, a person skilled in the art can use any known technique such as increasing the number of copies of the gene in the microorganism, by using a promoter inducing a high level of expression of the gene, i.e. a strong promoter, by using elements which stabilize the corresponding messenger RNA or sequences which sequester the ribosomal binding site (RBS) and the sequences surrounding same. In particular, overexpression may be obtained by increasing the number of copies of the gene in the microorganism. One or more copies of the gene may be introduced into the genome via recombination processes, known to those skilled in the art, including the replacement of the genes or multi-copy integration (see, for example, the international patent application WO 2015/092013). Preferably, an expression cassette comprising the gene, preferably placed under the control of a strong promoter, is integrated into the genome. As a variant, the gene may be carried by an expression vector, preferably a plasmid, comprising an expression cassette with the gene of interest preferably placed under the control of a strong promoter. The expression vector may be present in the microorganism in one or more copies, depending on the nature of the origin of replication. Overexpression of the gene may also be obtained by using a promoter which induces a high level of expression of the gene. For example, the promoter of an endogenous gene may be replaced with a stronger promoter, i.e. a promoter which induces a higher level of expression. The endogenous gene under the control of a promoter which is not the natural promoter is termed a heterologous nucleic acid. The promoters that are suitable for use in the present invention are known to those skilled in the art and may be constitutive or inducible, and may be endogenous or heterologous.

The term "comprising" also means "consisting of" or "consisting essentially of". The term "consisting essentially of" means that the sequence may contain 1, 2, 3, 4, 5, 6, 7, 8, 9 or 10 additions, substitutions or deletions relative to the sequences described in the SEQ ID NOs.

Recombinant Microorganisms

The microorganism according to the present invention may be a eukaryotic or prokaryotic microorganism.

In a first embodiment, the microorganism is a eukaryote. Preferably, it is a yeast of the Saccharomycetales, Sporidiobolales and Schizosaccharomycetales orders. The yeast may be selected, for example, from *Pichia, Kluyveromyces, Saccharomyces, Schizosaccharomyces, Candida, Lipomyces, Rhodotorula, Rhodosporidium, Yarrowia*, or *Debaryomyces*. In one embodiment, the yeast is chosen from *Pichia pastoris, Kluyveromyces lactis, Kluyveromyces marxianus, Saccharomyces cerevisiae, Saccharomyces carlsbergensis, Saccharomyces diastaticus, Saccharomyces douglasii, Saccharomyces kluyveri, Saccharomyces norbensis, Saccharomyces oviformis, Schizosaccharomyces pombe, Candida albicans, Candida tropicalis, Rhodotorula glutinis, Rhodosporidium toruloides, Yarrowia lipolytica, Debaryomyces hansenii* and *Lipomyces starkeyi*. In a preferred embodiment, the microorganism is a *Saccharomyces* yeast, preferably a *Saccharomyces cerevisiae* yeast. Alternatively, the microorganism may be a fungus, preferably a filamentous fungus. Preferably, it is chosen from *Aspergillus, Trichoderma, Neurospora, Podospora, Endothia, Mucor, Cochiobolus* or *Pyricularia*. Preferentially, the fungus is chosen from *Aspergillus nidulans, Aspergillus niger, Aspergillus awomari, Aspergillus oryzae, Aspergillus terreus, Neurospora crassa, Trichoderma reesei* and *Trichoderma viride*.

In a second embodiment, the microorganism is a prokaryote. Preferably, it is a bacterium, notably chosen from the phylum Acidobacteria, Actinobacteria, Aquificae, Bacterioidetes, Chlamydiae, Chlorobi, Chloroflexi, Chrysiogenetes, Cyanobacteria, Deferribacteres, Deinococcus-Thermus, Dictyoglomi, Fibrobacteres, Firmicutes, Fusobacteria, Gemmatimonadetes, Nitrospirae, Planctomycetes, Proteobacteria, Spirochaetes, Thermodesulfobacteria, Thermomicrobia, Thermotogae or Verrucomicrobia. Preferably, the bacterium belongs to the genus *Acaryochloris, Acetobacter, Actinobacillus, Agrobacterium, Alicyclobacillus, Anabaena, Anacystis, Anaerobiospirillum, Aquifex, Arthrobacter, Arthrospira, Azobacter, Bacillus, Brevibacterium, Burkholderia, Chlorobium, Chromatium, Chlorobaculum, Clostridium, Corynebacterium, Cupriavidus, Cyanothece, Enterobacter, Deinococcus, Erwinia, Escherichia, Geobacter, Gloeobacter, Gluconobacter, Hydrogenobacter, Klebsiella, Lactobacillus, Lactococcus, Mannheimia, Mesorhizobium, Methylobacterium, Microbacterium, Microcystis, Nitrobacter, Nitrosomonas, Nitrospina, Nitrospira, Nostoc, Phormidium, Prochlorococcus, Pseudomonas, Ralstonia, Rhizobium, Rhodobacter, Rhodococcus, Rhodopseudomonas, Rhodospirillum, Salmonella, Scenedesmun, Serratia, Shigella, Staphylococcus, Streptomyces, Synechoccus, Synechocystis, Thermosynechococcus, Trichodesmium* or *Zymomonas*. More preferably, the bacterium is chosen from the species *Agrobacterium tumefaciens, Anaerobiospirillum succiniciproducens, Actinobacillus succinogenes, Aquifex aeolicus, Aquifex pyrophilus, Bacillus subtilis, Bacillus amyloliquefacines, Brevibacterium ammoniagenes, Brevibacterium immariophilum, Clostridium pasteurianurn, Clostridium ljungdahlii, Clostridium acetobutylicum, Clostridium beigerinckii, Corynebacterium glutamicum, Cupriavidus necator, Cupriavidus metallidurans, Enterobacter sakazakii, Escherichia coli, Gluconobacter oxydans, Hydrogenobacter thermophilus, Klebsiella oxytoca, Lactococcus lactis, Lactobacillus plantarum, Mannheimia succiniciproducens, Mesorhizobium loti, Pseudomonas aeruginosa, Pseudomonas mevalonii, Pseudomonas pudica, Pseudomonas putida, Pseudomonas fluorescens, Rhizobium etli, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei, Staphylococcus aureus, Streptomyces coelicolor, Zymomonas mobilis, Acaryochloris marina, Anabaena variabilis, Arthrospira platensis, Arthrospira maxima, Chlorobium tepidum, Chlorobaculum* sp., *Cyanothece* sp., *Gloeobacter violaceus, Microcystis aeruginosa, Nostoc punctiforme, Prochlorococcus marinus, Synechococcus elongatus, Synechocystis* sp., *Thermosynechococcus elongatus, Trichodesmium erythraeum* and *Rhodopseudomonas palustris*. In a preferred embodiment, the microorganism is an *Escherichia coli* bacterium, for example *E. coli* BL21, *E. coli* BL21 (DE3), *E. coli* MG1655 or *E. coli* W31 10 and derivatives thereof. In an alternative embodiment, the microorganism is a bacterium of the *Streptomyces* genus, in particular *Streptomyces venezuelae*.

The microorganisms may have been modified to increase the production of tyrosine and/or phenylalanine, preferably tyrosine. Notably, the genes responsible for the feedback inhibition of the production of tyrosine and/or phenylalanine, preferably of tyrosine, may be inactivated. Alternatively or cumulatively, the pathway for the biosynthesis of tyrosine and/or phenylalanine, preferably of tyrosine, may be optimized, notably by redirecting the flow of carbon from other metabolic pathways toward that of tyrosine and/or phenylalanine, preferably of tyrosine. These modifications and these genes are well known to those skilled in the art (see U.S. Pat. No. 8,809,028; Pandey et al., 2016, Biotechnol. Adv., 34, 634-662).

Thus, in one embodiment, the microorganism produces large amounts of tyrosine and/or of phenylalanine, in particular from a simple carbon source such as glucose.

Modifications Enabling the Production of Hesperidin and/or Diosmin

The recombinant microorganism according to the present invention was modified to produce hesperidin and/or diosmin. Notably, to enable the microorganism to synthesize hesperidin and/or diosmin from hesperetin and/or from diosmetin, respectively, the microorganism was modified to introduce the enzymes required for the glycosylation of hesperetin and/or of diosmetin in position 7 and for the transfer of a rhamnose in position 6 of the glucose of hesperetin-7-O-glucoside and/or diosmetin-7-O-glucoside.

In a first embodiment, the recombinant microorganism is capable of producing hesperetin and/or diosmetin: in particular, it has been modified for this purpose. In an alternative embodiment, hesperetin and/or diosmetin may be provided to the microorganism, for example by adding these compounds to the culture medium.

In one particular embodiment, the microorganism produces hesperidin. Diosmin may then be prepared from hesperidin by chemical conversion, notably by oxidation.

In a preferred embodiment, the microorganism produces hesperidin and diosmin.

Thus, the recombinant microorganism comprises:

a. a heterologous nucleic acid sequence coding for a flavanone 7-O-beta-D-glucosyltransferase (UGT) which is capable of adding a glucose in position 7 of hesperetin and/or diosmetin;

b. a heterologous nucleic acid sequence coding for a 6-O-rhamnosyltransferase (RhaT) which is capable of transferring a rhamnose into position 6 of the glucose of hesperetin-7-O-glucoside and/or diosmetin-7-O-glucoside; and c. a heterologous nucleic acid sequence coding for a UDP-glucose 4,6-dehydratase/UDP-4-keto-6-deoxy-D-glucose 3,5-epimerase/UDP-4-keto-L-rhamnose-reductase (RHM) which is capable of producing UDP-rhamnose.

In one embodiment, the flavanone 7-O-beta-D-glucosyltransferase (UGT), 6"-O-rhamnosyltransferase (RhaT) and UDP-glucose 4,6-dehydratase/UDP-4-keto-6-deoxy-D-glucose 3,5-epimerase/UDP-4-keto-L-rhamnose-reductase (RHM) are enzymes that are heterologous to the microorganism.

UGT: Flavanone 7-O-beta-glucosyltransferase

UGT is an enzyme which performs the transfer of a glucose into position 7 of hesperetin and/or diosmetin. The name of UGT is UDP-glucose: flavanone 7-O-beta-D-glucosyltransferase or flavanone 7-O-beta-D-glucosyltransferase. It is also referred to by the following names: uridine diphosphoglucose-flavanone 7-O-glucosyltransferase, naringenin 7-O-glucosyltransferase, and hesperetin 7-O-glucosyl-transferase. This enzyme belongs to the class EC 2.4.1.185.

The inventors had to identify and select enzymes that are capable of accepting hesperetin and/or diosmetin as a substrate and of adding a glucose in position 7 of these compounds. Preferably, the enzyme is selected so as to have a preference for glycosylation in position 7 of hesperetin and/or diosmetin. In a preferred embodiment, the enzyme is specific for position 7 of hesperetin and/or diosmetin.

The microorganism thus comprises a heterologous nucleic acid sequence coding for a flavanone 7-O-beta-D-glucosyltransferase (UGT) which is capable of adding a glucose in position 7 of hesperetin and diosmetin.

The term "7-O-beta-glycosyltransferase activity" refers to a UGT enzyme which is capable of adding a glucose in position 7 of a flavonoid. To determine whether there is 7-O-beta-glycosyltransferase activity, an enzymatic test may be performed, which consists of the in vitro incubation of the flavanone 7-O-beta-D-glucosyltransferase enzyme in the presence of NAD(P)H, $O_2$, and of a flavonoid, under optimum conditions (pH, ions, etc.), and observation by UPLC-MS and comparison with the standard expected for the appearance of a flavonoid containing an additional glucose in position 7. Preferably, the flavonoid is hesperetin or diosmetin and the flavonoid containing an additional glucose in position 7 is their form with an additional glucose in position 7, i.e. hesperetin 7-O-glucoside and diosmetin 7-O-glucoside.

This enzyme is present only in higher eukaryotes, in particular in plants. For example, the enzyme may originate from plants of the genus *Citrus*, in particular *Citrus maxima, Citrus sinensis, Citrus clementina, Citrus mitis* and *Citrus* x *paradisi, Lysium*, in particular *Lysium barbarum, Petunia*, in particular *Petunia* x *hybrida, Arabidopsis*, in particular *Arabidopsis thaliana*, or *Scutellaria*, in particular *Scutellaria baicalensis.*

In one embodiment, the UGT is an enzyme from *Arabidopsis thaliana, Scutellaria baicalensis* or *Homo sapiens*. Preferably, the UGT is an enzyme from *Arabidopsis thaliana* or from *Scutellaria baicalensis.*

In a preferred embodiment, the UGT is an enzyme from *Citrus sinensis*, from *Citrus clementina*, from *Arabidopsis thaliana*, from *Scutellaria baicalensis* or from *Homo sapiens*, preferably from *Citrus sinensis* or from *Scutellaria baicalensis.*

In a particular embodiment, the UGT is selected from enzymes comprising a sequence chosen from SEQ ID NOs: 91, 93, 95, 97, 99 and 101 and polypeptides comprising a sequence having at least 60, 70, 80, 85, 90 or 95% sequence identity with one of these sequences and having flavanone 7-O-beta-D-glucosyltransferase activity, preferably selected from enzymes comprising a sequence chosen from SEQ ID NOs: 91, 93, 95 and 97 and polypeptides comprising a sequence having at least 60, 70, 80, 85, 90 or 95% sequence identity with one of these sequences and having flavanone 7-O-beta-D-glucosyltransferase activity, notably with hesperetin and/or diosmetin as substrate.

In a preferred embodiment, the UGT is selected from enzymes comprising a sequence chosen from SEQ ID NOs: 113, 115, 91, 93, 95, 97, 99 and 101 and polypeptides comprising a sequence having at least 60, 70, 80, 85, 90 or 95% sequence identity with one of these sequences and having flavanone 7-O-beta-D-glucosyltransferase activity, preferably selected from enzymes comprising a sequence chosen from SEQ ID NOs: 113, 115, 91, 93, 95 and 97 and polypeptides comprising a sequence having at least 60, 70, 80, 85, 90 or 95% sequence identity with one of these sequences and having flavanone 7-O-beta-D-glucosyltransferase activity. More particularly preferably, the UGT is selected from enzymes comprising a sequence chosen from SEQ ID NOs: 113, 115 and 95 and polypeptides comprising a sequence having at least 60, 70, 80, 85, 90 or 95% sequence identity with one of these sequences and having flavanone 7-O-beta-D-glucosyltransferase activity.

Thus, the UGT may be from *Arabidopsis thaliana*. The nucleic acid sequences coding for this enzyme and protein sequences are described in NCBI under the reference numbers NM_119576 and NP_567995.1, respectively, and more particularly in SEQ ID NO: 91. The protein is also described in UniProtKB/Swiss Prot under the reference number UGT73B1. Alternatively, the UGT is from *Scutellaria baicalensis*. In a first aspect, the nucleic acid sequences coding for a first UGT and protein sequences are described in NCBI under the reference numbers KU712253 and AMK52071.1, respectively, and more particularly in SEQ ID NO: 93. The protein is described in UniProtKB/Swiss Prot under the reference number A0A140DPB7. In a second aspect, the nucleic acid sequences coding for a second UGT and protein sequences are described in NCBI under the reference numbers KU712254 and AMK52072.1, respectively, and more particularly in SEQ ID NO: 95. The protein is described in UniProtKB/Swiss Prot under the reference number A0A140DPB8. In a third aspect, the nucleic acid sequences coding for a third UGT and protein sequences are described in NCBI under the reference numbers KU712255 and AMK52073.1, respectively, and more particularly in SEQ ID NO: 97. The protein is described in UniProtKB/Swiss Prot under the reference number A0A140DPB9.

Moreover, the UGT may be from *Homo sapiens*. In a first aspect, the UGT is UGT1A6 (UDP glucuronosyltransferase family 1 member A6). The protein is described in UniProtKB/Swiss Prot under the reference number P19224. The consensus coding sequence is described in NCBI under the number CCDS2507.1. The sequence of this enzyme is described in SEQ ID NO: 99. In a second aspect, the UGT is UGT1A7 (UDP glucuronosyltransferase family 1 member A7). The protein is described in UniProtKB/Swiss Prot under the reference number Q9HAW7. The consensus coding sequence is described in NCBI under the number CCDS2506.1. The sequence of this enzyme is described in SEQ ID NO: 101.

The UGT may also be from *Citrus*, in particular from *Citrus sinensis* or *Citrus clementina*. In particular, the UGT from *Citrus sinensis* is described in SEQ ID NO: 113. A nucleotide sequence coding for this enzyme is described in SEQ ID NO: 114. The UGT from *Citrus clementina* is described in SEQ ID NO: 115. A nucleotide sequence coding for this enzyme is described in SEQ ID NO: 116.

In a preferred embodiment, the UGT is selected from enzymes comprising a sequence chosen from SEQ ID NOs: 113 and 95 and polypeptides comprising a sequence having at least 60, 70, 80, 85, 90 or 95% sequence identity with one of these sequences and having flavanone 7-O-beta-D-glucosyltransferase activity, preferably selected from enzymes comprising a sequence chosen from SEQ ID NO: 113 and polypeptides comprising a sequence having at least 60, 70, 80, 85, 90 or 95% sequence identity with this sequence and having flavanone 7-O-beta-D-glucosyltransferase activity.

RhaT: 6-O-rhamnosyltransferase

RhaT is an enzyme which performs the transfer of a rhamnose into position 6 of the glucose of hesperetin-7-O-glucoside and/or diosmetin-7-O-glucoside. RhaT is a 6-O-rhamnosyltransferase. This enzyme belongs to the class EC 2.4.1.B53.

The inventors had to identify and select enzymes that are capable of accepting hesperetin-7-O-glucoside and/or diosmetin-7-O-glucoside as a substrate and of adding a rhamnose in position 6 of the glucose of these compounds.

The microorganism thus comprises a heterologous nucleic acid sequence coding for a 6-O-rhamnosyltransferase (RhaT) which is capable of transferring a rhamnose into position 6 of the glucose of hesperetin-7-O-glucoside and/or diosmetin-7-O-glucoside. This enzyme is present only in higher eukaryotes, in particular in plants.

The term "6-O-rhamnosyltransferase activity" means the addition of a rhamnose in position 6 of the glucose by the enzyme RhaT. To determine whether there is 6-O-rhamnosyltransferase activity, an enzymatic test may be performed, which consists of the in vitro incubation of the 6-O-rhamnosyltransferase enzyme in the presence of NAD(P)H, $O_2$, and of a flavonoid, under optimum conditions (pH, ions, etc.), and observation by UPLC-MS and comparison with the standard expected for the appearance of a flavonoid in which a rhamnose is added in position 6 of the glucose. Preferably, the flavonoid is hesperetin 7-O-glucoside or diosmetin 7-O-glucoside and the flavonoids in which a rhamnose is added in position 6 of the glucose are hesperidin and diosmin.

Preferably, this enzyme is an enzyme produced by a plant of the genus *Citrus* or *Petunia hybrida*, preferably of the species *Citrus sinensis, Citrus maxima*, or *Citrus clementina*. Preferably, the enzyme is an enzyme originating from *Citrus sinensis* or *Citrus clementina*.

In a particular embodiment, the 6-O-rhamnosyltransferase is selected from enzymes comprising a sequence chosen from SEQ ID NOs: 103, 105 and polypeptides comprising a sequence having at least 60, 70, 80, 85, 90 or 95% sequence identity with one of these sequences and having 6-O-rhamnosyltransferase activity.

Thus, the RhaT may be from *Citrus clementina*. It is described in the GenBank database from NCBI under the number XM_006420965 for the nucleic acid sequence and under the number XP_006421028 for the protein sequence, and more particularly in SEQ ID NO: 103. The protein is described in UniProtKB/Swiss Prot under the reference number V4RJL6.

The RhaT may also be from *Citrus sinensis*. It is described in the GenBank database from NCBI under the number DQ119035 for the nucleic acid sequence and under the number ABA18631.1 for the protein sequence, and more particularly in SEQ ID NO: 105. The protein is described in UniProtKB/Swiss Prot under the reference number A7ISD3.

In a particular embodiment, the RhaT is from *Citrus sinensis* and is an enzyme comprising the sequence SEQ ID NO: 105 or a polypeptide comprising a sequence having at least 60, 70, 80, 85, 90 or 95% sequence identity therewith and having 6"-O-rhamnosyltransferase activity.

In a preferred embodiment, the RhaT is selected from enzymes comprising a sequence chosen from SEQ ID NO: 103 and polypeptides comprising a sequence having at least 60, 70, 80, 85, 90 or 95% sequence identity with this sequence and having 6"-O-rhamnosyltransferase activity.

RHM: UDP-glucose 4,6-dehydratase/UDP-4-keto-6-deoxy-D-glucose 3,5-epimerase/UDP-4-keto-L-rhamnose-reductase RHM is a trifunctional enzyme UDP-glucose 4,6-dehydratase/UDP-4-keto-6-deoxy-D-glucose 3,5-epimerase/UDP-4-keto-L-rhamnose-reductase. This enzyme is capable of producing UDP-rhamnose from UDP-glucose. This enzyme belongs to the class EC 4.2.1.76. UDP-rhamnose is necessary for 6-O-rhamnosyltransferase (RhaT) activity.

The microorganism thus comprises a heterologous nucleic acid sequence coding for a UDP-glucose 4,6-dehydratase/UDP-4-keto-6-deoxy-D-glucose 3,5-epimerase/UDP-4-keto-L-rhamnose-reductase (RHM) which is capable of producing UDP-rhamnose. This enzyme is present only in higher eukaryotes, in particular in plants.

The term "UDP-glucose 4,6-dehydratase/UDP-4-keto-6-deoxy-D-glucose 3,5-epimerase/UDP-4-keto-L-rhamnose-reductase activity" means the transformation of UDP-glucose into UDP-rhamnose. To determine whether there is UDP-glucose 4,6-dehydratase/UDP-4-keto-6-deoxy-D-glucose 3,5-epimerase/UDP-4-keto-L-rhamnose-reductase activity, an enzymatic test may be performed, which consists of the in vitro incubation of the UDP-glucose enzyme, NAD(P)H and $O_2$, under optimum conditions (pH, ions, etc.), and observation by UPLC-MS and comparison with the standard expected for the appearance of a UDP-rhamnose.

Preferably, this enzyme is an enzyme produced by a plant of the genus *Citrus*, in particular *Citrus sinensis*, or by *Arabidopsis thaliana*.

In a particular embodiment, the UDP-glucose 4,6-dehydratase/UDP-4-keto-6-deoxy-D-glucose 3,5-epimerase/UDP-4-keto-L-rhamnose-reductase is selected from enzymes comprising a sequence chosen from SEQ ID NOs: 107, 109 and 111 and polypeptides comprising a sequence having at least 60, 70, 80, 85, 90 or 95% sequence identity with one of these sequences and having UDP-glucose 4,6- dehydratase/UDP-4-keto-6-deoxy-D-glucose 3,5-epimerase/UDP-4-keto-L-rhamnose-reductase activity.

The RHM may be from *Citrus sinensis*. It is described in the GenBank database from NCBI under the number XM_006477756 for the nucleic acid sequence and under the number XP_006477819.1 for the protein sequence, and more particularly in SEQ ID NO: 107.

The RHM may also be from *Arabidopsis thaliana*. In a first aspect, the protein is described in the GenBank database from NCBI under the number AY081471 for the nucleic acid sequence and under the number AAM10033.1 for the protein sequence, and more particularly in SEQ ID NO: 109. The protein is described in UniProtKB/Swiss Prot under the reference number Q9SYM5. In a second aspect, the protein is described in the GenBank database from NCBI under the number AJ565874 for the nucleic acid sequence and under the number CAD92667.1 for the protein sequence, and more particularly in SEQ ID NO: 111. The protein is described in UniProtKB/Swiss Prot under the reference number Q9LPG6.

In a particular embodiment, the RHM is an enzyme comprising a sequence chosen from SEQ ID NOs: 107 and 109 and polypeptides comprising a sequence having at least 60, 70, 80, 85, 90 or 95% sequence identity with one of these sequences and having UDP-glucose 4,6-dehydratase/UDP-4-keto-6-deoxy-D-glucose 3,5-epimerase/UDP-4-keto-L-rhamnose-reductase activity.

In a preferred embodiment, the RHM is selected from enzymes comprising a sequence chosen from SEQ ID NO: 107 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity.

Combination of Enzymes

In a particular embodiment, the recombinant microorganism comprises:

- a heterologous nucleic acid sequence coding for a flavanone 7-O-beta-D-glucosyltransferase (UGT) from *Arabidopsis thaliana, Scutellaria baicalensis* or *Homo sapiens*, preferably from *Arabidopsis thaliana* or from *Scutellaria baicalensis*, preferably a flavanone 7-O-beta-D-glucosyltransferase (UGT) selected from enzymes comprising a sequence chosen from SEQ ID NOs: 113, 115, 91, 93, 95, 97, 99 and 101 and polypeptides comprising a sequence having at least 60, 70, 80, 85, 90 or 95% sequence identity with one of these sequences and having flavanone 7-O-beta-D-glucosyltransferase activity; in particular a flavanone 7-O-beta-D-glucosyltransferase (UGT) comprising a sequence chosen from SEQ ID NOs: 113, 115, 91, 93, 95 and 97 and polypeptides comprising a sequence having at least 60, 70, 80, 85, 90 or 95% sequence identity with one of these sequences and having flavanone 7-O-beta-D-glucosyltransferase activity, and most particularly preferably comprising a sequence chosen from SEQ ID NOs: 113, 115 and 95 and polypeptides comprising a sequence having at least 60, 70, 80, 85, 90 or 95% sequence identity with one of these sequences and having flavanone 7-O-beta-D-glucosyltransferase activity, in particular comprising a sequence chosen from SEQ ID NOs: 113 and 95 and polypeptides comprising a sequence having at least 60, 70, 80, 85, 90 or 95% sequence identity with one of these sequences and having flavanone 7-O-beta-D-glucosyltransferase activity;
- a heterologous nucleic acid sequence coding for a 6-O-rhamnosyltransferase (RhaT) of the genus *Citrus* or *Petunia hybrida*, preferably *Citrus sinensis, Citrus maxima*, or *Citrus clementina*, even more preferably *Citrus sinensis* or *Citrus clementina*, preferably a 6-O-rhamnosyltransferase (RhaT) comprising a sequence chosen from SEQ ID NOs: 103 and 105 and polypeptides comprising a sequence having at least 60, 70, 80, 85, 90 or 95% sequence identity with one of these sequences and having 6-O-rhamnosyltransferase activity, and preferably an RhaT comprising a sequence chosen from SEQ ID NO: 103 and polypeptides comprising a sequence having at least 60, 70, 80, 85, 90 or 95% sequence identity with this sequence and having 6"-O-rhamnosyltransferase activity; and
- a heterologous nucleic acid sequence coding for a UDP-glucose 4,6-dehydratase/UDP-4-keto-6-deoxy-D-glucose 3,5-epimerase/UDP-4-keto-L-rhamnose-reductase (RHM) from *Citrus sinensis* or from *Arabidopsis thaliana*, preferably an RHM comprising a sequence chosen from SEQ ID NOs: 107, 109 and 111 and polypeptides comprising a sequence having at least 60, 70, 80, 85, 90 or 95% sequence identity with one of these sequences and having UDP-glucose 4,6-dehydratase/UDP-4-keto-6-deoxy-D-glucose 3,5-epimerase/UDP-4-keto-L-rhamnose-reductase activity, in particular an RHM comprising a sequence selected from SEQ ID NOs: 107 and 109 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity, and preferably an RHM comprising a sequence selected from SEQ ID NO: 107 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity.

In another particular embodiment, the recombinant microorganism comprises a heterologous nucleic acid sequence coding for a 6-O-rhamnosyltransferase (RhaT) and a heterologous nucleic acid sequence coding for a UDP-glucose 4,6-dehydratase/UDP-4-keto-6-deoxy-D-glucose 3,5-epimerase/UDP-4-keto-L-rhamnose-reductase (RHM) as defined in the preceding embodiment and a heterologous nucleic acid sequence coding for a flavanone 7-O-beta-D-glucosyltransferase (UGT) from *Arabidopsis thaliana, Scutellaria baicalensis* or *Homo sapiens*, preferably from *Arabidopsis thaliana* or from *Scutellaria baicalensis*, preferably a flavanone 7-O-beta-D-glucosyltransferase (UGT) selected from enzymes comprising a sequence chosen from SEQ ID NOs: 91, 93, 95, 97, 99 and 101 and polypeptides comprising a sequence having at least 60, 70, 80, 85, 90 or 95% sequence identity with one of these sequences and having flavanone 7-O-beta-D-glucosyltransferase activity; in particular a flavanone 7-O-beta-D-glucosyltransferase (UGT) comprising a sequence chosen from SEQ ID NOs: 91, 93, 95 and 97 and polypeptides comprising a sequence having at least 60, 70, 80, 85, 90 or 95% sequence identity with one of these sequences and having flavanone 7-O-beta-D-glucosyltransferase activity.

In a preferred embodiment, the microorganism comprises:

- a heterologous nucleic acid sequence coding for a flavanone 7-O-beta-D-glucosyltransferase (UGT) selected from enzymes comprising a sequence chosen from SEQ ID NOs: 113, 115 and 95 and polypeptides comprising a sequence having at least 60, 70, 80, 85, 90 or 95% sequence identity with one of these sequences and having flavanone 7-O-beta-D-glucosyltransferase activity, preferably selected from enzymes comprising a sequence chosen from SEQ ID NOs: 113 and 95 and polypeptides comprising a sequence having at least 60, 70, 80, 85, 90 or 95% sequence identity with one of these sequences and having flavanone 7-O-beta-D-glucosyltransferase activity, and more particularly preferably selected from enzymes comprising a sequence chosen from SEQ ID NO: 113 and polypeptides comprising a sequence having at least 60, 70, 80, 85, 90 or 95% sequence identity with this sequence and having flavanone 7-O-beta-D-glucosyltransferase activity; and a heterologous nucleic acid sequence coding for a 6"-O-rhamnosyltransferase selected from enzymes comprising a sequence chosen from SEQ ID NOs: 103 and polypeptides comprising a sequence having at least 60, 70, 80, 85, 90 or 95% sequence identity with this sequence and having 6"-O-rhamnosyltransferase activity; and a heterologous nucleic acid sequence coding for a UDP-glucose 4,6-dehydratase/UDP-4-keto-6-deoxy-D-glucose 3,5-epimerase/UDP-4-keto-L-rhamnose-reductase selected from enzymes comprising a sequence chosen from SEQ ID NO: 107 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity. In a particular embodiment, the enzymes described above are enzymes from higher eukaryotes, preferably plant enzymes. In a particular embodiment, the enzymes originate from plants of the same genus, for example of the same species.

Modifications Enabling the Production of Hesperetin and/or Diosmetin

As indicated previously, either hesperetin and/or diosmetin are supplied to the microorganism, or the microorganism is capable of producing hesperetin and/or diosmetin. In particular, the microorganism is capable or has been modified to be capable of producing hesperetin and/or diosmetin. The inventors thus also developed a biosynthetic pathway enabling the microorganism to produce hesperetin and/or diosmetin.

From Naringenin/Apigenin to Hesperetin/Diosmetin

Hesperetin and/or diosmetin may be obtained from naringenin and apigenin.

Several biosynthetic strategies were possible. To prepare hesperetin and/or diosmetin, it is necessary to make two modifications: methylation of the hydroxyl in position 4' and hydroxylation of position 3'. Thus, to increase the specificity of methylation of the hydroxyl in position 4', it appears logical to first perform methylation of the hydroxyl group already present before adding a second hydroxyl group in position 3'. On the contrary, the inventors arrived at the conclusion that it was necessary first to perform the hydroxylation and then the methylation, despite the risk of the problem of methylation specificity due to the introduction of the second hydroxyl.

F3'H: Flavonoid 3'-monooxygenase

Flavonoid 3'-monooxygenase (F3'H) is an enzyme which performs the addition of a hydroxyl group in position 3' of naringenin and/or apigenin. This enzyme belongs to the class EC 1.14.14.82. It is also known as flavone 3'-hydroxylase.

The inventors had to identify and select enzymes that are capable of accepting naringenin and/or apigenin as a substrate and of adding a hydroxyl group in position 3' of these compounds. Preferably, the enzyme is selected so as to have a preference for hydroxylation in position 3' of naringenin and/or apigenin. In a preferred embodiment, the enzyme is specific for the 3' position of naringenin and/or apigenin, in particular relative to the 5' position so as to avoid a double hydroxylation in positions 3' and 5', and preferably also to avoid hydroxylation in position 5'.

Flavonoid 3'-monooxygenase (F3'H) is an enzyme which performs the addition of a hydroxyl group in position 3' of naringenin and/or apigenin. This enzyme belongs to the class EC 1.14.14.82. It is also known as flavonoid 3'-hydroxylase.

The term "flavonoid 3'-monooxygenase activity" means the transformation of a flavonoid into a 3'-hydroxylated flavonoid by a CPR-dependent F3'H enzyme. To determine whether there is flavonoid 3'-monooxygenase activity, an enzymatic test may be performed, which consists of the in vitro incubation of the flavonoid 3'-monooxygenase enzyme in the presence of NAD(P)H, $O_2$, and of a flavonoid, under optimum conditions (pH, ions, etc.), and observation by UPLC-MS and comparison with the standard expected for the appearance of a 3'-hydroxylated flavonoid. Preferably, the flavonoid is naringenin or apigenin and the 3'-hydroxylated flavonoid is the 3'-hydroxylated form thereof, i.e. eriodictyol or luteolin.

The microorganism may thus comprise a heterologous nucleic acid sequence coding for a flavonoid 3'-monooxygenase (F3'H) which is capable of adding a hydroxyl in position 3' of naringenin and/or apigenin.

In one embodiment, the F3'H is a plant enzyme, notably from plants of the genus *Allium, Arabidopsis, Brassica, Callistephus, Columnea, Citrus, Dianthus, Gentiana, Gerbera, Glycine, Fragaria, Ipomoea, Malus, Matthiola, Osteospermum, Oryza, Phanerochaete, Perilla, Petroselinum, Pelargonium, Pilosella, Petunia, Sinningia, Sorghum, Torenia, Vitis* or *Zea*, for example *Allium cepa, Arabidopsis thaliana, Brassica napus, Columnea hybrida, Callistephus chinensis, Citrus sinensis, Citrus clementina, Dianthus caryophyllus, Fragaria vesca, Fragaria* x *ananassa, Gerbera hybrida, Glycine max, Gentiana triflora, Ipomoea nil, Ipomoea purpurea, Ipomoea tricolor, Matthiola incana, Malus domestica*, Osteospermum hybrid cultivar, *Oryza sativa, Phanerochaete chrysosporium, Pilosella officinarum, Petroselinum crispum, Pelargonium* x *hortorum, Perilla frutescens* var. *crispa, Petunia* x *hybrida, Sinningia cardinalis, Sorghum bicolor, Torenia* sp, Torenia hybrid cultivar, *Vitis vinifera* or *Zea mays*. In a more specific embodiment, the F3'H is an enzyme from plants of the genus *Allium, Brassica, Callistephus, Columnea, Citrus, Dianthus, Gentiana, Gerbera, Glycine, Fragaria, Ipomoea, Malus, Matthiola, Osteospermum, Oryza, Phanerochaete, Perilla, Petroselinum, Pelargonium, Pilosella, Petunia, Sinningia, Sorghum, Torenia, Vitis* or *Zea*, for example *Allium cepa, Brassica napus, Columnea hybrida, Callistephus chinensis, Citrus sinensis, Citrus clementina, Dianthus caryophyllus, Fragaria vesca, Fragaria* x *ananassa, Gerbera hybrida, Glycine max, Gentiana triflora, Ipomoea nil, Ipomoea purpurea, Ipomoea tricolor, Matthiola incana, Malus domestica*, Osteospermum hybrid cultivar, *Oryza sativa, Phanerochaete chrysosporium, Pilosella officinarum, Petroselinum crispum, Pelargonium* x *hortorum, Perilla frutescens* var. *crispa, Petunia* x *hybrida, Sinningia cardinalis, Sorghum bicolor, Torenia* sp, Torenia hybrid cultivar, *Vitis vinifera* or *Zea mays*.

Preferably, the F3'H is an enzyme from *Perilla frutescens* var. *crispa, Petunia* x *hybrida, Callistephus chinensis, Gerbera hybrida, Citrus clementina*, Osteospermum hybrid cultivar, *Phanerochaete chrysosporium, Streptomyces avermitilis, Citrus sinensis, Arabidopsis thaliana* or *Pilosella officinarum*. In particular, the F3'H may be an enzyme from *Perilla frutescens* var. *crispa, Petunia* x *hybrida, Callistephus chinensis, Gerbera hybrida, Citrus sinensis* and *Pilosella officinarum.*

In a particular embodiment, the F3'H is selected from enzymes comprising a sequence chosen from SEQ ID NOs: 1, 3, 5, 7, 9, 11, 13, 15, 17, 19, 21 and 121, in particular from SEQ ID NOs: 1, 3, 5, 7, 9, 11, 13, 15, 17, 19 and 21 and polypeptides comprising a sequence having at least 60, 70, 80, 85, 90 or 95% sequence identity with one of these sequences and having flavonoid 3'-monooxygenase activity, preferably selected from enzymes comprising a sequence chosen from SEQ ID NOs: 1, 5, 7, 11, 17, 19 and 121, in particular from SEQ ID NOs: 1, 5, 7, 11, 17 and 19 and polypeptides comprising a sequence having at least 60, 70, 80, 85, 90 or 95% sequence identity with one of these sequences and having flavonoid 3'-monooxygenase activity, notably with naringenin and/or apigenin as substrate and with hydroxylation in position 3'. In a particular embodiment, the F3'H is an enzyme comprising a sequence selected from SEQ ID NOs: 5, 7 and 17 and polypeptides comprising a sequence having at least 60, 70, 80, 85, 90 or 95% identity with one of these sequences and having flavonoid 3'-monooxygenase activity.

In a preferred embodiment, the F3'H is an enzyme comprising a sequence selected from SEQ ID NOs: 7, 11, 17 and 121 and polypeptides comprising a sequence having at least 60, 70, 75, 80, 85, 90 or 95% identity with one of these sequences and having flavonoid 3'-monooxygenase activity. Most particularly preferably, the F3'H may be an enzyme comprising a sequence selected from SEQ ID NOs: 7, 17 and 121 and polypeptides comprising a sequence having at least 60, 70, 75, 80, 85, 90 or 95% identity with one of these sequences and having flavonoid 3'-monooxygenase activity.

Thus, the F3'H may be from *Perilla frutescens* var. *crispa*. The nucleic acid sequences coding for this enzyme and protein sequences are described in NCBI under the reference numbers AB045593.1 and BAB59005.1, respectively, and more particularly in SEQ ID NOs: 2 and 1.

The F3'H may be from *Phanerochaete chrysosporium*. The nucleic acid sequences coding for this enzyme and protein sequences are described in NCBI under the reference numbers AB597870.1 and BAL05157.1, respectively, and more particularly in SEQ ID NOs: 4 and 3.

The F3'H may be from *Petunia* x *hybrida*. The nucleic acid sequences coding for this enzyme and protein sequences are described in NCBI under the reference numbers AF155332.1 and AAD56282.1, respectively, and more particularly in SEQ ID NOs: 6 and 5.

The F3'H may be from *Callistephus chinensis*. In one embodiment, the nucleic acid sequences coding for this enzyme and protein sequences are described in NCBI under the reference numbers AF313488.1 and AAG49298.1, respectively, and more particularly in SEQ ID NOs: 8 and 7. In another embodiment, the nucleic acid sequences coding for this enzyme and protein sequences are described in NCBI under the reference numbers AF313489.1 and AAG49299.1, respectively, and more particularly in SEQ ID NOs: 10 and 9. The F3'H may be from *Gerbera hybrida*. The nucleic acid sequences coding for this enzyme and protein sequences are described in NCBI under the reference numbers DQ218417.1 and ABA64468.1, respectively, and more particularly in SEQ ID NOs: 12 and 11.

The F3'H may be from Osteospermum hybrid cultivar. The nucleic acid sequences coding for this enzyme and protein sequences are described in NCBI under the reference numbers DQ250711.1 and ABB29899.1, respectively, and more particularly in SEQ ID NOs: 14 and 13.

The F3'H may be from *Citrus clementina*. The nucleic acid sequences coding for this enzyme and protein sequences are described in NCBI under the reference numbers XM_006440673.1 and XP 006440736.1, respectively, and more particularly in SEQ ID NOs: 16 and 15.

The F3'H may be from *Citrus sinensis*. The nucleic acid sequences coding for this enzyme and protein sequences are described in NCBI under the reference numbers XM_006477592.2 et XP 006477655.1, respectively, and more particularly in SEQ ID NOs: 18 and 17.

The F3'H may be from *Pilosella officinarum*. The nucleic acid sequences coding for this enzyme and protein sequences are described in NCBI under the reference numbers DQ319866.2 and ABC47161.1, respectively, and more particularly in SEQ ID NOs: 20 and 19.

The F3'H may be from *Streptomyces avermitilis*. The nucleic acid sequences coding for this enzyme and protein sequences are described in NCBI under the reference numbers SAV_4539 et WP 010985964.1, respectively, and more particularly in SEQ ID NOs: 22 and 21.

The F3'H may be from *Arabidopsis thaliana*. A nucleic acid sequence coding for this enzyme and the protein sequence are described in NCBI under the reference numbers NM_120881.2 and NP_196416.1, respectively, and more particularly in SEQ ID NOs: 122 and 121.

Preferably, the F3'H is an enzyme comprising a sequence selected from SEQ ID NOs: 7, 11, 17 and 121 and polypeptides comprising a sequence having at least 75%, at least 80%, at least 85%, at least 90% or at least 95% identity with one of these sequences and having flavonoid 3'-monooxygenase activity. Most particularly preferably, the F3'H is an enzyme comprising a sequence selected from SEQ ID NOs: 7, 17 and 121 and polypeptides comprising a sequence having at least 75%, at least 80%, at least 85%, at least 90% or at least 95% identity with one of these sequences and having flavonoid 3'-monooxygenase activity.

According to a preferred embodiment, the F3'H is an enzyme comprising a sequence chosen from SEQ ID NO: 7 and polypeptides comprising a sequence having at least 75%, at least 80%, at least 85%, at least 90% or at least 95% sequence identity with the sequence SEQ ID NO: 7 and having flavonoid 3'-monooxygenase activity.

According to another particular embodiment, the F3'H is an enzyme comprising a sequence chosen from SEQ ID NO: 17 and polypeptides comprising a sequence having at least 75%, at least 80%, at least 85%, at least 90% or at least 95% sequence identity with the sequence SEQ ID NO: 17 and having flavonoid 3'-monooxygenase activity.

According to another particular embodiment, the F3'H is an enzyme comprising a sequence chosen from SEQ ID NO: 121 and polypeptides comprising a sequence having at least 70%, at least 75%, at least 80%, at least 85%, at least 90% or at least 95% sequence identity with the sequence SEQ ID NO: 121 and having flavonoid 3'-monooxygenase activity.

According to another particular embodiment, the F3'H is an enzyme comprising a sequence chosen from SEQ ID NO: 11 and polypeptides comprising a sequence having at least 75%, at least 80%, at least 85%, at least 90% or at least 95% sequence identity with the sequence SEQ ID NO: 11 and having flavonoid 3'-monooxygenase activity.

CPR: Cytochrome P450 Reductase

Flavonoid 3'-monooxygenase (F3'H) requires the presence of NADPH to perform the addition of the hydroxyl group.

Thus, in a preferred embodiment, the microorganism comprises a heterologous nucleic acid coding for a cytochrome P450 reductase, an NADPH-cytochrome P450 reductase. This enzyme belongs to the class EC 1.6.2.4.

Cytochrome P450 reductase originates from a eukaryote, notably from a yeast, for example of the genus *Saccharomycetales*, or from a plant, for example a plant of the genus *Arabidopsis, Ammi, Avicennia, Camellia, Camptotheca, Catharanthus, Citrus, Glycine, Helianthus, Lotus, Mesembryanthemum, Phaseolus, Physcomitrella, Pinus, Populus, Ruta, Saccharum, Solanum, Vigna, Vitis* or *Zea.*

In a preferred embodiment, the cytochrome P450 reductase originates from a eukaryote, for example from yeast, in particular from *Saccharomyces cerevisiae*, or from a plant, for example from *Catharanthus roseus* or *Arabidopsis thaliana.*

In a particular embodiment, the cytochrome P450 reductase is selected from enzymes comprising a sequence chosen from SEQ ID NOs: 23, 25, 27, 29 and 31 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23, 25, 29 and 31 and polypeptides comprising a sequence having at least 60, 70, 80, 85, 90 or 95% sequence identity with one of these sequences and having cytochrome P450 reductase activity. In a very particular embodiment, the cytochrome P450 reductase may be selected from enzymes comprising a sequence chosen from SEQ ID NO: 25 and polypeptides comprising a sequence having at least 60, 70, 80, 85, 90 or 95% sequence identity with this sequence and having cytochrome P450 reductase activity.

For example, the cytochrome P450 reductase may be from *Catharanthus roseus*. It is described in the GenBank database from NCBI under the number X69791.1 for the nucleic acid sequence and under the number CAA49446.1 for the protein sequence, and more particularly in SEQ ID NOs: 24 and 23, respectively. The protein is described in UniProtKB/Swiss Prot under the reference number Q05001.

The cytochrome P450 reductase may be from *Saccharomyces cerevisiae*. It is described in the GenBank database from NCBI under the number NM_001179172.1 for the nucleic acid sequence and under the number NP_011908.1 for the protein sequence, and more particularly in SEQ ID NOs: 26 and 25, respectively. The protein is described in UniProtKB/Swiss Prot under the reference number P16603.

The cytochrome P450 reductase may be chimeric. It is described in the article by Aigrain et al. (2009, EMBO Reports, 10, 742-747). The nucleic acid sequence coding for this enzyme and the protein sequence are described in SEQ ID NOs: 28 and 27, respectively. Moreover, the cytochrome P450 reductase may be from *Arabidopsis thaliana.* When the cytochrome P450 originates from *Arabidopsis thaliana*, it may be named ATR. It is described in the GenBank database from NCBI under the number NM_118585.4 for the nucleic acid sequence and under the number NP_194183.1 for the protein sequence, and more particularly in SEQ ID NOs: 30 and 29, respectively. The protein is described in UniProtKB/Swiss Prot under the reference number Q9SB48.

In addition, the cytochrome P450 reductase may be from *Arabidopsis thaliana* and may be described in the GenBank database from NCBI under the number NM_179141.2 for the nucleic acid sequence and under the number NP_849472.2 for the protein sequence, and more particularly in SEQ ID NOs: 32 and 31, respectively. The protein is described in UniProtKB/Swiss Prot under the reference number Q9SUM3.

In one embodiment, a new copy of a sequence coding for CPR as defined above is introduced into the yeast. In another embodiment, when the yeast is *Saccharomyces cerevisiae* and when the CPR originates from the same yeast, the promoter of the endogenous gene coding for CPR is replaced with a strong promoter. Thus, the expression of the CPR is increased relative to the wild-type yeast; the CPR is thus overexpressed in the modified yeast.

In one particular embodiment, the F3'H and the CPR are from the same origin, the same species.

OMT: O-methyltransferase

O-methyltransferases (OMT) are a very large family of enzymes having targets that are difficult to define. The inventors had to identify and select O-methyltransferases that are capable of methylating eriodictyol and/or luteolin in position 4' (para position). Preferably, the enzyme was selected so as to have a preference for methylation in position 4' of eriodictyol and/or luteolin. In a preferred embodiment, the enzyme is specific for position 4' of eriodictyol and/or luteolin. The term "specific" means that the methyl group introduced by the enzyme onto eriodictyol and/or luteolin is found in position 4' in 60% of the cases, the remainder being introduced into position 3', preferably in 70% of the cases, and even more preferably in 80% of the cases.

The term "4'-O-methyltransferase activity" means the transformation of a 4'-hydroxyflavonoid into a 4'-methoxyflavonoid by a 4'-O-methyltransferase enzyme. To determine whether there is 4'-O-methyltransferase activity, an enzymatic test may be performed, which consists of the in vitro incubation of a mixture composed of the 4'-O-methyltransferase enzyme, a 4'-hydroxyflavonoid and S-adenosyl-L-methionine, under optimum conditions (pH, temperature, ions, etc.). After a certain incubation time, the appearance of the 4'-methoxyflavonoid is observed in UPLC-MS in comparison with the expected standard.

In the present case, the 4'-hydroxyflavonoid is eriodictyol or luteolin, which will be transformed, respectively, into their 4'-methoxyflavonoid form, i.e. into hesperetin or diosmetin.

The microorganism may thus comprise a heterologous nucleic acid sequence coding for an O-methyltransferase which is capable of methylating eriodictyol and/or luteolin in position 4'.

This enzyme is present only in higher eukaryotes, in particular in plants.

In one embodiment, the O-methyltransferase (OMT) is an enzyme from *Arabidopsis thaliana*. In another embodiment, the O-methyltransferase (OMT) originates from a higher eukaryote, preferably from a mammal. In particular, the O-methyltransferase (OMT) is of human origin (*Homo sapiens*).

In a particular embodiment, the OMT is selected from enzymes comprising a sequence chosen from SEQ ID NOs: 87 and 89 and polypeptides comprising a sequence having at least 60, 70, 80, 85, 90 or 95% identity with one of these sequences and having O-methyltransferase activity, notably with eriodictyol and/or luteolin as substrate and with methylation in position 4'.

In one embodiment, the OMT is selected from the enzyme comprising a sequence chosen from SEQ ID NO: 89 and polypeptides comprising a sequence having at least 60, 70, 80, 85, 90 or 95% identity with this sequence and having O-methyltransferase activity.

In another embodiment, the OMT is selected from the enzyme comprising a sequence chosen from SEQ ID NO: 87 and polypeptides comprising a sequence having at least 60, 70, 80, 85, 90 or 95% identity with this sequence and having O-methyltransferase activity. Thus, the OMT may be from *Arabidopsis thaliana*. The nucleic acid sequences coding for this enzyme and protein sequences are described in NCBI under the reference numbers NM_118755.4 and NP_567739.1, respectively. The protein is also described in UniProtKB/Swiss Prot under the reference number Q9C5D7, and more particularly in SEQ ID NO: 87.

Alternatively, the OMT is from *Homo sapiens*. The nucleic acid sequences coding for this enzyme and protein sequences are described in NCBI under the reference numbers NM_007310.2 and NP_009294.1, respectively. The protein is also described in UniProtKB/Swiss Prot under the reference number P21964, and more particularly in SEQ ID NO: 89.

The OMT from *Homo sapiens* has the advantage of accepting eriodictyol and luteolin as substrate for the methylation, whereas the OMT from *Arabidopsis thaliana* has a strong preference for eriodictyol. Conversely, if the synthesis of hesperetin is to be favored relative to that of diosmetin, the OMT from *Arabidopsis thaliana* might have an advantage.

In a preferred embodiment, the OMT is an OMT from *Citrus*, in particular *Citrus clementina* or *Citrus sinensis*. In a particularly preferred embodiment, the OMT is selected from an enzyme comprising a sequence chosen from SEQ ID NOs 117 and 119 and polypeptides comprising a sequence having at least 60, 70, 80, 85, 90 or 95% identity with one of these sequences and having O-methyltransferase activity.

Preferably, the OMT is selected from an enzyme comprising a sequence chosen from SEQ ID NO: 117 and polypeptides comprising a sequence having at least 60, 70, 80, 85, 90 or 95% identity with this sequence and having O-methyltransferase activity.

Alternatively, the OMT is selected from an enzyme comprising a sequence chosen from SEQ ID NO: 119 and polypeptides comprising a sequence having at least 60, 70, 80, 85, 90 or 95% identity with this sequence and having O-methyltransferase activity.

The OMTs from *Citrus* and from *Arabidopsis thaliana* described above have the advantage of specifically methylating eriodictyol in position 4'.

During the design of the microorganism, the inventors observed that this methylation step constituted one of the limiting steps. Surprisingly, despite the presence of the cofactor S-adenosyl-L-methionine in the microorganism, in particular the yeast, the addition of an enzyme which increases the synthesis of this cofactor made it possible to dispel the limiting aspect of this step. Thus, in a preferred embodiment, the microorganism also comprises a heterologous or endogenous sequence coding for an enzyme which synthesizes S-adenosyl-L-methionine, an S-adenosylmethionine synthetase (SAMT). This enzyme belongs to the class EC 2.5.1.6.

In one embodiment, the microorganism comprises a heterologous nucleic acid sequence coding for an O-methyltransferase (OMT), which is in particular capable of methylating eriodictyol and/or luteolin in position 4' and a heterologous or endogenous nucleic acid sequence coding for an S-adenosylmethionine synthetase (SAMT).

In one embodiment, the SAMT originates from a yeast, in particular from *Saccharomyces cerevisiae*, most particularly when the microorganism is a yeast.

In a particular embodiment, the S-adenosylmethionine synthetase is an enzyme comprising a sequence chosen from SEQ ID NO: 81 and a polypeptide comprising a sequence having at least 60, 70, 80, 85, 90 or 95% identity with this sequence and having S-adenosylmethionine synthetase activity.

For example, the S-adenosylmethionine synthase may be from *Saccharomyces cerevisiae. It is described in the GenBank database from NCBI under the number NM_*001180810.3 for the nucleic acid sequence and under the number NP_010790.3 for the protein sequence. The protein is described in UniProtKB/Swiss Prot under the reference number P19358.

In one embodiment, a new copy of a sequence coding for SAMT as defined above is introduced into the microorganism. In another embodiment, when the microorganism is *Saccharomyces cerevisiae*, the promoter of the endogenous gene coding for SAMT is replaced with a strong promoter. Thus, the expression of the SAMT is increased relative to the wild-type microorganism; the SAMT is thus overexpressed in the modified microorganism.

Thus, in a preferred embodiment, the microorganism comprises a heterologous nucleic acid sequence coding for an O-methyltransferase which is capable of methylating eriodictyol and/or luteolin in position 4' and a heterologous or endogenous nucleic acid sequence coding for an S-adenosylmethionine synthetase (SAMT) which is capable of producing S-adenosyl-L-methionine.

FNS: Flavone Synthase

Diosmetin may be produced from luteolin. It may also be obtained from eriodictyol, either by transforming it into luteolin and then preparing diosmetin from luteolin, or by transforming it into hesperetin and then preparing diosmetin from hesperetin. The enzyme that is capable of transforming eriodictyol into luteolin and/or hesperetin into diosmetin is a flavone synthase (FNS). In a particular embodiment, the flavone synthase is also capable of transforming eriodictyol into luteolin.

Thus, the microorganism may comprise a heterologous nucleic acid sequence coding for a flavone synthase, in particular a flavone synthase which is capable of producing luteolin from eriodictyol and/or diosmetin from hesperetin.

The term "flavone synthase activity" means the transformation of a flavanone into flavone by an FNSI enzyme (CPR-independent) or an FNSII enzyme (CPR-dependent).

To determine if there is flavone synthase activity, an enzymatic test may be performed, which consists of the in vitro incubation in the case of FNSI of a mixture composed of the flavone synthase enzyme (FNSI), a flavanone, 2-oxoglutarate and $O_2$, under optimum conditions (pH, temperature, ions, etc.) and in the case of FNSII of a mixture composed of the enzyme FNSII, a flavanone, NAD(P)H and $O_2$, under optimum conditions (pH, temperature, ions, etc.). After a certain incubation time, the appearance of the flavone corresponding to the flavanone is observed in UPLC-MS in comparison with the expected standard. Preferably, the flavanone is eriodictyol or hesperetin, which will be transformed, respectively, into their flavone form, i.e. into luteolin or diosmetin.

Thus, in a particular embodiment, the microorganism comprises a heterologous nucleic acid sequence coding for an O-methyltransferase (OMT), which is in particular capable of methylating eriodictyol and/or luteolin in position 4'; and a heterologous nucleic acid sequence coding for a flavone synthase, in particular a flavone synthase which is capable of producing luteolin from eriodictyol and/or diosmetin from hesperetin.

Preferably, the flavone synthase is an enzyme originating from a plant, for example of the genus *Aethusa, Angelica, Antirrhinum, Apium, Arabidopsis, Callistephus, Camellia, Conium, Cuminurn, Cynara, Dahlia, Dorcoceras, Erythranthe, Lonicera, Medicago, Oryza, Perilla, Petroselinum, Plectranthus, Populus, Saussurea, Scutellaria* or *Zea*, in particular of the genus *Arabidopsis, Lonicera, Medicago, Oryza, Petroselinum, Populus* or *Zea*, notably of *Arabidopsis thaliana, Lonicera japonica, Lonicera macranthoides, Medicago truncatula, Oryza sativa, Petroselinum crispum, Populus deltoides, Zea mays, Callistephus chinensis, Apium graveolens, Cuminum cyminurn, Aethusa cynapium, Angelica archangelica, Conium maculatum, Camellia sinensis, Cynara cardunculus* var *scolymus, Saussurea medusa, Plectranthus barbatus, Scutellaria baicalensis, Dorcoceras hygrometricum, Antirrhinum majus, Perilla frutescens* var *crispa, Dahlia pinnata* or *Erythranthe lewisii*, in particular of *Arabidopsis thaliana, Lonicera japonica, Lonicera macranthoides, Medicago truncatula, Oryza sativa, Petroselinum crispum, Populus deltoides* or *Zea mays*, preferably of *Petroselinum crispum*, or of the genus *Lonicera* for instance *Lonicera japonica* and *Lonicera macranthoides*.

In a particular embodiment, the flavone synthase (FNS) is selected from enzymes comprising a sequence chosen from SEQ ID NOs: 33, 35, 37, 127, 129, 131, 133, 135, 137, 139, 141, 143, 145, 147, 149, 151, 153, 155, 157 and 159 and polypeptides comprising a sequence having at least 60, 70, 80, 85, 90 or 95% sequence identity with one of these sequences and having flavone synthase activity. In particular, the flavone synthase (FNS) is selected from enzymes comprising a sequence chosen from SEQ ID NOs: 33, 35 and 37 and polypeptides comprising a sequence having at least 60, 70, 80, 85, 90 or 95% sequence identity with one of these sequences and having flavone synthase activity. Preferably, the FNS is selected from enzymes comprising a sequence chosen from SEQ ID NO: 37 and polypeptides comprising a sequence having at least 60, 70, 80, 85, 90 or 95% sequence identity with this sequence and having flavone synthase activity.

There are two types of flavone synthase (FNS): flavone synthase 1 (FNSI) and flavone synthase 2 (FNSII). Starting with a flavanone and 2-oxoglutarate, FNSI is capable of producing the corresponding flavone. The enzyme FNSI belongs to the class EC 1.14.11.22. FNSII belongs to the P450 group and requires the presence of a cytochrome P450 reductase. The enzyme FNSII belongs to the class EC 1.14.13.

In one embodiment, the FNS is a type I flavone synthase. In another embodiment, the FNS is a type II flavone synthase. In an additional embodiment, the microorganism comprises a type I flavone synthase and a type II flavone synthase.

In a preferred embodiment, the microorganism comprises a heterologous nucleic acid sequence coding for a type I flavone synthase (FNSI). The advantage of FNSI is that it functions without cytochrome P450 reductase.

The FNSI may be a flavone synthase from a plant such as *Petroselinum crispum, Oryza sativa, Populus deltoides, Medicago truncatula, Apium graveolens, Cuminum cyminum, Aethusa cynapium, Angelica archangelica*, or *Conium maculatum*, in particular from *Petroselinum crispum, Oryza sativa, Populus deltoides* or *Medicago truncatula*, preferably from *Petroselinum crispum*.

The FNSI may be an enzyme comprising a sequence chosen from SEQ ID NOs: 37, 127, 137, 141, 143 and 145 and polypeptides comprising a sequence having at least 60, 70, 80, 85, 90 or 95% sequence identity with one of these sequences and having flavone synthase activity. In a particular aspect, the FNSI may be an enzyme comprising a sequence chosen from SEQ ID NO: 37 and a polypeptide comprising a sequence having at least 60, 70, 80, 85, 90 or 95% sequence identity with this sequence and having flavone synthase activity. For example, the FNSI may be from *Petroselinum crispum*. It is described in the GenBank database from NCBI under the number AY817680.1 for the nucleic acid sequence and under the number AAX21541.1 for the protein sequence. The protein is described in UniProtKB/Swiss Prot under the reference number Q7XZQ8. The amino acid and nucleic acid sequences are described in SEQ ID NOs: 37 and 38, respectively.

The FNSI may also be from *Angelica archangelica*. It is described in the GenBank database from NCBI under the number DQ683352.1 for the nucleic acid sequence and under the number ABG78793.1 for the protein sequence. The amino acid and nucleic acid sequences are described in SEQ ID NOs: 127 and 128, respectively.

The FNSI may also be from *Apium graveolens*. It is described in the GenBank database from NCBI under the number AY817676.1 for the nucleic acid sequence and under the number AAX21537.1 for the protein sequence. The amino acid and nucleic acid sequences are described in SEQ ID NOs: 137 and 138, respectively.

The FNSI may also be from *Cuminum cyminum*. It is described in the GenBank database from NCBI under the number DQ683349.1 for the nucleic acid sequence and under the number ABG78790.1 for the protein sequence. The amino acid and nucleic acid sequences are described in SEQ ID NOs: 141 and 142, respectively.

The FNSI may also be from *Aethusa cynapium*. It is described in the GenBank database from NCBI under the number DQ683350.1 for the nucleic acid sequence and under the number DQ683350.1 for the protein sequence. The amino acid and nucleic acid sequences are described in SEQ ID NOs: 143 and 144, respectively.

The FNSI may also be from *Conium maculatum*. It is described in the GenBank database from NCBI under the number DQ683354.1 for the nucleic acid sequence and under the number ABG78795.1 for the protein sequence. The amino acid and nucleic acid sequences are described in SEQ ID NOs: 145 and 146, respectively.

In another embodiment, the microorganism comprises a heterologous nucleic acid sequence coding for a type II flavone synthase (FNSII).

The FNSII may be a flavone synthase from a plant, for example from *Arabidopsis thaliana, Zea mays*, of the genus *Lonicera* for instance *Lonicera japonica* and *Lonicera macranthoides, Callistephus chinensis, Medicago truncatula, Camellia sinensis, Cynara cardunculus* var *scolymus, Saussurea medusa, Plectranthus barbatus, Scutellaria baicalensis, Dorcoceras hygrometricum, Antirrhinum majus, Perilla frutescens* var *crispa, Dahlia pinnata* or *Erythranthe lewisii*, in particular a flavone synthase from *Arabidopsis thaliana, Zea mays* or of the genus *Lonicera*, for instance *Lonicera japonica* and *Lonicera macranthoides*.

In a particular embodiment, the flavone synthase (FNSII) is selected from enzymes comprising a sequence chosen from SEQ ID NOs: 33, 35, 129, 131, 133, 135, 139, 147, 149, 151, 153, 155, 157 and 159 and polypeptides comprising a sequence having at least 60, 70, 80, 85, 90 or 95% sequence identity with one of these sequences and having flavone synthase activity, preferably from enzymes comprising a sequence chosen from SEQ ID NOs: 33 and 35 and polypeptides comprising a sequence having at least 60, 70, 80, 85, 90 or 95% sequence identity with one of these sequences and having flavone synthase activity.

In one embodiment, the flavone synthase FNS is an FNSII originating from *Lonicera japonica*. In this embodiment, the enzyme may be an enzyme described in the GenBank database from NCBI under the number KU127576.1 for the nucleic acid sequence and under the number AMQ91109.1 for the protein sequence, and more particularly in SEQ ID NOs: 34 and 33, respectively.

In another embodiment, the flavone synthase FNS is an FNSII originating from *Lonicera macranthoides*. The nucleic acid sequences coding for this enzyme and protein sequences are described in NCBI under the reference numbers KU127580.1 and AMQ91113.1, respectively, and more particularly in SEQ ID NOs: 36 and 35, respectively.

In another embodiment, the flavone synthase FNS is an FNSII originating from *Cynara cardunculus* var *scolymus. The nucleic acid sequences coding for this enzyme and protein sequences are described in NCBI under the reference numbers JN*825735.1 and AFG31000.1, respectively, and more particularly in SEQ ID NOs: 130 and 129, respectively.

In another embodiment, the flavone synthase FNS is an FNSII originating from *Perilla frutescens* var *crispa*. The nucleic acid sequences coding for this enzyme and protein sequences are described in NCBI under the reference numbers AB045592.1 and BAB59004.1, respectively, and more particularly in SEQ ID NOs: 132 and 131, respectively.

In another embodiment, the flavone synthase FNS is an FNSII originating from *Dahlia pinnata*. The nucleic acid sequences coding for this enzyme and protein sequences are described in NCBI under the reference numbers AB769842.1 and BAM72335.1, respectively, and more particularly in SEQ ID NOs: 134 and 133, respectively.

In another embodiment, the flavone synthase FNS is an FNSII originating from *Callistephus chinensis*. The nucleic acid sequences coding for this enzyme and protein sequences are described in NCBI under the reference numbers AF188612.1 and AAF04115.1, respectively, and more particularly in SEQ ID NOs: 136 and 135, respectively.

In another embodiment, the flavone synthase FNS is an FNSII originating from *Medicago truncatula*. The nucleic acid sequences coding for this enzyme and protein sequences are described in NCBI under the reference numbers DQ354373.1 and ABC86159.1, respectively, and more particularly in SEQ ID NOs: 140 and 139, respectively.

In another embodiment, the flavone synthase FNS is an FNSII originating from *Camellia sinensis*. The nucleic acid sequences coding for this enzyme and protein sequences are described in NCBI under the reference numbers FJ169499.1 and ACH99109.1, respectively, and more particularly in SEQ ID NOs: 148 and 147, respectively.

In another embodiment, the flavone synthase FNS is an FNSII originating from *Saussurea medusa*. The nucleic acid sequences coding for this enzyme and protein sequences are described in NCBI under the reference numbers KF170286.1 and AGV40781.1, respectively, and more particularly in SEQ ID NOs: 150 and 149, respectively.

In another embodiment, the flavone synthase FNS is an FNSII originating from *Plectranthus barbatus*. The nucleic acid sequences coding for this enzyme and protein sequences are described in NCBI under the reference numbers KF606861.1 and AHJ89438.1, respectively, and more particularly in SEQ ID NOs: 152 and 151, respectively.

In another embodiment, the flavone synthase FNS is an FNSII originating from *Scutellaria baicalensis*. The nucleic acid sequences coding for this enzyme and protein sequences are described in NCBI under the reference numbers KT963454.1 and AMW91729.1, respectively, and more particularly in SEQ ID NOs: 154 and 153, respectively.

In another embodiment, the flavone synthase FNS is an FNSII originating from *Dorcoceras hygrometricum*. The nucleic acid sequences coding for this enzyme and protein sequences are described in NCBI under the reference numbers KV013332.1 and KZV23934.1, respectively, and more particularly in SEQ ID NOs: 156 and 155, respectively.

In another embodiment, the flavone synthase FNS is an FNSII originating from *Antirrhinum majus*. The nucleic acid sequences coding for this enzyme and protein sequences are described in NCBI under the reference numbers AB028151.1 and BAA84071.1, respectively, and more particularly in SEQ ID NOs: 158 and 157, respectively.

In another embodiment, the flavone synthase FNS is an FNSII originating from *Erythranthe lewisii*. The nucleic acid sequences coding for this enzyme and protein sequences are described in NCBI under the reference numbers KX710102.1 and AOR81894.1, respectively, and more particularly in SEQ ID NOs: 160 and 159, respectively.

In a particular embodiment, the microorganism comprises a heterologous nucleic acid sequence coding for a type II flavone synthase (FNSII) and a type I flavone synthase, for example a sequence chosen from SEQ ID NOs: 33, 35, 129, 131, 133, 135, 139, 147, 149, 151, 153, 155, 157 and 159 and polypeptides comprising a sequence having at least 60, 70, 80, 85, 90 or 95% sequence identity with one of these sequences and having flavone synthase activity, and an enzyme comprising a sequence chosen from SEQ ID NOs: 37, 127, 137, 141, 143 and 145 and a polypeptide comprising a sequence having at least 60, 70, 80, 85, 90 or 95% sequence identity with this sequence and having flavone synthase activity, preferably a sequence chosen from SEQ ID NOs: 33 and 35 and polypeptides comprising a sequence having at least 60, 70, 80, 85, 90 or 95% sequence identity with one of these sequences and having flavone synthase activity and an enzyme comprising a sequence chosen from SEQ ID NO: 37 and a polypeptide comprising a sequence having at least 60, 70, 80, 85, 90 or 95% sequence identity with this sequence and having flavone synthase activity.

The type II FNSs, FNSII, require the presence of a cytochrome P450 reductase (CPR). If the microorganism does not comprise cytochrome P450 reductase, it will thus be necessary to introduce a heterologous cytochrome P450 reductase. If the microorganism already comprises one, it is possible to envisage either the overexpression of an endogenous cytochrome P450 reductase (for example by replacing the promoter with a strong promoter or by adding one or more copies of the coding sequence) or by also introducing a heterologous cytochrome P450 reductase.

In a particular embodiment, the type II FNS and the CPR are from the same origin, the same species.

Combination of Enzymes

Thus, besides the enzymes required for the biosynthesis of hesperidin and/or diosmin from hesperetin and/or diosmetin, respectively, as described previously, the microorganism preferably comprises enzymes for producing hesperetin and/or diosmetin from naringenin and/or apigenin.

In a first particular embodiment, the recombinant microorganism comprises:

- a heterologous nucleic acid sequence coding for a flavanone 7-O-beta-D-glucosyltransferase (UGT) which is capable of adding a glucose in position 7 of hesperetin and/or diosmetin; preferably a flavanone 7-O-beta-D-glucosyltransferase (UGT) from *Arabidopsis thaliana, Citrus sinensis, Citrus clementina, Scutellaria baicalensis* or *Homo sapiens*, preferably from *Citrus sinensis* or *Scutellaria baicalensis*; preferably a flavanone 7-O-beta-D-glucosyltransferase (UGT) selected from enzymes comprising a sequence chosen from SEQ ID NOs: 113, 115, 91, 93, 95, 97, 99 and 101 and polypeptides comprising a sequence having at least 60, 70, 80, 85, 90 or 95% sequence identity with one of these sequences and having flavanone 7-O-beta-D-glucosyltransferase activity; in particular a flavanone 7-O-beta-D-glucosyltransferase (UGT) comprising a sequence chosen from SEQ ID NOs: 113, 115, 91, 93, 95 and 97 and polypeptides comprising a sequence having at least 60, 70, 80, 85, 90 or 95% sequence identity with one of these sequences and having flavanone 7-O-beta-D-glucosyltransferase activity;

a heterologous nucleic acid sequence coding for a 6-O-rhamnosyltransferase (RhaT) which is capable of transferring a rhamnose into position 6 of the glucose of hesperetin-7-O-glucoside and/or diosmetin-7-O-glucoside; preferably an RhaT of the genus *Citrus* or *Petunia hybrida*, preferably *Citrus sinensis, Citrus maxima*, or *Citrus clementina*, even more preferably *Citrus sinensis* or *Citrus clementina*, preferably a 6-O-rhamnosyltransferase (RhaT) comprising a sequence chosen from SEQ ID NOs: 103 and 105 and polypeptides comprising a sequence having at least 60, 70, 80, 85, 90 or 95% sequence identity with one of these sequences and having 6-O-rhamnosyltransferase activity;

a heterologous nucleic acid sequence coding for a UDP-glucose 4,6-dehydratase/UDP-4-keto-6-deoxy-D-glucose 3,5-epimerase/UDP-4-keto-L-rhamnose-reductase (RHM) which is capable of producing a UDP-rhamnose; preferably an RHM from *Citrus sinensis* or from *Arabidopsis thaliana*, preferably an RHM comprising a sequence chosen from SEQ ID NOs: 107, 109 and 111 and polypeptides comprising a sequence having at least 60, 70, 80, 85, 90 or 95% sequence identity with one of these sequences and having UDP-glucose 4,6-dehydratase/UDP-4-keto-6-deoxy-D-glucose 3,5-epimerase/UDP-4-keto-L-rhamnose-reductase activity, in particular an RHM comprising a sequence selected from SEQ ID NOs: 107 and 109 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity;

a heterologous nucleic acid sequence coding for a flavonoid 3'-monooxygenase (F3'H) which is capable of hydroxylating naringenin and/or apigenin in position 3'; in particular which is capable of hydroxylating naringenin and/or apigenin in position 3'; preferably from *Perilla frutescens* var. *crispa, Petunia* x *hybrida, Callistephus chinensis, Gerbera hybrida, Citrus sinensis, Citrus clementina*, Osteospermum hybrid cultivar, *Phanerochaete chrysosporium, Streptomyces avermitilis* or *Pilosella officinarum*, in particular from *Perilla frutescens* var. *crispa, Petunia* x *hybrida, Callistephus chinensis, Gerbera hybrida, Citrus sinensis* or *Pilosella officinarum*, preferably an F3'H comprising a sequence chosen from SEQ ID NOs: 1, 3, 5, 7, 9, 11, 13, 15, 17, 19, 21 and 121 and polypeptides comprising a sequence having at least 60, 70, 80, 85, 90 or 95% sequence identity with one of these sequences and having flavonoid 3'-monooxygenase activity, preferably selected from enzymes comprising a sequence chosen from SEQ ID NOs: 1, 5, 7, 11, 17, 19 and 121 and polypeptides comprising a sequence having at least 60, 70, 80, 85, 90 or 95% sequence identity with one of these sequences and having flavonoid 3'-monooxygenase activity, in particular an F3'H comprising a sequence selected from SEQ ID NOs: 7, 11, 17 and 121 and polypeptides comprising a sequence having at least 60, 70, 80, 85, 90 or 95% sequence identity with one of these sequences and having flavonoid 3'-monooxygenase activity;

optionally, a heterologous nucleic acid sequence coding for a cytochrome P450 reductase (CPR); preferably a CPR from *Saccharomyces cerevisiae*, or from a plant, for example from *Catharanthus roseus* or *Arabidopsis thaliana*; preferably a CPR comprising a sequence chosen from SEQ ID NOs: 23, 25, 27, 29 and 31 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23, 25, 29 and 31 and polypeptides comprising a sequence having at least 60, 70, 80, 85, 90 or 95% sequence identity with one of these sequences and having cytochrome P450 reductase activity;

a heterologous nucleic acid sequence coding for an O-methyltransferase (OMT) which is capable of methylating eriodictyol and/or luteolin in position 4'; preferably an OMT from *Arabidopsis thaliana* or *Homo sapiens*, preferably an OMT comprising a sequence chosen from SEQ ID NOs: 117, 119, 87 and 89 and polypeptides comprising a sequence having at least 60, 70, 80, 85, 90 or 95% sequence identity with one of these sequences and having O-methyltransferase activity, notably with eriodictyol and/or luteolin as substrate and with methylation in position 4', preferably selected from the enzyme comprising a sequence chosen from SEQ ID NOs: 117, 119 and 89 and polypeptides comprising a sequence having at least 60, 70, 80, 85, 90 or 95% sequence identity with one of these sequences and having O-methyltransferase activity; and optionally, a heterologous nucleic acid sequence coding for a flavone synthase (FNS) which is capable of producing a flavone from a flavanone, in particular which is capable of transforming naringenin into apigenin, and/or eriodictyol into luteolin, preferably of transforming eriodictyol into luteolin; preferably an FNS from *Arabidopsis thaliana, Lonicera japonica, Lonicera macranthoides, Medicago truncatula, Oryza sativa, Petroselinum crispum, Populus deltoides, Zea mays, Callistephus chinensis, Apium graveolens, Cuminum cyminum, Aethusa cynapium, Angelica archangelica, Conium maculatum, Camellia sinensis, Cynara cardunculus* var *scolymus, Saussurea medusa, Plectranthus barbatus, Scutellaria baicalensis, Dorcoceras hygrometricum, Antirrhinum majus, Perilla frutescens* var *crispa, Dahlia pinnata* or *Erythranthe lewisii*, in particular from *Arabidopsis thaliana, Lonicera japonica, Lonicera macranthoides, Medicago truncatula, Oryza sativa, Petroselinum crispum, Populus deltoides* or *Zea mays*, preferably from *Lonicera japonica, Lonicera macranthoides* and *Petroselinum crispum*; preferably an FNS comprising a sequence chosen from SEQ ID NOs: 33, 35, 37, 127, 129, 131, 133, 135, 137, 139, 141, 143, 145, 147, 149, 151, 153, 155, 157 and 159 and polypeptides comprising a sequence having at least 60, 70, 80, 85, 90 or 95% sequence identity with one of these sequences and having flavone synthase activity, preferably from enzymes comprising a sequence chosen from SEQ ID NOs: 33, 35 and 37 and polypeptides comprising a sequence having at least 60, 70, 80, 85, 90 or 95% sequence identity with one of these sequences and having flavone synthase activity, preferably a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity.

In another particular embodiment, the recombinant microorganism comprises:

a heterologous nucleic acid sequence coding for a flavanone 7-O-beta-D-glucosyltransferase (UGT) which is capable of adding a glucose in position 7 of hesperetin and/or diosmetin; preferably a flavanone 7-O-beta-D-glucosyltransferase (UGT) from *Arabidopsis thaliana, Scutellaria baicalensis* or *Homo sapiens*, preferably from *Arabidopsis thaliana* or *Scutellaria baicalensis*; preferably a flavanone 7-O-beta-D-glucosyltransferase (UGT) selected from enzymes comprising a sequence chosen from SEQ ID NOs: 91, 93, 95, 97, 99 and 101 and polypeptides comprising a sequence having at least 60, 70, 80, 85, 90 or 95% sequence identity with one of these sequences and having flavanone 7-O-beta-D-glucosyltransferase activity; in particular a flavanone 7-O-beta-D-glucosyltransferase (UGT) comprising a sequence chosen from SEQ ID NOs: 91, 93, 95 and 97 and polypeptides comprising a sequence having at least 60, 70, 80, 85, 90 or 95% sequence identity with one of these sequences and having flavanone 7-O-beta-D-glucosyltransferase activity;

a heterologous nucleic acid sequence coding for a 6-O-rhamnosyltransferase (RhaT) which is capable of transferring a rhamnose into position 6 of the glucose of hesperetin-7-O-glucoside and/or diosmetin-7-O-glucoside; preferably an RhaT of the genus *Citrus* or *Petunia hybrida*, preferably *Citrus sinensis, Citrus maxima*, or *Citrus clementina*, even more preferably *Citrus sinensis* or *Citrus clementina*, preferably a 6-O-rhamnosyltransferase (RhaT) comprising a sequence chosen from SEQ ID NOs: 103 and 105 and polypeptides comprising a sequence having at least 60, 70, 80, 85, 90 or 95% sequence identity with one of these sequences and having 6-O-rhamnosyltransferase activity;

a heterologous nucleic acid sequence coding for a UDP-glucose 4,6-dehydratase/UDP-4-keto-6-deoxy-D-glucose 3,5-epimerase/UDP-4-keto-L-rhamnose-reductase (RHM) which is capable of producing a UDP-rhamnose; preferably an RHM from *Citrus sinensis* or from *Arabidopsis thaliana*, preferably an RHM comprising a sequence chosen from SEQ ID NOs: 107, 109 and 111 and polypeptides comprising a sequence having at least 60, 70, 80, 85, 90 or 95% sequence identity with one of these sequences and having UDP-glucose 4,6-dehydratase/UDP-4-keto-6-deoxy-D-glucose 3,5-epimerase/UDP-4-keto-L-rhamnose-reductase activity, in particular an RHM comprising a sequence selected from SEQ ID NOs: 107 and 109 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity;

a heterologous nucleic acid sequence coding for a flavonoid 3'-monooxygenase (F3'H) which is capable of hydroxylating naringenin and/or apigenin in position 3'; in particular which is capable of hydroxylating naringenin and/or apigenin in position 3'; preferably from *Perilla frutescens* var. *crispa, Petunia* x *hybrida, Callistephus chinensis, Gerbera hybrida, Citrus sinensis* and *Pilosella officinarum*, preferably an F3'H comprising a sequence chosen from SEQ ID NOs: 1, 3, 5, 7, 9, 11, 13, 15, 17, 19 and 21 and polypeptides comprising a sequence having at least 60, 70, 80, 85, 90 or 95% sequence identity with one of these sequences and having flavonoid 3'-monooxygenase activity, preferably selected from enzymes comprising a sequence chosen from SEQ ID NOs: 1, 5, 7, 11, 17 and 19 and polypeptides comprising a sequence having at least 60, 70, 80, 85, 90 or 95% sequence identity with one of these sequences and having flavonoid 3'-monooxygenase activity, in particular an F3'H comprising a sequence selected from SEQ ID NOs: 5, 7 and 17 and polypeptides comprising a sequence having at least 60, 70, 80, 85, 90 or 95% sequence identity with this sequence and having flavonoid 3'-monooxygenase activity;

optionally, a heterologous nucleic acid sequence coding for a cytochrome P450 reductase (CPR); preferably a CPR from *Saccharomyces cerevisiae*, or from a plant, for example from *Catharanthus roseus* or *Arabidopsis thaliana*; preferably a CPR comprising a sequence chosen from SEQ ID NOs: 23, 25, 27, 29 and 31 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23, 25, 29 and 31 and polypeptides comprising a sequence having at least 60, 70, 80, 85, 90 or 95% sequence identity with one of these sequences and having cytochrome P450 reductase activity;

a heterologous nucleic acid sequence coding for an O-methyltransferase (OMT) which is capable of methylating eriodictyol and/or luteolin in position 4'; preferably an OMT from *Arabidopsis thaliana* or *Homo sapiens*, preferably an OMT comprising a sequence chosen from SEQ ID NOs: 87 and 89 and polypeptides comprising a sequence having at least 60, 70, 80, 85, 90 or 95% sequence identity with one of these sequences and having O-methyltransferase activity, notably with eriodictyol and/or luteolin as substrate and with methylation in position 4', preferably selected from the enzyme comprising the sequence SEQ ID NO: 89 and polypeptides comprising a sequence having at least 60, 70, 80, 85, 90 or 95% sequence identity with this sequence and having O-methyltransferase activity; and optionally, a heterologous nucleic acid sequence coding for a flavone synthase (FNS) which is capable of producing a flavone from a flavanone, in particular capable of transforming naringenin into apigenin, and/or eriodictyol into luteolin, preferably of transforming eriodictyol into luteolin; preferably an FNS from *Arabidopsis thaliana, Lonicera japonica, Lonicera macranthoides, Medicago truncatula, Oryza sativa, Petroselinum crispum, Populus deltoides* or *Zea mays*, preferably from *Lonicera japonica, Lonicera*

*macranthoides* and *Petroselinum crispum*; preferably an FNS comprising a sequence chosen from SEQ ID NOs: 33, 35 and 37 and polypeptides comprising a sequence having at least 60, 70, 80, 85, 90 or 95% sequence identity with one of these sequences and having flavone synthase activity, preferably a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity.

In a preferred embodiment, the microorganism comprises:

a heterologous nucleic acid sequence coding for a flavanone 7-O-beta-D-glucosyltransferase selected from enzymes comprising a sequence chosen from SEQ ID NOs: 113, 115 and 95 and polypeptides comprising a sequence having at least 60, 70, 80, 85, 90 or 95% sequence identity with one of these sequences and having flavanone 7-O-beta-D-glucosyltransferase activity, preferably selected from enzymes comprising a sequence chosen from SEQ ID NOs: 113 and 95 and polypeptides comprising a sequence having at least 60, 70, 80, 85, 90 or 95% sequence identity with one of these sequences and having flavanone 7-O-beta-D-glucosyltransferase activity, and most particularly preferably selected from enzymes comprising a sequence chosen from SEQ ID NO: 113 and polypeptides comprising a sequence having at least 60, 70, 80, 85, 90 or 95% sequence identity with this sequence and having flavanone 7-O-beta-D-glucosyltransferase activity; and a heterologous nucleic acid sequence coding for a 6"-O-rhamnosyltransferase selected from enzymes comprising a sequence chosen from SEQ ID NO: 103 and polypeptides comprising a sequence having at least 60, 70, 80, 85, 90 or 95% sequence identity with this sequence and having 6"-O-rhamnosyltransferase activity; and a heterologous nucleic acid sequence coding for a UDP-glucose 4,6-dehydratase/UDP-4-keto-6-deoxy-D-glucose 3,5-epimerase/UDP-4-keto-L-rhamnose-reductase selected from enzymes comprising a sequence chosen from SEQ ID NO: 107 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity; and a heterologous nucleic acid sequence coding for a flavonoid 3'-monooxygenase (F3'H) selected from enzymes comprising a sequence chosen from SEQ ID NOs: 7, 11, 17 and 121 and polypeptides comprising a sequence having at least 60, 70, 80, 85, 90 or 95% sequence identity with one of these sequences and having flavonoid 3'-monooxygenase activity, preferably a flavonoid 3'-monooxygenase (F3'H) comprising a sequence chosen from SEQ ID NOs: 7, 17 and 121 and polypeptides having at least 60, 70, 80, 85, 90 or 95% identity with one of these sequences and having flavonoid 3'-monooxygenase activity, and most particularly preferably a flavonoid 3'-monooxygenase (F3'H) comprising a sequence chosen from SEQ ID NO: 7 and polypeptides having at least 60, 70, 80, 85, 90 or 95% identity with this sequence and having flavonoid 3'-monooxygenase activity;

optionally, a heterologous nucleic acid sequence coding for a cytochrome P450 reductase (CPR) comprising a sequence chosen from SEQ ID NOs: 23, 25, 29 and 31 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23, 25 and 29 and polypeptides comprising a sequence having at least 60, 70, 80, 85, 90 or 95% sequence identity with one of these sequences and having cytochrome P450 reductase activity, and most particularly preferably from enzymes comprising a sequence chosen from SEQ ID NO: 25 and polypeptides comprising a sequence having at least 60, 70, 80, 85, 90 or 95% sequence identity with this sequence and having cytochrome P450 reductase activity; and a heterologous nucleic acid sequence coding for an O-methyltransferase (OMT) which is capable of methylating eriodictyol and/or luteolin in position 4' and comprising a sequence chosen from SEQ ID NOs: 117, 119 and 89 and polypeptides comprising a sequence having at least 60, 70, 80, 85, 90 or 95% sequence identity with one of these sequences and having O-methyltransferase activity, notably with eriodictyol and/or luteolin as substrate and with methylation in position 4', preferably selected from the enzyme comprising a sequence chosen from SEQ ID NOs: 117 and 119 and polypeptides comprising a sequence having at least 60, 70, 80, 85, 90 or 95% sequence identity with one of these sequences and having O-methyltransferase activity; and optionally, a heterologous nucleic acid sequence coding for a flavone synthase (FNS) which is capable of producing a flavone from a flavanone, in particular which is capable of transforming naringenin into apigenin, and/or eriodictyol into luteolin, preferably of transforming eriodictyol into luteolin and comprising a sequence chosen from SEQ ID NO: 37 and a polypeptide comprising a sequence having at least 60, 70, 80, 85, 90 or 95% sequence identity with this sequence and having flavone synthase activity. Preferably, the microorganism comprises each of these heterologous nucleic acid sequences.

In another particular embodiment, the recombinant microorganism comprises:

a heterologous nucleic acid sequence coding for a flavanone 7-O-beta-D-glucosyltransferase (UGT) which is capable of adding a glucose in position 7 of hesperetin and/or diosmetin;

a heterologous nucleic acid sequence coding for a 6"-O-rhamnosyltransferase (RhaT) which is capable of transferring a rhamnose into position 6 of the glucose of hesperetin-7-O-glucoside and/or diosmetin-7-O-glucoside;

a heterologous nucleic acid sequence coding for a UDP-glucose 4,6-dehydratase/UDP-4-keto-6-deoxy-D-glucose 3,5-epimerase/UDP-4-keto-L-rhamnose-reductase (RHM) which is capable of producing UDP-rhamnose;

a heterologous nucleic acid sequence coding for a flavonoid 3'-monooxygenase (F3'H) which is capable of hydroxylating naringenin and/or apigenin in position 3';

a heterologous nucleic acid sequence coding for a cytochrome P450 reductase;

a heterologous nucleic acid sequence coding for an O-methyltransferase which is capable of methylating eriodictyol and/or luteolin in position 4'; and a heterologous nucleic acid sequence coding for a flavone synthase (FNS) which is capable of producing a flavone from a flavanone, in particular which is capable of transforming naringenin into apigenin, eriodictyol into luteolin and/or hesperetin into diosmetin, preferably of transforming eriodictyol into luteolin.

In another particular embodiment, the recombinant microorganism also comprises a heterologous or endogenous nucleic acid sequence coding for an S-adenosylmethionine synthetase (SAMT), in particular from *Saccharomyces cerevisiae*, for example an SAMT comprising a sequence chosen from SEQ ID NO: 81 and a polypeptide comprising a sequence having at least 60, 70, 80, 85, 90 or 95% sequence identity with this sequence and having S-adenosylmethionine synthetase activity.

Each enzyme may be chosen from the enzymes described above.

Up to Naringenin and Apigenin

Various pathways for the biosynthesis of naringenin and apigenin are known in plants, in particular from glucose, tyrosine or phenylalanine. Microorganisms, notably *E. coli* and *Saccharomyces cerevisiae*, have been modified to produce naringenin and/or apigenin (Hwang E I, et al. 2003. Appl. Environ. Microbiol. 2003, 69(5): 2699-2706; Jiang H1, et al. 2005. Appl. Environ. Microbiol. 2005, 71(6): 2962-9; Pandey et al., 2016, Biotechnol. Adv., 34, 634-662).

For example, the pathway for the biosynthesis of naringenin and apigenin may be that described in FIG. 1.

In a first embodiment, the microorganism comprises the enzymes required for the synthesis of naringenin and/or apigenin from tyrosine.

In a second embodiment, the microorganism comprises the enzymes required for the synthesis of naringenin and/or apigenin from phenylalanine.

In a third embodiment, the microorganism comprises the enzymes required for the synthesis of naringenin and/or apigenin from tyrosine and phenylalanine.

TAL: Tyrosine Ammonia Lyase

TAL is a tyrosine ammonia lyase. This enzyme is capable of producing p-coumaric acid from tyrosine. This enzyme belongs to the class EC 4.3.1.23.

The term "phenylalanine ammonia lyase activity" means the transformation of phenylalanine into trans-cinnamic acid by means of the enzyme phenylalanine ammonia lyase. To determine whether there is phenylalanine ammonia lyase activity, an enzymatic test may be performed, which consists of the in vitro incubation of a mixture composed of the phenylalanine ammonia lyase enzyme and phenylalanine, under optimum conditions (pH, temperature, ions, etc.). After a certain incubation time, the appearance of trans-cinnamic acid is observed in UPLC-MS in comparison with the expected standard.

A tyrosine ammonia lyase (TAL) may also have phenylalanine ammonia lyase (PAL) activity as defined above and/or dihydroxyphenylalanine ammonia-lyase (DAL) activity.

The microorganism may thus comprise a heterologous nucleic acid sequence coding for a tyrosine ammonia lyase.

Preferably, this enzyme is an enzyme produced by a bacterium of the genus *Rhodobacter* or a bacterium of the genus Flavobacteriaceae. In a particular embodiment, this enzyme is produced by a *Rhodobacter capsulatus* or *Rhodobacter sphaeroides* bacterium. In another particular embodiment, this enzyme is produced by a *Flavobacterium johnsoniae* bacterium. In another embodiment, this enzyme is an enzyme produced by a yeast, in particular a yeast of the genus *Rhodotorula*, for example *Rhodotorula glutinis*. Other organisms also produce such an enzyme, for example *Camellia sinensis, Fragaria* x *ananassa, Ralstonia metallidurans* or *Zea mays.*

In a particular embodiment, the tyrosine ammonia lyase is selected from enzymes comprising a sequence chosen from SEQ ID NOs: 39 and 41 and polypeptides comprising a sequence having at least 60, 70, 80, 85, 90 or 95% sequence identity with one of these sequences and having tyrosine ammonia lyase activity.

In one embodiment, the TAL is from *Flavobacterium johnsoniae*. It is described in the GenBank database from NCBI under the number KR095306.1 for the nucleic acid sequence and under the number AKE50827.1 for the protein sequence, and more particularly in SEQ ID NOs: 40 and 39.

In a particularly preferred embodiment, the TAL is from *Rhodotorula glutinis*. It is described in the GenBank database from NCBI under the number KF765779.1 for the nucleic acid sequence and under the number AGZ04575.1 for the protein sequence, and more particularly in SEQ ID NOs: 42 and 41, respectively.

In a particularly preferred embodiment, the tyrosine ammonia lyase is selected from the enzyme comprising a sequence chosen from SEQ ID NO: 41 and polypeptides comprising a sequence having at least 60, 70, 80, 85, 90 or 95% sequence identity with this sequence and having tyrosine ammonia lyase activity.

4CL: 4-Coumarate-CoA Ligase

4CL is a 4-coumarate-CoA ligase. This enzyme is capable of producing 4-coumaroyl-CoA from p-coumaric acid and Coenzyme A and of producing caffeoyl-CoA from caffeic acid and Coenzyme A. This enzyme belongs to the class EC 6.2.1.12.

The term "4-coumarate-CoA ligase activity" means the transformation of p-coumaric acid into p-coumaroyl-CoA or of caffeic acid into caffeoyl-CoA by the enzyme 4-coumarate CoA ligase. To determine whether there is 4-coumarate CoA ligase activity, an enzymatic test may be performed, which consists of the in vitro incubation of a mixture composed of the 4-coumarate CoA ligase enzyme, p-coumaric acid or caffeic acid, ATP and CoA under optimum conditions (pH, temperature, ions, etc.). After a certain incubation time, the appearance of p-coumaroyl-CoA or of caffeoyl-CoA is observed on the UV spectrophotometer at a wavelength of 333 nm and 346 nm, respectively, in comparison with the expected standard.

The microorganism may thus comprise a heterologous nucleic acid sequence coding for a 4-coumarate-CoA ligase.

Preferably, this enzyme is an enzyme produced by a plant, for example *Abies, Arabidopsis, Agastache, Amorpha, Brassica, Citrus, Cathaya, Cedrus, Crocus, Larix, Festuca, Glycine, Juglans, Keteleeria, Lithospermum, Lolium, Lotus, Lycopersicon, Malus, Medicago, Mesembryanthemum, Nicotiana, Nothotsuga, Oryza, Phaseolus, Pelargonium, Petroselinum, Physcomitrella, Picea, Prunus, Pseudolarix, Pseudotsuga, Rosa, Rubus, Ryza, Saccharum, Suaeda, Pinus, Populus, Solanum, Thellungiella, Triticum, Tsuga, Vitis* or *Zea. Alternatively, this enzyme is an enzyme produced by a microorganism, for example Aspergillus, Mycosphaerella, Mycobacterium, Neisseria, Neurospora, Streptomyces, Rhodobacter* or *Yarrowia.*

In a preferred embodiment, this enzyme is an enzyme produced by a plant, preferably *Arabidopsis thaliana, Citrus clementina* or *Petroselinum crispum*, in particular *Arabidopsis thaliana* or *Petroselinum crispum*, or by a bacterium, preferably of the genus *Streptomyces*, in particular *Streptomyces clavuligerus.*

In a particular embodiment, the 4-coumarate-CoA ligase is selected from enzymes comprising a sequence chosen from SEQ ID NOs: 43, 45, 47, 49, 123 and 125 and polypeptides comprising a sequence having at least 60, 70, 80, 85, 90 or 95% sequence identity with one of these sequences and having 4-coumarate-CoA ligase activity.

In another particular embodiment, the 4-coumarate-CoA ligase is an enzyme comprising a sequence selected from SEQ ID NOs: 43, 45, 47 and 49, preferably SEQ ID NOs: 45 and 49 and polypeptides comprising a sequence having at least 60, 70, 80, 85, 90 or 95% sequence identity with one of these sequences and having 4-coumarate-CoA ligase activity.

In a first particular embodiment, the 4CL is from *Arabidopsis thaliana*. It is described in the GenBank database from NCBI under the number AY099747.1 for the nucleic acid sequence and under the number AAM20598.1 for the protein sequence, and more particularly in SEQ ID NOs: 44 and 43, respectively.

In a second particular embodiment, the 4CL is from *Petroselinum crispum*. It is described in the GenBank database from NCBI under the number X13324.1 or X13325.1 for the nucleic acid sequence and under the number CAA31696.1 or CAA31697.1 for the protein sequence, respectively. The proteins are described in UniProtKB/Swiss Prot under the reference numbers P14912 and P14913, respectively, and more particularly in SEQ ID NOs: 46 and 45, 48 and 47, respectively. Preferably, the 4CL is from *Petroselinum crispum* and is described in the GenBank database from NCBI under the number X13324.1 for the nucleic acid sequence and under the number CAA31696.1 for the protein sequence, and in UniProtKB/Swiss Prot under the reference number P14912, and more particularly in SEQ ID NOs: 46 and 45, respectively.

In a third particular embodiment, the 4CL is from *Streptomyces clavuligerus*. It is described in the GenBank database from NCBI under the number CP016559.1 for the nucleic acid sequence and under the number ANW18832.1 for the protein sequence, and more particularly in SEQ ID NOs: 50 and 49, respectively.

In a fourth particular embodiment, the 4CL is from *Arabidopsis thaliana*. A nucleotide sequence and the protein sequence of this enzyme are described, respectively, in SEQ ID NOs: 124 and 123.

In a fifth particular embodiment, the 4CL is from *Citrus clementina* and a nucleotide sequence and the protein sequence of this enzyme are described, respectively, in SEQ ID NOs: 126 and 125.

In a preferred embodiment, the 4CL is an enzyme comprising a sequence selected from SEQ ID NOs: 45, 123 and 125, preferably SEQ ID NOs: 123 and 45 and polypeptides comprising a sequence having at least 60, 70, 80, 85, 90 or 95% sequence identity with one of these sequences and having 4-coumarate-CoA ligase activity. Most particularly preferably, the 4CL is an enzyme comprising a sequence selected from SEQ ID NO: 45 and polypeptides comprising a sequence having at least 60, 70, 80, 85, 90 or 95% sequence identity with this sequence and having 4-coumarate-CoA ligase activity.

CHS: Chalcone Synthase

CHS is a chalcone synthase. This enzyme is capable of producing naringenin-chalcone from 4-coumaroyl-CoA and from malonyl-CoA and of producing eriodictyol-chalcone from caffeoyl-CoA and from malonyl-CoA. This enzyme belongs to the class EC 2.3.1.74.

The term "chalcone synthase activity" means the transformation of p-coumaroyl-CoA and of malonyl-CoA into naringenin chalcone or of caffeoyl-CoA and of malonyl-CoA- into eriodictyol chalcone by means of the chalcone synthase enzyme. To determine whether there is chalcone synthase activity, an enzymatic test may be performed, which consists of the in vitro incubation of a mixture composed of the chalcone synthase enzyme, coumaroyl-CoA or caffeoyl-CoA and malonyl-CoA, under optimum conditions (pH, temperature, ions, etc.). After a certain incubation time, the appearance of naringenin chalcone or of eriodictyol chalcone, respectively, is observed in HPLC-MS in comparison with the expected standard.

The microorganism thus comprises a heterologous nucleic acid sequence coding for a chalcone synthase.

This enzyme may be an enzyme produced by a plant, notably of the genus *Arabidopsis, Avena, Cosmos, Citrus, Daucus, Fagopyrum, Freesia, Glycine, Glycyrrhiza, Humulus, Hypericum, Hordeum, Juglans, Medicago, Phaseolus, Physcomitrella, Plagiochasma, Petroselinum, Pueraria, Rubus, Secale, Scutellaria, Silene, Sinapis, Spinacia, Stellaria, Triticum, Tulipa, Verbena, Vitis* or *Xanthisma*, for example *Arabidopsis thaliana, Avena sativa, Cosmos sulphureus, Citrus sinensis, Daucus carota, Fagopyrum esculentum*, Freesia hybrid cultivar, *Glycine max, Glycyrrhiza echinata, Humulus lupulus, Hypericum androsaemum, Hordeum vulgare, Juglans* sp., *Medicago sativa, Phaseolus vulgaris, Physcomitrella patens, Plagiochasma appendiculatum, Petroselinum crispum, Pueraria montana* var. *lobata, Rubus idaeus, Secale cereale, Scutellaria baicalensis, Silene* sp., *Sinapis alba, Spinacia oleracea, Stellaria longipes, Triticum aestivum*, Tulipa hybrid cultivar, *Verbena* sp., *Vitis vinifera* or *Xanthisma gracile*.

Preferably, this enzyme is an enzyme produced by a plant, for example of the genus *Citrus*, in particular *Citrus sinensis*, or *Hordeum vulgare* or by a bacterium, preferably of the genus *Streptomyces*, in particular *Streptomyces clavuligerus*.

In a particular embodiment, the chalcone synthase is selected from enzymes comprising a sequence chosen from SEQ ID NOs: 51, 53, 55 and 57 and polypeptides comprising a sequence having at least 60, 70, 80, 85, 90 or 95% sequence identity with one of these sequences and having chalcone synthase activity, preferably from enzymes comprising a sequence chosen from SEQ ID NOs: 53 and 55 and polypeptides comprising a sequence having at least 60, 70, 80, 85, 90 or 95% sequence identity with one of these sequences and having chalcone synthase activity.

In a particularly preferred embodiment, the chalcone synthase is an enzyme comprising a sequence chosen from SEQ ID NO: 53 and polypeptides comprising a sequence having at least 60, 70, 80, 85, 90 or 95% sequence identity with this sequence and having chalcone synthase activity.

In a first particular embodiment, the CHS is from *Hordeum vulgare*. It is described in the GenBank database from NCBI under the number Y09233.1 for the nucleic acid sequence and under the number CAA70435.1 for the protein sequence, and more particularly in SEQ ID NOs: 52 and 51, respectively. The protein is described in UniProtKB/Swiss Prot under the reference number Q96562.

In a second particular embodiment, the CHS is from *Citrus sinensis*. It is described in the GenBank database from NCBI under the number AB009351.1 for the nucleic acid sequence and under the number BAA81664.1 for the protein sequence, and more particularly in SEQ ID NOs: 54 and 53, respectively.

In a third particular embodiment, the CHS is from *Citrus sinensis*. It is described in the GenBank database from NCBI under the number XM_006489733.1 for the nucleic acid sequence and under the number XP_006489796.1 for the protein sequence, and more particularly in SEQ ID NOs: 56 and 55, respectively.

In a fourth particular embodiment, the CHS is from *Streptomyces clavuligerus*. It is described in the GenBank database from NCBI under the number CP016559.1 for the nucleic acid sequence and under the number ANW16917.1 for the protein sequence, and more particularly in SEQ ID NOs: 58 and 57, respectively.

Since the reaction catalyzed by chalcone synthase requires the presence of malonyl-CoA, the microorganism can be modified to increase the synthesis of malonyl-CoA.

CHI: Chalcone Isomerase

CHI is a chalcone isomerase. It is capable of producing naringenin from naringenin chalcone and of producing eriodictyol from eriodictyol chalcone. This enzyme belongs to the class EC 5.5.1.6.

The term "chalcone isomerase activity" means the transformation of naringenin chalcone or of eriodictyol chalcone into naringenin or eriodictyol by a chalcone isomerase enzyme. To determine whether there is chalcone isomerase activity, an enzymatic test may be performed, which consists of the in vitro incubation of a mixture composed of the chalcone isomerase enzyme, naringenin chalcone or eriodictyol chalcone under optimum conditions (pH, temperature, ions, etc.). After a certain incubation time, the appearance of naringenin or of eriodictyol, respectively, is observed in HPLC-MS in comparison with the expected standard.

The microorganism thus comprises a heterologous nucleic acid sequence coding for a chalcone isomerase.

This enzyme may originate from a plant, notably of the genus *Arabidopsis, Ginkgo, Oncidium, Perilla, Citrus* or *Trigonella*, for example *Arabidopsis thaliana, Ginkgo biloba, Oncidium Gower Ramsey, Perilla frutescens, Citrus Sinensis* or *Trigonella foenum-graecum*.

Preferably, this enzyme is an enzyme produced by a plant, for example *Arabidopsis thaliana* or by a bacterium, preferably of the genus *Streptomyces*, in particular *Streptomyces clavuligerus*.

In a particular embodiment, the chalcone isomerase is selected from enzymes comprising a sequence chosen from SEQ ID NOs: 59 and 61 and polypeptides comprising a sequence having at least 60, 70, 80, 85, 90 or 95% sequence identity with one of these sequences and having chalcone isomerase activity.

In a preferred embodiment, the chalcone isomerase is selected from enzymes comprising a sequence chosen from SEQ ID NO: 61 and polypeptides comprising a sequence having at least 60, 70, 80, 85, 90 or 95% sequence identity with this sequence and having chalcone isomerase activity.

In a first particular embodiment, the CHI is from *Streptomyces clavuligerus*. It is described in the GenBank database from NCBI under the number CP016559.1 for the nucleic acid sequence and under the number ANW16918.1 for the protein sequence, and more particularly in SEQ ID NOs: 60 and 59, respectively.

In a second particular embodiment, the CHI is from *Arabidopsis thaliana*. It is described in the GenBank database from NCBI under the number NM_115370.4 for the nucleic acid sequence and under the number NP_191072.1 for the protein sequence, and more particularly in SEQ ID NOs: 62 and 61, respectively.

FNS: Flavone Synthase

Apigenin may be prepared from naringenin using a flavone synthase (FNS). It is capable of producing apigenin from naringenin.

The microorganism may thus comprise a heterologous nucleic acid sequence coding for a flavone synthase, which is in particular capable of producing apigenin from naringenin and/or a heterologous nucleic acid sequence coding for a flavone synthase, which is in particular capable of producing luteolin from eriodictyol, and/or a heterologous nucleic acid sequence coding for a flavone synthase, which is in particular capable of producing diosmetin from hesperetin.

The FNS may be chosen from those described previously.

Starting with Phenylalanine

Alternatively or in addition, the microorganism may also comprise the enzymes required for the synthesis of p-coumaric acid from phenylalanine.

In this context, the microorganism may also comprise a heterologous nucleic acid sequence coding for a phenylalanine ammonia lyase (PAL) and a heterologous nucleic acid sequence coding for a cinnamate 4-hydroxylase (C4H).

The PAL belongs to the class EC 4.3.1.24. It is capable of producing cinnamic acid from phenylalanine.

The term "phenylalanine ammonia lyase activity" means the transformation of phenylalanine into trans-cinnamic acid by means of the enzyme phenylalanine ammonia lyase. To determine whether there is phenylalanine ammonia lyase activity, an enzymatic test may be performed, which consists of the in vitro incubation of a mixture composed of the phenylalanine ammonia lyase enzyme and phenylalanine, under optimum conditions (pH, temperature, ions, etc.). After a certain incubation time, the appearance of trans-cinnamic acid is observed in UPLC-MS in comparison with the expected standard.

Several enzymes have already been described in the prior art. Preferably, the enzyme originates from a plant, example a plant of the genus *Arabidopsis, Agastache, Ananas, Asparagus, Brassica, Bromheadia, Barnbusa, Beta, Betula, Citrus, Cucumis, Camellia, Capsicum, Cassia, Catharanthus, Cicer, Citrullus, Coffea, Cucurbita, Cynodon, Daucus, Dendrobium, Dianthus, Digitalis, Dioscorea, Eucalyptus, Gallus, Ginkgo, Glycine, Hordeum, Helianthus, Ipomoea, Lactuca, Lithospermum, Lotus, Lycopersicon, Medicago, Malus, Manihot, Medicago, Mesembryanthemum, Nicotiana, Olea, Oryza, Phaseolus, Pinus, Populus, Pisum, Persea, Petroselinum, Phalaenopsis, Phyllostachys, Physcomitrella, Picea, Pyrus, Prunus, Quercus, Raphanus, Rehmannia, Rubus, Solanum, Sorghum, Sphenostylis, Stellaria, Stylosanthes, Triticum, Trifolium, Vaccinium, Vigna, Vitis, Zea* or *Zinnia*. For example, mention may be made of those from *Arabidopsis thaliana* or from *Petroselinum crispum*. In a preferred embodiment, the PAL is from *Citrus sinensis*.

In addition, phenylalanine ammonia lyase (PAL) may also have tyrosine ammonia lyase (TAL) activity and/or dihydroxyphenylalanine ammonia-lyase (DAL) activity as defined below.

In a particular embodiment, the phenylalanine ammonia lyase (PAL) is selected from enzymes comprising a sequence chosen from SEQ ID NOs: 63, 65 and 77 and polypeptides comprising a sequence having at least 60, 70, 80, 85, 90 or 95% sequence identity with one of these sequences and having phenylalanine ammonia lyase activity.

In a preferred embodiment, the PAL is selected from enzymes comprising a sequence chosen from SEQ ID NOs: 65 and 77 and polypeptides comprising a sequence having at least 60, 70, 80, 85, 90 or 95% sequence identity with one of these sequences and having phenylalanine ammonia lyase activity. Most particularly preferably, the PAL is selected from enzymes comprising a sequence chosen from SEQ ID NOs: 65 and polypeptides comprising a sequence having at least 60, 70, 80, 85, 90 or 95% sequence identity with this sequence and having phenylalanine ammonia lyase activity.

In a particular embodiment, the PAL from *Citrus sinensis* is described in the GenBank database from NCBI under the number XM_006481431.2 for the nucleic acid sequence and under the number XP_006481494.1 for the protein sequence, and more particularly in SEQ ID NOs: 64 and 63, respectively.

In another particular embodiment, the PAL from *Citrus sinensis* is described in the GenBank database from NCBI under the number XM_006488000.2 for the nucleic acid sequence and under the number XP_006488063.1 for the protein sequence, and more particularly in SEQ ID NOs: 66 and 65, respectively.

In another particular embodiment, the PAL from *Arabidopsis thaliana* is described in the GenBank database from NCBI under the number NM_115186.4 for the nucleic acid sequence and under the number NP_190894.1 for the protein sequence, and more particularly in SEQ ID NOs: 78 and 77, respectively.

Optionally, if biosynthesis starting with tyrosine and phenylalanine is envisaged, the PAL and the TAL may be replaced or supplemented with a phenylalanine/tyrosine ammonia lyase (PTAL). PTAL belongs to the class EC 4.3.1.25.

C4H belongs to the class EC 1.14.13.11. It is capable of producing p-coumaric acid from cinnamic acid.

The term "trans-cinnamate 4-monooxygenase activity" means the transformation of trans-cinnamic acid into p-coumaric acid by a trans-cinnamate 4-monooxygenase enzyme (CPR-dependent). To determine whether there is trans-cinnamate 4-monooxygenase activity, an enzymatic test may be performed, which consists of the in vitro incubation of a mixture composed of the trans-cinnamate 4-monooxygenase enzyme, cinnamic acid, NADPH, $H^+$ and $O_2$, under optimum conditions (pH, temperature, ions, etc.). After a certain incubation time, the appearance of the 4-hydroxycinnamate (p-coumaric acid) is observed in UPLC-MS in comparison with the expected standard.

Several enzymes have already been described in the prior art. Preferably, the enzyme originates from a plant, for example a plant of the genus *Arabidopsis, Ammi, Avicennia, Camellia, Camptotheca, Catharanthus, Citrus, Glycine, Helianthus, Lotus, Mesembryanthemum, Physcomitreila, Phaseolus, Pinus, Populus, Ruta, Saccharum, Solanum, Vitis, Vigna* or *Zea*. In a preferred embodiment, the cinnamate 4-hydroxylase (C4H) is from *Citrus sinensis* or from *Arabidopsis thaliana*.

In a particular embodiment, the cinnamate 4-hydroxylase (C4H) is selected from enzymes comprising a sequence chosen from SEQ ID NOs: 67, 69 and 79 and polypeptides comprising a sequence having at least 60, 70, 80, 85, 90 or 95% sequence identity with one of these sequences and having cinnamate 4-hydroxylase activity.

In a preferred embodiment, the C4H is selected from enzymes comprising a sequence chosen from SEQ ID NO: 79 and polypeptides comprising a sequence having at least 60, 70, 80, 85, 90 or 95% sequence identity with this sequence and having cinnamate 4-hydroxylase activity.

In a particular embodiment, the C4H from *Citrus sinensis* is described in the GenBank database from NCBI under the number NM_001288840.1 for the nucleic acid sequence and under the number NP_001275769.1 for the protein sequence, and more particularly in SEQ ID NOs: 68 and 67, respectively.

In another particular embodiment, the C4H from *Citrus sinensis* is described in the GenBank database from NCBI under the number NM_001288895.1 for the nucleic acid sequence and under the number NP_001275824.1 for the protein sequence, and more particularly in SEQ ID NOs: 70 and 69, respectively.

In another particular embodiment, the C4H from *Arabidopsis thaliana* is described in the GenBank database from NCBI under the number NM_128601.3 for the nucleic acid sequence and under the number NP_180607.1 for the protein sequence, and more particularly in SEQ ID NOs: 80 and 79, respectively.

Proceeding Via Caffeic Acid

In an additional embodiment, the biosynthesis of eriodictyol may also comprise the synthesis of L-DOPA (3,4-dihydroxy-L-phenylalanine) from tyrosine and then of caffeic acid from L-DOPA (3,4-dihydroxy-L-phenylalanine). To do this, the following enzymes are necessary. To convert tyrosine into L-DOPA (3,4-dihydroxy-L-phenylalanine), two subunits are necessary, HpaB and HpaC.

HpaB is a 4-hydroxyphenylacetate 3-monooxygenase oxygenase subunit (HpaB).

Preferably, this enzyme is an enzyme produced by a bacterium, preferably *Escherichia coli*.

In a particular embodiment, the 4-hydroxyphenylacetate 3-monooxygenase oxygenase (HpaB) is an enzyme comprising a sequence chosen from SEQ ID NO: 83 and polypeptides comprising a sequence having at least 60, 70, 80, 85, 90 or 95% sequence identity with this sequence and having 4-hydroxyphenylacetate 3-monooxygenase activity.

In a particular embodiment, the HpaB is from *Escherichia coli*. It is described in the GenBank database from NCBI under the number CAQ34705.1 for the protein sequence, and more particularly in SEQ ID NO: 83. A nucleic acid sequence coding for this enzyme is described in SEQ ID NO: 84. The protein is described in UniProtKB/Swiss Prot under the reference number A0A140NG21.

HpaC is a 4-hydroxyphenylacetate 3-monooxygenase reductase subunit. The microorganism may thus comprise a heterologous nucleic acid sequence coding for a 4-hydroxyphenylacetate 3-monooxygenase reductase subunit (HpaC).

The term "p-coumarate 3-hydroxylase activity" means the transformation of p-coumaric acid into caffeic acid and/or of L-tyrosine into L-DOPA using an enzymatic complex composed of HpaB (4-hydroxyphenylacetate 3-hydroxylase oxidase) and HpaC (4-hydroxyphenylacetate 3-hydroxylase reductase). To determine whether there is p-coumarate 3-hydroxylase activity, an enzymatic test may be performed, which consists of the in vitro incubation of a mixture composed of the enzymes HpaB, HpaC, p-coumaric acid or L-tyrosine, FAD and NADH under optimum conditions (pH, temperature, ions, etc.). After a certain incubation time, the appearance of caffeic acid or of L-DOPA is observed in HPLC-MS in comparison with the expected standard.

Preferably, this enzyme is an enzyme produced by a bacterium, preferably *Escherichia* coll.

In a particular embodiment, the 4-hydroxyphenylacetate 3-monooxygenase reductase (HpaC) is an enzyme comprising a sequence chosen from SEQ ID NO: 85 and polypeptides comprising a sequence having at least 60, 70, 80, 85, 90 or 95% sequence identity with this sequence and having 4-hydroxyphenylacetate 3-monooxygenase activity.

In a particular embodiment, the HpaC is from *Escherichia coli*. It is described in the GenBank database from NCBI under the number CAQ34704.1 for the protein sequence, and more particularly in SEQ ID NO: 85. A nucleic acid sequence coding for this enzyme is described in SEQ ID NO: 86. The protein is described in UniProtKB/Swiss Prot under the reference number A0A140NG67.

Together, HpaB and HpaC are capable of producing L-DOPA (3,4-dihydroxy-L-phenylalanine) from tyrosine.

Thus, the microorganism may comprise a heterologous nucleic acid sequence coding for a 4-hydroxyphenylacetate 3-monooxygenase oxygenase (HpaB) and a heterologous nucleic acid sequence coding for 4-hydroxyphenylacetate 3-monooxygenase reductase (HpaC). Moreover, this pathway also requires the presence of an enzyme that is capable of synthesizing caffeic acid from L-DOPA (3,4-dihydroxy-L-phenylalanine), a dihydroxyphenylalanine ammonia-lyase (DAL). This enzyme belongs to the class EC 4.3.1.11.

The term "dihydroxyphenylalanine ammonia lyase activity" means the transformation of L-DOPA into trans-caffeic acid by means of a dihydroxyphenylalanine ammonia lyase enzyme. To determine whether there is dihydroxyphenylalanine ammonia lyase activity, an enzymatic test may be performed, which consists of the in vitro incubation of a mixture composed of the dihydroxyphenylalanine ammonia lyase enzyme and L-DOPA (levodopa) under optimum conditions (pH, temperature, ions, etc.). After a certain incubation time, the appearance of trans-caffeic acid is observed in UPLC-MS in comparison with the expected standard.

In addition, dihydroxyphenylalanine ammonia lyase (DAL) may also have tyrosine ammonia lyase (TAL) activity and/or phenylalanine ammonia-lyase (PAL) activity.

The microorganism may thus comprise a heterologous nucleic acid sequence coding for a 4-hydroxyphenylacetate 3-monooxygenase oxygenase subunit (HpaB), a heterologous nucleic acid sequence coding for a 4-hydroxyphenylacetate 3-monooxygenase reductase subunit (HpaC) and a heterologous nucleic acid sequence coding for a dihydroxyphenylalanine ammonia-lyase (DAL).

As an alternative to the use of HpaB and HpaC or in combination therewith, it is possible to use an enzyme for converting tyrosine into L-DOPA and an enzyme for converting p-coumaric acid into caffeic acid.

These are, respectively, a 4-methoxybenzoate 0-demethylase, also known as 4-methoxybenzoate monooxygenase (0-demethylating) which has L-tyrosine hydroxylase activity, belonging to the class EC 1.14.99.15, and a p-coumarate 3-hydroxylase having p-coumarate 3-hydroxylase activity, belonging to the class EC 1.14.13.

These various enzymes both form part of the cytochrome P450 (CYP) family.

The term "L-tyrosine hydroxylase activity" means the transformation of p-coumaric acid into caffeic acid and/or of L-tyrosine into L-DOPA using a p-coumarate 3-hydroxylase enzyme (CPR-dependent). To determine whether there is L-tyrosine hydroxylase activity, an enzymatic test may be performed, which consists of the in vitro incubation of a mixture composed of the p-coumarate 3-hydroxylase enzyme, p-coumaric acid or L-tyrosine and the necessary cofactors, under optimum conditions (pH, temperature, ions, etc.). After a certain incubation time, the appearance of caffeic acid or of L-DOPA is observed in HPLC-MS in comparison with the expected standard.

The term "p-coumarate 3-hydroxylase activity" means the transformation of p-coumaric acid into caffeic acid and/or of L-tyrosine into L-DOPA using a p-coumarate 3-hydroxylase enzyme (CPR-dependent). To determine whether there is p-coumarate 3-hydroxylase activity, an enzymatic test may be performed, which consists of the in vitro incubation of a mixture composed of the p-coumarate 3-hydroxylase enzyme, p-coumaric acid or L-Tyrosine under optimum conditions (pH, temperature, ions, etc.). After a certain incubation time, the appearance of caffeic acid or of L-DOPA is observed in HPLC-MS in comparison with the expected standard.

The recombinant microorganism may thus comprise a heterologous nucleic acid sequence coding for a 4-methoxybenzoate 0-demethylase (CYP) which is capable of converting tyrosine into L-DOPA and also p-coumaric acid into caffeic acid.

In one embodiment, the 4-methoxybenzoate 0-demethylase is a bacterial enzyme, notably from *Rhodopseudomonas palustris, Pseudomonas puticita* or *Escherichia coli*, plant enzyme, notably from *Beta vulgaris*, a mammalian enzyme, notably from *Oryctolagus cuniculus* or a fungal enzyme, notably from *Rhodotorula glutinis*. In a particular embodiment, the 4-methoxybenzoate O-demethylase is an enzyme from *Rhodopseudomonas palustris, Saccharothrix espanaensis* or *Beta vulgaris.*

In a particular embodiment, the 4-methoxybenzoate 0-demethylase is selected from enzymes comprising a sequence chosen from SEQ ID NOs: 73 and 75 and polypeptides comprising a sequence having at least 60, 70, 80, 85, 90 or 95% sequence identity with one of these sequences and having L-tyrosine hydrolase activity.

The 4-methoxybenzoate 0-demethylase may also be from *Beta vulgaris*. The nucleic acid sequences coding for this enzyme and the protein sequences are described in SEQ ID NOs: 74 and 73, respectively. The protein is described in UniProtKB/Swiss Prot under the reference number PODKI2.

In addition, the 4-methoxybenzoate O-demethylase may be from *Saccharothrix espanaensis*. The nucleic acid sequences coding for this enzyme and protein sequences are described in NCBI under the reference numbers NC_005296.1 and WP_011157377.1, respectively, and more particularly in SEQ ID NOs: 76 and 75. The protein is described in UniProtKB/Swiss Prot under the reference number Q6N8N2.

In one embodiment, the microorganism may comprise a heterologous nucleic acid sequence coding for a 4-methoxybenzoate 0-demethylase and a heterologous nucleic acid sequence coding for a dihydroxyphenylalanine ammonia-lyase (DAL).

The recombinant microorganism may thus comprise a heterologous nucleic acid sequence coding for a coumarate 3-hydroxylase (Coum3H) which is capable of converting p-coumaric acid into caffeic acid.

In one embodiment, the coumarate 3-hydroxylase is a bacterial enzyme, notably from *Saccharothrix.*

In a particular embodiment, the 4-methoxybenzoate 0-demethylase is selected from the enzyme comprising a sequence chosen from SEQ ID NO: 71 and polypeptides comprising a sequence having at least 60, 70, 80, 85, 90 or 95% sequence identity with one of these sequences and having coumarate 3-hydroxylase activity.

The nucleic acid sequence coding for this enzyme and the protein sequence are described in NCBI under the reference numbers DQ357071.1 and ABC88666.1, respectively, and more particularly in SEQ ID NOs: 72 and 71.

In one embodiment, the microorganism may comprise a heterologous nucleic add sequence coding for a coumarate 3-hydroxylase and a heterologous nucleic acid sequence coding for a dihydroxyphenylalanine ammonia-lyase (DAL).

Additional Combination of Enzymes

Thus, besides the enzymes required for the biosynthesis of hesperidin and/or diosmin from naringenin and/or apigenin as described previously, the microorganism preferably comprises enzymes for producing naringenin and/or apigenin from tyrosine and/or phenylalanine, preferably from tyrosine.

Thus, according to particular embodiments, the microorganism comprises a heterologous nucleic acid sequence coding for a flavanone 7-O-beta-D-glucosyltransferase (UGT) which is capable of adding a glucose in position 7 of hesperetin and/or diosmetin, a heterologous nucleic acid sequence coding for a 6"-O-rhamnosyltransferase (RhaT) which is capable of transferring a rhamnose into position 6 of the glucose of hesperetin-7-O-glucoside and/or diosmetin-7-O-glucoside, a heterologous nucleic acid sequence coding for a UDP-glucose 4,6-dehydratase/UDP-4-keto-6-deoxy-D-glucose 3,5-epimerase/UDP-4-keto-L-rhamnose-reductase (RHM) which is capable of producing UDP-rhamnose, a heterologous nucleic acid sequence coding for an O-methyltransferase (OMT) which is capable of methylating eriodictyol and/or luteolin in position 4', a heterologous nucleic acid sequence coding for an F3'H enzyme, and optionally a heterologous nucleic acid sequence coding for an FNS enzyme and a heterologous nucleic acid sequence coding for a CPR enzyme, and also comprises a heterologous nucleic acid sequence coding for a tyrosine ammonia lyase (TAL), a heterologous nucleic acid sequence coding for a 4-coumaroyl-CoA ligase (4CL), a heterologous nucleic acid sequence coding for a chalcone synthase (CHS) and a heterologous nucleic acid sequence coding for a chalcone isomerase (CHI).

In one embodiment, the microorganism comprises:

a heterologous nucleic acid sequence coding for an O-methyltransferase (OMT) which is capable of methylating eriodictyol and/or luteolin in position 4'; preferably an OMT from *Citrus clementina, Citrus sinensis, Arabidopsis thaliana* or *Homo sapiens*, preferably an OMT comprising a sequence chosen from SEQ ID NOs: 117, 119, 87 and 89 and polypeptides comprising a sequence having at least 60, 70, 80, 85, 90 or 95% sequence identity with one of these sequences and having O-methyltransferase activity, notably with eriodictyol and/or luteolin as substrate and methylation in position 4', preferably an OMT comprising a sequence chosen from SEQ ID NOs: 117 and 119 and polypeptides comprising a sequence having at least 60, 70, 80, 85, 90 or 95% sequence identity with one of these sequences and having O-methyltransferase activity, and most particularly preferably an OMT comprising a sequence chosen from SEQ ID NO: 117 and polypeptides comprising a sequence having at least 60, 70, 80, 85, 90 or 95% sequence identity with this sequence and having O-methyltransferase activity; and a heterologous nucleic acid sequence coding for a flavonoid 3'-monooxygenase (F3'H) which is capable of hydroxylating naringenin and/or apigenin in position 3' and comprising a sequence selected from SEQ ID NOs: 7, 11, 17 and 121 and polypeptides comprising a sequence having at least 75%, at least 80%, at least 85%, at least 90% or at least 95% identity with one of these sequences and having flavonoid 3'-monooxygenase activity, preferably an enzyme comprising a sequence selected from SEQ ID NOs: 7, 17 and 121 and polypeptides comprising a sequence having at least 75%, at least 80%, at least 85%, at least 90% or at least 95% identity with one of these sequences and having flavonoid 3'-monooxygenase activity, and most particularly preferably an enzyme comprising a sequence selected from SEQ ID NO: 7 and polypeptides comprising a sequence having at least 75%, at least 80%, at least 85%, at least 90% or at least 95% identity with this sequence and having flavonoid 3'-monooxygenase activity; and optionally, a heterologous nucleic acid sequence coding for a cytochrome P450 reductase (CPR) and comprising a sequence chosen from SEQ ID NOs: 23, 25, 27, 29 and 31 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23, 25 and 29 and polypeptides comprising a sequence having at least 60, 70, 80, 85, 90 or 95% sequence identity with one of these sequences and having cytochrome P450 reductase activity, and particularly from enzymes comprising a sequence chosen from SEQ ID NO: 25 and polypeptides comprising a sequence having at least 60, 70, 80, 85, 90 or 95% sequence identity with this sequence and having cytochrome P450 reductase activity; and optionally, a heterologous nucleic acid sequence coding for a flavone synthase (FNS) and comprising a sequence chosen from SEQ ID NOs: 33, 35, 37, 127, 129, 131, 133, 135, 137, 139, 141, 143, 145, 147, 149, 151, 153, 155, 157 and 159 and polypeptides comprising a sequence having at least 60, 70, 80, 85, 90 or 95% sequence identity with one of these sequences and having flavone synthase activity, in particular for a flavone synthase (FNS) and comprising a sequence chosen from SEQ ID NOs: 33, 35 and 37 and polypeptides comprising a sequence having at least 60, 70, 80, 85, 90 or 95% sequence identity with one of these sequences and having flavone synthase activity, preferably a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity; and a heterologous nucleic acid sequence coding for a tyrosine ammonia lyase (TAL) from *Rhodotorula glutinis* or *Flavobacterium johnsoniae*; in particular a TAL comprising a sequence chosen from SEQ ID NOs: 41 and 39 and polypeptides comprising a sequence having at least 60, 70, 80, 85, 90 or 95% sequence identity with one of these sequences and having tyrosine ammonia lyase activity; preferably a TAL comprising a sequence chosen from SEQ ID NO: 41 and polypeptides comprising a sequence having at least 60, 70, 80, 85, 90 or 95% sequence identity with this sequence and having tyrosine ammonia lyase activity; and a heterologous nucleic acid sequence coding for a 4-coumaroyl-CoA ligase (4CL) from *Arabidopsis thaliana, Citrus clementina, Petroselinum crispum* or *Streptomyces clavuligerus*; in particular a 4CL comprising a sequence chosen from SEQ ID NOs: 123, 125, 45, 43, 47 and 49 and polypeptides comprising a sequence having at least 60, 70, 80, 85, 90 or 95% sequence identity with one of these sequences and having 4-coumarate-CoA ligase activity; preferably a 4CL comprising a sequence selected from SEQ ID NOs: 123, 125 and 45 and polypeptides comprising a sequence having at least 60, 70, 80, 85, 90 or 95% sequence identity with one of these sequences and having 4-coumarate-CoA ligase activity; most particularly preferably a 4CL comprising a sequence selected from SEQ ID NO: 45 and polypeptides comprising a sequence having at least 60, 70, 80, 85, 90 or 95% sequence identity with this sequence and having 4-coumarate-CoA ligase activity, and a heterologous nucleic acid sequence coding for a chalcone synthase (CHS) from *Citrus sinensis, Hordeum vulgare* or *Streptomyces clavuligerus*, in particular a CHS comprising a sequence chosen from SEQ ID NOs: 53, 51, 55 and 57 and polypeptides comprising a sequence having at least 60, 70, 80, 85, 90 or 95% sequence identity with one of these sequences and having chalcone synthase activity, preferably a CHS comprising a sequence chosen from SEQ ID NO: 53 and polypeptides comprising a sequence having at least 60, 70, 80, 85, 90 or 95% sequence identity with this sequence and having chalcone synthase activity; and a heterologous nucleic acid sequence coding for a chalcone isomerase (CHI) from *Arabidopsis thaliana* or *Streptomyces clavuligerus*, in particular a CHI comprising a sequence chosen from SEQ ID NOs: 61 and 59 and polypeptides comprising a sequence having at least 60, 70, 80, 85, 90 or 95% sequence identity with one of these sequences and having chalcone isomerase activity; preferably a CHI comprising a sequence chosen from SEQ ID NO: 61 and polypeptides comprising a sequence having at least 60, 70, 80, 85, 90 or 95% sequence identity with this sequence and having chalcone isomerase activity.

Preferably, in this embodiment, the microorganism comprises one of the combinations of enzymes UGT, RhaT and RHM described above, in particular the flavanone 7-O-beta-D-glucosyltransferase selected from enzymes comprising a sequence chosen from SEQ ID NOs: 113 and 95 and polypeptides comprising a sequence having at least 60, 70, 80, 85, 90 or 95% sequence identity with one of these sequences and having flavanone 7-O-beta-D-glucosyltransferase activity, preferably selected from enzymes comprising a sequence chosen from SEQ ID NO: 113 and polypeptides comprising a sequence having at least 60, 70, 80, 85, 90 or 95% sequence identity with this sequence and having flavanone 7-O-beta-D-glucosyltransferase activity; and the 6"-O-rhamnosyltransferase selected from enzymes comprising a sequence chosen from SEQ ID NO: 103 and polypeptides comprising a sequence having at least 60, 70, 80, 85, 90 or 95% sequence identity with this sequence and having 6"-O-rhamnosyltransferase activity; and the UDP-glucose 4,6-dehydratase/UDP-4-keto-6-deoxy-D-glucose 3,5-epimerase/UDP-4-keto-L-rhamnose-reductase selected from enzymes comprising a sequence chosen from SEQ ID NO: 107 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity.

Preferably, in this embodiment, the microorganism also comprises:

a heterologous nucleic acid sequence coding for a phenylalanine ammonia lyase (PAL), in particular a PAL comprising a sequence chosen from SEQ ID NOs: 63, 65 and 77, preferably SEQ ID NOs: 65 and 77 and polypeptides comprising a sequence having at least 60, 70, 80, 85, 90 or 95% sequence identity with one of these sequences and having phenylalanine ammonia lyase activity, and more particularly preferably a phenylalanine ammonia lyase (PAL) comprising a sequence chosen from SEQ ID NO: 65 and polypeptides comprising a sequence having at least 60, 70, 80, 85, 90 or 95% sequence identity with this sequence and having phenylalanine ammonia lyase activity; and a heterologous nucleic acid sequence coding for a cinnamate 4-hydroxylase (C4H), in particular a C4H comprising a sequence chosen from SEQ ID NOs: 67, 69 and 79 and polypeptides comprising a sequence having at least 60, 70, 80, 85, 90 or 95% sequence identity with one of these sequences and having cinnamate 4-hydroxylase activity; and most particularly preferably a cinnamate 4-hydroxylase (C4H) comprising a sequence chosen from SEQ ID NO: 79 and polypeptides comprising a sequence having at least 60, 70, 80, 85, 90 or 95% sequence identity with this sequence and having cinnamate 4-hydroxylase activity.

In another embodiment, the microorganism comprises:

a heterologous nucleic acid sequence coding for an O-methyltransferase (OMT) comprising a sequence chosen from SEQ ID NOs: 117 and 119 and polypeptides comprising a sequence having at least 60, 70, 80, 85, 90 or 95% sequence identity with one of these sequences and having O-methyltransferase activity, and most particularly preferably an OMT comprising a sequence chosen from SEQ ID NO: 117 and polypeptides comprising a sequence having at least 60, 70, 80, 85, 90 or 95% sequence identity with this sequence and having O-methyltransferase activity; and a heterologous nucleic acid sequence coding for a flavonoid 3'-monooxygenase (F3'H) which is capable of hydroxylating naringenin and/or apigenin in position 3' and comprising a sequence selected from SEQ ID NOs: 7, 17 and 121 and polypeptides comprising a sequence having at least 75%, at least 80%, at least 85%, at least 90% or at least 95% identity with one of these sequences and having flavonoid 3'-monooxygenase activity, preferably an enzyme comprising a sequence selected from SEQ ID NO: 7 and polypeptides comprising a sequence having at least 75%, at least 80%, at least 85%, at least 90% or at least 95% identity with this sequence and having flavonoid 3'-monooxygenase activity; and optionally, a heterologous nucleic acid sequence coding for a cytochrome P450 reductase (CPR) and comprising a sequence chosen from SEQ ID NOs: 23, 25 and 29 and polypeptides comprising a sequence having at least 60, 70, 80, 85, 90 or 95% sequence identity with one of these sequences and having cytochrome P450 reductase activity, preferably chosen from enzymes comprising a sequence chosen from SEQ ID NO: 25 and polypeptides comprising a sequence having at least 60, 70, 80, 85, 90 or 95% sequence identity with this sequence and having cytochrome P450 reductase activity; and optionally, a heterologous nucleic acid sequence coding for a flavone synthase (FNS) and comprising a sequence chosen from SEQ ID NO: 37 and a polypeptide comprising a sequence having at least 60, 70, 80, 85, 90 or 95% sequence identity with this sequence and having flavone synthase activity; and a heterologous nucleic acid sequence coding for a tyrosine ammonia lyase (TAL) comprising a sequence chosen from SEQ ID NOs: 41 and polypeptides comprising a sequence having at least 60, 70, 80, 85, 90 or 95% sequence identity with this sequence and having tyrosine ammonia lyase activity;

a heterologous nucleic acid sequence coding for a 4-coumaroyl-CoA ligase (4CL) comprising a sequence selected from SEQ ID NOs: 123, 125 and 45 and polypeptides comprising a sequence having at least 60, 70, 80, 85, 90 or 95% sequence identity with these sequences and having 4-coumarate-CoA ligase activity, most particularly preferably a 4CL comprising a sequence selected from SEQ ID NO: 45 and polypeptides comprising a sequence having at least 60, 70, 80, 85, 90 or 95% sequence identity with this sequence and having 4-coumarate-CoA ligase activity; and a heterologous nucleic acid sequence coding for a chalcone synthase (CHS) comprising a sequence chosen from SEQ ID NO: 53 and polypeptides comprising a sequence having at least 60, 70, 80, 85, 90 or 95% sequence identity with this sequence and having chalcone synthase activity; and a heterologous nucleic acid sequence coding for a chalcone isomerase (CHI) comprising a sequence chosen from SEQ ID NO: 61 and polypeptides comprising a sequence having at least 60, 70, 80, 85, 90 or 95% sequence identity with this sequence and having chalcone isomerase activity.

Preferably, in this embodiment, the microorganism comprises one of the combinations of enzymes UGT, RhaT and RHM described above, in particular the flavanone 7-O-beta-D-glucosyltransferase selected from enzymes comprising a sequence chosen from SEQ ID NOs: 113 and 95 and polypeptides comprising a sequence having at least 60, 70, 80, 85, 90 or 95% sequence identity with one of these sequences and having flavanone 7-O-beta-D-glucosyltransferase activity, preferably selected from enzymes comprising a sequence chosen from SEQ ID NO: 113 and polypeptides comprising a sequence having at least 60, 70, 80, 85, 90 or 95% sequence identity with this sequence and having flavanone 7-O-beta-D-glucosyltransferase activity; and the 6"-O-rhamnosyltransferase selected from enzymes comprising a sequence chosen from SEQ ID NO: 103 and polypeptides comprising a sequence having at least 60, 70, 80, 85, 90 or 95% sequence identity with this sequence and having 6"-O-rhamnosyltransferase activity; and the UDP-glucose 4,6-dehydratase/UDP-4-keto-6-deoxy-D-glucose 3,5-epimerase/UDP-4-keto-L-rhamnose-reductase selected from enzymes comprising a sequence chosen from SEQ ID NO: 107 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity.

Preferably, in this embodiment, the microorganism also comprises a heterologous nucleic acid sequence coding for a phenylalanine ammonia lyase (PAL) and a heterologous nucleic acid sequence coding for a cinnamate 4-hydroxylase (C4H) as described in the preceding embodiment.

Optionally, in these various embodiments, the microorganism also comprises a heterologous or endogenous nucleic acid sequence coding for an S-adenosylmethionine synthetase (SAMT); in particular from *Saccharomyces cerevisiae*, for example an SAMT comprising a sequence chosen from SEQ ID NO: 81 and a polypeptide comprising a sequence having at least 60, 70, 80, 85, 90 or 95% sequence identity with this sequence and having S-adenosylmethionine synthetase activity.

In another particular embodiment, the microorganism comprises:

a heterologous nucleic acid sequence coding for a flavanone 7-O-beta-D-glucosyltransferase (UGT) from *Arabidopsis thaliana, Scutellaria baicalensis* or *Homo sapiens*, preferably from *Arabidopsis thaliana* or from *Scutellaria baicalensis*, preferably a flavanone 7-O-beta-D-glucosyltransferase (UGT) selected from enzymes comprising a sequence chosen from SEQ ID NOs: 91, 93, 95, 97, 99 and 101 and polypeptides comprising a sequence having at least 60, 70, 80, 85, 90 or 95% sequence identity with one of these sequences and having flavanone 7-O-beta-D-glucosyltransferase activity; in particular a flavanone 7-O-beta-D-glucosyltransferase (UGT) comprising a sequence chosen from SEQ ID NOs: 91, 93, 95 and 97 and polypeptides comprising a sequence having at least 60, 70, 80, 85, 90 or 95% sequence identity with one of these sequences and having flavanone 7-O-beta-D-glucosyltransferase activity, and preferably a UGT comprising a sequence chosen from SEQ ID NO: 113 and polypeptides comprising a sequence having at least 60, 70, 80, 85, 90 or 95% sequence identity with this sequence and having flavanone 7-O-beta-D-glucosyltransferase activity;

a heterologous nucleic acid sequence coding for a 6"-O-rhamnosyltransferase (RhaT) of the genus *Citrus* or *Petunia hybrida*, preferably *Citrus sinensis, Citrus maxima*, or *Citrus clementina*, even more preferably *Citrus sinensis* or *Citrus clementina*, preferably a 6"-O-rhamnosyltransferase (RhaT) comprising a sequence chosen from SEQ ID NOs: 103 and 105 and polypeptides comprising a sequence having at least 60, 70, 80, 85, 90 or 95% sequence identity with one of these sequences and having 6"-O-rhamnosyltransferase activity, and preferably an RhaT comprising a sequence chosen from SEQ ID NO: 103 and polypeptides comprising a sequence having at least 60, 70, 80, 85, 90 or 95% sequence identity with this sequence and having 6"-O-rhamnosyltransferase activity; and a heterologous nucleic acid sequence coding for a UDP-glucose 4,6-dehydratase/UDP-4-keto-6-deoxy-D-glucose 3,5-epimerase/UDP-4-keto-L-rhamnose-reductase (RHM) from *Citrus sinensis* or from *Arabidopsis thaliana*, preferably an RHM comprising a sequence chosen from SEQ ID NOs: 107, 109 and 111 and polypeptides comprising a sequence having at least 60, 70, 80, 85, 90 or 95% sequence identity with one of these sequences and having UDP-glucose 4,6-dehydratase/UDP-4-keto-6-deoxy-D-glucose 3,5-epimerase/UDP-4-keto-L-rhamnose-reductase activity, in particular an RHM comprising a sequence selected from SEQ ID NOs: 107 and 109 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity, and preferably an RHM comprising a sequence selected from SEQ ID NO: 107 and polypeptides comprising a sequence having at least 60, 70, 80, 85, 90 or 95% sequence identity with this sequence and having UDP-glucose 4,6-dehydratase/

UDP-4-keto-6-deoxy-D-glucose 3,5-epimerase/UDP-4-keto-L-rhamnose-reductase activity;

a heterologous nucleic acid sequence coding for a flavonoid 3'-monooxygenase (F3'H) which is capable of hydroxylating naringenin and/or apigenin in position 3'; preferably from *Perilla frutescens* var. *crispa, Petunia* x *hybrida, Callistephus chinensis, Gerbera hybrida, Citrus sinensis, Citrus clementina*, Osteospermum hybrid cultivar, *Phanerochaete chrysosporium, Streptomyces avermitilis* or *Pilosella officinarum*, in particular from *Perilla frutescens* var. *crispa, Petunia* x *hybrida, Callistephus chinensis, Gerbera hybrida, Citrus sinensis* or *Pilosella officinarum*, preferably an F3'H comprising a sequence chosen from SEQ ID NOs: 1, 3, 5, 7, 9, 11, 13, 15, 17, 19 and 21 and polypeptides comprising a sequence having at least 60, 70, 80, 85, 90 or 95% sequence identity with one of these sequences and having flavonoid 3'-monooxygenase activity, preferably selected from enzymes comprising a sequence chosen from SEQ ID NOs: 1, 5, 7, 11, 17 and 19 and polypeptides comprising a sequence having at least 60, 70, 80, 85, 90 or 95% sequence identity with one of these sequences and having flavonoid 3'-monooxygenase activity, in particular an F3'H comprising a sequence selected from SEQ ID NOs: 5, 7 and 17 and polypeptides comprising a sequence having at least 60, 70, 80, 85, 90 or 95% sequence identity with this sequence and having flavonoid 3'-monooxygenase activity, more particularly preferably an F3'H comprising a sequence chosen from SEQ ID NO: 7 and polypeptides comprising a sequence having at least 60, 70, 80, 85, 90 or 95% sequence identity with the sequence SEQ ID NO: 7 and having flavonoid 3'-monooxygenase activity;

optionally, a heterologous nucleic acid sequence coding for a cytochrome P450 reductase (CPR); preferably a CPR from *Saccharomyces cerevisiae*, or from a plant, for example from *Catharanthus roseus* or *Arabidopsis thaliana*; preferably a CPR comprising a sequence chosen from SEQ ID NOs: 23, 25, 27, 29 and 31 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23, 25 and 29 and polypeptides comprising a sequence having at least 60, 70, 80, 85, 90 or 95% sequence identity with one of these sequences and having cytochrome P450 reductase activity, and particularly a CPR comprising a sequence chosen from SEQ ID NO: 25 and polypeptides comprising a sequence having at least 60, 70, 80, 85, 90 or 95% sequence identity with this sequence and having cytochrome P450 reductase activity;

a heterologous nucleic acid sequence coding for an O-methyltransferase (OMT) which is capable of methylating eriodictyol and/or luteolin in position 4'; preferably an OMT from *Arabidopsis thaliana* or *Homo sapiens*, preferably an OMT comprising a sequence chosen from SEQ ID NOs: 87 and 89 and polypeptides comprising a sequence having at least 60, 70, 80, 85, 90 or 95% sequence identity with one of these sequences and having O-methyltransferase activity, notably with eriodictyol and/or luteolin as substrate and with methylation in position 4', preferably selected from the enzyme comprising a sequence chosen from SEQ ID NO: 89 and polypeptides comprising a sequence having at least 60, 70, 80, 85, 90 or 95% sequence identity with this sequence and having O-methyltransferase activity;

optionally, a heterologous or endogenous nucleic acid sequence coding for an S-adenosylmethionine synthetase (SAMT), in particular from *Saccharomyces cerevisiae*, for example an SAMT comprising a sequence chosen from SEQ ID NO: 81 and a polypeptide comprising a sequence having at least 60, 70, 80, 85, 90 or 95% sequence identity with this sequence and having S-adenosylmethionine synthetase activity; and optionally, a heterologous nucleic acid sequence coding for a flavone synthase (FNS) which is capable of transforming naringenin into apigenin, eriodictyol into luteolin, and/or hesperetin into diosmetin, preferably of transforming eriodictyol into luteolin; preferably an FNS from *Arabidopsis thaliana, Lonicera japonica, Lonicera macranthoides, Medicago truncatula, Oryza sativa, Petroselinum crispum, Populus deltoides, Zea mays, Callistephus chinensis, Apium graveolens, Medicago truncatula, Cuminum cyminum, Aethusa cynapium, Angelica archangelica, Conium maculatum, Camellia sinensis, Cynara cardunculus* var *scolymus, Saussurea medusa, Plectranthus barbatus, Scutellaria baicalensis, Dorcoceras hygrometricum, Antirrhinum majus, Perilla frutescens* var *crispa, Dahlia pinnata* or *Erythranthe lewisii*, in particular from *Arabidopsis thaliana, Lonicera japonica, Lonicera macranthoides, Medicago truncatula, Oryza sativa, Petroselinum crispum, Populus deltoides* or *Zea mays*, preferably from *Lonicera japonica, Lonicera macranthoides* and *Petroselinum crispum*; preferably an FNS comprising a sequence chosen from SEQ ID NOs: 33, 35, 37, 127, 129, 131, 133, 135, 137, 139, 141, 143, 145, 147, 149, 151, 153, 155, 157 and 159 and polypeptides comprising a sequence having at least 60, 70, 80, 85, 90 or 95% sequence identity with one of these sequences and having flavone synthase activity, preferably from enzymes comprising a sequence chosen from SEQ ID NOs: 33, 35 and 37 and polypeptides comprising a sequence having at least 60, 70, 80, 85, 90 or 95% sequence identity with one of these sequences and having flavone synthase activity, preferably a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity;

a heterologous nucleic acid sequence coding for a tyrosine ammonia lyase (TAL) which is capable of producing p-coumaric acid from tyrosine; preferably from *Rhodotorula glutinis* or *Flavobacterium johnsoniae*; in particular a TAL comprising a sequence chosen from SEQ ID NOs: 39 and 41 and polypeptides comprising a sequence having at least 60, 70, 80, 85, 90 or 95% sequence identity with one of these sequences and having tyrosine ammonia lyase activity; preferably a TAL comprising a sequence chosen from SEQ ID NO: 41 and polypeptides comprising a sequence having at least 60, 70, 80, 85, 90 or 95% sequence identity with this sequence and having tyrosine ammonia lyase activity;

a heterologous nucleic acid sequence coding for a 4-coumarate-CoA ligase (4CL) which is capable of producing coumaryl-CoA from p-coumaric acid and Coenzyme A; preferably from *Arabidopsis thaliana, Petroselinum crispum* or *Streptomyces clavuligerus*; a 4CL comprising a sequence chosen from SEQ ID NOs:

43, 45, 47 and 49 and polypeptides comprising a sequence having at least 60, 70, 80, 85, 90 or 95% sequence identity with one of these sequences and having 4-coumarate-CoA ligase activity, preferably a 4CL comprising a sequence selected from SEQ ID NO: 45 and polypeptides comprising a sequence having at least 60, 70, 80, 85, 90 or 95% sequence identity with this sequence and having 4-coumarate-CoA ligase activity;

a heterologous nucleic acid sequence coding for a chalcone synthase (CHS) which is capable of producing naringenin-chalcone from 4-coumaroyl-CoA and malonyl-CoA; preferably from *Citrus sinensis, Hordeum vulgare* or *Streptomyces clavuligerus*, in particular a CHS comprising a sequence chosen from SEQ ID NOs: 51, 53, 55 and 57 and polypeptides comprising a sequence having at least 60, 70, 80, 85, 90 or 95% sequence identity with one of these sequences and having chalcone synthase activity, preferably from enzymes comprising a sequence chosen from SEQ ID NOs: 53 and 55 and polypeptides comprising a sequence having at least 60, 70, 80, 85, 90 or 95% sequence identity with one of these sequences and having chalcone synthase activity, and more particularly preferably a CHS comprising a sequence chosen from SEQ ID NO: 53 and polypeptides comprising a sequence having at least 60, 70, 80, 85, 90 or 95% sequence identity with this sequence and having chalcone synthase activity;

a heterologous nucleic acid sequence coding for a chalcone isomerase (CHI) which is capable of producing naringenin from naringenin chalcone; preferably from *Arabidopsis thaliana* or *Streptomyces clavuligerus*, in particular a CHI comprising a sequence chosen from SEQ ID NOs: 59 and 61 and polypeptides comprising a sequence having at least 60, 70, 80, 85, 90 or 95% sequence identity with one of these sequences and having chalcone isomerase activity, and more particularly preferably a CHI comprising a sequence chosen from SEQ ID NO: 61 and polypeptides comprising a sequence having at least 60, 70, 80, 85, 90 or 95% sequence identity with this sequence and having chalcone isomerase activity.

In another particular embodiment, the microorganism comprises heterologous nucleic acid sequences coding for the enzymes UGT, RhaT, RHM, F3'H, OMT, 4CL, CHS and CHI, and optionally for the enzymes CPR, FNS and SAMT, as described in the preceding embodiment and also comprises:

a heterologous nucleic acid sequence coding for a phenylalanine ammonia lyase (PAL), in particular a PAL comprising a sequence chosen from SEQ ID NOs: 63, 65 and 77 and polypeptides comprising a sequence having at least 60, 70, 80, 85, 90 or 95% sequence identity with one of these sequences and having phenylalanine ammonia lyase activity, in particular a PAL comprising a sequence chosen from SEQ ID NO: 65 and polypeptides comprising a sequence having at least 60, 70, 80, 85, 90 or 95% sequence identity with this sequence and having phenylalanine ammonia lyase activity, and a heterologous nucleic acid sequence coding for a cinnamate 4-hydroxylase (C4H), in particular a C4H comprising a sequence chosen from SEQ ID NOs: 67, 69 and 79 and polypeptides comprising a sequence having at least 60, 70, 80, 85, 90 or 95% sequence identity with one of these sequences and having cinnamate 4-hydroxylase activity, which are capable of producing p-coumaric acid from phenylalanine, in particular a C4H comprising a sequence chosen from SEQ ID NO: 79 and polypeptides comprising a sequence having at least 60, 70, 80, 85, 90 or 95% sequence identity with this sequence and having cinnamate 4-hydroxylase activity.

In a third particular embodiment, the microorganism comprises heterologous nucleic acid sequences coding for the enzymes UGT, RhaT, RHM, F3'H, OMT, 4CL, CHS and CHI, and optionally for the enzymes CPR, FNS and SAMT, as described in the preceding embodiment and also comprises:

a heterologous nucleic acid sequence coding for a dihydroxyphenylalanine ammonia-lyase (DAL) which is capable of producing caffeic acid from L-DOPA (3,4-dihydroxy-L-phenylalanine);

a heterologous nucleic acid sequence coding for a 4-hydroxyphenylacetate 3-monooxygenase oxygenase subunit (HpaB), preferably comprising a sequence chosen from SEQ ID NO: 83 and polypeptides comprising a sequence having at least 60, 70, 80, 85, 90 or 95% sequence identity therewith and having 4-hydroxyphenylacetate 3-monooxygenase oxygenase activity, and a heterologous nucleic acid sequence coding for a 4-hydroxyphenylacetate 3-monooxygenase reductase subunit (HpaC), preferably comprising a sequence chosen from SEQ ID NO: 85 and polypeptides comprising a sequence having at least 60, 70, 80, 85, 90 or 95% sequence identity therewith and having 4-hydroxyphenylacetate 3-monooxygenase reductase activity; or a heterologous nucleic acid sequence coding for a 4-methoxybenzoate 0-demethylase which is capable of converting tyrosine into L-DOPA and also p-coumaric acid into caffeic acid, preferably comprising a sequence chosen from SEQ ID NOs: 73 and 75 and polypeptides comprising a sequence having at least 60, 70, 80, 85, 90 or 95% sequence identity with one of these sequences and having L-tyrosine hydroxylase activity; or a heterologous nucleic acid sequence coding for a p-coumarate 3-hydroxylase which is capable of converting p-coumaric acid into caffeic acid, preferably comprising a sequence chosen from SEQ ID NO: 71 and polypeptides comprising a sequence having at least 60, 70, 80, 85, 90 or 95% sequence identity with one of these sequences and having p-coumarate 3-hydroxylase activity.

In another particular embodiment, the microorganism comprises heterologous nucleic acid sequences coding for the enzymes UGT, RhaT, RHM, F3'H, OMT, 4CL, CHS and CHI, and optionally for the enzymes CPR, FNS and SAMT, as described in the preceding embodiment and also comprises:

a heterologous nucleic acid sequence coding for a tyrosine ammonia lyase (TAL) which is capable of producing p-coumaric acid from tyrosine; preferably from *Rhodotorula glutinis* or *Flavobacterium johnsoniae*; in particular a TAL comprising a sequence chosen from SEQ ID NOs: 39 and 41 and polypeptides comprising a sequence having at least 60, 70, 80, 85, 90 or 95% sequence identity with one of these sequences and having tyrosine ammonia lyase activity; preferably a TAL comprising a sequence chosen from SEQ ID NO: 41 and polypeptides comprising a sequence having at least 60, 70, 80, 85, 90 or 95% sequence identity with this sequence and having tyrosine ammonia lyase activity;

optionally, a heterologous nucleic acid sequence coding for a phenylalanine ammonia lyase (PAL), in particular a PAL comprising a sequence chosen from SEQ ID NOs: 63, 65 and 77 and polypeptides comprising a sequence having at least 60, 70, 80, 85, 90 or 95% sequence identity with one of these sequences and having phenylalanine ammonia lyase activity, preferably a PAL comprising a sequence chosen from SEQ ID NO: 65 and polypeptides comprising a sequence having at least 60, 70, 80, 85, 90 or 95% sequence identity with this sequence and having phenylalanine ammonia lyase activity; and a heterologous nucleic acid sequence coding for a cinnamate 4-hydroxylase (C4H), in particular a C4H comprising a sequence chosen from SEQ ID NOs: 67, 69 and 79 and polypeptides comprising a sequence having at least 60, 70, 80, 85, 90 or 95% sequence identity with one of these sequences and having cinnamate 4-hydroxylase activity, which are capable of producing p-coumaric acid from phenylalanine, preferably a C4H comprising a sequence chosen from SEQ ID NO: 79 and polypeptides comprising a sequence having at least 60, 70, 80, 85, 90 or 95% sequence identity with this sequence and having cinnamate 4-hydroxylase activity;

optionally, a heterologous nucleic acid sequence coding for a 4-hydroxyphenylacetate 3-monooxygenase oxygenase subunit (HpaB), preferably comprising a sequence chosen from SEQ ID NO: 83 and polypeptides comprising a sequence having at least 60, 70, 80, 85, 90 or 95% sequence identity therewith and having 4-hydroxyphenylacetate 3-monooxygenase oxygenase activity, and a heterologous nucleic acid sequence coding for a 4-hydroxyphenylacetate 3-monooxygenase reductase subunit (HpaC), preferably comprising a sequence chosen from SEQ ID NO: 85 and polypeptides comprising a sequence having at least 60, 70, 80, 85, 90 or 95% sequence identity therewith and having 4-hydroxyphenylacetate 3-monooxygenase reductase activity; or a heterologous nucleic acid sequence coding for a 4-methoxybenzoate 0-demethylase which is capable of converting tyrosine into L-DOPA and also p-coumaric acid into caffeic acid, preferably comprising a sequence chosen from SEQ ID NOs: 73 and 75 and polypeptides comprising a sequence having at least 60, 70, 80, 85, 90 or 95% sequence identity with one of these sequences and having L-tyrosine hydrolase activity; or a heterologous nucleic acid sequence coding for a p-coumarate 3-hydroxylase which is capable of converting p-coumaric acid into caffeic acid, preferably comprising a sequence chosen from SEQ ID NO: 71 and polypeptides comprising a sequence having at least 60, 70, 80, 85, 90 or 95% sequence identity with one of these sequences and having p-coumarate 3-hydroxylase activity;

optionally, a heterologous nucleic acid sequence coding for a dihydroxyphenylalanine ammonia-lyase (DAL) which is capable of producing caffeic acid from L-DOPA (3,4-dihydroxy-L-phenylalanine).

In another particular embodiment, the microorganism comprises:

a heterologous nucleic acid sequence coding for a flavanone 7-O-beta-D-glucosyltransferase (UGT) selected from enzymes comprising a sequence chosen from SEQ ID NO: 113 and polypeptides comprising a sequence having at least 60, 70, 80, 85, 90 or 95% sequence identity with this sequence and having flavanone 7-O-beta-D-glucosyltransferase activity;

a heterologous nucleic acid sequence coding for a 6"-O-rhamnosyltransferase (RhaT) comprising a sequence chosen from SEQ ID NO: 103 and polypeptides comprising a sequence having at least 60, 70, 80, 85, 90 or 95% sequence identity with this sequence and having 6"-O-rhamnosyltransferase activity; and a heterologous nucleic acid sequence coding for a UDP-glucose 4,6-dehydratase/UDP-4-keto-6-deoxy-D-glucose 3,5-epimerase/UDP-4-keto-L-rhamnose-reductase (RHM) comprising a sequence chosen from SEQ ID NO: 107 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity;

a heterologous nucleic acid sequence coding for a phenylalanine ammonia lyase (PAL) comprising a sequence chosen from SEQ ID NO: 65 and polypeptides comprising a sequence having at least 60, 70, 80, 85, 90 or 95% sequence identity with this sequence and having phenylalanine ammonia lyase activity;

a heterologous nucleic acid sequence coding for a cinnamate 4-hydroxylase (C4H), comprising a sequence chosen from SEQ ID NO: 79 and polypeptides comprising a sequence having at least 60, 70, 80, 85, 90 or 95% sequence identity with this sequence and having cinnamate 4-hydroxylase activity;

a heterologous nucleic acid sequence coding for a tyrosine ammonia lyase (TAL) comprising a sequence chosen from SEQ ID NO: 41 and polypeptides comprising a sequence having at least 60, 70, 80, 85, 90 or 95% sequence identity with this sequence and having tyrosine ammonia lyase activity;

a heterologous nucleic acid sequence coding for a 4-coumaroyl-CoA ligase (4CL) comprising a sequence selected from SEQ ID NO: 45 or 123 and polypeptides comprising a sequence having at least 60, 70, 80, 85, 90 or 95% sequence identity with one of these sequences and having 4-coumarate-CoA ligase activity, preferably a sequence selected from SEQ ID NO: 45 and polypeptides comprising a sequence having at least 60, 70, 80, 85, 90 or 95% sequence identity with this sequence and having 4-coumarate-CoA ligase activity;

a heterologous nucleic acid sequence coding for a chalcone synthase (CHS) comprising a sequence chosen from SEQ ID NO: 53 and polypeptides comprising a sequence having at least 60, 70, 80, 85, 90 or 95% sequence identity with this sequence and having chalcone synthase activity;

a heterologous nucleic acid sequence coding for a chalcone isomerase (CHI) comprising a sequence chosen from SEQ ID NO: 61 and polypeptides comprising a sequence having at least 60, 70, 80, 85, 90 or 95% sequence identity with this sequence and having chalcone isomerase activity;

a heterologous nucleic acid sequence coding for a flavonoid 3'-monooxygenase (F3'H) comprising a sequence chosen from SEQ ID NO: 7 and polypeptides comprising a sequence having at least 60, 70, 80, 85, 90 or 95% sequence identity with the sequence SEQ ID NO: 7 and having flavonoid 3'-monooxygenase activity;

a heterologous nucleic acid sequence coding for a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity; and a heterologous nucleic acid sequence coding for a cytochrome P450 reductase (CPR) comprising a sequence chosen from SEQ ID NO: 25 and polypeptides comprising a sequence having at least 60, 70, 80, 85, 90 or 95% sequence identity with one of these sequences and having cytochrome P450 reductase activity; and a heterologous nucleic acid sequence coding for an O-methyltransferase (OMT) which is capable of methylating eriodictyol and/or luteolin in position 4' and comprising a sequence chosen from SEQ ID NOs: 117 and 119 and polypeptides comprising a sequence having at least 60, 70, 80, 85, 90 or 95% sequence identity with one of these sequences and having O-methyltransferase activity, and preferably an OMT comprising a sequence chosen from SEQ ID NO: 117 and polypeptides comprising a sequence having at least 60, 70, 80, 85, 90 or 95% sequence identity with this sequence and having O-methyltransferase activity.

Preferably, the microorganism also comprises a heterologous or endogenous nucleic acid sequence coding for an S-adenosylmethionine synthetase (SAMT), in particular an SAMT comprising a sequence chosen from SEQ ID NO: 81 and a polypeptide comprising a sequence having at least 60, 70, 80, 85, 90 or 95% sequence identity with this sequence and having S-adenosylmethionine synthetase activity.

The origin of the enzymes or of a set of enzymes may be chosen so that their origin is the same or is similar. For example, the enzymes or the set of enzymes may be obtained from bacteria, for example from bacteria of the same genus or of the same species. In another example, the enzymes or the set of enzymes may be obtained from plants, for example from plants of the same genus or of the same species. The reason for this is that these common origins enable the enzymes to function together optimally.

In one embodiment, the microorganisms comprise a metabolic pathway for the biosynthesis of tyrosine. Notably, the microorganisms may have been modified to have increased production of tyrosine relative to a wild-type strain. Notably, the microorganisms may have been modified so that the carbon flow is redirected toward tyrosine biosynthesis. In addition, the microorganisms may have been modified to reduce or suppress the tyrosine biosynthesis feedback inhibitions.

In another embodiment, the microorganisms comprise a metabolic pathway for the biosynthesis of phenylalanine. Notably, the microorganisms may have been modified to have increased production of phenylalanine relative to a wild-type strain. Notably, the microorganisms may have been modified so that the carbon flow is redirected toward phenylalanine biosynthesis. In addition, the microorganisms may have been modified to reduce or suppress the phenylalanine biosynthesis feedback inhibitions.

In another embodiment, the microorganisms comprise a metabolic pathway for the biosynthesis of phenylalanine and tyrosine. Notably, the microorganisms may have been modified to have increased production of phenylalanine and tyrosine relative to a wild-type strain. Notably, the microorganisms may have been modified so that the carbon flow is redirected toward phenylalanine and tyrosine biosynthesis. In addition, the microorganisms may have been modified to reduce or suppress the phenylalanine and tyrosine biosynthesis feedback inhibitions.

Recombinant Nucleic Acid and Expression Cassette

Each nucleic acid sequence coding for an enzyme as described previously is included in an expression cassette. Preferably, the coding nucleic acid sequences have been optimized for expression in the host microorganism. The coding nucleic acid sequence is operatively linked to the elements required for the expression of the gene, notably for transcription and translation. These elements are chosen so as to be functional in the host recombinant microorganism. These elements may include, for example, transcription promoters, transcription activators, terminator sequences, and start and stop codons. The methods for selecting these elements as a function of the host cell in which expression is desired are well known to those skilled in the art.

Preferably, the promoter is a strong promoter. The promoter may optionally be inducible. For example, if the microorganism is prokaryotic, the promoter may be selected from the following promoters: LacI, LacZ, pLacT, ptac, pARA, pBAD, the RNA polymerase promoters of bacteriophage T3 or T7, the polyhedrin promoter, the PR or PL promoter of lambda phage. In one particular embodiment, the promoter is pLac. If the microorganism is eukaryotic and in particular a yeast, the promoter may be selected from the following promoters: the promoter pTDH3, the promoter pTEF1, the promoter pTEF2, the promoter pCCW12, the promoter pHHF2, the promoter pHTB2 and the promoter pRPL18B. Examples of inducible promoters that may be used in yeast are the promoters tetO-2, GAL10, GAL10-CYC1 and PHO5.

All or part of the expression cassettes comprising the nucleic acid sequences coding for the enzymes as described or a combination of some of them may be included in a common expression vector or in different expression vectors.

The present invention thus relates to a vector comprising two nucleic acid sequences chosen from a heterologous nucleic acid sequence coding for a flavanone 7-O-beta-D-glucosyltransferase (UGT), a heterologous nucleic acid sequence coding for a 6"-O-rhamnosyltransferase (RhaT) and a heterologous nucleic acid sequence coding for a UDP-glucose 4,6-dehydratase/UDP-4-keto-6-deoxy-D-glucose 3,5-epimerase/UDP-4-keto-L-rhamnose-reductase (RHM); preferably, a vector comprises these three sequences.

In particular, the present invention thus relates to a vector comprising two nucleic acid sequences chosen from (i) a heterologous nucleic acid sequence coding for a flavanone 7-O-beta-D-glucosyltransferase (UGT) from *Arabidopsis thaliana, Scutellaria baicalensis* or *Homo sapiens*, preferably from *Arabidopsis thaliana* or from *Scutellaria baicalensis*, preferably a flavanone 7-O-beta-D-glucosyltransferase (UGT) selected from enzymes comprising a sequence chosen from SEQ ID NOs: 113, 115, 91, 93, 95, 97, 99 and 101 and polypeptides comprising a sequence having at least 60, 70, 80, 85, 90 or 95% sequence identity with one of these sequences and having flavanone 7-O-beta-D-glucosyltransferase activity; in particular a flavanone 7-O-beta-D-glucosyltransferase (UGT) comprising a sequence chosen from SEQ ID NOs: 113, 115, 91, 93, 95 and 97 or from SEQ ID NOs: 113 and 95 and polypeptides comprising a sequence having at least 60, 70, 80, 85, 90 or 95% sequence identity with one of these sequences and having flavanone 7-O-beta-D-glucosyltransferase activity, preferably selected from enzymes comprising a sequence chosen from SEQ ID NO: 113 and polypeptides comprising a sequence having at least 60, 70, 80, 85, 90 or 95% sequence identity with this sequence and having flavanone 7-O-beta-D-glucosyltransferase activity;

(ii) a heterologous nucleic acid sequence coding for a 6"-O-rhamnosyltransferase (RhaT) of the genus *Citrus* or *Petunia hybrida*, preferably *Citrus sinensis, Citrus maxima* or *Citrus clementina*, even more preferably *Citrus sinensis* or *Citrus clementina*, preferably a 6"-O-rhamnosyltransferase (RhaT) comprising a sequence chosen from SEQ ID NOs: 103 and 105 and polypeptides comprising a sequence having at least 60, 70, 80, 85, 90 or 95% sequence identity with one of these sequences and having 6"-O-rhamnosyltransferase activity, and preferably an RhaT comprising a sequence chosen from SEQ ID NO: 103 and polypeptides comprising a sequence having at least 60, 70, 80, 85, 90 or 95% sequence identity with this sequence and having 6"-O-rhamnosyltransferase activity; and (iii) a heterologous nucleic acid sequence coding for a UDP-glucose 4,6-dehydratase/UDP-4-keto-6-deoxy-D-glucose 3,5-epimerase/UDP-4-keto-L-rhamnose-reductase (RHM) from *Citrus sinensis* or from *Arabidopsis thaliana*, preferably an RHM comprising a sequence chosen from SEQ ID NOs: 107, 109 and 111 and polypeptides comprising a sequence having at least 60, 70, 80, 85, 90 or 95% sequence identity with one of these sequences and having UDP-glucose 4,6-dehydratase/UDP-4-keto-6-deoxy-D-glucose 3,5-epimerase/UDP-4-keto-L-rhamnose-reductase activity, in particular an RHM comprising a sequence selected from SEQ ID NOs: 107 and 109 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity, and preferably an RHM comprising a sequence selected from SEQ ID NO: 107 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity.

In particular, the vector may comprise two nucleic acid sequences chosen from (i) a heterologous nucleic acid sequence coding for a flavanone 7-O-beta-D-glucosyltransferase (UGT) from *Arabidopsis thaliana, Scutellaria baicalensis* or *Homo sapiens*, preferably from *Arabidopsis thaliana* or from *Scutellaria baicalensis*, preferably a flavanone 7-O-beta-D-glucosyltransferase (UGT) selected from enzymes comprising a sequence chosen from SEQ ID NOs: 91, 93, 95, 97, 99 and 101 and polypeptides comprising a sequence having at least 60, 70, 80, 85, 90 or 95% sequence identity with one of these sequences and having flavanone 7-O-beta-D-glucosyltransferase activity; in particular a flavanone 7-O-beta-D-glucosyltransferase (UGT) comprising a sequence chosen from SEQ ID NOs: 91, 93, 95 and 97 and polypeptides comprising a sequence having at least 60, 70, 80, 85, 90 or 95% sequence identity with one of these sequences and having flavanone 7-O-beta-D-glucosyltransferase activity;

(ii) a heterologous nucleic acid sequence coding for a 6"-O-rhamnosyltransferase (RhaT) of the genus *Citrus* or *Petunia hybrida*, preferably *Citrus sinensis, Citrus maxima* or *Citrus clementina*, even more preferably *Citrus sinensis* or *Citrus clementina*, preferably a 6"-O-rhamnosyltransferase (RhaT) comprising a sequence chosen from SEQ ID NOs: 103 and 105 and polypeptides comprising a sequence having at least 60, 70, 80, 85, 90 or 95% sequence identity with one of these sequences and having 6"-O-rhamnosyltransferase activity; and (iii) a heterologous nucleic acid sequence coding for a UDP-glucose 4,6-dehydratase/UDP-4-keto-6-deoxy-D-glucose 3,5-epimerase/UDP-4-keto-L-rhamnose-reductase (RHM) from *Citrus sinensis* or from *Arabidopsis thaliana*, preferably an RHM comprising a sequence chosen from SEQ ID NOs: 107, 109 and 111 and polypeptides comprising a sequence having at least 60, 70, 80, 85, 90 or 95% sequence identity with one of these sequences and having UDP-glucose 4,6-dehydratase/UDP-4-keto-6-deoxy-D-glucose 3,5-epimerase/UDP-4-keto-L-rhamnose-reductase activity, in particular an RHM comprising a sequence selected from SEQ ID NOs: 107 and 109 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity.

Preferably, the vector comprises two nucleic acid sequences chosen from (I) a heterologous nucleic acid sequence coding for a flavanone 7-O-beta-D-glucosyltransferase (UGT) selected from enzymes comprising a sequence chosen from SEQ ID NOs: 113 and 95 and polypeptides comprising a sequence having at least 60, 70, 80, 85, 90 or 95% sequence identity with one of these sequences and having flavanone 7-O-beta-D-glucosyltransferase activity; preferably a flavanone 7-O-beta-D-glucosyltransferase (UGT) comprising a sequence chosen from SEQ ID NO: 113 and polypeptides comprising a sequence having at least 60, 70, 80, 85, 90 or 95% sequence identity with this sequence and having flavanone 7-O-beta-D-glucosyltransferase activity;

(ii) a heterologous nucleic acid sequence coding for a 6"-O-rhamnosyltransferase (RhaT) comprising a sequence chosen from SEQ ID NO: 103 and polypeptides comprising a sequence having at least 60, 70, 80, 85, 90 or 95% sequence identity with this sequence and having 6"-O-rhamnosyltransferase activity; and (iii) a heterologous nucleic acid sequence coding for a UDP-glucose 4,6-dehydratase/UDP-4-keto-6-deoxy-D-glucose 3,5-epimerase/UDP-4-keto-L-rhamnose-reductase (RHM) comprising a sequence chosen from SEQ ID NO: 107 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity.

In a preferred embodiment, the microorganism comprises all three.

The coding nucleic acid sequences and the enzyme sequences are as described above. The term "comprising a nucleic acid sequence" also means comprising an expression cassette comprising the nucleic acid sequence.

Optionally, the vector may also comprise one or more nucleic acid sequences chosen from: a nucleic acid sequence coding for an O-methyltransferase (OMT), a nucleic acid sequence coding for an F3'H, a nucleic acid sequence coding for a CPR, a nucleic acid sequence coding for an FNS, a nucleic acid sequence coding for an SAMT, a nucleic acid sequence coding for a TAL, a nucleic acid sequence coding for a 4CL, a nucleic acid sequence coding for a CHS, a nucleic acid sequence coding for a CHI, a nucleic acid sequence coding for a PAL, a nucleic acid sequence coding for a C4H, a nucleic acid sequence coding for an HpaB, and a nucleic acid sequence coding for a DAL, each of these enzymes being as defined above, and also combinations thereof.

Preferably, the vector also comprises one or more sequences chosen from a nucleic acid sequence coding for an OMT, a nucleic acid sequence coding for an F3'H, a nucleic acid sequence coding for a CPR, a nucleic acid sequence coding for an FNS, a nucleic acid sequence coding for a TAL, a nucleic acid sequence coding for a 4CL, a nucleic acid sequence coding for a CHS, a nucleic acid sequence coding for a CHI, a nucleic acid sequence coding for a PAL and a nucleic acid sequence coding for a C4H.

In particular, the vector may also comprise one or more nucleic acid sequences chosen from:

a heterologous nucleic acid sequence coding for a flavonoid 3'-monooxygenase (F3'H) which is capable of hydroxylating naringenin and/or apigenin in position 3'; preferably from *Perilla frutescens* var. *crispa, Petunia* x *hybrida, Callistephus chinensis, Gerbera hybrida, Citrus sinensis, Arabidopsis thaliana, Citrus clementina*, Osteospermum hybrid cultivar, *Phanerochaete chrysosporium, Streptomyces avermitilis* or *Pilosella officinarum*, in particular from *Perilla frutescens* var. *crispa, Petunia* x *hybrida, Callistephus chinensis, Gerbera hybrida, Citrus sinensis* or *Pilosella officinarum*, preferably an F3'H comprising a sequence chosen from SEQ ID NOs: 1, 3, 5, 7, 9, 11, 13, 15, 17, 19, 21 and 121 and polypeptides comprising a sequence having at least 60, 70, 80, 85, 90 or 95% sequence identity with one of these sequences and having flavonoid 3'-monooxygenase activity, preferably selected from enzymes comprising a sequence chosen from SEQ ID NOs: 1, 5, 7, 11, 17, 19 and 121 and polypeptides comprising a sequence having at least 60, 70, 80, 85, 90 or 95% sequence identity with one of these sequences and having flavonoid 3'-monooxygenase activity, in particular an F3'H comprising a sequence selected from SEQ ID NOs: 5, 7, 17 and 121 and polypeptides comprising a sequence having at least 60, 70, 80, 85, 90 or 95% sequence identity with this sequence and having flavonoid 3'-monooxygenase activity, and preferably an enzyme comprising a sequence selected from SEQ ID NO: 7 and polypeptides comprising a sequence having at least 75%, at least 80%, at least 85%, at least 90% or at least 95% identity with this sequence and having flavonoid 3'-monooxygenase activity;

a heterologous nucleic acid sequence coding for a cytochrome P450 reductase (CPR); preferably a CPR from *Saccharomyces cerevisiae*, or from a plant, for example from *Catharanthus roseus* or *Arabidopsis thaliana*; preferably a CPR comprising a sequence chosen from SEQ ID NOs: 23, 25, 27, 29 and 31 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23, 25 and 29 and polypeptides comprising a sequence having at least 60, 70, 80, 85, 90 or 95% sequence identity with one of these sequences and having cytochrome P450 reductase activity, and preferably a CPR comprising a sequence chosen from SEQ ID NO: 25 and polypeptides comprising a sequence having at least 60, 70, 80, 85, 90 or 95% sequence identity with this sequence and having cytochrome P450 reductase activity;

a heterologous nucleic acid sequence coding for an O-methyltransferase (OMT) which is capable of methylating eriodictyol and/or luteolin in position 4'; preferably an OMT from *Arabidopsis thaliana* or *Homo sapiens*, preferably an OMT comprising a sequence chosen from SEQ ID NOs: 117, 119, 87 and 89 and polypeptides comprising a sequence having at least 60, 70, 80, 85, 90 or 95% sequence identity with one of these sequences and having O-methyltransferase activity, notably with eriodictyol and/or luteolin as substrate and with methylation in position 4', preferably selected from the enzyme comprising a sequence chosen from SEQ ID NOs: 117, 119 and 89 and polypeptides comprising a sequence having at least 60, 70, 80, 85, 90 or 95% sequence identity with this sequence and having O-methyltransferase activity;

a heterologous nucleic acid sequence coding for a flavone synthase (FNS) which is capable of transforming naringenin into apigenin, eriodictyol into luteolin, and/or hesperetin into diosmetin, preferably of transforming eriodictyol into luteolin; preferably an FNS from *Arabidopsis thaliana, Lonicera japonica, Lonicera macranthoides, Medicago truncatula, Oryza sativa, Petroselinum crispum, Populus deltoides, Zea mays, Callistephus chinensis, Apium graveolens, Medicago truncatula, Cuminurn cyminum, Aethusa cynapium, Angelica archangelica, Conium maculatum, Camellia sinensis, Cynara cardunculus* var *scolymus, Saussurea medusa, Plectranthus barbatus, Scutellaria baicalensis, Dorcoceras hygrometricum, Antirrhinum majus, Perilla frutescens* var *crispa, Dahlia pinnata* or *Erythranthe lewisii*, in particular from *Arabidopsis thaliana, Lonicera japonica, Lonicera macranthoides, Medicago truncatula, Oryza sativa, Petroselinum crispum, Populus deltoides* or *Zea mays*, preferably from *Lonicera japonica, Lonicera macranthoides* and *Petroselinum crispum*; preferably an FNS comprising a sequence chosen from SEQ ID NOs: 33, 35, 37, 127, 129, 131, 133, 135, 137, 139, 141, 143, 145, 147, 149, 151, 153, 155, 157 and 159 and polypeptides comprising a sequence having at least 60, 70, 80, 85, 90 or 95% sequence identity with one of these sequences and having flavone synthase activity, preferably from enzymes comprising a sequence chosen from SEQ ID NOs: 33, 35 and 37 and polypeptides comprising a sequence having at least 60, 70, 80, 85, 90 or 95% sequence identity with one of these sequences and having flavone synthase activity, preferably a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity;

a heterologous or endogenous nucleic acid sequence coding for an S-adenosylmethionine synthetase (SAMT), in particular from *Saccharomyces cerevisiae*, for example an SAMT comprising a sequence chosen from SEQ ID NO: 81 and a polypeptide comprising a sequence having at least 60, 70, 80, 85, 90 or 95% sequence identity with this sequence and having S-adenosylmethionine synthetase activity;

a heterologous nucleic acid sequence coding for a tyrosine ammonia lyase (TAL) which is capable of producing p-coumaric acid from tyrosine; preferably from *Rho-*

*dotorula glutinis* or *Flavobacterium johnsoniae*; in particular a TAL comprising a sequence chosen from SEQ ID NOs: 39 and 41 and polypeptides comprising a sequence having at least 60, 70, 80, 85, 90 or 95% sequence identity with one of these sequences and having tyrosine ammonia lyase activity; preferably a TAL comprising a sequence chosen from SEQ ID NO: 41 and polypeptides comprising a sequence having at least 60, 70, 80, 85, 90 or 95% sequence identity with this sequence and having tyrosine ammonia lyase activity;

a heterologous nucleic acid sequence coding for a 4-coumarate-CoA ligase (4CL) which is capable of producing coumaryl-CoA from p-coumaric acid and Coenzyme A; preferably from *Arabidopsis thaliana, Citrus clementina, Petroselinum crispum* or *Streptomyces clavuligerus*; a 4CL comprising a sequence chosen from SEQ ID NOs: 43, 45, 47, 49, 123 and 125 and polypeptides comprising a sequence having at least 60, 70, 80, 85, 90 or 95% sequence identity with one of these sequences and having 4-coumarate-CoA ligase activity, preferably a 4CL comprising a sequence selected from SEQ ID NOs: 123, 125 and 45 and polypeptides comprising a sequence having at least 60, 70, 80, 85, 90 or 95% sequence identity with one of these sequences and having 4-coumarate-CoA ligase activity, and in particular a 4CL comprising a sequence selected from SEQ ID NO: 45 and polypeptides comprising a sequence having at least 60, 70, 80, 85, 90 or 95% sequence identity with this sequence and having 4-coumarate-CoA ligase activity;

a heterologous nucleic acid sequence coding for a chalcone synthase (CHS) which is capable of producing naringenin-chalcone from 4-coumaroyl-CoA and malonyl-CoA; preferably from *Citrus sinensis, Hordeum vulgare* or *Streptomyces clavuligerus*, in particular a CHS comprising a sequence chosen from SEQ ID NOs: 51, 53, 55 and 57 and polypeptides comprising a sequence having at least 60, 70, 80, 85, 90 or 95% sequence identity with one of these sequences and having chalcone synthase activity, preferably from enzymes comprising a sequence chosen from SEQ ID NOs: 53 and 55 and polypeptides comprising a sequence having at least 60, 70, 80, 85, 90 or 95% sequence identity with one of these sequences and having chalcone synthase activity, and preferably a CHS comprising a sequence chosen from SEQ ID NO: 53 and polypeptides comprising a sequence having at least 60, 70, 80, 85, 90 or 95% sequence identity with this sequence and having chalcone synthase activity;

a heterologous nucleic acid sequence coding for a chalcone isomerase (CHI) which is capable of producing naringenin from naringenin chalcone; preferably from *Arabidopsis thaliana* or *Streptomyces clavuligerus*, in particular a CHI comprising a sequence chosen from SEQ ID NOs: 59 and 61 and polypeptides comprising a sequence having at least 60, 70, 80, 85, 90 or 95% sequence identity with one of these sequences and having chalcone isomerase activity, and preferably a CHI comprising a sequence chosen from SEQ ID NO: 61 and polypeptides comprising a sequence having at least 60, 70, 80, 85, 90 or 95% sequence identity with this sequence and having chalcone isomerase activity;

a heterologous nucleic acid sequence coding for a phenylalanine ammonia lyase (PAL), in particular a PAL comprising a sequence chosen from SEQ ID NOs: 63, 65 and 77 and polypeptides comprising a sequence having at least 60, 70, 80, 85, 90 or 95% sequence identity with one of these sequences and having phenylalanine ammonia lyase activity, preferably a PAL comprising a sequence chosen from SEQ ID NO: 65 and polypeptides comprising a sequence having at least 60, 70, 80, 85, 90 or 95% sequence identity with this sequence and having phenylalanine ammonia lyase activity; and a heterologous nucleic acid sequence coding for a cinnamate 4-hydroxylase (C4H), in particular a C4H comprising a sequence chosen from SEQ ID NOs: 67, 69 and 79 and polypeptides comprising a sequence having at least 60, 70, 80, 85, 90 or 95% sequence identity with one of these sequences and having cinnamate 4-hydroxylase activity, which are capable of producing p-coumaric acid from phenylalanine, and preferably a C4H comprising a sequence chosen from SEQ ID NO: 79 and polypeptides comprising a sequence having at least 60, 70, 80, 85, 90 or 95% sequence identity with this sequence and having cinnamate 4-hydroxylase activity;

a nucleic acid sequence coding for a 4-hydroxyphenylacetate 3-monooxygenase oxygenase subunit (HpaB), preferably comprising a sequence chosen from SEQ ID NO: 83 and polypeptides comprising a sequence having at least 60, 70, 80, 85, 90 or 95% sequence identity therewith and having 4-hydroxyphenylacetate 3-monooxygenase oxygenase activity, and a nucleic acid sequence coding for a 4-hydroxyphenylacetate 3-monooxygenase reductase subunit (HpaC), preferably comprising a sequence chosen from SEQ ID NO: 85 and polypeptides comprising a sequence having at least 60, 70, 80, 85, 90 or 95% sequence identity therewith and having 4-hydroxyphenylacetate 3-monooxygenase reductase activity; or a nucleic acid sequence coding for a 4-methoxybenzoate 0-demethylase which is capable of converting tyrosine into L-DOPA and also p-coumaric acid into caffeic acid, preferably comprising a sequence chosen from SEQ ID NOs: 73 and 75 and polypeptides comprising a sequence having at least 60, 70, 80, 85, 90 or 95% sequence identity with one of these sequences and having L-tyrosine hydrolase activity; or a heterologous nucleic acid sequence coding for a p-coumarate 3-hydroxylase which is capable of converting p-coumaric acid into caffeic acid, preferably comprising a sequence SEQ ID NO: 71 and polypeptides comprising a sequence having at least 60, 70, 80, 85, 90 or 95% sequence identity with one of these sequences and having p-coumarate 3-hydroxylase activity, and a nucleic acid sequence coding for a dihydroxyphenylalanine ammonia-lyase (DAL).

In particular, the vector may also comprise one or more nucleic acid sequences chosen from:

a heterologous nucleic acid sequence coding for a flavonoid 3'-monooxygenase (F3'H) which is capable of hydroxylating naringenin and/or apigenin in position 3'; preferably from *Perilla frutescens* var. *crispa, Petunia* x *hybrida, Callistephus chinensis, Gerbera hybrida, Citrus sinensis* and *Pilosella officinarum*, preferably an F3'H comprising a sequence chosen from SEQ ID NOs: 1, 3, 5, 7, 9, 11, 13, 15, 17, 19 and 21 and polypeptides comprising a sequence having at least 60, 70, 80, 85, 90 or 95% sequence identity with one of these sequences and having flavonoid 3'-monooxygenase activity, preferably selected from enzymes comprising a sequence chosen from SEQ ID NOs: 1, 5, 7, 11, 17 and 19 and polypeptides comprising a sequence having at least 60, 70, 80, 85, 90 or 95% sequence identity with one of these sequences and having flavonoid 3'-monooxygenase activity, in particular an F3'H comprising a sequence selected from SEQ ID NOs: 5, 7 and 17 and polypeptides comprising a sequence having at least 60, 70, 80, 85, 90 or 95% sequence identity with this sequence and having flavonoid 3'-monooxygenase activity;

a heterologous nucleic acid sequence coding for a cytochrome P450 reductase (CPR); preferably a CPR from *Saccharomyces cerevisiae*, or from a plant, for example from *Catharanthus roseus* or *Arabidopsis thaliana*; preferably a CPR comprising a sequence chosen from SEQ ID NOs: 23, 25, 27, 29 and 31 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23, 25 and 29 and polypeptides comprising a sequence having at least 60, 70, 80, 85, 90 or 95% sequence identity with one of these sequences and having cytochrome P450 reductase activity;

a heterologous nucleic acid sequence coding for an O-methyltransferase (OMT) which is capable of methylating eriodictyol and/or luteolin in position 4'; preferably an OMT from *Arabidopsis thaliana* or *Homo sapiens*, preferably an OMT comprising a sequence chosen from SEQ ID NOs: 87 and 89 and polypeptides comprising a sequence having at least 60, 70, 80, 85, 90 or 95% sequence identity with one of these sequences and having O-methyltransferase activity, notably with eriodictyol and/or luteolin as substrate and with methylation in position 4', preferably selected from the enzyme comprising the sequence SEQ ID NO: 89 and polypeptides comprising a sequence having at least 60, 70, 80, 85, 90 or 95% sequence identity with this sequence and having O-methyltransferase activity;

a heterologous nucleic acid sequence coding for a flavone synthase (FNS) which is capable of transforming naringenin into apigenin, eriodictyol into luteolin and/or hesperetin into diosmetin, preferably of transforming eriodictyol into luteolin; preferably an FNS from *Arabidopsis thaliana, Lonicera japonica, Lonicera macranthoides, Medicago truncatula, Oryza sativa, Petroselinum crispum, Populus deltoides* or *Zea mays*, preferably from *Lonicera japonica, Lonicera macranthoides* and *Petroselinum crispum*; preferably an FNS comprising a sequence chosen from SEQ ID NOs: 33, 35 and 37 and polypeptides comprising a sequence having at least 60, 70, 80, 85, 90 or 95% sequence identity with one of these sequences and having flavone synthase activity, preferably from enzymes comprising a sequence chosen from SEQ ID NOs: 33, 35 and 37 and polypeptides comprising a sequence having at least 60, 70, 80, 85, 90 or 95% sequence identity with one of these sequences and having flavone synthase activity, preferably a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity;

a heterologous or endogenous nucleic acid sequence coding for an S-adenosylmethionine synthetase (SAMT), in particular from *Saccharomyces cerevisiae*, for example an SAMT comprising a sequence chosen from SEQ ID NO: 81 and a polypeptide comprising a sequence having at least 60, 70, 80, 85, 90 or 95% sequence identity with this sequence and having S-adenosylmethionine synthetase activity;

a heterologous nucleic acid sequence coding for a tyrosine ammonia lyase (TAL) which is capable of producing p-coumaric acid from tyrosine; preferably from *Rhodotorula glutinis* or *Flavobacterium johnsoniae*; in particular a TAL comprising a sequence chosen from SEQ ID NOs: 39 and 41 and polypeptides comprising a sequence having at least 60, 70, 80, 85, 90 or 95% sequence identity with one of these sequences and having tyrosine ammonia lyase activity; preferably a TAL comprising a sequence chosen from SEQ ID NO: 41 and polypeptides comprising a sequence having at least 60, 70, 80, 85, 90 or 95% sequence identity with this sequence and having tyrosine ammonia lyase activity;

a heterologous nucleic acid sequence coding for a 4-coumarate-CoA ligase (4CL) which is capable of producing coumaryl-CoA from p-coumaric acid and Coenzyme A; preferably from *Arabidopsis thaliana, Petroselinum crispum* or *Streptomyces clavuligerus*; a 4CL comprising a sequence chosen from SEQ ID NOs: 43, 45, 47 and 49 and polypeptides comprising a sequence having at least 60, 70, 80, 85, 90 or 95% sequence identity with one of these sequences and having 4-coumarate-CoA ligase activity;

a heterologous nucleic acid sequence coding for a chalcone synthase (CHS) which is capable of producing naringenin-chalcone from 4-coumaroyl-CoA and malonyl-CoA; preferably from *Citrus sinensis, Hordeum vulgare* or *Streptomyces clavuligerus*, in particular a CHS comprising a sequence chosen from SEQ ID NOs: 51, 53, 55 and 57 and polypeptides comprising a sequence having at least 60, 70, 80, 85, 90 or 95% sequence identity with one of these sequences and having chalcone synthase activity, preferably from enzymes comprising a sequence chosen from SEQ ID NOs: 53 and 55 and polypeptides comprising a sequence having at least 60, 70, 80, 85, 90 or 95% sequence identity with one of these sequences and having chalcone synthase activity;

a heterologous nucleic acid sequence coding for a chalcone isomerase (CHI) which is capable of producing naringenin from naringenin chalcone; preferably from *Arabidopsis thaliana* or *Streptomyces clavuligerus*, in particular a CHI comprising a sequence chosen from SEQ ID NOs: 59 and 61 and polypeptides comprising a sequence having at least 60, 70, 80, 85, 90 or 95% sequence identity with one of these sequences and having chalcone isomerase activity;

a heterologous nucleic acid sequence coding for a phenylalanine ammonia lyase (PAL), in particular a PAL comprising a sequence chosen from SEQ ID NOs: 63, 65 and 77 and polypeptides comprising a sequence having at least 60, 70, 80, 85, 90 or 95% sequence identity with one of these sequences and having phenylalanine ammonia lyase activity; and a heterologous nucleic acid sequence coding for a cinnamate 4-hydroxylase (C4H), in particular a C4H comprising a sequence chosen from SEQ ID NOs: 67, 69 and 79 and polypeptides comprising a sequence having at least 60, 70, 80, 85, 90 or 95% sequence identity with one of these sequences and having cinnamate 4-hydroxylase activity, which are capable of producing p-coumaric acid from phenylalanine;

a nucleic acid sequence coding for a 4-hydroxyphenylacetate 3-monooxygenase oxygenase subunit (HpaB), preferably comprising a sequence chosen from SEQ ID NO: 83 and polypeptides comprising a sequence having at least 60, 70, 80, 85, 90 or 95% sequence identity therewith and having 4-hydroxyphenylacetate 3-monooxygenase oxygenase activity, and a nucleic acid sequence coding for a 4-hydroxyphenylacetate 3-monooxygenase reductase subunit (HpaC), preferably comprising a sequence chosen from SEQ ID NO: 85 and polypeptides comprising a sequence having at least 60, 70, 80, 85, 90 or 95% sequence identity therewith and having 4-hydroxyphenylacetate 3-monooxygenase reductase activity; or a nucleic acid sequence coding for a 4-methoxybenzoate 0-demethylase which is capable of converting tyrosine into L-DOPA and also p-coumaric acid into caffeic acid, preferably comprising a sequence chosen from SEQ ID NOs: 73 and 75 and polypeptides comprising a sequence having at least 60, 70, 80, 85, 90 or 95% sequence identity with one of these sequences and having L-tyrosine hydrolase activity; or a heterologous nucleic acid sequence coding for a p-coumarate 3-hydroxylase which is capable of converting p-coumaric acid into caffeic acid, preferably comprising a sequence SEQ ID NO: 71 and polypeptides comprising a sequence having at least 60, 70, 80, 85, 90 or 95% sequence identity with one of these sequences and having p-coumarate 3-hydroxylase activity, and a nucleic acid sequence coding for a dihydroxyphenylalanine ammonia-lyase (DAL).

Preferably, the vector may also comprise one or more nucleic acid sequences chosen from:

a heterologous nucleic acid sequence coding for a flavonoid 3'-monooxygenase (F3'H) comprising a sequence chosen from SEQ ID NOs: 7, 11, 17 and 121 and polypeptides comprising a sequence having at least 60, 70, 80, 85, 90 or 95% sequence identity with one of these sequences and having flavonoid 3'-monooxygenase activity, preferably selected from enzymes comprising a sequence chosen from SEQ ID NOs: 7, 17 and 121 and polypeptides comprising a sequence having at least 60, 70, 80, 85, 90 or 95% sequence identity with one of these sequences and having flavonoid 3'-monooxygenase activity, and most particularly preferably an F3'H comprising a sequence selected from SEQ ID NO: 7 and polypeptides comprising a sequence having at least 60, 70, 80, 85, 90 or 95% sequence identity with this sequence and having flavonoid 3'-monooxygenase activity;

a heterologous nucleic acid sequence coding for a cytochrome P450 reductase (CPR) comprising a sequence chosen from SEQ ID NOs: 23, 25, 27, 29 and 31 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23, 25 and 29 and polypeptides comprising a sequence having at least 60, 70, 80, 85, 90 or 95% sequence identity with one of these sequences and having cytochrome P450 reductase activity, and most particularly preferably from enzymes comprising a sequence chosen from SEQ ID NO: 25 and polypeptides comprising a sequence having at least 60, 70, 80, 85, 90 or 95% sequence identity with this sequence and having cytochrome P450 reductase activity;

a heterologous nucleic acid sequence coding for an O-methyltransferase (OMT) which is capable of methylating eriodictyol and/or luteolin in position 4' and comprising a sequence chosen from SEQ ID NOs: 117 and 119 and polypeptides comprising a sequence having at least 60, 70, 80, 85, 90 or 95% sequence identity with one of these sequences and having O-methyltransferase activity, notably with eriodictyol and/or luteolin as substrate and with methylation in position 4', preferably selected from the enzyme comprising a sequence chosen from SEQ ID NO: 117 and polypeptides comprising a sequence having at least 60, 70, 80, 85, 90 or 95% sequence identity with this sequence and having O-methyltransferase activity;

a heterologous nucleic acid sequence coding for a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity;

a heterologous or endogenous nucleic acid sequence coding for an S-adenosylmethionine synthetase (SAMT) comprising a sequence chosen from SEQ ID NO: 81 and a polypeptide having at least 60, 70, 80, 85, 90 or 95% sequence identity with this sequence and having S-adenosylmethionine synthetase activity;

a heterologous nucleic acid sequence coding for a tyrosine ammonia lyase (TAL) which is capable of producing p-coumaric acid from tyrosine and comprising a sequence chosen from SEQ ID NO: 41 and polypeptides comprising a sequence having at least 60, 70, 80, 85, 90 or 95% sequence identity with this sequence and having tyrosine ammonia lyase activity;

a heterologous nucleic acid sequence coding for a 4-coumarate-CoA ligase (4CL) which is capable of producing coumaryl-CoA from p-coumaric acid and Coenzyme A and comprising a sequence chosen from SEQ ID NOs: 123, 125 and 45 and polypeptides comprising a sequence having at least 60, 70, 80, 85, 90 or 95% sequence identity with one of these sequences and having 4-coumarate-CoA ligase activity, preferably comprising a sequence selected from SEQ ID NO: 45 and polypeptides comprising a sequence having at least 60, 70, 80, 85, 90 or 95% sequence identity with this sequence and having 4-coumarate-CoA ligase activity;

a heterologous nucleic acid sequence coding for a chalcone synthase (CHS) which is capable of producing naringenin-chalcone from 4-coumaroyl-CoA and malonyl-CoA and comprising a sequence chosen from SEQ ID NO: 53 and polypeptides comprising a sequence having at least 60, 70, 80, 85, 90 or 95% sequence identity with this sequence and having chalcone synthase activity;

a heterologous nucleic acid sequence coding for a chalcone isomerase (CHI) which is capable of producing naringenin from naringenin chalcone and comprising a sequence chosen from SEQ ID NO: 61 and polypeptides comprising a sequence having at least 60, 70, 80, 85, 90 or 95% sequence identity with this sequence and having chalcone isomerase activity;

a heterologous nucleic acid sequence coding for a phenylalanine ammonia lyase (PAL) and comprising a sequence chosen from SEQ ID NOs: 65 and 77 and polypeptides comprising a sequence having at least 60, 70, 80, 85, 90 or 95% sequence identity with one of these sequences and having phenylalanine ammonia lyase activity, preferably comprising a sequence chosen from SEQ ID NO: 65 and polypeptides comprising a sequence having at least 60, 70, 80, 85, 90 or 95% sequence identity with this sequence and having phenylalanine ammonia lyase activity; and a heterologous nucleic acid sequence coding for a cinnamate 4-hydroxylase (C4H) and comprising a sequence chosen from SEQ ID NO: 79 and polypeptides comprising a sequence having at least 60, 70, 80, 85, 90 or 95% sequence identity with this sequence and having cinnamate 4-hydroxylase activity, which are capable of producing p-coumaric acid from phenylalanine.

In a particular embodiment, the vector comprises:

a nucleic acid sequence coding for an O-methyltransferase, in particular which is capable of methylating eriodictyol and/or luteolin in position 4' and a heterologous nucleic acid sequence coding for a flavonoid 3'-monooxygenase (F3'H), in particular which is capable of adding a hydroxyl in position 3' of naringenin and/or apigenin; or a nucleic acid sequence coding for an O-methyltransferase (OMT), in particular which is capable of methylating eriodictyol and/or luteolin in position 4'; a heterologous nucleic acid sequence coding for a flavonoid 3'-monooxygenase (F3'H), in particular which is capable of adding a hydroxyl in position 3' of naringenin and/or apigenin; and a heterologous nucleic acid sequence coding for a cytochrome P450 reductase; or a heterologous nucleic acid sequence coding for an O-methyltransferase (OMT), in particular which is capable of methylating eriodictyol and/or luteolin in position 4'; and a heterologous nucleic acid sequence coding for a flavone synthase (FNS), which is capable of transforming naringenin into apigenin, eriodictyol into luteolin and/or hesperetin into diosmetin, preferably of transforming eriodictyol into luteolin; or a heterologous nucleic acid sequence coding for an O-methyltransferase which is capable of methylating eriodictyol and/or luteolin in position 4'; a heterologous nucleic acid sequence coding for a flavonoid 3'-monooxygenase (F3'H) which is capable of hydroxylating in position 3' of naringenin and/or apigenin; a heterologous nucleic acid sequence coding for a cytochrome P450 reductase; and a heterologous nucleic acid sequence coding for flavone synthase (FNS) which is capable of transforming naringenin into apigenin, eriodictyol into luteolin and/or hesperetin into diosmetin, preferably of transforming eriodictyol into luteolin.

The vector may thus comprise several nucleic acid sequences chosen therefrom, notably 1, 2, 3, 4, 5, 6, 7, 8, 9 or 10 nucleic acid sequences chosen therefrom.

The vector may notably comprise combinations of particular coding sequences as described above.

The vectors comprise coding sequences that are heterologous insofar as the coding sequences may be optimized for the host microorganism, may be under the control of a heterologous promoter and/or may combine coding sequences which do not originate from the same original organism and/or which are not present in the same arrangement.

The vector may be any DNA sequence in which it is possible to insert foreign nucleic acids, the vectors making it possible to introduce foreign DNA into the host microorganism. For example, the vector may be a plasmid, a phagemid, a cosmid, an artificial chromosome, notably a YAC, or a BAC.

The expression vectors may comprise nucleic acid sequences coding for selection markers. The selection markers may be genes for resistance to one or more antibiotics or auxotrophic genes. The auxotrophic gene may be, for example, URA3, LEU2, HIS3 or TRP1. The antibiotic-resistance gene may preferably be, for example, a gene for resistance to ampicillin, kanamycin, hygromycin, geneticin and/or nourseothricin.

The introduction of vectors into a host microorganism is a process that is widely known to those skilled in the art. Several methods are notably described in "Current Protocols in Molecular Biology", 13.7.1-13.7.10; or in Ellis T. et al., Integrative Biology, 2011, 3(2), 109-118.

The host microorganism may be transiently or stably transformed/transfected and the nucleic acid, the cassette or the vector may be contained therein in episomal form or in a form incorporated into the genome of the host microorganism.

The expression vector may also comprise one or more sequences allowing the targeted insertion of the vector, of the expression cassette or of the nucleic acid into the genome of the host microorganism.

All or part of the expression cassettes comprising the nucleic acid sequences coding for the enzymes as described above or a combination of some of them may be inserted into the/a chromosome of the recombinant microorganism.

Conversely, all or part of the expression cassettes comprising the nucleic acid sequences coding for the enzymes as described or a combination of some of them may be conserved in episomal form, notably in plasmid form.

Optionally, the microorganism may comprise several copies of nucleic acid sequences coding for an enzyme as described previously. Notably, it may comprise 2 to 10 copies, for example 2, 3, 4, 5, 6, 7, 8, 9 or 10 copies of a nucleic acid sequence coding for an enzyme as described previously.

The present invention relates to a method for preparing a microorganism according to the present invention, comprising the introduction of nucleic acid sequences coding for a flavanone 7-O-beta-D-glucosyltransferase (UGT), in particular which is capable of adding a glucose in position 7 of hesperetin and diosmetin; for a 6"-O-rhamnosyltransferase (RhaT), in particular which is capable of transferring a rhamnose in position 6 of the glucose of hesperetin-7-O-glucoside and/or diosmetin-7-O-glucoside; and for a UDP-glucose 4,6-dehydratase/UDP-4-keto-6-deoxy-D-glucose 3,5-epimerase/UDP-4-keto-L-rhamnose-reductase (RHM), in particular which is capable of producing UDP-rhamnose in the microorganism and the selection of microorganisms comprising said nucleic acid sequences.

The method may also comprise the introduction of one or more nucleic acid sequences chosen from:

a heterologous nucleic acid sequence coding for a flavonoid 3'-monooxygenase (F3'H) which is capable of hydroxylating naringenin and/or apigenin in position 3'; preferably from *Perilla frutescens* var. *crispa, Petunia* x *hybrida, Callistephus chinensis, Gerbera hybrida, Citrus sinensis, Citrus clementina*, Osteospermum hybrid cultivar, *Phanerochaete chrysosporium, Streptomyces avermitilis* or *Pilosella officinarum*, in particular from *Perilla frutescens* var. *crispa, Petunia* x *hybrida, Callistephus chinensis, Gerbera hybrida, Citrus sinensis* or *Pilosella officinarum*, preferably an F3'H comprising a sequence chosen from SEQ ID NOs:

1, 3, 5, 7, 9, 11, 13, 15, 17, 19 and 21 and polypeptides comprising a sequence having at least 60, 70, 80, 85, 90 or 95% sequence identity with one of these sequences and having flavonoid 3'-monooxygenase activity, preferably selected from enzymes comprising a sequence chosen from SEQ ID NOs: 1, 5, 7, 11, 17 and 19 and polypeptides comprising a sequence having at least 60, 70, 80, 85, 90 or 95% sequence identity with one of these sequences and having flavonoid 3'-monooxygenase activity, in particular an F3'H comprising a sequence selected from SEQ ID NOs: 5, 7 and 17 and polypeptides comprising a sequence having at least 60, 70, 80, 85, 90 or 95% sequence identity with this sequence and having flavonoid 3'-monooxygenase activity, preferably an F3'H comprising a sequence chosen from SEQ ID NOs: 7 and polypeptides comprising a sequence having at least 60, 70, 80, 85, 90 or 95% sequence identity with the sequence SEQ ID NO: 7 and having flavonoid 3'-monooxygenase activity;

a heterologous nucleic acid sequence coding for a cytochrome P450 reductase (CPR); preferably a CPR from *Saccharomyces cerevisiae*, or from a plant, for example from *Catharanthus roseus* or *Arabidopsis thaliana*; preferably a CPR comprising a sequence chosen from SEQ ID NOs: 23, 25, 27, 29 and 31 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23, 25, 29 and 31 and polypeptides comprising a sequence having at least 60, 70, 80, 85, 90 or 95% sequence identity with one of these sequences and having cytochrome P450 reductase activity, and particularly a CPR comprising a sequence chosen from SEQ ID NO: 25 and polypeptides comprising a sequence having at least 60, 70, 80, 85, 90 or 95% sequence identity with this sequence and having cytochrome P450 reductase activity;

a heterologous nucleic acid sequence coding for an O-methyltransferase (OMT) which is capable of methylating eriodictyol and/or luteolin in position 4'; preferably an OMT from *Arabidopsis thaliana* or *Homo sapiens*, preferably an OMT comprising a sequence chosen from SEQ ID NOs: 87 and 89 and polypeptides comprising a sequence having at least 60, 70, 80, 85, 90 or 95% sequence identity with one of these sequences and having O-methyltransferase activity, notably with eriodictyol and/or luteolin as substrate and with methylation in position 4', preferably selected from the enzyme comprising a sequence chosen from SEQ ID NO: 89 and polypeptides comprising a sequence having at least 60, 70, 80, 85, 90 or 95% sequence identity with this sequence and having O-methyltransferase activity;

a heterologous nucleic acid sequence coding for a flavone synthase (FNS) which is capable of transforming naringenin into apigenin, eriodictyol into luteolin, and/or hesperetin into diosmetin, preferably of transforming eriodictyol into luteolin; preferably an FNS from *Arabidopsis thaliana, Lonicera japonica, Lonicera macranthoides, Medicago truncatula, Oryza sativa, Petroselinum crispum, Populus deltoides, Zea mays, Callistephus chinensis, Apium graveolens, Medicago truncatula, Cuminurn cyminum, Aethusa cynapium, Angelica archangelica, Conium maculatum, Camellia sinensis, Cynara cardunculus* var *scolymus, Saussurea medusa, Plectranthus barbatus, Scutellaria baicalensis, Dorcoceras hygrometricum, Antirrhinum majus, Perilla frutescens* var *crispa, Dahlia pinnata* or *Erythranthe lewisii*, in particular from *Arabidopsis thaliana, Lonicera japonica, Lonicera macranthoides, Medicago truncatula, Oryza sativa, Petroselinum crispum, Populus deltoides* or *Zea mays*, preferably from *Lonicera japonica, Lonicera macranthoides* and *Petroselinum crispum*; preferably an FNS comprising a sequence chosen from SEQ ID NOs: 33, 35, 37, 127, 129, 131, 133, 135, 137, 139, 141, 143, 145, 147, 149, 151, 153, 155, 157 and 159 and polypeptides comprising a sequence having at least 60, 70, 80, 85, 90 or 95% sequence identity with one of these sequences and having flavone synthase activity, preferably from enzymes comprising a sequence chosen from SEQ ID NOs: 33, 35 and 37 and polypeptides comprising a sequence having at least 60, 70, 80, 85, 90 or 95% sequence identity with one of these sequences and having flavone synthase activity, preferably a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity;

a heterologous or endogenous nucleic acid sequence coding for an S-adenosylmethionine synthetase (SAMT), in particular from *Saccharomyces cerevisiae*, for example an SAMT comprising a sequence chosen from SEQ ID NO: 81 and a polypeptide comprising a sequence having at least 60, 70, 80, 85, 90 or 95% sequence identity with this sequence and having S-adenosylmethionine synthetase activity;

a heterologous nucleic acid sequence coding for a tyrosine ammonia lyase (TAL) which is capable of producing p-coumaric acid from tyrosine; preferably from *Rhodotorula glutinis* or *Flavobacterium johnsoniae*; in particular a TAL comprising a sequence chosen from SEQ ID NOs: 39 and 41 and polypeptides comprising a sequence having at least 60, 70, 80, 85, 90 or 95% sequence identity with one of these sequences and having tyrosine ammonia lyase activity; preferably a TAL comprising a sequence chosen from SEQ ID NO: 41 and polypeptides comprising a sequence having at least 60, 70, 80, 85, 90 or 95% sequence identity with this sequence and having tyrosine ammonia lyase activity;

a heterologous nucleic acid sequence coding for a 4-coumarate-CoA ligase (4CL) which is capable of producing coumaryl-CoA from p-coumaric acid and Coenzyme A; preferably from *Arabidopsis thaliana, Petroselinum crispum* or *Streptomyces clavuligerus*; a 4CL comprising a sequence chosen from SEQ ID NOs: 43, 45, 47 and 49 and polypeptides comprising a sequence having at least 60, 70, 80, 85, 90 or 95% sequence identity with one of these sequences and having 4-coumarate-CoA ligase activity, and preferably a 4CL comprising a sequence selected from SEQ ID NO: 45 and polypeptides comprising a sequence having at least 60, 70, 80, 85, 90 or 95% sequence identity with this sequence and having 4-coumarate-CoA ligase activity;

a heterologous nucleic acid sequence coding for a chalcone synthase (CHS) which is capable of producing naringenin-chalcone from 4-coumaroyl-CoA and malonyl-CoA; preferably from *Citrus sinensis, Hordeum vulgare* or *Streptomyces clavuligerus*, in particular a CHS comprising a sequence chosen from SEQ ID NOs: 51, 53, 55 and 57 and polypeptides comprising a sequence having at least 60, 70, 80, 85, 90 or 95% sequence identity with one of these sequences and having chalcone synthase activity, preferably from enzymes comprising a sequence chosen from SEQ ID NOs: 53 and 55 and polypeptides comprising a sequence having at least 60, 70, 80, 85, 90 or 95% sequence identity with one of these sequences and having chalcone synthase activity, and more particularly preferably a CHS comprising a sequence chosen from SEQ ID NO: 53 and polypeptides comprising a sequence having at least 60, 70, 80, 85, 90 or 95% sequence identity with this sequence and having chalcone synthase activity;

a heterologous nucleic acid sequence coding for a chalcone isomerase (CHI) which is capable of producing naringenin from naringenin chalcone; preferably from *Arabidopsis thaliana* or *Streptomyces clavuligerus*, in particular a CHI comprising a sequence chosen from SEQ ID NOs: 59 and 61 and polypeptides comprising a sequence having at least 60, 70, 80, 85, 90 or 95% sequence identity with one of these sequences and having chalcone isomerase activity, and preferably a CHI comprising a sequence chosen from SEQ ID NO: 61 and polypeptides comprising a sequence having at least 60, 70, 80, 85, 90 or 95% sequence identity with this sequence and having chalcone isomerase activity;

a heterologous nucleic acid sequence coding for a phenylalanine ammonia lyase (PAL), in particular a PAL comprising a sequence chosen from SEQ ID NOs: 63, 65 and 77 and polypeptides comprising a sequence having at least 60, 70, 80, 85, 90 or 95% sequence identity with one of these sequences and having phenylalanine ammonia lyase activity, in particular a PAL comprising a sequence chosen from SEQ ID NO: 65 and polypeptides comprising a sequence having at least 60, 70, 80, 85, 90 or 95% sequence identity with this sequence and having phenylalanine ammonia lyase activity; and a heterologous nucleic acid sequence coding for a cinnamate 4-hydroxylase (C4H), in particular a C4H comprising a sequence chosen from SEQ ID NOs: 67, 69 and 79 and polypeptides comprising a sequence having at least 60, 70, 80, 85, 90 or 95% sequence identity with one of these sequences and having cinnamate 4-hydroxylase activity, which are capable of producing p-coumaric acid from phenylalanine, in particular a C4H comprising a sequence chosen from SEQ ID NO: 79 and polypeptides comprising a sequence having at least 60, 70, 80, 85, 90 or 95% sequence identity with this sequence and having cinnamate 4-hydroxylase activity;

a nucleic acid sequence coding for a 4-hydroxyphenylacetate 3-monooxygenase oxygenase subunit (HpaB), preferably comprising a sequence chosen from SEQ ID NO: 83 and polypeptides comprising a sequence having at least 60, 70, 80, 85, 90 or 95% sequence identity therewith and having 4-hydroxyphenylacetate 3-monooxygenase oxygenase activity, and a nucleic acid sequence coding for a 4-hydroxyphenylacetate 3-monooxygenase reductase subunit (HpaC), preferably comprising a sequence chosen from SEQ ID NO: 85 and polypeptides comprising a sequence having at least 60, 70, 80, 85, 90 or 95% sequence identity therewith and having 4-hydroxyphenylacetate 3-monooxygenase reductase activity; or a nucleic acid sequence coding for a 4-methoxybenzoate 0-demethylase which is capable of converting tyrosine into L-DOPA and also p-coumaric acid into caffeic acid, preferably comprising a sequence chosen from SEQ ID NOs: 73 and 75 and polypeptides comprising a sequence having at least 60, 70, 80, 85, 90 or 95% sequence identity with one of these sequences and having L-tyrosine hydrolase activity; or a heterologous nucleic acid sequence coding for a p-coumarate 3-hydroxylase which is capable of converting p-coumaric acid into caffeic acid, preferably comprising a sequence SEQ ID NO: 71 and polypeptides comprising a sequence having at least 60, 70, 80, 85, 90 or 95% sequence identity with one of these sequences and having p-coumarate 3-hydroxylase activity, and a nucleic acid sequence coding for a dihydroxyphenylalanine ammonia-lyase (DAL).

According to a preferred embodiment, the method comprises the introduction of:

(i) a heterologous nucleic acid sequence coding for a flavanone 7-O-beta-D-glucosyltransferase (UGT) from *Arabidopsis thaliana, Scutellaria baicalensis* or *Homo sapiens*, preferably from *Arabidopsis thaliana* or from *Scutellaria baicalensis*, preferably a flavanone 7-O-beta-D-glucosyltransferase (UGT) selected from enzymes comprising a sequence chosen from SEQ ID NOs: 113, 115, 91, 93, 95, 97, 99 and 101 and polypeptides comprising a sequence having at least 60, 70, 80, 85, 90 or 95% sequence identity with one of these sequences and having flavanone 7-O-beta-D-glucosyltransferase activity; in particular a flavanone 7-O-beta-D-glucosyltransferase (UGT) comprising a sequence chosen from SEQ ID NOs: 113 and 95 and polypeptides comprising a sequence having at least 60, 70, 80, 85, 90 or 95% sequence identity with one of these sequences and having flavanone 7-O-beta-D-glucosyltransferase activity;

(ii) a heterologous nucleic acid sequence coding for a 6"-O-rhamnosyltransferase (RhaT) of the genus *Citrus* or *Petunia hybrida*, preferably *Citrus sinensis, Citrus maxima*, or *Citrus clementina*, even more preferably *Citrus sinensis* or *Citrus clementina*, preferably an RhaT comprising a sequence chosen from SEQ ID NOs: 103 and 105 and polypeptides comprising a sequence having at least 60, 70, 80, 85, 90 or 95% sequence identity with one of these sequences and having 6"-O-rhamnosyltransferase activity, in particular a 6"-O-rhamnosyltransferase (RhaT) comprising a sequence chosen from SEQ ID NO: 103 and polypeptides comprising a sequence having at least 60, 70, 80, 85, 90 or 95% sequence identity with this sequence and having 6"-O-rhamnosyltransferase activity; and (iii) a heterologous nucleic acid sequence coding for a UDP-glucose 4,6-dehydratase/UDP-4-keto-6-deoxy-D-glucose 3,5-epimerase/UDP-4-keto-L-rhamnose-reductase (RHM) from *Citrus sinensis* or from *Arabidopsis thaliana*, preferably an RHM comprising a sequence chosen from SEQ ID NOs: 107, 109 and 111 and polypeptides comprising a sequence having at least 60, 70, 80, 85, 90 or 95% sequence identity with one of these sequences and having UDP-glucose 4,6-dehydratase/UDP-4-keto-6-deoxy-D-glucose 3,5-epimerase/UDP-4-keto-L-rhamnose-reductase activity, in particular an RHM comprising a sequence selected from SEQ ID NO: 107 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity;

and of at least one nucleic acid sequence chosen from:

a heterologous nucleic acid sequence coding for an O-methyltransferase (OMT) which is capable of methylating eriodictyol and/or luteolin in position 4'; preferably an OMT from *Citrus clementina, Citrus sinensis, Arabidopsis thaliana* or *Homo sapiens*, preferably an OMT comprising a sequence chosen from SEQ ID NOs: 117, 119, 87 and 89 and polypeptides comprising a sequence having at least 60, 70, 80, 85, 90 or 95% sequence identity with one of these sequences and having O-methyltransferase activity, notably with eriodictyol and/or luteolin as substrate and methylation in position 4', preferably an OMT comprising a sequence chosen from SEQ ID NOs: 117 and 119 and polypeptides comprising a sequence having at least 60, 70, 80, 85, 90 or 95% sequence identity with one of these sequences and having O-methyltransferase activity, and most particularly preferably an OMT comprising a sequence chosen from SEQ ID NO: 117 and polypeptides comprising a sequence having at least 60, 70, 80, 85, 90 or 95% sequence identity with this sequence and having O-methyltransferase activity;

a heterologous nucleic acid sequence coding for a flavonoid 3'-monooxygenase (F3'H) which is capable of hydroxylating naringenin and/or apigenin in position 3' and comprising a sequence selected from SEQ ID NOs: 7, 11, 17 and 121 and polypeptides comprising a sequence having at least 75%, at least 80%, at least 85%, at least 90% or at least 95% identity with one of these sequences and having flavonoid 3'-monooxygenase activity, preferably an enzyme comprising a sequence selected from SEQ ID NOs: 7, 17 and 121 and polypeptides comprising a sequence having at least 75%, at least 80%, at least 85%, at least 90% or at least 95% identity with one of these sequences and having flavonoid 3'-monooxygenase activity, and most particularly preferably an enzyme comprising a sequence selected from SEQ ID NO: 7 and polypeptides comprising a sequence having at least 75%, at least 80%, at least 85%, at least 90% or at least 95% identity with this sequence and having flavonoid 3'-monooxygenase activity; and a heterologous nucleic acid sequence coding for a cytochrome P450 reductase (CPR) and comprising a sequence chosen from SEQ ID NOs: 23, 25, 27, 29 and 31 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23, 25 and 29 and polypeptides comprising a sequence having at least 60, 70, 80, 85, 90 or 95% sequence identity with one of these sequences and having cytochrome P450 reductase activity, and particularly a CPR comprising a sequence chosen from SEQ ID NO: 25 and polypeptides comprising a sequence having at least 60, 70, 80, 85, 90 or 95% sequence identity with this sequence and having cytochrome P450 reductase activity; and a heterologous nucleic acid sequence coding for an FNS comprising a sequence chosen from SEQ ID NOs: 33, 35, 37, 127, 129, 131, 133, 135, 137, 139, 141, 143, 145, 147, 149, 151, 153, 155, 157 and 159 and polypeptides comprising a sequence having at least 60, 70, 80, 85, 90 or 95% sequence identity with one of these sequences and having flavone synthase activity, in particular a flavone synthase (FNS) and comprising a sequence chosen from SEQ ID NOs: 33, 35 and 37 and polypeptides comprising a sequence having at least 60, 70, 80, 85, 90 or 95% sequence identity with one of these sequences and having flavone synthase activity, preferably a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity; and a nucleic acid sequence coding for an S-adenosylmethionine synthetase (SAMT); in particular from *Saccharomyces cerevisiae*, for example an SAMT comprising a sequence chosen from SEQ ID NO: 81 and a polypeptide comprising a sequence having at least 60, 70, 80, 85, 90 or 95% sequence identity with this sequence and having S-adenosylmethionine synthetase activity, and a heterologous nucleic acid sequence coding for a tyrosine ammonia lyase (TAL) from *Rhodotorula glutinis* or *Flavobacterium johnsoniae*; in particular a TAL comprising a sequence chosen from SEQ ID NOs: 41 and 39 and polypeptides comprising a sequence having at least 60, 70, 80, 85, 90 or 95% sequence identity with one of these sequences and having tyrosine ammonia lyase activity; preferably a TAL comprising a sequence chosen from SEQ ID NO: 41 and polypeptides comprising a sequence having at least 60, 70, 80, 85, 90 or 95% sequence identity with this sequence and having tyrosine ammonia lyase activity;

a heterologous nucleic acid sequence coding for a 4-coumaroyl-CoA ligase (4CL) from *Arabidopsis thaliana, Citrus clementina, Petroselinum crispum* or *Streptomyces clavuligerus*; in particular a 4CL comprising a sequence chosen from SEQ ID NOs: 123, 125, 45, 43, 47 and 49 and polypeptides comprising a sequence having at least 60, 70, 80, 85, 90 or 95% sequence identity with one of these sequences and having 4-coumarate-CoA ligase activity; preferably a 4CL comprising a sequence selected from SEQ ID NOs: 123, 125 and 45 and polypeptides comprising a sequence having at least 60, 70, 80, 85, 90 or 95% sequence identity with one of these sequences and having 4-coumarate-CoA ligase activity; most particularly preferably a 4CL comprising a sequence selected from SEQ ID NO: 45 and polypeptides comprising a sequence having at least 60, 70, 80, 85, 90 or 95% sequence identity with this sequence and having 4-coumarate-CoA ligase activity, and a heterologous nucleic acid sequence coding for a chalcone synthase (CHS) from *Citrus sinensis, Hordeum vulgare* or *Streptomyces clavuligerus*, in particular a CHS comprising a sequence chosen from SEQ ID NOs: 53, 51, 55 and 57 and polypeptides comprising a sequence having at least 60, 70, 80, 85, 90 or 95% sequence identity with one of these sequences and having chalcone synthase activity, preferably a CHS comprising a sequence chosen from SEQ ID NO: 53 and polypeptides comprising a sequence having at least 60, 70, 80, 85, 90 or 95% sequence identity with this sequence and having chalcone synthase activity; and a heterologous nucleic acid sequence coding for a chalcone isomerase (CHI) from *Arabidopsis thaliana* or *Streptomyces clavuligerus*, in particular a CHI comprising a sequence chosen from SEQ ID NOs: 61 and 59 and polypeptides comprising a sequence having at least 60, 70, 80, 85, 90 or 95% sequence identity with one of these sequences and having chalcone isomerase activity; preferably a CHI comprising a sequence chosen from SEQ ID NO: 61 and polypeptides comprising a sequence having at least 60, 70, 80, 85, 90 or 95% sequence identity with this sequence and having chalcone isomerase activity.

Preferably, the method comprises the introduction of all these sequences.

Preferably, the method also comprises the introduction of:

a heterologous nucleic acid sequence coding for a phenylalanine ammonia lyase (PAL), in particular a PAL comprising a sequence chosen from SEQ ID NOs: 63, 65 and 77, preferably SEQ ID NOs: 65 and 77 and polypeptides comprising a sequence having at least 60, 70, 80, 85, 90 or 95% sequence identity with one of these sequences and having phenylalanine ammonia lyase activity, and more particularly preferably a phenylalanine ammonia lyase (PAL) comprising a sequence chosen from SEQ ID NO: 65 and polypeptides comprising a sequence having at least 60, 70, 80, 85, 90 or 95% sequence identity with this sequence and having phenylalanine ammonia lyase activity; and a heterologous nucleic acid sequence coding for a cinnamate 4-hydroxylase (C4H), in particular a C4H comprising a sequence chosen from SEQ ID NOs: 67, 69 and 79 and polypeptides comprising a sequence having at least 60, 70, 80, 85, 90 or 95% sequence identity with one of these sequences and having cinnamate 4-hydroxylase activity, and most particularly preferably a cinnamate 4-hydroxylase (C4H) comprising a sequence chosen from SEQ ID NO: 79 and polypeptides comprising a sequence having at least 60, 70, 80, 85, 90 or 95% sequence identity with this sequence and having cinnamate 4-hydroxylase activity.

Preferably, the method comprises the introduction of combinations of particular coding sequences as described above.

Production of Diosmin and/or Hesperidin

The present invention relates to the use of a microorganism according to the present invention for producing diosmin and/or hesperidin. In a first preferred embodiment, the invention relates to the use of a microorganism according to the present invention for producing diosmin. In a second preferred embodiment, the invention relates to the use of a microorganism according to the present invention for producing hesperidin. In a preferred embodiment, the invention relates to the use of a microorganism according to the present invention for producing diosmin and hesperidin.

The present invention also relates to a method for producing diosmin and/or hesperidin, comprising the cultivation of a microorganism according to the present invention, notably under conditions allowing or that are favourable for the production of diosmin and/or hesperidin and optionally the recovery and/or purification of the diosmin and/or hesperidin produced.

The conditions for cultivating the microorganism according to the invention may be adapted according to the conventional techniques that are well known to those skilled in the art.

The microorganism is cultivated in a suitable culture medium. The term "suitable culture medium" generally denotes a culture medium providing the nutrients that are essential for or beneficial to the maintenance and/or growth of said microorganism, such as carbon sources; nitrogen sources such as ammonium sulfate; phosphorus sources, for example monobasic potassium phosphate; trace elements, for example copper, iodide, iron, magnesium, zinc or molybdate salts; vitamins and other growth factors such as amino acids or other growth promoters. An antifoam may be added if need be. According to the invention, this suitable culture medium may be chemically defined or complex. The culture medium may thus be identical or similar in composition to that of a synthetic medium, as defined by Verduyn et al., (Yeast. 1992. 8: 501-17), adapted by Visser et al., (Biotechnology and Bioengineering. 2002. 79: 674-81), or commercially available such as the YNB medium (Yeast Nitrogen Base, MP Biomedicals or Sigma-Aldrich). Notably, the culture medium may comprise a simple carbon source, such as glucose, fructose, xylose, ethanol, glycerol, galactose, sucrose, cellulose, cellobiose, starch, glucose polymers, molasses, or byproducts of these sugars.

Preferably, the production of diosmin and/or hesperidin by the microorganism according to the invention is obtained without supplying naringenin, apigenin, eriodictyol, luteolin, hesperetin and/or diosmetin to the culture medium, preferably without supplying naringenin, apigenin, eriodictyol, luteolin, hesperetin and diosmetin to the culture medium.

According to the invention, any cultivation method for the industrial-scale production of molecules of interest may be envisioned. Advantageously, the cultivation is performed in bioreactors, notably in batch, fed-batch, chemostat and/or continuous cultivation mode. Controlled feeding with vitamins during the process may also be beneficial to the productivity (Alfenore et al., Appl. Microbiol. Biotechnol. 2002. 60: 67-72).

The cultivation is generally performed in bioreactors, with possible solid and/or liquid preculturing steps in Erlenmeyer flasks, with a suitable culture medium.

In general, the conditions for cultivating the microorganisms according to the invention are readily adaptable by a person skilled in the art, as a function of the microorganism. For example, the cultivation temperature is notably, for yeasts, between 20° C. and 40° C., preferably between 28° C. and 35° C., and more particularly about 30° C. for *S. cerevisiae*. The microorganism according to the present invention may be cultivated for 1 to 30 days and preferably for 1 to 10 days.

A microorganism according to the present invention is capable of producing diosmin and/or hesperidin in a minimum amount of 1 mg/l of culture medium, preferably 10, 20, 25, 30, 35, 40, 45, 50, 55, 60, 65, 70, 75, 80, 85, 90, 95 or 100 mg/l of culture medium, optionally 150, 200, 250, 300, 350, 400, 450, 500, 600, 700, 800, 900 or 1000 mg/l of culture medium.

DESCRIPTION OF THE FIGURES

FIG. 1: Description of the metabolic pathways for producing hesperidin and diosmin.

FIG. 2: Production of eriodictyol from naringenin by the strain FL_405 (F3'H4+CPR2). Control strain: CF235. Observation of disappearance of the naringenin peak and appearance of an eriodictyol peak in the strain FL-405.

FIG. 3: Production of luteolin from apigenin by the strain FL_405 (F3'H4+CPR2). Control strain: CF235. Observation of disappearance of the apigenin peak and appearance of a luteolin peak in the strain FL-405.

FIG. 4: Production of apigenin from naringenin by the strain SC744 (FNSII1+CPR2). Control strain: CF234. Observation of disappearance of the naringenin peak and appearance of an apigenin peak in the strain.

FIG. 5: Production of luteolin from eriodictyol SC744 (FNSII1+CPR2). Control strain: CF234. Observation of disappearance of the eriodictyol peak and appearance of a luteolin peak in the strain.

FIG. 6: Production of eriodictyol and luteolin by the strain SC1500. Control strain: CF237. Observation of the eriodictyol and luteolin peaks.

FIG. 7: Production of hesperetin from eriodictyol by the strains SC 1612 (MET+SAM) and SC 1614 (MET+SAM). Control strain: CF235. Observation of disappearance of the eriodictyol peak and appearance of a hesperetin peak in the strains.

FIG. 8: Production of diosmetin from luteolin by the strains SC 1612 (MET+SAM) and SC 1614 (MET+SAM). Control strain: CF235. Observation of disappearance of the luteolin peak and appearance of a diosmetin peak in the strains.

FIG. 9: Production of diosmetin from hesperetin by the strain SC744 (FNSII+CPR). Control strain: CF234. Observation of disappearance of the hesperetin peak and appearance of a diosmetin peak in the strain.

FIG. 10: Production of hesperetin from eriodictyol by *E. coli* EC26 (MET+SAM). Control strain: *E. coli* MH1. Observation of disappearance of the eriodictyol peak and appearance of a hesperetin peak in the strain.

FIG. 11: Production of diosmetin from luteolin by *E. coli* EC26 (MET+SAM). Control strain: *E. coli* MH1. Observation of disappearance of the luteolin peak and appearance of a diosmetin peak in the strain.

FIG. 12: Production of diosmetin from hesperetin by *E. coli* EC30 (FNSII). Control strain: *E. coli* MH1. Observation of disappearance of the hesperetin peak and appearance of a diosmetin peak in the strain.

FIG. 13: Production of hesperetin and diosmetin by the strain SC1508. Control strain: CF237. Observation of the hesperetin and diosmetin peaks.

FIG. 14: Production of hesperidin from hesperetin by the strain FL 547 (GT+RHM+RHAT). Control strain: CF 233. Observation of disappearance of the hesperetin peak and appearance of the hesperidin peak.

FIG. 15: Production of diosmin from diosmetin by the strain FL 547 (GT+RHM+RHAT). Control strain: CF 233. Observation of disappearance of the diosmetin peak and appearance of the diosmin peak.

FIG. 16: Production of hesperidin from hesperetin by *E. coli* EC38, EC45 and EC47 (GT+RHM+RHAT). Control strain: *E. coli* MH1. Observation of disappearance of the hesperetin peak and appearance of the hesperidin peak.

FIG. 17: Production of diosmin from diosmetin by *E. coli* EC38, EC45 and EC47 (GT+RHM+RHAT). Control strain: *E. coli* MH1. Observation of disappearance of the diosmetin peak and appearance of the diosmin peak.

FIG. 18: Production of hesperidin and diosmin by the strains SC1509, SC1530, SC1529, SC1568 and SC2410. Control strain: CF237. Observation of the hesperidin and diosmin peaks.

FIG. 19: Production of eriodictyol and luteolin by the strains SC2424, SC2425, SC2426, SC2427, SC2428 and SC1500. Control strain: CF237.

FIG. 20: Production of hesperetin and homoeriodictyol by the strains SC2147, SC2151, SC1612 and SC1614. Control strain: CF235.

FIG. 21: Production of diosmetin and chrysoeriol by the strains SC2147, SC2151, SC1612 and SC1614. Control strain: CF235.

FIG. 22: Production of hesperetin from eriodictyol by *E. coli* EC41 (MET+SAM). Control strain: *E. coli* MH1. Observation of disappearance of the eriodictyol peak and appearance of a hesperetin peak in the strain.

FIG. 23: Production of hesperetin from eriodictyol by *E. coli* EC43 (MET+SAM). Control strain: *E. coli* MH1. Observation of disappearance of the eriodictyol peak and appearance of a hesperetin peak in the strain.

FIG. 24: Production of diosmetin from luteolin by *E. coli* EC43 (MET+SAM). Control strain: *E. coli* MH1. Observation of disappearance of the luteolin peak and appearance of a diosmetin peak in the strain.

FIG. 25: Production of hesperetin and diosmetin by the strain SC2408. Control strain: CF237. Observation of the hesperetin and diosmetin peaks.

FIG. 26: Production of hesperetin and diosmetin by the strain SC2409. Control strain: CF237. Observation of the hesperetin and diosmetin peaks.

FIG. 27: Production of hesperetin and diosmetin by the strains SC2408, SC2409 and SC1508. Control strain: CF237.

FIG. 28: Production of hesperidin and diosmin by the strains SC1579, SC1584, SC1621 and SC1626.

FIG. 29: Production of diosmetin from naringenin by the strains SC2429 to SC2434, SC2436 to SC2444, SC2446 to SC2454, SC2456 to SC2464 and SC2466.

TABLE 1

SEQUENCE DESCRIPTION

| SEQ ID NO | Description |
|---|---|
| 39 | Amino acid sequence of tyrosine ammonia lyase from *Flavobacterium johnsoniae* |
| 40 | Nucleic acid sequence coding for tyrosine ammonia lyase from *Flavobacterium johnsoniae* |
| 41 | Amino acid sequence of tyrosine ammonia lyase from *Rhodotorula glutinis* |
| 42 | Nucleic acid sequence coding for tyrosine ammonia lyase from *Rhodotorula glutinis* |
| 43 | Amino acid sequence of 4-coumarate-CoA ligase from *Arabidopsis thaliana* |
| 44 | Nucleic acid sequence coding for 4-coumarate-CoA ligase from *Arabidopsis thaliana* |
| 45 | Amino acid sequence of 4-coumarate-CoA ligase from *Petroselinum crispum* |
| 46 | Nucleic acid sequence coding for 4-coumarate-CoA ligase from *Petroselinum crispum* |
| 47 | Amino acid sequence of 4-coumarate-CoA ligase from *Petroselinum crispum* |
| 48 | Nucleic acid sequence coding for 4-coumarate-CoA ligase from *Petroselinum crispum* |
| 49 | Amino acid sequence of 4-coumarate-CoA ligase from *Streptomyces clavuligerus* |
| 50 | Nucleic acid sequence coding for 4-coumarate-CoA ligase from *Streptomyces clavuligerus* |
| 51 | Amino acid sequence of chalcone synthase from *Hordeum vulgare* |
| 52 | Nucleic acid sequence coding for chalcone synthase from *Hordeum vulgare* |
| 53 | Amino acid sequence of chalcone synthase from *Citrus sinensis* |
| 54 | Nucleic acid sequence coding for chalcone synthase from *Citrus sinensis* |
| 55 | Amino acid sequence of chalcone synthase from *Citrus sinensis* |
| 56 | Nucleic acid sequence coding for chalcone synthase from *Citrus sinensis* |
| 57 | Amino acid sequence of chalcone synthase from *Streptomyces clavuligerus* |
| 58 | Nucleic acid sequence coding for chalcone synthase from *Streptomyces clavuligerus* |
| 59 | Amino acid sequence of chalcone isomerase from *Streptomyces clavuligerus* |
| 60 | Nucleic acid sequence coding for chalcone isomerase from *Streptomyces clavuligerus* |

TABLE 1-continued

| SEQUENCE DESCRIPTION | |
|---|---|
| SEQ ID NO | Description |
| 61 | Amino acid sequence of chalcone isomerase from *Arabidopsis thaliana* |
| 62 | Nucleic acid sequence coding for chalcone isomerase from *Arabidopsis thaliana* |
| 33 | Amino acid sequence of flavone synthase from *Lonicera japonica* |
| 34 | Nucleic acid sequence coding for flavone synthase from *Lonicera japonica* |
| 35 | Amino acid sequence of flavone synthase from *Lonicera macranthoides* |
| 36 | Nucleic acid sequence coding for flavone synthase from *Lonicera macranthoides* |
| 37 | Amino acid sequence of flavone synthase from *Petroselinum crispum* |
| 38 | Nucleic acid sequence coding for flavone synthase from *Petroselinum crispum* |
| 1 | Amino acid sequence of flavonoid 3'-monooxygenase from *Perilla frutescens* var. *crispa* |
| 2 | Nucleic acid sequence coding for flavonoid 3'-monooxygenase from *Perilla frutescens* var. *crispa* |
| 3 | Amino acid sequence of flavonoid 3'-monooxygenase from *Phanerochaete chrysosporium* |
| 4 | Nucleic acid sequence coding for flavonoid 3'-monooxygenase from *Phanerochaete chrysosporium* |
| 5 | Amino acid sequence of flavonoid 3'-monooxygenase from *Petunia* x *hybrida* |
| 6 | Nucleic acid sequence coding for flavonoid 3'-monooxygenase from *Petunia* x *hybrida* |
| 7 | Amino acid sequence of flavonoid 3'-monooxygenase from *Callistephus chinensis* |
| 8 | Nucleic acid sequence coding for flavonoid 3'-monooxygenase from *Callistephus chinensis* |
| 9 | Amino acid sequence of flavonoid 3'-monooxygenase from *Callistephus chinensis* |
| 10 | Nucleic acid sequence coding for flavonoid 3'-monooxygenase from *Callistephus chinensis* |
| 11 | Amino acid sequence of flavonoid 3'-monooxygenase from *Gerbera hybrida* |
| 12 | Nucleic acid sequence coding for flavonoid 3'-monooxygenase from *Gerbera hybrida* |
| 13 | Amino acid sequence of flavonoid 3'-monooxygenase from *Osteospermum hybrid cultivar* |
| 14 | Nucleic acid sequence coding for flavonoid 3'-monooxygenase from *Osteospermum hybrid cultivar* |
| 15 | Amino acid sequence of flavonoid 3'-monooxygenase from *Citrus clementina* |
| 16 | Nucleic acid sequence coding for flavonoid 3'-monooxygenase from *Citrus clementina* |
| 17 | Amino acid sequence of flavonoid 3'-monooxygenase from *Citrus sinensis* |
| 18 | Nucleic acid sequence coding for flavonoid 3'-monooxygenase from *Citrus sinensis* |
| 19 | Amino acid sequence of flavonoid 3'-monooxygenase from *Pilosella officinarum* |
| 20 | Nucleic acid sequence coding for flavonoid 3'-monooxygenase from *Pilosella officinarum* |
| 21 | Amino acid sequence of flavonoid 3'-monooxygenase from *Streptomyces avermitilis* |
| 22 | Nucleic acid sequence coding for flavonoid 3'-monooxygenase from *Streptomyces avermitilis* |
| 23 | Amino acid sequence of cytochrome P450 reductase from *Catharanthus roseus* |
| 24 | Nucleic acid sequence coding for cytochrome P450 reductase from *Catharanthus roseus* |
| 25 | Amino acid sequence of cytochrome P450 reductase from *Saccharomyces cerevisiae* |
| 26 | Nucleic acid sequence coding for cytochrome P450 reductase from *Saccharomyces cerevisiae* |
| 27 | Amino acid sequence of chimeric cytochrome P450 reductase |
| 28 | Nucleic acid sequence coding for chimeric cytochrome P450 reductase |
| 29 | Amino acid sequence of cytochrome P450 reductase from *Arabidopsis thaliana* |

TABLE 1-continued

| SEQUENCE DESCRIPTION | |
|---|---|
| SEQ ID NO | Description |
| 30 | Nucleic acid sequence coding for cytochrome P450 reductase from *Arabidopsis thaliana* |
| 31 | Amino acid sequence of cytochrome P450 reductase from *Arabidopsis thaliana* |
| 32 | Nucleic acid sequence coding for cytochrome P450 reductase from *Arabidopsis thaliana* |
| 63 | Amino acid sequence of phenylalanine ammonia lyase from *Citrus sinensis* |
| 64 | Nucleic acid sequence coding for phenylalanine ammonia lyase from *Citrus sinensis* |
| 65 | Amino acid sequence of phenylalanine ammonia lyase from *Citrus sinensis* |
| 66 | Nucleic acid sequence coding for phenylalanine ammonia lyase from *Citrus sinensis* |
| 67 | Amino acid sequence of cinnamate 4-hydroxylase from *Citrus sinensis* |
| 68 | Nucleic acid sequence coding for cinnamate 4-hydroxylase from *Citrus sinensis* |
| 69 | Amino acid sequence of cinnamate 4-hydroxylase from *Citrus sinensis* |
| 70 | Nucleic acid sequence coding for cinnamate 4-hydroxylase from *Citrus sinensis* |
| 71 | Amino acid sequence of coumarate 3-hydroxylase from *Saccharothrix espanaensis* |
| 72 | Nucleic acid sequence coding for coumarate 3-hydroxylase from *Saccharothrix espanaensis* |
| 73 | Amino acid sequence of 4-methoxybenzoate O-demethylase from *Beta vulgaris* |
| 74 | Nucleic acid sequence coding for 4-methoxybenzoate O-demethylase from *Beta vulgaris* |
| 75 | Amino acid sequence of 4-methoxybenzoate O-demethylase from *Rhodopseudomonas palustris* |
| 76 | Nucleic acid sequence coding for 4-methoxybenzoate O-demethylase from *Rhodopseudomonas palustris* |
| 77 | Amino acid sequence of phenylalanine ammonia lyase from *Arabidopsis thaliana* |
| 78 | Nucleic acid sequence coding for phenylalanine ammonia lyase from *Arabidopsis thaliana* |
| 79 | Amino acid sequence of cinnamate 4-hydroxylase from *Arabidopsis thaliana* |
| 80 | Nucleic acid sequence coding for cinnamate 4-hydroxylase from *Arabidopsis thaliana* |
| 81 | Amino acid sequence of S-adenosylmethionine synthetase from *Saccharomyces cerevisiae* |
| 82 | Nucleic acid sequence coding for S-adenosylmethionine synthetase from *Saccharomyces cerevisiae* |
| 83 | Amino acid sequence of 4-hydroxyphenylacetate 3-monooxygenase oxygenase from *Escherichia coli* |
| 84 | Nucleic acid sequence coding for 4-hydroxyphenylacetate 3-monooxygenase oxygenase from *Escherichia coli* |
| 85 | Amino acid sequence of 4-hydroxyphenylacetate 3-monooxygenase reductase from *Escherichia coli* |
| 86 | Nucleic acid sequence coding for 4-hydroxyphenylacetate 3-monooxygenase reductase from *Escherichia coli* |
| 87 | Amino acid sequence of O-methyltransferase from *Arabidopsis thaliana* |
| 88 | Nucleic acid sequence coding for O-methyltransferase from *Arabidopsis thaliana* |
| 89 | Amino acid sequence of O-methyltransferase from *Homo sapiens* |
| 90 | Nucleic acid sequence coding for O-methyltransferase from *Homo sapiens* |
| 91 | Amino acid sequence of flavanone 7-O-beta-D-glucosyltransferase from *Arabidopsis thaliana* |
| 92 | Nucleic acid sequence coding for flavanone 7-O-beta-D-glucosyltransferase from *Arabidopsis thaliana* |
| 93 | Amino acid sequence of flavanone 7-O-beta-D-glucosyltransferase from *Scutellaria baicalensis* |
| 94 | Nucleic acid sequence coding for flavanone 7-O-beta-D-glucosyltransferase from *Scutellaria baicalensis* |
| 95 | Amino acid sequence of flavanone 7-O-beta-D-glucosyltransferase from *Scutellaria baicalensis* |
| 96 | Nucleic acid sequence coding for flavanone 7-O-beta-D-glucosyltransferase from *Scutellaria baicalensis* |

TABLE 1-continued

| SEQUENCE DESCRIPTION | |
|---|---|
| SEQ ID NO | Description |
| 97 | Amino acid sequence of flavanone 7-O-beta-D-glucosyltransferase from *Scutellaria baicalensis* |
| 98 | Nucleic acid sequence coding for flavanone 7-O-beta-D-glucosyltransferase from *Scutellaria baicalensis* |
| 99 | Amino acid sequence of flavanone 7-O-beta-D-glucosyltransferase from *Homo sapiens* |
| 100 | Nucleic acid sequence coding for flavanone 7-O-beta-D-glucosyltransferase from *Homo sapiens* |
| 101 | Amino acid sequence of flavanone 7-O-beta-D-glucosyltransferase from *Homo sapiens* |
| 102 | Nucleic acid sequence coding for flavanone 7-O-beta-D-glucosyltransferase from *Homo sapiens* |
| 103 | Amino acid sequence of 6-O-rhamnosyltransferase from *Citrus clementina* |
| 104 | Nucleic acid sequence coding for 6-O-rhamnosyltransferase from *Citrus clementina* |
| 105 | Amino acid sequence of 6-O-rhamnosyltransferase from *Citrus sinensis* |
| 106 | Nucleic acid sequence coding for 6-O-rhamnosyltransferase from *Citrus sinensis* |
| 107 | Amino acid sequence of UDP-glucose 4,6-dehydratase/UDP-4-keto-6-deoxy-D-glucose 3,5-epimerase/UDP-4-keto-L-rhamnose-reductase from *Citrus sinensis* |
| 108 | Nucleic acid sequence coding for UDP-glucose 4,6-dehydratase/UDP-4-keto-6-deoxy-D-glucose 3,5-epimerase/UDP-4-keto-L-rhamnose-reductase from *Citrus sinensis* |
| 109 | Amino acid sequence of UDP-glucose 4,6-dehydratase/UDP-4-keto-6-deoxy-D-glucose 3,5-epimerase/UDP-4-keto-L-rhamnose-reductase from *Arabidopsis thaliana* |
| 110 | Nucleic acid sequence coding for UDP-glucose 4,6-dehydratase/UDP-4-keto-6-deoxy-D-glucose 3,5-epimerase/UDP-4-keto-L-rhamnose-reductase from *Arabidopsis thaliana* |
| 111 | Amino acid sequence of UDP-glucose 4,6-dehydratase/UDP-4-keto-6-deoxy-D-glucose 3,5-epimerase/UDP-4-keto-L-rhamnose-reductase from *Arabidopsis thaliana* |
| 112 | Nucleic acid sequence coding for UDP-glucose 4,6-dehydratase/UDP-4-keto-6-deoxy-D-glucose 3,5-epimerase/UDP-4-keto-L-rhamnose-reductase from *Arabidopsis thaliana* |
| 113 | Amino acid sequence of flavanone 7-O-beta-D-glucosyltransferase from *Citrus sinensis* |
| 114 | Nucleic acid sequence coding for flavanone 7-O-beta-D-glucosyltransferase from *Citrus sinensis* |
| 115 | Amino acid sequence of flavanone 7-O-beta-D-glucosyltransferase from *Citrus clementina* |
| 116 | Nucleic acid sequence coding for flavanone 7-O-beta-D-glucosyltransferase from *Citrus clementina* |
| 117 | Amino acid sequence of O-methyltransferase from *Citrus clementina* |
| 118 | Nucleic acid sequence coding for O-methyltransferase from *Citrus clementina* |
| 119 | Amino acid sequence of O-methyltransferase from *Citrus sinensis* |
| 120 | Nucleic acid sequence coding for O-methyltransferase from *Citrus sinensis* |
| 121 | Amino acid sequence of flavonoid 3'-monooxygenase from *Arabidopsis thaliana* |
| 122 | Nucleic acid sequence coding for flavonoid 3'-monooxygenase from *Arabidopsis thaliana* |
| 123 | Amino acid sequence of a 4-coumarate-CoA ligase from *Arabidopsis thaliana* |
| 124 | Nucleic acid sequence coding for a 4-coumarate-CoA ligase from *Arabidopsis thaliana* |
| 125 | Amino acid sequence of a 4-coumarate-CoA ligase from *Citrus clementina* |
| 126 | Nucleic acid sequence coding for 4-coumarate-CoA ligase from *Citrus clementina* |
| 127 | Amino acid sequence of flavone synthase from *Angelica archangelica* |
| 128 | Nucleic acid sequence coding for flavone synthase from *Angelica archangelica* |
| 129 | Amino acid sequence of flavone synthase from *Cynara cardunculus* var. *scolymus* |
| 130 | Nucleic acid sequence coding for flavone synthase from *Cynara cardunculus* var. *scolymus* |
| 131 | Amino acid sequence of flavone synthase from *Perilla frutescens* var. *crispa* |
| 132 | Nucleic acid sequence coding for flavone synthase from *Perilla frutescens* var. *crispa* |
| 133 | Amino acid sequence of flavone synthase from *Dahlia pinnata* |
| 134 | Nucleic acid sequence coding for flavone synthase from *Dahlia pinnata* |
| 135 | Amino acid sequence of flavone synthase from *Callistephus chinensis* |
| 136 | Nucleic acid sequence coding for flavone synthase from *Callistephus chinensis* |
| 137 | Amino acid sequence of flavone synthase from *Apium graveolens* |
| 138 | Nucleic acid sequence coding for flavone synthase from *Apium graveolens* |
| 139 | Amino acid sequence of flavone synthase from *Medicago truncatula* |
| 140 | Nucleic acid sequence coding for flavone synthase from *Medicago truncatula* |
| 141 | Amino acid sequence of flavone synthase from *Cuminum cyminum* |
| 142 | Nucleic acid sequence coding for flavone synthase from *Cuminum cyminum* |
| 143 | Amino acid sequence of flavone synthase from *Aethusa cynapium* |
| 144 | Nucleic acid sequence coding for flavone synthase from *Aethusa cynapium* |
| 145 | Amino acid sequence of flavone synthase from *Conium maculatum* |
| 146 | Nucleic acid sequence coding for flavone synthase from *Conium maculatum* |
| 147 | Amino acid sequence of flavone synthase from *Camellia sinensis* |
| 148 | Nucleic acid sequence coding for flavone synthase from *Camellia sinensis* |
| 149 | Amino acid sequence of flavone synthase from *Saussurea medusa* |
| 150 | Nucleic acid sequence coding for flavone synthase from *Saussurea medusa* |
| 151 | Amino acid sequence of flavone synthase from *Plectranthus barbatus* |
| 152 | Nucleic acid sequence coding for flavone synthase from *Plectranthus barbatus* |
| 153 | Amino acid sequence of flavone synthase from *Scutellaria baicalensis* |
| 154 | Nucleic acid sequence coding for flavone synthase from *Scutellaria baicalensis* |
| 155 | Amino acid sequence of flavone synthase from *Dorcoceras hygrometricum* |
| 156 | Nucleic acid sequence coding for flavone synthase from *Dorcoceras hygrometricum* |
| 157 | Amino acid sequence of flavone synthase from *Antirrhinum majus* |
| 158 | Nucleic acid sequence coding for flavone synthase from *Antirrhinum majus* |
| 159 | Amino acid sequence of flavone synthase from *Erythranthe lewisii* |
| 160 | Nucleic acid sequence coding for flavone synthase from *Erythranthe lewisii* |

Examples

Materials and Methods

Strains

The yeasts used in the examples were obtained from *Saccharomyces cerevisiae* FY1679-28A (Tettelin et al., 1995 doi.org/10.1016/S1067-2389(06)80008-7). This yeast is quadruply auxotrophic for uracil, tryptophan, histidine and leucine. The bacterial strains used in the examples were obtained from *Escherichia coli* MH1.

Standards

The standards were acquired from the supplier Extrasynthese, France (naringenin, apigenin, eriodictyol, luteolin, hesperetin, hesperidin, diosmetin and diosmin).

Gene Cloning

The genes optimized to express in the yeast were synthesized by Eurofins Genomics, Ebersberg, Germany or Biomatik, Cambridge, Canada or Twist Biosciences, San Francisco, USA or DC Biosciences, Dundee, UK. By PCR, the gene cpr2 (SEQ ID NO: 26) from *S. cerevisiae* was amplified from the genomic DNA.

The genes obtained by synthesis or by PCR comprise at the 5' and 3' ends a Bbsl (GAAGAC) or Bsal (GGTCTC) restriction site.

All the genes, promoters and terminators were restriction-cloned in the vector pSBK for expression in the yeast or in the vector pSB1K3 for expression in *E. coli*. The promoters and terminators (Wargner et al., 2015 DOI: 10.1016/j.fgb.2015.12.001) were recovered by PCR from the genomic DNA of the yeast *S. cerevisiae* or of *E. coli.*

The vector pSBK comprises a URA or LEU or TRP or HIS selection marker for the yeast and the vector pSB1K3 comprises a kanamycin-resistance marker.

Culture Conditions

The strains were cultivated in 1 ml of minimum nitrogen base medium (Dutscher, Brumath, Fr) supplemented with glucose at 20 g/l for the yeasts and in 1 ml of M9 supplemented with glucose at 4 $g \cdot l^{-1}$ for *E. coli* in 24-well plates (Starlab, Orsay, Fr) at 30° C. for 72 hours with continuous stirring at 200 rpm. In certain cases, naringenin or apigenin was added at a concentration of 100 $mg \cdot l^{-1}$ to determine the activity of the F3'Hs, naringenin or eriodictyol was added at a concentration of 100 $mg \cdot l^{-1}$ to determine the activity of the FNSIIs, eriodictyol or luteolin was added at a concentration of 100 $mg \cdot l^{-1}$ to determine the activity of the METs, hesperetin or diosmetin was added at a concentration of 100 $mg \cdot l^{-1}$ to determine the activity of the GTs, and hesperetin 7-O-glucoside and/or diosmetin 7-O-glucoside was added to determine the activity of the RHMs and RHATs.

Each strain was inoculated at an OD of 0.2 using a 24-hour preculture cultivated under the same conditions.

Analytical Method

Preparation of the samples: The 1 mL cultures are frozen at −80° C. and then lyophilized for 12 hours at 0.10 mbar. The samples are then taken up in 1 mL of dimethyl sulfoxide (DMSO), stirred for 30 seconds at 1000 rpm and then centrifuged for 5 minutes at 3000 rpm at room temperature. After centrifugation, a known volume of supernatant is added to a known volume of a mixture of internal standards dissolved in methanol.

The final concentrations of the internal standards are:

| | |
|---|---|
| Diosmin C13 | 0.5 mg/L |
| Diosmetin C13 | 0.015 mg/L |

Analysis by UHPLC-TQ: The samples were analysed using a Vanquish-H UHPLC machine (Thermo) coupled to a Quantis triple-quadrupole MS (Thermo). The column is a Waters Acquity UPLC@ USST3 column (8 μm 2.1×100 mm) combined with an HSST3 1.8 μm 2.1×5 mm precolumn.

The mobile phase A is a 0.1% solution of formic acid in LC/MS-grade water and the mobile phase B is a 0.1% solution of formic acid in pure LC/MS-grade acetonitrile. The column temperature is 50° C. and the temperature of the sample changer is 10° C.

Two chromatographic conditions were used for detecting the flavonoids of interest:

TABLE 2

| Chromatographic conditions method 1 | | | |
|---|---|---|---|
| Time (min) | Flow rate (ml/min) | Mobile phase A (%) | Mobile phase B (%) |
| 0 | 0.5 | 73 | 27 |
| 8 | 0.5 | 73 | 27 |

TABLE 3

| Chromatographic conditions method 2 | | | |
|---|---|---|---|
| Time (min) | Flow rate (ml/min) | Mobile phase A (%) | Mobile phase B (%) |
| 0 | 0.5 | 83 | 17 |
| 3.75 | 0.5 | 83 | 17 |
| 4 | 0.5 | 73 | 27 |
| 8.5 | 0.5 | 73 | 27 |
| 11.0 | 0.5 | 50 | 50 |
| 13.0 | 0.5 | 0 | 100 |
| 13.5 | 0.5 | 83 | 17 |
| 15.0 | 0.5 | 83 | 17 |

The ions monitored and the fragmentation conditions for the molecules of interest are:

TABLE 4

| For method 1 | | | | | | | |
|---|---|---|---|---|---|---|---|
| Molecules | Retention time (min) | Polarity | Precursor ion | Daughter ion | Collision energy | Lens RF (V) | Reference internal standard |
| Naringenin | 3.3 | Negative | 271.0 | 119.0 | 27 | 169 | Diosmetin |
| | | | | 150.9 | 18 | 169 | C13 |
| Apigenin | 3.5 | Negative | 269.0 | 117.1 | 35 | 201 | Diosmetin |
| | | | | 150.9 | 24 | 201 | C13 |
| Eriodictyol | 1.9 | Negative | 287.1 | 135.1 | 26 | 147 | Diosmetin |
| | | | | 150.9 | 14 | 147 | C13 |
| Luteolin | 2.1 | Negative | 285.0 | 133.0 | 34 | 213 | Diosmetin |
| | | | | | | | C13 |

TABLE 5

| For method 2 | | | | | | | |
|---|---|---|---|---|---|---|---|
| Molecules | Retention time (min) | Polarity | Precursor ion | Daughter ion | Collision energy | Lens RF (V) | Reference internal standard |
| Naringenin | 7.8 | Negative | 271.0 | 119.0 | 27 | 169 | Diosmetin |
| | | | | 150.9 | 18 | 169 | C13 |
| Apigenin | 8.2 | Negative | 269.0 | 117.1 | 35 | 201 | Diosmetin |
| | | | | 150.9 | 24 | 201 | C13 |
| Eriodictyol | 6.2 | Negative | 287.1 | 135.1 | 26 | 147 | Diosmetin |
| | | | | 150.9 | 14 | 147 | C13 |
| Luteolin | 6.6 | Negative | 285.0 | 133.0 | 34 | 213 | Diosmetin |
| | | | | 150.9 | 25 | 213 | C13 |
| Hesperetin | 8.7 | Negative | 301.0 | 164.0 | 24 | 169 | Diosmetin |
| | | | | 150.9 | 17 | 169 | C13 |
| Diosmetin | 9.1 | Negative | 299.0 | 256.0 | 30 | 192 | Diosmetin |
| | | | | 284.1 | 21 | 192 | C13 |
| Hesperetin 7-O-glucoside | 4.9 | Negative | 463.2 | 286.0 | 32 | 141 | Diosmin C13 |
| | | | | 301.1 | 15 | 141 | |
| Hesperidin | 3.9 | Negative | 609.2 | 286.0 | 42 | 211 | Diosmin C13 |
| | | | | 301.1 | 25 | 211 | |
| Diosmetin 7-O-glucoside | 5.0 | Negative | 461.1 | 284.0 | 36 | 194 | Diosmin C13 |
| | | | | 299.1 | 10 | 194 | |
| Diosmin | 4.0 | Negative | 607.2 | 284.0 | 50 | 274 | Diosmin C13 |
| | | | | 299.0 | 25 | 274 | |

F3'H

Constructs for each of the F3'Hs were made in a vector bearing the URA selection marker (Table 6). Constructs including each SAM2 and only one of the various CPRs were created in a vector bearing the LEU selection marker (Table 7). Two vectors including only the URA or LEU selection marker were also created as controls. The marker genes make it possible to detect and to select the cells that have incorporated the gene of interest.

TABLE 6

| List of the various F3'H constructs tested | | |
|---|---|---|
| Names | Assembled genes | Markers |
| FL 23 | F3'H from *Perilla frutescens* var. *crispa* (SEQ ID NO: 2) | URA |
| FL 24 | F3'H from *Phanerochaete chrysosporium* (SEQ ID NO: 4) | URA |
| FL 25 | F3'H from *Petunia* x *hybrida* (SEQ ID NO: 6) | URA |
| FL 26 | F3'H from *Callistephus chinensis* (SEQ ID NO: 8) | URA |
| FL 27 | F3'H from *Callistephus chinensis* (SEQ ID NO: 10) | URA |
| FL 28 | F3'H from *Gerbera hybrida* (SEQ ID NO: 12) | URA |
| FL 29 | F3'H from *Osteospermum hybrid cultivar* (SEQ ID NO: 14) | URA |
| FL 30 | F3'H from *Citrus clementina* (SEQ ID NO: 16) | URA |
| FL 31 | F3'H from *Citrus sinensis* (SEQ ID NO: 18) | URA |
| FL 32 | F3'H from *Pilosella officinarum* (SEQ ID NO: 20) | URA |
| FL 1031 | F3'H from *Arabidopsis thaliana* (SEQ ID NO: 122) | URA |
| TT URA | — | URA |

TABLE 7

| List of constructs made with the various CPRs | | |
|---|---|---|
| Names | Assembled genes | Markers |
| FL 121 (CPR + SAM) | CPR from *Catharanthus roseus* (SEQ ID NO: 24), SAM from *Saccharomyces cerevisiae* (SEQ ID NO: 82) | LEU |
| FL 274 (CPR + SAM) | chimeric CPR (SEQ ID NO: 28), SAM from *Saccharomyces cerevisiae* (SEQ ID NO: 82) | LEU |

TABLE 7-continued

| List of constructs made with the various CPRs | | |
|---|---|---|
| Names | Assembled genes | Markers |
| FL 275 (ATR + SAM) | ATR from *Arabidopsis thaliana* (SEQ ID NO: 30), SAM from *Saccharomyces cerevisiae* (SEQ ID NO: 82) | LEU |
| FL 401 (CPR + SAM) | CPR from *Saccharomyces cerevisiae* (SEQ ID NO: 26), SAM from *Saccharomyces cerevisiae* (SEQ ID NO: 82) | LEU |
| FL 463 (ATR + SAM) | ATR from *Arabidopsis thaliana* (SEQ ID NO: 32), SAM from *Saccharomyces cerevisiae* (SEQ ID NO: 82) | LEU |
| TT LEU | — | LEU |

Several strains were created with, respectively, all the F3'Hs listed in Table 6 so that they could each be tested with the constructs of Table 7.

These various assemblies make it possible to check the enzymatic activity of the F3'Hs and also make it possible to determine the most efficient F3'H-CPR pairs.

For example, the strain FL 405 contains the constructs FL 26 and FL 401.

The control strain (without the genes) containing the constructs TT URA and TT LEU is called CF235.

FNSII

For each of the following FNSIIs, constructs in a TRP vector were prepared (Table 8). The same vectors with the LEU selection marker each containing SAM2 and a different CPR were used to test the FNSIIs (Table 9).

TABLE 8

| Constructs including the various FNSIIs tested | | |
|---|---|---|
| Names | Assembled genes | Markers |
| FL 620 (TAL + 4CL + CHS + | TAL from *Rhodotorula glutinis* (SEQ ID NO: 42), 4CL from *Petroselinum crispum* (SEQ ID NO: 46), CHS from *Citrus sinensis* (SEQ ID NO: 54), CHI from *Arabidopsis thaliana* (SEQ ID NO: 62) | TRP |

TABLE 8-continued

| Constructs including the various FNSIIs tested | | |
|---|---|---|
| Names | Assembled genes | Markers |
| CHI + FNSII) | FNSII from *Lonicera japonica* (SEQ ID NO: 34) | |
| FL 621 (TAL + 4CL + CHS + CHI + FNSII) | TAL from *Rhodotorula glutinis* (SEQ ID NO: 42), 4CL from *Petroselinum crispum* (SEQ ID NO: 46), CHS from *Citrus sinensis* (SEQ ID NO: 54), CHI from *Arabidopsis thaliana* (SEQ ID NO: 62) FNSII from *Lonicera macranthoides* (SEQ ID NO: 36) | TRP |
| FL 112 (TAL + 4CL + CHS + CHI + FNSII) | TAL from *Flavobacetrium jonhsoniae* (SEQ ID NO: 40), 4CL from *Petroselinum crispum* (SEQ ID NO: 46), CHS from *Citrus sinensis* (SEQ ID NO: 54), CHI from *Arabidopsis thaliana* (SEQ ID NO: 62) FNSII from *Petroselinum crispum* (SEQ ID NO: 38) | TRP |
| TT TRP | — | TRP |

TABLE 9

| List of constructs made with the various CPRs | | |
|---|---|---|
| Names | Assembled genes | Markers |
| FL 121 (CPR + SAM) | CPR from *Catharanthus roseus* (SEQ ID NO: 24), SAM from *Saccharomyces cerevisiae* (SEQ ID NO: 82) | LEU |
| FL 274 (CPR + SAM) | Chimeric CPR (SEQ ID NO: 28), SAM from *Saccharomyces cerevisiae* (SEQ ID NO: 82) | LEU |
| FL 275 (ATR + SAM) | ATR from *Arabidopsis thaliana* (SEQ ID NO: 30), SAM from *Saccharomyces cerevisiae* (SEQ ID NO: 82) | LEU |
| FL 401 (CPR + SAM) | CPR from *Saccharomyces cerevisiae* (SEQ ID NO: 26), SAM from *Saccharomyces cerevisiae* (SEQ ID NO: 82) | LEU |
| FL 463 (ATR + SAM) | ATR from *Arabidopsis thaliana* (SEQ ID NO: 32), SAM from *Saccharomyces cerevisiae* (SEQ ID NO: 82) | LEU |
| TT LEU | — | LEU |

Several strains were created with, respectively, each of the constructs of the FNSIIs listed in Table 8 and each of the constructs of the CPRs of Table 9.

These various assemblies make it possible to check the enzymatic activity of the FNSIIs and also make it possible to determine the most efficient FNSIIs.

For example, the strain SC 744 contains the constructs FL 620 and FL 401.

The control strain (without the genes) containing the constructs TT TRP and TT LEU is called CF234.

Similar constructs were made to test the FNSIIs of SEQ ID NOs: 127, 129, 131, 133, 135, 137, 139, 141, 143, 145, 147, 149, 151, 153, 155, 157 and 159.

Yeast Up to Eriodictyol/Luteolin

Strains including the pathway up to eriodictyol and luteolin were also tested:

- the strain SC1500 comprises the constructs FL 26, FL 602, FL 808 and FL 822;
- the strain SC2424 comprising the constructs FL 1031+FL 602+FL 822+TT HIS;
- the strain SC2425 comprising the constructs FL 26+FL 602+FL 822+TT HIS;
- the strain SC2426 comprising the constructs FL 31+FL 602+FL 822+TT HIS;
- the strain SC2427 comprises the constructs FL 1031, FL 602, FL 808 and FL 822; and
- the strain SC2428 comprising the constructs FL 31+FL 602+FL 808+FL 822.

TABLE 10

| Lists of constructs used for the strains including the pathway up to eriodictyol and luteolin | | |
|---|---|---|
| Names | Assembled genes | Markers |
| FL 26 (F3'H) | F3'H from *Callistephus chinensis* (SEQ ID NO: 8) | URA |
| FL 1031 (F3'H) | F3'H from *Arabidopsis thaliana* (SEQ ID NO: 122) | URA |
| FL 31 (F3'H) | F3'H from *Citrus sinensis* (SEQ ID NO: 18) | URA |
| FL 602 (TAL + 4CL + CHS + CHI + FNS) | TAL from *Rhodotorula glutinis* (SEQ ID NO: 42), 4CL from *Petroselinum crispum* (SEQ ID NO: 46), CHS from *Citrus sinensis* (SEQ ID NO: 54), CHI from *Arabidopsis thaliana* (SEQ ID NO: 62) FNSII from *Petroselinum crispum* (SEQ ID NO: 38) | TRP |
| FL 808 (PAL + C4H) | PAL from *Arabidopsis thaliana* (SEQ ID NO: 78), C4H from *Arabidopsis thalian*a (SEQ ID NO: 80), | HIS |
| FL 822 (CPR + CAF) | CPR from *Catharanthus roseus* (SEQ ID NO: 24), CAF from *Rhodopseudomonas palustris* (SEQ ID NO: 76) | LEU |
| TT HIS | | HIS |

The control strain (without the genes) containing the constructs TT URA, TT TRP, TT HIS and TT LEU is called CF237.

MET:

In order to test each of the METs, constructs were made and are presented in Table 11. The marker genes make it possible to detect and to select the cells that have incorporated the gene of interest.

TABLE 11

| List of constructs made to test the various METs | | |
|---|---|---|
| Names | Assembled genes | Markers |
| FL 121 (CPR + SAM) | CPR from *Catharanthus roseus* (SEQ ID NO: 24), SAM from *Saccharomyces cereyisiae* (SEQ ID NO: 82) | LEU |
| FL 266 (F3'H + MET) | F3'H from *Callistephus chinensis* (SEQ ID NO: 8), MET from *Arabidopsis thaliana* (SEQ ID NO: 88) | URA |
| FL 268 (F3'H + MET) | F3'H from *Callistephus chinensis* (SEQ ID NO: 8), MET from *Homo sapiens* (SEQ ID NO: 90) | URA |
| FL 469 (F3'H + MET) | F3'H from *Callistephus chinensis* (SEQ ID NO: 8) MET from *Citrus clementina* (SEQ ID NO: 118) | URA |
| FL 475 (F3'H + MET) | F3'H from *Callistephus chinensis* (SEQ ID NO: 8) MET from *Citrus sinensis* (SEQ ID NO: 120) | URA |

Four strains SC1612, SC1614, SC2147 and SC2151 were created, with FL 121 and FL 266 for SC1612, FL 121 and FL 268 for SC1614, FL 475 and FL 121 for SC2147 and FL 469 and FL 121 for SC2151 for the conversion of eriodictyol into hesperetin in order to determine which MET is the most efficient.

The control strain (without the genes) containing the constructs TT LEU and TT URA is called CF235.

F3'H, MET, FNS, CPR: Production of Diosmetin from Naringenin

TABLE 12

List of constructs used to test the enzymes in *Saccharomyces cerevisiae* (SC)

| Names | Assembled genes | Markers |
|---|---|---|
| FL 121 (CPR + SAM) | CPR from *Catharanthus roseus* (SEQ ID NO: 24), SAM from *Saccharomyces cerevisiae* (SEQ ID NO: 82) | LEU |
| TT LEU | — | LEU |
| FL 26 (F3'H) | F3'H from *Callistephus chinensis* (SEQ ID NO: 8), | URA |
| FL 1031 (F3'H) | F3'H from *Arabidopsis thaliana* (SEQ ID NO: 122), | URA |
| FL 1111 (FNS + MET) | FNSII from *Petroselinum crispum* (SEQ ID NO: 33) MET from *Citrus clementina* (SEQ ID NO: 118) | TRP |
| FL 1112 (FNS + MET) | FNSII from *Angelica archangelica* (SEQ ID NO: 128) MET from *Citrus clementina* (SEQ ID NO: 118) | TRP |
| FL 1113 (FNS + MET) | FNSII from *Cynara cardunculus var. scolymus* (SEQ ID NO: 130) MET from *Citrus clementina* (SEQ ID NO: 118) | TRP |
| FL 1114 (FNS + MET) | FNSII from *Perilla frutescens var. crispa* (SEQ ID NO: 132) MET from *Citrus clementina* (SEQ ID NO: 118) | TRP |
| FL 1115 (FNS + MET) | FNSII from *Dahlia pinnata* (SEQ ID NO: 134) MET from *Citrus clementina* (SEQ ID NO: 118) | TRP |
| FL 1116 (FNS + MET) | FNSII from *Petroselinum crispum* (SEQ ID NO: 33) MET from *Citrus sinensis* (SEQ ID NO: 120) | TRP |
| FL 1118 (FNS + MET) | FNSII from *Cynara cardunculus var. scolymus* (SEQ ID NO: 130) MET from *Citrus sinensis* (SEQ ID NO: 120) | TRP |
| FL 1119 (FNS + MET) | FNSII from *Perilla frutescens var. crispa* (SEQ ID NO: 132) MET from *Citrus sinensis* (SEQ ID NO: 120) | TRP |
| FL 1120 (FNS + MET) | FNSII from *Dahlia pinnata* (SEQ ID NO: 134) MET from *Citrus sinensis* (SEQ ID NO: 120) | TRP |

The following strains were constructed:

| |
|---|
| SC2429: FL 1111 + FL 1031 + FL 121 |
| SC2430: FL 1112 + FL 1031 + FL 121 |
| SC2431: FL 1113 + FL 1031 + FL 121 |
| SC2432: FL 1114 + FL 1031 + FL 121 |
| SC2433: FL 1115 + FL 1031 + FL 121 |
| SC2439: FL 1111 + FL 1031 + TT LEU |
| SC2440: FL 1112 + FL 1031 + TT LEU |
| SC2441: FL 1113 + FL 1031 + TT LEU |
| SC2442: FL 1114 + FL 1031 + TT LEU |
| SC2443: FL 1115 + FL 1031 + TT LEU |
| SC2434: FL 1116 + FL 1031 + FL 121 |
| SC2436: FL 1118 + FL 1031 + FL 121 |
| SC2437: FL 1119 + FL 1031 + FL 121 |
| SC2438: FL 1120 + FL 1031 + FL 121 |
| SC2444: FL 1116 + FL 1031 + TT LEU |
| SC2446: FL 1118 + FL 1031 + TT LEU |
| SC2447: FL 1119 + FL 1031 + TT LEU |
| SC2448: FL 1120 + FL 1031 + TT LEU |
| SC2449: FL 1111 + FL 26 + FL 121 |
| SC2450: FL 1112 + FL 26 + FL 121 |
| SC2451: FL 1113 + FL 26 + FL 121 |
| SC2452: FL 1114 + FL 26 + FL 121 |
| SC2453: FL 1115 + FL 26 + FL 121 |
| SC2459: FL 1111 + FL 26 + TT LEU |

-continued

| |
|---|
| SC2460: FL 1112 + FL 26 + TT LEU |
| SC2461: FL 1113 + FL 26 + TT LEU |
| SC2462: FL 1114 + FL 26 + TT LEU |
| SC2463: FL 1115 + FL 26 + TT LEU |
| SC2454: FL 1116 + FL 26 + FL 121 |
| SC2456: FL 1118 + FL 26 + FL 121 |
| SC2457: FL 1119 + FL 26 + FL 121 |
| SC2458: FL 1120 + FL 26 + FL 121 |
| SC2464: FL 1116 + FL 26 + TT LEU |
| SC2466: FL 1118 + FL 26 + TT LEU |
| SC2467: FL 1119 + FL 26 + TT LEU |
| SC2468: FL 1120 + FL 26 + TT LEU |

The control strain (without the genes) containing the constructs TT URA, TT TRP, TT HIS and TT LEU is called CF237.

*E. coli* Up to Hesperetin/Diosmetin

TABLE 13

List of constructs used to test the enzymes in *E. coli*

| Names | Assembled genes |
|---|---|
| EC26 (SAM + MET) | SAM from *Saccharomyces cereyisiae* (SEQ ID NO: 82) MET from *Homo sapiens* (SEQ ID NO: 90) |
| EC41 (SAM + MET) | SAM from *Saccharomyces cereyisiae* (SEQ ID NO: 82) MET from *Citrus clementina* (SEQ ID NO: 118) |
| EC43 (SAM + MET) | SAM from *Saccharomyces cereyisiae* (SEQ ID NO: 82) MET from *Citrus sinensis* (SEQ ID NO: 120) |
| EC30 (FNSII) | FNSII from *Petroselinum crispum* (SEQ ID NO: 38) |

Yeast Up to Hesperetin/Diosmetin

Three strains including the pathway up to hesperetin/diosmetin were also tested. The strain SC1508 comprises the constructs FL 121+FL 268+FL 602+FL 808 of Table 14. The strain SC2408 comprises the constructs FL 121+FL 469+FL 602+FL 808 of Table 14. The strain SC2409 comprises the constructs FL 121+FL 475+FL 602+FL 808 of Table 14.

TABLE 14

List of constructs used in the examples

| Names | Assembled genes | Markers |
|---|---|---|
| FL 121 (CPR + SAM) | CPR from *Catharanthus roseus* (SEQ ID NO: 24), SAM from *Saccharomyces cereyisiae* (SEQ ID NO: 82) | LEU |
| FL 268 (F3'H + MET) | F3'H from *Catllistephus chinensis* (SEQ ID NO: 8), MET from *Homo sapiens* (SEQ ID NO: 90) | URA |
| FL 469 (F3'H + MET) | F3'H from *Callistephus chinensis* (SEQ ID NO: 8) MET from *Citrus clementina* (SEQ ID NO: 118) | URA |
| FL 475 (F3'H + MET) | F3'H from *Callistephus chinensis* (SEQ ID NO: 8) MET from *Citrus sinensis* (SEQ ID NO: 120) | URA |
| FL 602 (TAL + 4CL + CHS + CHI + FNSII) | TAL from *Rhodotorula glutinis* (SEQ ID NO: 42), 4CL from *Petroselinum crispum* (SEQ ID NO: 46), CHS from *Citrus sinensis* (SEQ ID NO: 54), CHI from *Arabidopsis thaliona* (SEQ ID NO: 62) FNSII from *Petroselinum crispum* (SEQ ID NO: 38) | TRP |
| FL 808 (PAL + C4H) | PAL from *Arabidopsis thaliona* (SEQ ID NO: 78), C4H from *Arabidopsis thaliona* (SEQ ID NO: 80), | HIS |

TABLE 14-continued

List of constructs used in the examples

| Names | Assembled genes | Markers |
|---|---|---|
| TT LEU | — | LEU |
| TT URA | — | URA |
| TT TRP | — | TRP |
| TT HIS | — | HIS |

The control strain (without the genes) containing the constructs TT LEU, TT URA, TT TRP and TT HIS is called CF237.

GT

In order to test each of the GTs, constructs were made and are presented in Table 15. The marker genes make it possible to detect and to select the cells that have incorporated the gene of interest.

TABLE 15

List of constructs used to test the various GTs

| Names | Assembled genes | Markers |
|---|---|---|
| FL 545 (F3'H + MET + GT + RHM + RHAT) | F3'H from *Callistephus chinensis* (SEQ ID NO: 8), MET from *Citrus sinensis* (SEQ ID NO: 120), GT from *Arabidopsis thaliana* (SEQ ID NO: 92), RHM from *Citrus sinensis* (SEQ ID NO: 108) RHAT from *Citrus clementina* (SEQ ID NO: 104) | URA |
| FL 546 (F3'H + MET + GT + RHM + RHAT) | F3'H from *Callistephus chinensis* (SEQ ID NO: 8), MET from *Citrus sinensis* (SEQ ID NO: 120), GT from *Scutellaria baicalensis* (SEQ ID NO: 94), RHM from *Citrus sinensis* (SEQ ID NO: 108) RHAT from *Citrus clementina* (SEQ ID NO: 104) | URA |
| FL 547 (F3'H + MET + GT + RHM + RHAT) | F3'H from *Callistephus chinensis* (SEQ ID NO: 8), MET from *Citrus sinensis* (SEQ ID NO: 120), GT from *Scutellaria baicalensis* (SEQ ID NO: 96), RHM from *Citrus sinensis* (SEQ ID NO: 108) RHAT from *Citrus clementina* (SEQ ID NO: 104) | URA |
| FL 548 (F3'H + MET + GT + RHM + RHAT) | F3'H from *Callistephus chinensis* (SEQ ID NO: 8), MET from *Citrus sinensis* (SEQ ID NO: 120), GT from *Scutellaria baicalensis* (SEQ ID NO: 98), RHM from *Citrus sinensis* (SEQ ID NO: 108 RHAT from *Citrus clementina* (SEQ ID NO: 104) | URA |
| FL 549 (F3'H + MET + GT + RHM + RHAT) | F3'H from *Callistephus chinensis* (SEQ ID NO: 8), MET from *Citrus sinensis* (SEQ ID NO: 120), GT from *Homo sapiens* (SEQ ID NO: 100), RHM from *Citrus sinensis* (SEQ ID NO: 108) RHAT from *Citrus clementina* (SEQ ID NO: 104) | URA |
| FL 550 (F3'H + MET + GT + RHM + RHAT) | F3'H from *Callistephus chinensis* (SEQ ID NO: 8), MET from *Citrus sinensis* (SEQ ID NO: 120), GT from *Homo sapiens* (SEQ ID NO: 102), RHM from *Citrus sinensis* (SEQ ID NO: 108) RHAT from *Citrus clementina* (SEQ ID NO: 104) | URA |
| FL 554 (F3'H + MET + GT + UDPRHA + RHAT) | F3'H from *Callistephus chinensis* (SEQ ID NO: 8), MET from *Citrus sinensis* (SEQ ID NO: 120), GT from *Citrus sinensis* (SEQ ID NO: 114), UDPRHA from *Citrus sinensis* (SEQ ID NO: 108), RHAT from *Citrus clementina* (SEQ ID NO: 104) | URA |
| FL 556 (F3'H + MET + GT + UDPRHA + RHAT) | F3'H from *Callistephus chinensis* (SEQ ID NO: 8), MET from *Citrus sinensis* (SEQ ID NO: 120), GT from *Citrus clementina* (SEQ ID NO: 116), UDPRHA from *Citrus sinensis* (SEQ ID NO: 108), RHAT from *Citrus clementina* (SEQ ID NO: 104) | URA |
| TT URA | — | URA |

The various constructs with the various GTs make it possible to check the enzymatic activity of the GTs and also make it possible to determine the most efficient GTs.

The control strain (without the genes) containing the construct TT URA is called CF233.

RHM

In order to test each of the RHMs, constructs were made and are presented in Table 16.

TABLE 16

List of constructs used to test the various RHMs

| Names | Assembled genes | Markers |
|---|---|---|
| FL 545 (F3'H + MET + GT + RHM + RHAT) | F3'H from *Callistephus chinensis* (SEQ ID NO: 8), MET from *Citrus sinensis* (SEQ ID NO: 120), GT from *Arabidopsis thaliana* (SEQ ID NO: 98), RHM from *Citrus sinensis* (SEQ ID NO: 108), RHAT from *Citrus clementina* (SEQ ID NO: 104) | URA |
| FL 512 (F3'H + MET + GT + RHM + RHAT) | F3'H from *Callistephus chinensis* (SEQ ID NO: 8), MET from *Homo sapiens* (SEQ ID NO: 90), GT from *Arabidopsis thaliana* (SEQ ID NO: 98), RHM from *Arabidopsis thaliana* (SEQ ID NO: 110), RHAT from *Citrus clementina* (SEQ ID NO: 104) | URA |
| TT URA | — | URA |

The various constructs with the various RHMs make it possible to check the enzymatic activity of the RHMs and also make it possible to determine the most efficient RHMs.

The control strain (without the genes) containing the construct TT URA is called CF233.

RHAT

In order to test each of the RHATs, constructs were made and are presented in Table 17.

TABLE 17

List of constructs used to test the various RHATs

| Names | Assembled genes | Markers |
|---|---|---|
| FL 512 (F3'H + MET + GT3 + RHM + RHAT) | F3'H from *Callistephus chinensis* (SEQ ID NO: 8), MET from *Homo sapiens* (SEQ ID NO: 90), GT from *Arabidopsis thaliana* (SEQ ID NO: 92), RHM from *Arabidopsis thaliana* (SEQ ID NO: 110) RHAT from *Citrus clementina* (SEQ ID NO: 104) | URA |
| FL 165 (F3'H + MET + GT + RHM + RHAT) | F3'H from *Callistephus chinensis* (SEQ ID NO: 8), MET from *Homo sapiens* (SEQ ID NO: 90), GT from *Arabidopsis thaliana* (SEQ ID NO: 92), RHM from *Arabidopsis thaliana* (SEQ ID NO: 110) RHAT from *Citrus sinensis* (SEQ ID NO: 106) | URA |
| TT URA2 | — | URA |

The various assemblies made with the various RHATs make it possible to check the enzymatic activity of the RHATs and also make it possible to determine the most efficient RHATs.

The control strain (without the genes) containing the construct TT URA is called CF233.

*E. coli* Up to Hesperidin/Diosmin

TABLE 18

List of strains created to test the pathway in *E. coli*

| Names | Assembled genes |
|---|---|
| EC38 (GT + RHM + RHAT) | GT from *Arabidopsis thaliona* (SEQ ID NO: 92), RHM from *Citrus sinensis* (SEQ ID NO: 108) RHAT from *Citrus clementina* (SEQ ID NO: 104) |
| EC45 (GT + UDPRHA + RHAT) | GT from *Citrus sinensis* (SEQ ID NO: 114), UDPRHA from *Citrus sinensis* (SEQ ID NO: 108), RHAT from *Citrus clementina* (SEQ ID NO: 104) |
| EC47 | GT from *Citrus clementina* (SEQ ID NO: 116), |

TABLE 18-continued

| List of strains created to test the pathway in *E. coli* | |
|---|---|
| Names | Assembled genes |
| (GT + UDPRHA + RHAT) | UDPRHA from *Citrus sinensis* (SEQ ID NO: 108), RHAT from *Citrus clementina* (SEQ ID NO: 104) |

Yeast Up to Hesperidin/Diosmin

Nine strains including the full pathway were also created.

The strain SC1509 comprises the constructs FL 121+FL 511+FL 602+FL 808.

The strain SC1530 comprises the constructs FL 121+FL 603+FL 602+FL 808.

The strain SC1529 comprises the constructs FL 121+FL 554+FL 602+FL 808.

The strain SC1568 comprises the constructs FL 121+FL 556+FL 602+FL 808.

The strain SC2410 comprises the constructs FL 121+FL 1100+FL 602+FL 808.

The strain SC1579 comprises the constructs FL 401+FL 547+FL 602+FL 828.

The strain SC1584 comprises the constructs FL 401+FL 554+FL 602+FL 828.

The strain SC1621 comprises the constructs FL 401+FL 556+FL 602+FL 828.

The strain SC1626 comprises the constructs FL 401+FL 603+FL 602+FL 828.

TABLE 19

| Lists of constructs used to create the strains up to hesperidin/diosmin | | |
|---|---|---|
| Names | Assembled genes | Markers |
| FL 121 (CPR + SAM) | CPR from *Catharanthus roseus* (SEQ ID NO: 24), SAM from *Saccharomyces cereyisiae* (SEQ ID NO: 82) | LEU |
| FL 401 (CPR + SAM) | CPR from *Saccharomyces cereyisiae* (SEQ ID NO: 26), SAM from *Saccharomyces cereyisiae* (SEQ ID NO: 82) | LEU |
| FL 547 (F3'H + MET + GT + RHM + RHAT) | F3'H from *Callistephus chinensis* (SEQ ID NO: 8), MET from *Citrus sinensis* (SEQ ID NO: 120), GT from *Scutellaria baicalensis* (SEQ ID NO: 96), RHM from *Citrus sinensis* (SEQ ID NO: 108) RHAT from *Citrus clementina* (SEQ ID NO: 104) | URA |
| FL 511 (F3'H + MET + GT + RHM + RHAT) | F3'H from *Callistephus chinensis* (SEQ ID NO: 8), MET from *Homo sapiens* (SEQ ID NO: 90), GT from *Arabidopsis thaliana* (SEQ ID NO: 92), RHM from *Citrus sinensis* (SEQ ID NO: 108) RHAT from *Citrus clementina* (SEQ ID NO: 104) | URA |

TABLE 19-continued

| Lists of constructs used to create the strains up to hesperidin/diosmin | | |
|---|---|---|
| Names | Assembled genes | Markers |
| FL 603 (F3'H + MET + GT + UDPRHA + RHAT) | F3'H from *Callistephus chinensis* (SEQ ID NO: 8), MET from *Citrus clementina* (SEQ ID NO: 118), GT from *Citrus sinensis* (SEQ ID NO: 114), UDPRHA from *Citrus sinensis* (SEQ ID NO: 108), RHAT from *Citrus clementina* (SEQ ID NO: 104) | URA |
| FL 554 (F3'H + MET + GT + UDPRHA + RHAT) | F3'H from *Callistephus chinensis* (SEQ ID NO: 8), MET from *Citrus sinensis* (SEQ ID NO: 120), GT from *Citrus sinensis* (SEQ ID NO: 114), UDPRHA from *Citrus sinensis* (SEQ ID NO: 108), RHAT from *Citrus clementina* (SEQ ID NO: 104) | URA |
| FL 556 (F3'H + MET + GT + UDPRHA + RHAT) | F3'H from *Callistephus chinensis* (SEQ ID NO: 8), MET from *Citrus sinensis* (SEQ ID NO: 120), GT from *Citrus clementina* (SEQ ID NO: 116), UDPRHA from *Citrus sinensis* (SEQ ID NO: 108), RHAT from *Citrus clementina* (SEQ ID NO: 104) | URA |
| FL 1100 (F3'H + MET + GT + UDPRHA + RHAT) | F3'H from *Callistephus chinensis* (SEQ ID NO: 8), MET from *Citrus clementina* (SEQ ID NO: 118), GT from *Citrus clementina* (SEQ ID NO: 116), UDPRHA from *Citrus sinensis* (SEQ ID NO: 108), RHAT from *Citrus clementina* (SEQ ID NO: 104) | URA |
| FL 602 (TAL + 4CL + CHS + CHI + FNS) | TAL from *Rhodotorula glutinis* (SEQ ID NO: 42), 4CL from *Petroselinum crispum* (SEQ ID NO: 46), CHS from *Citrus sinensis* (SEQ ID NO: 54), CHI from *Arabidopsis thaliona* (SEQ ID NO: 62) FNSII from *Petroselinum crispum* (SEQ ID NO: 38) | TRP |
| FL 808 (PAL + C4H) | PAL from *Arabidopsis thaliona* (SEQ ID NO: 78), C4H from *Arabidopsis thaliona* (SEQ ID NO: 80), | HIS |
| FL 828 (PAL + C4H) | PAL from *Citrus sinensis* (SEQ ID NO: 66), C4H from *Arabidopsis thaliona* (SEQ ID NO: 80), | HIS |
| TT LEU | — | LEU |
| TT URA | — | URA |
| TT TRP | — | TRP |
| TT HIS | — | HIS |

The control strain (without the genes) containing the constructs TT LEU, TT URA, TT TRP and TT HIS is called CF237.

Results

F3'H

Tables 20 and 21 below show the production of eriodictyol (Table 20) and of luteolin (Table 21) obtained by cultivating the strains comprising the F3'Hs listed in Table 6 and the constructs of Table 7, in the presence of naringenin and apigenin, respectively.

TABLE 20

| Concentration of eriodictyol (in $mg.l^{-1}$) | | | | | | |
|---|---|---|---|---|---|---|
| F3'H (SEQ ID No) | WITHOUT CPR (TT LEU) | CPR (SEQ ID No 24; FL121) | CPR (SEQ ID No 26; FL401) | CPR (SEQ ID No 28; FL274) | ATR (SEQ ID No 30; FL275) | ATR (SEQ ID No 32; FL463) |
| 2 (FL23) | 35.5 ± 2.9 | 42.1 ± 4.3 | 49.9 ± 4.2 | 43.6 ± 4.2 | 38.8 ± 4.1 | 43.3 ± 5.1 |
| 4 (FL24) | 1 ± 0.8 | 6.4 ± 0.5 | 4.0 ± 0.5 | 4.7 ± 0.3 | 5.1 ± 0.4 | 5.3 ± 0.4 |
| 6 (FL25) | 115.2 ± 3.2 | 76.8 ± 4.2 | 42.3 ± 2.6 | 70.2 ± 8.6 | 71.1 ± 8.7 | 71.3 ± 7.4 |
| 8 (FL26) | 108.3 ± 4.0 | 71.1 ± 7.1 | 89.2 ± 9.5 | 87.4 ± 5.0 | 75.8 ± 5.2 | 90.0 ± 6.1 |
| 10 (FL27) | 28.8 ± 1.2 | 57.7 ± 2.6 | 69.3 ± 10.6 | 79.1 ± 4.2 | 52.3 ± 0.5 | 69.7 ± 2.3 |
| 12 (FL28) | 108.0 ± 2.0 | 7.0 ± 1.4 | 9.1 ± 5.9 | 4.6 ± 0.3 | 7.4 ± 2.8 | 9.2 ± 0.6 |
| 14 (FL29) | 119.9 ± 1.1 | 39.9 ± 4.7 | 56.1 ± 16.3 | 64.8 ± 4.1 | 36.8 ± 4.4 | 46.1 ± 5.5 |
| 16 (FL30) | <QL | 76.3 ± 2.6 | 70.9 ± 6.2 | 70.4 ± 4.4 | 58.5 ± 10.9 | 76.9 ± 1.7 |

TABLE 20-continued

| Concentration of eriodictyol (in mg.l$^{-1}$) | | | | | | |
|---|---|---|---|---|---|---|
| F3'H (SEQ ID No) | WITHOUT CPR (TT LEU) | CPR (SEQ ID No 24; FL121) | CPR (SEQ ID No 26; FL401) | CPR (SEQ ID No 28; FL274) | ATR (SEQ ID No 30; FL275) | ATR (SEQ ID No 32; FL463) |
| 18 (FL31) | 107.3 ± 8.0 | 82.3 ± 17.2 | 102.2 ± 7.1 | 98.8 ± 5.9 | 96.6 ± 4.7 | 101.3 ± 4.0 |
| 20 (FL32) | 33.7 ± 4.0 | 68.9 ± 2.7 | 81.5 ± 3.4 | 63.6 ± 3.7 | 69.5 ± 0.9 | 69.7 ± 1.1 |
| 122 (FL1031) | 4.8 ± 0.3 | 60.5 ± 3.4 | 34.4 ± 2.8 | 25.8 ± 5.8 | 59.0 ± 1.7 | 40.0 ± 9.5 |

QL: below the quantification limit

The various strains are indeed capable of producing eriodictyol from naringenin, in different concentrations according to the F3'Hs and the CPR used (see FIG. 2).

TABLE 21

| Concentration of luteolin (in mg.l$^{-1}$) | | | | | | |
|---|---|---|---|---|---|---|
| F3'H (SEQ ID No) | WITHOUT CPR (TT LEU) | CPR (SEQ ID No 24; FL121) | CPR (SEQ ID No 26; FL401) | CPR (SEQ ID No 28; FL274) | ATR (SEQ ID No 30; FL275) | ATR (SEQ ID No 32; FL463) |
| 2 (FL23) | 3.5 ± 0.1 | 11.7 ± 0.7 | 9.1 ± 2.1 | 11.01 ± 0.4 | 10.8 ± 1.7 | 10.2 ± 1.4 |
| 4 (FL24) | <QL | <QL | <QL | <QL | <QL | <QL |
| 6 (FL25) | 10.2 ± 0.9 | 12.8 ± 0.7 | 7.8 ± 1.4 | 11.9 ± 0.8 | 10.1 ± 1.2 | 12.9 ± 1.4 |
| 8 (FL26) | 9.5 ± 0.4 | 13.2 ± 1.1 | 8.2 ± 0.7 | 10.9 ± 0.7 | 12.2 ± 0.4 | 12.1 ± 0.7 |
| 10 (FL27) | <QL | 2.5 ± 0.3 | <QL | 0.5 ± 0 | 2.7 ± 0.1 | 2.77 ± 0.4 |
| 12 (FL28) | 12.1 ± 0.4 | 13.3 ± 1.2 | 14.7 ± 1.8 | 14.1 ± 1.7 | 12.5 ± 3.8 | 15.3 ± 0.9 |
| 14 (FL29) | 1.5 ± 0.1 | 0.6 ± 0.04 | 1.1 ± 0.2 | 0.8 ± 0.03 | 0.7 ± 0.06 | 1.0 ± 0.08 |
| 16 (FL30) | 0.5 ± 0.02 | 1.3 ± 0.1 | 2.5 ± 1.5 | 1.6 ± 0.1 | 1.5 ± 0.5 | 2.0 ± 0.1 |
| 18 (FL31) | 12.2 ± 0.7 | 13.2 ± 0.8 | 13.7 ± 1.2 | 12.7 ± 0.4 | 14.0 ± 1.8 | 12.7 ± 0.6 |
| 20 (FL32) | 1.2 ± 0.2 | 9.9 ± 1.4 | 2.8 ± 0.4 | 4.3 ± 0.1 | 11.0 ± 0.9 | 9.3 ± 1.8 |
| 122 (FL1031) | 0.4 ± 0.1 | 10.9 ± 0.1 | 3.0 ± 0.6 | 3.0 ± 0.9 | 11.4 ± 0.4 | 9.5 ± 1.6 |

QL: below the quantification limit

The various strains are indeed capable of producing luteolin from apigenin, in different concentrations according to the F3'Hs and the CPR used (see FIG. 3).

FNS

Tables 22 and 23 below show the production of apigenin (Table 22) and of luteolin (Table 23) obtained by cultivating the strains comprising the FNSIIs listed in Table 8 and the constructs of Table 9, in the presence of naringenin and eriodictyol, respectively.

TABLE 22

| Concentration of apigenin (in mg.l$^{-1}$) | | | | | | |
|---|---|---|---|---|---|---|
| FNSII (SEQ ID No) | WITHOUT CPR (TT LEU) | CPR (SEQ ID No 24; FL121) | CPR (SEQ ID No 26; FL401) | CPR (SEQ ID No 28; FL274) | ATR (SEQ ID No 30; FL275) | ATR (SEQ ID No 32; FL463) |
| 34 (FL620) | 11.6 ± 0.3 | 34.7 ± 1.0 | 47.6 ± 5.7 | 37.7 ± 1.6 | 50.5 ± 1.5 | 51.3 ± 3.4 |
| 36 (FL621) | 3.5 ± 0.1 | 35.6 ± 0.2 | 14.9 ± 1.3 | 16.4 ± 1.4 | 29.8 ± 3.9 | 33.2 ± 1.5 |
| 38 (FL112) | 2.9 ± 0.1 | 40.7 ± 1.2 | 41.4 ± 1.5 | 34.2 ± 1.7 | 38.0 ± 0.9 | 43.5 ± 0.0 |

TABLE 23

| Concentration of luteolin (in mg.l$^{-1}$) | | | | | | |
|---|---|---|---|---|---|---|
| FNSII (SEQ ID No) | WITHOUT CPR (TT LEU) | CPR (SEQ ID No 24; FL121) | CPR (SEQ ID No 26; FL401) | CPR (SEQ ID No 28; FL274) | ATR (SEQ ID No 30; FL275) | ATR (SEQ ID No 32; FL463) |
| 34 (FL620) | 2.5 ± 0.2 | 1.4 ± 0.3 | 7.8 ± 1.4 | 4.5 ± 0.9 | 4.5 ± 2.9 | 8.5 ± 0.8 |
| 36 (FL621) | 0.2 ± 0.2 | 1.5 ± 0.1 | 1.3 ± 0.2 | 0.9 ± 0.1 | 1.3 ± 0.3 | 1.2 ± 0.2 |
| 38 (FL112) | 0.2 ± 0.0 | 4.5 ± 1.9 | 2.3 ± 0.5 | 2.6 ± 1.2 | 1.4 ± 0.0 | 1.6 ± 0.0 |

The various strains are indeed capable of producing apigenin and luteolin from naringenin and eriodictyol, in different concentrations according to the FNS used (FIGS. 4 and 5). Similar results were obtained with the FNSIIs of SEQ ID NOs: 127, 129, 131, 133, 135, 137, 139, 141, 143, 145, 147, 149, 151, 153, 155, 157 and 159.

F3'H, MET, FNS, CPR: Production of Diosmetin from Naringenin

The results for the production of diosmetin from naringenin by the strains SC2429 to SC2434, SC2436 to SC2444, SC2446 to SC2454, SC2456 to SC2464 and SC2466 to SC2468 are presented in FIG. 29.

All the strains are capable of producing diosmetin from naringenin. The production of diosmetin is largely increased by adding a CPR.

Yeast Up to Eriodictyol/Luteolin

The strains SC2424, SC2425, SC2426, SC2427, SC1500 and SC2428 contain all the enzymes of the pathway up to eriodictyol and luteolin and are capable of producing luteolin and eriodictyol from glucose.

The results for the strain SC1500 correspond to FIG. 6, in which the eriodictyol and luteolin peaks are observed. Similar results are obtained for the strains SC2424, SC2425, SC2426, SC2427 and SC2428. The production of eriodictyol and of luteolin for each of the strains SC2424, SC2425, SC2426, SC2427, SC1500 and SC2428 is presented in FIG. 19.

It should be noted that the addition of the enzymes PAL and C4H to the biosynthetic pathway makes it possible to obtain markedly higher eriodictyol and luteolin concentrations. These concentrations may be up to six times higher than the concentrations obtained with the strains containing the same enzymes with the exception of PAL and C4H (cf. FIG. 19, for example by comparing the strain SC2425 without PAL/C4H and the strain SC1500 with PAL/C4H or the strain SC2426 without PAL/C4H and the strain SC2428 with PAL/C4H).

MET

The results for the production of hesperetin and diosmetin from eriodictyol and luteolin by the strains SC1612, SC1614, SC2147 and SC2151 are presented, respectively, in FIGS. 7, 8, 20 and 21.

The yeast strains SC1612, SC1614, SC2147 and SC2151 are indeed capable of producing hesperetin and/or diosmetin.

Starting with eriodictyol, the strains SC2147, SC2151 and SC1612 are capable of specifically producing hesperetin, i.e. of specifically methylating the hydroxyl in position 4' of eriodictyol (FIG. 20). The strain SC1614 produces, for its part, a mixture of hesperetin and of homoeriodictyol.

In a noteworthy manner, the strain SC2151 is moreover capable of producing about 40 mg/L of hesperetin (FIG. 20). The strains SC2147, SC1612 and SC1614, for their part, are capable of producing diosmetin from luteolin (FIG. 21).

FNSII

The results for the production of diosmetin from hesperetin by the strain SC744 are presented in FIG. 9.

The yeast strain SC744 is indeed capable of producing diosmetin from hesperetin.

*E. coli* Up to Hesperetin/Diosmetin

The results for the production of hesperetin from eriodictyol by the strains EC26, EC41 and EC43 are presented in FIGS. 10, 22 and 23 and the production of diosmetin from luteolin by the strains EC26 and EC43 are presented in FIGS. 11 and 24.

The *E. coli* strains EC26, EC41 and EC43 are indeed capable of producing hesperetin and/or diosmetin.

The results for the production of diosmetin from hesperetin by the strain EC30 are presented in FIG. 12.

The *E. coli* strain EC30 is indeed capable of producing diosmetin from hesperetin.

Yeast Up to Hesperetin/Diosmetin

The results for the production of hesperetin and diosmetin from glucose by the strains SC1508, SC2408 and SC2409 are presented in FIGS. 13, 25 and 26.

The yeast strains SC1508, SC2408 and SC2409 containing all the enzymes of the pathway up to hesperetin and diosmetin are capable of producing hesperetin and/or diosmetin from glucose (FIG. 27). In a noteworthy manner, the strain SC2408 produces about 25 mg/L of hesperetin and about 5 mg/L of diosmetin.

GT

TABLE 24

Concentration of hesperetin, hesperetin 7-O-glucoside and hesperidin according to the GTs used (in $mg.l^{-1}$)

| | Hesperetin | Hesperetin 7-O-glucoside | Hesperidin |
|---|---|---|---|
| medium | 90 ± 8.1 | N/D | N/D |
| Control - | 84.2 ± 4.6 | N/D | N/D |
| FL 545 - GT SEQ ID No 92 | 59.2 ± 1.1 | 7.1 ± 0.2 | 70.4 ± 2.2 |
| FL 546 - GT SEQ ID No 94 | 85.1 ± 1.4 | N/D | 22.2 ± 1.2 |
| FL 547 - GT SEQ ID No 96 | N/D | 6 ± 0.5 | 109.9 ± 4.8 |
| FL 548 - GT SEQ ID No 98 | 46.7 ± 2.4 | N/D | 71.9 ± 2.1 |
| FL 554 - GT SEQ ID No 114 | 46.7 ± 1.7 | // | 70.4 ± 5.0 |
| FL 556 - GT SEQ ID No 116 | 107.0 ± 3.0 | // | 11.3 ± 1.1 |

// amount not determined

TABLE 25

Concentration of diosmetin, diosmetin 7-O-glucoside and diosmin according to the GTs used (in $mg.l^{-1}$)

| | Diosmetin | Diosmetin 7-O-glucoside | Diosmin |
|---|---|---|---|
| medium | 82.1 ± 3.9 | N/D | N/D |
| Control - | 75.3 ± 6.1 | N/D | N/D |
| FL 545 - GT SEQ ID No 92 | 67.1 ± 2.6 | N/D | 21.8 ± 0.4 |
| FL 546 - GT SEQ ID No 94 | 61.9 ± 3.3 | N/D | 23.2 ± 3.2 |
| FL 547 - GT SEQ ID No 96 | 2.4 ± 0.4 | 7.1 ± 0.5 | 122.8 ± 8.5 |
| FL 548 - GT SEQ ID No 98 | 17.7 ± 0.7 | N/D | 76 ± 4.1 |
| FL 554 - GT SEQ ID No 114 | 61.4 ± 4.2 | 7.1 ± 1.1 | 108.5 ± 8.3 |
| FL 556 - GT SEQ ID No 116 | 138.6 ± 3.5 | N/D | N/D |

The various strains are indeed capable of producing hesperidin and/or diosmin from hesperetin and diosmetin, in different concentrations according to the GT used.

RHM

TABLE 26

Concentration of hesperetin, hesperetin 7-O-glucoside and hesperidin according to the RHMs used (in $mg.l^{-1}$)

| | Hesperetin | Hesperetin 7-O-glucoside | Hesperidin |
|---|---|---|---|
| medium | 90 ± 8.1 | N/D | N/D |
| Control - | 84.2 ± 4.6 | N/D | N/D |
| FL 545 - RHM SEQ ID No 108 | 59.2 ± 1.1 | 7.1 ± 0.3 | 70.4 ± 2.2 |
| FL 512 - RHM SEQ ID No 110 | 45.6 ± 2.4 | N/D | 82.2 ± 5.2 |

TABLE 27

| Concentration of diosmetin, diosmetin 7-O-glucoside and diosmin according to the RHMs used (in mg.$l^{-1}$) | | | |
|---|---|---|---|
| | Diosmetin | Diosmetin 7-O-glucoside | Diosmin |
| medium | 82.1 ± 3.9 | N/D | N/D |
| Control - | 75.3 ± 6.1 | N/D | N/D |
| FL 545 - RHM SEQ ID No 108 | 67.1 ± 2.6 | N/D | 21.8 ± 0.4 |
| FL 512 - RHM SEQ ID No 110 | 61.4 ± 3.6 | N/D | 23.7 ± 1 |

The various strains are indeed capable of producing hesperidin and diosmin from hesperetin and diosmetin, in different concentrations according to the RHMs used.

RHAT

TABLE 28

| Concentration of hesperetin, hesperetin 7-O-glucoside and hesperidin according to the RHATs used (in mg.$l^{-1}$) | | | |
|---|---|---|---|
| | Hesperetin | Hesperetin 7-O-glucoside | Hesperidin |
| medium | 90 ± 8.1 | N/D | N/D |
| Control - | 84.2 ± 4.6 | N/D | N/D |
| FL 512 - RHAT SEQ ID No 104 | 45.6 ± 2.4 | N/D | 82.2 ± 5.2 |
| FL 165 - RHAT SEQ ID No 106 | 46 ± 1.5 | 8.1 ± 0.2 | 69.8 ± 1.4 |

TABLE 29

| Concentration of diosmetin, diosmetin 7-O-glucoside and diosmin according to the RHATs used (in mg.$l^{-1}$) | | | |
|---|---|---|---|
| | Diosmetin | Diosmetin 7-O-glucoside | Diosmin |
| medium | 82.1 ± 3.9 | N/D | N/D |
| Control - | 75.3 ± 6.1 | N/D | N/D |
| FL 512 - RHAT SEQ ID No 104 | 61.4 ± 3.6 | N/D | 23.7 ± 1 |
| FL 165 - RHAT SEQ ID No 106 | 66.7 ± 2.5 | N/D | 23 ± 1.5 |

The various strains are indeed capable of producing hesperidin and diosmin from hesperetin and diosmetin, in different concentrations according to the GTs, the RHMs and the RHATs used.

The results for the production of hesperidin and diosmin from hesperetin and diosmetin by the strain FL 547 are presented, respectively, in FIGS. 14 and 15.

The yeasts tested with the various constructs are indeed capable of producing hesperidin and diosmin.

*E. coli* Up to Hesperidin/Diosmin

The results for the production of hesperidin from hesperetin by the strains EC38, EC45 and EC47 are presented in FIG. 16.

These strains are indeed capable of producing hesperidin from hesperetin.

The results for the production of diosmin from diosmetin by the strains EC38, EC45 and EC47 are presented in FIG. 17.

These strains are indeed capable of producing diosmin from diosmetin.

Yeast Up to Hesperidin/Diosmin

The results for the production of hesperidin and diosmin from glucose by the strains SC1509, SC1530, SC1529, SC1568 and SC2410 are presented in FIG. 18. The results for the production of hesperidin from diosmin by the strains SC1579, SC1584, SC1621 and SC1626 are presented in FIG. 28.

All the strains containing all the enzymes of the pathway are capable of producing hesperidin and/or diosmin.

The invention claimed is:

1. A recombinant microorganism comprising:

a heterologous nucleic acid sequence coding for a flavanone 7-O-beta-D-glucosyltransferase (UGT) belonging to EC 2.4.1.185, which is capable of adding a glucose in position 7 of hesperetin and/or diosmetin; and a heterologous nucleic acid sequence coding for a 6"-O-rhamnosyltransferase (RhaT) belonging to EC 2.4.1.653, which is capable of transferring a rhamnose into position 6 of the glucose of hesperetin-7-O-glucoside and/or diosmetin-7-O-glucoside; and a heterologous nucleic acid sequence coding for a UDP-glucose 4,6-dehydratase/UDP-4-keto-6-deoxy-D-glucose 3,5-epimerase/UDP-4-keto-L-rhamnose-reductase (RHM) belonging to EC 4.2.1.76, which is capable of producing UDP-rhamnose.

2. The microorganism as claimed in claim 1, in which the flavanone 7-O-beta-D-glucosyltransferase is selected from the group consisting of SEQ ID NOs: 113, 115, 91, 93, 95, 97, 99 and 101 and polypeptides comprising a sequence having at least 60% sequence identity with one of these sequences and having flavanone 7-O-beta-D-glucosyltransferase activity.

3. The microorganism as claimed in claim 1, in which the 6"-O-rhamnosyltransferase is selected from the group consisting of SEQ ID NOs: 103 and 105 and polypeptides comprising a sequence having at least 60% sequence identity with one of these sequences and having 6"-O-rhamnosyltransferase activity.

4. The microorganism as claimed in claim 1, in which the UDP-glucose 4,6-dehydratase/UDP-4-keto-6-deoxy-D-glucose 3,5-epimerase/UDP-4-keto-L-rhamno se-reductase is selected from the group consisting of SEQ ID NOs: 107, 109 and 111 and polypeptides comprising a sequence having at least 60% sequence identity with one of these sequences and having UDP-glucose 4,6-dehydratase/UDP-4-keto-6-deoxy-D-glucose 3,5-epimerase/UDP-4-keto-L-rhamnose-reductase activity.

5. The microorganism as claimed in claim 1, in which the flavanone 7-O-beta-D-glucosyltransferase is selected from the group consisting of SEQ ID NOs: 113 and 95 and polypeptides comprising a sequence having at least 60% sequence identity with one of these sequences and having flavanone 7-O-beta-D-glucosyltransferase activity; and the 6"-O-rhamnosyltransferase is selected from the group consisting of SEQ ID NO: 103 and polypeptides comprising a sequence having at least 60% sequence identity with this sequence and having 6"-O-rhamnosyltransferase activity; and the UDP-glucose 4,6-dehydratase/UDP-4-keto-6-deoxy-D-glucose 3,5-epimerase/UDP-4-keto-L-rhamnose-reductase is selected from the group consisting of SEQ ID NO: 107 and polypeptides comprising a sequence having at least 60% sequence identity with this sequence and having UDP-glucose 4,6-dehydratase/UDP-4-keto-6-deoxy-D-glucose 3,5-epimerase/UDP-4-keto-L-rhamnose-reductase activity.

6. The microorganism as claimed in claim 1, the microorganism also comprising:

a heterologous nucleic acid sequence coding for a tyrosine ammonia lyase (TAL);

a heterologous nucleic acid sequence coding for a 4-coumarin-CoA ligase (4CL);

a heterologous nucleic acid sequence coding for a naringenin-chalcone synthase (CHS); and a heterologous nucleic acid sequence coding for a chalcone isomerase (CHI).

7. The microorganism as claimed in claim 6, characterized in that it comprises:

a heterologous nucleic acid sequence coding for a tyrosine ammonia lyase (TAL) comprising a sequence selected from the group consisting of SEQ ID NOs: 41 and 39 and polypeptides comprising a sequence having at least 60% sequence identity with one of these sequences and having tyrosine ammonia lyase activity;

a heterologous nucleic acid sequence coding for a 4-coumaroyl-CoA ligase (4CL) comprising a sequence selected from the group consisting of SEQ ID NOs: 123, 125, 43, 45, 47 and 49 and polypeptides comprising a sequence having at least 60% sequence identity with one of these sequences and having 4-coumarate-CoA ligase activity;

a heterologous nucleic acid sequence coding for a chalcone synthase (CHS) comprising a sequence selected from the group consisting of SEQ ID NOs: 53, 51, 55 and 57 and polypeptides comprising a sequence having at least 60% sequence identity with one of these sequences and having chalcone synthase activity; and a heterologous nucleic acid sequence coding for a chalcone isomerase (CHI) comprising a sequence selected from the group consisting of SEQ ID NOs: 61 and 59 and polypeptides comprising a sequence having at least 60% sequence identity with one of these sequences and having chalcone isomerase activity.

8. The microorganism as claimed in claim 1, characterized in that it also comprises a heterologous nucleic acid sequence coding for a flavonoid 3'-monooxygenase (F3 'H).

9. The microorganism as claimed in claim 8, characterized in that the microorganism comprises a heterologous nucleic acid sequence coding for a flavonoid 3'-monooxygenase (F3'H) comprising a sequence selected from the group consisting of SEQ ID NOs: 7, 1, 3, 5, 9, 11, 13, 15, 17, 19, 21 and 121 and polypeptides comprising a sequence having at least 60% sequence identity with one of these sequences and having flavonoid 3'-monooxygenase activity.

10. The microorganism as claimed in claim 1, characterized in that it also comprises a heterologous nucleic acid sequence coding for an O-methyltransferase (OMT).

11. The microorganism as claimed in claim 10, characterized in that the microorganism comprises a heterologous nucleic acid sequence coding for an O-methyltransferase (OMT) comprising a sequence selected from the group consisting of SEQ ID NOs: 119, 117, 87 and 89 and polypeptides comprising a sequence having at least 60% sequence identity with one of these sequences and having O-methyltransferase activity.

12. The microorganism as claimed in claim 1, also comprising:

a heterologous nucleic acid sequence coding for a phenylalanine ammonia lyase (PAL) comprising a sequence selected from the group consisting of SEQ ID NOs: 63, 65 and 77 and polypeptides comprising a sequence having at least 60% sequence identity with one of these sequences and having phenylalanine ammonia lyase activity; and a heterologous nucleic acid sequence coding for a cinnamate 4-hydroxylase (C4H) comprising a sequence selected from the group consisting of SEQ ID NOs: 67, 69 and 79 and polypeptides comprising a sequence having at least 60% sequence identity with one of these sequences and having cinnamate 4-hydroxylase activity.

13. The microorganism as claimed in claim 1, also comprising a heterologous or endogenous nucleic acid sequence coding for a flavone synthase (FNS).

14. The microorganism as claimed in claim 13, characterized in that it comprises a heterologous nucleic acid sequence coding for a flavone synthase (FNS) comprising a sequence selected from the group consisting of SEQ ID NOs: 33, 35, 37, 127, 129, 131, 133, 135, 137, 139, 141, 143, 145, 147, 149, 151, 153, 155, 157 and 159 and polypeptides comprising a sequence having at least 60% sequence identity with one of these sequences and having flavone synthase activity.

15. The microorganism as claimed in claim 1, also comprising:

a heterologous nucleic acid sequence coding for a cytochrome P450 reductase (CPR); and/or a heterologous or endogenous nucleic acid sequence coding for an S-adenosylmethionine synthetase (SAMT).

16. The microorganism as claimed in claim 15, characterized in that the microorganism comprises a heterologous nucleic acid sequence coding for a cytochrome P450 reductase (CPR) comprising a sequence selected from the group consisting of SEQ ID NOs: 25, 23, 27, 29 and 31 and polypeptides comprising a sequence having at least 60% sequence identity with one of these sequences and having cytochrome P450 reductase activity.

17. The microorganism as claimed in claim 1, characterized in that the microorganism comprises:

a heterologous nucleic acid sequence coding for a phenylalanine ammonia lyase (PAL) comprising SEQ ID NO: 65 or a polypeptide comprising a sequence having at least 60% sequence identity with this sequence and having phenylalanine ammonia lyase activity;

a heterologous nucleic acid sequence coding for a cinnamate 4-hydroxylase (C4H) comprising SEQ ID NO:

79 or a polypeptide comprising a sequence having at least 60% sequence identity with this sequence and having cinnamate 4-hydroxylase activity;

a heterologous nucleic acid sequence coding for a tyrosine ammonia lyase (TAL) comprising SEQ ID NO: 41 or a polypeptide comprising a sequence having at least 60% sequence identity with this sequence and having tyrosine ammonia lyase activity;

a heterologous nucleic acid sequence coding for a 4-coumaroyl-CoA ligase (4CL) comprising SEQ ID NO: 45, 123 or a polypeptide comprising a sequence having at least 60% sequence identity with one of these sequences and having 4-coumarate-CoA ligase activity;

a heterologous nucleic acid sequence coding for a chalcone synthase (CHS) comprising SEQ ID NO: 53 or a polypeptide comprising a sequence having at least 60% sequence identity with this sequence and having chalcone synthase activity;

a heterologous nucleic acid sequence coding for a chalcone isomerase (CHI) comprising SEQ ID NO: 61 or a polypeptide comprising a sequence having at least 60% sequence identity with this sequence and having chalcone isomerase activity;

a heterologous nucleic acid sequence coding for a flavonoid 3'-monooxygenase (F3'H) comprising SEQ ID NOs: 7, 17, 121 or a polypeptide comprising a sequence having at least 60% sequence identity with one of these sequences and having flavonoid 3'-monooxygenase activity;

a heterologous nucleic acid sequence coding for a flavone synthase (FNS) comprising SEQ ID NO: 37 or a polypeptide comprising a sequence having at least 60% sequence identity with this sequence and having flavone synthase activity;

a heterologous nucleic acid sequence coding for a cytochrome P450 reductase (CPR) comprising SEQ ID NO: 25 or a polypeptide comprising a sequence having at least 60% sequence identity with this sequence and having cytochrome P450 reductase activity;

a heterologous nucleic acid sequence coding for an O-methyltransferase (OMT) comprising SEQ ID NOs: 117, 119 or a polypeptide comprising a sequence having at least 60% identity with one of these sequences and having O-methyltransferase activity;

a heterologous nucleic acid sequence coding for a flavanone 7-O-beta-D-glucosyltransferase comprising SEQ ID NOs: 113, 95 or a polypeptide comprising a sequence having at least 60% sequence identity with one of these sequences and having flavanone 7-O-beta-D-glucosyltransferase activity;

a heterologous nucleic acid sequence coding for a 6"-O-rhamnosyltransferase comprising SEQ ID NO: 103 or a polypeptide comprising a sequence having at least 60% sequence identity with this sequence and having 6"-O-rhamnosyltransferase activity; and a heterologous nucleic acid sequence coding for a UDP-glucose 4,6-dehydratase/UDP-4-keto-6-deoxy-D-glucose 3,5-epimerase/UDP-4-keto-L-rhamnose-reductase comprising SEQ ID NO: 107 or a polypeptide comprising a sequence having at least 60% sequence identity with this sequence and having UDP-glucose 4,6-dehydratase/UDP-4-keto-6-deoxy-D-glucose 3,5-epimerase/UDP-4-keto-L-rhamnose-reductase activity.

18. The microorganism as claimed in claim 1, in which the microorganism is a yeast or a bacterium.

* * * * *